US010538487B2

(12) United States Patent
O'Neill et al.

(10) Patent No.: US 10,538,487 B2
(45) Date of Patent: Jan. 21, 2020

(54) SULFONYLUREAS AND RELATED COMPOUNDS AND USE OF SAME

(71) Applicants: THE UNIVERSITY OF QUEENSLAND, Queensland (AU); THE PROVOST, FELLOWS, FOUNDATION SCHOLARS, AND THE OTHER MEMBERS OF THE BOARD OF THE COLLEGE OF THE HOLY AND UNDIVIDED TRINITY OF QUEEN ELIZABETH NEAR DUBLIN, Dublin (IE)

(72) Inventors: Luke O'Neill, Dublin (IE); Rebecca Coll, West End (AU); Matthew Cooper, Chapel Hill (AU); Avril Robertson, Kenmore (AU); Kate Schroder, Fairfield (AU)

(73) Assignees: THE UNIVERSITY OF QUEENSLAND, Queensland (AU); THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE)

( * ) Notice: Subject to any disclaimer, the term of this patent is extended or adjusted under 35 U.S.C. 154(b) by 0 days.

(21) Appl. No.: 15/551,264

(22) PCT Filed: Feb. 16, 2016

(86) PCT No.: PCT/AU2016/050103
§ 371 (c)(1),
(2) Date: Aug. 15, 2017

(87) PCT Pub. No.: WO2016/131098
PCT Pub. Date: Aug. 25, 2016

(65) Prior Publication Data
US 2018/0044287 A1 Feb. 15, 2018

(30) Foreign Application Priority Data
Feb. 16, 2015 (AU) ................... 2015900507

(51) Int. Cl.
*C07C 311/56* (2006.01)
*C07D 307/18* (2006.01)
(Continued)

(52) U.S. Cl.
CPC .............. *C07C 311/56* (2013.01); *A61P 1/00* (2018.01); *A61P 3/00* (2018.01); *A61P 5/00* (2018.01); *A61P 17/00* (2018.01); *A61P 25/00* (2018.01); *A61P 35/00* (2018.01); *A61P 37/00* (2018.01); *C07C 311/60* (2013.01); *C07D 207/38* (2013.01); *C07D 213/71* (2013.01);

*C07D 215/36* (2013.01); *C07D 217/02* (2013.01); *C07D 217/22* (2013.01); *C07D 217/24* (2013.01); *C07D 221/18* (2013.01); *C07D 231/18* (2013.01); *C07D 235/02* (2013.01); *C07D 241/42* (2013.01); *C07D 241/44* (2013.01); *C07D 249/04* (2013.01); *C07D 249/06* (2013.01); *C07D 249/12* (2013.01); *C07D 261/18* (2013.01); *C07D 271/12* (2013.01); *C07D 277/36* (2013.01); *C07D 307/18* (2013.01); *C07D 307/64* (2013.01); *C07D 307/68* (2013.01); *C07D 307/82* (2013.01); *C07D 309/08* (2013.01); *C07D 311/16* (2013.01); *C07D 311/18* (2013.01); *C07D 311/60* (2013.01); *C07D 317/62* (2013.01); *C07D 333/34* (2013.01); *C07D 333/52* (2013.01); *C07D 333/62* (2013.01); *C07D 401/06* (2013.01); *C07D 401/12* (2013.01); *C07D 403/12* (2013.01); *C07D 405/12* (2013.01); *C07D 407/12* (2013.01); *C07D 413/12* (2013.01); *C07D 417/12* (2013.01); *C07D 487/04* (2013.01); *C07D 493/04* (2013.01); *C07D 495/04* (2013.01);

(Continued)

(58) Field of Classification Search
None
See application file for complete search history.

(56) References Cited

U.S. PATENT DOCUMENTS 4,018,929 A  4/1977 Delarge et al.
4,723,991 A  2/1988 Holyoke, Jr. et al.
(Continued)

FOREIGN PATENT DOCUMENTS

CA   1292738 C    12/1991
CN   104513239 A   4/2015
(Continued)

OTHER PUBLICATIONS

WIPO Application No. PCT/AU2016/050103, PCT International Preliminary Report on Patentability dated Aug. 31, 2017.
Laliberte et al., "Glutathione S-Transferase Omega 1-1 Is a Target of Cytokine Release Inhibitory Drugs and May Be Responsible for Their Effect on Interleukin-1fi Posttranslational Processing," J Biol Chem, 278(19):16567-16578, doi: 10.1074/jbc.M211596200, (2003).
(Continued)

Primary Examiner — Kristin A Vajda
(74) Attorney, Agent, or Firm — Alston & Bird LLP

(57) ABSTRACT

The present invention provides for certain sulfonyl ureas and related compounds which have advantageous properties and show useful activity in the inhibition of activation of the NLRP3 inflammasome. Such compounds are useful in the treatment of a wide range of disorders in which the inflammation process, or more specifically the NLRP3 inflammasome, have been implicated as being a key factor.

34 Claims, 3 Drawing Sheets

(51) Int. Cl.
| | |
|---|---|
| C07D 307/64 | (2006.01) |
| C07D 407/12 | (2006.01) |
| C07D 493/04 | (2006.01) |
| C07D 405/12 | (2006.01) |
| C07D 333/34 | (2006.01) |
| C07D 277/36 | (2006.01) |
| C07D 249/12 | (2006.01) |
| C07D 249/04 | (2006.01) |
| C07D 231/18 | (2006.01) |
| C07D 403/12 | (2006.01) |
| C07C 311/60 | (2006.01) |
| C07D 333/52 | (2006.01) |
| C07D 249/06 | (2006.01) |
| C07D 413/12 | (2006.01) |
| C07D 495/04 | (2006.01) |
| C07D 401/12 | (2006.01) |
| C07D 241/24 | (2006.01) |
| C07D 307/68 | (2006.01) |
| C07D 271/12 | (2006.01) |
| C07D 311/16 | (2006.01) |
| C07D 317/62 | (2006.01) |
| C07D 487/04 | (2006.01) |
| C07D 215/36 | (2006.01) |
| C07D 217/02 | (2006.01) |
| C07D 241/42 | (2006.01) |
| C07D 498/04 | (2006.01) |
| C07D 307/82 | (2006.01) |
| C07D 333/62 | (2006.01) |
| C07D 217/24 | (2006.01) |
| C07D 207/38 | (2006.01) |
| C07D 261/18 | (2006.01) |
| C07D 213/71 | (2006.01) |
| C07D 221/18 | (2006.01) |
| C07D 309/08 | (2006.01) |
| A61P 1/00 | (2006.01) |
| C07D 417/12 | (2006.01) |
| C07D 495/06 | (2006.01) |
| C07D 311/60 | (2006.01) |
| A61P 35/00 | (2006.01) |
| A61P 3/00 | (2006.01) |
| C07D 235/02 | (2006.01) |
| C07D 311/18 | (2006.01) |
| A61P 17/00 | (2006.01) |
| A61P 5/00 | (2006.01) |
| C07D 401/06 | (2006.01) |
| A61P 37/00 | (2006.01) |
| A61P 25/00 | (2006.01) |
| C07D 217/22 | (2006.01) |
| C07D 241/44 | (2006.01) |

(52) U.S. Cl.
CPC ......... C07D 495/06 (2013.01); C07D 498/04 (2013.01); *C07C 2601/02* (2017.05); *C07C 2601/08* (2017.05); *C07C 2601/14* (2017.05); *C07C 2601/16* (2017.05); *C07C 2602/08* (2017.05); *C07C 2602/10* (2017.05); *C07C 2603/10* (2017.05)

(56) References Cited

U.S. PATENT DOCUMENTS

| | | | |
|---|---|---|---|
| 4,741,760 | A | 5/1988 | Meyer et al. |
| 4,802,908 | A | 2/1989 | Hillemann |
| 5,169,860 | A | 12/1992 | Mohamadi et al. |
| 2002/0034764 | A1 | 3/2002 | Gabel et al. |
| 2002/0077486 | A1 | 6/2002 | Scarborough et al. |
| 2006/0069093 | A1 | 3/2006 | Scarborough et al. |

FOREIGN PATENT DOCUMENTS

| | | |
|---|---|---|
| DK | 2006/00313 L | 3/2006 |
| EP | 125864 A1 | 5/1984 |
| EP | 177163 A2 | 4/1986 |
| EP | 189069 A2 | 7/1986 |
| EP | 224842 A2 | 6/1987 |
| EP | 249938 A2 | 12/1987 |
| EP | 262096 A1 | 3/1988 |
| EP | 318602 A1 | 6/1989 |
| EP | 176304 A1 | 6/1991 |
| EP | 0467613 A1 | 1/1992 |
| EP | 795548 A1 | 9/1997 |
| EP | 885890 A1 | 12/1998 |
| EP | 0885890 A1 | 12/1998 |
| EP | 976742 A1 | 2/2000 |
| EP | 1236468 | 9/2002 |
| EP | 1236468 A1 | 9/2002 |
| EP | 1995240 A1 | 11/2008 |
| EP | 2543670 A1 | 1/2013 |
| EP | 2781216 A1 | 9/2014 |
| EP | 2962692 A1 | 1/2016 |
| FR | 2063472 A | 8/1971 |
| FR | 2063472 A1 | 8/1971 |
| GB | 1322980 A | 7/1973 |
| GB | 1322980 A | 11/1973 |
| JP | H06-045573 | 3/1985 |
| JP | S62-148482 | 7/1987 |
| JP | H06-199053 A | 7/1994 |
| JP | H06-199054 A | 7/1994 |
| JP | 2000-053649 A | 2/2000 |
| RU | 2022963 C1 | 11/1994 |
| WO | WO 1991/10668 A1 | 7/1991 |
| WO | WO 1992/04319 A | 3/1992 |
| WO | WO 1992/04319 A1 | 3/1992 |
| WO | WO 98/032733 A1 | 7/1998 |
| WO | WO 1998/032733 | 7/1998 |
| WO | WO 2016/119349 A1 | 12/1998 |
| WO | WO 01/019390 A1 | 3/2001 |
| WO | WO 2001/019390 | 3/2001 |
| WO | WO 2001/19390 A1 | 3/2001 |
| WO | WO 2001/57037 A1 | 8/2001 |
| WO | WO 2003/031397 A1 | 4/2003 |
| WO | WO 2003/045400 A1 | 6/2003 |
| WO | WO 2005/032488 A2 | 4/2005 |
| WO | WO 2005/035520 A1 | 4/2005 |
| WO | WO 2006/039212 A2 | 4/2006 |
| WO | WO 2006/085815 A1 | 8/2006 |
| WO | WO 2006/097293 A2 | 9/2006 |
| WO | WO 2008/090382 A1 | 7/2008 |
| WO | WO 16/119349 A1 | 8/2016 |
| WO | WO 2016/138473 A1 | 9/2016 |
| WO | WO 2017/106957 A1 | 6/2017 |
| WO | WO 2017/129897 A1 | 8/2017 |
| WO | WO 1998/32733 A1 | 4/2019 |
| WO | WO 1998/32733 A1 | 7/2019 |

OTHER PUBLICATIONS

Ouf et al., "Thiophene Sulphonylureas Structurally Related to Antidiabetic Drugs," Journal of Drug Research and Control Centre, Giza, Egypt, 6(2):123-129, (1974).
Urban et al., "Novel Synthesis of 1-(1,2,3,5,6,7-Hexahydro-s-indacen-4-yl)-3-[4-(1hydroxy-1-methyl-ethyl)-furan-2-sulfonyl]urea, an Anti-inflammatory Agent," Synthetic Communications, 33(12):2029-2043, doi: 10.1081/SCC-120021029 (2003).
EPO Application No. 16751821.6, Supplementary European Search Report and European Search Opinion dated Jun. 21, 2018.
CAS RN 309742-96-9; STN Entry date Dec. 19, 2000; N-[[(4-chlorophenyl)amino]carbonyl]-1-(phenylmethyl)-1H-1,2,4-Triazole-3-sulfonamide.
CAS RN 663215-37-0; STN Entry date Mar. 15, 2004; N-(2-chlorophenyl)-5-[[[[(2-chlorophenyl)amino]carbonyl]amino]sulfonyl]-1H-1,2,4-Triazole-1-carboxamide.
Baldwin, et al, "Inhibiting the Inflammasome: A Chemical Perspective," J. of Medicinal Chemistry, DOI: 10.1021/acs.jmedchem.5b01091, received Jul. 13, 2015.

(56) References Cited

OTHER PUBLICATIONS

Braddock, et al., "Targeting IL-1 in Inflammatory Disease: New Opportunities for Therapeutic Intervention," Nature Reviews, Drug Discovery, vol. 3, (Apr. 2004).
Coll, et al., "A small-molecule inhibitor of the NLRP3 inflammasome for the treatment of inflammatory diseases," Nature Medicine, vol. 21, No. 3, pp. 248-257, (Mar. 2015).
Cubrilovic, et al., "Determination of Protein-Ligand Binding Constants of a Cooperatively Regulated Tetrameric Enzyme Using Electrospray Mass Spectrometry," ACS Chem Biol., 9, 219-226, (2014).
El-Telbany, et al., "Synthesis of Thiophenesulphonylureas and Thioureas Structurally Related to Certain Oral Hypoglycemic drugs. Part 1," Egypt J. Pharm. Sci., vol. 16, No. 4, pp. 397-401, (1975).
Hebeisen, et al., "Orally active Aminopyridines as inhibitors of tetrameric fructose-1, 6-bisphosphase," Bioorganic & Medicinal Chemistry Letters, 21: 3237-3242, (2011).
Krishnan, et al., "Inflammasome activity is essential for one kidney/ deoxycorticosterone acetate/salt-induced hypertension in mice," British Journal of Pharmacacology, 173:752-765, (2016).
Laporte, et al., "Tetrahydrobenzothiophen inhibitors of hepatitis C Virus NS5B polymerase," Bioorganic & Medicinal Chemistry Letters, 16: 100-133, (2006).
Ouf, et al., "Sulphonyl Ureas and Thioureas of 1, 3, 4-Thiodiazole to be tested as Hypoglycomie Agents," Egypt. J. Pharm. Sci., vol. 21, No. 3-4, pp. 189-198, (1980).
Ouf, et al., Thiophene Sulphonylureas Structurally Related to Antidiabetic Drugs, J. Drug Res. Egypt, vol. 6, No. 2, (1974).
Rotroll, et al., "Predictive Endocrne Testing in the 21st Centry Using in Vitro Assays of Estrogen Receptor Signaling Responses," American Chemical Society, vol. 48, Issue 15, pp. 8706-8716, (2014).
Shah, et al., Analysis of Pfizer Compounds in EPA's ToxCast Chemicals-Assay Space, Published by ACS American Chemical Society, vol. 27, pp. 86-88, (2014).
Sipes, et al., "Profiling 976 ToxCast Chemicals across 331 Enzymatic and Receptor Signaling Assays," American Chemical Society, vol. 26, Issue 6, pp. 878-895, (2013).
Wambaaugh, et al., "High-Throughput Models for Exposure-Based chemical Prioritization in the ExpoCast Project," American Chemical Society, vol. 47, p. 8479, (2013).
Waterman, et al., "Improved Protocol and Data Analysis for Accelerated Shelf-Life Estimation of Solid Dosage Forms," Pharmaceutical Research, vol. 24, No. 4, (Apr. 2007).
Youssef, et al., "Synthesis of Sulofenur Analoges as Antitumour Agents: Part II," Med Chem Res, 11:9, pp. 481-503, (2002).
Alsante, et al., "Pharmaceutical Impurity Identification: A Case Study Using a Multidisciplinary Approach," Journal of Pharmaceutical Sciences, vol. 93, No. 9, pp. 2296-2309, (Sep. 2004).
Baldwin, et al, "Inhibiting the Inflammasome: A Chemical Perspective," J. of Medicinal Chemistry, DOI: 10.1021/acs.jmedchem. 5b01091, received Jul. 13, 2015, vol. 59, pp. 1691-1710, (2016).
Braddock, et al., "Targeting IL-1 in Inflammatory Disease: New Opportunities for Therapeutic Intervention," Nature Reviews, Drug Discovery, vol. 3, pp. 1-10, (Apr. 2004).
Coll, et al., "A small-molecule inhibitor of the NLRP3 inflammasome for the treatment of inflammatory diseases," Nature Medicine, vol. 21, No. 3, pp. 248-255, (Mar. 2015).
Cubrilovic, et al., "Determination of Protein-Ligand Binding Constants of a Cooperatively Regulated Tetrameric Enzyme Using Electrospray Mass Spectrometry," ACS Chem Biol., 9, 218-226, (2014).
El-Telbany, et al., "Synthesis of Thiophenesulphoynlureas and Thioureas Structurally Related to Certain Oral Hypoglycemic drugs. Part 1," Egypt. J. Pharm. Sci., vol. 16, No. 4, pp. 397-401, (1975).
Hebeisen, et al., "Orally active Aminopyridines as inhibitors of tetrameric fructose-1, 6-bisphosphatase," Bioorganic & Medicinal Chemistry Letters, 21: 3237-3242, (2011).

Holland, "Preparation of Some Additional Sulfonylureas1," Journal of organic chemistry, American Chenical Society, vol. 26, pp. 1662-1665, (1961).
Khuntwal, et al., "Credential Role of van der Waal Volumes and Atomic Masses in Modeling Hepatitis C Virus NS5B Polymerase Inhibition by Tetrahydrobenzo-Thiophenes Using SVM and MLR Aided QSAR Studies," Current Bioinformatics, 8, 465-471, (2013).
Krishnan, et al., "Inflammasome activity is essential for one kidney/ deoxycorticosterone acetate/salt-induced hypertension in mice," British Journal of Pharmacology, 173:752-765, (2016).
Laporte, et al., "Tetrahydrobenzothiophene inhibitors of hepatitis C Virus NS5B polymerase," Bioorganic & Medicinal Chemistry Letters, 16: 100-103, (2006).
Luckhurst, et al., "A convenient synthesis of sulfonylureas from carboxylic acids and sulfonamides via an in situ Curtius rearrangement," Tetrahedron Letters, 48, pp. 8878-8882, (2007).
Ouf, et al., "Sulphonyl Ureas and Thioureas of 1, 3, 4-Thiodiazole to be tested as Hypoglycomic Agents," Egypt J. Pharm. Sci., vol. 21, No. 3-4, pp. 189-198, (1980).
Ouf, et al., Thiophene Sulphonylureas Structurally Related to Antidiabetic Drugs, J. Drug Res. Egypt, vol. 6, No. 2, pp. 123-129, (1974).
Rotroff, et al., "Predictive Endocrne Testing in the 21st Centry Using in Vitro Assays of Estrogen Receptor Signaling Responses," Environmental Science & Technology, vol. 48, Issue 15, pp. 8706-8716, (2014), published by American Chemical Society.
Saczewski, et al., "Synthesis of Novel Aryl(heteroaryl)sulfonyl Ureas of Possible Biological Interest," Molecules, 15, pp. 1113-1126, (2010).
Shah, et al., Analysis of Pfizer Compounds in EPA's ToxCast Chemicals-Assay Space, Chemical Research in Toxicology, vol. 27, pp. 86-98, (2014), published by American Chemical Society.
Shah, et al., "Setting Clinical Exposure Levels of Concern for Drug-Induced Liver Injury (DILI) Using Mechanistic in vitro Assays," Toxicological Sciences, 147(2), pp. 500-514, (2015).
Sipes, et al., "Profiling 976 ToxCast Chemicals across 331 Enzymatic and Receptor Signaling Assays," Chemical Research in Toxicology, vol. 26, Issue 6, pp. 878-895, (2013), published by American Chemical Society.
Wambaugh, et al., High-Throughput Models for Exposure-Based chemical Prioritization in the ExpoCast Project, Environmental Science & Technology, vol. 47, pp. 8479-8488, (2013), published by American Chemical Society.
Waterman, et al., "Improved Protocol and Data Analysis for Accelerated Shelf-Life Estimation of Solid Dosage Forms," Pharmaceutical Research, vol. 24, No. 4, pp. 780-790, (Apr. 2007).
Youssef, et al., "N1, N3-Diaryl sulfonylureas as Possible Anticancer Agents," Alex. J. Pharm. Sci., vol. 8(3), pp. 223-225, (Oct. 1994).
Youssef, et al., "Synthesis of Sulofenur Analogues as Antitumor Agents: Part II," Med Chem Res, 11:9, pp. 481-503, (2002).
Cook et al., "Immunotherapy and vaccine—The NLRP3 inflammasome, a target for therapy in diverse disease states," Eur. J. Immunol., 40: 595-653, (2010).
Doitsh et al., "Cell death by pyroptosis drives CD4 T-cell depletion in HIV-1 infection," Nature, 505:509-514, doi:10.1038/nature12940, (2014).
Grishman et al., "Toll-like receptors, the NLRP3 inflammasome, and interleukin-1β in the development and progression of type 1 diabetes," Pediatric Research, 71(6):626-632, (2012).
Lamkanfi et al., "Glyburide inhibits the Cryopyrin/Nalp3 inflammasome," J. Cell Biol., 187(1):61-70, (2009).
Lo'Pez-Castejo'n et al., "Current status of inflammasome blockers as anti-inflammatory drugs," Expert Opin. Investig. Drugs, 21(7):995-1007, (2012).
Ozaki et al., "Targeting the NLRP3 inflammasome in chronic inflammatory diseases: current perspectives," Journal of Inflammation Research, 8:15-27, (2015).
Wen et al., "A role for the NLRP3 inflammasome in metabolic diseases did Warburg miss inflammation?," Nature Immunology, 13(4):352-357, (2012).
CAS RN 309742-96-9; STN Entry date Dec. 19, 2000; N-[[(4-chlorophenyl)amino]carbonyl]-1-(phenylmethyl)-1H-1,2,4-Triazole-3-sulfonamide.

(56) References Cited

OTHER PUBLICATIONS

CAS RN 663215-37-0; STN Entry date Mar. 15, 2004; N-(2-chlorophenyl)-5-[[[[(2-chloropheny2)amino]carbonyl]amino]sulfonyl]-1H-1,2,4-Triazole-1-carboxamide.

Foroumadi et al, "Synthesis of certain diarylsulfonylurea derivatives as new potential antitumor agents," Chemistry: An Indian Journal, 1(12):745-748, (2005).

Goda et al, "Development of some 1,2,4-triazole derivatives as potential hypoglycemic agents," Alex Journal of Pharml Sci, 1(2):63-66, (1987).

Mohamadi et al., "Sulfonylureas: A New Class of Cancer Chemotherapeutic Agents," J Med Chem, 35:3012-3016, (1992).

Youssef et al, "Synthesis of certain diarylsulfonylureas as antitumor agents," Medicinal Chemistry Research, 10(6):404-418, (2001).

WIPO Application No. PCT/AU2016/050103, PCT International Search Report dated May 17, 2016.

WIPO Application No. PCT/AU2016/050103, PCT Written Opinion of the International Searching Authority dated May 17, 2016.

Eggler et al., "Synthesis of Covalent (14c)-Labeled Diarylsulfonylurea (Dasu) Inhibitors of the Processing and Release of II-1," Journal of Labelled Compounds and Radiopharmaceuticals, 45(9):785-794, doi: 10.1002/JLCR.602, (2002).

Howbert et al., "Novel Agents Effective Against Solid Tumors: The Diarylsulfonylureas Synthesis, Activities, and Analysis of Quantitative Structure-Activity Relationships," J Med Chem, 33(9):2393-2407, doi: 10.1021/JM00171A013, (1990).

Laliberte et al., "Glutathione S-Transferase Omega 1-1 Is a Target of Cytokine Release Inhibitory Drugs and May Be Responsible for Their Effect on Interleukin-1β Posttranslational Processing," J Biol Chem, 278(19):16567-16578, doi: 10.1074/jbc.M211596200, (2003).

Ouf et al., "Thiophene Sulphonylureas Structurally Related to Antidiabetic Drugs," Journal of Drug Research, Egypt, 6(2):123-129, (1974).

Urban et al., "Novel Synthesis of 1-(1,2,3,5,6,7-Hexahydro-s-indacen-4-y1)-3-[4-(1hydroxy-1-methyl-ethyl)-furan-2-sulfonyl]urea, an Anti-inflammatory Agent," Synthetic Communications, 33(12):2029-2043, doi: 10.1081/SCC-120021029 (2003).

Application No. 16751821.6, Supplementary European Search Report and European Search Opinion dated Jun. 21, 2018.

Singapore Application No. 11201706664Q, Written Opinion dated Jun. 7, 2018.

Croker, et al., "C5a, but not C5a-des Arg, induces upregulation of heteromer formation between complement C5a receptors C5aR and C5L2," Immunology and Cell Biology, (2013) 91, 625-633.

Kumar, et al., "Sulfonamide bearing oligonucleotides: Simple synthesis and efficient RNA recognition," Bioorganic & Medicinal Chemistry, 20, (2012), 384-3849.

Li, et al., "Click Chemistry to Fluorescent Amino Esters: Synthesis and Spectroscopic Studies," Eur. J. Org. Chem. 2395-2405, (2010).

Menu, et al., "The NLRP3 inflammasome in health and disease: the good, the bad, and the ugly," 2011 British Society for Immunology, Clinical and Experimental Immunology, 166, 1015, (2011).

Monte, et al., "Dihydrobenzofuran Analogues of Hallucinogens. 3.[1] Models of 4-Substituted (2,5-Dimethoxyphenyl)alkylamine Derivatives with Rigidified Methoxy Groups[2]," J. Med. Chem. 1996, 39, 2953-2961.

Mu, et al., "Fluorescent Logic Gates Chemically Attached to Silicon Nanowires," Angew. Chem. Int. Ed., 48, 3469-3472, (2009).

Nair, et al., "Unexpected binding Mode of the Sulfonamide Fluorophore 5-Dimethylamino-1-naphthalene Sulfonamide to Human Carbonic Anhydrase II," The Journal of Biological Chemistry, vol. 271, No. 2, Issue of Jan. 12, pp. 1003-1007, (1996).

Perregaux, et al., "Identification and Characterization of a Novel Class of Interleukin-1 Post-Translational Processing Inhibitors," The Journal of Pharmacology and Experimental Therapeutics, vol. 299, No. 1, 187-197, 2001.

Plé, et al., "Discovery of a New Class of Anilinoquinazoline Inhibitors with High Affinity and Specificity for the Tyrosine Kinase Domain of c-Src," J. Med. Chem. 47, 871-887, (2004).

AU 2015900507 Australian Patent Office International-Type Search Report dated Jul. 30, 2015.

EP Application No. 16751821.6 Examination Report dated Feb. 1, 2019.

RU Application No. 2017128287, Exam Report dated Jul. 31, 2019.

SULFONYLUREAS AND RELATED COMPOUNDS AND USE OF SAME

CROSS-REFERENCE TO RELATED APPLICATIONS

This application is the US national stage of PCT/AU2016/050103 filed Feb. 16, 2016, which claims the benefit of AU2015900507 filed Feb. 16, 2015.

FIELD OF THE INVENTION

The invention relates to the field of medical treatment and diagnosis of disease. More particularly, this invention relates to novel sulfonylurea and related compounds and their use in treating, or identifying a disease or condition responsive to modulation of NLRP3 or inhibition of the activation of NLRP3 or related components of the inflammatory process.

BACKGROUND TO THE INVENTION

Any reference to background art herein is not to be construed as an admission that such art constitutes common general knowledge in Australia or elsewhere.

The NOD-like receptor (NLR) family, pyrin domain-containing protein 3 (NLRP3) inflammasome is a component of the inflammatory process, and its aberrant activation is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the proinflammatory cytokines IL-1β and IL-18 to their active forms and mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-10 signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cell driving a Th1 response.

Other intracellular pattern recognition receptors (PRRs) are also capable of forming inflammasomes. These include other NLR family members such as NLRP1 and NLRC4, as well as non-NLR PRRs such as the double-stranded DNA (dsDNA) sensors absent in melanoma 2 (AIM2) and interferon, gamma inducible protein 16 (IFI16). NLRP3-dependent IL-1β processing can also be activated by an indirect, non-canonical pathway downstream of caspase-11.

The inherited CAPS diseases Muckle-Wells syndrome (MWS), familial cold autoinflammatory syndrome and neonatal-onset multisystem inflammatory disease are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using $Nlrp3^{-/-}$ mice, but there have also been insights into the specific activation of NLRP3 in these diseases. In type 2 diabetes, the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised NLRP3 inhibitors include parthenolide, 3,4-methylenedioxy-β-nitrostyrene and dimethyl sulfoxide (DMSO), although these agents have limited potency and are nonspecific Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Several small molecules have been shown to inhibit the NLRP3 inflammasome. Glyburide inhibits IL-1β production at micromolar concentrations in response to the activation of NLRP3 but not NLRC4 or NLRP1. Other previously characterised NLRP3 inhibitors include parthenolide, 3,4-methylenedioxy-1-nitrostyrene and dimethyl sulfoxide (DMSO), although these agents have limited potency and are nonspecific.

Certain diarylsulfonylurea-containing compounds have been identified as cytokine release inhibitory drugs (CRIDs) (Perregaux et al.; J. Pharmacol. Exp. Ther. 299, 187-197, 2001). CRIDs are a class of diarylsulfonylurea containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

There is a need to provide compounds with improved pharmacological and/or physiological and or physicochemical properties and/or those that provide a useful alternative to known compounds.

SUMMARY OF INVENTION

According to a first aspect of the invention, there is provided a compound of formula (I), or a pharmaceutically acceptable salt, solvate or prodrug thereof:

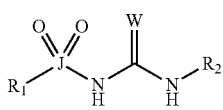

Formula (I)

wherein, W is selected from O, S and Se;
J is selected from S and Se;
$R_1$ is selected from the group consisting of cycloalkyl, aryl, heteroaryl and heterocyclyl, all of which may be optionally substituted;
$R_2$ is selected from the group consisting of cycloalkyl, aryl, heteroaryl and heterocyclyl, all of which may be optionally substituted; and
both $R_1$ is directly bonded to J and $R_2$ is directly bonded to the adjacent nitrogen, via a carbon atom.

According to a second aspect of the invention there is provided a pharmaceutical composition comprising a compound of the first aspect, or a pharmaceutically acceptable salt, solvate or prodrug thereof, and a pharmaceutically acceptable carrier, diluent and/or excipient.

A third aspect of the invention resides in a method of treatment or prevention of a disease, disorder or condition including the step of administering an effective amount of a compound of the first aspect, or a pharmaceutically effective salt, solvate or prodrug thereof, or the pharmaceutical composition of the second aspect to thereby treat or prevent the disease disorder or condition.

A fourth aspect of the invention provides for a compound of the first aspect, or a pharmaceutically effective salt, solvate or prodrug thereof, or the pharmaceutical composition of the second aspect for use in the treatment or prevention of a disease, disorder or condition.

A fifth aspect of the invention provides for use of a compound of the first aspect, or a pharmaceutically effective salt, solvate or prodrug thereof, in the manufacture of a medicament for the treatment or prevention of a disease, disorder or condition.

In one embodiment, the disease, disorder or condition is responsive to inhibition of activation of the NLRP3 inflammasome.

In particular non-limiting embodiments of the above aspects, the disease, disorder or condition is a disease, disorder or condition of the immune system, the cardiovascular system, the endocrine system, the gastrointestinal tract, the renal system, the respiratory system, the central nervous system, is a cancer or other malignancy and/or is caused by or associated with a pathogen.

In a sixth aspect of the invention there is provided a method of diagnosing a disease, disorder or condition in a mammal including the step of administering a labelled compound of formula (I), (Ia), (Ib), (Ic) or (II), or a pharmaceutically effective salt, solvate or prodrug thereof, to the mammal or to a biological sample obtained from the mammal to facilitate diagnosis of the disease disorder or condition in the mammal.

A seventh aspect of the invention resides in a method of modulating the activity of a biological target comprising the step of exposing the biological target to a compound of the first aspect, or a pharmaceutically acceptable salt thereof.

The biological target may be selected from the group consisting of the NLRP3 inflammasome, IL-1β, IL-17, IL-18, IL-1α, IL-37, IL-33 and Th17 cells.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein.

DETAILED DESCRIPTION

Figure 1A:
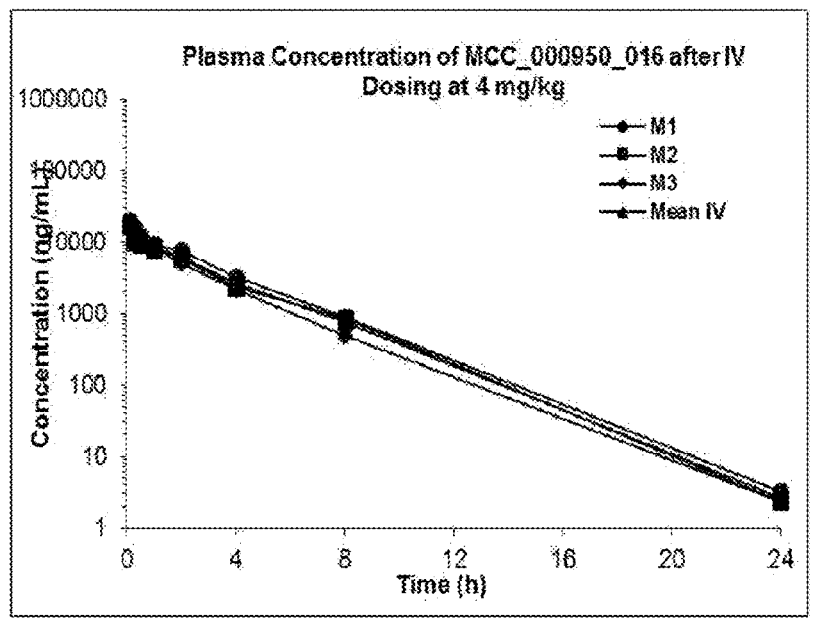
FIG. 1A to 1C is a series of graphical representations of the plasma concentrations of a known sulfonylurea (MCC950) following different dosing levels in mice.

The present invention is predicated, at least in part, on the finding that certain sulfonyl ureas and related compounds have advantageous properties and show useful activity in the inhibition of activation of the NLRP3 inflammasome and/or inhibition of IL-1β and/or IL-17 and/or IL-18, and/or IL-1α, and/or IL-37, and/or IL-33 as well as interfere with or modulate the activity of T helper cells such as Th17. Particularly, the compounds of the invention are useful in the treatment of a wide range of disorders in which the inflammation process, or the NLRP3 inflammasome and/or IL-1β and/or IL-17 and/or IL-18, and/or IL-1α, and/or IL-37, and/or IL-33 and/or Th17 cells play a part.

Evidence from human CAPS patients and mouse models of CAPS has lead the present inventors to believe that NLRP3 inhibition will be a superior treatment over IL-1 biologics, as inhibition of all NLRP3-dependent processes will be more effective than inhibition of a single NLRP3-dependent process, such as IL-1 signalling.

Individuals with CAPS display dysregulated secretion of both IL-1β and IL-18, and CAPS patients treated with anti-IL-1 biologics have residual disease. Symptoms such as bony overgrowth and joint deformity are not prevented by IL-1 biologics. In addition, symptoms involving the central nervous system such as hearing loss are difficult to control using IL-1 biologics, which appear to poorly penetrate the central nervous system. Studies in mouse models of CAPS indicate that deficiency in either IL-1 signalling or IL-18 alone is insufficient to block systemic inflammation, particularly in older animals. In a severe model of CAPS, only a complete loss of caspase-1 signalling fully rescued the disease.

Specific inhibition of NLRP3 by sulfonylurea-containing compounds, such as those of the first aspect, may block all processes downstream of NLRP3, including ASC speck formation and caspase-8 and caspase-1 activation. Consequently, NLRP3 inhibition will block all caspase-1 dependent processes such as IL-1β, IL-18 and IL-37 processing and secretion, gasdermin D cleavage, pyroptosis, and release of IL-1α, IL-33 and HMGB. Furthermore, NLRP3-dependent extracellular release of the ASC speck will be blocked, and caspase-8-dependent pro-IL-1β and pro-IL-18 cleavage and apoptotic cell death will be prevented. Thus, specific inhibition of NLRP3 by compounds of the first aspect will prevent multiple downstream inflammatory signals and should therefore prove more effective anti-inflammatory therapy than IL-1 blockade alone.

Anti-IL-1 biologics block IL-1 derived from NLRP3-independent sources, such IL-1 produced by other inflammasomes (e.g. NLRC4, NLRP1, NLRP6, AIM2) and IL-1 generated by the latter pathways may be important for host defence against pathogens. For example, patients receiving IL-1/IL-1R antagonists exhibit increased incidence of upper airway infections. Specific inhibition of NLRP3 by the present compounds may thus exert less generalised immunosuppression compared to anti-IL-1 biologics.

IL-1β and IL-18, generated by the Nlrp3/caspase-1 axis, play critical roles in driving IL-17 production by CD4 Th17 cells and γδ T cells. IL-1β and IL-18 synergise with IL-23 to induce IL-17 production by memory CD4 Th17 cells and by γδ T cells in the absence of TCR engagement. IL-1-driven IL-17 has also been implicated in psoriasis, type I diabetes, rheumatoid arthritis, type 2 diabetes mellitus, atherosclerosis, obesity, gout, and recently, asthma.

In essence, each of these diseases has been shown to involve the activation of tissue macrophages, dendritic cells, or brain microglia, driven by either soluble alarmins, or the frustrated phagocytosis of metabolites that accumulate extracellularly. NLRP3 senses these events, leading to IL-1 release, triggering inflammation to clear the offensive material. Disease will result if this process becomes chronic or over-activated, which explains why so many diseases have been shown to involve NLRP3. Inhibitors that act to prevent NLRP3 activation hence can have utility in IL-17 driven, as well as IL-1 driven diseases.

In this patent specification, the terms 'comprises', 'comprising', 'includes', 'including', or similar terms are intended to mean a non-exclusive inclusion, such that a method or composition that comprises a list of elements does not include those elements solely, but may well include other elements not listed.

Unless defined otherwise, all technical and scientific terms used herein have the same meaning as would be commonly understood by those of ordinary skill in the art to which this invention belongs.

The term "pharmaceutically acceptable salt", as used herein, refers to salts which are toxicologically safe for systemic or localised administration such as salts prepared from pharmaceutically acceptable non-toxic bases or acids including inorganic or organic bases and inorganic or organic acids. The pharmaceutically acceptable salts may be selected from the group including alkali and alkali earth, ammonium, aluminium, iron, amine, glucosamine, chloride, sulphate, sulphonate, bisulphate, nitrate, citrate, tartrate, bitarate, phosphate, carbonate, bicarbonate, malate, maleate, napsylate, fumarate, succinate, acetate, benzoate, terephthalate, palmoate, piperazine, pectinate and S-methyl methionine salts and the like.

The term "alkyl" refers to a straight-chain or branched alkyl substituent containing from, for example, 1 to about 12 carbon atoms, preferably 1 to about 9 carbon atoms, more preferably 1 to about 6 carbon atoms, even more preferably from 1 to about 4 carbon atoms, still yet more preferably from 1 to 2 carbon atoms. Examples of such substituents may be selected from the group consisting of methyl, ethyl, propyl, isopropyl, n-butyl, sec-butyl, isobutyl, tert-butyl, pentyl, isoamyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl and the like. The number of carbons referred to relates to the carbon backbone and carbon branching but does not include carbon atoms belonging to any substituents, for example the carbon atoms of an alkoxy substituent branching off the main carbon chain. Substituted alkyl includes alkyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of 'optionally substituted'.

The term "alkenyl" refers to optionally substituted unsaturated linear or branched hydrocarbon groups, having 2 to 12 carbon atoms, preferably 2 to 9 carbon atoms, more preferably 2 to 6 carbon atoms and having at least one carbon-carbon double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. The number of carbons referred to relates to the carbon backbone and carbon branching but does not include carbon atoms belonging to any substituents. Examples of such substituents may be selected from the group consisting of ethenyl, propenyl, isopropenyl, butenyl, s- and t-butenyl, pentenyl, hexenyl, hept-1,3-diene, hex-1,3-diene, non-1,3,5-triene and the like. Substituted alkenyl includes alkenyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of 'optionally substituted'.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The terms "cycloalkyl" and "cycloalkenyl" refers to optionally substituted saturated and unsaturated mono-cyclic, bicyclic or tricyclic carbon groups. Where appropriate, the cycloalkyl or cycloalkenyl group may have a specified number of carbon atoms, for example, $C_3$-$C_6$ cycloalkyl or cycloalkenyl includes within its scope a carbocyclic group having 3, 4, 5 or 6 carbon atoms. Examples of such substituents may be selected from the group consisting of cyclopropyl, cyclobutyl, cyclopentyl, cyclopentenyl, cyclohexyl, cyclohexenyl, cyclohexadienyl and the like. Substituted cycloalkyl or cycloalkenyl includes substitutions with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of 'optionally substituted'.

The term "alkylthio" as used herein means a thio group with one or more alkyl substituents, where alkyl is defined as above.

The term "amino" as used herein means a moiety represented by the structure $NR_{23}$, and includes primary amines, and secondary and tertiary amines substituted by alkyl (i.e., alkylamino). Thus, $R_{23}$ may represent, for example, two hydrogen atoms, two alkyl moieties, or one hydrogen atom and one alkyl moiety.

The term "aryl" refers to a stable monocyclic, bicyclic, or tricyclic carbon ring of up to 8 members in each ring, wherein at least one ring is aromatic as defined by the Hückel 4n+2 rule. The term includes polycyclic systems comprising saturated carbon rings or heteroaryl or heterocyclic groups so long as at least one ring is aryl, as described.

The terms "aralkyl" and "arylalkyl" as used herein mean an aryl group as defined above linked to the molecule through an alkyl group as defined above.

The term "heteroaryl" refers to an aryl group containing from one or more (particularly one to four) non-carbon atom(s) (particularly N, O or S) or a combination thereof, which heteroaryl group is optionally substituted at one or more carbon or nitrogen atom(s). Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having four heteroatoms (e.g., tetrazoles); 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. "Substituted heteroaryl" means a heteroaryl having one or more non-interfering groups as substituents and including those defined under 'optionally substituted'.

"Heterocyclyl" as used herein refers to a non-aromatic ring having 5 to 8 atoms in the ring and of those atoms 1 to 4 are heteroatoms. Heterocyclic rings may also be fused with one or more cyclic hydrocarbon, heterocyclic, aryl, or heteroaryl rings. Heterocyclic includes partially and fully saturated heterocyclic groups. Heterocyclic systems may be attached to another moiety via any number of carbon atoms or heteroatoms of the radical and may be both saturated and unsaturated. Non-limiting examples of heterocyclic include $C_4$-$C_6$ selenocycles, pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

"Optionally substituted" in reference to a substituent group refers to substituent groups optionally substituted with one or more moieties, for example, those selected from the group consisting of optionally substituted C1-10 alkyl (e.g., optionally substituted C1-6 alkyl); optionally substituted C3-6 cycloalkyl (e.g., optionally substituted cyclopropyl); optionally substituted hydroxyalkyl; optionally substituted C1-10 alkoxy (e.g., optionally substituted C1-6 alkoxy); optionally substituted C2-10 alkenyl; optionally substituted C2-10 alkynyl; optionally substituted C6-C12 aryl; aryloxy; optionally substituted heteroaryl; optionally substituted heterocyclyl; halo (e.g., Cl, F, Br, and I); hydroxyl; halogenated alkyl (e.g., $CF_3$, 2-Br-ethyl, $CH_2F$, $CH_2CF_3$, and $CF_2CF_3$); amino (e.g., $NH_2$, $NR_{12}H$, and $NR_{12}R_{13}$); alkylamino; arylamino; acyl; amido; CN; $NO_2$; $N_3$; $CH_2OH$; $CONH_2$; $CONR_{24}R_{25}$; $CO_2R_{24}$; $CH_2OR_{24}$; $NHCOR_{24}$; $NHCO_2R_{24}$; $C_{1-3}$ alkylthio; sulfate; sulfonic acid; sulfonate esters such as alkyl or aralkyl sulfonyl, including methanesulfonyl; phosphonic acid; phosphate; phosphonate; mono-, di-, or triphosphate esters; trityl or monomethoxytrityl; $R_{24}SO$; $R_{24}SO_2$; $CF_3S$; and $CF_3SO_2$; trialkylsilyl such as dimethyl-t-butylsilyl or diphenylmethylsilyl; and $R_{24}$ and $R_{25}$ are each independently selected from H or optionally substituted C1-10 alkyl, C1-6 alkyl or C1-4 alkyl.

Whenever a range of the number of atoms in a structure is indicated (e.g., a $C_1$-$C_{12}$, $C_1$-$C_{10}$, $C_1$-$C_9$, $C_1$-$C_6$, $C_1$-$C_4$, or $C_2$-$C_{20}$, $C_2$-$C_{12}$, $C_2$-$C_{10}$, $C_2$-$C_9$, $C_2$-$C_8$, $C_2$-$C_6$, $C_2$-$C_4$ alkyl, alkenyl, etc.), it is specifically contemplated that any subrange or individual number of carbon atoms falling within the indicated range also can be used. Thus, for instance, the recitation of a range of 1-12 carbon atoms (e.g., $C_1$-$C_{12}$), 1-9 carbon atoms (e.g., $C_1$-$C_9$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

According to a first aspect of the invention, there is provided a compound of formula (I), or a pharmaceutically acceptable salt, solvate or prodrug thereof:

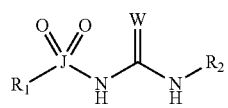

Formula (I)

wherein, W is selected from O, S and Se;
J is selected from S and Se;
$R_1$ is selected from the group consisting of cycloalkyl, aryl, heteroaryl and heterocyclyl, all of which may be optionally substituted;
$R_2$ is selected from the group consisting of cycloalkyl, aryl, heteroaryl and heterocyclyl, all of which may be optionally substituted; and
both $R_1$ is directly bonded to J and $R_2$ is directly bonded to the adjacent nitrogen, via a carbon atom.
In one preferred embodiment, W is O.
In one preferred embodiment, J is S.
In a particularly preferred embodiment, W is O and J is S.
In one embodiment, $R_1$ is selected from the group consisting of $C_5$ or $C_6$ cycloalkyl, 5-membered or 6-membered heteroaryl, bicyclic heteroaryl wherein at least one ring is heteroaryl, phenyl, biphenyl, phenylheterocyclyl, 5-membered or 6-membered heterocyclyl, and heterocyclylcycloalkyl, all of which may be optionally substituted.

In certain embodiments, W is O, J is S and $R_1$ is selected from the group consisting of pyrazole, furan, tetrahydrofuran, tetrahydropyran, pyran, pyrrolidine, pyrrole, triazole, tetrazole, imidazole, pyridine, morpholine, piperazine, piperidine, substituted phenyl, phenylheteroaryl, phenylheterocyclyl, biphenyl, quinoline, isoquinoline, naphthyl, pyrazine and pyrimidine, all of which may be optionally substituted as appropriate.

In one embodiment, when W is O, J is S and $R_1$ is 2-furan or 2-thiophene it is selected from unsubstituted 2-furan or 2,5-substituted furan and unsubstituted 2-thiophene or 2,5-substituted thiophene.

In one embodiment, when W is O, J is S, and $R_1$ is 2,5-substituted furan or 2,5-substituted thiophene then the 2,5-substituted furan or 2,5-substituted thiophene is not substituted with a tertiary alcohol group.

In certain embodiments it has been found that when $R_1$ is an unsubstituted furan then it has the ability to cross the blood brain barrier at levels about 10 times greater than CRID3, a prior art sulfonylurea.

In the above embodiments, reference to 2,5-substituted does not preclude the presence of further substitutions on the ring but merely indicates that the numbered substitutions must be present. For example, 2,4,5-substitutions are considered within the scope of such terms.

Reference to 2-furan and 2-thiophene means that the ring is connected to the sulfonyl sulphur at the 2-ring position, as shown below:

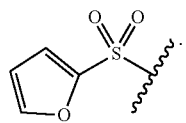 [SMILES: *S(=O)(=O)c1ccco1]

In one embodiment, $R_1$ is 5-membered heterocyclyl or heteroaryl, each of which may be optionally substituted, comprising at least one, preferably at least two ring heteroatoms selected from N, O and S.

In certain embodiments, $R_1$ is a nitrogen heterocyclyl or nitrogen heteroaryl, each of which may be optionally substituted.

In one embodiment, $R_1$ is 5-membered nitrogen heterocyclyl or 5-membered nitrogen heteroaryl, each of which may be optionally substituted.

In an embodiment, $R_1$ is 5-membered heterocyclyl or 5-membered heteroaryl, each comprising at least two ring nitrogen atoms and each of which rings may be optionally substituted.

In one embodiment, W is O, J is S and $R_1$ is selected from the group consisting of quinoline, isoquinoline, naphthyl, pyrazine, tetrazole, imidazole, pyrrolidine, pyrrole, tetrahydropyran, pyran, piperidine, piperazine, pyrazole, pyridine, pyrimidine and triazole, each of which may be optionally substituted.

In one embodiment $R_1$ and/or $R_2$ may comprise a selenocycle.

In one embodiment, $R_2$ may be selected from bicyclic and tricyclic hydrocarbons, 5-, 6- and 7-membered heterocycle or heteroaryl, each of which rings may be optionally substituted, and substituted phenyl.

Suitably, the tricyclic hydrocarbon may be an indacene.

In one embodiment, $R_2$ may be selected from 5-, 6- or 7-membered nitrogen heterocycles, 6-membered nitrogen heteroaryl and aryl with fused cycloalkyl ring.

In one embodiment of the compound of formula (I), W is O, J is S and $R_1$ may be selected from the group consisting of:

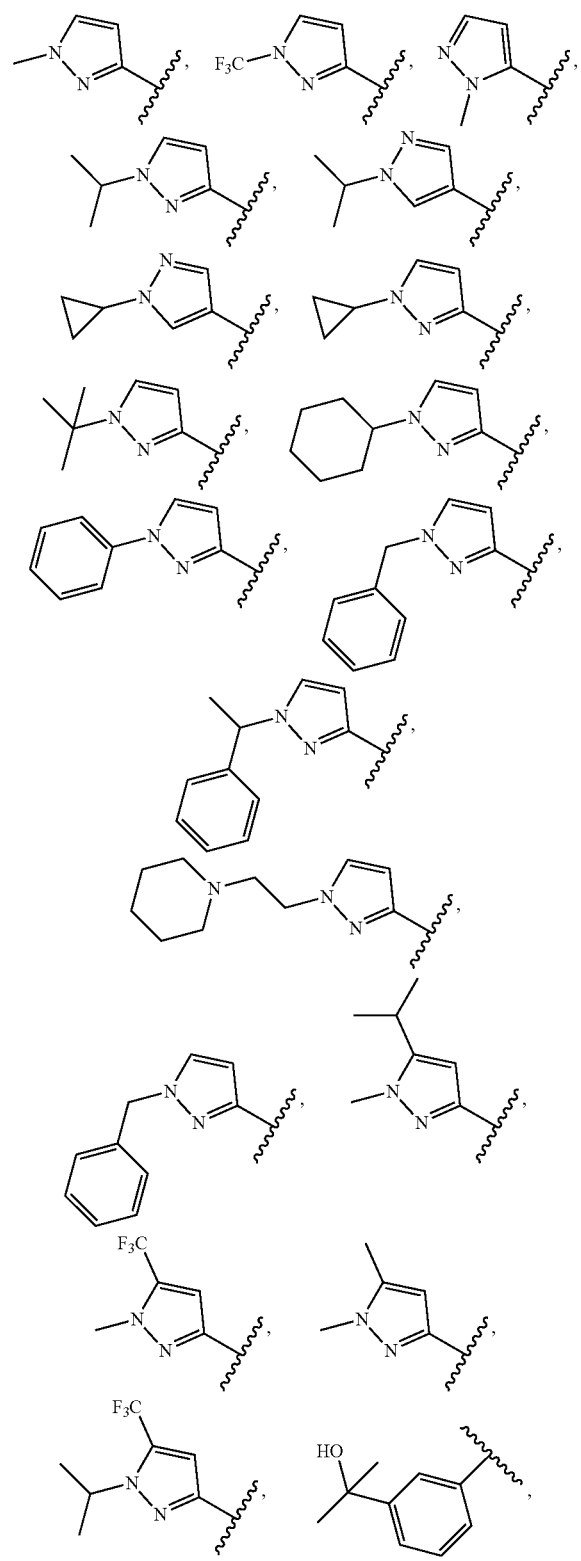

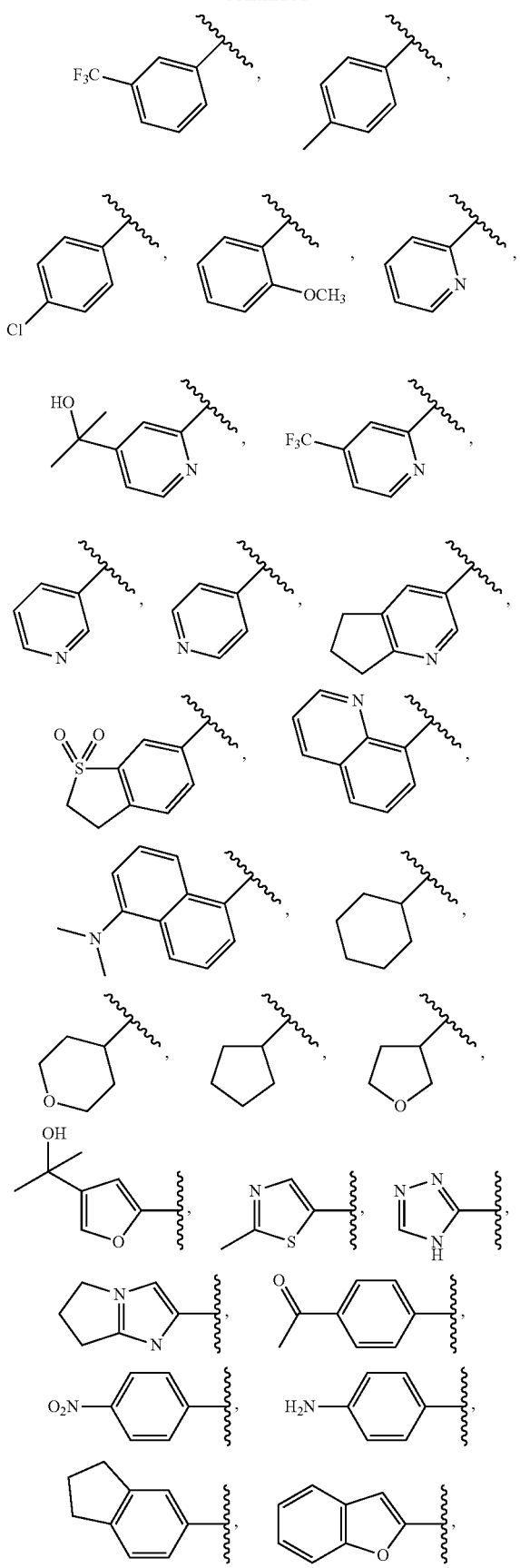
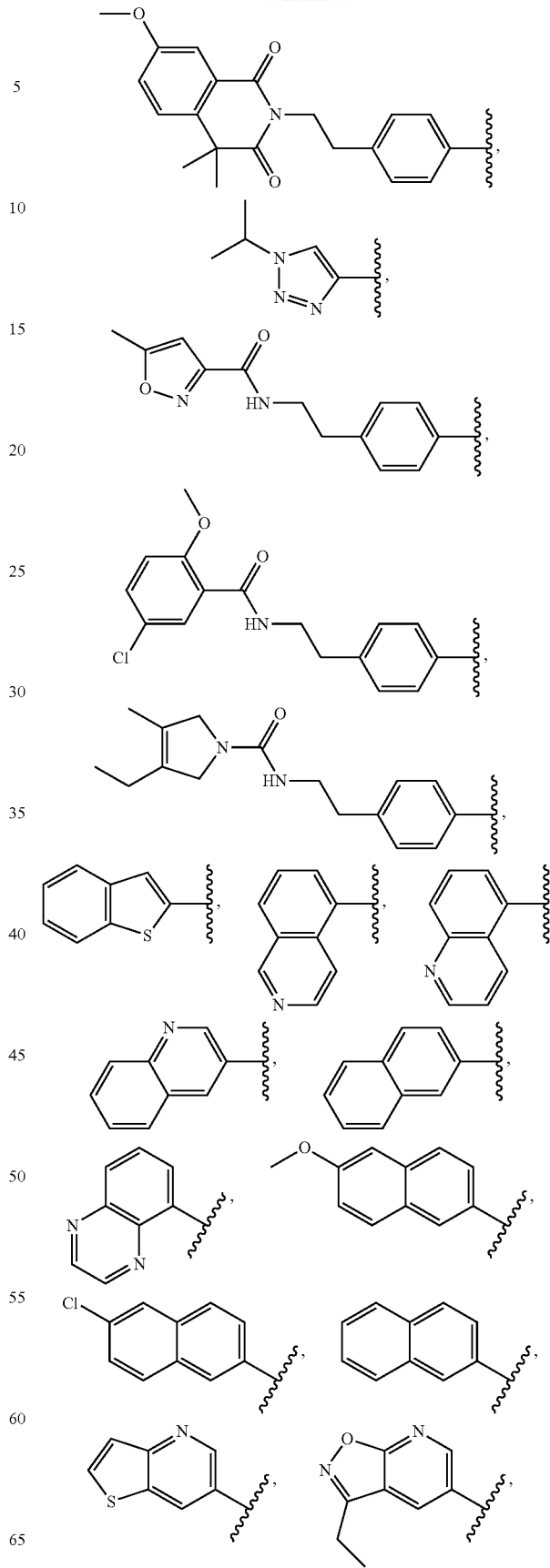

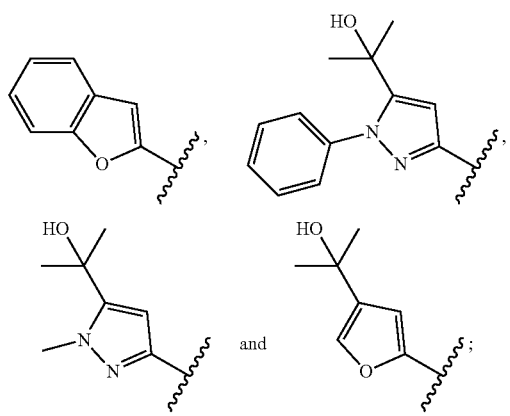
and for each of these $R_1$ groups, $R_2$ may be independently selected from the group consisting of:
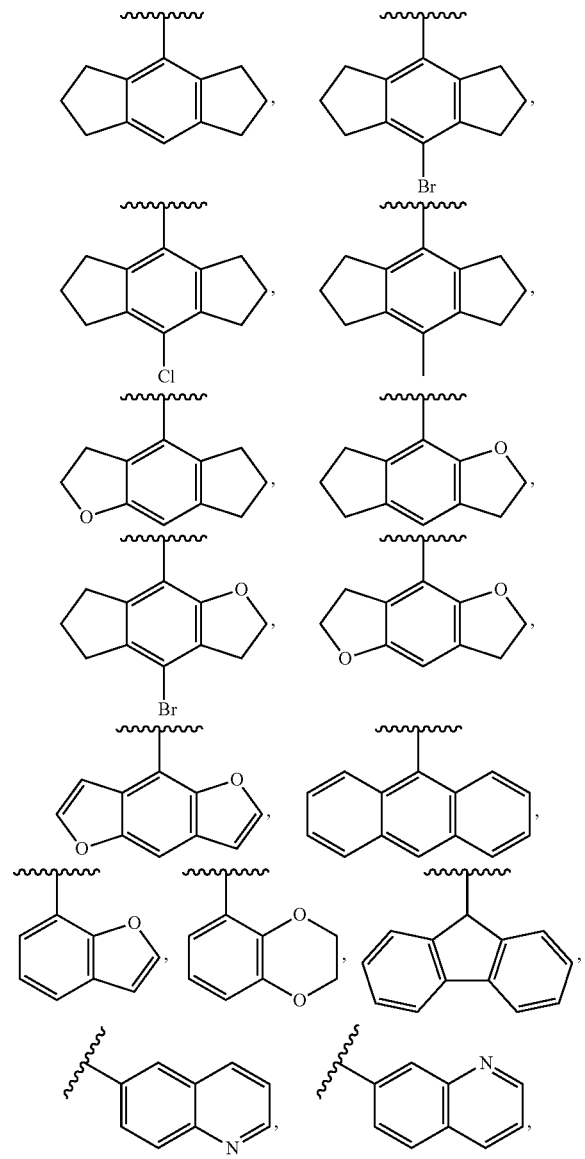
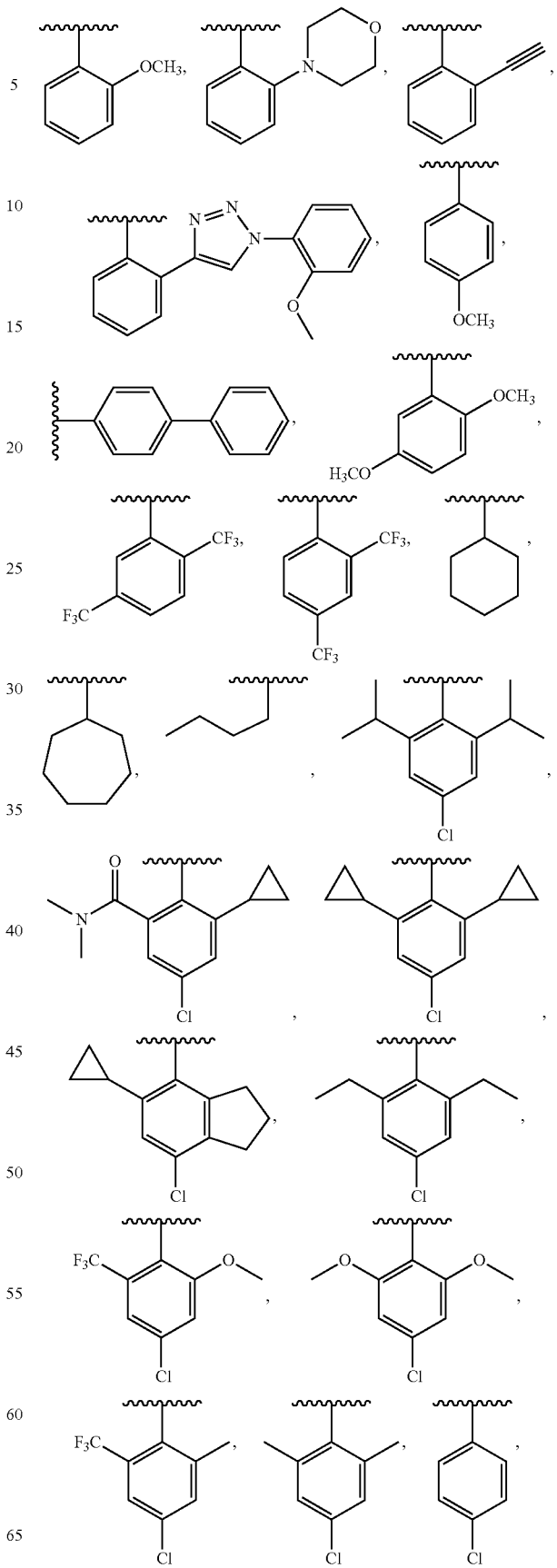

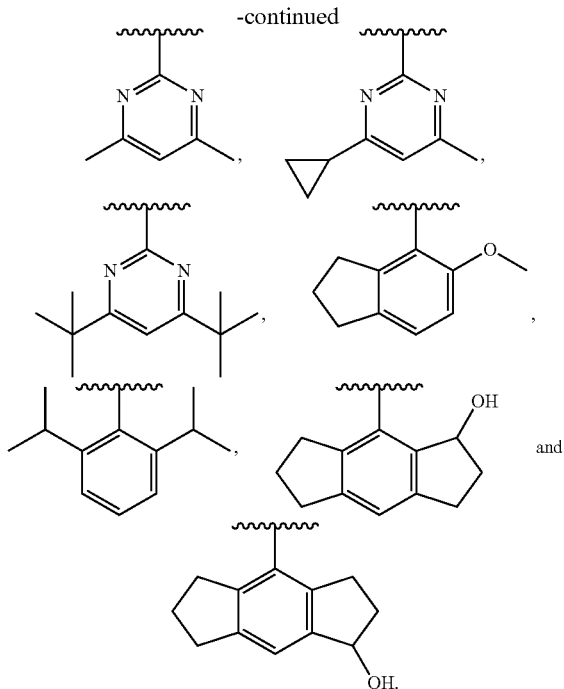

In any embodiment of the first aspect, when J is S and W is O, and in combination with any of the R₁ groups listed above, R₂ may be selected from:

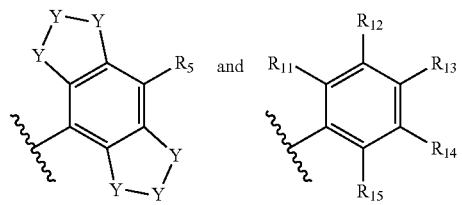

wherein, each incidence of Y is independently selected from C, N, S and O, and which may be optionally substituted, as appropriate;

$R_5$, $R_{11}$, $R_{12}$, $R_{13}$, $R_{14}$ and $R_{15}$ are independently selected from the group consisting of hydrogen, halo, cyano, amide, sulphonamide, acyl, hydroxyl, $C_1$-$C_6$ alkyl, $C_1$-$C_6$ haloalkyl, $C_3$-$C_5$ cycloalkyl, and $C_1$-$C_6$ alkoxy, all of which groups may be optionally substituted, as appropriate, with halo, cyano or $C_1$-$C_6$ alkoxy; and wherein $R_{11}$ and $R_{12}$ may combine to form phenyl, a 5- or 6-membered oxygen heterocycle or a 5- or 6-membered nitrogen heteroaryl, each of which may be optionally substituted;

$R_{12}$ and $R_{13}$ may combine to form a 5- or 6-membered nitrogen heteroaryl, which may be optionally substituted; and $R_{14}$ and $R_{15}$ may combine to form a 5- or 6-membered cycloalkyl ring, phenyl, a 5- or 6-membered oxygen heterocycle or a 5- or 6-membered nitrogen heteroaryl, each of which may be optionally substituted.

Suitably, each incidence of Y is a carbon and $R_5$ is hydrogen or halo.

In one embodiment, $R_{12}$ and $R_{14}$ are hydrogen, $R_{11}$ and $R_{15}$ are $C_1$-$C_6$ alkyl and $R_{13}$ is hydrogen or halo.

Preferably, $R_2$ is selected from a substituted or hydrogenated indacene, a 2,6-dialkylphenyl, a 2,6-dialkyl-4-halophenyl, 2,6-dicycloalkylphenyl, and a 2,6-dicycloalkyl-4-halophenyl.

In certain preferred embodiments, and in combination with any $R_1$ group described for any of the formulae of the first aspect, $R_2$ is selected from hexahydroindacene, 2,6-diisopropylphenyl 2,6-diisopropyl-4-chlorophenyl, 2,6-dicyclopropylphenyl and 2,6-dicyclopropyl-4-chlorophenyl.

In one embodiment, W is O and J is S, $R_1$ is heteroaryl and $R_2$ is

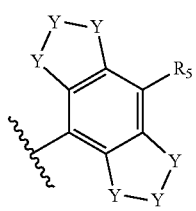

wherein each Y is CH and $R_5$ is H or halogen, preferably $R_5$ is H.

In one embodiment, W is O and J is S, $R_1$ is heteroaryl and $R_2$ is

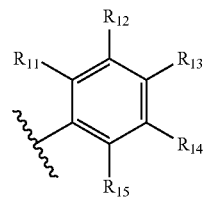

wherein
$R_{11}$ and $R_{15}$ are $C_{1-6}$ alkyl, preferably isopropyl;
$R_{12}$ and $R_{14}$ are H,
$R_{13}$ is H or halogen, preferably H or Cl.

In one embodiment W is O and J is S, $R_1$ is heteroaryl and $R_2$ is

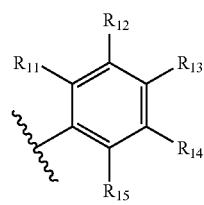

wherein $R_{11}$ and $R_{15}$ are isopropyl, $R_{12}$ and $R_{14}$ are H, and $R_{13}$ is H or Cl.

In particular embodiments, the compound of formula (I) may be selected from a compound of formula (Ia), (Ib) and (Ic), or a pharmaceutically acceptable salt, solvate or prodrug thereof:

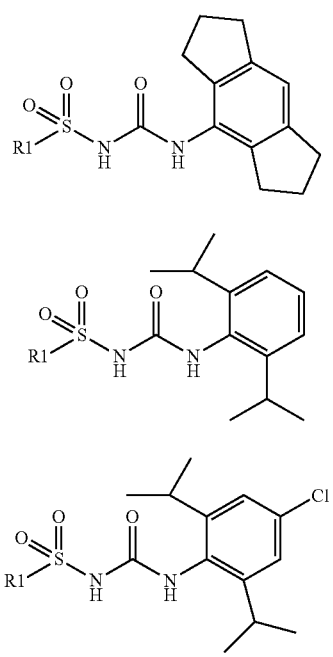

formula (Ia)

formula (Ib)

formula (Ic)

wherein, $R_1$ is as previously described for any embodiment of formula (I).

In one embodiment of the compound of formula (Ia), (Ib) and (Ic), $R_1$ is selected from the group consisting of pyrazole, furan, tetrahydrofuran, tetrahydropyran, pyran, pyrrolidine, pyrrole, triazole, tetrazole, imidazole, pyridine, morpholine, piperazine, piperidine, substituted phenyl, phenylheteroaryl, phenylheterocyclyl, biphenyl, quinoline, isoquinoline, naphthyl, pyrazine and pyrimidine, all of which may be optionally substituted as appropriate.

In one embodiment of the compound of formula (Ia), (Ib) and (Ic), $R_1$ is selected from the group consisting of:

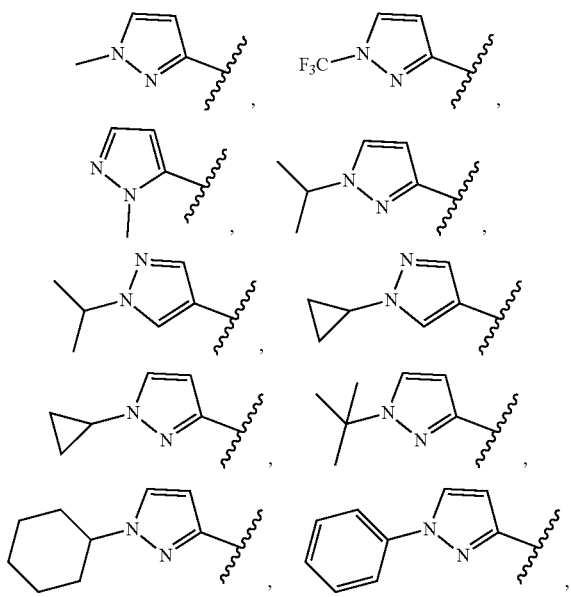

-continued

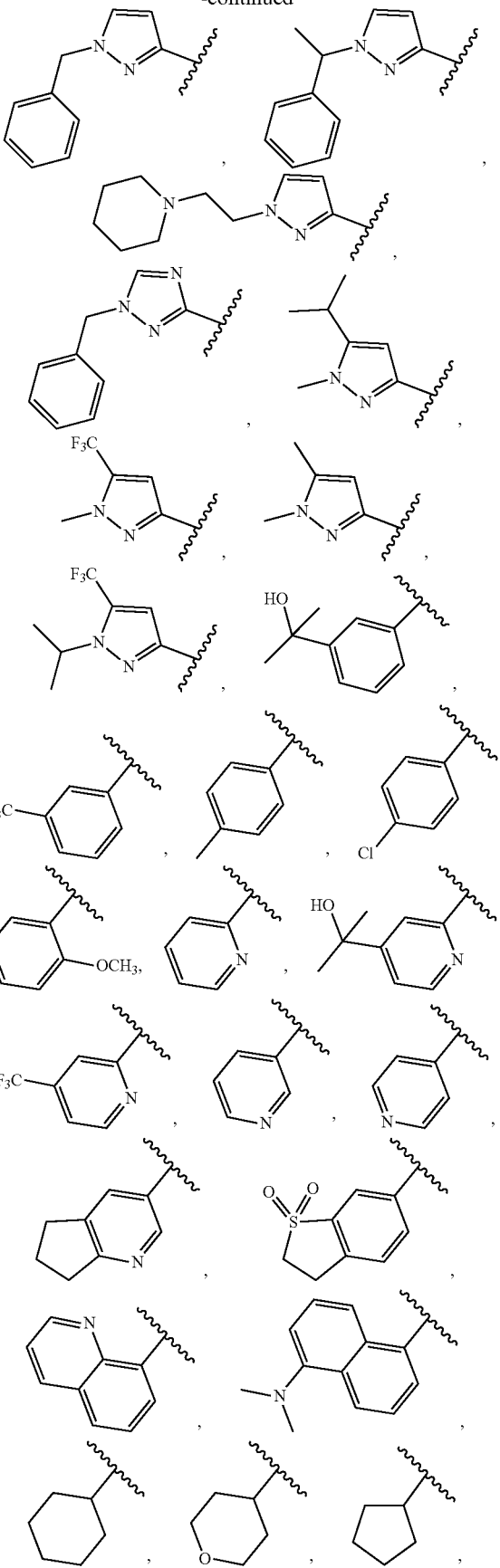

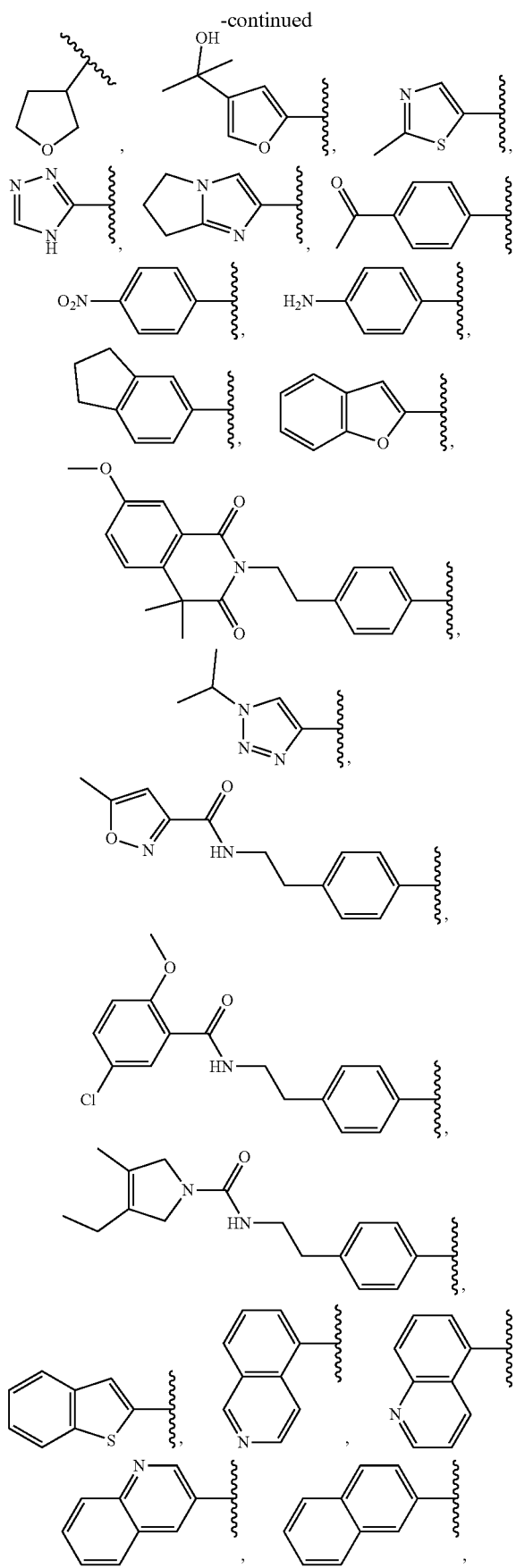

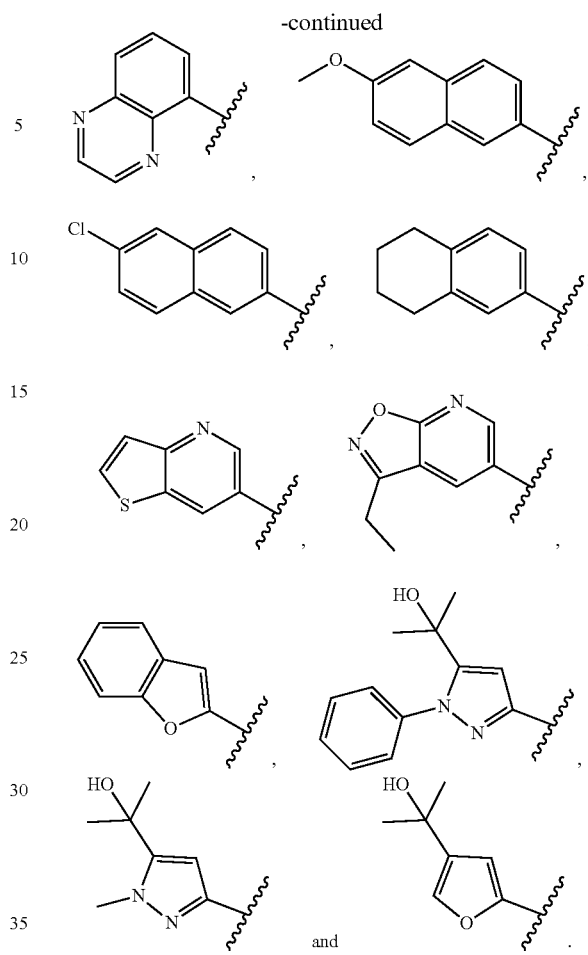

and

In one embodiment, the compound of formula (I) may be selected from a compound of formula (II), or a pharmaceutically acceptable salt, solvate or prodrug thereof:

Formula (II)

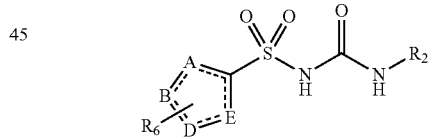

wherein, A, B, D and E are independently selected from C, N, O, S and Se but at least one thereof is C;

each dashed line may represent a bond;

$R_2$ is as previously defined for any embodiment of formula (I), (Ia), (Ib) or (Ic), or may be a fluorescent group;

each incidence of $R_6$ is independently selected from the group consisting of hydrogen, halo, cyano, $C_1$-$C_6$ alkyl, $C_1$-$C_6$ alkylamino, $C_1$-$C_6$ alkylhydroxy, $C_3$-$C_6$ cycloalkyl, alkylphenyl, phenyl, benzyl, $C_1$-$C_6$ ester, $C_2$-$C_6$ alkenyl, $C_1$-$C_6$ trifluoroalkyl and $C_1$-$C_6$ alkoxy, each of which may be optionally substituted, or $R_6$ may be a fluorescent group.

In one preferred embodiment of the compound of formula (II), at least one of A, B, D and E is N (i.e. nitrogen).

In a further preferred embodiment of the compound of formula (II), at least two of A, B, D and E are N.

In one embodiment of the compound of formula (II), A, B, D and E are selected from N and C.

In a further embodiment of the compound of formula (II), A is C and at least two of B, D and E are N.

In one embodiment, A, B, D and E form a ring selected from a pyrazole, an imidazole, a triazole, and a tetrazole.

Preferably, A, B, D, and E form a ring selected from a pyrazole or an imidazole ring, most preferably a pyrazole ring.

In one embodiment A, B, D and E and/or $R_2$ may comprise a selenocycle.

In one embodiment, the compound of formula (I) may be selected from a compound of formula (IIa), or a pharmaceutically acceptable salt, solvate or prodrug thereof:

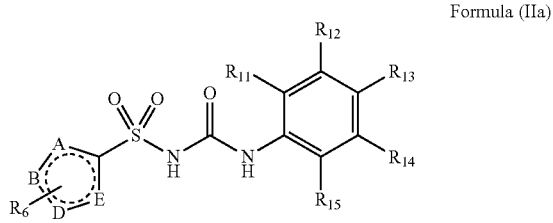

Formula (IIa)

wherein $R_{11}$ $R_{12}$ $R_{13}$ $R_{14}$ and $R_{15}$ are as previously defined;

A, B, D and E are selected from N and C and at least two of A, B, D, and E are N;

each incidence of $R_6$ is independently selected from the group consisting of hydrogen, halide, cyano, $C_1$-$C_6$ alkyl, $C_1$-$C_6$ alkylamino, $C_1$-$C_6$ alkylhydroxy, $C_3$-$C_6$ cycloalkyl, alkylphenyl, phenyl, benzyl, $C_1$-$C_6$ ester, $C_2$-$C_6$ alkenyl, $C_1$-$C_6$ trifluoroalkyl and $C_1$-$C_6$ alkoxy, each of which may be optionally substituted.

In one embodiment, the compound of formula (I) may be selected from a compound of formula (IIb), or a pharmaceutically acceptable salt, solvate or prodrug thereof:

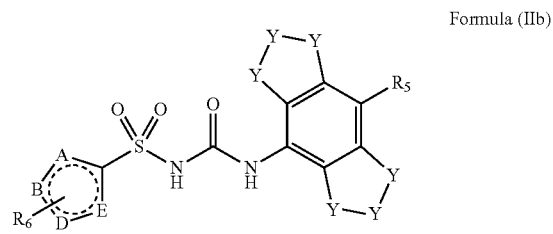

Formula (IIb)

wherein Y and $R_5$ are as previously defined;

A, B, D and E are selected from N and C and at least two of A, B, D, and E are N;

each incidence of $R_6$ is independently selected from the group consisting of hydrogen, halide, cyano, $C_1$-$C_6$ alkyl, $C_1$-$C_6$ alkylamino, $C_1$-$C_6$ alkylhydroxy, $C_3$-$C_6$ cycloalkyl, alkylphenyl, phenyl, benzyl, $C_1$-$C_6$ ester, $C_2$-$C_6$ alkenyl, $C_1$-$C_6$ trifluoroalkyl and $C_1$-$C_6$ alkoxy, each of which may be optionally substituted.

In one embodiment the compound of formula (II), is selected from:

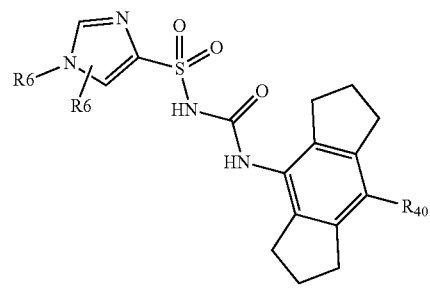

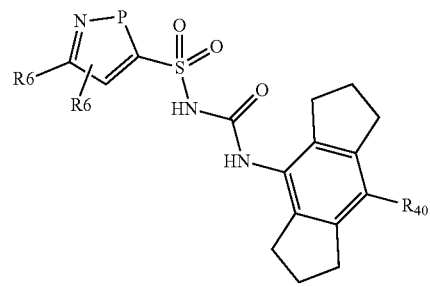

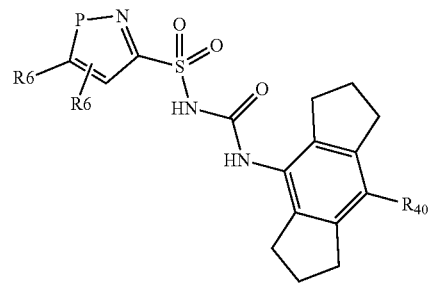

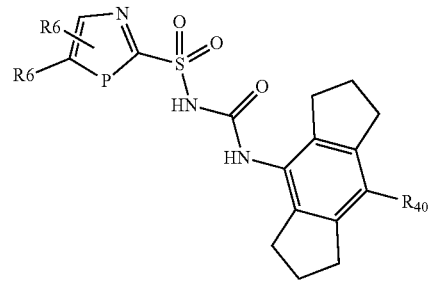

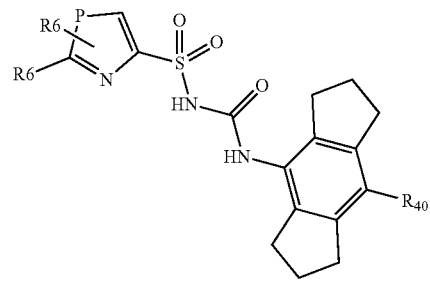

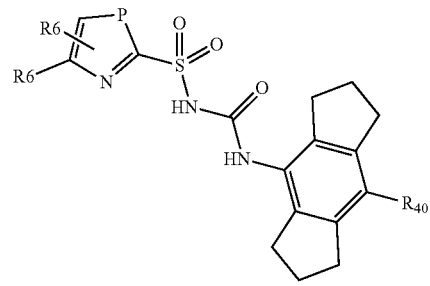

-continued
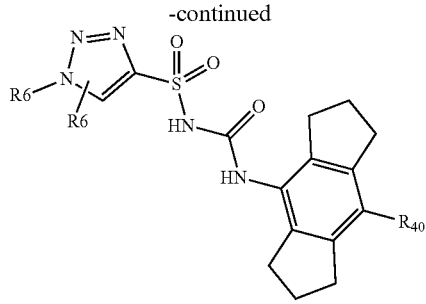
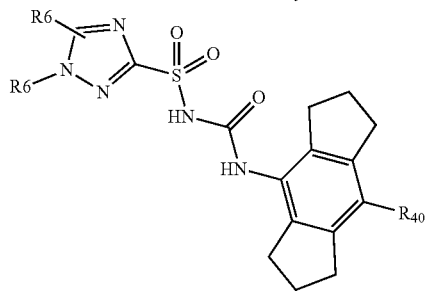
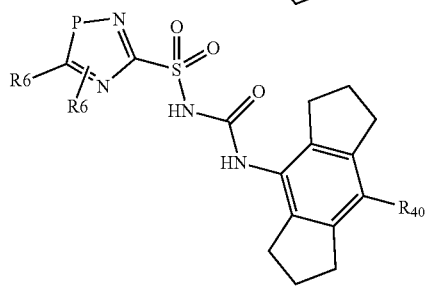
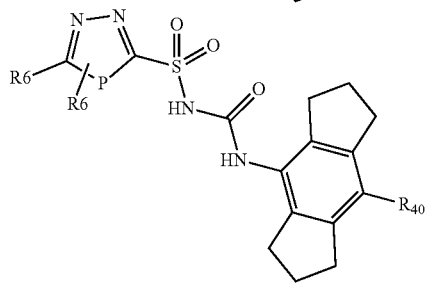
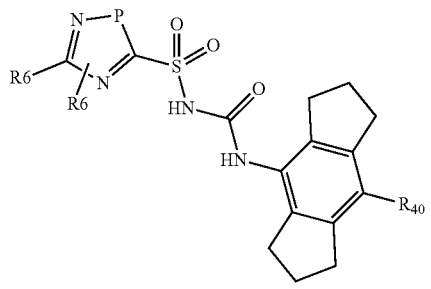
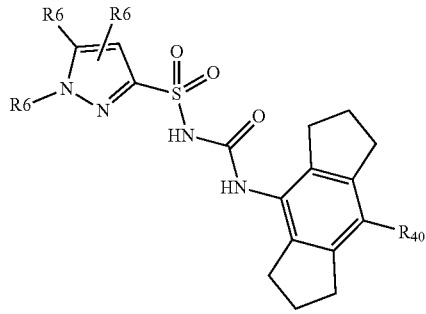
-continued
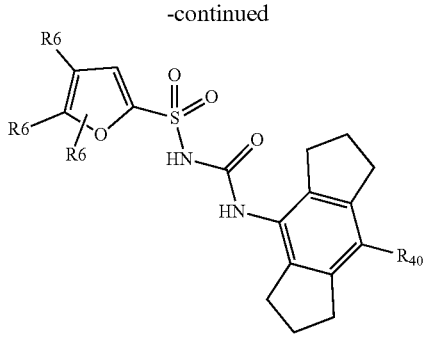
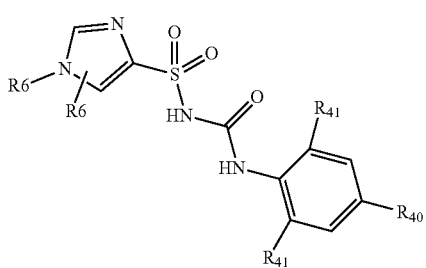
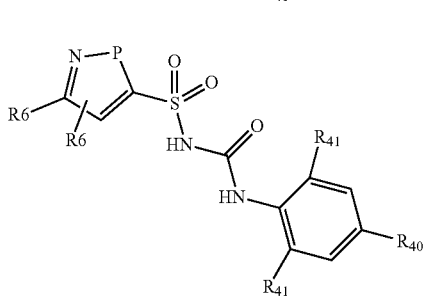
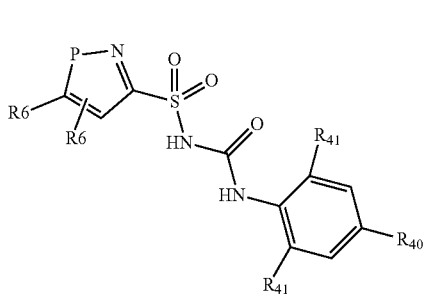
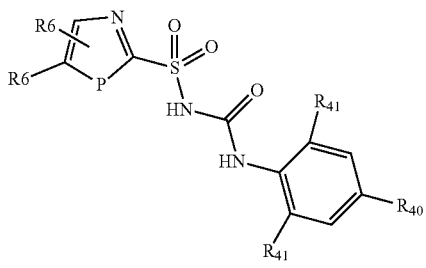
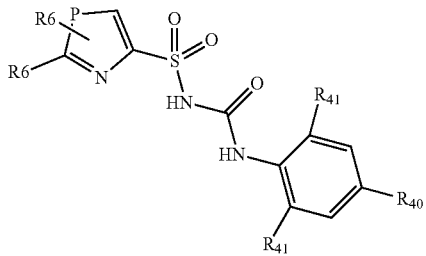

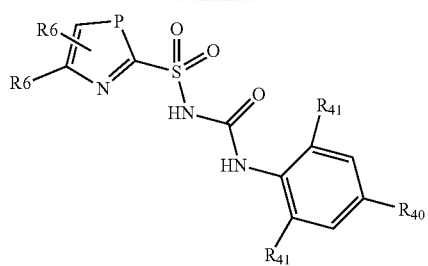

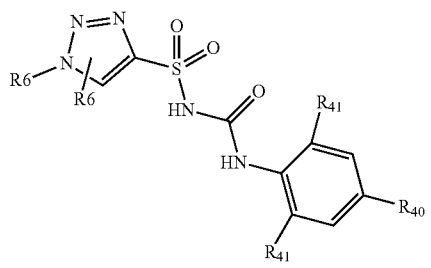

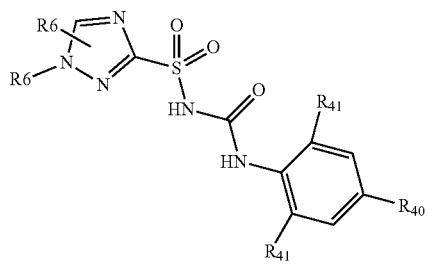

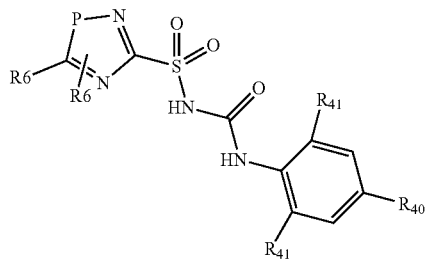

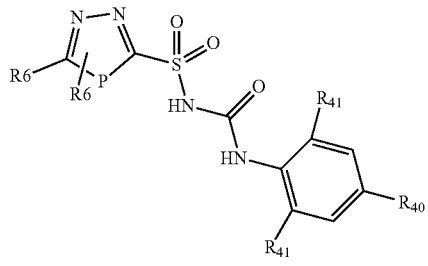

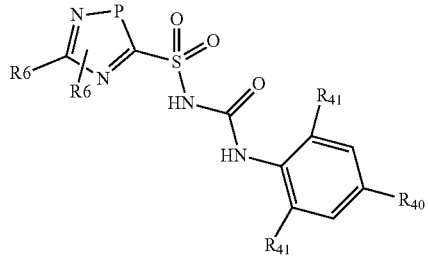

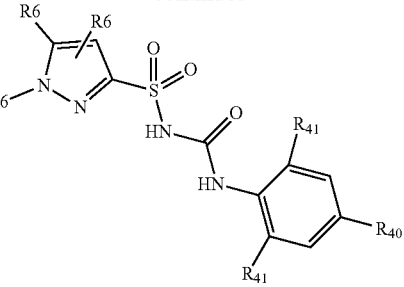

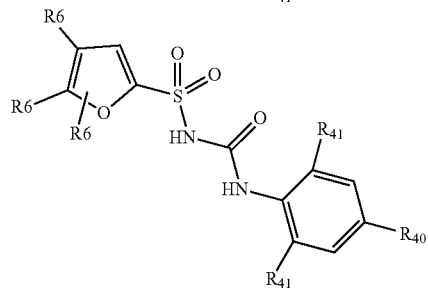

wherein, $R_{40}$ is selected from H, alkyl and halo;

$R_{41}$ is selected from H and alkyl;

each incidence of P is independently selected from C, O or S; and wherein each incidence of $R_6$, when present, is independently selected from those groups defined for formula (II).

It will be understood that the $R_6$ moiety extending from the centre of each ring may represent a group bonded to the ring carbons or ring heteroatoms, as appropriate taking valency into consideration, or may not be present.

In one embodiment of formula (II), $R_6$ is $C_1$-$C_6$ alkyl or $C_1$-$C_6$ alkylhydroxy.

In certain embodiments of the compound of formula (II), for example when $R_2$ is hexahydraindacene and $R_1$ is furan, $R_6$ may not be a tertiary alcohol substituent.

In one embodiment, the compound of the first aspect may be selected from a compound of formula (IIIa), (IIIb) or (IIIc), or a pharmaceutically acceptable salt, solvate or prodrug thereof:

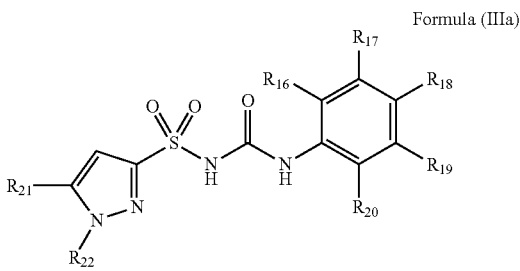

Formula (IIIa)

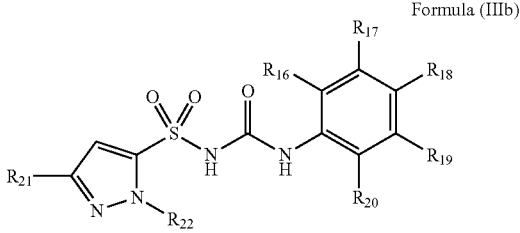

Formula (IIIb)

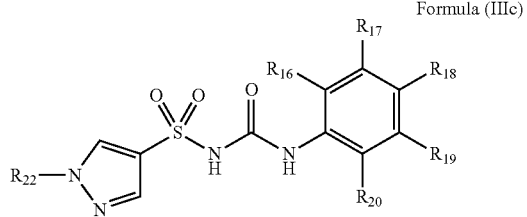

Formula (IIIc)

wherein, $R_{21}$ is selected from H, alkyl, perhaloalkyl or hydroxylalkyl;

$R_{22}$ is selected from H, alkyl, perhaloalkyl, $C_3$-$C_6$ cycloalkyl, phenyl or benzyl;

$R_{18}$ is H or halogen;

$R_{16}$ and $R_{17}$ are H or alkyl; or $R_{16}$ and $R_{17}$, together with the carbon atoms to which they are attached, form a 5 or 6 membered ring, said ring being saturated, partially unsaturated or unsaturated, said ring optionally comprising one or two heteroatoms selected from N, O and S;

$R_{19}$ and $R_{20}$ are H or alkyl; or $R_{19}$ and $R_{20}$, together with the carbon atoms to which they are attached, form a 5 or 6 membered ring, said ring being saturated, partially unsaturated or unsaturated, said ring optionally comprising one or two heteroatoms selected from N, O and S;

provided that $R_{21}$ and $R_{22}$ are not both H; and provided that $R_{16}$, $R_{17}$, $R_{18}$, $R_{19}$ and $R_{20}$ are not all H.

In a preferred embodiment of compounds of formulae (IIIa), (IIIb) and (IIIc):

$R_{21}$ is selected from H, alkyl, perhaloalkyl or hydroxylalkyl; preferably $C_{1-6}$ perhaloalkyl or hydroxylalkyl;

$R_{22}$ is selected from H, alkyl, perhaloalkyl, $C_3$-$C_6$ cycloalkyl, phenyl or benzyl;

$R_{16}$ and $R_{17}$, together with the atoms to which they are attached, form a cyclopentyl ring;

$R_{19}$ and $R_{20}$, together with the atoms to which they are attached, form a cyclopentyl ring;

$R_{18}$ is H or halogen, preferably $R_{18}$ is H; and provided that $R_{21}$ and $R_{22}$ are not both H.

In another preferred embodiment of the compounds of formulae (IIIa), (IIIb) and (IIIc):

$R_{21}$ is selected from H, alkyl, perhaloalkyl or hydroxylalkyl; preferably $C_{1-6}$ perhaloalkyl or hydroxylalkyl;

$R_{22}$ is selected from H, alkyl, perhaloalkyl, $C_3$-$C_6$ cycloalkyl, phenyl and benzyl;

$R_{16}$ and $R_{20}$ are $C_{1-6}$ alkyl, preferably isopropyl;

$R_{17}$ and $R_{19}$ are H, $R_{18}$ is H or halogen; preferably $R_{18}$ is H or Cl; and provided that $R_{21}$ and $R_{22}$ are not both H.

In one embodiment, the compound of the first aspect may be selected from a compound of formula (IVa), (IVb) or (IVc), or a pharmaceutically acceptable salt, solvate or prodrug thereof:

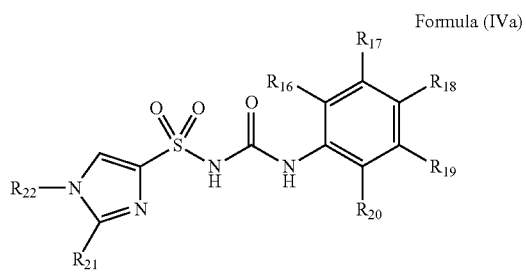

Formula (IVa)

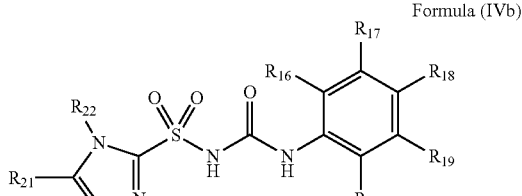

Formula (IVb)

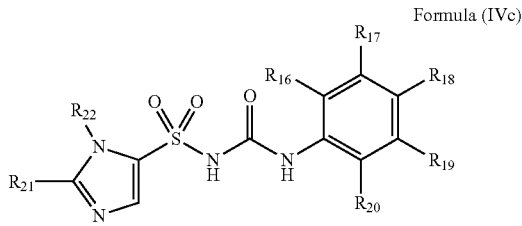

Formula (IVc)

wherein, $R_{21}$ and $R_{22}$ are selected from H, alkyl, perhaloalkyl, hydroxylalkyl, $C_3$-$C_6$ cycloalkyl, phenyl and benzyl or $R_{21}$ and $R_{22}$, together with the carbon atoms to which they are attached, may form a cyclopentyl or a cyclohexyl ring;

$R_{18}$ is H or halogen;

$R_{16}$ and $R_{17}$ are H or alkyl; or $R_{16}$ and $R_{17}$, together with the carbon atoms to which they are attached, form a 5 or 6 membered ring, said ring being saturated, partially unsaturated or unsaturated, said ring optionally comprising one or two heteroatoms selected from N, O and S;

$R_{19}$ and $R_{20}$ are H or alkyl; or $R_{19}$ and $R_{20}$, together with the carbon atoms to which they are attached, form a 5 or 6 membered ring, said ring being saturated, partially unsaturated or unsaturated, said ring optionally comprising one or two heteroatoms selected from N, O and S;

provided that $R_{21}$ and $R_{22}$ are not both H; and provided that $R_{16}$, $R_{17}$, $R_{18}$, $R_{19}$ and $R_{20}$ are not all H.

In a preferred embodiment of compounds of formulae (IVa), (IVb) and (IVc):

$R_{21}$ and $R_{22}$ are selected from H, alkyl, perhaloalkyl, hydroxylalkyl, $C_3$-$C_6$ cycloalkyl, phenyl and benzyl; preferably the perhaloalkyl and hydroxylalkyl are $C_{1-6}$ perhaloalkyl and hydroxylalkyl;

$R_{16}$ and $R_{17}$, together with the atoms to which they are attached, form a cyclopentyl ring;

$R_{19}$ and $R_{20}$, together with the atoms to which they are attached, form a cyclopentyl ring;

$R_{18}$ is H or halogen; preferably $R_{18}$ is H; and provided that $R_{21}$ and $R_{22}$ are not both H.

In another preferred embodiment of compounds of formulae (IVa), (IVb) and (IVc):

$R_{21}$ and $R_{22}$ are selected from H, alkyl, perhaloalkyl, hydroxylalkyl, $C_3$-$C_6$ cycloalkyl, phenyl and benzyl; preferably the perhaloalkyl and hydroxylalkyl are $C_{1-6}$ perhaloalkyl and hydroxylalkyl;

$R_{16}$ and $R_{20}$ are $C_{1-6}$ alkyl, preferably isopropyl;

$R_{17}$ and $R_{19}$ are H, $R_{18}$ is H or halogen; preferably $R_{18}$ is H or Cl;

provided that $R_{21}$ and $R_{22}$ are not both H.

In one embodiment, the compound of the first aspect may be selected from a compound of formula (Va), (Vb) or (Vc), or a pharmaceutically acceptable salt, solvate or prodrug thereof:

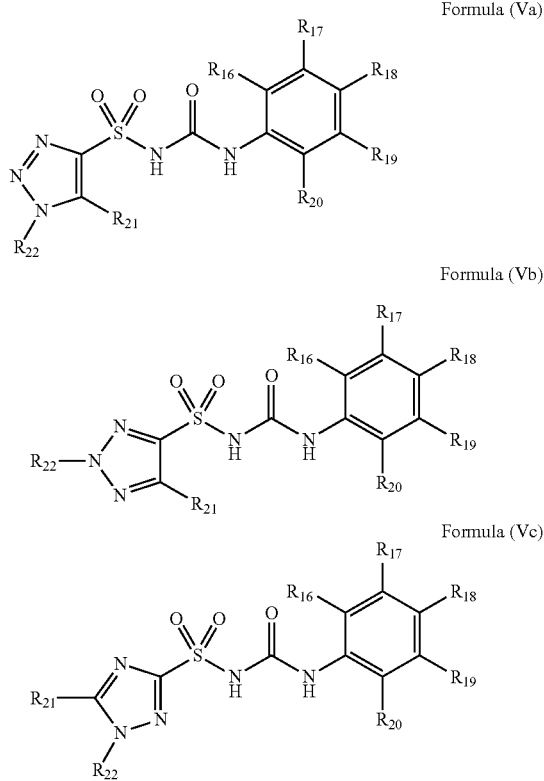

Formula (Va)

Formula (Vb)

Formula (Vc)

wherein, $R_{21}$ and $R_{22}$ are selected from H, alkyl, perhaloalkyl, hydroxylalkyl, $C_3$-$C_6$ cycloalkyl, phenyl and benzyl;

$R_{18}$ is H or halogen;

$R_{16}$ and $R_{17}$ are H or alkyl; or $R_{16}$ and $R_{17}$, together with the carbon atoms to which they are attached, form a 5 or 6 membered ring, said ring being saturated, partially unsaturated or unsaturated, said ring optionally comprising one or two heteroatoms selected from N, O and S;

$R_{19}$ and $R_{20}$ are H or alkyl; or $R_{19}$ and $R_{20}$, together with the carbon atoms to which they are attached, form a 5 or 6 membered ring, said ring being saturated, partially unsaturated or unsaturated, said ring optionally comprising one or two heteroatoms selected from N, O and S;

provided that $R_{21}$ and $R_{22}$ are not both H; and provided that $R_{16}$, $R_{17}$, $R_{18}$, $R_{19}$ and $R_{20}$ are not all H.

In a preferred embodiment of compounds of formulae (Va), (Vb) and (Vc):

$R_{21}$ and $R_{22}$ are selected from H, alkyl, perhaloalkyl, hydroxylalkyl, $C_3$-$C_6$ cycloalkyl, phenyl and benzyl; preferably the perhaloalkyl and hydroxylalkyl are $C_{1-6}$ perhaloalkyl and hydroxylalkyl;

$R_{16}$ and $R_{17}$, together with the atoms to which they are attached, form a cyclopentyl ring;

$R_{19}$ and $R_{20}$, together with the atoms to which they are attached, form a cyclopentyl ring;

$R_{18}$ is H or halogen; preferably $R_{18}$ is H; and provided that $R_{21}$ and $R_{22}$ are not both H.

In another preferred embodiment of compounds of formulae (Va), (Vb) and (Vc):

$R_{21}$ and $R_{22}$ are selected from H, alkyl, perhaloalkyl, hydroxylalkyl, $C_3$-$C_6$ cycloalkyl, phenyl and benzyl; preferably the perhaloalkyl and hydroxylalkyl are $C_{1-6}$ perhaloalkyl and hydroxylalkyl;

$R_{16}$ and $R_{20}$ are $C_{1-6}$ alkyl, preferably isopropyl;

$R_{17}$ and $R_{19}$ are H;

$R_{18}$ is H or halogen; preferably $R_{18}$ is H or Cl; and provided that $R_{21}$ and $R_{22}$ are not both H.

In one embodiment, the compound of the first aspect may be selected from a compound of formula (VIa) or (VIb), or a pharmaceutically acceptable salt, solvate or prodrug thereof:

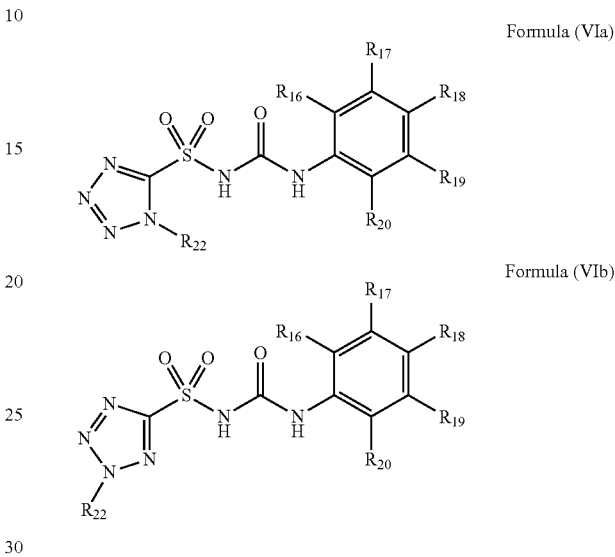

Formula (VIa)

Formula (VIb)

wherein, $R_{22}$ is selected from alkyl, perhaloalkyl, hydroxylalkyl, $C_3$-$C_6$ cycloalkyl, phenyl and benzyl;

$R_{18}$ is H or halogen;

$R_{16}$ and $R_{17}$ are H or alkyl; or $R_{16}$ and $R_{17}$, together with the carbon atoms to which they are attached, form a 5 or 6 membered ring, said ring being saturated, partially unsaturated or unsaturated, said ring optionally comprising one or two heteroatoms selected from N, O and S;

$R_{19}$ and $R_{20}$ are H or alkyl; or $R_{19}$ and $R_{20}$, together with the carbon atoms to which they are attached, form a 5 or 6 membered ring, said ring being saturated, partially unsaturated or unsaturated, said ring optionally comprising one or two heteroatoms selected from N, O and S; and provided that $R_{16}$, $R_{17}$, $R_{18}$, $R_{19}$ and $R_{20}$ are not all H.

In a preferred embodiment of compounds of formulae (VIa) and (VIb):

$R_{22}$ is selected from alkyl, perhaloalkyl, hydroxylalkyl, $C_3$-$C_6$ cycloalkyl, phenyl and benzyl; preferably the perhaloalkyl and hydroxylalkyl are $C_{1-6}$ perhaloalkyl and hydroxylalkyl;

$R_{16}$ and $R_{17}$, together with the atoms to which they are attached, form a cyclopentyl ring;

$R_{19}$ and $R_{20}$, together with the atoms to which they are attached, form a cyclopentyl ring; and $R_{18}$ is H or halogen; preferably $R_{18}$ is H.

In another preferred embodiment of compounds of formulae (VIa) and (VIb):

$R_{22}$ is selected from alkyl, perhaloalkyl, hydroxylalkyl, $C_3$-$C_6$ cycloalkyl, phenyl and benzyl; preferably the perhaloalkyl and hydroxylalkyl are $C_{1-6}$ perhaloalkyl and hydroxylalkyl;

$R_{16}$ and $R_{20}$ are $C_{1-6}$ alkyl, preferably isopropyl;

$R_{17}$ and $R_{19}$ are H; and $R_{18}$ is H or halogen; preferably $R_{18}$ is H or Cl.

In one embodiment, the compound of the first aspect may be selected from a compound of formula (VII), or a pharmaceutically acceptable salt, solvate or prodrug thereof:

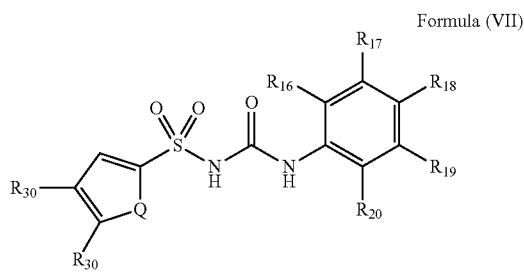

Formula (VII)

wherein, Q is O or S;

each incidence of $R_{30}$ is independently selected from alkyl, perhaloalkyl, hydroxylalkyl, $C_3$-$C_6$ cycloalkyl, and alkylamino;

$R_{18}$ is H or halogen;

$R_{16}$ and $R_{17}$ are H or alkyl; or $R_{16}$ and $R_{17}$, together with the carbon atoms to which they are attached, form a 5 or 6 membered ring, said ring being saturated, partially unsaturated or unsaturated, said ring optionally comprising one or two heteroatoms selected from N, O and S;

$R_{19}$ and $R_{20}$ are H or alkyl; or $R_{19}$ and $R_{20}$, together with the carbon atoms to which they are attached, form a 5 or 6 membered ring, said ring being saturated, partially unsaturated or unsaturated, said ring optionally comprising one or two heteroatoms selected from N, O and S;

provided that $R_{16}$, $R_{17}$, $R_{18}$, $R_{19}$ and $R_{20}$ are not all H; and provided that when Q is O and $R_{16}$ and $R_{17}$, and separately $R_{19}$ and $R_{20}$, together with the respective carbon atoms to which they are attached, form a cyclopentyl ring then $R_{30}$ is not $C_{-3}$ hydroxylalkyl.

In a preferred embodiment of compounds of formulae (VII):

Q is O or S;

each incidence of $R_{30}$ is independently selected from alkyl, perhaloalkyl, hydroxylalkyl, $C_3$-$C_6$ cycloalkyl, and alkylamino; preferably $C_{1-6}$ alkyl, perhaloalkyl, hydroxylalkyl, and alkylamino;

$R_{16}$ and $R_{17}$, together with the atoms to which they are attached, form a cyclopentyl ring;

$R_{19}$ and $R_{20}$, together with the atoms to which they are attached, form a cyclopentyl ring; and $R_{18}$ is H or halogen; preferably $R_{18}$ is H and provided that when Q is O then $R_{30}$ is not $C_{-3}$ hydroxylalkyl.

In another preferred embodiment of compounds of formulae (VII):

Q is O or S;

each incidence of $R_{30}$ is independently selected from alkyl, perhaloalkyl, hydroxylalkyl, $C_3$-$C_6$ cycloalkyl, and alkylamino; preferably $C_{1-6}$ alkyl, perhaloalkyl, hydroxylalkyl, and alkylamino;

$R_{16}$ and $R_{20}$ are $C_{1-6}$ alkyl, preferably isopropyl;

$R_{17}$ and $R_{19}$ are H; and $R_{18}$ is H or halogen; preferably $R_{18}$ is H or Cl.

The compounds of the first aspect, and particularly those of formulae (II) to (VI), provide a range of unexpected benefits over those sulfonylureas of the prior art, which benefits may be selected from: Improved microsomal stability; Improved permeability; Reduced Pgp liability; Reduced plasma protein binding; Increased half-life; Improved oral bioavailability; Improved AUC; Improved Cmax; Reduced Cyp inhibition; Improved inhibition of activation of the NLRP3 inflammasome; and Improved solubility. The solubility, and certain other, improvements may be seen particularly in an aqueous environment.

In one embodiment, the compounds of the first aspect offer improved pharmacokinetic characteristics. CRID3, a known sulfonylurea, has a half life of 3.2 hours (mouse) which may lead to substantial trough levels from QD or BD dosing when the t1/2 is extrapolated to man. The compounds of the first aspect may differ in, for example, their protein binding, metabolism and oral availability.

Particularly it has been found that compounds of the first aspect, especially those wherein A, B, D and E form a 5-membered nitrogen heteroaryl, for example a pyrazole ring, are less metabolically labile and/or have improved pharmacokinetic properties over otherwise structurally similar furans and thiophenes seen in the prior art.

In one embodiment, the compounds of of the first aspect have a tPSA of less than 90 Å$^2$.

It is one advantage of the present compounds of the first aspect that they may demonstrate a significantly lowered polar surface area in comparison to prior art sulfonylureas, such as CRID3.

In one further embodiment, the compounds of the first aspect have a tPSA of less than 90 Å$^2$ and a molecular weight of less than 405.

The absence of a tertiary alcohol group, in some embodiments, increases plasma concentration and aids in decreasing both MW and polar surface area thereby giving an overall improvement in blood brain barrier penetration.

In any of the embodiments described for the compound of the first aspect, including the compounds of formula (I) to (VII), one or more hydrogens of the substituents or optional substitutions thereupon may be deuterated.

Deuterated analogues of the compounds of the invention may exhibit increased metabolic stability due to the kinetic isotope effect.

In one embodiment, the compound of the first aspect is selected from the group consisting of:

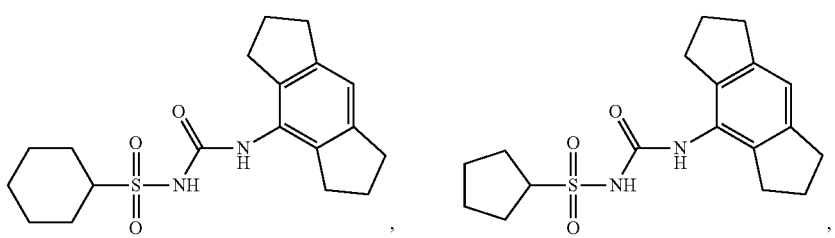

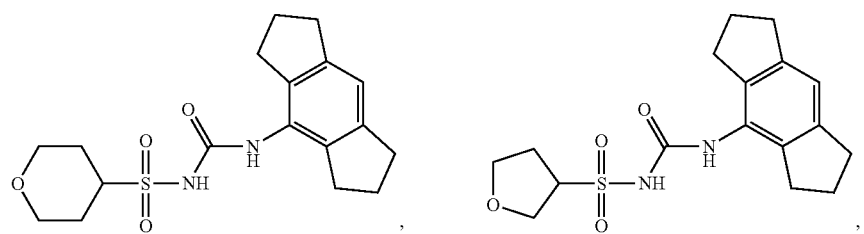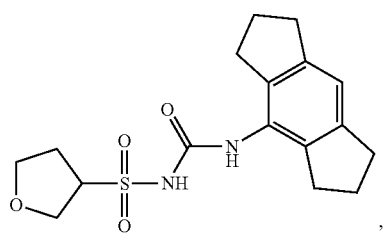
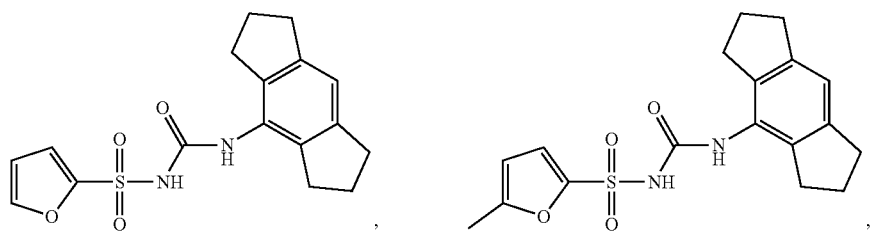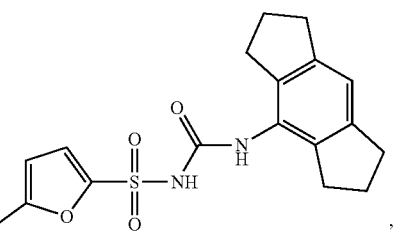
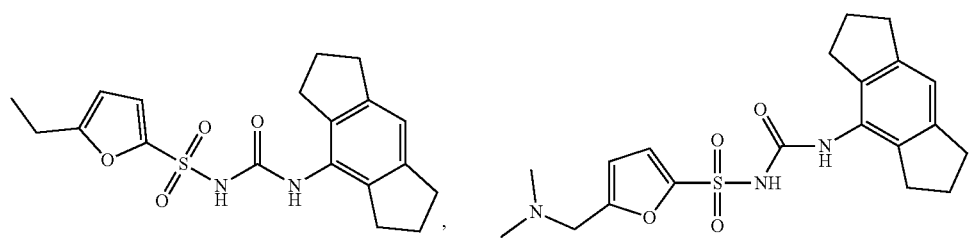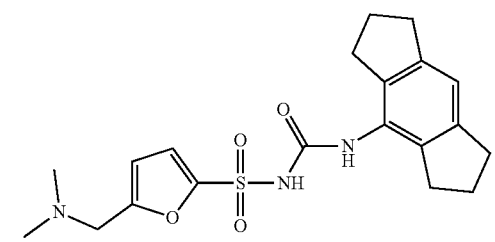
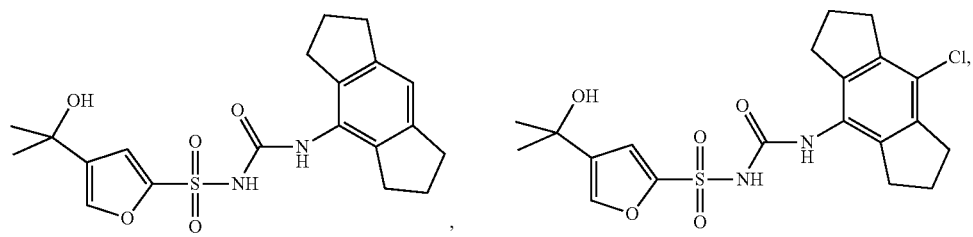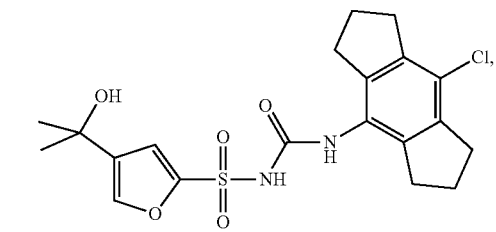
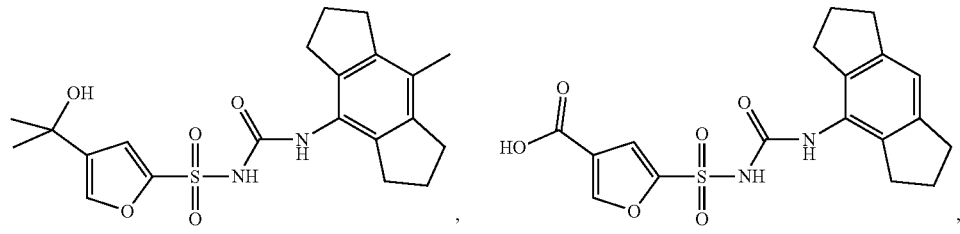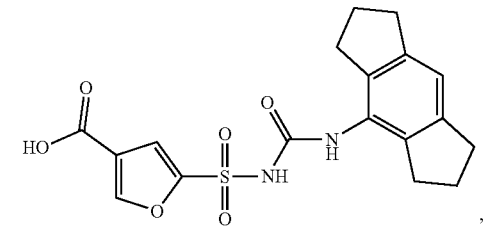
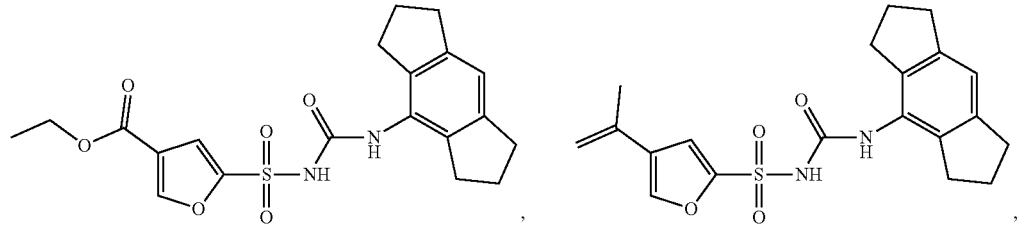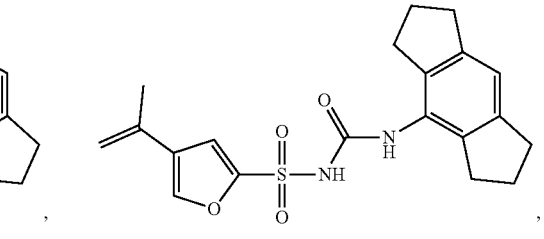
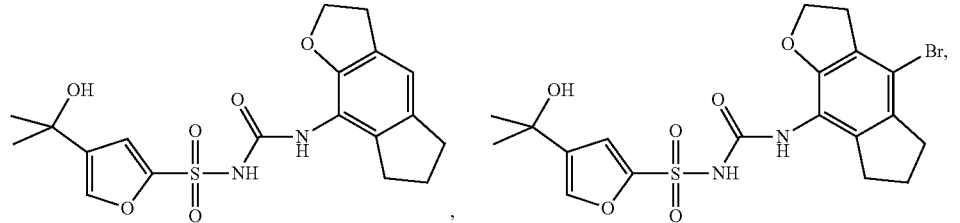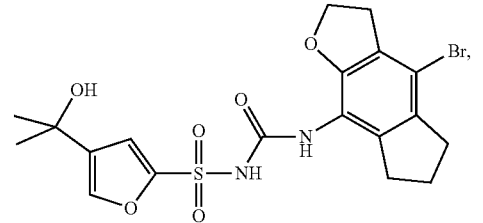

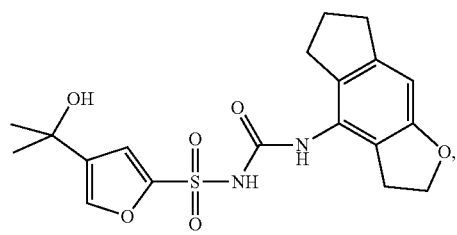
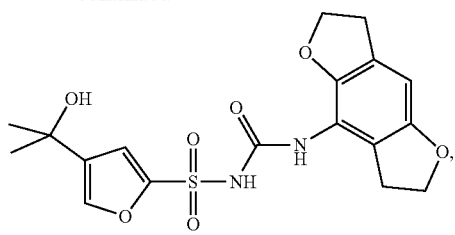
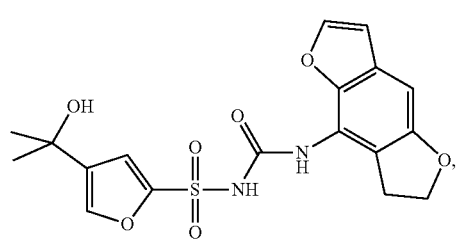
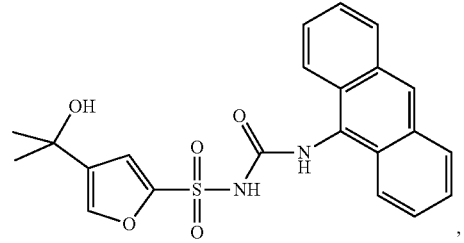
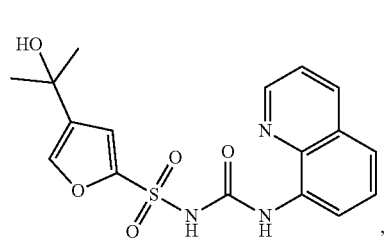
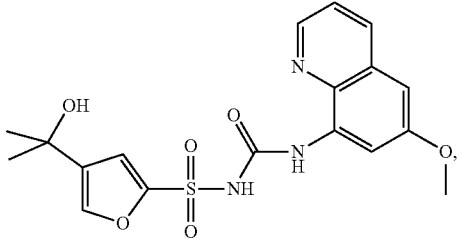
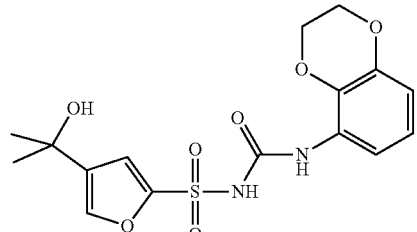
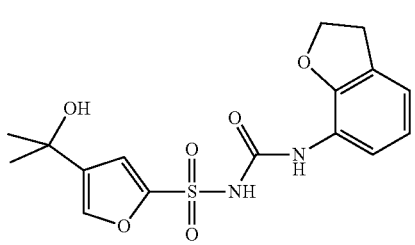
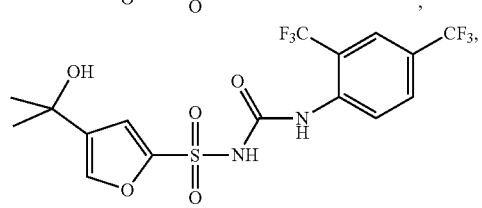
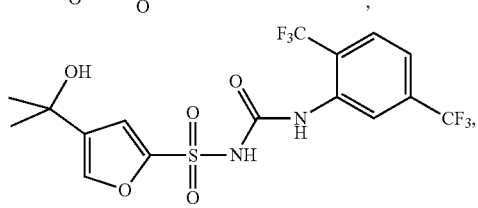
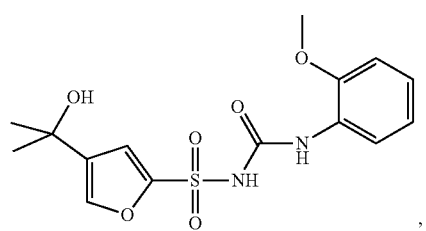
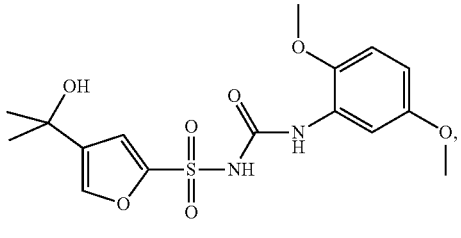
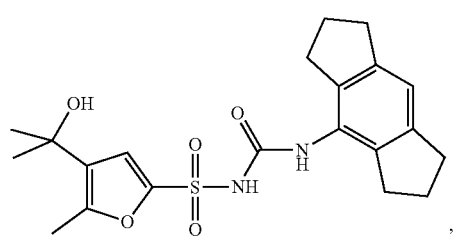
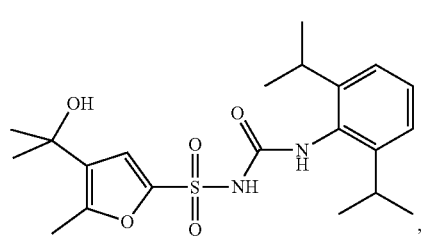

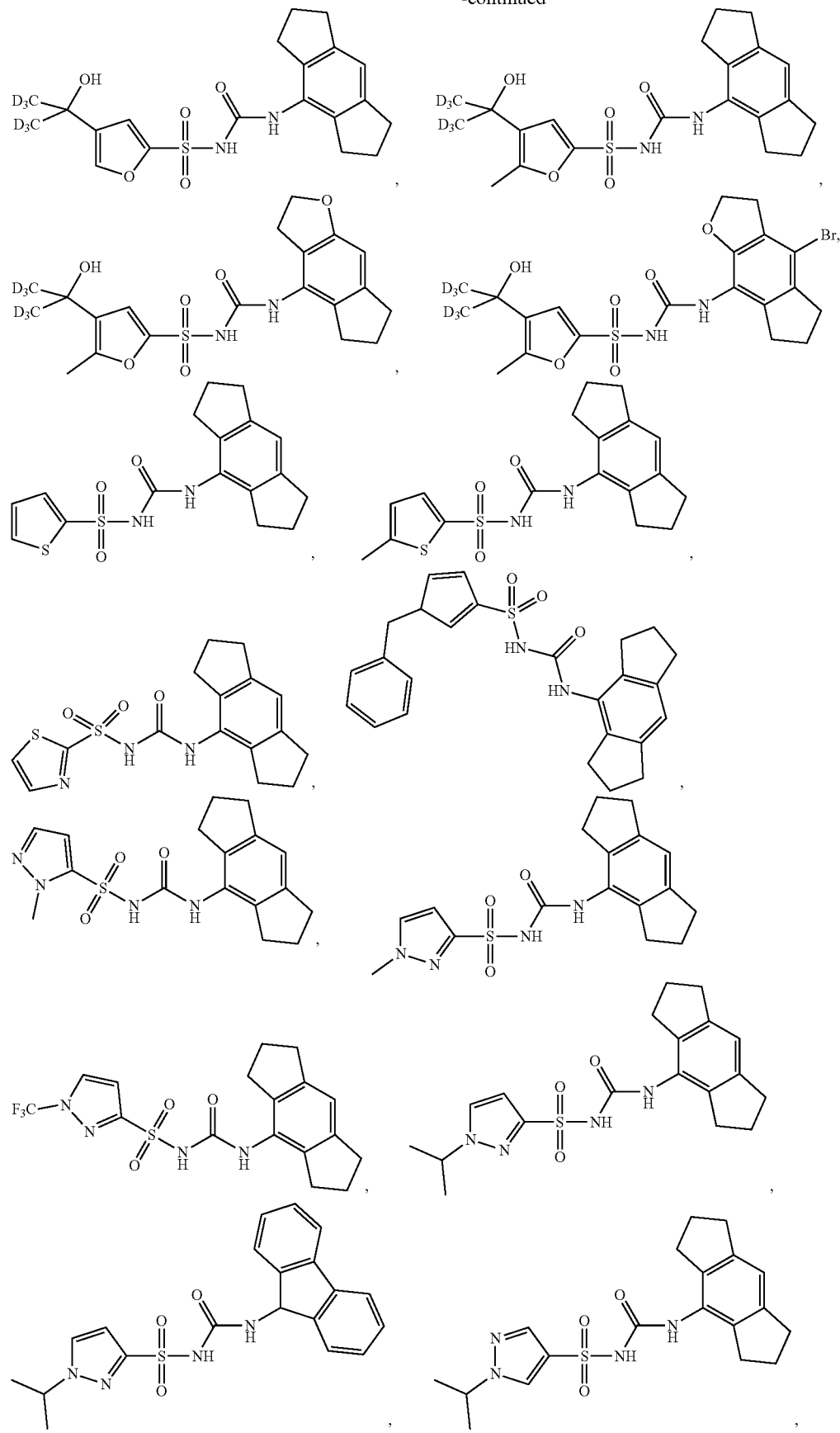

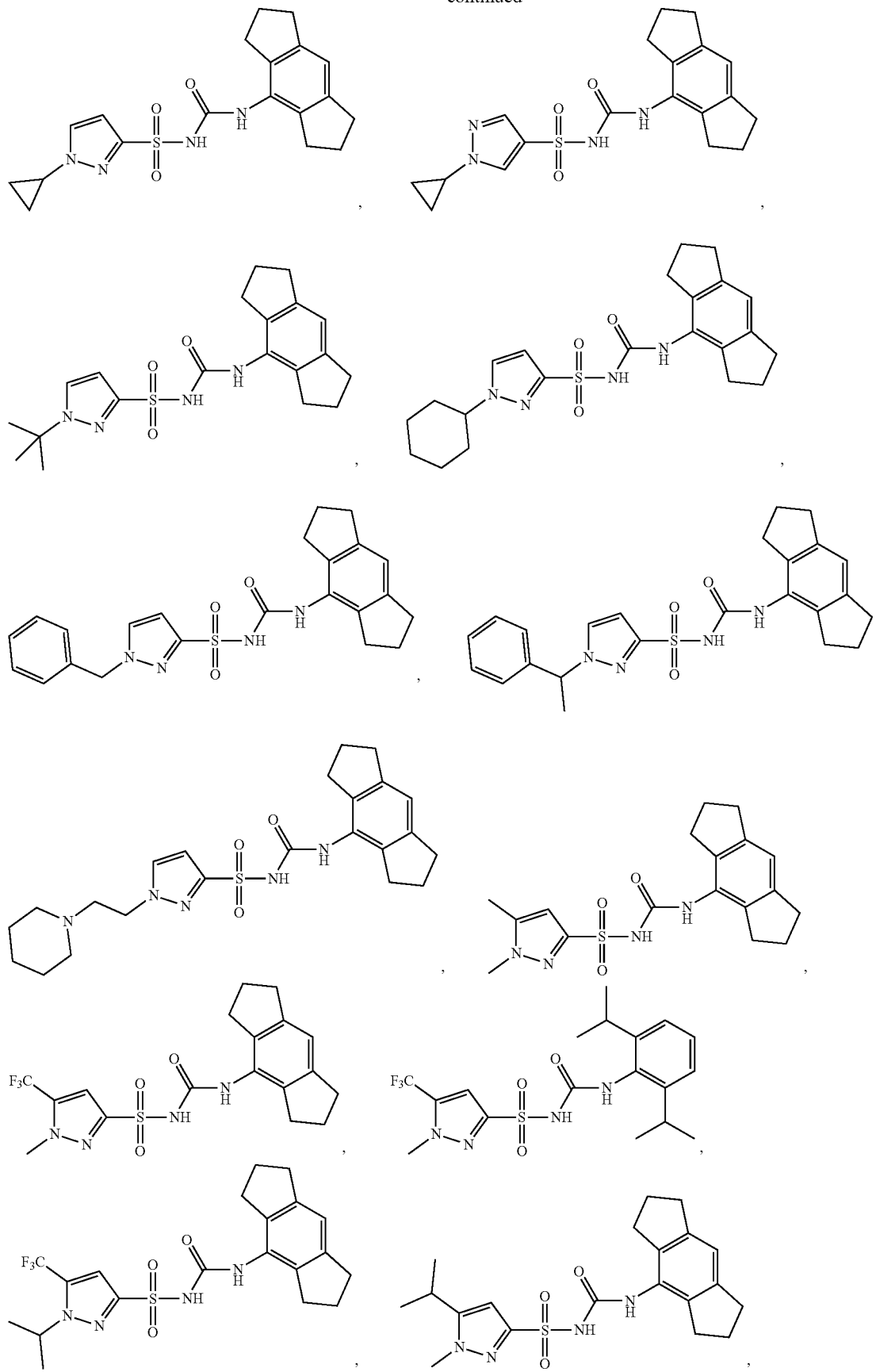

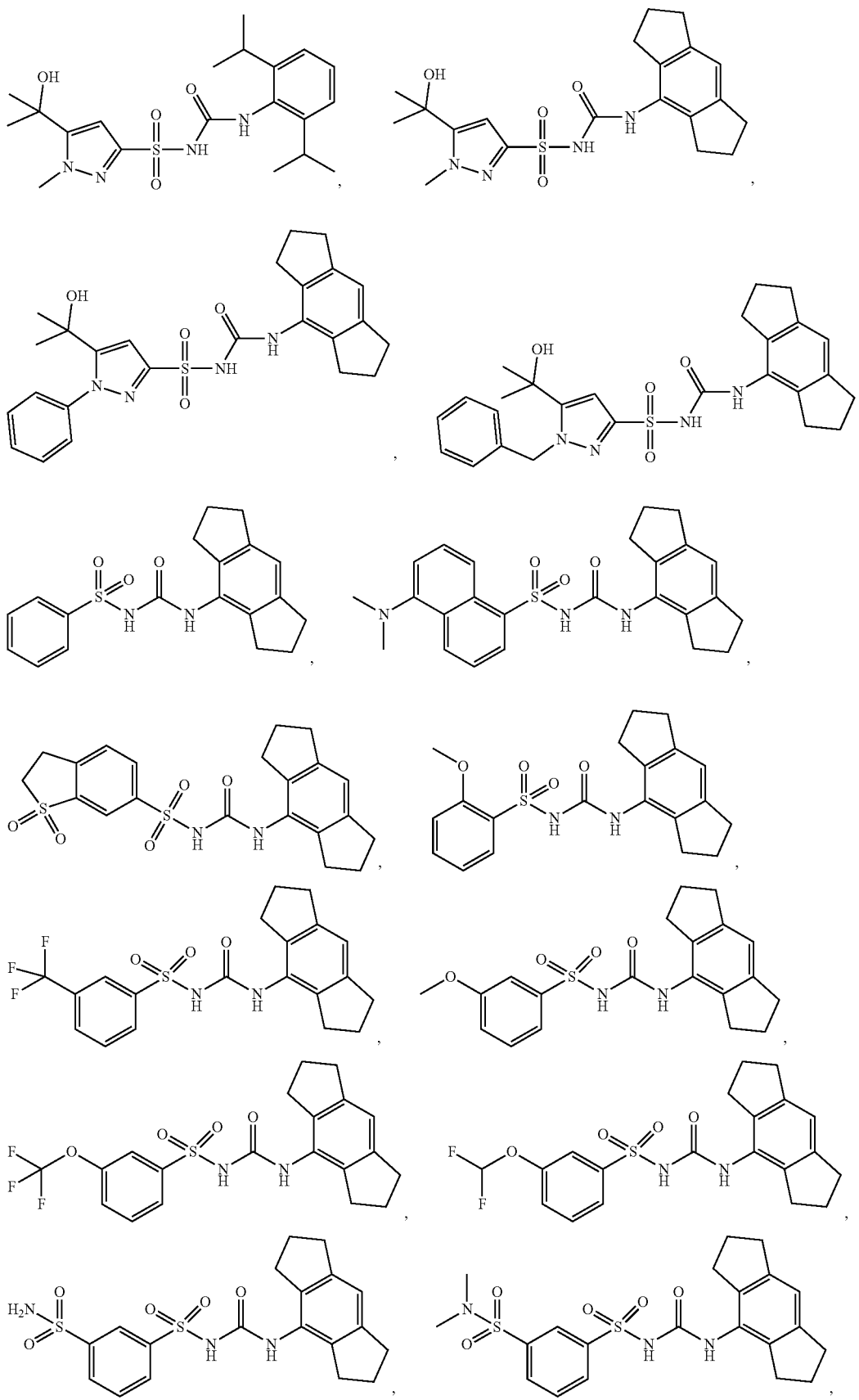

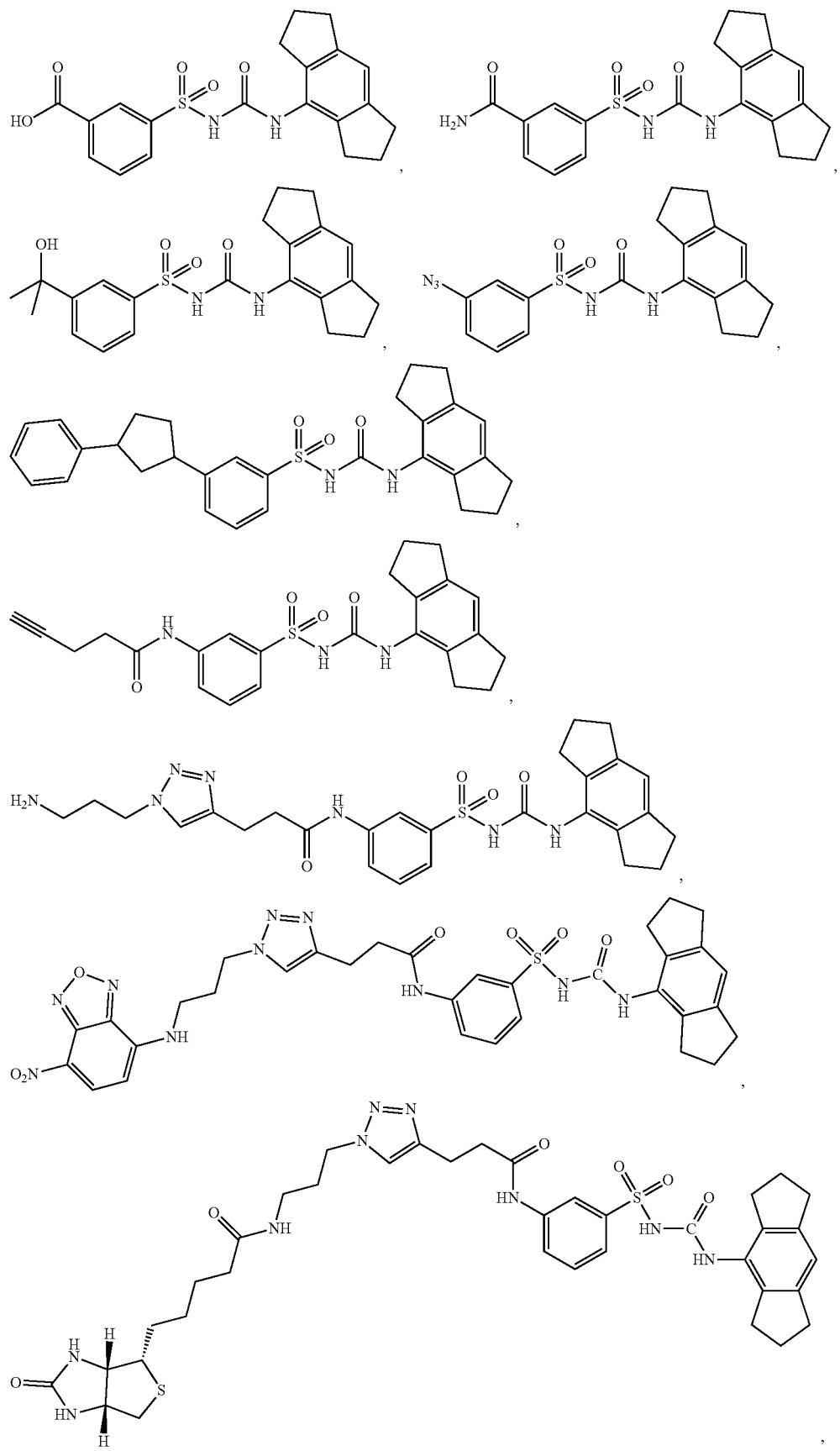

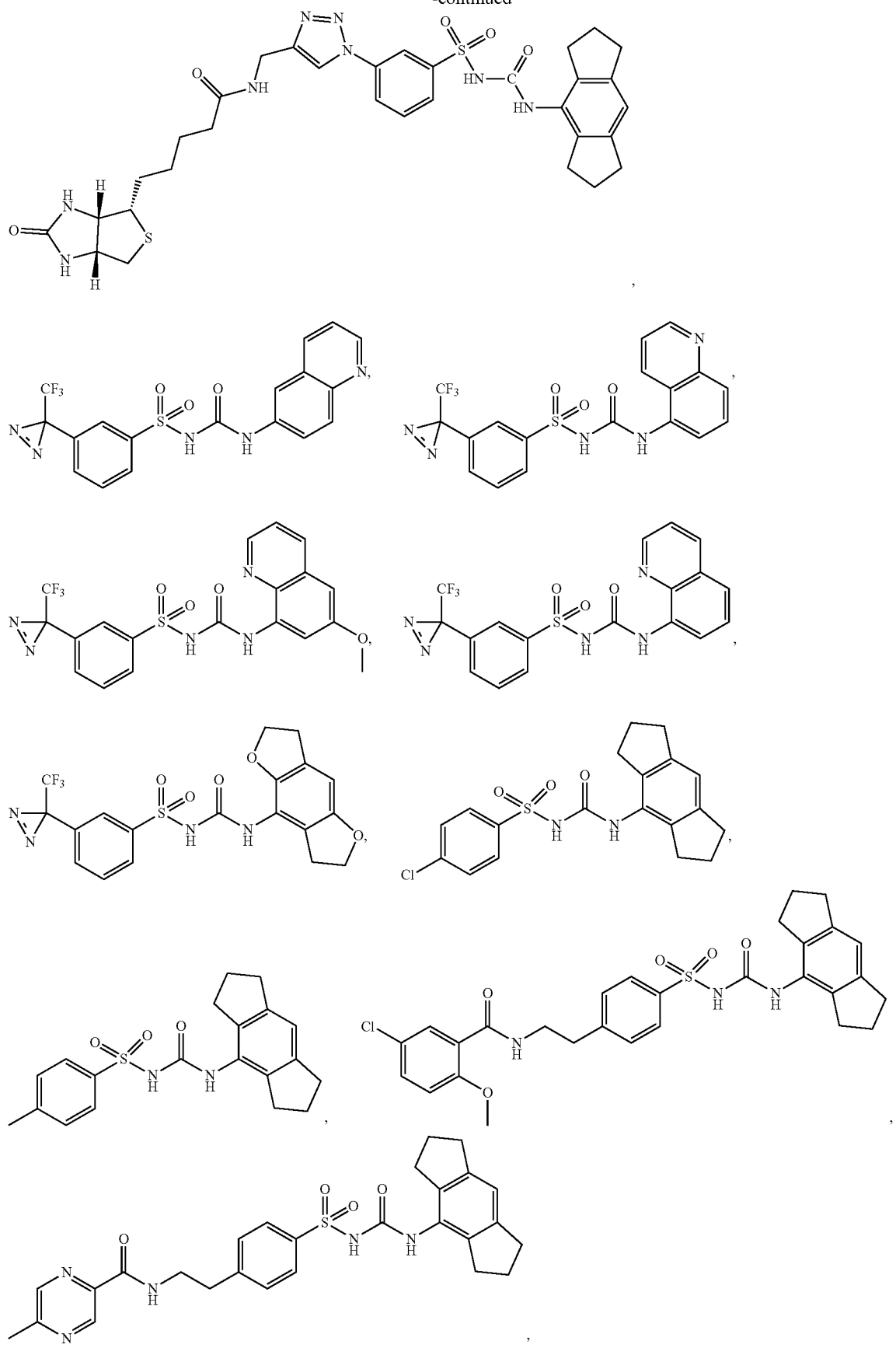

-continued
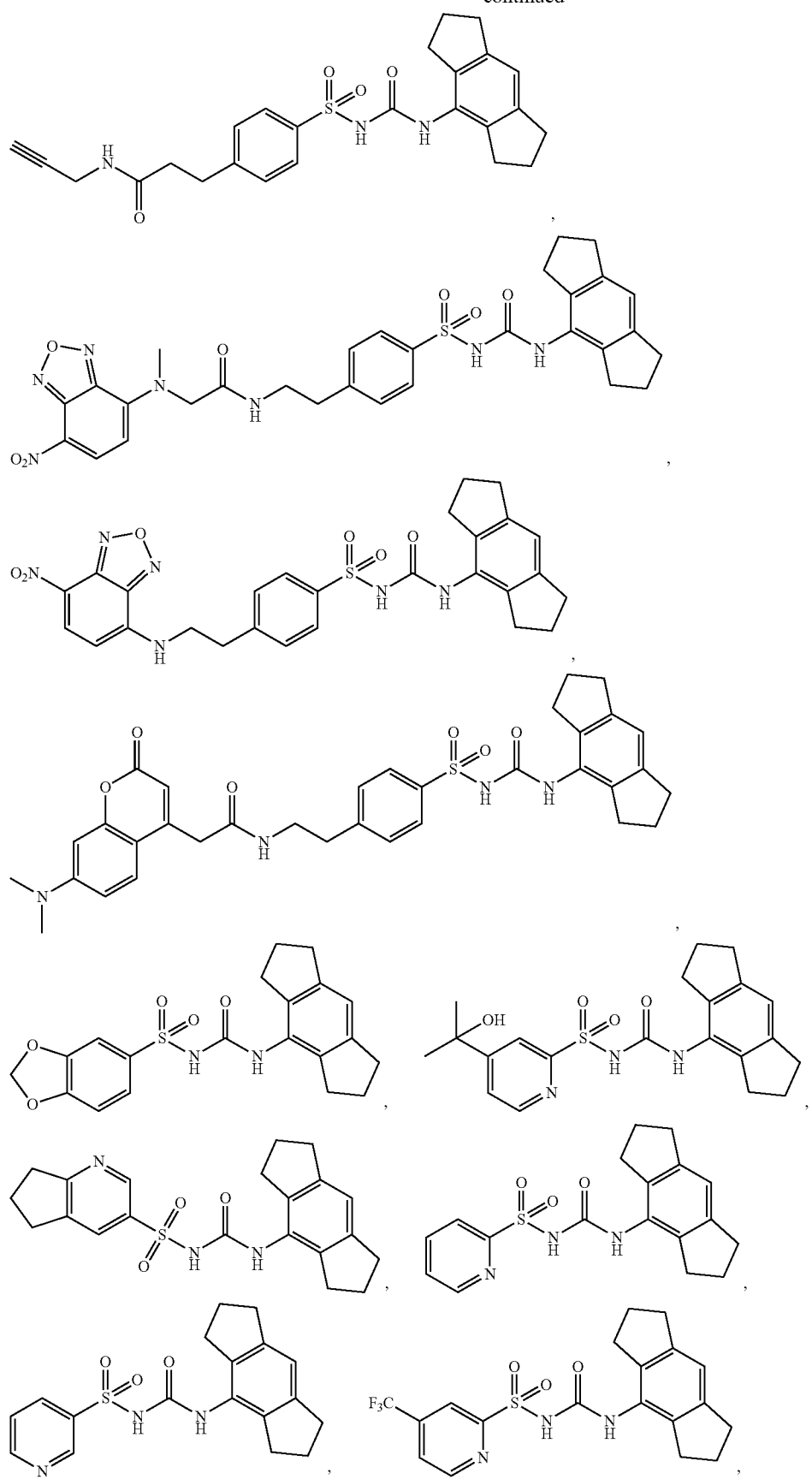

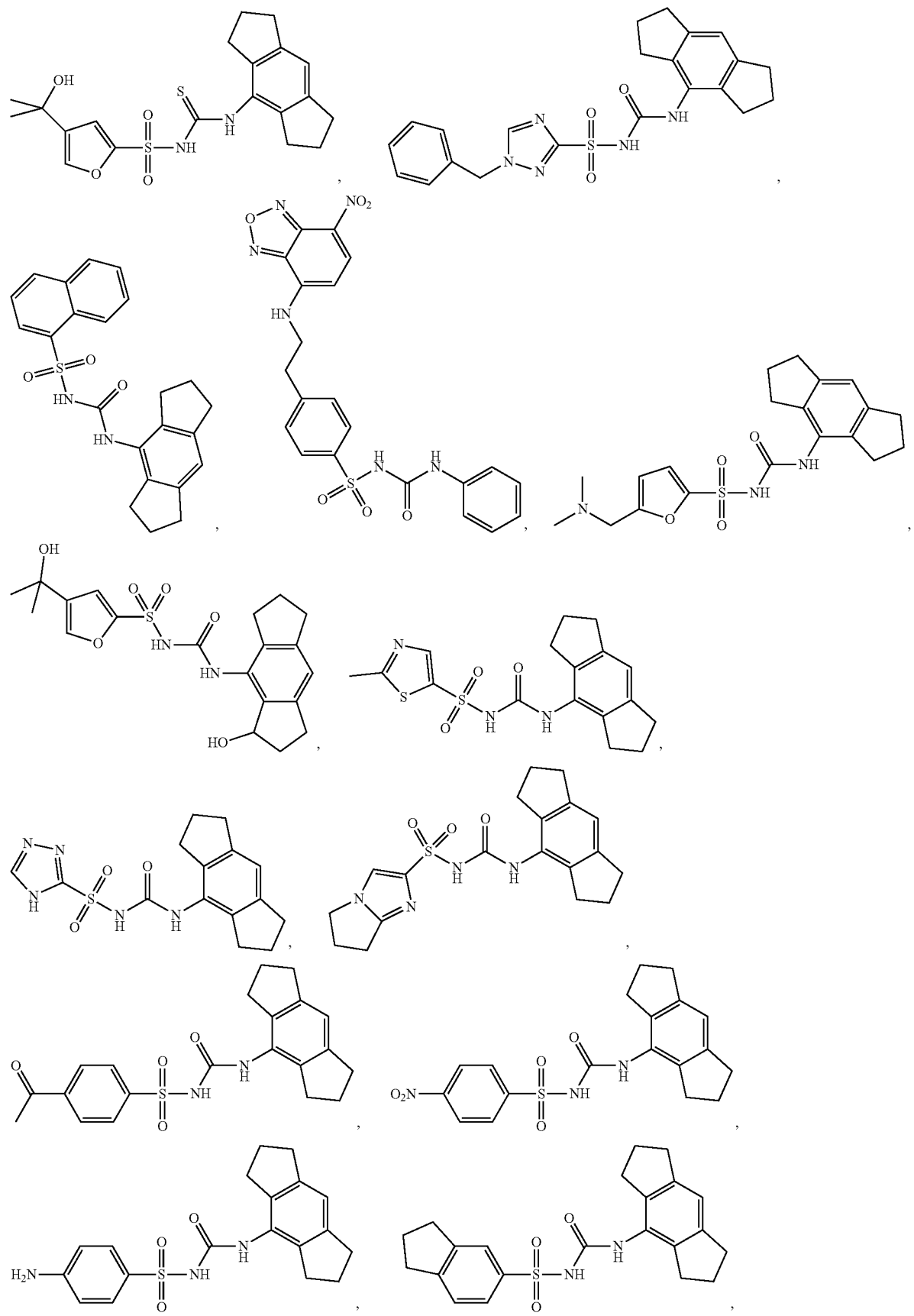

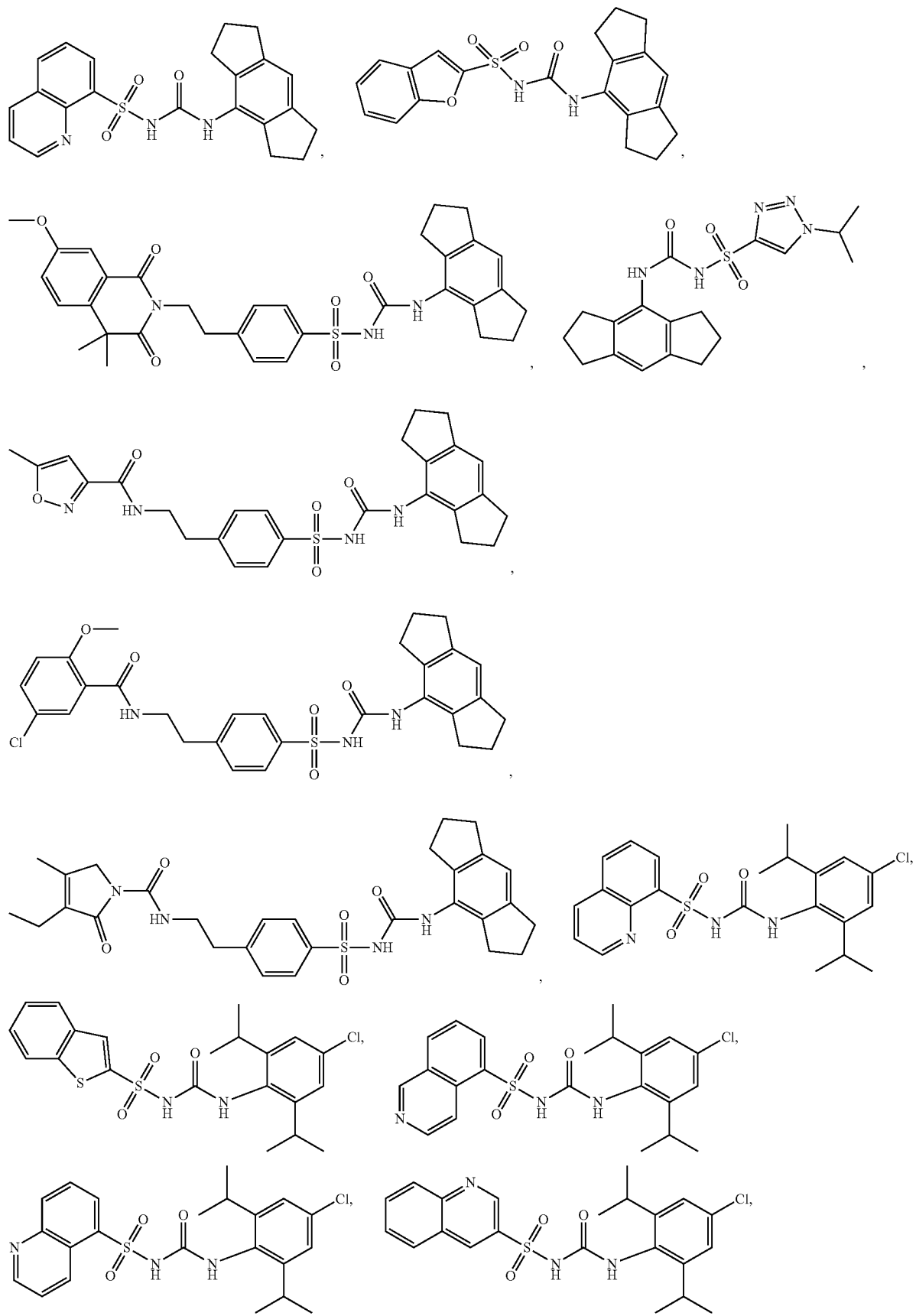

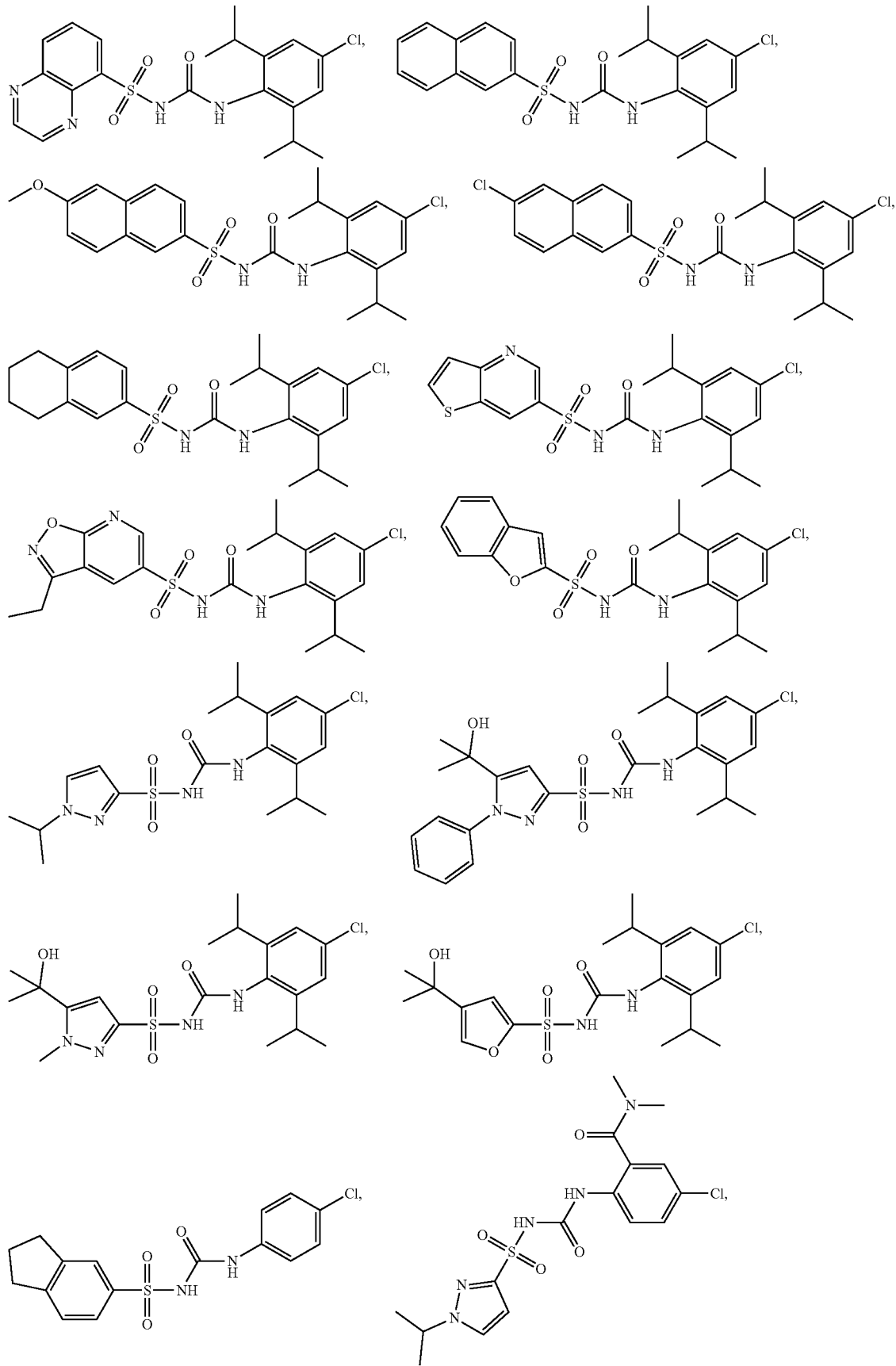
-continued

-continued
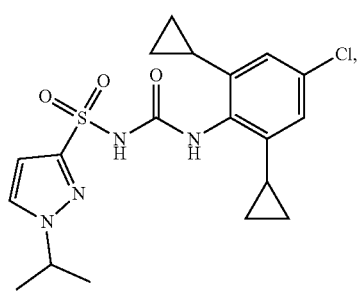 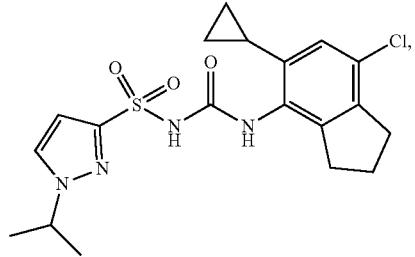
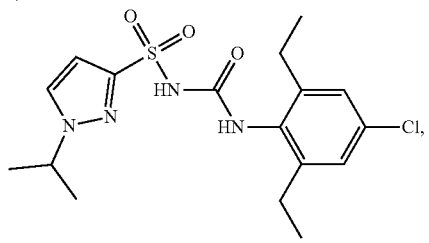 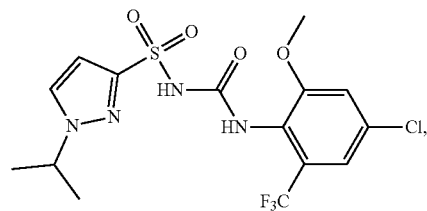
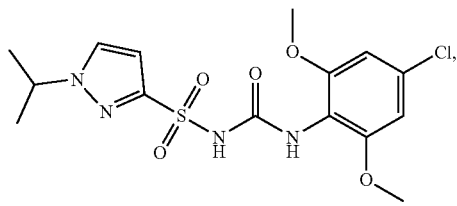 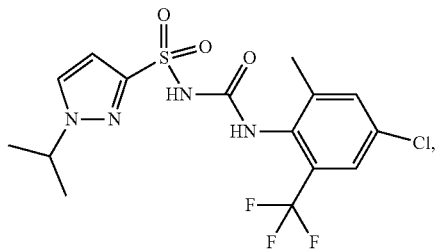
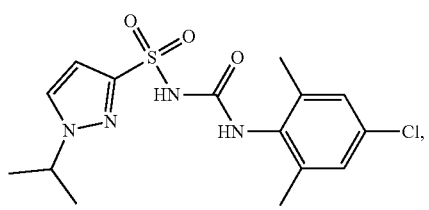 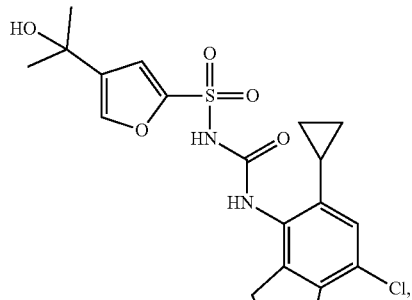
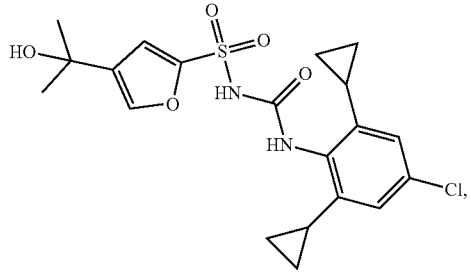 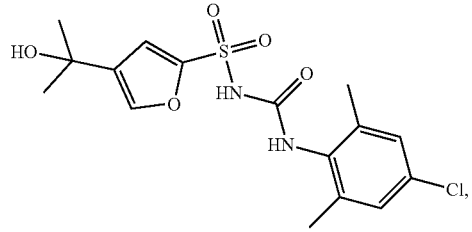
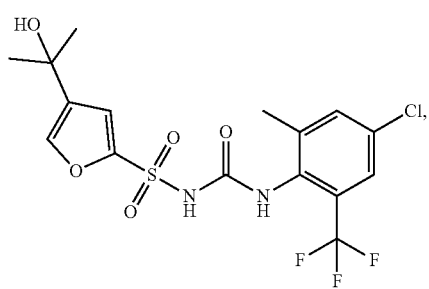 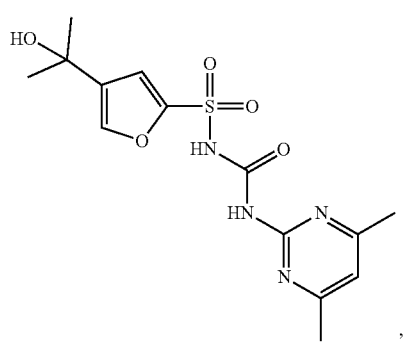

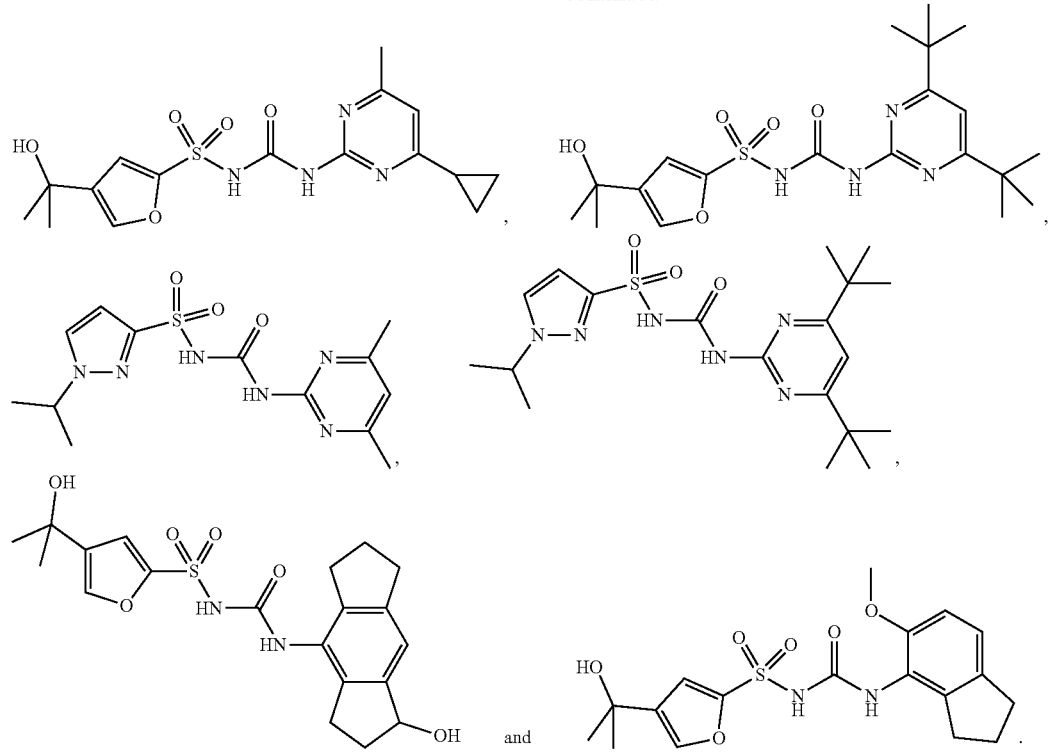
In certain embodiments, the compounds of the first aspect may exhibit improved properties compared to known anti-diabetes drugs. Examples of such compounds may include those below:
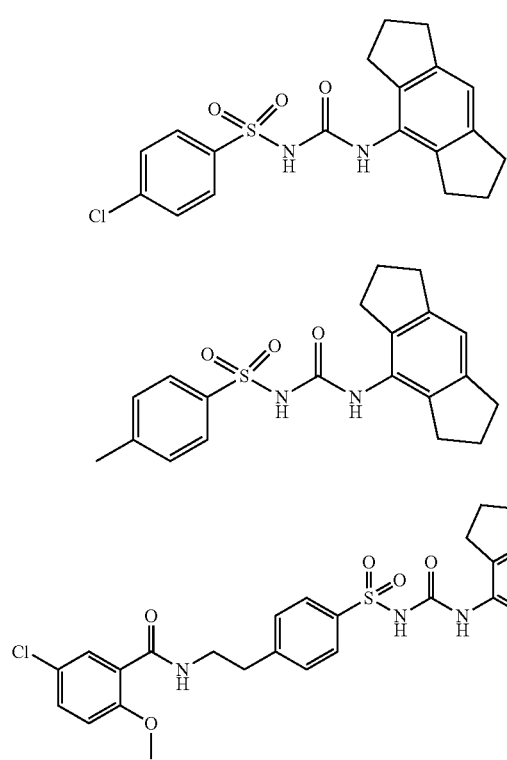
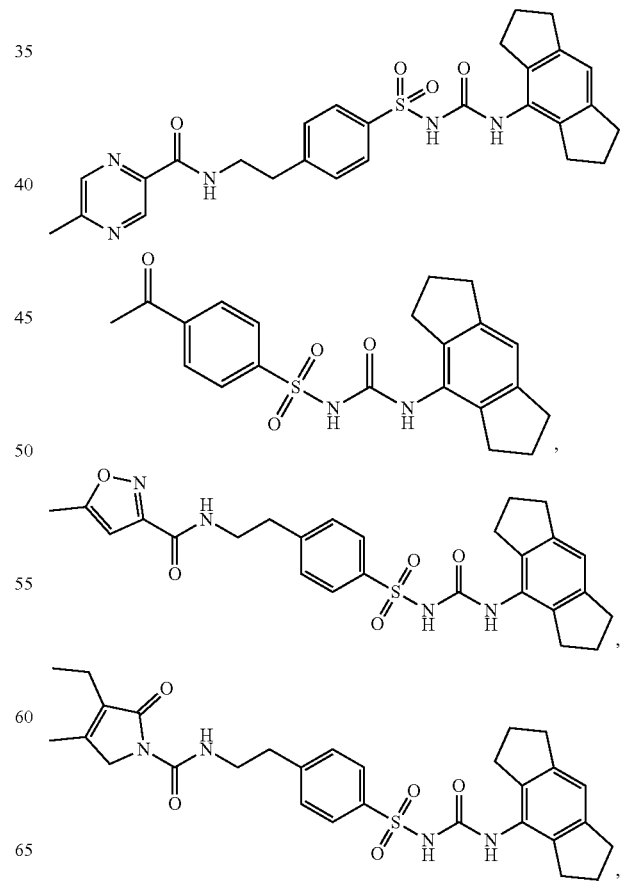

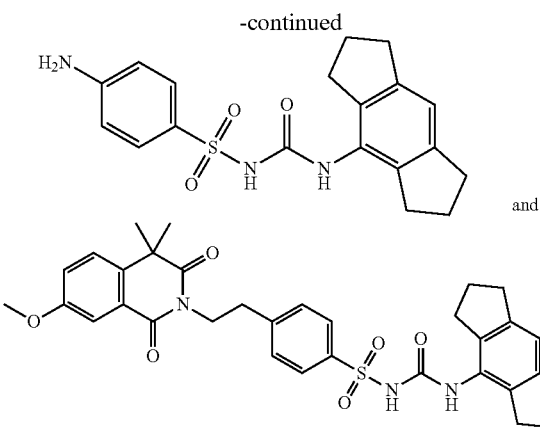

and

These four compounds of formula (I) may be viewed as very potent versions of current sulfonylurea anti-diabetes drugs. The IC50 data presented in the experimental section reflects this view. It is believed that known drugs do not target NLRP3 to any therapeutically significant extent and so it would be necessary to use very high doses to have any significant effect on the NLRP3 inflammasome. The four compounds shown above, and others of the first aspect, show advantageously improved properties in a significant decrease in IC50 versus the NLRP3 inflammasome and additionally have the benefits, not realised by existing diabetes and other drugs, associated with NLRP3 inhibition such as improved wound healing and other advantages described herein.

In any one or more embodiments of the first aspect and in relation to any one or more of the compounds of formula (I) to (VII), the compound is an inhibitor of activation of the NLRP3 inflammasome.

Therefore it will be appreciated that the present invention provides for sulfonyl urea and related drugs exhibiting significantly lower NLRP3 $IC_{50}$ values in cell based assay using HMDM (see experimental section for protocols) than the above comparator compounds. Currently known diabetes drugs are not potent inhibitors of the NLRP3 inflammasome at therapeutic doses and to achieve any such inhibition would require dosing outside of recommended levels. The present compounds allow lower doses to be used and therefore limit the risk of toxic effects.

In a further embodiment, one or more of the compounds of the first aspect may be useful as photoswitchable compounds which may be applied in a range of uses including but not limited to insulin release. Such compounds may, in one embodiment, be selected from the group consisting of:

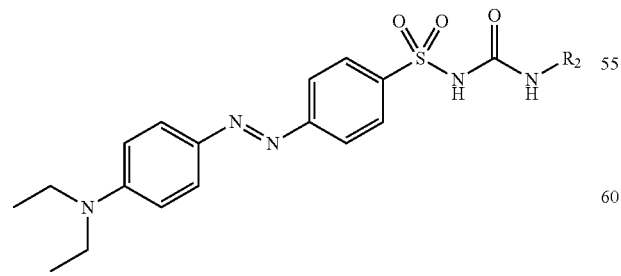

wherein, $R_2$ is as defined in any one or more of the embodiments of compounds of formula (I) to (VII) described previously.

In certain embodiments of the invention one or more compounds of the first aspect may be appropriate for use as probes, such as photoaffinity probes, or as reactive intermediates which can be modified either directly or by means of a linking moiety to give biotinylated, fluorescent or photoaffinity probes including, but not limited to, those shown below:

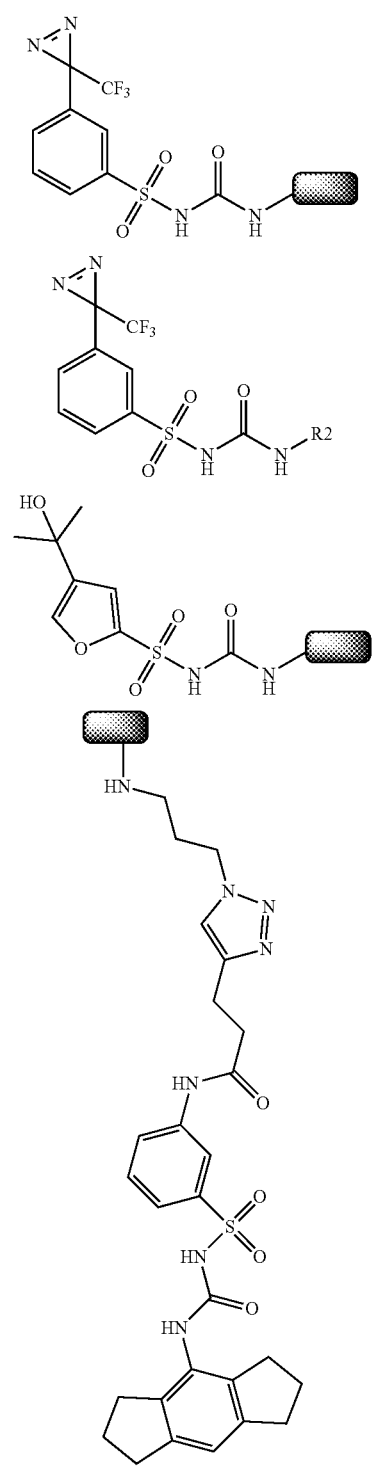

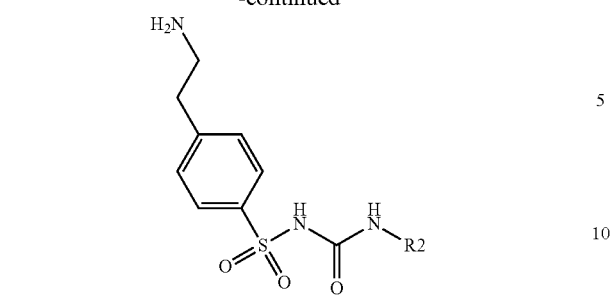
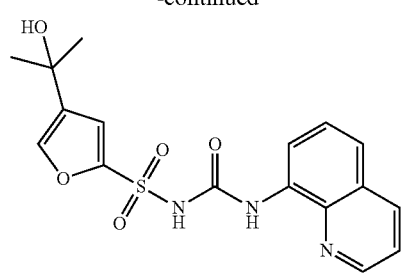
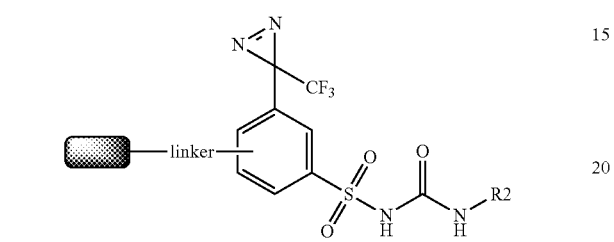
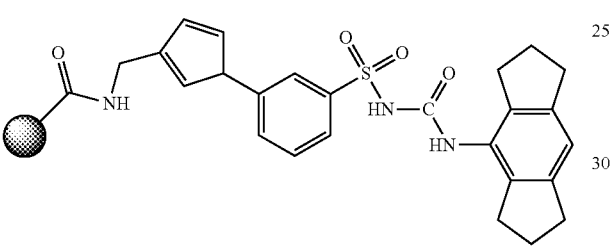
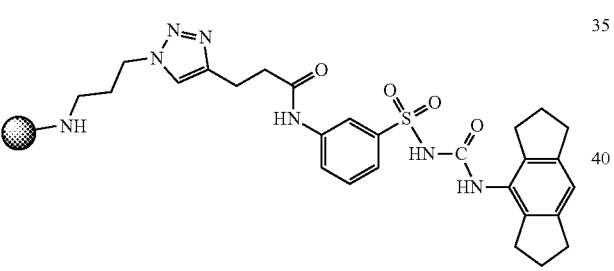
= Biotin
= fluorescent moiety
wherein, R₂ is as defined in any one or more of the embodiments described for formula (I) to (VII).
Particularly, such compounds as probes or reactive intermediates may be selected from those below:
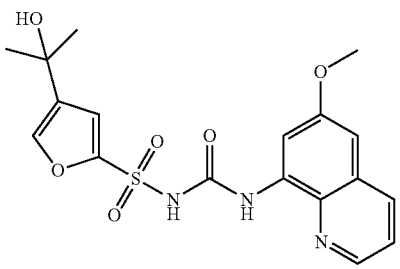
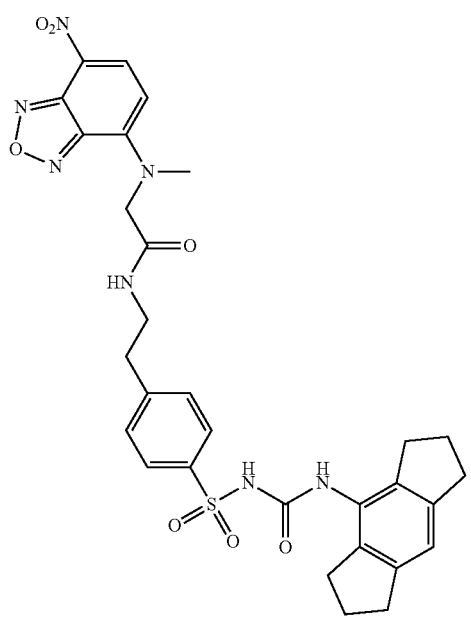

-continued

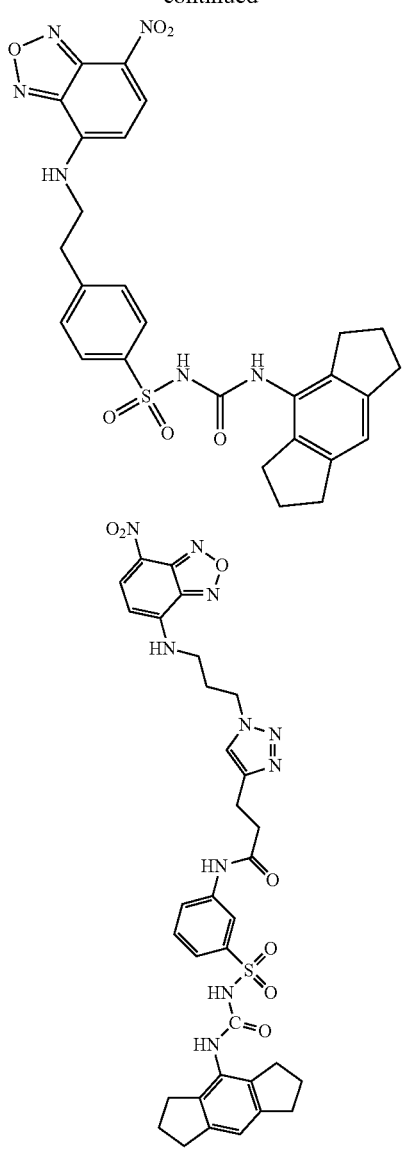

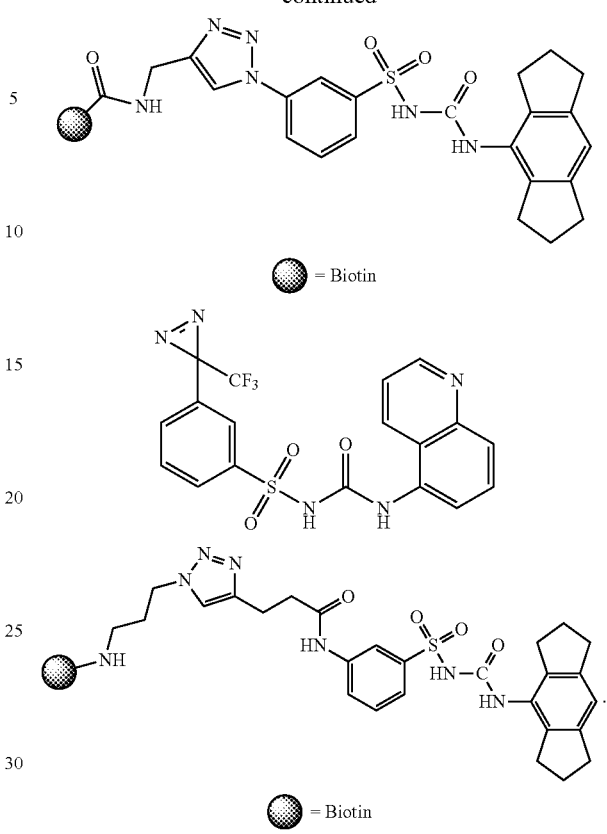

= Biotin

It will be appreciated that the compounds of the first aspect may be modified or derivatised by means well understood in the art to allow linkage to a molecule such as biotin, or a fluorescent group or photoaffinity label, as shown with certain of the compounds above.

In one embodiment, the compound of formula (I) or (II) does not comprise a structure selected from the groups below shown attached to the sulfonyl moiety (i.e. as an $R_1$ group):

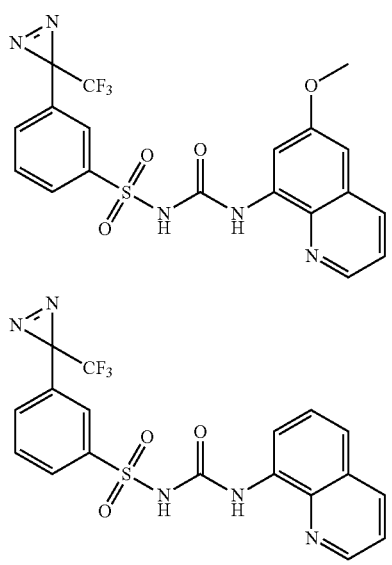

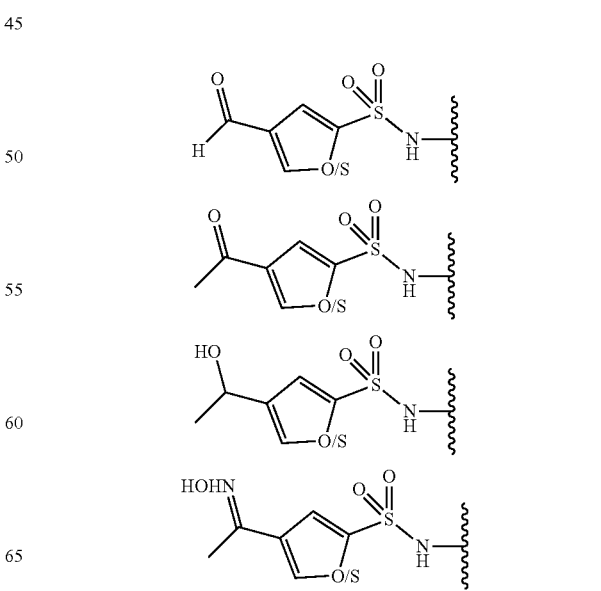

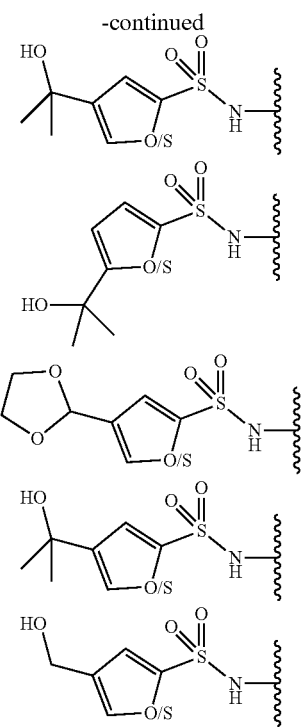

In one embodiment, wherein the compound of the first aspect, including any compound of formula (I) to (VII), has J as S, W as O and $R_2$ is selected from hexahydroindacene, 2,6-diisopropylphenyl and 2,6-diisopropyl-4-chlorophenyl then $R_1$ is not one of 2,4-disubstituted furan, 2,4-disubstituted thiophene, 2,5-disubstituted furan and 2,5-disubstituted thiophene.

In one embodiment, wherein the compound of the first aspect, including any compound of formula (I) to (VII), has J as S, W as O and $R_1$ is selected from substituted triazole, thiadiazole, 4-substituted pyridine and 1,2-disubstituted imidazole then $R_2$ is not unsubstituted phenyl, 2- or 4-chlorophenyl or 3,4-substituted phenyl, substituted with one or more of halo, trifluoromethyl, nitro or thiomethyl.

In one embodiment, wherein the compound of the first aspect, including any compound of formula (I) to (VII), has J as S, W as O and $R_1$ is selected from substituted triazole, thiadiazole, benzothiazole and substituted pyrimidine then $R_2$ is not thiophene, 3-chlorophenyl, 4-ethoxyphenyl, substituted benzimidazole or substituted benzothiazole.

In one embodiment, wherein the compound of the first aspect, including any compound of formula (I) to (VII), has J as S, W as O and $R_1$ is ethoxy substituted benzothiazole, then $R_2$ is not 2,6-diisopropylphenyl.

In one embodiment, wherein the compound of the first aspect, including any compound of formula (I) to (VII), has J as S, W as O and $R_1$ is selected from benzofuran, benzothiophene and indole then $R_2$ is not 3- or 3,4-halo, methyl, ethyl or trifluoromethyl substituted phenyl.

In one embodiment, wherein the compound of the first aspect, including any compound of formula (I) to (VII), has J as S, W as O and $R_2$ is substituted pyrimidine, then $R_1$ is not pyrazole substituted with ester or carboxy.

In one embodiment, wherein the compound of the first aspect, including any compound of formula (I) to (VII), has J as S and W as O then the carbon atom of $R_2$ which is directly bonded to the urea nitrogen is not a carbonyl carbon.

In one embodiment, wherein the compound of the first aspect, including any compound of formula (I) to (VII), has J as S and W as O, then the carbon atom of $R_2$ which is directly bonded to the urea nitrogen is an aryl, heteroaryl or heterocyclic ring carbon.

In one embodiment, wherein the compound of the first aspect, including any compound of formula (I) to (VII), has J as S and W as O, $R_2$ is a substituted phenyl and $R_1$ is a pyrazole then the $R_1$ pyrazole is not substituted with an aryl or heteroaryl group.

In one embodiment, wherein the compound of the first aspect, including any compound of formula (I) to (VII), has J as S, W as O, and $R_1$ is a pyrazole and the sulfonylurea linker is branched in position 4 thereof, the pyrazole is not fused in positions 1 and 5 with a 6-membered heterocycle to form a pyrazolopyrimidine derivative.

In one embodiment, the compound of the first aspect, including any compound of formula (I) to (VII) is not a compound selected from the group consisting of:

1. 1-(4-Chloro-2,6-diisopropyl-phenyl)-3-[3-(1-hydroxy-1-methyl-ethyl)-benzenesulfonyl]-urea;
2. 1-(1,2,3,5,6,7-Hexahydro-s-indacen-4-yl)-3-[4-(1-hydroxy-1-methyl-ethyl)-furan-2-sulfonyl]-urea;
3. 1-(1,2,3,5,6,7-Hexahydro-4-aza-s-indacen-8-yl)-3-[4-(1-hydroxy-1-methyl-ethyl)-furan-2-sulfonyl]-urea;
4. 1-(1,2,3,5,6,7-Hexahydro-s-indacen-4-yl)-3-[4-(1-hydroxy-1-methyl-ethyl)-thiophene-2-sulfonyl]-urea;
5. 1-(4-[1,3]Dioxolan-2-yl-furan-2-sulfonyl)-3-(1,2,3,5,6,7-hexahydro-s-indacen-4-yl)-urea;
6. 1-(2,6-Diisopropyl-phenyl)-3-[4-(1-hydroxy-1-methyl-ethyl)-furan-2-sulfonyl]-urea;
7. 1-(2,6-Diisopropyl-phenyl)-3-[4-(1-hydroxy-1-methyl-ethyl)-thiophene-2-sulfonyl]-urea;
8. 1-(4-Acetyl-thiophene-2-sulfonyl)-3-(1,2,3,5,6,7-hexahydro-s-indacen-4-yl)-urea;
9. 1-(1H-Benzoimidazole-5-sulfonyl)-3-(1,2,3,5,6,7-hexahydro-s-indacen-4-yl)-urea;
10. 1-(1,2,3,5,6,7-Hexahydro-s-indacen-4-yl)-3-[4-(1-hydroxy-1-methyl-ethyl)-thiophene-2-sulfonyl]-urea;
11. 1-(8-Chloro-1,2,3,5,6,7-hexahydro-s-indacen-4-yl)-3-[4-(1-hydroxy-1-methyl-ethyl)-furan-2-sulfonyl]-urea;
12. 1-(4-Acetyl-furan-2-sulfonyl)-3-(1,2,3,5,6,7-hexahydro-s-indacen-4-yl)-urea;
13. 1-(8-Fluoro-1,2,3,5,6,7-hexahydro-s-indacen-4-yl)-3-[4-(1-hydroxy-1-methyl-ethyl)-furan-2-sulfonylj-urea;
14. 1-(4-Fluoro-2,6-diisopropyl-phenyl)-3-[3-(1-hydroxy-1-methyl-ethyl)-benzenesulfonyl]-urea; and
15. 1-(6-Fluoro-1H-benzoimidazole-5-sulfonyl)-3-(1,2,3,5,6,7-hexahydro-s-indacen-4-yl)-urea;
16. 1-(4-Chloro-2,6-diisopropyl-phenyl)-3-(1H-indole-6-sulfonyl)-urea;
17. 1-(4-Chloro-2,6-diisopropyl-phenyl)-3-(5-fluoro-1H-indole-6-sulfonyl)-urea;
18. 1-[1,2,3,5,6,7-Hexahydro-s-indacen-u-yl)-3-(1H-indole-6-sulfonyl)-urea;
19. 1-(5-Fluoro-1H-indole-6-sulfonyl)-3-(1,2,3,5,6,7-hexahydro-5-indacen-4-yl)-urea;
20. 1-[4-Chloro-2,6-diisopropyl-phenyl]-3-[2-fluoro-5-(2-methyl-(1,3)dioxolan-2-yl)-benzenesulfonyl]-urea;
21. 3-[3-[4-Chloro-2,6-diisopropyl-phenyl]-ureidosulfonyl]-N-methyl-benzenesulfonamide;
22. 1-[2-Fluoro-5-(2-methyl-(1,3)dioxolan-2-yl)benzenesulfonyl]-3-1,2,3,5,6,7-hexahydro-indacen-4-yl)-urea;
23. 3-[3-(1,2,3,5,6,7-Hexahydro-S-indacen-4-yl)-ureidosulfonyl]-N-methyl-benzenesulfonamide;
24. 4-(1-hydroxy-1-methyl-ethyl)-furan-2-sulfonamide.

In some embodiments of the present invention, therapeutically inactive prodrugs of the compounds of the first aspect are provided. Prodrugs are compounds which, when administered to a mammal, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

A number of prodrug ligands are known. In general, alkylation, acylation, or other lipophilic modification of one or more heteroatoms of the compound, such as a free amine or carboxylic acid residue, may reduce polarity and allow for the compound's passage into cells. Examples of substituent groups that can replace one or more hydrogen atoms on a free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphatidylcholine; phosphocholine; amino acid residues or derivatives; amino acid acyl residues or derivatives; peptides; cholesterols; or other pharmaceutically acceptable leaving groups which, when administered in vivo, provide the free amine. Any of these moieties can be used in combination with the disclosed active agents to achieve a desired effect.

In some embodiments, compounds with one or more chiral centers are provided. While racemic mixtures of compounds of the invention may be active, selective, and bioavailable, isolated isomers may be of interest as well.

The compounds of the first aspect may contain chiral centers, which may be either of the (R) or (S) configuration, or which may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds and prodrugs of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein and other similar tests which are well known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, such as a mixture of enantiomers in which one enantiomer is present in excess, in particular, to the extent of 95% or more, 96% or more, 97% or more, 98% or more, or 99% or more, including 100%.

The terms (R), (S), (R,R), (S,S), (R,S) and (S,R) as used herein mean that the composition contains a greater proportion of the named isomer of the compound in relation to other isomers. In a preferred embodiment, these terms indicate that the composition contains at least 90% by weight of the named isomer and 10% by weight or less of the one or more other isomers; or more preferably about 95% by weight of the named isomer and 5% or less of the one or more other isomers. In some embodiments, the composition may contain at least 99% by weight of the named isomer and 1% or less by weight of the one or more other isomers, or may contain 100% by weight of the named isomer and 0% by weight of the one of more other isomers. These percentages are based on the total amount of the compound of the present invention present in the composition.

The compounds of the first aspect may be utilized per se or in the form of a pharmaceutically acceptable ester, amide, salt, solvate, prodrug, or isomer, as appropriate. For example, the compound may be provided as a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound or prodrug useful according to the present invention may be prepared in a similar manner using a pharmaceutically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from an anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound useful as an active agent according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound described herein as an active agent is an acid, the desired salt may be prepared by any suitable method known in the art, including treatment of the free acid with an inorganic or organic base, such as an am ine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

According to a second aspect of the invention there is provided a pharmaceutical composition comprising a compound of formula (I) to (VII), or a pharmaceutically acceptable salt, solvate or prodrug thereof, and a pharmaceutically acceptable carrier, diluent and/or excipient.

Suitably, the pharmaceutically acceptable carrier, diluent and/or excipient may be or include one or more of diluents, solvents, pH buffers, binders, fillers, emulsifiers, disintegrants, polymers, lubricants, oils, fats, waxes, coatings, viscosity-modifying agents, glidants and the like.

The salt forms of the compounds of the invention may be especially useful due to their improved solubility.

In one embodiment, the pharmaceutical composition includes a cyclodextrin.

The cyclodextrin may be selected from alpha, beta or gamma cyclodextrins.

In one embodiment, the cyclodextrin is selected from a methyl cyclodextrin, a hydroxypropyl cyclodextrin and a sulfobutylether cyclodextrin.

It has been found that cyclodextrins provide significant advantages in formulation and delivery of the compounds of the invention.

Cyclodextrin formulations such as for example, one or more compounds of the invention with hydroxypropyl beta cyclodextrin or methyl beta cyclodextrin, may have uses in cholesterol sequestration/cholesterol lowering or via NLRP3 inhibition for Non-alcoholic steatohepatitis (NASH), alcoholic liver disease, atherosclerosis and also in Alzheimer's Disease (AD).

Diluents may include one or more of microcrystalline cellulose, lactose, mannitol, calcium phosphate, calcium sulfate, kaolin, dry starch, powdered sugar, and the like. Binders may include one or more of povidone, starch, stearic acid, gums, hydroxypropylmethyl cellulose and the like. Disintegrants may include one or more of starch, croscarmellose sodium, crospovidone, sodium starch glycolate and the like. Solvents may include one or more of ethanol, methanol, isopropanol, chloroform, acetone, methylethyl ketone, methylene chloride, water and the like. Lubricants may include one or more of magnesium stearate, zinc stearate, calcium stearate, stearic acid, sodium stearyl fumarate, hydrogenated vegetable oil, glyceryl behenate and the like. A glidant may be one or more of colloidal silicon dioxide, talc or cornstarch and the like. Buffers may include phosphate buffers, borate buffers and carbonate buffers, although without limitation thereto. Fillers may include one or more gels inclusive of gelatin, starch and synthetic polymer gels, although without limitation thereto. Coatings may comprise one or more of film formers, solvents, plasticizers and the like. Suitable film formers may be one or more of hydroxypropyl methyl cellulose, methyl hydroxyethyl cellulose, ethyl cellulose, hydroxypropyl cellulose, povidone, sodium carboxymethyl cellulose, polyethylene glycol, acrylates and the like. Suitable solvents may be one or more of water, ethanol, methanol, isopropanol, chloroform, acetone, methylethyl ketone, methylene chloride and the like. Plasticizers may be one or more of propylene glycol, castor oil, glycerin, polyethylene glycol, polysorbates, and the like.

Reference is made to the Handbook of Excipients 6$^{th}$ Edition, Eds. Rowe, Sheskey & Quinn (Pharmaceutical Press), which provides non-limiting examples of excipients which may be useful according to the invention.

It will be appreciated that the choice of pharmaceutically acceptable carriers, diluents and/or excipients will, at least in part, be dependent upon the mode of administration of the formulation. By way of example only, the composition may be in the form of a tablet, capsule, caplet, powder, an injectable liquid, a suppository, a slow release formulation, an osmotic pump formulation or any other form that is effective and safe for administration.

Suitably, the pharmaceutical composition is for the treatment or prevention of a disease, disorder or condition in a mammal.

A third aspect of the invention resides in a method of treatment or prevention of a disease, disorder or condition including the step of administering an effective amount of a compound of formula (I) to (VII), or a pharmaceutically effective salt, solvate or prodrug thereof, or the pharmaceutical composition of the second aspect to thereby treat or prevent the disease disorder or condition.

A fourth aspect of the invention provides for a compound of formula (I) to (VII), or a pharmaceutically effective salt, solvate or prodrug thereof, or the pharmaceutical composition of the second aspect for use in the treatment or prevention of a disease, disorder or condition.

A fifth aspect of the invention provides for use of a compound of formula (I) to (VII), or a pharmaceutically effective salt, solvate or prodrug thereof, in the manufacture of a medicament for the treatment or prevention of a disease, disorder or condition.

As generally used herein, the terms "administering" or "administration", and the like, describe the introduction of the compound or composition to a mammal such as by a particular route or vehicle. Routes of administration may include topical, parenteral and enteral which include oral, buccal, sub-lingual, nasal, anal, gastrointestinal, subcutaneous, intramuscular and intradermal routes of administration, although without limitation thereto.

By "treat", "treatment" or treating" is meant administration of the compound or composition to a subject to at least ameliorate, reduce or suppress existing signs or symptoms of the disease, disorder or condition experienced by the subject.

By "prevent", "preventing" or "preventative" is meant prophylactically administering the formulation to a subject who does not exhibit signs or symptoms of a disease disorder or condition, but who is expected or anticipated to likely exhibit such signs or symptoms in the absence of prevention. Preventative treatment may at least lessen or partly ameliorate expected symptoms or signs.

As used herein, "effective amount" refers to the administration of an amount of the relevant compound or composition sufficient to prevent the occurrence of symptoms of the condition being treated, or to bring about a halt in the worsening of symptoms or to treat and alleviate or at least reduce the severity of the symptoms. The effective amount will vary in a manner which would be understood by a person of skill in the art with patient age, sex, weight etc. An appropriate dosage or dosage regime can be ascertained through routine trial.

As used herein, the terms "subject" or "individual" or "patient" may refer to any subject, particularly a vertebrate subject, and even more particularly a mammalian subject, for whom therapy is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment for a disease, disorder or condition as described herein. However, it will be understood that the aforementioned terms do not imply that symptoms are necessarily present.

In one particular embodiment, the disease, disorder or condition is one which is responsive to inhibition of activation of the NLRP3 inflammasome.

According to this embodiment, the compound of the first aspect, or pharmaceutically effective salt, solvate or prodrug thereof is a specific inhibitor of NLRP3.

In a further embodiment, the disease, disorder or condition is responsive to modulation of one or more of IL-1β, IL-17, IL-18, IL-1α, IL-37, IL-33 and Th17 cells.

In one embodiment, the modulation is inhibition of one or more of IL-1β, IL-17, IL-18, IL-1α, IL-37, and IL-33.

In one embodiment, the modulation of Th17 cells, is by inhibition of production and/or secretion of IL-17.

In general embodiments, the disease, disorder or condition is a disease, disorder or condition of the immune system, the cardiovascular system, the endocrine system, the gastrointestinal tract, the renal system, the respiratory system, the central nervous system, is a cancer or other malignancy and/or is caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is Type I diabetes which is an autoimmune disease and a disease of the endocrine system.

In one embodiment, the disease, disorder or condition is of the immune system. In particular embodiments, the disease disorder or condition is an inflammatory disease disorder or condition or an autoimmune disease disorder or condition.

In one embodiment, the disease, disorder or condition is of the skin.

In one embodiment, the disease, disorder or condition is of the cardiovascular system.

In one embodiment, the disease, disorder or condition is a cancer, tumour or other malignancy. As used herein, cancers tumours and malignancies, refer to diseases disorders or conditions, or to cells or tissues associated with the diseases, disorders or conditions, characterized by aberrant or abnormal cell proliferation, differentiation and/or migration often accompanied by an aberrant or abnormal molecular phenotype that includes one or more genetic mutations or other genetic changes associated with oncogenesis, expression of tumour markers, loss of tumour suppressor expression or activity and/or aberrant or abnormal cell surface marker expression. In general embodiments, cancers, tumours and malignancies may include sarcomas, lymphomas, leukemias, solid tumours, blastomas, gliomas, carcinomas, melanomas and metastatic cancers, although without limitation thereto. A more comprehensive listing of cancers tumours and malignancies may be found at the National Cancer Institutes website http://www.cancer.gov/cancertopics/types/alphalist.

In one embodiment, the disease, disorder or condition is of the renal system.

In one embodiment, the disease, disorder or condition is of the gastro-intestinal tract.

In one embodiment, the disease, disorder or condition is of the respiratory system.

In a further embodiment, the disease, disorder or condition is of the endocrine system.

In one embodiment, the disease, disorder or condition is of the central nervous system (CNS).

In one embodiment, the disease, disorder or condition is caused by, or is associated with, a pathogen. The pathogen may be a virus, a bacterium, a protist, a worm or a fungus or any other organism capable of infecting a mammal, although without limitation thereto.

Non-limiting examples of viruses include influenza virus, cytomegalovirus, Epstein Barr Virus, human immunodeficiency virus (HIV), alphavirus such as Chikungunya and Ross River virus, flaviviruses such as Dengue virus, Zika virus and papillomavirus, although without limitation thereto.

Non-limiting examples of pathogenic bacteria include *Staphylococcus aureus, Helicobacter pylori, Bacillus anthracis, Bordatella pertussis, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* and *Yersinia pestis*, although without limitation thereto.

Non-limiting examples of protists include *Plasmodium, Babesia, Giardia, Entamoeba, Leishmania* and Trypanosomes, although without limitation thereto.

Non-limiting examples of worms include helminths inclusive of schistisimes, roundworms, tapeworms and flukes, although without limitation thereto.

Non-limiting examples of fungi include *Candida* and *Aspergillus* species, although without limitation thereto.

Further relevant disease, disorder or conditions may be selected from the group consisting of those recited in the journal article found at: http://onlinelibrary.wiley.com/store/10.1111/j.1365-2249.2011.04440.x/asset/j.1365-2249.2011.04440.x.pdf?v=1&t=i60c1phf&s=d26f50a2622926cc6b4bc855bd911ae9dc9750cf.

In particular embodiments, the disease, disorder or condition is selected from the group consisting of constitutive inflammation including the cryopyrin-associated periodic syndromes (CAPS): Muckle-Wells syndrome (MWS), familial cold autoinflammatory syndrome (FCAS) and neonatal-onset multisystem inflammatory disease (NOMID); including autoinflammatory diseases: familial Mediterranean fever (FMF), TNF receptor associated periodic syndrome (TRAPS), mevalonate kinase deficiency (MKD), hyperimmunoglobulinemia D and periodic fever syndrome (H IDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, and developmental delay (SIFD); Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO); autoimmune diseases including multiple sclerosis (MS), type-1 diabetes, psoriasis, rheumatoid arthritis, Behcet's disease, Sjogren's syndrome and Schnitzler syndrome; respiratory diseases including chronic obstructive pulmonary disorder (COPD), steroid-resistant asthma, asbestosis, silicosis and cystic fibrosis; central nervous system diseases including Parkinson's disease, Alzheimer's disease, motor neuron disease, Huntington's disease, cerebral malaria and brain injury from pneumococcal meningitis; metabolic diseases including Type 2 diabetes, atherosclerosis, obesity, gout, pseudo-gout; ocular diseases including those of the ocular epithelium, age-related macular degeneration (AMD), corneal infection, uveitis and dry eye; kidney disease including chronic kidney disease, oxalate nephropathy and diabetic nephropathy; liver disease including non-alcoholic steatohepatitis and alcoholic liver disease; inflammatory reactions in skin including contact hypersensitivity and sunburn; inflammatory reactions in the joints including osteoarthritis, systemic juvenile idiopathic arthritis, adult-onset Still's disease, relapsing polychondritis; viral infections including alpha virus (Chikungunya, Ross River) and flavivirus (Dengue and Zika Virus), flu, HIV; hidradenitis suppurativa (HS) and other cyst-causing skin diseases; cancers including lung cancer metastasis, pancreatic cancers, gastric cancers, myelodisplastic syndrome, leukemia; polymyositis; stroke; myocardial infarction; Graft versus Host Disease; hypertension; colitis; helminth infection; bacterial infection; abdominal aortic aneurism; wound healing; depression, psychological stress; pericarditis including Dressler's syndrome, ischaemia reperfusion injury and any disease where an individual has been determined to carry a germline or somatic non-silent mutation in NLRP3.

In one non-limiting example of those described, the disease, disorder or condition being treated is NASH. NLRP3 inflammasome activation is central to inflammatory recruitment in NASH, and inhibition of NLRP3 may both prevent and reverse liver fibrosis. Compounds of the present invention, by interrupting the function of NLRP3 inflammasomes in liver tissue, can cause histological reductions in liver inflammation, decreased recruitment of macrophages and neutrophils, and suppression of NF-κB activation. Inhibition of the NLRP3 can reduce hepatic expression of pro-IL-1β and normalized hepatic and circulating IL-1β, IL-6 and MCP-1 levels thereby assisting in treatment of the disease.

In a further non-limiting example of those described, the disease, disorder or condition being treated is severe steroid resistant (SSR) asthma. Respiratory infections induce an NLRP3 inflammasome/caspase-1/IL-1β signaling axis in the lungs that promotes SSR asthma. The NLRP3 inflammasome recruits, and activates, pro-caspase-1 to induce IL-1β responses. NLRP3 inflammasome-induced IL-1β responses are therefore important in the control of infections, however, excessive activation results in aberrant inflammation and has been associated with the pathogenesis of SSR asthma and COPD. The administration of compounds of the first aspect that target specific disease processes, are more therapeutically attractive than non-specifically inhibiting inflammatory responses with steroids or IL-1β. Targeting the NLRP3 inflammasome/caspase-1/IL-1β signaling axis with the compounds of the first aspect may therefore be useful in the treatment of SSR asthma and other steroid-resistant inflammatory conditions.

In one further non-limiting example of those described, the disease, disorder or condition being treated is Parkinson's disease. Parkinson's is the most common neurodegenerative movement disorder and is characterized by a selective loss of dopaminergic neurons, accompanied by the accumulation of mis-folded α-synuclein (Syn) into Lewy bodies that are pathological hallmarks of the disease. Chronic microglial neuroinflammation is evident early in the disease, and has been proposed to drive pathology.

A central role for microglial NLRP3 is postulated in Parkinson's progression. The NLRP3 inflammasome is activated by fibrillar Syn via a Syk kinase dependent mechanism, and also occurs in the absence of Syn pathology at the early stages of dopaminergic degeneration, and drives neuronal loss. The compounds of the first aspect may block NLRP3 inflammasome activation by fibrillar Syn or mitochondrial dysfunction and thereby confer effective neuroprotection of the nigrostriatal dopaminergic system and assist with treatment of Parkinson's.

In a sixth aspect of the invention there is provided a method of diagnosing a disease, disorder or condition in a mammal including the step of administering a labelled compound of formula (I) to (VII), or a pharmaceutically effective salt, solvate or prodrug thereof, to the mammal or to a biological sample obtained from the mammal to facilitate diagnosis of the disease disorder or condition in the mammal.

Inflammasome activation, in particular that of the NLRP3 inflammasome, is known to drive initiation, progression and chronic development of a vast number of inflammatory diseases. The sulfonylureas and related compounds of the first aspect are potent and specific direct inhibitors of NLRP3. Accordingly, a chemical probe specific for NLRP3, which is present in immune cells during inflammation has potential utility in diagnosing inflammatory and other related diseases. An NRLP3 activation probe comprising a compound of the first aspect could act as an effective surrogate biomarker of inflammatory disease for ex vivo (blood) or in vivo (MRI, PET etc.) diagnostics.

The use of the compounds of the first aspect in diagnosing inflammatory and other related diseases, such as those listed above, may be achieved by near infrared fluorescent imaging and ex vivo characterisation of immune cells by degree of inhibition of IL-1beta, pro-caspase 1 cleavage and IL-18 levels. In particular, peripheral blood monocytes (PMBCs), macrophages, dendritic cells, $CD^+$ T cells, Th17 cells, Th1 cells and Th2 cells are relevant. In vivo diagnostics using magnetic resonance imaging (MRI). H2 (deuterium) $^{13}C$, $^{19}F$, $^{15}N$ labelled variants of [compound classes] given to a patient IV, IM, SC, PO, topical, IT, etc.

In vivo diagnostics using positron emission tomography (PET) are also appropriate. PET is a molecular imaging technique that requires specific probes radiolabelled with short-lived positron emitting radionuclides. Typical isotopes include $^{11}C$, $^{13}N$, $^{15}O$, $^{18}F$, $^{64}Cu$, $^{62}Cu$, $^{124}I$, $^{76}Br$, $^{82}Rb$ and $^{68}Ga$, with $^{18}F$ being the most clinically utilized. In particular it is possible to produce in a simple manner a stable $^{64}Cu$ or $^{62}Cu$ salt of one or more of the compounds of formula (I) by simple ion exchange with a sodium (or other monovalent cation) salt of said compounds. This enables rapid preparation of a diagnostic probe for radioimaging, PET and the like whereby the intensity, location and temporal accretion of the diagnostic probe is able to identify the degree and/or the location of immune cells with activated NLRP3 as a surrogate biomarker of the patient's inflammatory state, and site of inflammation within the body. They will also be useful for application to biological samples removed from the body i.e. in vitro diagnosis.

A seventh aspect of the invention resides in a method of modulating the activity of a biological target comprising the step of exposing the biological target to a compound of formula (I) to (VII), or a pharmaceutically effective salt, solvate or prodrug thereof.

The biological target may be selected from the group consisting of NLRP3 inflammasome, IL-1β, IL-17, IL-18, IL-1α, IL-37, IL-33 and Th17 cells.

The modulation may be as described previously for the third to fifth aspects.

As generally used herein, a biological sample may include cells, tissues, fluids, molecules or other biological materials obtained, or obtainable, from a mammal. Non-limiting examples include urine, blood and fractions thereof such as serum, plasma, lymphocytes and erythrocytes, cerebrospinal fluid, PAP smears, nasal and ocular secretions, amniotic fluid, faeces, semen, tissue and/or organ biopsies and nucleic acid (e.g. DNA, RNA) or protein samples, although without limitation thereto.

The following experimental section describes in more detail the characterisation of certain of the compounds of the invention and their efficacy. The intention is to illustrate certain specific embodiments of the compounds of the invention and their efficacy without limiting the invention in any way.

EXPERIMENTAL

General Synthetic Methods

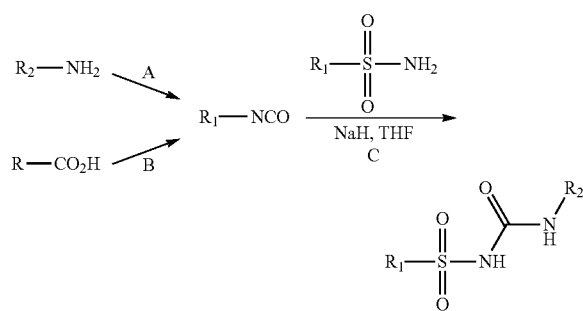

Method A:

A1: To a solution of R2 amine intermediate (1 eq.) with or without base such as, but not exclusively, triethylamine (1.2 eq.) in an anhydrous aprotic solvent such as, but not exclusively, tetrahydrofuran or dichloromethane was added triphosgene (0.4 to 1.1 eq.). The reaction was stirred at ambient temperature or, where necessary, heated at reflux until completion, typically from 2 to 18 h.

A2: To di-t-butyldicarbonate (1.2-1.4 eq.) in anhydrous acetonitrile or THF was added DMAP (15-100 mol %), after 5 minutes, a solution of R2 amine intermediate (1.0 eq.) in acetonitrile was added. The reaction mixture was stirred for 30-60 min at room temperature.

Method B:

B1: The R2 carboxylic acid intermediate (1 eq.) was dissolved in an aprotic solvent such as toluene with or without 2 drops of DMF and a chlorinating agent such as thionyl chloride (2 eq.) added. The reaction mixture was heated at reflux until completion, then concentrated in vacuo. To give the corresponding R2 acid chloride intermediate.

Alternative methods or forming the acid chloride are also equally useful here for example the above procedure can be carried out without toluene and DMF thereby using thionyl chloride as both solvent and chlorinating agent.

The R2 acid chloride intermediate was dissolved in acetone and added drop-wise to a solution of sodium azide (1.5 eq) in a water:acetone (50:50) solution at 0° C. Iced water was added to precipitate the resulting R2 acylazide intermediate which was dissolved in toluene and dried (MgSO4) prior to adding the solution in a drop-wise fashion to anhydrous toluene at reflux while maintaining a constant flow of inert gas. The reaction was heated until completion, typically 2 h, to give the R2 isocyanate.

B2: The R2 acid chloride (formed as indicated in method B1) in dry $CH_2Cl_2$ was added $NaN_3$ (2.0 eq.) at 0° C. The reaction mixture was stirred at room temperature for 1 h and extracted into EtOAc. The organic layer was washed with $H_2O$ (15 mL), dried (MgSO4), and carefully evaporated to give acyl azide. The acyl azide was dissolved in dry toluene and heated to 100° C. for 2 h. The solvent was removed to give crude R2 isocyanate.

Method C:

C1: R1 sulfonamide intermediate (1 eq.) was dissolved in anhydrous THF and treated with NaH (1 eq.) under reduced pressure. The mixture was heated to reflux for 2 h then cooled to room temperature and R2 isocyanate intermediate in THF added under nitrogen atmosphere. The reaction mixture was stirred at reflux until completion.

C2: R1 sulfonamide intermediate (1 eq.) was dissolved in anhydrous THF or anhydrous methanol and treated with NaH (1 eq.) under reduced pressure. Once effervescence ceased the R2 isocyanate intermediate was added and the reaction mixture was stirred at ambient temperature overnight.

C3: To R1 sulfonamide intermediate (1 eq) in anhydrous THF (5 mL/mmol) was added NaH (1 eq) at 0° C. and stirred for 30 min to 2 h, or until completion, at ambient temperature under nitrogen atmosphere. Again cooled to 0° C., R2 isocyanate (1.0 eq) in THF was added and stirred at ambient temperature until completion, typically 2 to 16 h.

C4: To crude R2 isocyanate (1.0 eq) in anhydrous THF or DCM (5-11 mL/mmol) was added R1 sulfonamide (1.0 eq) followed by base such as triethylamine, DIPEA, or DBU (1-2 eq) and the reaction mixture stirred at ambient temperature overnight.

C5: To R1 sulfonamide intermediate (1 eq) in anhydrous MeOH (5 mL/mmol) was added NaOMe (1 eq) [alternatively: a 1.0 mM solution of freshly prepared sodium methoxide (1 eq) was added to a 1.0 mM solution of R1 sulfonamide (1 eq) in anhydrous methanol]. The solvent was then removed in vacuo. The salt was suspended in anhydrous aprotic solvent such as acetonitrile or THF, the R2 isocyanate (1.0 eq) in anhydrous aprotic solvent such as acetonitrile or THF was added and the mixture stirred at ambient temperature overnight. The solution was then heated at reflux until completion, typically 90 min.

C6: R1 sulfonamide (1.0 eq.) was dissolved in anhydrous THF under a nitrogen atmosphere. Solid sodium methoxide (1.0 eq mmol) was added in one portion. This mixture was stirred at ambient temperature for 3 h. A solution of the R2 isocyanate (1.17 eq) in THF was added drop wise. The reaction mixture was stirred at room temperature overnight.

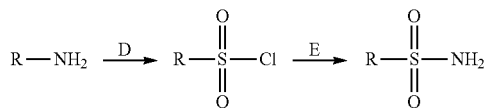

Method D:

A solution of amine (1.0 eq) in acetonitrile (7-12 mL/mmol) at 0° C. was treated with c. HCl (1.25-2.25 m L/mmol) in $H_2O$ (0.5-1.2 mL/mmol) followed by aqueous solution of $NaNO_2$ (1.2 eq) dissolved in $H_2O$ (0.3-0.5 mL/mmol of $NaNO_2$). The resulting solution was stirred at 0° C. for 45 min. AcOH (0.5-1.2 mL/mmol), $CuCl_2.2H_2O$ (0.5 eq) and CuCl (0.05 eq) were sequentially added to the above mixture and purged with SO$_2$ gas for 20 min at 0° C. The resulting reaction mixture was stirred at 0° C.-10° C. until completion.

Method E:

E1: A solution of sulfonyl chloride (1 eq) in THF (10-20 mL/mmol) was cooled to −78° C. and ammonia gas was bubbled through the solution for 15 min, stirring was continued for a further 30 min then allowed to warm to ambient temperature and stirred for 2 h or until completion.

E2: A solution of sulfonyl chloride (1 eq) in acetone (20 mL/mmol) was treated with a solution of NH$_4$HCO$_3$ (4 eq) dissolved in water 1.5 mL/mmol of NH$_4$HCO$_3$) at ambient temperature and stirred for 4 h or until completion.

E3: A solution of sulfonyl chloride (1 eq) in acetone (2.5 mL/mmol) was treated with NH$_3$ (3.5 mL/mmol, NH$_4$OH in H$_2$O, 28% NH$_3$ basis) at 0° C. and stirred for 2 h or until completion.

Method F

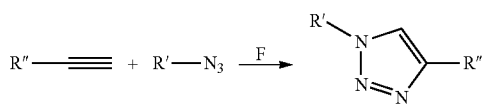

General Procedure for the Synthesis of Triazoles

Alkyne (1 eq) and azide (1.2 eq), 5 mol % CuSO$_4$, 10 mol % NaAsc solution in DMSO (500 μL) were stirred at room temperature until completion, typically 12 h.

an off-white solid (30 mg, 34%). $^1$H NMR (400 MHz, DMSO-d$_6$): δ=6.61 (br s, 2H), 2.76-2.70 (m, 1H), 2.09-2.04 (m, 2H), 1.80-1.76 (m, 2H), 1.65-1.60 (m, 1H), 1.31-1.19 (m, 4H), 1.16-1.06 (m, 1H).

Cyclopentanesulfonamide

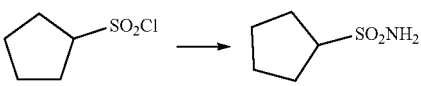

To a solution of cyclopentanesulfonyl chloride (0.1 g, 0.59 mmol) in acetone (1 mL) was added aq NH$_3$ (1 mL, 28% NH$_4$OH in H$_2$O) at 0° C., and the reaction mixture stirred at room temperature for ~2 h. The solvent was removed in vacuo and MeOH/dichloromethane (1:9) (5 mL) added the NH$_4$Cl by-product was removed by filtration and remaining solution concentrated in vacuo. The crude product was purified by column chromatography on silica gel using 35% EtOAc-hexanes eluent to give cyclopentanesulfonamide as an off-white solid (72 mg, 81%). $^1$H NMR (400 MHz, DMSO-d$_6$): 5=6.69 (br s, 2H), 3.42-3.32 (m, 1H), 1.89-1.84 (m, 4H), 1.68-1.64 (m, 2H), 1.61-1.52 (m, 2H).

5-((dimethylamino)methyl)furan-2-sulfonamide

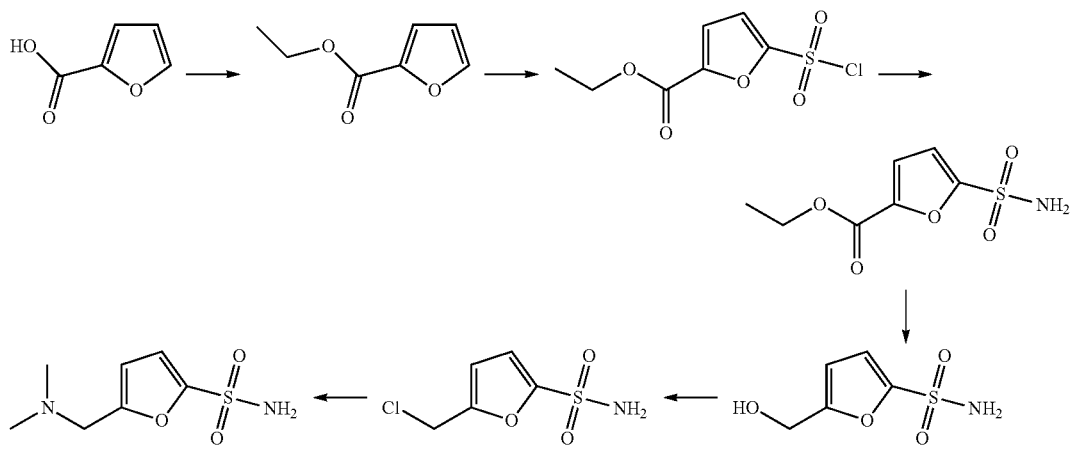

Synthesis of R1 Sulfonamide Intermediates:
Cyclohexanesulfonamide

To a solution of cyclohexanesulfonyl chloride (0.1 g, 0.54 mmol) in acetone (1 mL) was added aq NH$_3$ (2 mL, 28% NH$_4$OH in H$_2$O) at 0° C. and the reaction mixture stirred at room temperature for ~2 h. The solvent was removed in vacuo and MeOH/dichloromethane (1:9) (5 mL) added the NH$_4$Cl by-product was removed by filtration and remaining solution concentrated in vacuo. The crude product was purified by column chromatography on silica gel using 0.2% MeOH—CH$_2$Cl$_2$ eluent to give cyclohexanesulfonamide as Furan-2-carboxylic acid (5 g, 44.6 mmol) was dissolved in ethanol (100 mL), c.H$_2$SO$_4$ (1.0 mL) was added and the solution heated to reflux overnight. The reaction mixture was concentrated in vacuo then partitioned between ethyl acetate (100 mL) and saturated NaHCO$_3$ (100 mL). The organic phase was washed using water then brine, dried (MgSO$_4$) and concentrated in vacuo to give ethyl furan-2-carboxylate (4.5 g, 80%). $^1$H NMR (400 MHz, CDCl$_3$): δ=7.57 (d, J=1.2 Hz, 1H), 7.18 (d, J=3.5 Hz, 1H), 6.51 (dd, J=3.5, 1.2 Hz, 1H), 4.37 (q, J=7.1 Hz, 2H), 1.38 (t, J=7.1 Hz, 3H).

Ethyl furan-2-carboxylate (9.0 g, 64.3 mmol) was dissolved in dichloromethane (200 mL) and chlorosulfonic acid (7.5 g, 64.3 mmol) added. The reaction was stirred at ambient temperature for 6 hours, or until completion, then pyridine (5.6 g, 70.7 mmol) and PCl5 (14.7 g, 70.7 mmol) were added portionwise. The reaction mixture was stirred at ambient temperature for 16 hours then quenched using ice-water and stirred for 30 mins. The mixture was extracted using DCM and the combined organics washed with water, brine, dried (Na$_2$SO$_4$) and concentrated in vacuo. The crude product, ethyl 5-(chlorosulfonyl)furan-2-carboxylate (7 g, 46%) was used directly without further purification. $^1$H NMR (300 MHz, CDCl$_3$) δ=7.33 (d, J=3.9 Hz, 1H), 7.27 (d, J=3.9 Hz, 1H), 4.44 (q, J=7.1 Hz, 1H), 1.42 (t, J=7.1 Hz, 2H).

The crude ethyl 5-(chlorosulfonyl)furan-2-carboxylate (7 g) was converted using general method E1 to give ethyl 5-sulfamoylfuran-2-carboxylate (5 g, 78%). $^1$H NMR (300 MHz, DMSO-d$_6$) δ=8.05 (s, 2H), 7.38 (d, J=3.7 Hz, 1H), 7.09 (d, J=3.7 Hz, 1H), 4.32 (q, J=7.1 Hz, 2H), 1.29 (t, J=7.1 Hz, 3H).

Ethyl 5-sulfamoylfuran-2-carboxylate (2 g, 9.13 mmol) in dry THF (40 mL) was cooled to 0° C. and lithium aluminium hydride (1.05 g, 27.3 mmol) was added portion-wise over a period of 30 mins. The reaction was heated to 70° C. for 4 hours. The reaction was cooled to 0° C. and saturated NH$_4$Cl was added (20 mL) dropwise with great care over a period of 30 mins. The reaction mixture was diluted using ethyl acetate (100 mL) and filtered through a pad of celite. The organic phase was washed with water (100 mL), brine (100 mL), dried (MgSO$_4$) and concentrated in vacuo to give 5-(hydroxymethyl)furan-2-sulfonamide (1.25 g, 78%) as a pale brown liquid. 1H NMR (400 MHz, DMSO-d6) δ 7.71 (s, 2H), 6.88 (d, J=3.5 Hz, 1H), 6.44 (d, J=3.4 Hz, 1H), 5.47 (s, 1H), 4.44 (d, J=5.7 Hz, 2H), 3.36 (s, 7H), 2.51 (q, J=1.8 Hz, 5H), 1.36 (s, 1H).

5-(hydroxymethyl)furan-2-sulfonamide (0.3 g, 1.7 mmol) in THF (5 mL) was cooled to 0° C. and POCl$_3$ (0.4 g, 2.54 mmol) added slowly. The reaction mixture was stirred at 75° C. for 2 hours then cooled to ambient temperature. The crude mixture was partitioned between ethylacetate (50 mL) and sat. aq. NaHCO$_3$ (50 mL) and the organic phase washed with water (50 mL), brine (50 mL), dried (Na$_2$SO$_4$) and concentrated in vacuo. The crude product was purified by column chromatography on silica gel using 30% EtOAc-hexanes eluent to give 5-(chloromethyl)furan-2-sulfonamide as a pale-brown semi-solid (0.25 g, 76%). $^1$H NMR (300 MHz, DMSO-d6) δ=7.85 (s, 2H), 6.93 (dd, J=3.5, 1.3 Hz, 1H), 6.69 (dd, J=3.5, 1.3 Hz, 1H), 4.89 (d, J=1.3 Hz, 2H). 5-(chloromethyl)furan-2-sulfonamide (0.4 g, 2.05 mmol) in THF (20 mL) was cooled to 0° C., c.HCl (7.5 mg, 2.05 mmol) was added and the solution stirred for 20 mins at this same temperature. 5.6 M N,N-dimethylamine in ethanol (0.28 g, 6.15 mmol, 3 eq.) was added at 0° C. and the reaction tube sealed before stirring at room temperature overnight. The solvents were removed in vacuo and azeotroped using toluene (×2) to give 5-((dimethylamino)methyl)furan-2-sulfonamide as a gum (0.25 g, 60%). The crude product was used directly without further purification.

Furan-2-sulfonamide

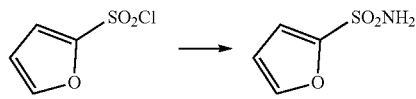

Furan-2-sulfonyl chloride (0.30 g, 1.8 mmol) was added to aqueous ammonia (1.0 mL) at 0° C. and the mixture was stirred at ambient temperature for 1 h. Upon completion of the reaction, the excess aqueous ammonia was removed in vacuo. The residue was azeotroped with isopropanol and triturated with pentane to afford the titled compound as a light brown solid (0.21 g, 79%). $^1$H NMR (400 MHz, DMSO-d$_6$): δ=7.91 (s, 1H), 7.45 (br.s., 2H), 6.95 (d, J=3.6 Hz, 1H), 6.63 (dd, J=2.8, 1.6 Hz, H). LC-MS 97.4% (ELSD); m/z 146.11 [M−H]$^+$.

5-methylfuran-2-sulfonamide

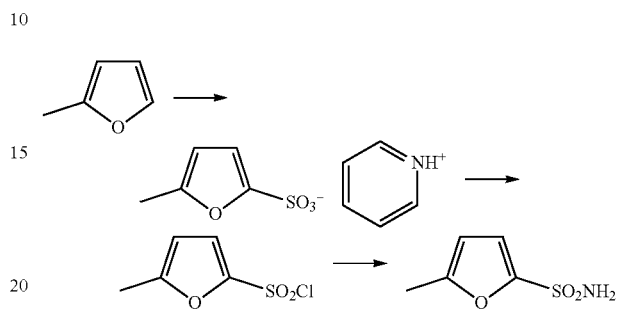

To a solution of 2-methylfuran (2.0 g, 24.3 mmol) in anhydrous acetonitrile (4 mL) was added SO$_3$.Py complex (5.0 g, 31.6 mmol) and the reaction mixture heated at 40° C. under nitrogen overnight. The reaction mixture was diluted with EtOAc (5 mL) and stirred for 2 h at 0° C., the resulting precipitates were removed by filtration and dried to give pyridinium 5-methylfuran-2-sulfonate as an off-white solid (2.93 g, 50%). $^1$H NMR (400 MHz, DMSO): δ=8.90 (dd, J$_1$=4 Hz, J$_2$=8 Hz, 2H), 8.57 (tt, J$_1$=1.5 Hz, J$_2$=8.1 Hz, 1H), 8.04 (dd, J$_1$=4 Hz, J$_2$=8 Hz, 2H), 6.27 (d, J=3.0 Hz, 1H), 5.98-5.94 9 m, 1H), 2.19 (s, 3H).

A slurry of pyridinium 5-methylfuran-2-sulfonate (1.0 g, 4.41 mmol) in anhydrous DME was treated with oxalyl chloride (0.53 mL, 6.21 mmol) then DMF (0.32 mL, 4.41 mmol) at 0° C. under argon and the reaction stirred at room temperature until completion. The reaction was quenched with ice-water and extracted with toluene (2×50 mL), the combined organics were washed with aqueous saturated NaHCO$_3$ (20 mL), brine (20 mL), dried (MgSO$_4$) and concentrated in vacuo to give 5-methylfuran-2-sulfonyl chloride as pale-yellow oil (350 mg, 47%). $^1$H NMR (400 MHz, CDCl$_3$): δ=7.23-7.21 (m, 1H), 6.27-6.25 (m, 1H), 2.47 (s, 3H).

To a solution of 5-methylfuran-2-sulfonyl chloride (0.2 g, 1.10 mmol) in acetone (1 mL) was added aq. NH$_3$ (1 mL, 28% NH$_4$OH in H$_2$O) at 0° C. The reaction mixture was stirred at ambient temperature for ~2 h then concentrated in vacuo. The residue was suspended in dichloromethane (5 mL) the NH$_4$Cl by-product was removed by filtration and remaining solution concentrated in vacuo. The crude product purified by column chromatography on silica gel using 40% EtOAc-hexanes eluent to give 5-methylfuran-2-sulfonamide as an off-white solid (130 mg, 73%). $^1$H NMR (400 MHz, DMSO-d$_6$): δ=7.60 (s, 2H), 6.83-6.82 (d, J=4.0 Hz, 1H), 6.26-6.25 (d, J=4.0 Hz, 1H), 2.34 (s, 3H).

5-ethyl-N-((1,2,3,5,6,7-hexahydro-s-indacen-4-yl)carbamoyl)furan-2-sulfonamide

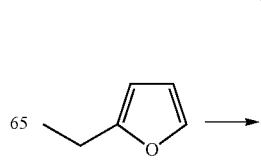

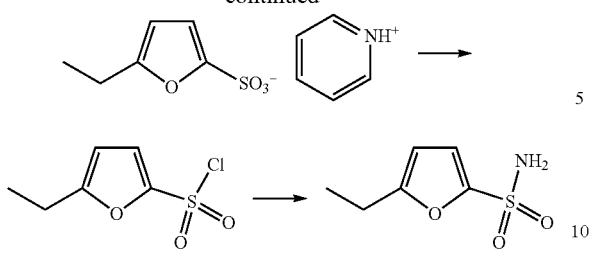

To a solution of 2-ethylfuran (2.0 g, 20.8 mmol) in anhydrous acetonitrile (3 mL) was added SO₃.Py complex (4.30 g, 27.0 mmol). The resulting reaction mixture was heated at 40° C. under nitrogen atmosphere for 23 h or until completion. EtOAc (5 mL) was added and the solution stirred for 2 h at 0° C. The resulting precipitate was removed by filtration and dried to give pyridin-1-ium 5-ethylfuran-2-sulfonate as a brown coloured hygroscopic solid (3.2 g, 60%) which was used directly in the next step without purification.

To a slurry of pyridinium 5-ethylfuran-2-sulfonate (3.2 g, 12.5 mmol) in DME (15 mL) was added oxalyl chloride (1.62 mL, 27.0 mmol) and then DMF (0.97 mL, 12.5 mmol) at 0° C. under argon atmosphere, the resulting reaction mixture was stirred at room temperature until completion. The reaction mixture was quenched with ice-water and then extracted with toluene (2×50 mL), organic layer was washed with aqueous saturated NaHCO₃(20 mL) and brine (20 mL), dried (MgSO₄) and concentrated in vacuo to give 5-ethylfuran-2-sulfonyl chloride as light brown oil (510 mg, 21%). $^1$H NMR (400 MHz, CDCl₃): δ 7.23 (d, J=4 Hz, 1H), 6.26 (d, J=8 Hz, 1H), 2.80 (q, J=8 Hz, 2H), 1.33 (t, J=8 Hz, 3H).

To a solution of 5-ethylfuran-2-sulfonyl chloride in acetone (1 mL) was added aq NH₃ (1.5 mL, NH₄OH in H₂O, 28% NH₃ basis) at 0° C., resulting reaction mixture was stirred at room temperature for 2 h or until completion. The solvent was removed in vacuo and azeotroped with toluene (×2). The residue was purified by column chromatography on silica using 1% MeOH/DCM eluant to give 5-ethylfuran-2-sulfonamide as brown coloured gum (0.36 g, 78%). $^1$H NMR (400 MHz, DMSO-d₆): δ 7.63 (bs, 2H), 6.85 (d, J=4 Hz, 1H), 6.28 (d, J=4 Hz, 1H), 2.70 (q, J=8 Hz, 2H), 1.21 (t, J=6 Hz, 3H).

4-(prop-1-en-2-yl)furan-2-sulfonamide

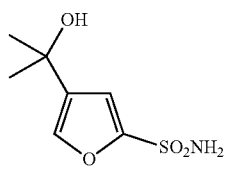

Synthesis of 4-(prop-1-en-2-yl)furan-2-sulfonamide was carried out from ethyl furan-3-carboxylate using procedures detailed by Urban et. al. *Synth. Commun.* 2003, 33(12), 2029-2043 to give the titled compound as a white solid with all spectral data consistent with the specified literature reference.

d₆-4-(prop-1-en-2-yl)furan-2-sulfonamide

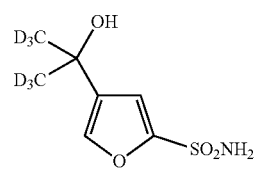 [SMILES: [2H]C([2H])([2H])C(O)(c1coc(S(N)(=O)=O)c1)C([2H])([2H])[2H]]

Modification of the procedures contained within Urban et. al. *Synth. Commun.* 2003, 33(12), 2029-2043 to use methyl-d₃-magnesium iodide in place of methyl magnesium chloride gives the corresponding d₆-4-(prop-1-en-2-yl)furan-2-sulfonamide.

4-(prop-1-en-2-yl)furan-2-sulfonamide

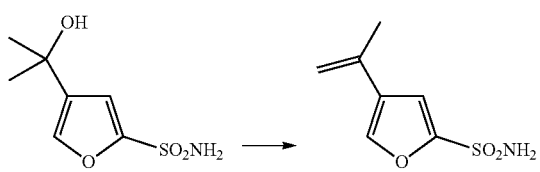

To a solution of triphenylphosphine (0.3 g, 1.16 mmol) in anhydrous THF (5.0 mL) was added iodine (1.0 eq.) and the mixture stirred at room temperature for 10 min. A solution of 4-(2-hydroxypropan-2-yl)furan-2-sulfonamide in THF (3.0 ml) was added slowly and stirring was continued for 2 h or until completion. The solution was diluted with EtOAc (20 mL), washed with 10% aq. sodium bisulfite (20 mL), water (20 mL). The organic layer was separated, dried (MgSO₄) and concentrated in vacuo. The crude product was purified by column chromatography on silica gel using 20% EtOAc:hexanes eluent to give the titled compound as a white solid (0.1 g, 58%). $^1$H NMR (400 MHz, CDCl₃) δ=7.51 (s, 1H), 7.16 (s, 1H), 5.27 (s, 2H), 2.02 (s, 3H). $^{13}$C NMR (101 MHz, CDCl₃) b 149.3, 140.7, 140.7, 132.3, 127.8, 112.1, 111.9, 76.0, 7.7, 28.7, 19.8.

4-(2-hydroxypropan-2-yl)-5-methylfuran-2-sulfonamide

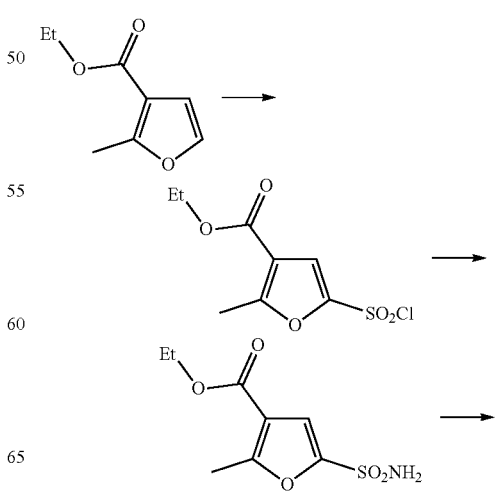

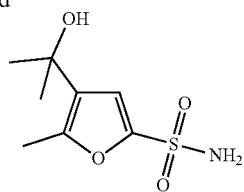

To a solution of ethyl 2-methyl-3-furoate (30 g, 0.195 M) in DCM (300 mL) at −10° C. was added chlorosulfonic acid (23.8 g, 0.204 M) drop-wise over ~15 min. The reaction was allowed to warm to ambient temperature and stirred for 72 hours. The solution was cooled to −10° C. and anhydrous pyridine (16.9 g, 0.214 M) added drop wise followed by phosphorous pentachloride (44.6 g, 0.214 M) added in ~10 g portions over 10 min. Stirred at <0° C. for 30 min then stirred at ambient temperature overnight. The reaction mixture was added drop-wise to water (550 mL) with stirring and stirring continued for 2 hours. The organic phase was separated and the aqueous phase extracted using DCM (150 mL). The combined organics were washed using water (300 mL), dried (Na$_2$SO$_4$) and concentrated in vacuo to give 44 g dark red oil. The crude product was purified by column chromatography on silica gel using 10% EtOAc-hexane eluent to give ethyl 5-(chlorosulfonyl)-2-methylfuran-3-carboxylate as an orange oil (36 g, 73%). $^1$H NMR (400 MHz, CDCl$_3$) δ=7.55 (s, 1H), 4.63 (q, J=7.2 Hz, 2H), 2.75 (s, 3H), 1.38 (t, J=7.2 Hz, 3H).

Ethyl 5-(chlorosulfonyl)-2-methylfuran-3-carboxylate (30 g, 0.12 M) in acetone (200 mL) was added drop-wise over 15 min to a solution of ammonium bicarbonate (37.6 g, 0.475 M) in water (630 mL). The reaction mixture was stirred at ambient temperature until completion (~3 h). EtOAc (250 mL) was added and the pH adjusted using drop-wise addition of cHCl to pH~2. The organics were separated and the remaining aqueous phase saturated with sodium chloride and re-extracted using EtOAc (250 mL). The combined organics were washed with brine (300 mL), dried (Na$_2$SO$_4$) and concentrated in vacuo to give a brown oily solid which was recrystallized using EtOAc-hexane to give ethyl 2-methyl-5-sulfamoylfuran-3-carboxylate as a beige solid (11.4 g, 41%). $^1$H NMR (400 MHz, DMSO-d$_6$) δ=7.8 (s, 2H), 7.02 (s, 1H), 4.26 (q, J=7.2 Hz, 2H), 2.62 (s, 3H), 1.3 (t, J=7.2 Hz, 3H).

Ethyl 2-methyl-5-sulfamoylfuran-3-carboxylate (10 g, 0.043 M) in anhydrous THF (400 mL) at −10° C. was treated with methyl magnesium chloride solution (3.0 M in THF, 64.3 mL) drop-wise over 5 minutes with vigorous stirring. The solution was then stirred at ambient temperature for 6 hours then cooled to −5° C. and treated drop-wise with a solution of ammonium chloride (51.8 g in 265 mL water). The aqueous solution was extracted using EtOAc (2×250 mL), the combined organics washed with brine (250 mL), dried (Na$_2$SO$_4$) and concentrated in vacuo to an orange oil (10 g). The crude product was purified by column chromatography on silica gel using 40% EtOAc-hexane eluent to give the titled compound as a white solid (6.1 g, 42%). $^1$H NMR (400 MHz, DMSO-d$_6$) δ=7.54 (br.s., 2H), 6.78 (s, 1H), 4.95 (s, 1H), 2.42 (s, 3H), 1.4 (s, 6H).

d$_6$-4-(2-hydroxypropan-2-yl)-5-methylfuran-2-sulfonamide

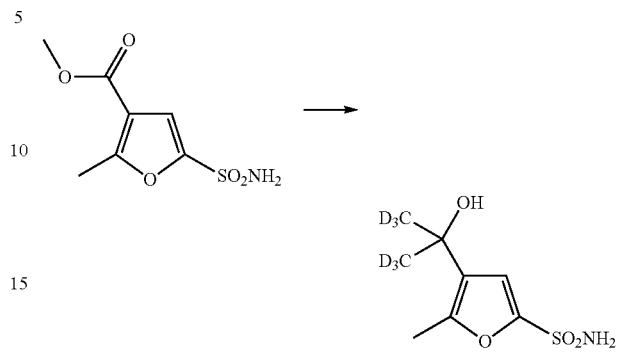

Methyl 2-methyl-5-sulfamoylfuran-3-carboxylate can be prepared by modification of procedures used to synthesise ethyl 2-methyl-5-sulfamoylfuran-3-carboxylate but using methyl 2-methylfuran-3-carboxylate as starting material in place of ethyl 2-methylfuran-3-carboxylate. Methyl 2-methyl-5-sulfamoylfuran-3-carboxylate was obtained as a white solid (3 g, 29%) 1H NMR (400 MHz, DMSO-d$_6$) δ=7.89 (s, 2H), 7.03 (s, 1H), 3.79 (s, 3H), 2.61 (s, 3H).

Methyl 2-methyl-5-sulfamoylfuran-3-carboxylate (0.7 g, 3.2 mmol) in anhydrous THF (20 mL) at −10° C. was treated with d$_3$-methyl magnesium iodide solution (1.0 M in Et$_2$O, 26 mL) drop-wise over 10 minutes with vigorous stirring. The solution was then stirred at ambient temperature for 12 h then cooled to 0° C. and treated drop-wise with a solution of sat. ammonium chloride. The aqueous solution was extracted using EtOAc (2×25 mL), the combined organics washed with brine (25 mL), dried (Na$_2$SO$_4$) and concentrated in vacuo. The crude product was purified by column chromatography on silica gel using a gradient of 40-70% EtOAc-hexane eluent to give the titled compound as a white solid (0.37 g, 51%). $^1$H NMR (400 MHz, DMSO-d$_6$) δ=7.57 (s, 2H), 6.79 (s, 1H), 4.99 (s, 1H), 2.4 (s, 3H). $^{13}$C NMR (100 MHz, CD$_3$OD) δ=150.3, 147.3, 128.4, 113.4, 67.3, 28.5 (multiplet), 12.2.

1-benzyl-1H-1,2,4-triazole-3-sulfonamide

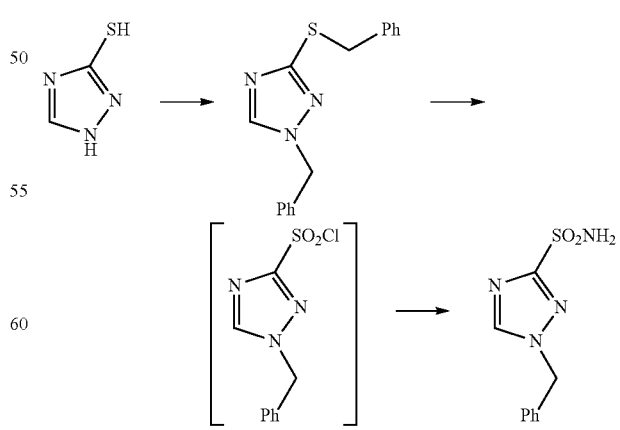

A solution of 1H-1,2,4-triazole-3-thiol (1 g, 9.90 mmol) in DMF (20 mL) was treated with K$_2$CO$_3$ (4.8 g, 34.7 mmol), cooled to 0° C. then benzyl bromide (4.2 g, 24.8 mmol) was added drop-wise over 5 min. The resulting reaction mixture was warmed to ambient temperature and stirred for 12 h. The reaction mixture was diluted with water (25 mL) and extracted with ethyl acetate (2×25 mL). The combined organics were washed with water (20 mL), brine (20 mL), dried (Na$_2$SO$_4$) and concentrated in vacuo. The crude product was purified by column chromatography on silica gel using 20% EtOAc-hexanes eluent to give 1-benzyl-3-(benzylthio)-1H-1,2,4-triazole as a white solid (1.5 g 54%). $^1$H NMR (400 MHz, DMSO-d$_6$): δ=8.67 (s, 1H), 7.39-7.32 (m, 5H), 7.27-7.21 (m, 5H), 5.36 (s, 2H), 4.29 (s, 2H).

To a solution of 1-benzyl-3-(benzylthio)-1H-1,2,4-triazole, 2 (0.5 g, 1.77 mmol) in acetonitrile (5 mL) at 0° C. was added AcOH (3 mL) and H$_2$O (2 mL) then and Cl$_2$ gas was bubbled through the solution for 45 min. Stirring was continued at 0° C. for 30 min then at 20° C. for 1.5 h. The reaction mixture was diluted with water (20 mL) and extracted with EtOAc (2×20 mL). The combined organics were washed with water (20 mL), brine (20 mL), dried (Na$_2$SO$_4$) and concentrated in vacuo to give a colorless liquid. The residue was diluted with THF and cooled to −78° C. Ammonia gas was bubbled through the solution for 20 min and stirring continued for a further 30 min before warming to ambient temperature and stirring for 1 h. The reaction mixture was diluted with water (25 mL) and extracted with ethyl acetate (2×25 mL). The combined organics were washed with water (20 mL), brine (20 mL), dried (Na$_2$SO$_4$) and concentrated in vacuo. The residue was triturated with diethyl ether to give 1-benzyl-1H-1,2,4-triazole-3-sulfonamide as an off-white solid (0.25 g, 60%). $^1$H NMR (400 MHz, DMSO-d$_6$): δ=8.88 (s, 1H), 7.77 (s, 2H), 7.39-7.33 (m, 5H), 5.45 (s, 2H).

1-isopropyl-1H-1,2,3-triazole-4-sulfonamide

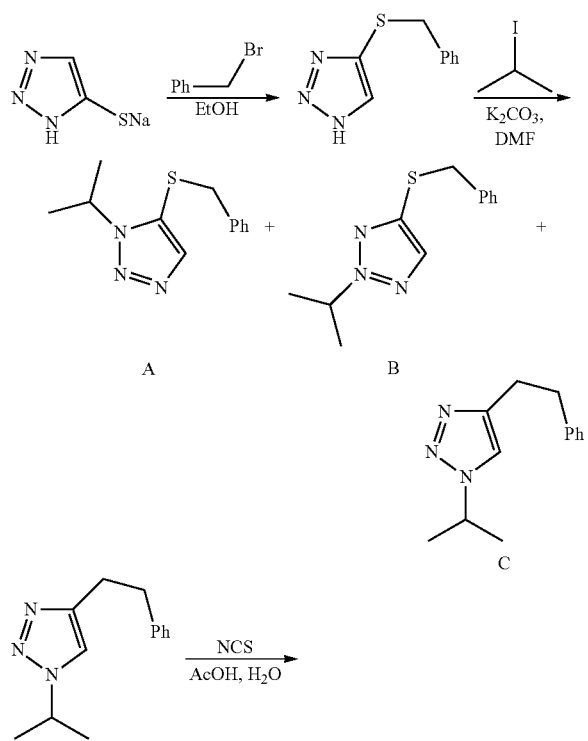

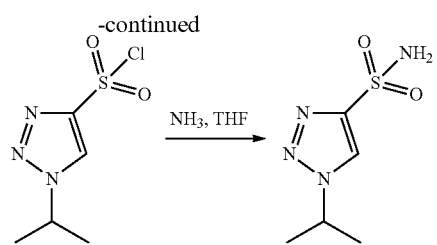

(5 mL) and cooled to 0° C. Benzyl bromide (0.69 g, 4.06 mmol) was added drop wise over a period of 5 min. The resulting reaction mixture was warmed to RT and stirred for 1 h. Upon completion, the reaction mixture was concentrated in vacuo and residue obtained was diluted with saturated NaHCO$_3$ solution and extracted with EtOAc (2×20 mL). The combined organic extract was washed with water, brine, dried (Na$_2$SO$_4$) and concentrated in vacuo. The residue obtained was stirred with n-pentane (30 mL), filtered and dried in vacuo to give 4-(benzylthio)-1H-1,2,3-triazole as a white solid (0.7 g, 90%) which was used without further purification. $^1$H NMR (400 MHz, CDCl$_3$): δ=7.40-7.38 (m, 1H), 7.35-7.21 (m, 5H), 4.12 (s, 2H). LCMS (m/z): 192.0 [M+H]$^+$ A solution of 4-(benzylthio)-1H-1,2,3-triazole (5 g, 26.1 mmol) in DMF (50 mL) was cooled to 0° C. and treated with K$_2$CO$_3$ (9.03 g, 65.4 mmol). The reaction mixture was stirred for 5 minutes at same temperature. Isopropyl iodide (8.89 g, 52.3 mmol) was added drop wise to the above mixture over 5 min. The resulting reaction mixture was warmed to RT and stirred for 2 h. Upon completion, the reaction mixture was diluted with water (30 mL) and extracted with ethyl acetate (50 mL). The organic extract was washed with water, brine and dried over anhydrous Na$_2$SO$_4$. The crude product was purified by column chromatography on silica using, 8% EtOAc-hexane eluent to give 5-(benzylthio)-1-isopropyl-1H-1,2,3-triazole A (0.9 g), 4-(benzylthio)-2-isopropyl-2H-1,2,3-triazole B (1 g) and the desired product 4-(benzylthio)-1-isopropyl-1H-1,2,3-triazole C (1.4 g, 23%). $^1$H NMR (400 MHz, DMSO-d$_6$): δ=7.29-7.18 (m, 5H), 4.78-4.71 (m, 1H), 4.09 (s, 2H), 1.4 (d, J=6.8 Hz, 6H). LCMS (m/z): 234.30 [M+H]$^+$.

A solution of 4-(benzylthio)-1-isopropyl-1H-1,2,3-triazole (75 mg, 0.32 mmol) in acetic acid (2.25 mL) and H$_2$O (1.12 mL) was cooled to 0° C. N-chlorosuccinimide (170 mg, 1.28 mmol) was added at 0° C. The resulting reaction mixture was warmed to RT and stirred for 1 h. Upon completion, the reaction mixture was diluted with water and extracted with ethyl acetate (2×10 mL). The combined organic extracts were washed with water, brine, dried (Na$_2$SO$_4$) and concentrated in vacuo. The crude product was purified by column chromatography on silica using, 8% EtOAc-hexanes eluant to give 1-isopropyl-1H-1,2,3-triazole-4-sulfonyl chloride (0.1 g, 100%) as a pale brown liquid used without further purification. LCMS (m/z): 210.10 [M+H]+.

A solution of 1-isopropyl-1H-1,2,3-triazole-4-sulfonyl chloride (100 mg) in THF (5 mL) was cooled to −40° C. Ammonia gas was purged through the aforementioned solution for 15 min. The reaction mixture was warmed to RT and stirred for 2 h. Upon completion, the reaction mixture was concentrated in vacuo and residue obtained was diluted with ethyl acetate (25 mL) and water (10 mL). The organic extract was washed with water, brine, dried (Na$_2$SO$_4$) and concentrated in vacuo to give 1-isopropyl-1H-1,2,3-triazole-4-sulfonamide (0.07 g, 78%) as brown solid. $^1$H NMR (400

MHz, DMSO-$d_6$): δ=8.71 (s, 1H), 7.66 (s, 2H), 4.91-4.87 (m, 1H), 1.5 (d, J=6.8 Hz, 6H). LCMS (m/z): 191.30 [M+H]$^+$.

1-methyl-1H-pyrazole-3-sulfonamide

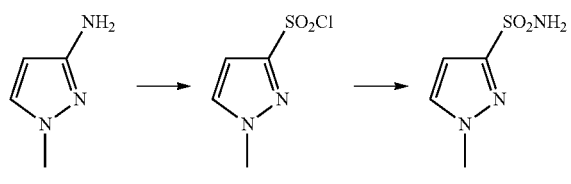

1-Methyl-1H-pyrazol-3-amine hydrochloride was reacted to 1-methyl-1H-pyrazole-3-sulfonyl chloride, a pale-yellow liquid, using general method D (0.7 g, 38%). $^1$H NMR (300 MHz, CDCl$_3$): δ=7.51-7.50 (d, J=2.1 Hz, 1H), 6.89-6.88 (d, J=2.4 Hz, 1H), 4.06 (s, 3H). LCMS (m/z): 160.9 (M−1)$^−$. The sulfonyl chloride was converted using general method E1 to give the titled compound as an off-white solid (0.4 g, 69%). $^1$H NMR (400 MHz, DMSO-$d_6$): δ=7.80 (d, J=2.1 Hz, 1H), 7.36 (s, 2H), 6.53 (d, J=2.1 Hz, 1H), 3.88 (s, 3H). LCMS (m/z): 162.05 (M+1)$^+$.

1-(trifluoromethyl)-1H-pyrazole-3-sulfonamide

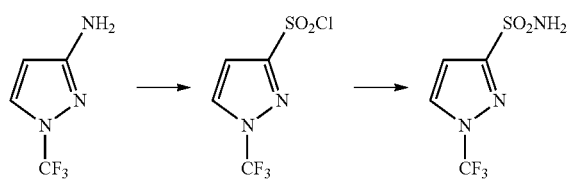 [SMILES: Nc1ccn(C(F)(F)F)n1 ; O=S(=O)(Cl)c1ccn(C(F)(F)F)n1 ; NS(=O)(=O)c1ccn(C(F)(F)F)n1]

1-(trifluoromethyl)-1H-pyrazol-3-amine was reacted to 1-(trifluoromethyl)-1H-pyrazole-3-sulfonyl chloride, a brown liquid, using general method D (0.4 g, 43%). $^1$H NMR (300 MHz, CDCl$_3$) δ=8.02 (d, J=2.8 Hz, 1H), 7.06 (d, J=2.8 Hz, 1H). $^{19}$F NMR (282 MHz, CDCl$_3$) δ=−60.46.

The sulfonyl chloride was converted using general method E1 to give the titled compound (0.22 g, 46%). $^1$H NMR (300 MHz, CDCl$_3$) δ=7.92 (dd, J=2.8, 0.3 Hz, 1H), 6.91 (dd, J=2.8, 0.7 Hz, 1H), 5.28 (s, 2H). $^{19}$F NMR (282 MHz, CDCl$_3$) δ=−60.41.

1-isopropyl-1H-pyrazole-3-sulfonamide

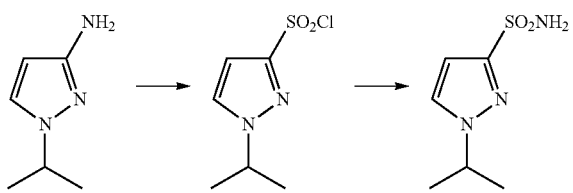

1-Isopropyl-1H-pyrazol-3-amine was reacted to 1-isopropyl-1H-pyrazole-3-sulfonyl chloride, a brown liquid, using general method D (0.5 g, 43%). $^1$H NMR (400 MHz, CDCl$_3$): δ=7.55 (s, 1H), 6.88 (s, 1H), 4.66-4.63 (m, 1H), 3.6 (br.s., 2H), 1.59 (d, J=6.8 Hz, 6H). LCMS (m/z): 209.0 (M+1)$^+$. The sulfonyl chloride was converted using general method E1 to give the titled compound as yellow solid (0.45 g, 82%). $^1$H NMR (300 MHz, DMSO-$d_6$): δ=7.9 (d, J=2.4 Hz, 1H), 7.36 (s, 2H), 6.55 (d, J=2.1 Hz, 1H), 4.57-4.53 (m, 1H), 1.42 (d, J=6.9 Hz, 6H). LCMS (m/z): 190.0 (M+1)$^+$.

1-isopropyl-1H-pyrazole-4-sulfonamide

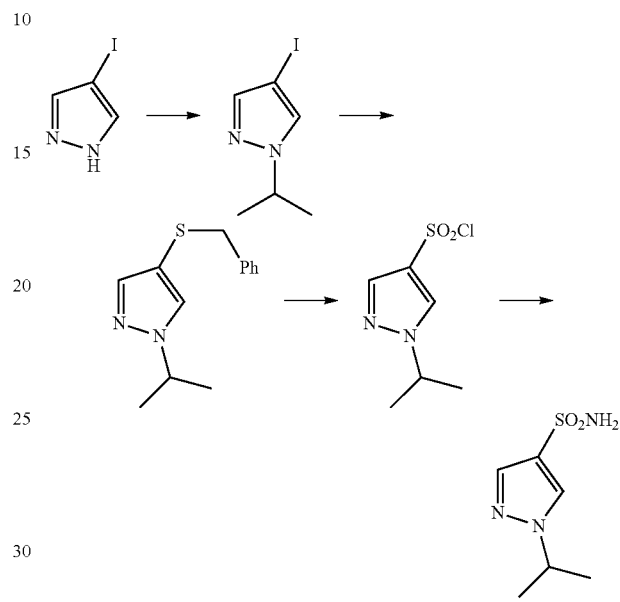

A solution of 4-iodo-1H-pyrazole (1 g, 5.15 mmol) in DMF (20 mL) was treated with K$_2$CO$_3$ (1.42 g, 10.30 mmol) and isopropyl iodide (1.05 g, 6.19 mmol) at ambient temperature under nitrogen atmosphere. The resulting reaction mixture was heated to 90° C. and stirred for 12 h. The mixture was cooled, diluted with water (50 mL) and extracted with diethyl ether (2×50 mL). The combined organics were washed with water (2×50 mL), brine (50 mL), dried (Na$_2$SO$_4$) and concentrated in vacuo. The crude product was purified by column chromatography on silica gel using 10% EtOAc-hexanes eluent to give 4-iodo-1-isopropyl-1H-pyrazole as a colorless liquid (1.1 g, 92%). $^1$H NMR (400 MHz, CDCl$_3$): δ=7.50-7.46 (m, 2H), 4.53-4.47 (m, 1H), 1.50 (d, J=6.8 Hz, 6H). LCMS (m/z): 237.2 (M+1)$^+$.

A solution of 4-iodo-1-isopropyl-1H-pyrazole (1 g, 4.24 mmol) in dioxane (20 mL) was treated sequentially with benzyl mercaptan (0.8 g, 6.35 mmol) and DIPEA (1.1 g, 8.47 mmol) under nitrogen atmosphere. The solution was degassed by purging with argon gas for 15 min. Pd$_2$(dba)$_3$ (40 mg, 0.0423 mmol) and Xantphos (50 mg, 0.0847 mmol) were added under argon atmosphere then the resulting mixture was sealed in the reaction vessel and heated at 75° C. for 6 h. The reaction mixture was cooled, concentrated in vacuo, diluted with water (20 mL) and extracted with EtOAc (2×20 mL). The combined organics were washed with water (2×50 mL), brine (50 mL), dried (Na$_2$SO$_4$) and concentrated in vacuo. The crude product was purified by column chromatography on silica gel using 10% EtOAc-hexanes eluent to give 4-(benzylthio)-1-isopropyl-1H-pyrazole as a yellow liquid (650 mg, 66%). H NMR (400 MHz, CDCl$_3$): δ=7.36 (s, 1H), 7.26-7.22 (m, 4H), 7.11-7.09 (m, 2H), 4.41-4.36 (m, 1H), 3.76 (s, 2H), 1.42 (d, J=6.8 Hz, 6H). LCMS (m/z): 233.3 (M+1)

To a solution of 4-(benzylthio)-1-isopropyl-1H-pyrazole, 3 (0.35 g, 1.508 mmol) in acetonitrile (10 mL) at 0° C. was added AcOH (0.7 mL) and H₂O (0.35 mL) then DCDMH (0.6 g, 3.017 mmol) was added portion-wise over 5 min. The solution was stirred for 30 min then warmed to ambient temperature and stirred for a further 2 h. The reaction mixture was diluted with water (20 mL) and extracted with EtOAc (2×20 mL). The combined organics were washed with water (20 mL), brine (20 mL), dried (Na₂SO₄) and concentrated in vacuo to give 1-isopropyl-1H-pyrazole-4-sulfonyl chloride as a colorless liquid. The sulfonyl chloride was diluted with THF and cooled to −78° C. then NH₃ gas was bubbled through the solution for 15 minutes. The reaction mixture was stirred at −78° C. for 1 h and at ambient temperature for 2 h. The reaction mixture was diluted with water and compound extracted with ethyl acetate (2×25 mL). The combined organic extracts were washed with water (20 mL), brine (20 mL), dried (Na₂SO₄) and concentrated in vacuo. The residue obtained was triturated with diethyl ether and dried under reduced pressure give 1-isopropyl-1H-pyrazole-4-sulfonamide as a light brown solid (0.2 g, 71%). ¹H NMR (400 MHz, DMSO-d₆): δ=8.21 (s, 1H), 7.71 (s, 1H), 7.22 (s, 2H), 4.59-4.53 (m, 1H), 1.4 (d, J=6.8 Hz, 6H). LCMS (m/z): 190.2 (M+1)⁺.

1-cyclopropyl-1H-pyrazole-3-sulfonamide

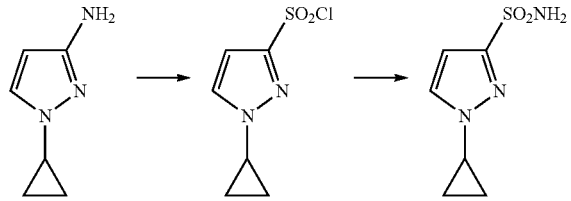 [SMILES: Nc1ccn(C2CC2)n1 ; O=S(=O)(Cl)c1ccn(C2CC2)n1 ; NS(=O)(=O)c1ccn(C2CC2)n1]

1-Cyclopropyl-1H-pyrazole-3-amine was reacted to 1-cyclopropyl-1H-pyrazole-3-sulfonyl chloride using general method D then converted using general method E1 to give the titled compound as a light brown solid (0.2 g, 33%). ¹H NMR (400 MHz, CDCl₃) δ=7.51 (d, J=2.4 Hz, 1H), 6.69 (d, J=2.4 Hz, 1H), 5.04 (s, 2H), 3.67 (m, 1H), 1.28-1.05 (m, 4H).

1-(tert-butyl)-1H-pyrazole-3-sulfonamide

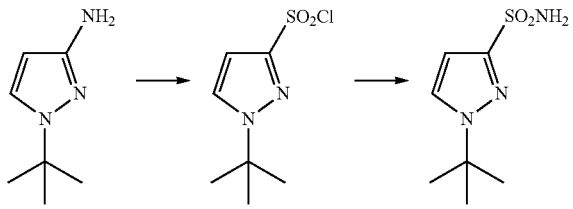

1-(tert-butyl)-1H-pyrazol-3-amine was reacted to 1-(tert-butyl)-1H-pyrazole-3-sulfonyl chloride using general method D then converted using general method E1 to give the titled compound as a light brown solid (150 mg, 26%). ¹H NMR (400 MHz, DMSO-d₆): δ=7.56 (d, J=3.6 Hz, 1H), 6.7 (d, J=3.2 Hz, 1H), 4.75 (br.s., 1H), 1.60 (s, 9H). LCMS (m/z): 204.15 (M+1)⁺.

1-cyclohexyl-1H-pyrazole-3-sulfonamide


1-Cyclohexyl-1H-pyrazole-3-amine was reacted to 1-cyclohexyl-1H-pyrazole-3-sulfonyl chloride using general method D then converted using general method E1 to give the titled compound as a white solid (0.35 mg, 50%). ¹H NMR (300 MHz, DMSO-d₆) δ=7.89 (d, J=2.3 Hz, 1H), 7.36 (s, 2H), 6.55 (d, J=2.3 Hz, 1H), 4.28-4.08 (m, 1H), 2.0-1.1 (m, 6H).

1-phenyl-1H-pyrazole-3-sulfonamide


1-phenyl-1H-pyrazol-3-amine was reacted to 1-phenyl-1H-pyrazole-3-sulfonyl chloride, a yellow liquid, using general method D (0.5 g, 47%). ¹H NMR (400 MHz, CDCl₃): δ=8.04 (d, J=2.4 Hz, 1H), 7.73 (d, J=9.2 Hz, 2H), 7.58 (t, J=7.6 Hz, 2H), 7.47 (t, J=7.2 Hz, 1H), 7.08 (d, J=2.8 Hz, 1H). The sulfonyl chloride was converted using general method E1 to give the titled compound as a yellow solid (0.4 g, 87%). ¹H NMR (400 MHz, DMSO-d₆): δ=8.62 (d, J=2.7 Hz, 1H), 7.86 (d, J=8.7 Hz, 2H), 7.61 (br.s., 2H), 7.57 (t, J=7.8 Hz, 2H), 7.41 (t, J=7.2 Hz, 1H), 6.85 (d, J=2.4 Hz, 1H). LCMS (m/z): 224.1 (M+1)⁺.

1-benzyl-1H-pyrazole-3-sulfonyl chloride

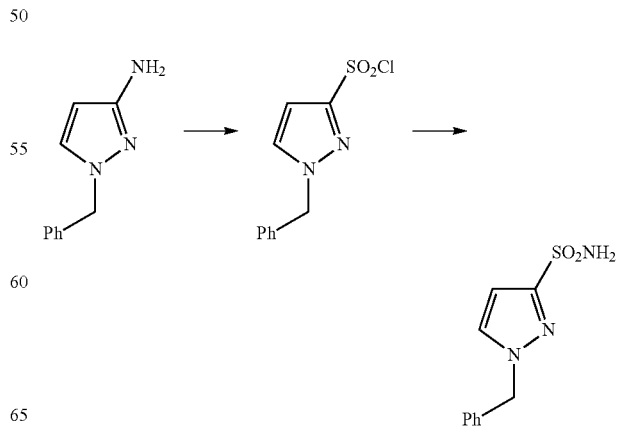

1-benzyl-1H-pyrazol-3-amine was reacted to 1-benzyl-1H-pyrazole-3-sulfonyl chloride, a light brown liquid, using general method D (0.2 g, 45%). $^1$H NMR (300 MHz, CDCl$_3$): δ7.42-7.38 (m, 3H), 7.33-7.28 (m, 3H), 6.8 (d, J=2.4 Hz, 1H), 5.42 (s, 2H). The sulfonyl chloride was converted using general method E1 to give the titled compound as a light brown liquid (0.15 g, 81%). $^1$H NMR (400 MHz, CDCl$_3$): δ=7.42-7.36 (m, 4H), 7.24 (d, J=1.6 Hz, 2H), 6.7 (d, J=2.4 Hz, 1H), 5.35 (s, 2H), 5.10 (s, 2H). LCMS (m/z): 238.10 (M+1)$^+$ 1-(1-phenylethyl)-1H-pyrazole-3-sulfonamide

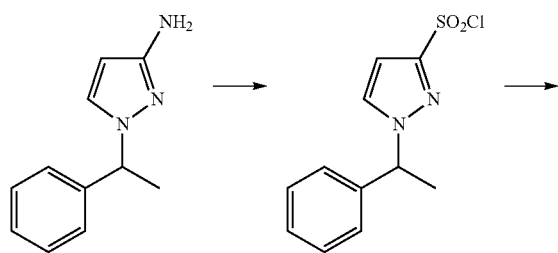

1-(1-phenylethyl)-1H-pyrazol-3-amine was reacted to 1-(1-phenylethyl)-1H-pyrazole-3-sulfonyl chloride using general method D then converted using general method E1 to give the titled compound as a white solid (0.25 mg, 68%). $^1$H NMR (300 MHz, CDCl3) δ=7.43-7.18 (m, 6H), 6.72 (d, J=2.4 Hz, 1H), 5.57 (q, J=7.1 Hz, 1H), 5.02 (s, 2H), 1.92 (d, J=7.1 Hz, 3H).

1-(2-(piperidin-1-yl)ethyl)-1H-pyrazole-3-sulfonamide

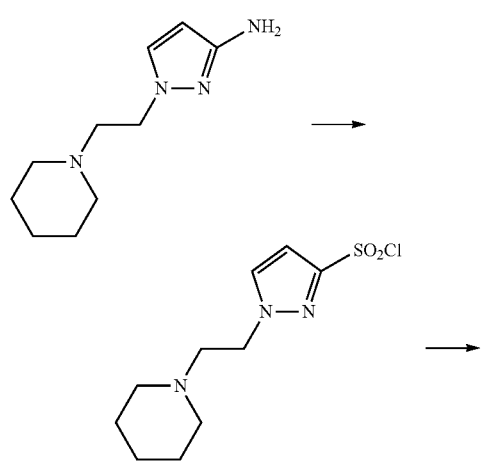

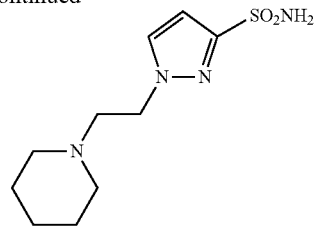

1-(2-(piperidin-1-yl)ethyl)-1H-pyrazol-3-amine was reacted to 1-(2-(piperidin-1-yl)ethyl)-1H-pyrazole-3-sulfonyl chloride, a pale-brown liquid, using general method D then converted using general method E1 to give the titled compound as an off-white solid (0.3 g, 46%). $^1$H NMR (300 MHz, DMSO-d$_6$): δ=7.84 (d, J=2.1 Hz, 1H), 7.36 (s, 2H), 6.54 (s, J=2.4 Hz, 1H), 4.26 (t, J=6.9 Hz, 2H), 2.66 (t, J=6.6 Hz, 2H), 2.36 (s, 4H), 1.46-1.34 (m, 6H). LCMS (m/z): 259.10 (M+1)$^+$.

1,5-dimethyl-1H-pyrazole-3-sulfonamide

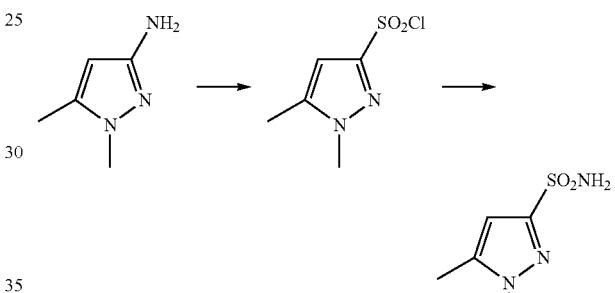

1,5-dimethyl-1H-pyrazol-3-amine was reacted to 1,5-dimethyl-1H-pyrazole-3-sulfonyl chloride, a yellow liquid, using general method D (0.45 g, 26%). $^1$H NMR (300 MHz, CDCl$_3$): δ=5.92 (s, 1H), 3.71 (s, 3H), 2.23 (s, 3H). LCMS (m/z):217 (M+Na)$^+$. The sulfonyl chloride was converted using general method E1 to give the titled compound as an off-white solid (0.25 g, 55%). $^1$H NMR (400 MHz, DMSO-d$_6$): δ=7.30 (s, 2H), 6.36 (s, 1H), 3.76 (s, 3H), 2.27 (s, 3H). LCMS (m/z): 175.9 (M+1)$^+$.

1-methyl-5-(trifluoromethyl)-1H-pyrazole-3-sulfonamide

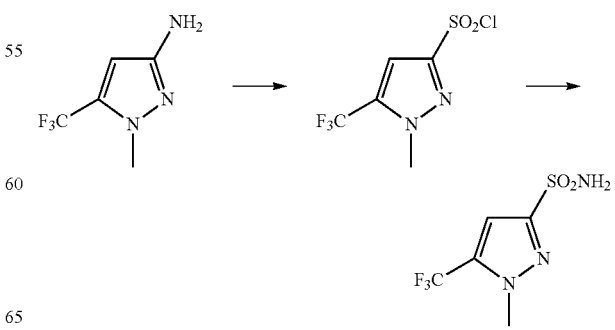

1-methyl-5-(trifluoromethyl)-1H-pyrazol-3-amine was reacted to 1-methyl-5-(trifluoromethyl)-1H-pyrazole-3-sulfonyl chloride, a pale-brown liquid, using general method D (1.1 g, 37%). ¹H NMR (300 MHz, CDCl₃): δ=7.21 (s, 1H), 4.16 (s, 3H). The sulfonyl chloride was converted using general method E1 to give the titled compound as a yellow solid (0.45 mg, 82%). ¹H NMR (300 MHz, CDCl₃): δ=7.06 (s, 1H), 5.02 (br.s., 2H), 4.03 (s, 3H).

1-isopropyl-5-(trifluoromethyl)-1H-pyrazole-3-sulfonamide

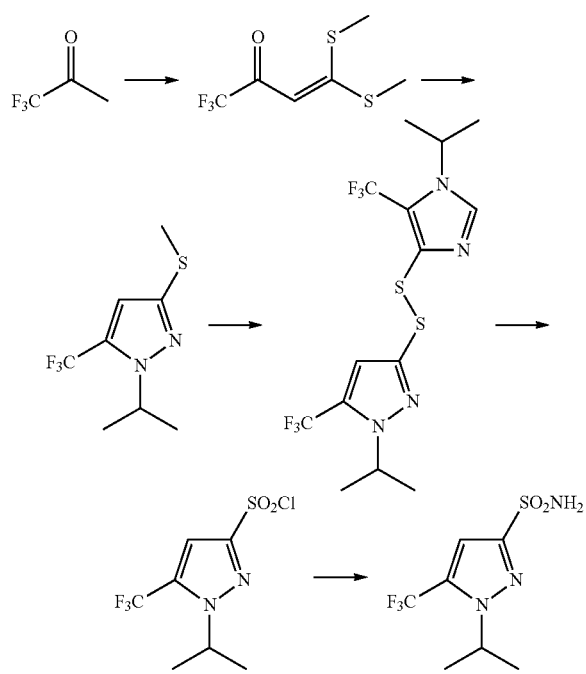

A mixture of NaH (2.14 g, 89.3 mmol) in DMF (20 mL) was cooled to −10° C. A solution of 1,1,1-trifluoropropan-2-one (5 g, 44.6 mmol) in DMF (80 mL) was added very carefully to the above mixture and stirred at −10° C. for 5 min. CS₂ (10.2 g, 133.9 mmol) was added drop-wise to the above mixture over 30 min then the reaction mixture was warmed to ambient temperature and stirred for 1 h. The reaction mixture was cooled to 0° C. and treated with CH₃I (7.5 mL) over 10 min. The resulting reaction mixture was warmed to ambient temperature and stirred for 12 h. The reaction mixture was diluted with cold water (50 mL) and extracted with diethyl ether (2×100 mL). The combined organic extracts were washed with water (50 mL), brine (50 mL), dried (Na₂SO₄) and concentrated in vacuo. The crude product was purified by column chromatography on silica gel using 5% EtOAc-hexanes eluent to give 1,1,1-trifluoro-4,4-bis(methylthio)but-3-en-2-one as a light brown solid (3.5 g, 36%). ¹H NMR (300 MHz, CDCl₃): δ=6.24 (s, 1H), 2.57 (m, 6H). LCMS (m/z): 217.20 (M+1)⁺.

A solution of 1,1,1-trifluoro-4,4-bis(methylthio)but-3-en-2-one (2.5 g, 11.6 mmol) in EtOH (25 mL) was treated with isopropyl hydrazine hydrochloride (2 g, 13.9 mmol) at 0° C., Et₃N (2.4 g, 40.98 mmol) was added and the mixture heated at 80° C. for 12 h. The reaction mixture was concentrated in vacuo, diluted with sat. aq. NaHCO₃ solution and extracted with EtOAc (2×250 mL). The combined organics were washed with water (200 mL), brine (200 mL), dried (Na₂SO₄) and concentrated in vacuo. The crude product was purified by column chromatography on silica gel using 100% EtOAc eluent to give 1-isopropyl-3-(methylthio)-5-(trifluoromethyl)-1H-pyrazole as a light brown liquid (1.5 g, 58%). ¹H NMR (400 MHz, CDCl₃): δ=6.47 (s, 1H), 4.58-4.53 (m, 1H), 2.49 (s, 3H), 1.50 (d, J=6.8 Hz, 6H). LCMS (m/z): 225.20 (M+1)⁺.

A solution of 1-isopropyl-3-(methylthio)-5-(trifluoromethyl)-1H-pyrazole (0.5 g, 2.23 mmol) in chloroform (10 mL) at 0° C. was treated with mCPBA (0.38 g, 2.23 mmol) and stirred at 10° C. for 1 h. The reaction mixture was diluted with saturated NaHCO₃ solution (10 mL) and extracted with CHCl₃ (2×30 mL). The combined organics were washed with water (30 mL), brine (30 mL), dried (Na₂SO₄) and concentrated in vacuo The residue obtained was dissolved in CHCl₃ (10 mL) and treated with trifluoroacetic anhydride (1.4 g, 6.7 mmol) the reaction mixture was heated at 50° C. for 3 h, cooled to ambient temperature and concentrated in vacuo. The residue obtained was diluted with MeOH (5 mL)-THF (5 mL)-H₂O (5 mL), cooled to 0° C., treated with Na₂CO₃ (0.7 g, 6.7 mmol) and stirred for 3 h. The solution was diluted with water (30 mL) and extracted with CHCl₃ (2×50 mL). The combined organics were washed with water (50 mL), brine (50 mL), dried (Na₂SO₄) and concentrated in vacuo. The crude residue (0.2 g) containing 1-isopropyl-3-((1-isopropyl-5-(trifluoromethyl)-1H-imidazol-4-yl)disulfanyl)-5-(trifluoromethyl)-1H-pyrazole was used in the next in step without further purification. ¹H NMR (400 MHz, CDCl₃): δ=6.85 (s, 2H), 6.70 (s, 1H), 6.60 (s, 1H), 4.6 (m, 2H), 1.53 (m, 6H). LCMS (m/z): 416.75 (M−1)⁻.

A solution of crude 1-isopropyl-3-((1-isopropyl-5-(trifluoromethyl)-1H-imidazol-4-yl)disulfanyl)-5-(trifluoromethyl)-1H-pyrazole (0.2 g crude, 0.478 mmol) in acetonitrile (10 mL) was cooled to 0° C. and treated with AcOH (1 mL) and H₂O (1.5 mL). DCDMH (0.19 g, 0.956 mmol) was added portion-wise over 5 minutes and stirred for 2 h. The mixture was diluted with water (20 mL) and extracted with DCM (2×20 mL). The combined organics were washed with water (50 mL), brine (50 mL), dried (Na₂SO₄) and concentrated in vacuo to give 1-isopropyl-5-(trifluoromethyl)-1H-pyrazole-3-sulfonyl chloride as a colorless liquid. The (1-isopropyl-5-(trifluoromethyl)-1H-pyrazole-3-sulfonyl chloride) was diluted with THF, cooled to −78° C. and NH₃ gas was bubbled through the solution for 10 min then stirred for 1 h before warming to ambient temperature and stirring for a further 1 h. The reaction mixture was diluted with water and extracted with ethyl acetate (2×25 mL). The combined organics were washed with water (50 mL), brine (50 mL), dried (Na₂SO₄) and concentrated in vacuo. The residue obtained was triturated with diethyl ether and n-pentane to give 1-isopropyl-5-(trifluoromethyl)-1H-pyrazole-3-sulfonamide as a white solid (75 mg, 61%). ¹H NMR (400 MHz, CDCl₃): δ=7.01 (s, 1H), 5.06 (s, 2H), 4.73-4.70 (m, 1H), 1.5 (d, J=6.8 Hz, 6H). LCMS (m/z): 256.0 (M−1)⁻.

5-isopropyl-1-methyl-1H-pyrazole-3-sulfonamide

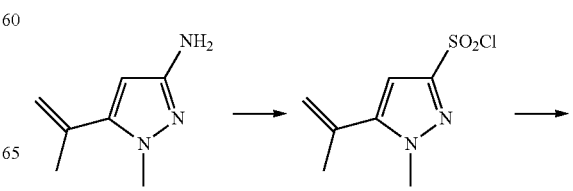

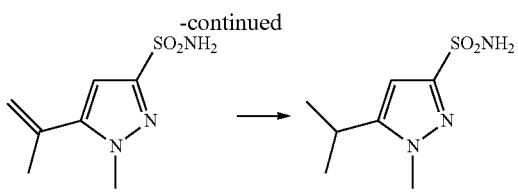

A solution of 1-methyl-5-(prop-1-en-2-yl)-1H-pyrazol-3-amine (0.25 g, 1.824 mmol) in acetonitrile (10 mL) at 0° C. was treated with c.HCl (1.2 mL) in $H_2O$ (0.5 mL) followed by aqueous solution of $NaNO_2$ (0.15 g, 2.19 mmol) dissolved in $H_2O$ (2 mL). The resulting solution was stirred at 0° C. for 45 min. AcOH (0.25 mL), $CuCl_2.2H_2O$ (0.15 g, 0.91 mmol) and CuCl (10 mg, 0.091 mmol) were sequentially added to the above mixture and purged with $SO_2$ gas for 20 min at 0° C. The resulting reaction mixture was stirred at 0° C.-10° C. for 60 min. Upon completion, the reaction mixture was diluted with water (20 mL) and extracted with EtOAc (2×20 mL). The combined organics were washed with water (20 mL), brine (20 mL), dried ($Na_2SO_4$) and concentrated in vacuo. The crude product was purified by column chromatography on silica gel using 20% EtOAc-hexanes eluent to give 1-methyl-5-(prop-1-en-2-yl)-1H-pyrazole-3-sulfonyl chloride as a colourless liquid (0.15 g, 38%). $^1$H NMR (300 MHz, $CDCl_3$): δ=6.77 (s, 1H), 5.51 (s, 1H), 5.28 (s, 1H), 4.02 (s, 3H), 2.11 (s, 3H).

A solution of 1-methyl-5-(prop-1-en-2-yl)-1H-pyrazole-3-sulfonyl chloride (0.075 g, 0.34 mmol) in THF (7 mL) was cooled to −78° C. and ammonia gas was bubbled through the solution for 15 min, stirring was continued for a further 30 min then allowed to warm to ambient temperature and stirred for 2 h or until completion. The reaction mixture was diluted with ethyl acetate (25 mL) and filtered through a pad of celite. The filtrate was dried ($Na_2SO_4$) and concentrated in vacuo to give 1-methyl-5-(prop-1-en-2-yl)-1H-pyrazole-3-sulfonamide as an off-white solid used without purification 0.04 g (crude).

A solution of crude 1-methyl-5-(prop-1-en-2-yl)-1H-pyrazole-3-sulfonamide (0.12 g, 0.6 mmol) in MeOH (10 mL)-EtOAc (4 mL) was treated with 10% palladium on carbon (30 mg) under nitrogen atmosphere. The reaction flask was evacuated, filled with hydrogen (balloon) and stirred for 4 h. The reaction mixture was diluted with ethyl acetate (25 mL), filtered through a pad of celite, dried ($Na_2SO_4$) and concentrated in vacuo. The solid obtained was further washed with diethyl ether to give 5-isopropyl-1-methyl-1H-pyrazole-3-sulfonamide as an off-white solid (0.11 g, 91%). $^1$H NMR (400 MHz, $CDCl_3$): δ=6.50 (s, 1H), 5.00 (br.s., 2H), 3.87 (s, 3H), 2.97-2.93 (m, 1H), 1.28 (d, J=7.2 Hz, 6H).

5-(2-hydroxypropan-2-yl)-1-methyl-1H-pyrazole-3-sulfonamide

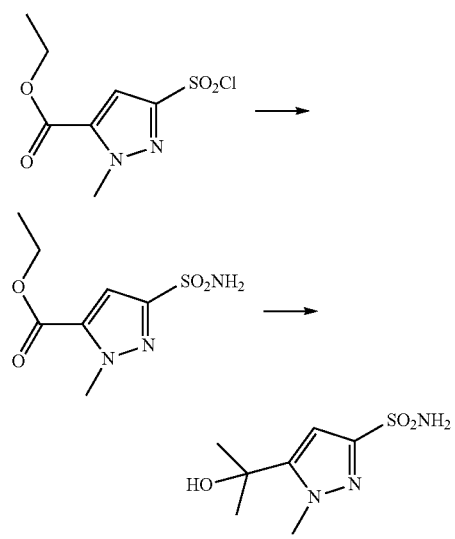

ethyl 3-amino-1-methyl-1H-pyrazole-5-carboxylate was reacted to ethyl 3-(chlorosulfonyl)-1-methyl-1H-pyrazole-5-carboxylate, a light-yellow liquid, using general method D (0.35 g, 47%). $^1$H NMR (300 MHz, Chloroform-d) δ 7.39 (s, 1H), 4.40 (q, J=7.1 Hz, 2H), 4.32 (s, 3H), 1.40 (t, J=7.1 Hz, 3H). The sulfonyl chloride was converted using general method E2 to give ethyl 1-methyl-3-sulfamoyl-1H-pyrazole-5-carboxylate as an off-white solid (0.3 g, 94%). $^1$H NMR (300 MHz, DMSO-$d_6$) δ=7.59 (s, 2H), 7.09 (s, 1H), 4.33 (q, J=7.1 Hz, 2H), 4.14 (s, 3H), 1.31 (t, J=7.1 Hz, 3H).

To a solution of ethyl 1-methyl-3-sulfamoyl-1H-pyrazole-5-carboxylate (0.25 g, 1.07 mmol) in anhydrous THF (10 mL) at 0° C. was added methyl magnesium chloride (3 M in THF, 5 equivalents) drop-wise. The resulting reaction mixture was gradually warmed to ambient temperature and stirred for 6 h or until completion. The solution was cooled to 0° C., quenched with sat. aq. $NH_4Cl$ (2.0 mL) then diluted with cold water (20 mL) and extracted with EtOAc (2×25 mL). The combined organics were washed with brine (50 mL), dried ($Na_2SO_4$) and concentrated in vacuo. The crude product was purified by column chromatography on silica gel using 50% gradient of EtOAc in hexanes eluent to give the titled compound as a white solid. (0.2 g, 87%). $^1$H NMR (400 MHz, DMSO-$d_6$) δ=7.34 (s, 2H), 6.40 (s, 1H), 5.48 (s, 1H), 4.0 (s, 3H), 1.50 (s, 6H).

1-benzyl-5-(2-hydroxypropan-2-yl)-1H-pyrazole-3-sulfonamide

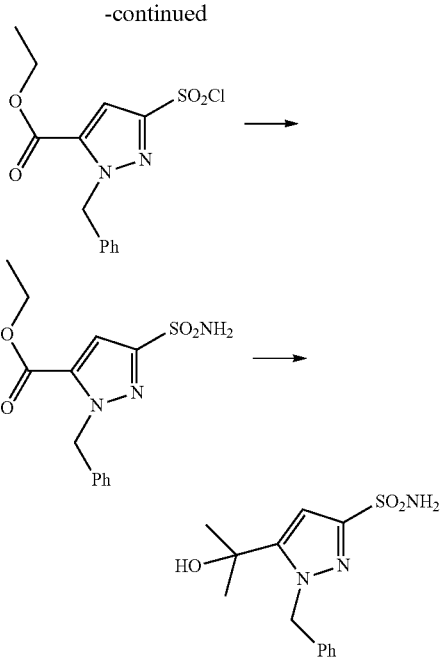

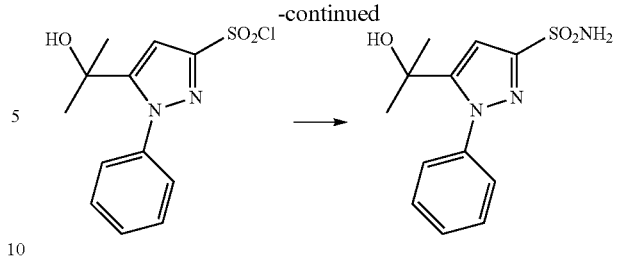

2-(3-amino-1-phenyl-1H-pyrazol-5-yl)propan-2-ol was reacted to 5-(2-hydroxypropan-2-yl)-1-phenyl-1H-pyrazole-3-sulfonyl chloride, a yellow liquid, using method D (0.4 g, 36%). $^1$H NMR (300 MHz, CDCl$_3$): δ=7.55-7.45 (m, 5H), 6.91 (s, 1H), 1.51 (s, 6H). The sulfonyl chloride was converted using general method E2 to give the titled compound as a yellow solid (0.32 g, 87%). $^1$H NMR (300 MHz, DMSO-d$_6$): δ=7.5 (s, 5H), 7.47 (s, 2H), 6.65 (s, 1H), 5.41 (s, 1H), 1.30 (s, 6H).

5-(dimethylamino)naphthalene-1-sulfonamide

Ethyl 3-amino-1-benzyl-1H-pyrazole-5-carboxylate was reacted to ethyl 1-benzyl-3-(chlorosulfonyl)-1H-pyrazole-5-carboxylate, a light-brown liquid, using method D (0.35 g, 47%). $^1$H NMR (400 MHz, CDCl$_3$): δ=7.41 (s, 1H), 7.34-7.26 (m, 5H), 5.87 (s, 2H), 4.37 (q, J=7.2 Hz, 2H), 1.38 (t, J=7.2 Hz, 3H). The sulfonyl chloride was converted using general method E2 to give ethyl 1-benzyl-3-sulfamoyl-1H-pyrazole-5-carboxylate as a white solid (0.7 g, 88%). $^1$H NMR (400 MHz, DMSO-d$_6$): δ=7.66 (s, 2H), 7.39-7.27 (m, 3H), 7.2-7.18 (m, 3H), 5.77 (s, 2H), 4.33 (q, J=7.2 Hz, 2H), 1.29 (t, J=7.2 Hz, 3H). LCMS (m/z): 310.05 (M+1)$^+$.

To a solution of ethyl 1-benzyl-3-sulfamoyl-1H-pyrazole-5-carboxylate (0.5 g, 1.62 mmol) in anhydrous THF (10 mL) at 0° C. was added methyl magnesium chloride (3 M in THF, 2.77 mL, 8.1 mmol) drop-wise. The resulting reaction mixture was gradually warmed to ambient temperature and stirred for 4 h or until completion. The solution was cooled to 0° C., quenched with sat. aq. NH$_4$Cl (2.0 mL) then diluted with cold water (20 mL) and extracted with EtOAc (2×25 mL). The combined organics were washed with brine (50 mL), dried (Na$_2$SO$_4$) and concentrated in vacuo. The crude product was purified by column chromatography on silica gel using 70-100% gradient of EtOAc in hexanes eluent to give the titled compound as a white solid. (0.27 g, 57%). $^1$H NMR (300 MHz, DMSO-d$_6$): δ=7.37 (s, 2H), 7.39-7.27 (m, 3H), 7.2-7.18 (m, 2H), 6.45 (s, 1H), 5.66 (s, 2H), 5.60 (s, 1H), 1.44 (s, 6H). LCMS (m/z): 296.1 (M+1)$^+$.

5-(2-hydroxypropan-2-yl)-1-phenyl-1H-pyrazole-3-sulfonamide

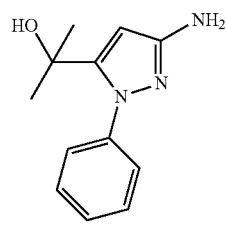

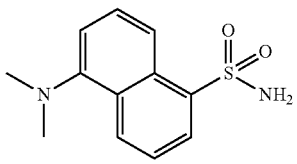 [SMILES: CN(C)c1cccc2c(S(N)(=O)=O)cccc12]

5-(dimethylamino)naphthalene-1-sulfonamide 3-azido-benzenesulfonamide was synthesized according to procedures contained in Satish K. Nair, Daniel Elbaum and David W. Christianson. *J. Biol. Chem.* 1996, 271:1003-100 and Lixuan Mu, Wensheng Shi, Guangwei She, Jack C. Chang, and Shuit-Tong Lee. *Angew. Chem. Int. Ed.* 2009, 48, 3469-3472.

A solution of 5-(dimethylamino)naphthalene-1-sulfonyl chloride (0.12 g, 0.44 mmol) in acetone (5 mL) was added drop-wise to a solution of ammonium bicarbonate (0.17 g, 1.76 mmol) in water (1.0 mL) and the reaction stirred at ambient temperature for 2 h, or until completion. The pH was adjusted using c.HCl to pH 2.0. The organic phase was separated and the aqueous phase was saturated with NaCl and extracted with ethyl acetate. The combined organic phases were washed with brinem dried (MgSO$_4$) and concentrated in vacuo to give the titled compound as a white solid (0.075 g, 67% yield). $^1$H NMR (600 MHz, CD$_3$OD) δ=8.54 (d, J=8.5 Hz, OH), 8.36 (d, J=8.7 Hz, 1H), 8.23 (d, J=7.3 Hz, 1H), 7.58 (ddd, J=17.0, 8.6, 7.4 Hz, 2H), 7.28 (d, J=7.6 Hz, 1H), 2.89 (s, 6H). $^{13}$C NMR (151 MHz, CD3OD) δ=151.6, 138.9, 129.7, 129.4, 129.2, 127.4, 126.6, 122.9, 119.5, 114.8, 44.4.

N-((1,2,3,5,6,7-hexahydro-s-indacen-4-yl)carbamoyl)-2,3-dihydrobenzo[b]thiophene-6-sulfonamide 1,1-dioxide

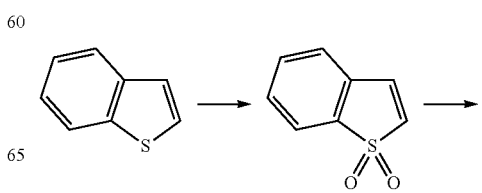

101

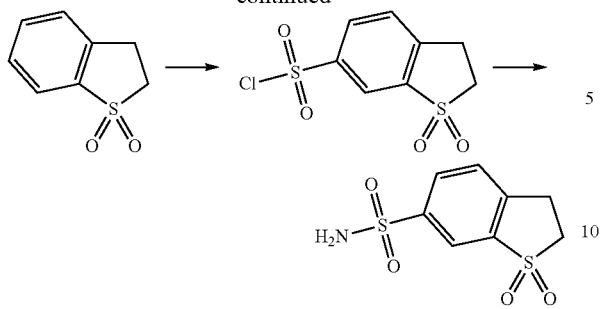

m-Chloroperbenzoic acid (77%, 6.35 g, 27.9 mmol) was added portion wise to a solution of benzo[b]thiophene (1.50 g, 11.1 mmol) in anhydrous dichloromethane (100 mL) at room temperature with vigorous stirring, the resulting reaction mixture was stirred for 16 h at the same temperature. A saturated aqueous $NaHCO_3$ solution (250 mL) was added and aqueous layer was extracted with dichloromethane (2×100 mL), organic layer was separated, combined organic layers dried ($MgSO_4$) and concentrated in vacuo. Crystallization from ethanol afforded benzo[b]thiophene 1,1-dioxide (1.56 g, 84%) as an off-white solid. $^1$H NMR (600 MHz, $CDCl_3$): δ=7.73 (d, J=6 Hz, 1H), 7.58-7.53 (m, 2H), 7.38 (d, J=12 Hz, 1H), 7.23 (d, J=6 Hz, 1H), 6.73 (d, J=6 Hz, 1H). LCMS (m/z): 167 [M+H]$^+$ A solution of benzo[b]thiophene 1,1-dioxide (0.75 g, 4.51 mmol) in ethanol (55 mL) was degassed with nitrogen for 10 minutes then 10% Pd/C (10 mg) was added and the mixture stirred under hydrogen atmosphere (1 atm) for 24 h. The reaction mixture was filtered through a Celite pad, filtrate was concentrated to give 2,3-dihydrobenzo[b]thiophene 1,1-dioxide (0.74 g, 97%) as an off-white solid. $^1$H NMR (600 MHz, $CDCl_3$): δ=7.75 (d, J=6 Hz, 1H), 7.59 (t, J=9 Hz, 1H), 7.49 (t, J=6 Hz, 1H), 7.40 (d, J=6 Hz, 1H), 3.51 (t, J=6 Hz, 2H), 3.41 (t, J=6 Hz, 2H). LCMS (m/z): 169 [M+H]$^+$ 2,3-dihydrobenzo[b]thiophene 1,1-dioxide (0.75 g, 4.45 mmol) was heated in chlorosulfonic acid (1.5 mL, 22.2 mmol) at 80° C. for 4 h. Reaction mixture was poured onto crushed ice and stirred for 5 minutes. The aqueous solution was extracted with dichloromethane (2×50 mL) and the combined organics dried ($MgSO_4$) and concentrated in vacuo to give 2,3-dihydrobenzo[b]thiophene-6-sulfonyl chloride 1,1-dioxide (0.45 g, 38%) as a light brown oil. The crude product was used directly in the next step without purification. 1H NMR (600 MHz, $CDCl_3$): δ=8.42 (s, 1H), 8.25 (d, J=12 Hz, 1H), 7.69 (d, J=6 Hz, 1H), 3.64 (t, J=9 Hz, 2H), 3.55 (t, J=6 Hz, 2H).

To a solution of 2,3-dihydrobenzo[b]thiophene-6-sulfonyl chloride 1,1-dioxide (0.45 g, 1.68 mmol) in acetone (1 mL) was added aq $NH_3$ (2 mL, 28% $NH_4OH$ in $H_2O$) at 0° C., the resulting reaction mixture was stirred at room temperature for 2 h or until completion. The solvent was removed in vacuo and azeotroped with toluene (×2). The crude residue was purified by column chromatography on silica using 4% $MeOH/CH_2Cl_2$ eluent to give 2,3-dihydrobenzo[b]thiophene-6-sulfonamide 1,1-dioxide (0.16 mg, 39%) as an off-white solid. $^1$H-NMR (DMSO-$d_6$): δ=8.09 (s, 1H), 8.06 (d, J=12 Hz, 1H), 7.75 (d, J=6 Hz, 1H), 7.60 (bs, 2 h) 3.70 (t, J=6 Hz, 2H), 3.44 (t, J=9 Hz, 2H).

102

3-azidobenzenesulfonamide

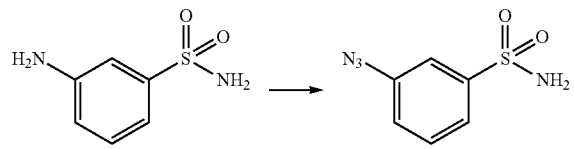 [SMILES: Nc1cccc(S(N)(=O)=O)c1 ; [N-]=[N+]=Nc1cccc(S(N)(=O)=O)c1]

Synthesised according to procedure contained in Pawan Kumar, Navneet Chandak, Poul Nielsen, Pawan K. Sharma. *Bioorg. Med. Chem.* 2012, 20, 3843-3849. A solution of 3-aminobenzenesulfonamide (0.3 g, 1.7 mmol) in $CH_3CN$ (8 mL) was cooled to 0° C. To this stirred mixture was added t-BuONO (250 µL, 2.1 mmol) followed by $TMSN_3$ (276 uL, 2.1 mmol). The resulting solution was stirred at room temperature for 1 h. The reaction mixture was concentrated in vacuo and the crude product purified by column chromatography on silica gel using 100% hexanes eluant to give the titled compound as a pale yellow solid (0.31 g, 91%). $^1$H NMR (600 MHz, $CD_3OD$) b 7.68-7.62 (m, 1H), 7.56 (d, J=1.8 Hz, 1H), 7.47 (d, J=7.8 Hz, 1H), 7.19-7.15 (m, 1H). $^{13}$C NMR (151 MHz, DMSO-$d_6$) δ 146.2, 140.8, 131.2, 122.9, 122.4, 116.5.

N-(3-Sulfamoylphenyl)pent-4-ynamide

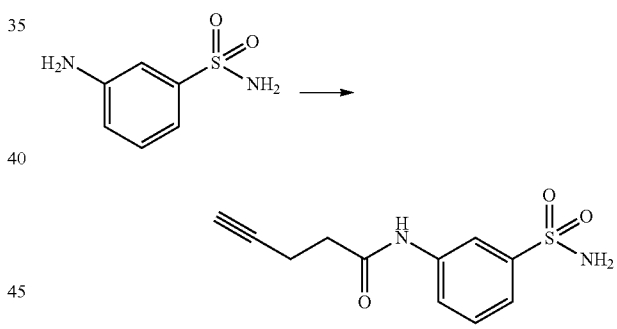

To a solution of pent-4-ynoic acid (0.1 g, 1.02 mmol) and 3-aminobenzenesulfonamide (0.21 g, 1.22 mmol) in dry DMF (5.0 ml) was added HBTU (0.46 g, 1.22 mmol) followed by DIPEA (212 uL, 1.22 mmol). The reaction mixture was stirred at ambient temperature for 2 h, or until completion. The mixture was diluted with EtOAc (30 mL), washed with $H_2O$ (20 mL), brine (20 mL) then the organics dried ($MgSO_4$) and concentrated in vacuo. The crude product was purified by column chromatography on silica gel using 100% hexanes eluant to give the titled compound as a to give the titled compound as a pale-yellow solid (0.2 g, 79%). $^1$H NMR (400 MHz, $CD_3OD$) δ=8.22 (dd, J=2.2, 1.7 Hz, 1H), 7.75-7.68 (m, 1H), 7.65-7.58 (m, 1H), 7.51-7.42 (m, 2H), 2.64-2.59 (m, 2H), 2.58-2.54 (m, 2H), 2.32-2.25 (m, 1H). $^{13}$C NMR (101 MHz, $CD_3OD$) δ=171.3, 143.8, 138.9, 129.2, 122.9, 121.0, 117.1, 82.1, 69.1, 35.4, 14.0.

103
Benzene-1,3-disulfonamide

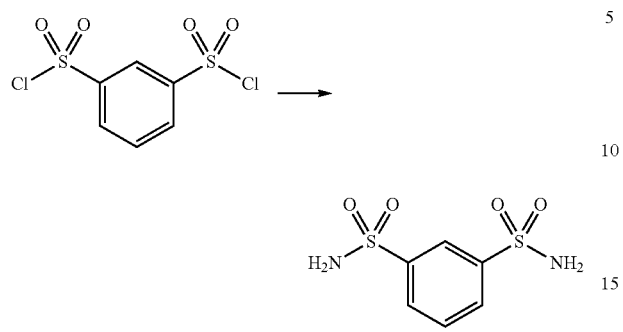

Benzene-1,3-disulfonyl dichloride (0.50 g, 0.726 mmol) was dissolved in tetrahydrofuran (4 mL) and the solution was cooled to 0° C. aqueous ammonia (0.4 mL) was added at 0° C. and the mixture was stirred at ambient temperature for 1 h. Upon completion of the reaction, the mixture was poured into chilled water and extracted with ethyl acetate. The combined organic extracts were washed with brine, dried (Na$_2$SO$_4$) and concentrated in vacuo. The resulting solid was triturated with pentane to afford the titled compound as a light brown solid (0.16 g, 87%). $^1$H NMR (400 MHz, DMSO-d$_6$): δ=8.27 (t, J=2.0 Hz, 1H), 8.06 (dd, J=2.0, 8.0 Hz, 2H), 7.81 (t, J=8.0 Hz, 1H), 7.64 (s, 4H).

N$^1$,N$^1$-dimethylbenzene-1,3-disulfonamide

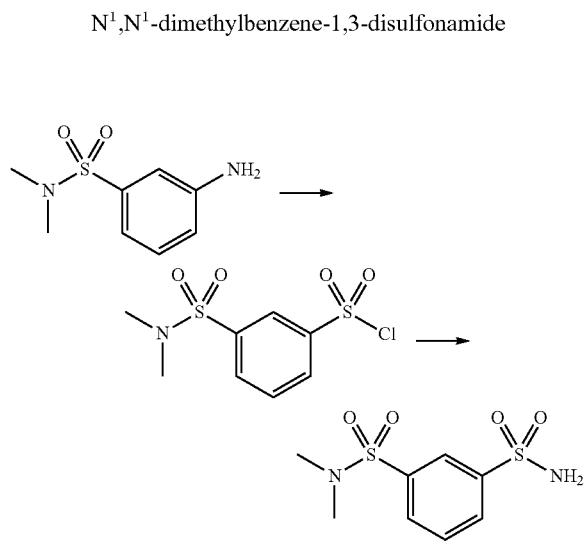

3-amino-N,N-dimethylbenzenesulfonamide was converted to 3-(N,N-dimethylsulfamoyl)benzenesulfonyl chloride (0.45 g, 80%) using method D. $^1$H NMR (300 MHz, CDCl$_3$) δ=8.42 (t, J=2.0 Hz, 1H), 8.27 (d, J=7.9 Hz, 1H), 8.14 (d, J=7.9 Hz, 1H), 7.85 (t, J=7.9 Hz, 1H), 2.79 (s, 6H). The sulfonyl chloride was converted using general method E1 to give the titled compound as a yellow solid (0.45 g, 93%). $^1$H NMR (400 MHz, DMSO-d$_6$) δ=8.13 (m, 2H), 7.98 (d, J=7.9 Hz, 1H), 7.87 (t, J=7.9 Hz, 1H), 7.65 (s, 2H), 2.65 (s, 6H).

104
Methyl 3-sulfamoylbenzoate

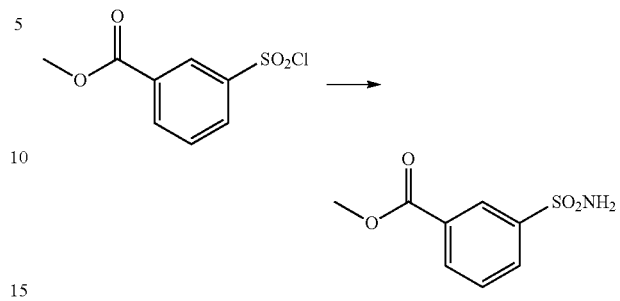

Methyl 3-(chlorosulfonyl)benzoate (1.00 g, 4.26 mmol) was dissolved in anhydrous tetrahydrofuran (15 mL) and the solution was cooled to 0° C. Aqueous ammonia (5.0 mL) was added drop-wise and the mixture stirred at ambient temperature for 2 h. Upon completion the reaction mixture was poured into chilled water and extracted with ethyl acetate. The combined organic extracts were washed with brine, dried (Na$_2$SO$_4$) and concentrated in vacuo. The resulting solid was triturated with pentane to afford the titled compound as a light brown solid (0.75 g, 82%). H NMR (400 MHz, DMSO-d$_6$): δ=8.40 (s, 1H), 8.19 (d, J=8 Hz, 1H), 8.1 (d, J=8 Hz, 1H), 7.77 (t, J=8 Hz, 1H), 7.6 (s, 2H), 3.92 (s, 3H); m/z 214.0 [M−H+]$^-$.

3-(4-phenyl-1H-1,2,3-triazol-1-yl)benzenesulfonamide

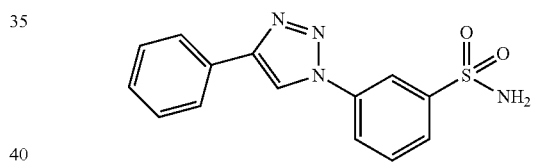

Ethynylbenzene (1 eq) and 3-azidobenzenesulfonamide (1.2 eq), 5 mol % CuSO$_4$, 10 mol % NaAsc solution in DMSO (500 µL) were stirred at room temperature for 12 h. The crude product was purified directly from the reaction mixture using reverse phase column chromatography (Reveleris flash column chromatography, 4 g, 18 mL/min.) and freeze dried to give the product as a white solid (32 mg, 70%). $^1$H NMR (400 MHz, DMSO-d$_6$) δ=9.57-9.36 (m, 1H), 8.46 (d, J=5.7 Hz, 1H), 8.20 (s, 1H), 7.98 (d, J=8.1 Hz, 3H), 7.88 (d, J=7.6 Hz, 1H), 7.62 (s, 2H), 7.53 (d, J=7.4 Hz, 2H), 7.42 (d, J=7.5 Hz, 1H).

N-(prop-2-yn-1-yl)-3-(4-sulfamoylphenyl)propanamide

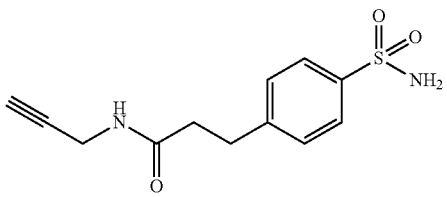 [SMILES: C#CCNC(=O)CCc1ccc(S(N)(=O)=O)cc1]

To a solution of 3-(4-sulfamoylphenyl)propanoic acid (0.3 g, 1.5 mmol) and propargyl amine (0.11 g, 1.5 mmol) in dry DMF (5.0 ml) was added HBTU (0.74 g, 1.5 mmol) followed by DIPEA (342 uL, 1.22 mmol). The reaction mixture was stirred at RT for 2 h. The reaction was monitored by LCMS and after the completion of reaction, it was diluted with EtOAc (30 mL) washed with H2O (20 mL), brine (20 mL). The organic layer was separated; dried (MgSO$_4$) and evaporated to give the crude product. The crude product was purified by silica gel column chromatography (1:1, EtOAc:Hexane) to isolate the title compound as a white solid (0.22 g, 63%). $^1$H NMR (400 MHz, CD$_3$OD) δ=7.85 (d, J=7.9 Hz, 2H), 7.38 (d, J=7.9 Hz, 2H), 3.97 (t, J=2.4 Hz, 2H), 3.04 (t, J=7.6 Hz, 2H), 2.55 (t, J=7.6 Hz, 2H), 2.33 (d, J=2.8 Hz, 1H).

benzo[d][1,3]dioxole-5-sulfonamide

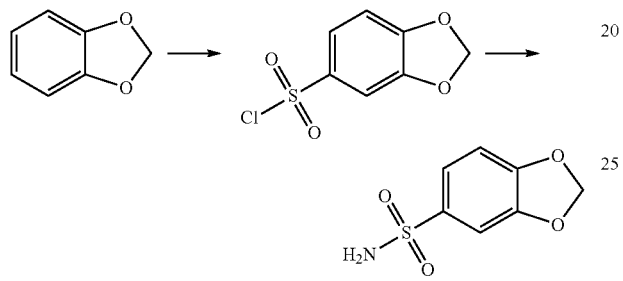

Sulfuryl chloride (2.18 ml, 26.7 mmol) was added to anhydrous DMF (2.10 ml, 26.7 mmol) at 0° C. under nitrogen atmosphere, then the ice bath was removed and the solution stirred for 15 minutes. The solution was cooled once more to 0° C. and benzo[d][1,3]dioxole was added. The reaction mixture was allowed to reach room temperature then heated at 100° C. for 2 h. The reaction mixture was poured onto crushed ice, stirred for 5 minutes, then extracted with dichloromethane (100 ml then 2×50 mL). The combined organics were dried (MgSO$_4$) and concentrated in vacuo. The crude product was purified by column chromatography on silica gel using 15% DCM-hexanes eluent to give benzo[d][1,3]dioxole-5-sulfonyl chloride as an off-white solid (1.78 g, 33%). $^1$H NMR (400 MHz, CDCl$_3$): δ=7.64 (d, J=8.0 Hz, 1H), 7.43 (s, 1H), 6.95 (d, J=8.0 Hz, 1H), 6.16 (s, 2H).

To a solution of benzo[d][1,3]dioxole-5-sulfonyl chloride (0.30 g, 1.35 mmol) in acetone (1 mL) was added aq. NH$_3$ (1.5 mL, 28% NH$_4$OH in H$_2$O) at 0° C., the reaction mixture was stirred at room temperature until completion, typically 2 h, then concentrated in vacuo. The crude product was purified by column chromatography on silica gel using 2% MeOH-DCM eluent to give the titled compound as an off-white solid (210 mg, 77%). $^1$H NMR (400 MHz, DMSO-d$_6$): δ=7.32 (d, J=8.0 Hz, 1H), 7.25 (s, 1H), 7.21 (bs, 2H), 7.02 (d, J=8.0 Hz, 1H), 6.11 (s, 2H).

Pyridine-4-sulfonamide

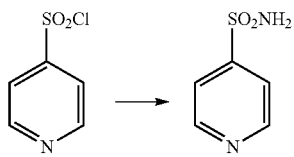 [SMILES: O=S(=O)(Cl)c1ccncc1 ; NS(=O)(=O)c1ccncc1]

Pyridine-4-sulfonyl chloride was converted using general method E3 to give the titled compound as a pale-yellow solid (50 mg, 56%). $^1$H NMR (300 MHz, DMSO-d$_6$): δ=8.56 (d, J=4.5 Hz, 1H), 7.49 (d, J=4.5 Hz, 1H), 7.24 (br.s., 2H).

Pyridine-3-sulfonamide

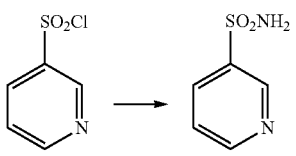 [SMILES: O=S(=O)(Cl)c1cccnc1 ; NS(=O)(=O)c1cccnc1]

Pyridine-3-sulfonyl chloride was converted using general method E3 to give the titled compound as a pale-yellow solid (0.7 g, 79%). $^1$H NMR (300 MHz, DMSO-d$_6$) δ=8.96 (dd, J=2.5, 0.9 Hz, 1H), 8.77 (dd, J=4.8, 1.6 Hz, 1H), 8.17 (ddd, J=8.0, 2.4, 1.6 Hz, 1H), 7.67-7.56 (m, 3H).

Pyridine-2-sulfonamide

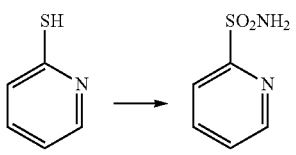 [SMILES: Sc1ccccn1 ; NS(=O)(=O)c1ccccn1]

A 1.0 M solution of HCl (45 mL) and DCM (45 mL) was cooled to −10° C. and pyridine-2-thiol (1.0 g, 9.0 mmol) added. After 10 min, NaOCl (6% solution, 47 mL, 3.3 eq.) was added drop-wise over 5 min and stirring continued at −10° C. for 10 min. The organic phase was separated, dried using Na$_2$SO$_4$ and filtered. The resulting solution was added drop-wise to a pre-cooled solution of sat. methanolic ammonia and DCM (1:1, 40 mL) at 0° C. then allowed to warm to ambient temperature and stirred until completion, typically 2 h. The solvent was removed in vacuo to give a white solid which was dissolved in hot EtOAc and filtered to remove solid impurities. The solvent was removed in vacuo and recrystallized with EtOAc-hexanes to give the titled compound as a yellow solid (0.5 g, 35%). $^1$H NMR (300 MHz, DMSO-d$_6$) δ=8.70 (ddd, J=4.7, 1.7, 0.9 Hz, 1H), 8.05 (td, J=7.7, 1.7 Hz, 1H), 7.91 (dt, J=7.9, 1.1 Hz, 1H), 7.62 (ddd, J=7.6, 4.7, 1.2 Hz, 1H), 7.45 (s, 2H).

4-(trifluoromethyl)pyridine-2-sulfonamide

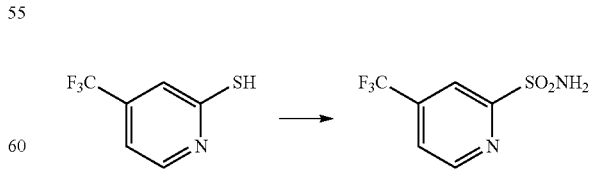

4-(trifluoromethyl)pyridine-2-sulfonamide was synthesized according to the procedures used to synthesise pyridine-2-sulfonamide but using 4-(trifluoromethyl)pyridine-2-thiol in place of pyridine-2-thiol. The product 4-(trifluoromethyl)pyridine-2-sulfonamide was given as a solid (0.7 g, 56%). $^1$H NMR (300 MHz, DMSO-$d_6$) δ=9.02 (d, J=5.0 Hz, 1H), 8.16 (s, 1H), 8.07 (d, J=5.0 Hz, 1H), 7.68 (s, 2H).

3-(3-(trifluoromethyl)-3H-diazirin-3-yl)benzenesulfonamide

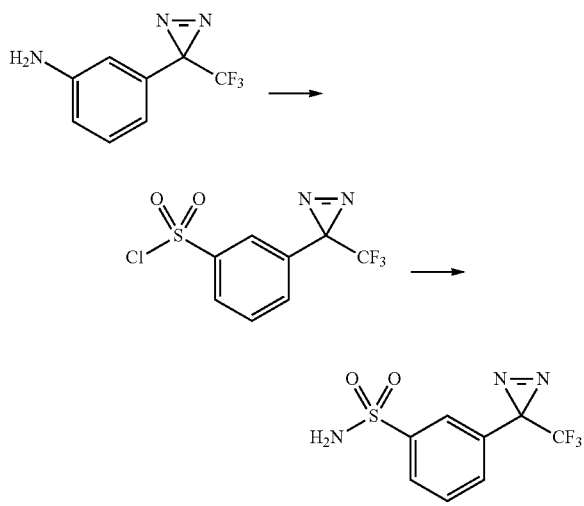

3-(3-(trifluoromethyl)-3H-diazirin-3-yl)aniline was converted using general method D to 3-(3-(trifluoromethyl)-3H-diazirin-3-yl)benzenesulfonyl chloride, a yellow liquid (1.1 g, 52%). $^1$H NMR (300 MHz, CDCl$_3$) δ=8.15-8.08 (m, 1H), 7.82-7.77 (m, 1H), 7.76-7.68 (m, 1H), 7.68-7.61 (m, 1H). $^{19}$F NMR (282 MHz, CDCl$_3$) δ −65.06.

3-(3-(trifluoromethyl)-3H-diazirin-3-yl)benzenesulfonyl chloride was converted using general method E2 to the titled compound as a white solid (0.6 g, 60%). $^1$H NMR (300 MHz, CDCl$_3$) δ=7.99 (dt, J=7.9, 1.5 Hz, 1H), 7.71 (t, J=2.0 Hz, 1H), 7.60 (t, J=7.9 Hz, 1H), 7.49 (d, J=7.9 Hz, 1H), 4.87 (s, 2H). 19F NMR (282 MHz, CDCl$_3$) δ −65.13.

2-(methyl(7-nitrobenzo[c][1,2,5]oxadiazol-4-yl)amino)-N-(4-sulfamoylphenethyl)acetamide

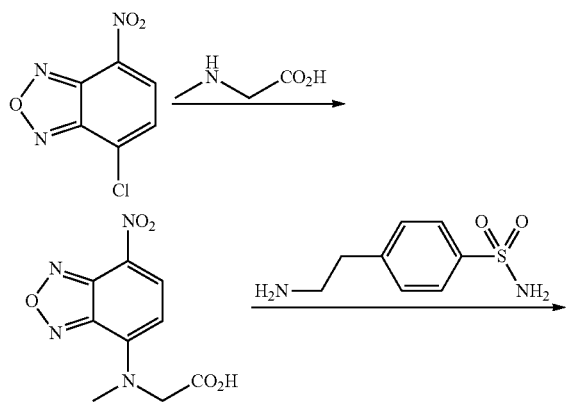

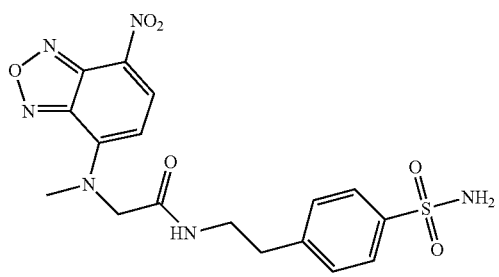

2-(Methylamino)acetic acid (0.24 g, 2.75 mmol) and sodium hydrogencarbonate (0.694 g, 8.26 mmol) were dissolved in a mixture of water (10 mL) and MeOH (20 mL). Then, 4-chloro-7-nitrobenzo[c][1,2,5]oxadiazole (0.50 g, 2.50 mmol) was added and the mixture stirred at 60° C. for 2 h. Upon completion of the reaction, volatiles were removed under reduced pressure and the crude residue obtained was purified by column chromatography on silica gel using 0-5% gradient of methanol in dichloromethane to obtain 2-(methyl(7-nitrobenzo[c][1,2,5]oxadiazol-4-yl)amino)acetic acid as a brick-red solid (1.10 g, 87%).

2-(Methyl(7-nitrobenzo[c][1,2,5]oxadiazol-4-yl)amino) acetic acid (1.00 g, 3.96 mmol) was dissolved in anhydrous tetrahydrofuran (25 mL) under nitrogen atmosphere and the solution was cooled to 0° C. Diisopropylethylamine (0.76 g, 5.55 mmol) and 1,1'-carbonyldiimidazole (0.90 g, 4.75 mmol) were added and the mixture stirred at 50° C. until all of the 2-(methyl(7-nitrobenzo[c][1,2,5]oxadiazol-4-yl)amino)acetic acid had reacted. The reaction mixture was then cooled to 0° C., 4-(2-aminoethyl)benzenesulfonamide (0.95 g, 4.75 mmol) was added and stirred at ambient temperature until completion, typically 6 h. The solvents were removed in vacuo and the residue was purified by reverse phase preparative HPLC to afford the titled compound as a brick-red solid (1.20 g, 70%). LCMS (m/z): 435.4 (M+1)$^+$.

4-(2-(7-Nitrobenzo[c][1,2,5]oxadiazol-4-ylamino)ethyl)benzenesulfonamide

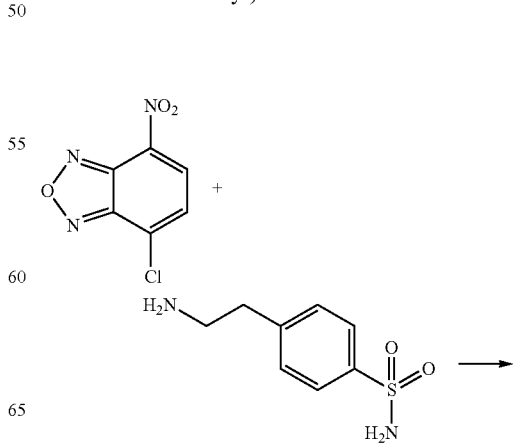

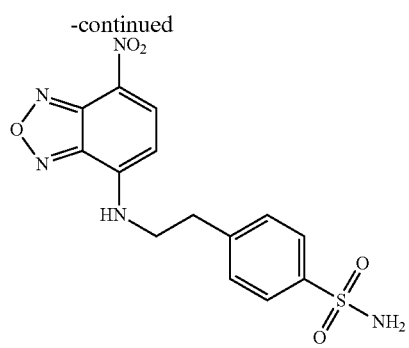

4-(2-aminoethyl)benzenesulfonamide (0.55 g, 2.75 mmol) and diisopropylethylamine (0.64 g, 2.75 mmol) were dissolved in ethanol (20 mL) and the solution cooled to 0° C. 4-Chloro-7-nitrobenzo[c][1,2,5]oxadiazole (0.50 g, 2.50 mmol) was added at 0° C. and the mixture was stirred at ambient temperature for 16 h. Upon completion of the reaction, the reaction mass was poured into brine and extracted with ethyl acetate. Solvents evaporated from the combined organic extract under reduced pressure and the crude obtained was purified by reverse phase prep HPLC to afford the titled product as a dark yellow solid (0.250 g, 7%). $^1$H NMR (400 MHz, CD$_3$OD) δ=8.5 (d, J=8.8 Hz, 1H), 7.82 (d, J=8.4 Hz, 2H), 7.47 (d, J=8.4 Hz, 2H), 6.35 (d, J=8.8 Hz, 1H), 3.83 (m, 2H), 3.15 (t, J=7.6 Hz, 2H).

2-(7-(Dimethylamino)-2-oxo-2H-chromen-4-yl)-N-(4-sulfamoylphenethyl)acetamide (17I)

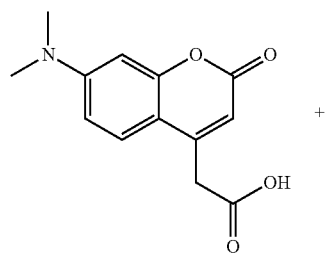

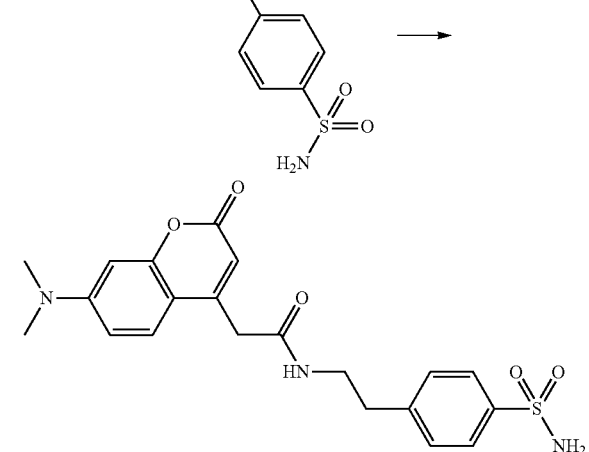

Molecular Weight 429.49

2-(7-(dimethylamino)-2-oxo-2H-chromen-4-yl)acetic acid (0.50 g, 2.02 mmol), EDC.HCl (0.47 g, 3.03 mmol), HOBt (0.464 g, 3.03 mmol) and N-methylmorpholine (0.409 g, 4.04 mmol) were mixed in anhydrous tetrahydrofuran (5 mL) and stirred at 0° C. for 30 min. 4-(2-Aminoethyl)benzenesulfonamide (0.445 g, 2.224 mmol) was added and stirring continued at ambient temperature for 18 h. Upon completion, the reaction was poured onto chilled water and extracted with ethyl acetate. The solvent was removed in vacuo and the residue was purified by column chromatography on silica gel using a gradient of 0-5% methanol in dichloromethane to give 2-(7-(dimethylamino)-2-oxo-2H-chromen-4-yl)-N-(4-sulfamoylphenethyl)acetamide as a greenish-yellow solid (0.25 g, 29%). LCMS (m/z): 430.2 (M+1)$^+$.

6,7-dihydro-5H-pyrrolo[1,2-a]imidazole-2-sulfonamide

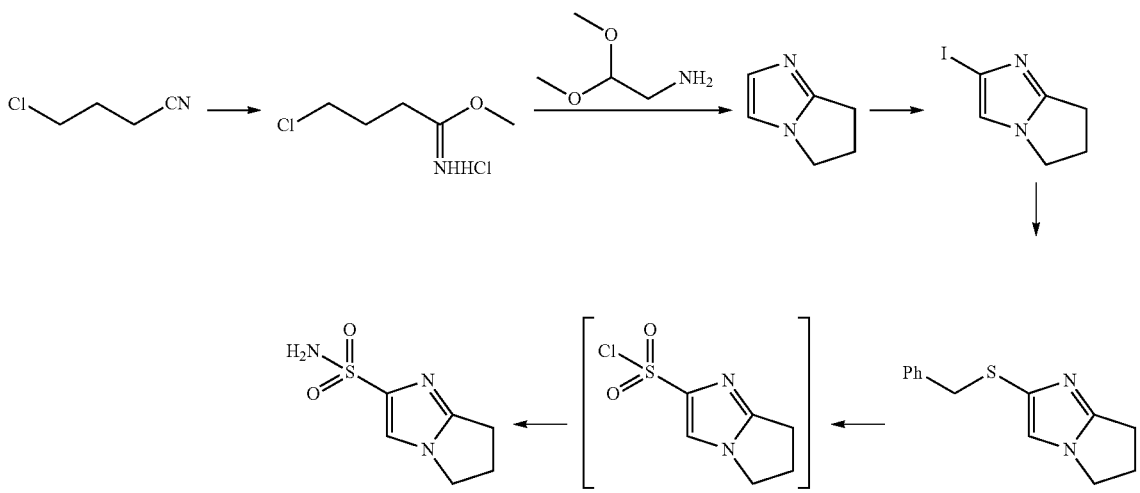

A solution of 3-chlorobutanenitrile (20 g, 193.1 mmol) in diethyl ether (100 mL) was treated with MeOH (7.41 g, 231.7 mmol) and cooled to 0° C. HCl gas was bubbled into the reaction mixture for 4 h at 0° C. The reaction mixture was stirred at −20° C. for 24 h and reaction mixture was concentrated in vacuo. The solid residue obtained was washed with diethyl ether (3×100 mL), n-pentane (2×100 mL) and dried in vacuo at 45° C. to give methyl 4-chlorobutanimidate hydrochloride as a white solid.

Methyl 4-chlorobutanimidate hydrochloride (25 g, 146.1 mmol) was dissolved in DCM (250 mL) treated with $Et_3N$ (44.3 g, 4.38 mmol) and resulting solution was cooled to 0° C. 2,2-Dimethoxyethan-1-amine (12.2 g, 116.9 mmol) was added dropwise to the above mixture over a period of 5 min. The resulting reaction mixture was warmed to 60° C. and stirred for 3 h. The reaction mixture was concentrated in vacuo and residue obtained was treated with in formic acid (150 mL) and heated at 80° C. for 24 h. Upon completion, the reaction mixture was concentrated in vacuo and residue obtained azeotroped with toluene (2×100 mL). The crude mixture was basified with saturated $NaHCO_3$ solution and extracted with DCM (3×200 mL). The combined organic extract was washed with water, brine, dried ($Na_2SO_4$) and concentrated in vacuo to give 6,7-dihydro-5H-pyrrolo[1,2-a]imidazole (8 g, 39% over 3 steps) as a low melting dark solid. $^1$H NMR (300 MHz, $CDCl_3$): δ=7.0 (s, 1H), 6.83 (s, 1H), 3.95 (t, J=7.2 Hz, 2H), 2.84 (t, J=7.2 Hz, 2H), 2.61-2.51 (m, 2H).

A solution of 6, 7-dihydro-5H-pyrrolo[1,2-a]imidazole (4 g, 37.0 mmol) in acetonitrile (120 m L) was cooled to 0° C. N-Iodosuccinimide (9.16 g, 40.7 mmol) was added portion wise at 0° C. The resulting reaction mixture was warmed to RT and stirred for 12 h. Upon completion, the reaction mixture was diluted with saturated $Na_2S_2O_3$ solution and extracted with ethyl acetate (2×50 mL). The combined organic extract was washed with water, brine, dried ($Na_2SO_4$) and concentrated in vacuo. The crude product was purified by column chromatography on silica gel using 4-40% EtOAc-hexanes eluant to give 2-iodo-6,7-dihydro-5H-pyrrolo[1,2-a]imidazole (1.0 g, 19%) as a white solid. $^1$H NMR (300 MHz, $CDCl_3$): δ=7.03 (s, 1H), 3.89 (t, J=7.2 Hz, 2H), 3.02 (t, J=7.2 Hz, 2H), 2.65-2.55 (m, 2H). LCMS (m/z): 235 [M+H]$^+$.

In a 50 mL re-sealable reaction tube, a solution of 2-iodo-6,7-dihydro-5H-pyrrolo[1,2-a]imidazole (0.3 g, 1.28 mmol) and phenylmethane thiol (0.24 g, 1.92 mmol) in 1,4-dioxane (10 mL) was treated with DIPEA (0.41 g, 3.20 mmol) at RT under nitrogen atmosphere. Nitrogen gas was purged through the solution for 5 minutes. Xantphos (74 mg, 0.128 mmol) and $Pd_2(dba)_3$ (60 mg, 0.064 mmol) were sequentially added to the aforementioned solution and the vessel purged with nitrogen gas for 5 minutes. The resulting mixture was stirred at 110° C. for 12 h. Upon completion, the reaction mixture was cooled to RT, diluted with EtOAc (25 mL) and filtered through celite. The filtrate was dried ($Na_2SO_4$) and concentrated in vacuo. The crude product was purified by column chromatography on silica gel (60-120 mesh) using 50-70% EtOAc-hexanes eluant to give 2-(benzylthio)-6,7-dihydro-5H-pyrrolo[1,2-a]imidazole, (0.15 g, 51%) as a brown liquid. $^1$H NMR (300 MHz, $CDCl_3$): δ=7.26-7.22 (m, 3H), 7.12 (s, 1H), 7.05-7.02 (m, 2H), 3.73 (s, 2H), 3.14 (t, J=6.9 Hz, 2H), 2.81 (t, J=7.2 Hz, 2H), 2.32-2.27 (m, 2H). LCMS (m/z): 231.3 [M+H]$^+$.

A solution of 2-(benzylthio)-6,7-dihydro-5H-pyrrolo[1,2-a]imidazole (250 mg, 1.08 mmol) in acetonitrile (2.5 mL), acetic acid (0.5 mL) and $H_2O$ (1.2 mL) was cooled to 0° C. DCDMH (170 mg, 0.869 mmol) was added at 0° C. and resulting reaction mixture was stirred at 0° C. for 2 h. The reaction mixture was diluted with water and extracted with ethyl acetate (2×20 mL). The combined organic extract was washed with water, brine, dried ($Na_2SO_4$) and concentrated in vacuo to give 6,7-dihydro-5H-pyrrolo[1,2-a]imidazole-2-sulfonyl chloride as a pale brown liquid used directly in the next step.

A solution of 6,7-dihydro-5H-pyrrolo[1,2-a]imidazole-2-sulfonyl chloride (300 mg) in THF (15 mL) was cooled to −40° C. Ammonia gas was purged through the aforementioned solution for 15 min and solution was stirred at −40° C. for 1 h. The reaction mixture was warmed to RT, stirred for 1 h then, upon completion, concentrated in vacuo. The crude product was purified by column chromatography on silica gel (60-120 mesh) using 10% MeOH—$CHCl_3$ eluant to give 6,7-dihydro-5H-pyrrolo[1,2-a]imidazole-2-sulfonamide (117 mg, 88%) as a white solid. $^1$H NMR (300 MHz, DMSO-$d_6$): δ=7.54 (bs, 2H), 7.26 (s, 1H), 4.06 (s, 2H), 2.80 (s, 2H), 2.32 (s, 2H). LCMS (m/z): 187.95 [M+H]$^+$.

4-Nitrobenzenesulfonamide

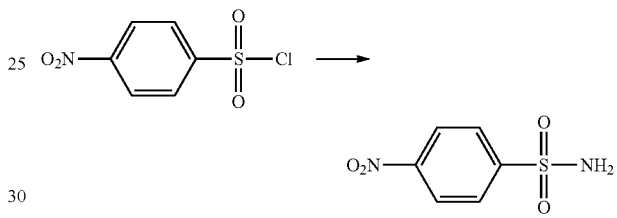

4-Nitrobenzenesulfonyl chloride (1.0 eq.) dissolved in acetone (0.8 mL/mmol) was added drop-wise to Ammonium bicarbonate (4.0 eq) dissolved in water (0.8 mL/mmol). The reaction mixture was stirred at room temperature for 2 h before acidification with 1 M HCl (pH ~2). The mixture was extracted with ethyl acetate (3×10 mL), dried ($MgSO_4$) and concentrated in vacuo to give the titled compound as a pale orange solid (157 mg, 57%). $^1$H NMR (600 MHz, DMSO-$d_6$) δ=8.42 (d, J=8.8 Hz, 2H), 8.06 (d, J=8.8 Hz, 2H), 7.74 (s, 2H). HRMS calculated for $C_6H_5N_2O_4S_1$ [M−H]$^−$ 200.9976, found 200.9984.

5-Methyl-N-(4-sulfamoylphenethyl)isoxazole-3-carboxamide

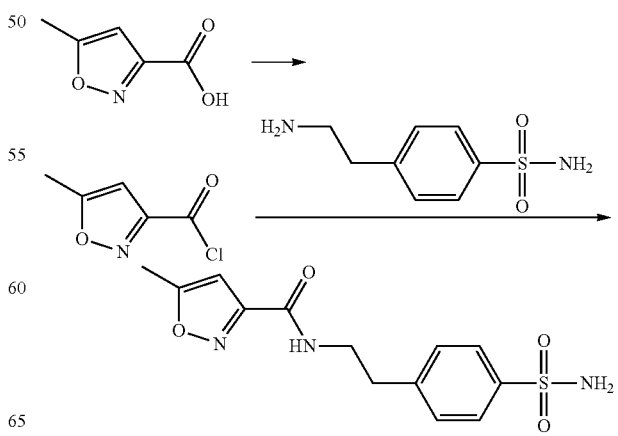

5-Methylisoxazole-3-carbonyl chloride (1.0 eq) (prepared using general method B1) was dissolved in anhydrous THF (4 mL/mmol) and treated with triethylamine (1.0 eq). After stirring for 5 minutes 4-(2-aminoethyl)benzenesulfonamide (1.0 eq) was added to the acid chloride solution. The reaction was stirred at room temperature, under an argon atmosphere overnight. The solvent was removed in vacuo, and the residue purified by reverse phase column chromatography using acetonitrile/10 mM ammonium bicarbonate (aq) as mobile phase to give the titled compound as a white solid (205 mg, 48%). $^1$H NMR (600 MHz, DMSO-d$_6$) δ=8.79 (t, J=5.8 Hz, 1H), 7.74 (d, J=8.3 Hz, 2H), 7.41 (d, J=8.3 Hz, 2H), 7.30 (s, 2H), 6.50 (q, J=0.6 Hz, 1H), 3.52-3.46 (m, 2H), 2.91 (t, J=7.2 Hz, 2H), 2.45 (d, J=0.6 Hz, 3H). HRMS calculated for C$_{13}$H$_{14}$N$_3$O$_4$S$_1$ [M-H]$^-$ 308.0711, found 308.0708.

4-(2-(7-Methoxy-4,4-dimethyl-1,3-dioxo-3,4-dihydroisoquinolin-2(1H)-yl)ethyl)benzenesulfonamide

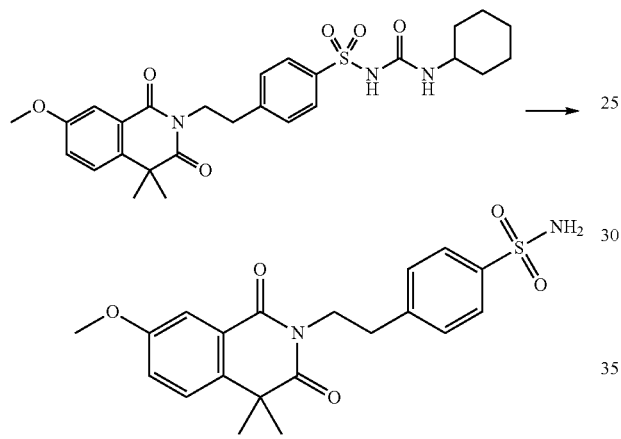

N-(cyclohexylcarbamoyl)-4-(2-(7-methoxy-4,4-dimethyl-1,3-dioxo-3,4-dihydroisoquinolin-2(1H)-yl)ethyl)benzenesulfonamide (1.0 eq) dissolved in anhydrous pyridine (8 mL/mmol) was treated with phthalic anhydride (1 eq.) and DMAP (0.1 eq) and heated to reflux under an inert atmosphere for 4 hours. The solvent was removed in vacuo, and the residue purified by reverse phase column chromatography using acetonitrile/10 mM ammonium bicarbonate (aq) as mobile phase to give the titled compound as a white solid (291 mg, 75%). $^1$H NMR (600 MHz, DMSO-d$_6$) δ=7.72 (d, J=8.4 Hz, 2H), 7.61 (d, Jf=8.7 Hz, 1H), 7.53 (d, J=2.8 Hz, 1H), 7.40 (d, J=8.2 Hz, 2H), 7.33-7.25 (m, 3H), 4.13 (d, J=7.5 Hz, 2H), 3.83 (s, 3H), 2.93 (t, J=7.3 Hz, 2H), 1.45 (s, 6H). HRMS calculated for C$_{20}$H$_{21}$N$_2$O$_5$S$_1$ [M-H]$^-$ 401.1177, found 401.1174.

Synthesis of R1 and R2 amine intermediates:
1-methyl-1H-pyrazol-3-amine HCl

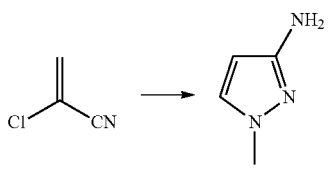

In a 20 mL microwave vial, a solution of 2-chloroacrylonitrile (2 g, 22.85 mmol) in EtOH (10 mL) was treated with methyl hydrazine (1.93 g, 41.13 mmol). The resulting reaction mixture was heated at 100° C. for 10 minutes in a Biotage microwave synthesizer. The reaction mixture was left at <5° C. for 12 h during this time a solid precipitated. The precipitate was removed by filtration and dried in vacuo to give the titled compound as white solid (0.12 g, 55%). $^1$H NMR (400 MHz, DMSO-d$_6$): δ 7.76 (s, 1H), 6.13 (s, 1H), 3.80 (s, 3H), 2.58 (s, 2H). LCMS (m/z): 98.3 (M+1)$^+$.

1-(trifluoromethyl)-1H-pyrazol-3-amine

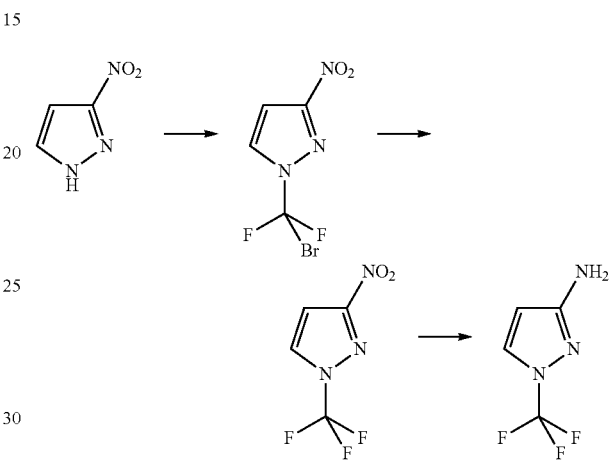

3-Nitro-1H-pyrazole (5 g, 44 mmol) was dissolved in N,N-dimethylformamide (100 mL), cooled to −5° C. and NaH (3.8 g, 93.6 mmol) added portionwise. The reaction mixture was stirred for 15 mins before adding dibromodifluoromethane (8.6 g, 44 mmol) and allowing to warm to ambient temperature overnight. The reaction mixture was quenched using ice-water and extracted using ethyl acetate. The organic phase was washed using water, brine, dried (Na$_2$SO$_4$) and concentrated in vacuo to give 3-nitro-1-(trifluoromethyl)-1H-pyrazole (2.1 g, 22%) which was used without further purification. $^{19}$F NMR (282 MHz, CDCl$_3$) δ=−34.20.

1-(bromodifluoromethyl)-3-nitro-1H-pyrazole (2.1 g, 9.76 mmol) was dissolved in DCM (50 mL) and cooled to −78° C. before adding AgBF$_4$ (5.7 g, 28.3, 3 equivalents). The reaction mixture was allowed to warm to ambient temperature overnight then cooled to 0° C. and quenched by addition of sat.aq. NaHCO3 (50 mL). The aqueous phase was extracted using DCM and the combined organics washed with water, brine, dried (Na$_2$SO$_4$) and concentrated in vacuo to give 3-nitro-1-(trifluoromethyl)-1H-pyrazole (0.9 g, 51%). $^{19}$F NMR (282 MHz, CDCl$_3$) δ=−60.96.

3-nitro-1-(trifluoromethyl)-1H-pyrazole (1.0 g) was dissolved in THF:EtOAc (1:1, 50 mL), Pd/C (200 mg) was added and the mixture stirred under a hydrogen atmosphere (balloon) overnight. The mixture was filtered through celite and washed through using ethyl acetate. The solvent was removed in vacuo and the residue purified by column chromatography on silica gel using 40% EtOAc in hexanes eluant to give the titled product (0.75 g, 87%). $^1$H NMR (300 MHz, CDCl$_3$) δ=7.54 (d, J=2.7 Hz, 1H), 5.84 (d, J=2.7 Hz, 1H). $^{19}$F NMR (282 MHz, CDCl$_3$) δ=−61.13.

1-isopropyl-1H-pyrazol-3-amine

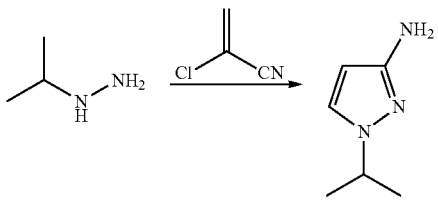

Isopropyl hydrazine hydrochloride (5 g, 45.45 mmol) in water (40 mL) was treated sequentially with K₂CO₃ (12.5 g, 91 mmol) and 2-chloroacrylonitrile (4 g, 45.45 mmol). The resulting reaction mixture was stirred at 50° C. for 1 h, cooled to RT and extracted with ethyl acetate (50 mL). The organic extract was washed with water (40 mL), brine (40 mL), dried (Na₂SO₄) and concentrated in vacuo to give the titled compound as a yellow solid (3.5 g, 62%). $^1$H NMR (400 MHz, CDCl₃): δ=7.15 (s, 1H), 5.56 (s, 1H), 4.27-4.23 (m, 1H), 3.6 (br.s., 2H), 1.43 (d, J=6.4 Hz, 6H). LCMS (m/z): 126.0 (M+1)$^+$.

1-cyclopropyl-1H-pyrazol-3-amine

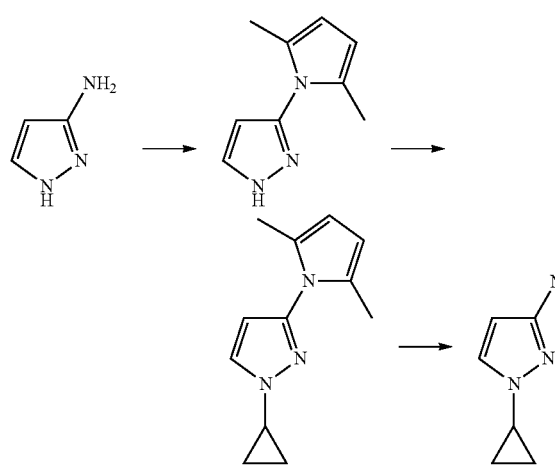

A solution of 1H-pyrazol-3-amine (2 g, 24.1 mmol) in AcOH (20 mL) was treated with 2,5-hexane dione (5.7 g, 50.6 mmol) at ambient temperature under nitrogen atmosphere. The resulting reaction mixture was heated to 100° C. for 6 h. The reaction mixture was concentrated under reduced pressure and azeotroped with toluene. The crude product was purified by column chromatography on silica gel using a gradient of 50-100% EtOAc-hexanes eluent to give 3-(2,5-dimethyl-1H-pyrrol-1-yl)-1H-pyrazole as a red solid (2.25 g, 59%). $^1$H NMR (400 MHz, DMSO-d₆) δ 12.92 (s, 1H), 7.85 (t, J=1.8 Hz, 1H), 6.28 (t, J=2.1 Hz, 1H), 5.75 (s, 2H), 2.00 (s, 6H).

Copper (II) acetate (0.56 g, 3.1 mmol), 2,2;-bipyridine (0.48 g, 3.1 mmol) and dichloroethane (10 mL) were heated to 75° C. for 20 min. 5 mL of this pre-prepared solution was added to a mixture of 3-(2,5-dimethyl-1H-pyrrol-1-yl)-1H-pyrazole (0.5 g, 3.1 mmol), potassium cyclopropyltrifluoroborate (2 eq) and sodium carbonate (2eq.), in dichloroethane (5 mL) then the reaction stirred at 75° C. for 6 h. The reaction mixture was diluted using DCM, washed using water, brine, dried (Na₂SO₄) and concentrated in vacuo. The crude product was purified by column chromatography on silica gel using 10% EtOAc-hexanes eluent to give 1-cyclopropyl-3-(2,5-dimethyl-1H-pyrrol-1-yl)-1H-pyrazole as a yellow liquid (0.2 g, 32%). $^1$H NMR (300 MHz, Chloroform-d) δ 7.48 (dd, J=2.3, 0.5 Hz, 1H), 6.12 (d, J=2.3 Hz, 1H), 5.84 (s, 2H), 3.61 (tt, J=7.3, 3.6 Hz, 1H), 2.09 (s, 6H), 1.22-0.95 (m, 4H).

To a solution of ammonium hydroxide hydrochloride (1.64 g, 11.8 mmol) in ethanol ((10 mL) was added a solution of potassium hydroxide (0.66 g) in water (10 mL) at 0° C. After 10 min stirring a solution of 1-cyclopropyl-3-(2,5-dimethyl-1H-pyrrol-1-yl)-1H-pyrazole (0.95 g) in ethanol (10 mL) was added and the reaction heated at 100° C. for 20 h. The solvent was removed in vacuo and the residue partitioned between ethyl acetate and water. The organic phase was washed with water, brine, dried (Na₂SO₄) and concentrated in vacuo. The crude product was purified by column chromatography on silica gel using a gradient of 70-100% EtOAc-hexanes eluent to give the titled product as a brown solid (0.4 g, 69%). $^1$H NMR (400 MHz, CDCl3) δ=7.51 (d, J=2.4 Hz, 1H), 6.69 (d, J=2.4 Hz, 1H), 5.04 (s, 2H), 3.67 (m, 1H), 1.19 (m, 2H), 1.12 (m, 2H).

1-(tert-butyl)-1H-pyrazol-3-amine

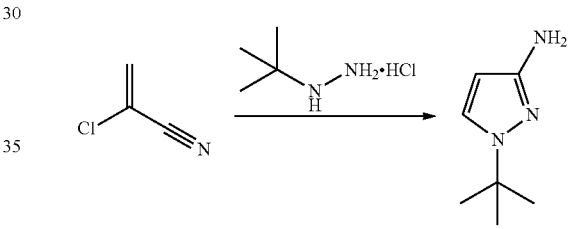

Isopropyl hydrazine hydrochloride (1.42 g, 11.4 mmol) in water (25 mL) at 0° C. was treated sequentially with K₂CO₃ (1.57 g, 11.4 mmol), NaHCO₃ (1.91 g, 22.9 mmol) and 2-chloroacrylonitrile (1 g, 11.4 mmol) then warmed to ambient temperature and stirred for 12 h. The reaction mixture was diluted with water (20 mL) and extracted with ethyl acetate (2×25 mL). The combined organics were washed with water (30 mL), brine (30 mL), dried (Na₂SO₄) and concentrated in vacuo to give the titled compound as a brown liquid (0.9 g, 60%). $^1$H NMR (400 MHz, DMSO-d₆): δ=7.34 (s, 1H), 5.35 (s, 1H), 4.51 (br.s., 2H), 1.40 (s, 9H). LCMS (m/z): 140.10 (M+1)$^+$.

1-cyclohexyl-1H-pyrazol-3-amine

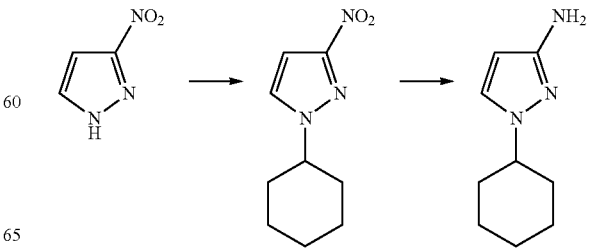

3-nitro-1H-pyrazole (1 g, 8.85 mmol) was dissolved in N,N-dimethylformamide (20 mL) and treated with potassium carbonate (1.47 g, 10.62 mmol) and bromocyclohexane (1.8 g, 10.62 mmol). The mixture was heated to 100° C. for 16 hours (or until completion) then cooled to ambient temperature diluted using water (100 mL) and extracted using ethyl acetate (2×75 mL). The combined organics were washed using water (100 mL), brine (100 mL), dried (Na$_2$SO$_4$) and concentrated in vacuo. The crude product was purified by column chromatography on silica gel using a gradient of 10% EtOAc-hexanes eluent to give 1-cyclohexyl-3-nitro-1H-pyrazole as a colourless liquid (1.3 g, 76%). $^1$H NMR (300 MHz, CDCl$_3$) δ=7.47 (d, J=2.5 Hz, 1H), 6.88 (d, J=2.5 Hz, 1H), 4.26-4.11 (m, 1H), 2.18 (m, 2H), 1.93 (m, 2H), 1.82-1.20 (m, 6H).

In a 100 mL Parr shaker reaction vessel, a solution of 1,5-dimethyl-3-nitro-1H-pyrazole (0.65 g, 3.3 mmol) in MeOH (4 mL) and EtOAc (20 mL) was treated with 10% palladium on carbon (200 mg) under nitrogen atmosphere. The flask was evacuated then filled with hydrogen gas (60 psi) and stirred at ambient temperature for 12 h. The reaction mixture was diluted with ethyl acetate (50 mL) and filtered through a bed of Celite. The filtrate was dried (Na$_2$SO$_4$) and concentrated in vacuo to give 1-cyclohexyl-1H-pyrazol-3-amine as a light brown solid (0.3 g 55%). $^1$H NMR (300 MHz, CDCl$_3$) δ=7.15 (d, J=2.3 Hz, 1H), 5.56 (d, J=2.3 Hz, 1H), 3.85 (m, 1H), 3.62 (s, 1H), 2.1 (m, 2H), 1.8 (m, 2H), 1.77-1.10 (m, 6H).

1-phenyl-1H-pyrazol-3-amine

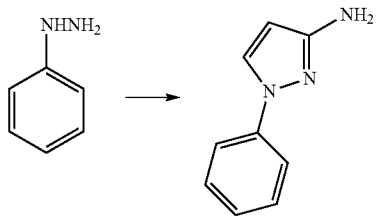 [SMILES: NNc1ccccc1 ; Nc1ccn(-c2ccccc2)n1]

Potassium tert-butoxide (11.9 g, 106.3 mmol) was dissolved in tBuOH (100 mL) and the solution was heated to 100° C. Phenyl hydrazine (5 g, 46.2 mmol) and 3-ethoxy acrylonitrile (4.5 g, 46.2 mmol) were sequentially added and heating continued for 16 h. The mixture was concentrated in vacuo. The residue obtained was partitioned between water (500 mL) and ethyl acetate (500 mL). The organic extract was washed with water (250 mL), brine (250 mL), dried (Na$_2$SO$_4$) and concentrated in vacuo. The crude product was purified by column chromatography on silica gel using 25% EtOAc-hexanes eluent to give 1-phenyl-1H-pyrazol-3-amine as a pale brown solid (3.5 g, 48%). $^1$H NMR (400 MHz, CDCl$_3$): δ=7.69 (s, 1H), 7.57 (d, J=8.0 Hz, 2H), 7.41 (d, J=8.0 Hz, 2H), 7.2 (t, J=7.6 Hz, 1H), 5.85 (s, 1H), 3.83 (br.s., 2H). LCMS (m/z): 160.3 (M+1)$^+$.

1-benzyl-1H-pyrazol-3-amine

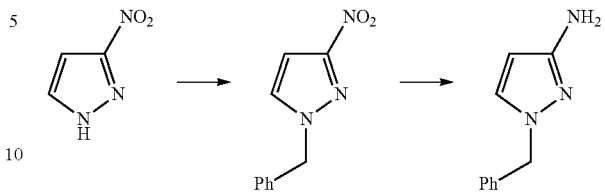

A solution of 3-nitro-1H-pyrazole (1 g, 8.85 mmol) in THF (20 mL) was cooled to 0° C. and NaH (0.53 g, 13.27 mmol) was added. The suspension was stirred for 20 min then benzyl bromide (1.5 g, 8.85 mmol) was added dropwise. The reaction was stirred until completion ~6 h, diluted with saturated NaHCO$_3$ solution (20 mL) and extracted with EtOAc (2×50 mL). The organics were washed with water (30 mL), brine (30 mL), dried (Na$_2$SO$_4$) and concentrated in vacuo to give 1-benzyl-3-nitro-1H-pyrazole as a white solid (1.5 g, 84%). $^1$H NMR (300 MHz, CDCl$_3$): δ=7.40-7.36 (m, 4H), 7.31-7.27 (m, 2H), 6.90 (d, J=2.7 Hz, 1H), 5.37 (s, 2H). LCMS (m/z): 204.20 (M+1)$^+$.

A solution of 1-benzyl-3-nitro-1H-pyrazole (1.5 g, 7.39 mmol) in THF (20 mL) and MeOH (5 mL) was cooled to 0° C. Zinc powder (2.4 g, 36.9 mmol) and NH$_4$Cl solution (1.97 g, 36.94 mmol; in 5 mL of water) was added. The resulting reaction mixture was heated at 70° C. for 12 h. The reaction mixture was cooled to ambient temperature, diluted with EtOAc (50 mL) and filtered through a bed of Celite. The filtrate was dried (Na$_2$SO$_4$) and concentrated in vacuo. The crude product was purified by column chromatography on silica gel using 50% EtOAc-hexanes eluent to give 1-benzyl-1H-pyrazol-3-amine as light brown liquid (0.85 g, 67%). $^1$H NMR (300 MHz, CDCl$_3$): δ=7.34-7.26 (m, 3H), 7.14-7.11 (m, 2H), 7.05 (d, J=2.4 Hz, 1H), 5.59 (d, J=2.4 Hz, 1H), 5.14 (s, 2H). LCMS (m/z): 174.10 (M+1)$^+$ 1-(1-phenylethyl)-1H-pyrazol-3-amine

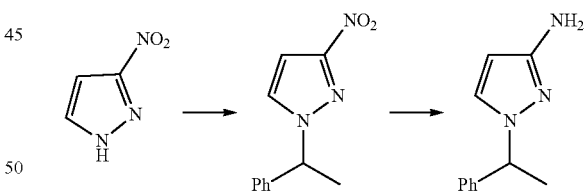

A solution of 3-nitro-1H-pyrazole (1 g, 8.85 mmol) in THF (20 mL) was cooled to 0° C. and NaH (0.7 g, 17.7 mmol) was added. The suspension was stirred for 30 min then (1-bromoethyl)benzene (1.96 g, 10.6 mmol) was added drop-wise. The reaction was heated to 80° C. overnight or until completion, cooled to ambient temperature, diluted using water (40 mL) and extracted with EtOAc (2×50 mL). The organics were washed with water (30 mL), brine (30 mL), dried (Na$_2$SO$_4$) and concentrated in vacuo. The crude product was purified by column chromatography on silica gel using 20% EtOAc-hexanes eluent to give 3-nitro-1-(1-phenylethyl)-1H-pyrazole as a yellow liquid (1.2 g, 63%). $^1$H NMR (300 MHz, CDCl$_3$) δ 7.46-7.18 (m, 6H), 6.88 (d, J=2.5 Hz, 1H), 5.59 (q, J=7.1 Hz, 1H), 1.96 (d, J=7.1 Hz, 3H).

A solution of 3-nitro-1-(1-phenylethyl)-1H-pyrazole (1 g, 4.6 mmol) in THF (20 mL) and MeOH (5 mL) was cooled to 0° C. Zinc powder (1.49 g, 23.04 mmol) and NH$_4$Cl solution (1.23 g, 23.04 mmol; in 5 mL of water) was added. The resulting reaction mixture was stirred for 30 mins then heated at 80° C. for 6 h. The reaction mixture was cooled to ambient temperature, diluted with EtOAc (50 mL) and filtered through a bed of Celite. The organic phase was washed using water (20 mL), brine (20 mL), dried (Na$_2$SO$_4$) and concentrated in vacuo. The crude product was purified by column chromatography on silica gel using 50% EtOAc-hexanes eluent to give 1-(1-phenylethyl)-1H-pyrazol-3-amine as a yellow liquid (0.85 g, 67%). $^1$H NMR (300 MHz, CDCl$_3$) δ=7.39-7.04 (m, 6H), 5.59 (d, J=2.4 Hz, 1H), 5.35 (q, J=7.1 Hz, 1H), 3.83 (s, 2H), 1.78 (d, J=7.1 Hz, 3H).

1-(2-(piperidin-1-yl)ethyl)-1H-pyrazol-3-amine

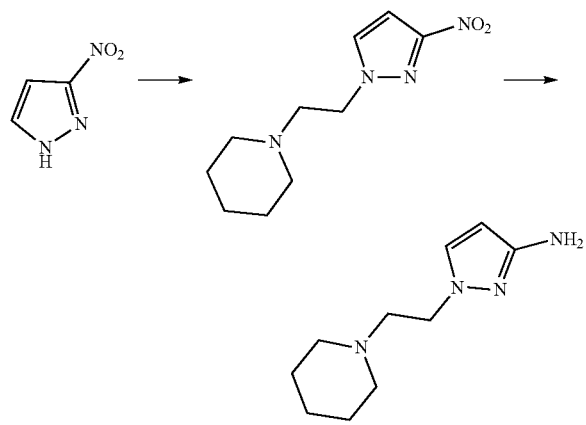

A solution of 3-nitro-1H-pyrazole (2 g, 17.7 mmol) in DMF (20 mL) was treated with 1-(2-chloroethyl)piperidine hydrochloride (4.8 g, 26.5 mmol) at ambient temperature. The solution was cooled to 0° C., and treated with K$_2$CO$_3$ (6.1 g, 44.27 mmol) in portions over a period of 5 min. The resulting reaction mixture was stirred at ambient temperature for 4 h. The reaction mixture was diluted with water and extracted with ethyl acetate (2×40 mL). The combined organics were washed with water (40 mL), brine (40 mL), dried (Na$_2$SO$_4$) and concentrated in vacuo. The crude product was purified by column chromatography on silica gel using 25% EtOAc-hexanes eluent to give 1-(2-(3-nitro-1H-pyrazol-1-yl)ethyl)piperidine as a pale yellow solid (2.5 g, 64%). $^1$H NMR (400 MHz, CDCl$_3$): δ=7.60 (d, J=2.4 Hz, 1H), 6.81 (d, J=2.4 Hz, 1H), 4.29 (t, J=6.4 Hz, 2H), 2.78 (t, J=6.4 Hz, 2H), 2.41 (s, 4H), 1.57-1.53 (m, 4H), 1.45 (t, J=6 Hz, 2H). LCMS (m/z): 225.10 (M+1)$^+$.

A solution of 1-(2-(3-nitro-1H-pyrazol-1-yl)ethyl)piperidine 3 (2.5 g, 11.16 mmol) in THF (20 mL) and MeOH (5 mL) was cooled to 0° C. The solution was sequentially treated with zinc powder (3.6 g, 55.8 mmol) and aqueous NH$_4$Cl (3 g, 55.8 mmol) solution then warmed to ambient temperature and stirred for 5 h. The reaction mixture was diluted with ethyl acetate (50 mL), filtered through a bed of Celite and concentrated in vacuo. The residue was diluted with ethyl acetate (60 mL) and washed with water (40 mL), brine (40 mL), dried (Na$_2$SO$_4$) and concentrated in vacuo to give 1-(2-(piperidin-1-yl)ethyl)-1H-pyrazol-3-amine as light yellow liquid (1.75 g, 81%). $^1$H NMR (400 MHz, DMSO-d$_6$): δ=7.28 (d, J=2 Hz, 1H), 5.30 (s, J=2 Hz, 1H), 4.50 (s, 2H), 3.90 (t, J=6.8 Hz, 2H), 2.5-2.53 (m, 4H), 2.39-2.33 (m, 6H), 1.2 (s, 2H). LCMS (m/z): 195.10 (M+1)$^+$.

1,5-dimethyl-1H-pyrazol-3-amine

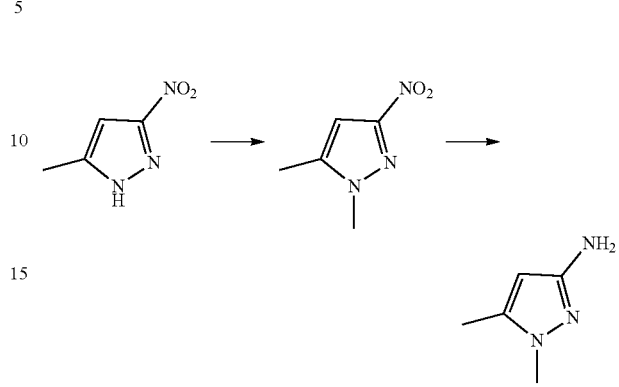

A solution of 5-methyl-3-nitro-1H-pyrazole (2 g, 15.7 mmol) in THF (20 mL) was cooled to 0° C. NaH (0.7 g, 17.32 mmol) was added portion-wise over 10 min under nitrogen atmosphere. The resulting suspension was stirred for 10 min then treated with MeI (2.2 g, 15.7 mmol), warmed to ambient temperature and stirred for 4 h. The reaction mixture was diluted with saturated NH$_4$Cl solution (20 mL) and extracted with EtOAc (2×30 mL). The organics were washed with water (30 mL), brine (30 mL), dried (Na$_2$SO$_4$) and concentrated in vacuo to give 1,5-dimethyl-3-nitro-1H-pyrazole as a white solid (2 g, 91%). $^1$H NMR (300 MHz, CDCl$_3$): δ=6.71 (s, 1H), 3.87 (s, 3H), 2.34 (s, 3H).

In a 100 mL Parr shaker reaction vessel, a solution of 1,5-dimethyl-3-nitro-1H-pyrazole (2 g, 14.18 mmol) in MeOH (4 mL) and EtOAc (20 mL) was treated with 10% palladium on carbon (400 mg) under nitrogen atmosphere. The flask was evacuated then filled with hydrogen gas (60 psi) and stirred at ambient temperature for 12 h. The reaction mixture was diluted with ethyl acetate (50 mL) and filtered through a bed of Celite. The filtrate was dried (Na$_2$SO$_4$) and concentrated in vacuo to give 1,5-dimethyl-1H-pyrazol-3-amine as a light brown solid (1.36 g 87%). $^1$H NMR (400 MHz, DMSO-d$_6$): δ=5.19 (s, 1H), 4.33 (br.s., 2H), 3.43 (s, 3H), 2.07 (s, 3H). LCMS (m/z): 112.3 (M+1)$^+$ 1-methyl-5-(trifluoromethyl)-1H-pyrazol-3-amine

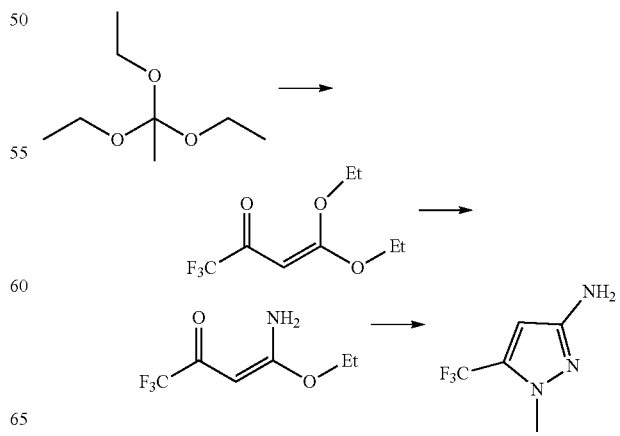

A solution of 1,1,1-triethoxyethane (20 g, 123 mmol) in DCM (250 mL) and pyridine (20.5 g, 259 mmol) was cooled to 0° C. A solution of trifluoroacetic anhydride (52 g, 246 mmol) in DCM (50 mL) was added drop-wise over a period of 30 min. The reaction mixture was warmed to ambient temperature, stirred for 12 h, then diluted with sat. aq. NaHCO$_3$ solution and extracted with DCM (2×250 mL). The combined organics were washed with water (20 mL), brine (20 mL), dried (Na$_2$SO$_4$) and concentrated in vacuo to give 4,4-diethoxy-1,1,1-trifluorobut-3-en-2-one as a pale brown liquid (20 g, 76%). $^1$H NMR (400 MHz, CDCl$_3$): δ=4.93 (s, 1H), 4.39 (q, J=7.2 Hz, 2H), 4.18 (q, J=7.2 Hz, 4H), 1.46-1.40 (m, 6H).

A solution of 4,4-diethoxy-1,1,1-trifluorobut-3-en-2-one (10 g, 47.16 mmol) in acetonitrile (100 mL) was treated with aqueous NH$_3$ solution (15 mL) at 0° C. then stirred at RT for 12 h. The reaction mixture was concentrated in vacuo then the residue was treated with water (250 mL) and extracted with DCM (2×250 mL). The combined organics were washed with water (250 mL), brine (250 mL), dried (Na$_2$SO$_4$) and concentrated in vacuo to give (E)-4-amino-4-ethoxy-1,1,1-trifluorobut-3-en-2-one as an off white solid (7.5 g, 87%). $^1$H NMR (300 MHz, CDCl$_3$): δ=5.6 (br.s., 1H), 4.17 (q, J=7.2 Hz, 2H), 1.42 (t, J=7.2 Hz, 3H).

A solution of (E)-4-amino-4-ethoxy-1,1,1-trifluorobut-3-en-2-one (5 g, 27.3 mmol) in EtOH (30 mL) was treated with methylhydrazine sulphate (4.72 g, 32.8 mmol) and Et$_3$N (4.1 g, 41.0 mmol) at ambient temperature. The resulting reaction mixture was heated at 85° C. for 12 h then cooled to ambient temperature and concentrated in vacuo. The residue obtained was diluted with sat. aq. NaHCO$_3$ solution (250 mL) and extracted with EtOAc (2×250 mL). The combined organics were washed with water (250 mL), brine (250 mL), dried (Na$_2$SO$_4$) and concentrated in vacuo. The crude product was purified by column chromatography on silica gel using 20% EtOAc-hexanes eluent to give 1-methyl-5-(trifluoromethyl)-1H-pyrazol-3-amine as a pale brown liquid (0.17 g, 38%). $^1$H NMR (400 MHz, CDCl$_3$): δ=5.93 (s, 1H), 3.79 (s, 3H), 3.68 (br.s., 2H).

1-methyl-5-(prop-1-en-2-yl)-1H-pyrazol-3-amine

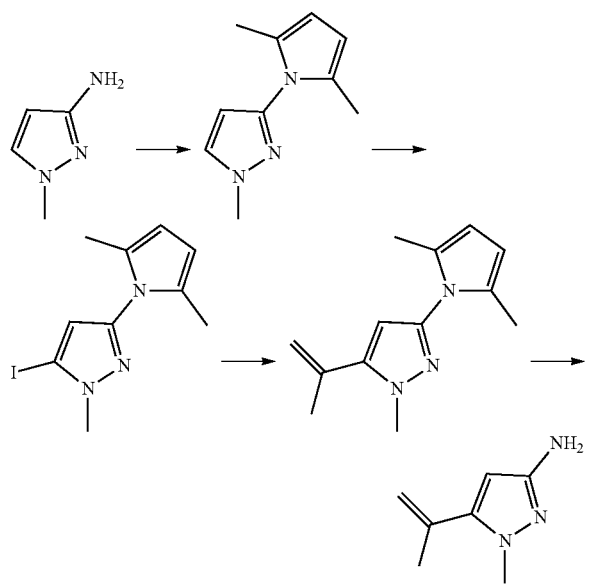

A solution of 1-methyl-1H-pyrazol-3-amine (2 g, 20.6 mmol) in AcOH (50 mL) was treated with 2,5-hexane dione (4.9 g, 43.29 mmol) at ambient temperature under nitrogen atmosphere. The resulting reaction mixture was heated to 100° C. for 1 h then stirred at ambient temperature for 5 h. The reaction mixture was concentrated under reduced pressure and azeotroped with toluene. The crude product was purified by column chromatography on silica gel using 10% EtOAc-hexanes eluent to give 3-(2,5-dimethyl-1H-pyrrol-1-yl)-1-methyl-1H-pyrazole as a liquid (2.5 g, 69%). $^1$H NMR (300 MHz, CDCl$_3$): δ=7.39 (d, J=2.1 Hz, 1H), 6.15 (d, J=2.4 Hz, 1H), 5.84 (s, 2H), 3.92 (s, 3H), 2.10 (s, 6H).

A solution of 3-(2,5-dimethyl-1H-pyrrol-1-yl)-1-methyl-1H-pyrazole (1 g, 5.71 mmol) in dry THF (10 mL) was cooled to −78° C. under nitrogen atmosphere, n-BuLi (1.6 M in hexanes, 4.4 mL, 6.86 mmol) was added drop-wise to the above solution over a period of 10 minutes then stirred at −78° C. for 1 h before treating with a solution of I$_2$ (1.54 g, 5.71 mmol) in THF (5 mL) at −78° C. stirring was continued at this temperature until completion (2 h). The reaction mixture was quenched with sat. aq. NH$_4$Cl solution and extracted with ethyl acetate (2×25 mL). The combined organics were washed with water (20 mL), brine (20 mL), dried (Na$_2$SO$_4$) and concentrated in vacuo. The crude product was purified by column chromatography on silica gel using 50% EtOAc-hexanes eluent to give 3-(2,5-dimethyl-1H-pyrrol-1-yl)-5-iodo-1-methyl-1H-pyrazole as an off-white solid (0.75 g, 43.6%). $^1$H NMR (400 MHz, CDCl$_3$): δ=6.33 (s, 1H), 5.84 (s, 2H), 3.95 (s, 3H), 2.09 (s, 6H).

A solution of 3-(2,5-dimethyl-1H-pyrrol-1-yl)-5-iodo-1-methyl-1H-pyrazole (1 g, 3.32 mmol) in DME:water (8:2, 10 mL) was treated with 4,4,5,5-tetramethyl-2-(prop-1-en-2-yl)-1,3,2-dioxaborolane (0.67 g, 3.98 mmol) and Na$_2$CO$_3$ (0.52 g, 4.98 mmol) at ambient temperature under nitrogen atmosphere. The resulting solution was degassed by purging with argon for 15 min then treated with Pd(PPh$_3$)$_4$ (190 mg, 0.166 mmol) under argon atmosphere. The resulting mixture was heated at 90° C. for 24 h then cooled to ambient temperature and concentrated in vacuo. The residue obtained was diluted with cold water (20 mL) and extracted with EtOAc (2×20 mL). The combined organics were washed with water (20 mL), brine (20 mL), dried (Na$_2$SO$_4$) and concentrated in vacuo. The crude product was purified by column chromatography on silica gel using 5% EtOAc-hexanes eluent to give 3-(2,5-dimethyl-1H-pyrrol-1-yl)-1-methyl-5-(prop-1-en-2-yl)-1H-pyrazole as a pale-yellow liquid (0.765 g, 92%). $^1$H NMR (300 MHz, CDCl$_3$): δ=6.08 (s, 1H), 5.84 (s, 2H), 5.39 (s, 1H), 5.23 (s, 1H), 3.92 (s, 3H), 2.12 (s, 9H).

A solution of 3-(2,5-dimethyl-1H-pyrrol-1-yl)-1-methyl-5-(prop-1-en-2-yl)-1H-pyrazole (0.7 g, 3.25 mmol) in EtOH—H$_2$O (8:2, 12 mL) was treated with NH$_2$OH.HCl (2.26 g, 32.55 mmol) and KOH (1.8 g, 32.55 mmol). The resulting reaction mixture was heated at 100° C. for 48 h. The reaction mixture was cooled and concentrated in vacuo. The residue was treated with saturated NaHCO$_3$ to give a solution of pH-8 then extracted with EtOAc (2×50 mL). The combined organics were washed with water (20 mL), brine (20 mL), dried (Na$_2$SO$_4$) and concentrated in vacuo. The crude product was purified by column chromatography on silica gel using 100% EtOAc eluent to give 1-methyl-5-(prop-1-en-2-yl)-1H-pyrazol-3-amine as a light brown liquid (0.4 g, 91%). $^1$H NMR (400 MHz, CDCl$_3$): δ=5.54 (s, 1H), 5.27 (s, 1H), 5.08 (s, 1H), 3.71 (s, 3H), 2.41 (s, 2H), 1.92 (s, 3H).

123

Ethyl 1-benzyl-3-nitro-1H-pyrazole-5-carboxylate

124

Ethyl 1-benzyl-3-nitro-1H-pyrazole-5-carboxylate

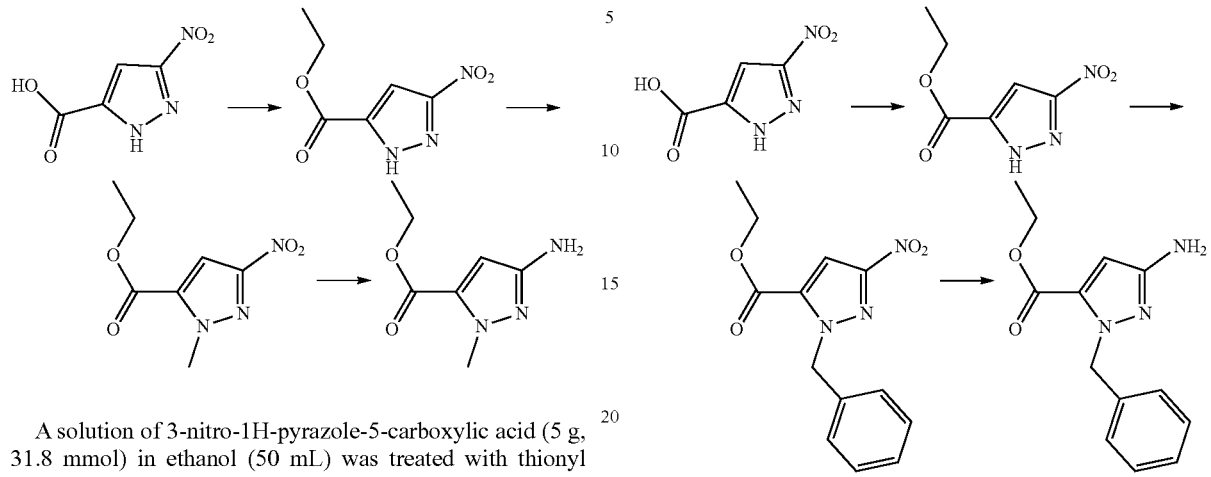

A solution of 3-nitro-1H-pyrazole-5-carboxylic acid (5 g, 31.8 mmol) in ethanol (50 mL) was treated with thionyl chloride (4.5 g, 38.2 mmol) drop wise over a period of 10 min at 0° C. under a nitrogen atmosphere. The resulting mixture was stirred at 80° C. for 6 h then cooled to ambient temperature and concentrated in vacuo. The residue obtained was basified to pH 8 with saturated NaHCO$_3$ solution before extracting with ethyl acetate (2×100 mL). The combined organics were washed with water (100 mL), brine (100 mL), dried (Na$_2$SO$_4$) and concentrated in vacuo. The crude product was triturated with diethyl ether, filtered and dried under reduced pressure to give ethyl 3-nitro-1H-pyrazole-5-carboxylate as a white solid (5 g, 85%). $^1$H NMR (400 MHz, DMSO-d$_6$): δ=7.44 (s, 1H), 4.36 (q, J=6.8 Hz, 2H), 1.33 (t, J=7.2 Hz, 3H). LCMS (m/z): 184 (M−1)$^-$.

Ethyl 3-nitro-1H-pyrazole-5-carboxylate (1 g, 5.4 mmol) was dissolved in DMF (10 mL) at ambient temperature and treated with K$_2$CO$_3$ (1.34 g, 9.7 mmol). The resulting mixture was cooled to 0° C. and methyl iodide (1.15 g, 8.1 mmol) was added drop-wise, the reaction mixture was sealed, allowed to warm to ambient temperature and stirred for 12 h. The reaction mixture was diluted with water (20 mL) and extracted with EtOAc (2×30 mL). The combined organics were washed with water (30 mL), brine (30 mL), dried (Na$_2$SO$_4$) and concentrated in vacuo. The crude product was purified by column chromatography on silica gel using 5% EtOAc-hexanes eluent to give ethyl 1-methyl-3-nitro-1H-pyrazole-5-carboxylate as a white solid (0.65 g, 61%). $^1$H NMR (400 MHz, DMSO-d$_6$) δ=7.54 (s, J=1.1 Hz, 1H), 4.35 (q, J=7.1 Hz, 2H), 4.19 (d, J=1.2 Hz, 3H), 1.33 (t, J=7.1 Hz, 3H).

Ethyl 1-methyl-3-nitro-1H-pyrazole-5-carboxylate (0.65 g, 3.3 mmol) was dissolved in THF (20 mL) and MeOH (5 mL) at 0° C. Zinc powder (1.0 g, 16.3 mmol) and aqueous NH$_4$Cl (0.87 g, 16.3 mmol) were added sequentially. The resulting reaction mixture was stirred at ambient temperature for 4 h, then heated to 70 C for 1 hour. The solvents were removed in vacuo. The residue obtained was dissolved in EtOAc (30 mL) and filtered through a bed of Celite. The filtrate was washed with water (30 mL), brine (30 mL), dried (Na$_2$SO$_4$) and concentrated in vacuo to give ethyl 3-amino-1-methyl-1H-pyrazole-5-carboxylate as a white solid (0.5 g, 91%). $^1$H NMR (400 MHz, DMSO-d$_6$) δ 5.95 (s, 1H), 4.24 (q, J=7.1 Hz, 2H), 3.83 (s, 3H), 3.41 (s, 2H), 1.27 (t, J=7.1 Hz, 4H).

A solution of 3-nitro-1H-pyrazole-5-carboxylic acid (5 g, 31.8 mmol) in ethanol (50 mL) was treated with thionyl chloride (4.5 g, 38.2 mmol) drop wise over a period of 10 min at 0° C. under a nitrogen atmosphere. The resulting mixture was stirred at 80° C. for 6 h then cooled to ambient temperature and concentrated in vacuo. The residue obtained was basified to pH 8 with saturated NaHCO$_3$ solution before extracting with ethyl acetate (2×100 mL). The combined organics were washed with water (100 mL), brine (100 mL), dried (Na$_2$SO$_4$) and concentrated in vacuo. The crude product was triturated with diethyl ether, filtered and dried under reduced pressure to give ethyl 3-nitro-1H-pyrazole-5-carboxylate as a white solid (5 g, 85%). $^1$H NMR (400 MHz, DMSO-d$_6$): δ=7.44 (s, 1H), 4.36 (q, J=6.8 Hz, 2H), 1.33 (t, J=7.2 Hz, 3H). LCMS (m/z): 184 (M−1)$^-$.

Ethyl 3-nitro-1H-pyrazole-5-carboxylate (2 g, 10.8 mmol) was dissolved in DMF (10 mL) at ambient temperature and treated with K$_2$CO$_3$ (3 g, 21.6 mmol). The resulting mixture was cooled to 0° C. and benzyl bromide (2.7 g, 16.2 mmol) was added drop-wise, the reaction mixture was allowed to warm to ambient temperature and stirred for 2 h. The reaction mixture was diluted with water (20 mL) and extracted with EtOAc (2×30 mL). The combined organics were washed with water (30 mL), brine (30 mL), dried (Na$_2$SO$_4$) and concentrated in vacuo. The crude product was purified by column chromatography on silica gel using 5% EtOAc-hexanes eluent to give ethyl 1-benzyl-3-nitro-1H-pyrazole-5-carboxylate as a white solid (1.2 g, 40%). $^1$H NMR (400 MHz, CDCl$_3$): δ=7.44 (s, 1H), 7.34-7.31 (m, 5H), 5.83 (s, 2H), 4.39 (q, J=7.2 Hz, 2H), 1.38 (t, J=7.2 Hz, 3H). LCMS (m/z): 276.15 (M+1)$^+$.

Ethyl 1-benzyl-3-nitro-1H-pyrazole-5-carboxylate (1.2 g, 4.36 mmol) was dissolved in THF (20 mL) and MeOH (5 mL) at 0° C. Zinc powder (1.4 g, 21.8 mmol) and aqueous NH$_4$Cl (1.16 g, 21.8 mmol) were added sequentially. The resulting reaction mixture was stirred at ambient temperature for 4 h, then concentrated in vacuo. The residue obtained was dissolved in EtOAc (30 mL) and filtered through a bed of Celite. The filtrate was washed with water (30 mL), brine (30 mL), dried (Na$_2$SO$_4$) and concentrated in vacuo to give ethyl 3-amino-1-benzyl-1H-pyrazole-5-carboxylate as a white solid (1 g, 94%). $^1$H NMR (300 MHz, DMSO-d$_6$): δ=7.30-7.19 (m, 3H), 7.11-7.08 (m, 2H), 6.00

(s, 1H), 5.43 (s, 2H), 4.91 (s, 2H), 4.23 (q, J=7.2 Hz, 2H), 1.24 (t, J=7.2 Hz, 3H). LCMS (m/z): 245.9 (M+1)$^+$.

3-(2,5-dimethyl-1H-pyrrol-1-yl)-1-phenyl-1H-pyrazole

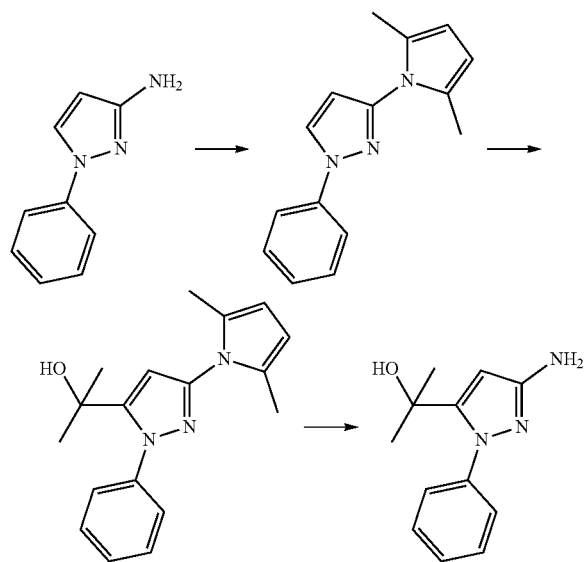

A solution of 1-phenyl-1H-pyrazol-3-amine (3.5 g, 21.9 mmol) in acetic acid (20 mL) was treated with 2,5-hexadione (5.2 g, 45.9 mmol) and heated to 100° C. for 4 h. The mixture was cooled and concentrated in vacuo. The crude product was purified by column chromatography on silica gel using 5% EtOAc-hexanes eluent to give 3-(2,5-dimethyl-1H-pyrrol-1-yl)-1-phenyl-1H-pyrazole as a colorless liquid (2.8 g, 54%). $^1$H NMR (400 MHz, CDCl$_3$): δ=7.98 (s, 1H), 7.74 (d, J=8.4 Hz, 2H), 7.49 (d, J=8.4 Hz, 2H), 7.32 (t, J=7.6 Hz, 1H), 6.39 (s, 1H), 5.9 (s, 2H), 2.19 (s, 6H).

A solution of 3-(2,5-dimethyl-1H-pyrrol-1-yl)-1-phenyl-1H-pyrazole (2.7 g, 11.4 mmol) in THF (70 mL) at −78° C. was treated drop-wise with n-BuLi (1.6 M in THF, 10 mL, 23.91 mmol) over 10 min. The reaction mixture was stirred at −78° C. for 1.5 h then treated with freshly dried acetone (1 g, 17.0 mmol) and stirring continued at −78° C. for 1.5 h. The reaction mixture was quenched with sat. ammonium chloride (2 mL), concentrated in vacuo then partitioned between water (100 mL) and ethyl acetate (100 mL). The organic extract was washed with water (100 mL), brine (100 mL), dried (Na$_2$SO$_4$) and concentrated in vacuo. The crude product was purified by column chromatography on silica gel using 20% EtOAc-hexanes eluent to give 2-(3-(2,5-dimethyl-1H-pyrrol-1-yl)-1-phenyl-1H-pyrazol-5-yl)propan-2-ol as an off white solid (1.4 g, 42%). $^1$H NMR (400 MHz, CDCl$_3$): δ=7.57-7.56 (m, 2H), 7.47-7.46 (m, 3H), 6.23 (s, 1H), 5.85 (s, 2H), 2.19 (s, 6H), 1.52 (s, 6H). LCMS (m/z): 296.1 (M+1)$^+$.

In an 100 mL re-sealable reaction tube, 2-(3-(2,5-dimethyl-1H-pyrrol-1-yl)-1-phenyl-1H-pyrazol-5-yl)propan-2-ol (1.4 g, 4.74 mmol) was dissolved in EtOH—H$_2$O (1:1, 50 mL) at ambient temperature. Hydroxyl amine hydrochloride (3.3 g, 47.45 mmol), and KOH (2.6 g, 47.45 mmol) were added sequentially and resulting reaction mixture was heated at 120° C. for 16 h. The reaction mixture was concentrated in vacuo, diluted with water (50 mL) and extracted with ethyl acetate (2×50 mL). The organic extracts were washed with water (50 mL), brine (50 mL), dried (Na$_2$SO$_4$) and concentrated in vacuo. The crude product was purified by column chromatography on silica gel using 50% EtOAc-hexanes eluent to give 2-(3-amino-1-phenyl-1H-pyrazol-5-yl)propan-2-ol as a colorless liquid (0.8 g, 78%). LCMS (m/z): 218.1 (M+1)$^+$.

8-bromo-1,2,3,5,6,7-hexahydro-s-indacen-4-amine

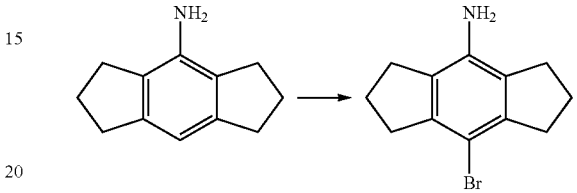

N-Bromosuccinimide (1.02 g, 5.78 mmol) was added portion-wise to a solution of 1,2,3,5,6,7-hexahydro-s-indacen-4-amine (1 g, 5.78 mmol) in DCM (20 mL) at 0° C. The solution was gradually warmed to ambient temperature and stirred for 12 h. The reaction mixture was diluted with sat. aqueous Na$_2$S$_2$O$_3$ (50 mL) and extracted with DCM (2×25 mL). The combined organic extracts were washed with water (25 mL), brine (25 mL), dried (Na$_2$SO$_4$) and concentrated in vacuo. The crude product was purified by column chromatography on silica gel using 5% EtOAc-hexane eluent to give 8-bromo-1,2,3,5,6,7-hexahydro-s-indacen-4-amine as a brown solid (1.2 g, 83%). $^1$H NMR (300 MHz, CDCl$_3$): δ=3.45 (br.s., 2H), 2.92-2.88 (m, 4H), 2.81-2.77 (m, 4H), 2.16-2.09 (m, 4H); LC-MS 94% (210 nM); m/z 252.15 [M+H]$^+$.

8-chloro-1,2,3,5,6,7-hexahydro-s-indacen-4-amine

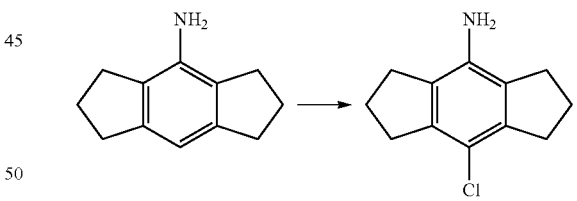

N-Chlorosuccinimide (0.46 g, 3.46 mmol) was added portion-wise to a solution of 1,2,3,5,6,7-hexahydro-s-indacen-4-amine, 1 (0.6 g, 3.46 mmol) in CHCl$_3$ (10 mL) at 0° C. The solution was gradually warmed to ambient temperature and stirred for 10 h. The reaction mixture was diluted with sat. aqueous Na$_2$S$_2$O$_3$ (50 mL) and extracted with DCM (2×25 mL). The combined organic extracts were washed with water (25 mL), brine (25 mL), dried (Na$_2$SO$_4$) and concentrated in vacuo. The crude product was purified by column chromatography on silica gel using 10% EtOAc-hexane eluent to give 8-chloro-1,2,3,5,6,7-hexahydro-s-indacen-4-amine as a brown solid (0.45 g, 63%). $^1$H NMR (300 MHz, CDCl$_3$): δ=2.94 (t, J=7.2 Hz, 4H), 2.77 (t, J=8.1 Hz, 4H), 2.18 (m, 4H); m/z 207.8 [M+H]$^+$.

8-methyl-1,2,3,5,6,7-hexahydro-s-indacen-4-amine

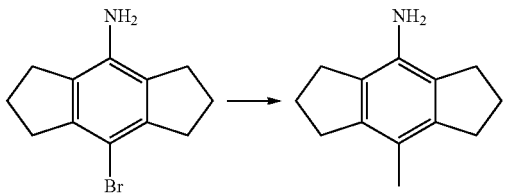

8-Bromo-1,2,3,5,6,7-hexahydro-s-indacen-4-amine (400 mg, 1.59 mmol) was dissolved in 1,4-dioxane-water (8:2, 10 mL) and the reaction flask purged with argon gas for 15 min. $K_2CO_3$ (650 mg, 4.78 mmol), methyl boronic acid (100 mg, 1.75 mmol) and $Pd(PPh_3)_4$ (100 mg, 0.079 mmol) were sequentially added under argon atmosphere. The resulting mixture was sealed and heated at 100° C. for 2 h. The reaction mixture was cooled, diluted with water and extracted using EtOAc (2×20 mL). The combined organic extracts were washed with water (25 mL), brine (25 mL), dried ($Na_2SO_4$) and concentrated in vacuo. The crude product was purified by column chromatography on silica gel using 5% EtOAc-hexane eluent to give 8-methyl-1,2,3,5,6,7-hexahydro-s-indacen-4-amine as a colorless liquid (0.220 g, 76%). $^1$H NMR (400 MHz, $CDCl_3$): δ=3.41 (br.s., 2H), 2.88-2.8 (m, J=7.5 Hz, 4H), 2.75-2.67 (m, 4H), 2.18-2.09 (m, 7H); m/z 188.2 $[M+H]^+$.

3,5,6,7-tetrahydro-2H-indeno[5,6-b]furan-8-amine

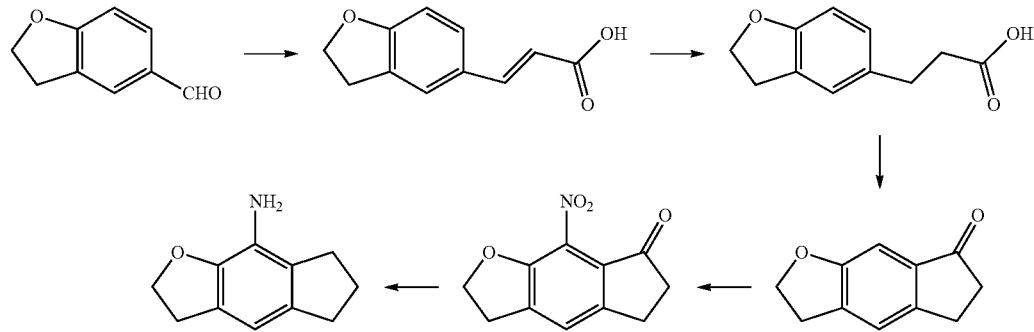

A solution of 2,3-dihydrobenzofuran-5-carbaldehyde (10 g, 67.6 mmol), malonic acid (10.5 g, 101.35 mmol) and piperidine (0.47 mL, 4.73 mmol, 0.07 eq) was heated in pyridine (60 m L) at 100° C. for 5 h. The reaction mixture was acidified to ~pH 3 using 1N HCl and the product extracted using 10% IPA/chloroform (2×250 mL). The combined organic extracts were washed with water (250 mL), brine (250 mL), dried ($Na_2SO_4$) and concentrated in vacuo. The crude product was triturated using diethyl ether to give (E)-3-(2,3-dihydrobenzofuran-5-yl)acrylic acid as a yellow solid (10 g, 78%). $^1$H NMR (300 MHz, Chloroform-d) δ=7.73 (d, J=15.9 Hz, 1H), 7.43 (s, 1H), 7.33 (dd, J=8.1, 1.8 Hz, 1H), 6.80 (d, J=8.1 Hz, 1H), 6.29 (d, J=15.9 Hz, 1H), 4.64 (t, J=8.7 Hz, 2H), 3.24 (t, J=8.7 Hz, 2H).

A solution of (E)-3-(2,3-dihydrobenzofuran-5-yl)acrylic acid (8.0 g, 42.1 mmol) in acetic acid (80 mL) and water (1.0 mL) was treated with 10% palladium on carbon (1.0 g) in two portions. The reaction mixture was stirred under an atmosphere or hydrogen gas (balloon) until completion, typically 4 h. The mixture was diluted using ethyl acetate (100 mL) and filtered through a bed of celite washing through with further ethyl acetate. The solvents were removed in vacuo and the crude residue azeotroped using toluene (2×50 mL) to give an off white solid which was triturated using diethyl ether (50 mL) to give 3-(2,3-dihydrobenzofuran-5-yl)propanoic acid as a white solid (6.5 g, 80%). $^1$H NMR (400 MHz, $CDCl_3$) δ=7.04 (s, 1H), 6.93 (d, J=8.4, 1H), 6.7 (d, J=8.4 Hz, 1H), 4.55 (t, J=8.4 Hz, 2H), 3.18 (t, J=8.4 Hz, 2H), 2.89 (t, J=7.6 Hz, 2H), 2.64 (t, J=7.6 Hz, 2H).

A solution of 3-(2,3-dihydrobenzofuran-5-yl)propanoic acid (6.0 g, 31 mmol) in thionyl chloride (8 mL) was heated at 80° C. for 1 h. On completion of the reaction the thionyl chloride was removed in vacuo and the crude 3-(2,3-dihydrobenzofuran-5-yl)propanoyl chloride dissolved in anhydrous 1,2-dichloroethane (30 mL). In a separate flask aluminium trichloride (2 g, 15 mmol) was added to anhydrous 1,2-dichloroethane (40 mL) at 0° C. followed by the acid chloride solution (10 mL) drop-wise over 5 min and the resulting solution was stirred for 30 min at 0° C. A further portion of aluminium trichloride (3 g, 22.5 mmol) was added followed by drop-wise addition of the remaining acid chloride solution (20 mL) at 0° C. The reaction mixture was stirred at room temperature for 1 h or until completion, diluted with water and extracted using EtOAc (2×50 mL). The combined organic extracts were washed with 1N HCl (50 mL), 1N NaOH (50 mL), water (25 mL), brine (25 mL), dried ($Na_2SO_4$) and concentrated in vacuo. The crude product was purified by column chromatography on silica gel using 10% EtOAc-hexanes eluent to give 2,3,5,6-tetrahydro-7H-indeno[5,6-b]furan-7-one as a white solid (3.8 g, 70%). $^1$H NMR (300 MHz, $CD_3OD$) δ=7.36 (s, 1H), 6.91 (s, 1H), 4.61 (t, J=8.6 Hz, 3H), 3.26 (t, J=8.6 Hz, 2H), 3.05 (t, J=5.5 Hz, 3H), 2.68 (t, J=5.5 Hz, 2H).

2,3,5,6-tetrahydro-7H-indeno[5,6-b]furan-7-one (1.5 g, 8.61 mmol) was dissolved in $c.H_2SO_4$ (6.0 mL) at 0° C. followed by drop-wise addition of $f.HNO_3:c.H_2SO_4$, 1:1 (1.2 mL) stirring was continued at 0° C. for 1 h. The reaction mixture was added to ice-cold water (60 mL) and stirred for 10 min, the resulting light brown ppt was removed by filtration, washed with ice cold water (20 mL) and dried in vacuo to give 8-nitro-2,3,5,6-tetrahydro-7H-indeno[5,6-b]furan-7-one (1.2 g, 64%). $^1$H NMR (300 MHz, $CD_3OD$) δ=7.54 (s, 1H), 4.80 (t, J=8.6 Hz, 2H), 3.42 (t, J=8.6 Hz, 2H), 3.09 (t, J=5.6 Hz, 2H), 2.74 (t, J=5.6 Hz, 2H).

A solution of 8-nitro-2,3,5,6-tetrahydro-7H-indeno[5,6-b]furan-7-one (1.0 g, 4.57 mmol) in methanol (20 mL) 0° C. was treated with methane sulfonic acid (0.2 mL) followed by 20% palladium hydroxide (0.5 g). The reaction mixture was stirred under an atmosphere or hydrogen gas at 60 psi until completion. The reaction mixture was filtered through a bed of celite washing through with methanol (50 mL) and concentrated in vacuo. The residue was diluted with ethyl acetate (50 mL) and washed using sat. aq. NaHCO3 (50 mL), water (20 mL), brine (20 mL), dried (Na$_2$SO$_4$) and concentrated in vacuo. The crude product was purified by column chromatography on silica gel using 10% EtOAc-hexanes eluent to give 3,5,6,7-tetrahydro-2H-indeno[5,6-b]furan-8-amine as a white solid (0.5 g, 63%). $^1$H NMR (300 MHz, CDCl$_3$) δ=6.54 (s, 1H), 5.30 (s, 2H), 4.61 (t, J=8.7 Hz, 2H), 3.21 (t, J=8.7 Hz, 2H), 2.95 (t, J=5.5 Hz, 2H), 2.66 (t, J=5.5 Hz, 2H).

4-bromo-3,5,6,7-tetrahydro-2H-indeno[5,6-b]furan-8-amine

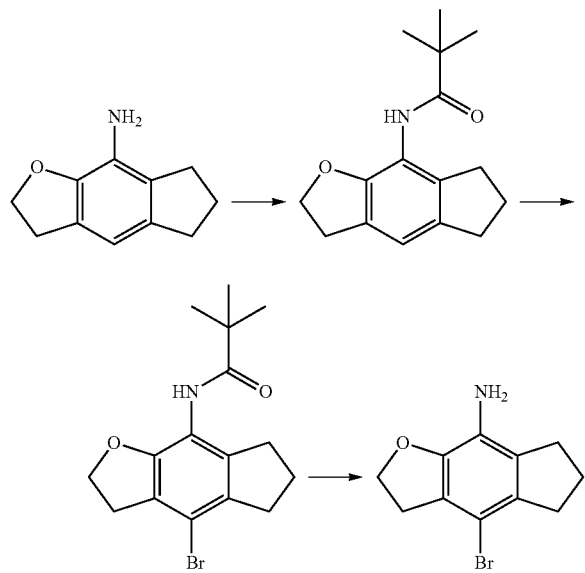

3,5,6,7-tetrahydro-2H-indeno[5,6-b]furan-8-amine (0.5 g, 2.86 mmol) and triethylamine (0.51 mL, 3.71 mmol) in dichloromethane (6.0 mL) at 0° C. was treated drop-wise with a solution of pivolyl chloride (0.41 g, 3.43 mmol) in DCM (4.0 mL). The reaction was stirred at ambient temperature for 6 h. The reaction mixture was added to sat. aq. NaHCO$_3$ (30 mL), and extracted using DCM (2×25 mL). The combined organics were washed with water (25 mL), brine (25 mL), dried (Na$_2$SO$_4$) and concentrated in vacuo to give N-(3,5,6,7-tetrahydro-2H-indeno[5,6-b]furan-8-yl) pivalamide as a white solid (0.55 g, 74%). $^1$H NMR (300 MHz, Chloroform-d) δ=6.91 (s, 1H), 4.56 (t, J=8.6 Hz, 2H), 3.17 (t, J=8.6 Hz, 2H), 2.83 (t, J=7.4 Hz, 2H), 2.75 (t, J=7.4 Hz, 2H), 2.04 (p, J=7.4 Hz, 2H), 1.32 (s, 9H).

N-(3,5,6,7-tetrahydro-2H-indeno[5,6-b]furan-8-yl)pivalamide (0.55 g, 2.12 mmol) in acetic acid (10 mL) was treated drop-wise with a solution of bromine (0.4 g, 2.55 mmol) in acetic acid (2.0 mL) and the reaction stirred at ambient temperature for 3 h. Ice cold water was added to the reaction mixture and stirred for 10 min. The resulting precipitate was removed by filtration, washed with water (20 mL) and dried in vacuo to give N-(4-bromo-3,5,6,7-tetrahydro-2H-indeno [5,6-b]furan-8-yl)pivalamide as a pale-brown solid (0.65 g, 91%). $^1$H NMR (300 MHz, Chloroform-d) δ=6.94 (s, 1H), 4.61 (t, J=8.7 Hz, 2H), 3.18 (t, J=8.7 Hz, 2H), 2.92-2.80 (m, 4H), 2.06 (p, J=7.4 Hz, 2H), 1.31 (s, 9H).

N-(4-bromo-3,5,6,7-tetrahydro-2H-indeno[5,6-b]furan-8-yl)pivalamide (0.6 g, 1.78 mmol) in EtOH (10 mL) and cHCl (15 mL) was heated at 90° C. for 36 h. The solution was concentrated in vacuo then basified using aq NH$_4$OH solution. The aqueous phase was extracted using ethyl acetate (2×20 mL) and the combined organics dried (Na$_2$SO$_4$) and concentrated in vacuo to give 4-bromo-3,5,6,7-tetrahydro-2H-indeno[5,6-b]furan-8-amine as a brown solid (0.3 g, 67%). H NMR (400 MHz, Chloroform-d) δ=4.61 (t, J=8.6 Hz, 2H), 3.49 (s, 2H), 3.17 (t, J=8.6 Hz, 2H), 2.84 (t, J=7.4 Hz, 2H), 2.78 (t, J=7.4 Hz, 2H), 2.12 (p, J=7.4 Hz, 2H).

3,5,6,7-tetrahydro-2H-indeno[5,6-b]furan-4-amine

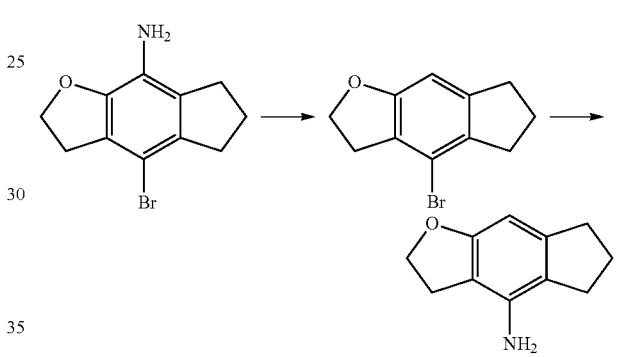

3,5,6,7-tetrahydro-2H-indeno[5,6-b]furan-8-amine (0.5 g, 1.98 mmol) in ethanol (10 mL) and acetic acid (1.5 mL) was treated with a solution of sodium nitrate (1.3 g, 19.8 mmol) in water (3.0 mL) and the reaction stirred at ambient temperature for 4 h. The ethanol was removed in vacuo then the residue diluted with water (30 mL), extracted using 10% IPA/chloroform (2×25 mL), dried (Na$_2$SO$_4$) and concentrated in vacuo. The crude product was purified by column chromatography on silica gel using 5% EtOAc-hexanes eluent to give 4-bromo-3,5,6,7-tetrahydro-2H-indeno[5,6-b] furan as a yellow solid (0.28 g, 60%).

4-bromo-3,5,6,7-tetrahydro-2H-indeno[5,6-b]furan (0.28 g, 1.18 mmol) in DMSO (10 mL) was treated with copper iodide (0.22 g, 1.18 mmol), L-proline (0.21 g, 1.88 mmol) and sodium azide (0.19 g, 2.94 mmol). The reaction mixture was heated in a sealed tube at 135° C. for 36 h. The reaction mixture was cooled, diluted with water and extracted using EtOAc (2×25 mL). The combined organic extracts were washed with water (25 mL), brine (25 mL), dried (Na$_2$SO$_4$) and concentrated in vacuo. The crude product was purified by column chromatography on silica gel using 10% EtOAc-hexanes eluent to give 3,5,6,7-tetrahydro-2H-indeno[5,6-b] furan-4-amine as a grey solid (0.17 g, 85%). $^1$H NMR (300 MHz, Chloroform-d) δ=6.21 (s, 1H), 4.59 (t, J=8.5 Hz, 2H), 3.51 (s, 1H), 2.98 (t, J=8.5 Hz, 2H), 2.83 (t, J=7.5 Hz, 2H), 2.64 (t, J=7.5 Hz, 2H), 2.10 (p, J=7.5 Hz, 2H).

benzo[1,2-b:4,5-b']difuran-4-amine

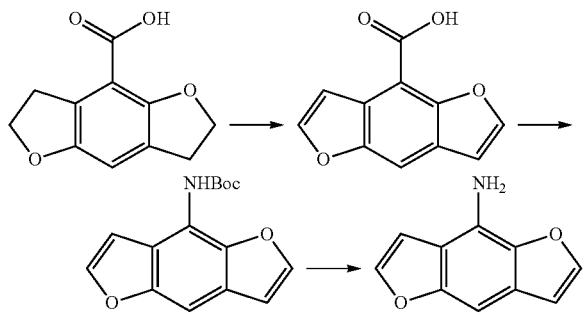

2,3,6,7-tetrahydrobenzo[1,2-b:4,5-b']difuran-4-carboxylic acid (0.8 g, 3.88 mmol), 2,3-dichloro-5,6-dicyanobenzoquinone (2.64 g, 11.65 mmol) in anhydrous dioxane (20 mL) was heated in a sealed tube at 120° C. for 18 h. The reaction mixture was cooled to room temperature and sat. aq. $Na_2S_2O_3$ (30 mL) added before extraction with ethyl acetate (2×25 mL). The combined organics dried ($Na_2SO_4$) and concentrated in vacuo to give the crude benzo[1,2-b:4,5-b']difuran-4-carboxylic acid (1.5 g). The crude acid (1.5 g), triethylamine (2.05 mL) and diphenylphosphoryl azide (4.08 g, 14.85 mmol) in tertiary butanol (20 mL) was heated in a sealed tube at 90° C. for 12 h. The solution was cooled to room temperature, diluted with water (50 mL) and extracted using EtOAc (2×50 mL). The combined organic extracts were washed with water (25 mL), brine (25 mL), dried ($Na_2SO_4$) and concentrated in vacuo. The crude product was purified by column chromatography on silica gel using 10% EtOAc-hexanes eluent to give tert-butyl benzo[1,2-b:4,5-b']difuran-4-ylcarbamate (0.75 g) with minor impurities from the phosphine reagent, the product was dissolved in DCM (10 mL) and TFA (3.0 mL) added drop-wise over 5 min at 0° C. The reaction was stirred at ambient temperature for 2 h then added carefully to sat. aq. $NaHCO_3$ (50 mL). The aqueous phase was extracted using DCM (2×30 mL) and the combined organic extracts were washed with water (25 mL), brine (25 mL), dried ($Na_2SO_4$) and concentrated in vacuo. The crude product was purified by column chromatography on silica gel using 10% EtOAc-hexanes eluent to give benzo[1,2-b:4,5-b']difuran-4-amine as an off-white solid (0.2 g, 30% over three steps). $^1$H NMR (400 MHz, $CDCl_3$): δ=7.6 (d, J=2.2 Hz, 1H), 7.53 (d, J=2.2 Hz, 1H), 7.12 (s, 1H), 6.78 (m, 2H), 4.17 (br.s., 1H).

3-(3-(trifluoromethyl)-3H-diazirin-3-yl)aniline

To a solution of 2,2,2-trifluoro-1-phenylethan-1-one (5 g, 28.7 mmol) in $c.H_2SO_4$ (10 mL) at −5° C. was added a solution of $c.H_2SO_4$ and $f.HNO_3$ (1:1, 16 mL) and the reaction mixture was stirred for 3 hours. The resulting solution was poured onto ice/water (100 mL) and extracted using ethyl acetate (2×100 mL). The combined organics were washed with water (100 mL), brine (100 mL), dried ($Na_2SO_4$) and concentrated in vacuo. The crude product was purified by column chromatography on silica gel using 20% EtOAc-hexanes eluent to give 2,2,2-trifluoro-1-(3-nitrophenyl)ethan-1-one as a yellow liquid (4.2 g, 67%). $^1$H NMR (400 MHz, $CDCl_3$) δ=8.92 (s, 1H), 8.59 (dd, J=8.1, 1.4 Hz, 1H), 8.41 (d, J=7.8 Hz, 1H), 7.82 (t, J=8.1 Hz, 1H). $^{19}$F NMR (233.33 MHz, $CDCl_3$): −71.82 (s, 3F).

A solution of 2,2,2-trifluoro-1-(3-nitrophenyl)ethan-1-one (4.2 g, 19.2 mmol), hydroxylamine hydrochloride (4.0 g, 57.5 mmol) and pyridine (25 mL) in ethanol (25 mL) were heated at reflux for 3 h. or until completion. The solvent was removed in vacuo and the crude product was purified by column chromatography on silica gel using 40% EtOAc-hexanes eluent to give 2,2,2-trifluoro-1-(3-nitrophenyl)ethan-1-one oxime as a colourless liquid (4.0 g, 89%). $^{19}$F NMR (233.33 MHz, $CDCl_3$): −66.42 and 62.28 (E and Z oxime).

To a solution of 2,2,2-trifluoro-1-(3-nitrophenyl)ethan-1-one oxime (4.0 g, 17.1 mmol) in dichloromethane (20 mL) was cooled to 0° C. treated with triethylamine (1.5 eq), N,N-dimethylamine pyridine (0.5 eq), tosylchloride (1.1 eq) and stirred at ambient temperature until completion, typically 16 h. The reaction mixture was diluted using dichloromethane (50 mL), washed with sat.aq. $NH_4Cl$ (100 mL), water (100 mL), brine (100 mL), dried ($Na_2SO_4$) and concentrated in vacuo. The crude product was purified by column chromatography on silica gel using 5% EtOAc-hexanes eluent to give 2,2,2-trifluoro-1-(3-nitrophenyl)ethan-1-one O-tosyl oxime as a white solid (4.0 g, 60%). $^1$H NMR (300 MHz, $CDCl_3$) δ=8.41 (ddd, J=5.6, 3.5, 2.2 Hz, 1H), 8.21 (t, J=1.5 Hz, 1H), 7.89 (d, J=8.3 Hz, 2H), 7.81-7.65 (m, 2H), 7.42 (d, J=7.8 Hz, 2H), 2.50 (s, 3H). $^{19}$F NMR (282 MHz, $cdcl_3$) δ−61.55, −66.90.

A solution of 2,2,2-trifluoro-1-(3-nitrophenyl)ethan-1-one O-tosyl oxime (4.0 g, 10.3 mmol) in diethyl ether was cooled to −78° C. and a solution of ammonia gas was bubbled through for 30 min. The reaction mixture was sealed, allowed to warm to ambient temperature then stirred for 16 h. The mixture was filtered through a pad of celite and concentrated in vacuo. The crude product was purified by column chromatography on silica gel using 7% EtOAc-

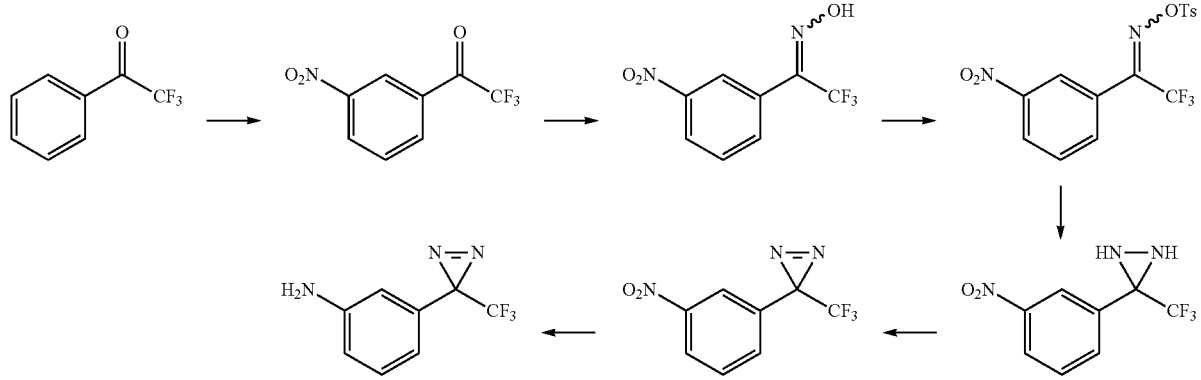

hexanes eluent to give 3-(3-nitrophenyl)-3-(trifluoromethyl) diaziridine as a colourless liquid (2.4 g, 100%). ¹H NMR (300 MHz, CDCl₃) δ=8.52 (t, J=2.0 Hz, 1H), 8.33 (ddd, J=8.3, 2.3, 1.1 Hz, 1H), 7.99 (d, J=8.0 Hz, 1H), 7.65 (tt, J=7.8, 0.4 Hz, 1H), 2.95 (d, J=8.8 Hz, 1H), 2.31 (d, J=8.9 Hz, 1H). 19F NMR (282 MHz, CDCl₃) δ=−75.10.

A solution of 3-(3-nitrophenyl)-3-(trifluoromethyl)diaziridine (2.4 g, 10.3 mmol) in methanol (30 mL) was treated with triethylamine (2 eq.) and iodine (1 eq.) and the reaction mixture stirred until completion, typically 2 h. The solution was diluted using diethyl ether, washed with 10% aq citric acid, water, aq. sodium thiosulfate, brine then dried (Na₂SO₄) and concentrated in vacuo. The crude product was purified by column chromatography on silica gel using 10% EtOAc-hexanes eluent to give 3-(3-nitrophenyl)-3-(trifluoromethyl)-3H-diazirine as a colourless liquid (2.1 g, 88%). ¹H NMR (300 MHz, CDCl₃) δ 8.30 (ddd, J=7.9, 2.2, 1.4 Hz, 1H), 8.09-8.01 (m, 1H), 7.70-7.54 (m, 2H). 19F NMR (282 MHz, CDCl₃) δ=−65.14.

3-(3-nitrophenyl)-3-(trifluoromethyl)-3H-diazirine (3.0 g, 13 mmol) in THF (70 mL) was treated with a solution of sodium dithionate (10 eq.) in water (30 mL) and the mixture was stirred at ambient temperature until completion, typically overnight. The solution was diluted using water, extracted using ethyl acetate (×2), washed with water, brine then dried (Na₂SO₄) and concentrated in vacuo. The crude product was purified by column chromatography on silica gel using 40% EtOAc-hexanes eluent to give the titled compound, 3-(3-(trifluoromethyl)-3H-diazirin-3-yl)aniline, as a yellow solid (1.5 g, 58%). ¹H NMR (300 MHz, CDCl₃) δ=7.16 (t, J=7.9 Hz, 1H), 6.70 (ddd, J=8.1, 2.3, 0.9 Hz, 1H), 6.52 (ddt, J=7.9, 1.9, 0.9 Hz, 1H), 6.45 br. (s, 1H), 3.77 (s, 2H). 19F NMR (282 MHz, CDCl₃) δ −65.07.

4,6-di-tert-butylpyrimidin-2-amine

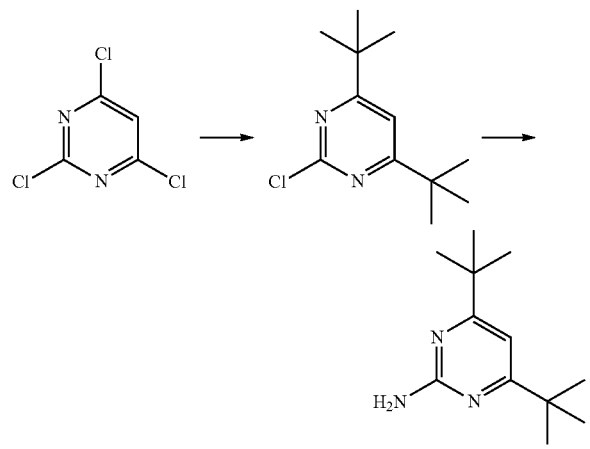

2,4,6-Trichloropyrimidine (2.7 g, 14.7 mmol) was dissolved in anhydrous THF (30 mL) at 0° C. under nitrogen atmosphere. CuI (280 mg, 1.47 mmol) was added to the aforementioned solution and subsequently treated with 2M tert-butylmagnesium chloride in THF (3.78 g, 16.15 mL, 32.3 mmol) at 0° C. under nitrogen atmosphere. The resulting mixture was stirred at RT for 3 h. Upon completion, the reaction mixture was diluted with saturated NH₄Cl solution and extracted with EtOAc (2×50 mL). The combined organic extract was washed with water, brine, dried (Na₂SO₄) and concentrated in vacuo. The crude product was purified by column chromatography on silica gel (60-120 mesh) using 100% hexanes eluent to give 4,6-di-tert-butyl-2-chloropyrimidine (1.3 g, 39%) as a pale brown liquid. ¹H NMR (300 MHz, CDCl₃): δ=7.20 (s, 1H), 1.33 (s, 18H). LCMS (m/z): 227.3 [M+H]⁺

In a 100 mL re-sealable reaction tube, a solution of 4,6-di-tert-butyl-2-chloropyrimidine (1.3 g) in EtOH (15 mL) was cooled to −50° C. Ammonia gas was purged through the aforementioned solution for 15 min. The reaction mixture was warmed to 70° C. and stirred for 12 h. Upon completion, the reaction mixture was concentrated in vacuo and the residue obtained was diluted with water and extracted with ethyl acetate (50 mL). The organic extract was washed with water, brine, dried (Na₂SO₄) and concentrated in vacuo to give 4,6-di-tert-butylpyrimidin-2-amine (0.7 g, 59%) as a white solid. ¹H NMR (300 MHz, CDCl₃): δ=6.64 (s, 1H), 4.83 (s, 2H), 1.26 (s, 18H). LCMS (m/z): 208.4 [M+H]⁺

4-chloro-2,6-diisopropylaniline

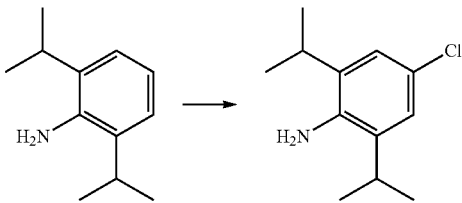

2,6-Diisopropylaniline (5.0 g, 28.2 mmol) in DMF (100 mL) was treated with N-chlorosuccinimide (3.97 g, 29.7 mmol) and the reaction mixture stirred at room temperature overnight. The solution was poured onto water (500 mL) and extracted using diethyl ether (2×150 mL). The combined organics were washed with water (2×200 mL), brine (200 mL), dried (MgSO₄) and concentrated in vacuo. The product was purified by short path distillation to give the titled compound as a red oil (3.0 g, 50%). ¹H NMR (600 MHz, DMSO-d₆): δ=6.84 (s, 2H), 4.75 (s, 2H), 3.01 (hept, J=6.8 Hz, 2H), 1.13 (d, J=6.8 Hz, 12H). ¹³C NMR (151 MHz, DMSO-d₆): δ=141.1, 133.8, 122.5, 120.5, 27.2, 22.8.

4-chloro-2,6-dicyclopropylaniline

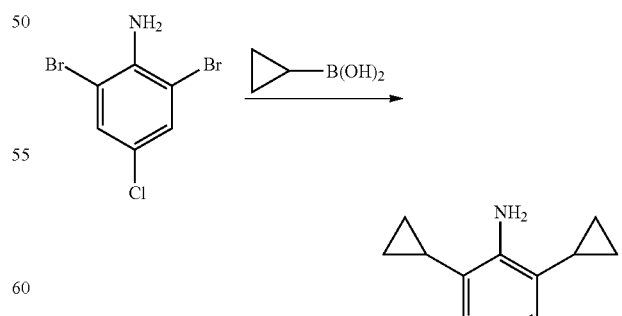

In a 50 mL re-sealable reaction tube, a solution of 2,6-dibromo-4-chloroaniline (0.25 g, 0.88 mmol) and cyclopropyl boronic acid (0.22 g, 2.62 mmol) along with K₃PO₄ (0.74 g, 3.50 mmol) was dissolved in toluene:water (10 mL:1 mL). The resulting solution was degassed by purging with nitrogen gas for 5 minutes. Pd(OAc)$_2$ (20 mg, 0.087 mmol) and tricyclohexylphospine (25 mg, 0.087 mmol) were added and the solution was purged with nitrogen gas for another 5 minutes. The resulting mixture was stirred at 100° C. for 12 h. Upon completion of reaction the mixture was diluted with water (25 mL), extracted with EtOAc (2×25 mL) and the combined organic extract washed with water, brine, dried (Na$_2$SO$_4$) and concentrated in vacuo. The crude product was purified by column chromatography on silica gel (60-120 mesh) using 5% EtOAc-hexanes eluant to give 4-chloro-2,6-dicyclopropylaniline (150 mg, 83%) as brown liquid. $^1$H NMR (300 MHz, DMSO-d$_6$): δ=6.69 (s, 2H), 4.98 (s, 2H), 1.74-1.64 (m, 2H), 0.90-0.84 (m, 4H), 0.52-0.47 (m, 4H). LCMS (m/z): 208.30 [M+H]$^+$.

Synthesis of
4-chloro-2-methyl-6-(trifluoromethyl)aniline

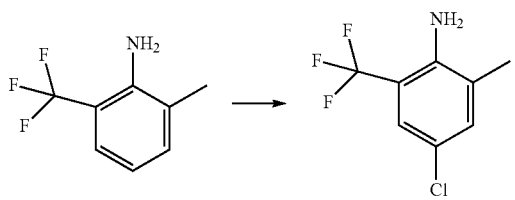

A solution of 2-methyl-6-(trifluoromethyl)aniline (0.4 g, 2.20 mmol) in acetonitrile (4 mL) and AcOH (0.3 mL) was cooled to 0° C. N-Chlorosuccinimide (0.36 g, 2.70 mmol) was added at 0° C. and the solution then allowed to warm to RT and stirred for 12 h. Upon completion of reaction the reaction mixture was diluted with ice cold water and the resulting precipitate removed by filtration and washed sequentially with saturated NaHCO$_3$, Na$_2$S$_2$O$_3$ solution, n-pentane and dried in vacuo to give 4-chloro-2-methyl-6-(trifluoromethyl)aniline (0.25 g, 52%) as a white solid. $^1$H NMR (400 MHz, CDCl$_3$): δ=7.30 (d, J=2.4 Hz, 1H), 7.18 (d, J=2.0 Hz, 1H), 2.17 (s, 3H). 19F NMR (400 MHz, CDCl$_3$): δ=−63.03

4-chloro-2,6-diethylaniline

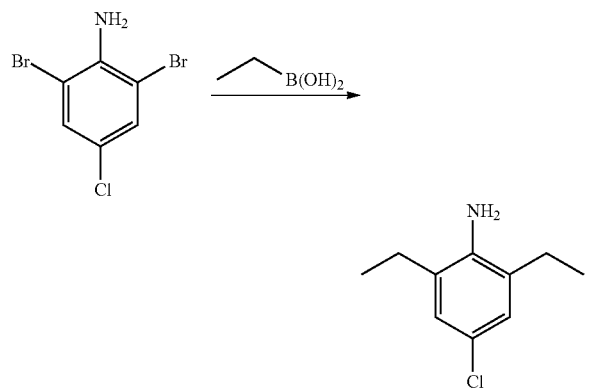

A solution of 2,6-dibromo-4-chloroaniline (0.5 g, 1.75 mmol) and ethyl boronic acid (0.4 g, 5.25 mmol) in toluene (15 mL) and water (4 mL) was treated with K$_3$PO$_4$ (1.5 g, 7.0 mmol) at RT under argon atmosphere. Argon gas was used to purge the solution for 5 minutes before treating with Pd(OAc)$_2$ (40 mg, 0.175 mmol) and tricyclohexyl phosphine (50 mg, 0.175 mmol). The reaction mixture was again purged with argon for 5 minutes. The resulting mixture was stirred at 100° C. for 12 h. Upon completion the reaction mixture diluted with water extracted with EtOAc (2×25 mL) and the combined organic extract washed with water, brine, dried (Na$_2$SO$_4$) and concentrated in vacuo. The crude product was purified by column chromatography on silica gel (60-120 mesh) using 8% EtOAc-hexanes eluant to give 4-chloro-2,6-dicyclopropylaniline (100 mg, 31%) as yellow liquid. $^1$H NMR (300 MHz, CDCl$_3$): δ=6.94 (s, 2H), 3.61 (s, 2H), 2.53 (q, J=7.5 Hz, 4H), 1.27 (t, J=7.5 Hz, 6H). LCMS (m/z): 184.00 [M+H]$^+$.

4-chloro-2,6-dimethoxyaniline

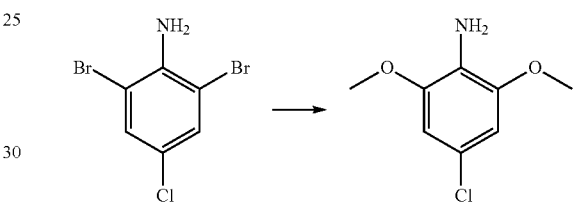

2,6-dibromo-4-chloroaniline (4 g, 14.0 mmol) was dissolved in 25% NaOMe soln in MeOH (48 mL) and treated with CuI (2.9 g, 15.4 mmol) at RT under nitrogen atmosphere. The resulting mixture was stirred at 70° C. for 12 h under nitrogen atmosphere. Upon completion, the reaction mixture was cooled to RT and concentrated in vacuo. The residue obtained was diluted with saturated NH$_4$Cl solution, extracted with EtOAc (2×50 mL) and the combined organic extract washed with water, brine, dried (Na$_2$SO$_4$) and concentrated in vacuo. The crude product was purified by column chromatography on silica gel (60-120 mesh) using 1% EtOAc-hexanes to give 4-chloro-2,6-dimethoxyaniline (1.0 g, 38%) as a pale brown liquid. $^1$H NMR (300 MHz, CDCl$_3$): δ=6.52 (s, 2H), 3.83 (s, 6H). LCMS (m/z): 187.9 [M+H]$^+$ 2-amino-5-chloro-3-cyclopropyl-N,N-dimethylbenzamide

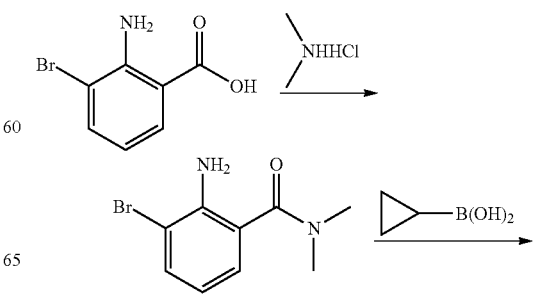

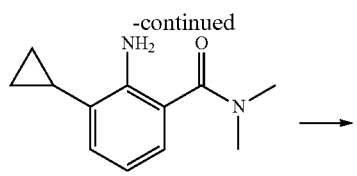

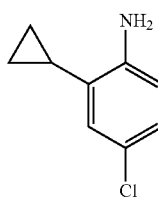

In a 50 mL resealable reaction tube, 2-amino-3-bromobenzoic acid (2.0 g, 9.25 mmol) was dissolved in DMF (20 mL) and cooled to 0° C. EDC-HCl (2.1 g, 11.0 mmol), HOBt (1.49 g, 11.0 mmol), DIPEA (2.8 mL, 27.7 mmol) and dimethylamine hydrochloride (1.13 g, 13.8 mmol) were sequentially added at 0° C. The reaction mixture was warmed to 70° C. and stirred for 12 h. Upon completion the reaction mixture was diluted with water extracted with EtOAc (2×50 mL) and the combined organic extract washed with water, brine, dried (Na$_2$SO$_4$) and concentrated in vacuo to give 2-amino-3-bromo-N,N-dimethylbenzamide (2.0 g, 89%) as a white solid. $^1$H NMR (300 MHz, CDCl$_3$): δ=7.44 (dd, J=7.8, 1.5 Hz, 1H), 7.06 (dd, J=7.8, 1.5 Hz, 1H), 6.61 (t, J=7.8 Hz, 1H), 4.82 (bs, 2H), 3.05 (s, 6H). LCMS (m/z): 243.10, 245.10 [M+H]$^+$.

In a 50 mL resealable reaction tube, a solution of 2-amino-3-bromo-N,N-dimethylbenzamide (2 g, 8.23 mmol), cyclopropyl boronic acid (850 mg, 9.87 mmol) and K$_3$PO$_4$ (5.23 g, 24.06 mmol) were dissolved in toluene (30 mL) and water (3 mL). The solution was degassed by purging with nitrogen gas for 5 minutes then Pd(OAc)$_2$ (184 mg, 0.823 mmol) and tricyclohexylphospine (230 mg, 0.823 mmol) were added and solution was once again purged with nitrogen gas for 5 minutes. The resulting mixture was stirred at 100° C. for 12 h. Upon completion the reaction mixture was diluted with saturated NH$_4$Cl solution, extracted with EtOAc (2×50 mL) and the combined organic extract washed with water, brine, dried (Na$_2$SO$_4$) and concentrated in vacuo. The crude product was purified by column chromatography on silica gel (60-120 mesh) using 20% EtOAc-hexanes to give 2-amino-3-cyclopropyl-N,N-dimethylbenzamide (1.0 g, 60%) as light brown color solid. $^1$H NMR (300 MHz, CDCl$_3$): δ=7.06 (d, J=7.5 Hz, 1H), 6.99 (dd, J=7.8, 1.5 Hz, 1H), 6.66 (t, J=7.8 Hz, 1H), 4.70 (bs, 2H), 3.05 (s, 6H), 1.68-1.61 (m, 1H), 0.94-0.88 (m, 2H), 0.62-0.57 (m, 2H). LCMS (m/z): 205.3 [M+H]$^+$.

A solution of 2-amino-3-cyclopropyl-N,N-dimethylbenzamide (0.5 g, 2.44 mmol) in acetonitrile (10 mL) and AcOH (0.3 mL) was cooled to 0° C. N-Chlorosuccinimide (0.5 g, 3.67 mmol) was added at 0° C. and the resulting reaction mixture was warmed to RT and stirred for 12 h. Upon completion the reaction mixture was diluted with saturated Na$_2$S$_2$O$_3$ solution and extracted with ethyl acetate (2×50 mL). The combined organic extracts were washed with NaHCO$_3$ solution, brine, dried (Na$_2$SO$_4$) and concentrated in vacuo. The crude product was purified by column chromatography on silica gel (60-120 mesh) using 25% EtOAc-hexanes eluant to give 2-amino-5-chloro-3-cyclopropyl-N,N-dimethylbenzamide (0.2 g, 34%) as a brown solid. $^1$H NMR (300 MHz, CDCl$_3$): δ=7.02 (d, J=1.5 Hz, 1H), 6.96 (d, J=2.7 Hz, 1H), 4.66 (bs, 2H), 3.05 (s, 6H), 1.68-1.61 (m, 1H), 0.94-0.88 (m, 2H), 0.62-0.57 (m, 2H). LCMS (m/z): 239.0 [M+H]$^+$.

4-chloro-2-methoxy-6-(trifluoromethyl)aniline

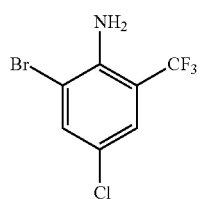

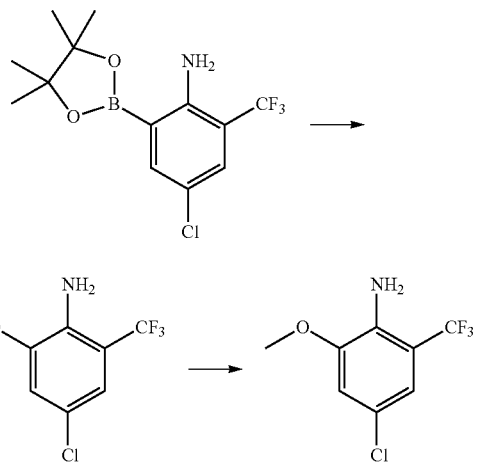

In a 50 mL resealable reaction tube, a solution of 2-bromo-4-chloro-6-(trifluoromethyl)aniline (0.5 g, 1.82 mmol), bis(pinacolato diborane) (0.92 g, 3.64 mmol) and KOAc (0.44 g, 4.55 mmol) in 1,4-dioxane (10 mL) was degassed by purging with nitrogen gas for 5 minutes. Pd(dppf)Cl$_2$ (015 g, 0.182 mmol) was added and the solution purged again with nitrogen gas for 5 minutes. The resulting mixture was stirred at 110° C. for 12 h. Upon completion, the reaction mixture diluted with water, extracted with EtOAc (2×50 mL) and the combined organic extract washed with water, brine, dried (Na$_2$SO$_4$) and concentrated in vacuo. The crude product was purified by column chromatography on silica gel (60-120 mesh) using 2% EtOAc-hexanes eoluant to give 4-chloro-2-(4,4,5,5-tetramethyl-1,3,2-dioxaborolan-2-yl)-6-(trifluoromethyl)aniline (0.5 g, 85%). LCMS (m/z): 324.10 [M+H]$^+$.

4-Chloro-2-(4,4,5,5-tetramethyl-1,3,2-dioxaborolan-2-yl)-6-(trifluoromethyl)aniline (500 mg, 1.55 mmol) was dissolved in THF (5 mL) and H$_2$O (2 mL) at RT. NaBO$_3$.H$_2$O (0.62 g, 6.23 mmol) was added portion-wise and the reaction stirred at RT for 4 h. Upon completion the reaction mixture was diluted with water extracted with EtOAc (2×50 mL) and the combined organic extract washed with water, brine, dried (Na$_2$SO$_4$) and concentrated in vacuo. The crude product was purified by column chromatography on silica gel (60-120 mesh) using 15% EtOAc-hexanes eluant to give 2-amino-5-chloro-3-(trifluoromethyl) phenol (0.5 g, 100%) as a yellow liquid. $^1$H NMR (300 MHz, DMSO-d$_6$): δ=10.50 (s, 1H), 6.85 (s, 2H), 5.12 (bs, 2H). $^{19}$F NMR (300 MHz, DMSO-d$_6$): δ=−61.46. LCMS (m/z): 211.6 [M+H]$^+$.

2-amino-5-chloro-3-(trifluoromethyl)phenol (250 mg, 1.18 mmol) was dissolved in anhydrous DMF (5 mL) and treated with K$_2$CO$_3$ (240 mg, 1.77 mmol). The resulting mixture was stirred at RT for 30 minutes. Methyl iodide (185 mg, 1.303 mmol) was added dropwise and the reaction stirred at RT for 2 h. Upon completion the reaction mixture was diluted with water extracted with EtOAc (2×50 mL) and the combined organic extract washed with water, brine, dried (Na$_2$SO$_4$) and concentrated in vacuo. The crude product was purified by column chromatography on silica gel (60-120 mesh) using 10% EtOAc-hexanes eluant to give 4-chloro-2-methoxy-6-(trifluoromethyl)aniline (0.2 g, 75%) as a pale brown solid. $^1$H NMR (400 MHz, DMSO-d$_6$): δ=7.10 (d, J=2.0 Hz, 1H), 6.98 (d, J=2.0 Hz, 1H), 5.34 (bs, 2H) 3.85 (s, 3H). $^{19}$F NMR (400 MHz, DMSO-d$_6$): δ=−61.45.

7-chloro-5-cyclopropyl-2,3-dihydro-1H-inden-4-amine

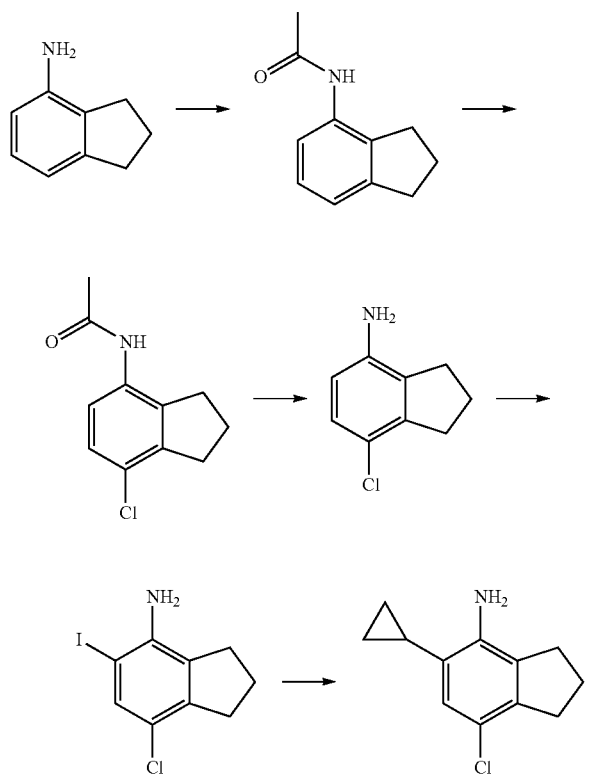

A solution of 2,3-dihydro-1H-inden-4-amine, 1 (500 mg, 3.75 mmol) in EtOH (5 mL) was cooled to 0° C. and treated dropwise with acetic anhydride (0.95 g, 9.37 mmol) under nitrogen atmosphere. The resulting reaction mixture was warmed to RT and stirred for 3 h. Upon completion of reaction, (TLC, 30% ethyl acetate-hexanes, R$_f$, 0.2), the reaction mixture was concentrated in vacuo. The residue obtained was diluted with diethyl ether, filtered and dried in vacuo to give N-(2,3-dihydro-1H-inden-4-yl)acetamide (0.3 g, 45%) as a white solid. 1H NMR (400 MHz, DMSO-d$_6$): δ=9.29 (s, 1H), 7.41 (d, J=8.0 Hz, 1H), 7.08 (t, J=7.6 Hz, 1H), 6.99 (d, J=6.8 Hz, 1H), 2.87 (t, J=7.2 Hz, 2H), 2.80 (t, J=7.2 Hz, 2H), 2.04 (s, 3H), 1.99-1.95 (m, 2H). LCMS (m/z): 176.40 [M+H]$^+$ N-(2,3-dihydro-1H-inden-4-yl)acetamide (200 mg, 1.11 mmol) was dissolved in AcOH (5 mL) and cooled to 0° C. N-Chlorosuccinimide (220 mg, 1.69 mmol) was added then the reaction mixture was warmed to RT and stirred overnight. Upon completion the reaction mixture was diluted with ice cold water and the solid formed removed by filtration, washed saturated NaHCO$_3$, Na$_2$S$_2$O$_3$ solution and dried in vacuo to give N-(7-chloro-2,3-dihydro-1H-inden-4-yl)acetamide (0.12 g, 50%) as a white solid. $^1$H NMR (300 MHz, CDCl$_3$): δ=7.73 (d, J=8.4 Hz, 1H), 7.14 (d, J=8.4 Hz, 1H), 6.86 (s, 1H), 3.02-2.85 (m, 4H), 2.19 (s, 3H), 1.99 (m, 2H). LCMS (m/z): 209.80 [M+H]$^+$ N-(7-chloro-2,3-dihydro-1H-inden-4-yl)acetamide (120 mg, 0.57 mmol) was dissolved in 3 M HCl (5 mL) and warmed to 90° C. for 4 h. Upon completion the reaction mixture was cooled to RT and basified (pH ~8) with saturated NaHCO$_3$ solution before extracting with EtOAc (2×20 mL). The combined organic extracts were washed with water, brine, dried (Na$_2$SO$_4$) and concentrated in vacuo to give 7-chloro-2,3-dihydro-1H-inden-4-amine (70 mg, 74%) as a white solid. $^1$H NMR (300 MHz, DMSO-d$_6$): δ=6.85 (d, J=8.4 Hz, 1H), 6.40 (d, J=8.4 Hz, 1H), 4.97 (s, 2H), 2.82 (t, J=8.1 Hz, 2H), 2.71 (t, J=7.5 Hz, 2H), 2.01-1.96 (m, 2H). LCMS (m/z): 168.20 [M+H]$^+$.

A solution of 7-chloro-2,3-dihydro-1H-inden-4-amine (0.8 g, 4.79 mmol) in acetonitrile (10 mL) was cooled to 0° C. and treated with N-iodosuccinimide (1.61 g, 7.18 mmol) at 0° C. The resulting reaction mixture was warmed to RT and stirred for 12 h. Upon completion the reaction mixture was diluted with saturated Na$_2$S$_2$O$_3$ solution and extracted with ethyl acetate (2×50 mL). The combined organic extract was washed with water, brine, dried (Na$_2$SO$_4$) and concentrated in vacuo. The crude product was purified by column chromatography on silica gel (60-120 mesh) using 4-5% EtOAc-hexanes eluant to give 7-chloro-5-iodo-2,3-dihydro-1H-inden-4-amine (0.45 g, 32%) as a pale brown solid. $^1$H NMR (300 MHz, DMSO-d$_6$): δ=7.36 (s, 1H), 5.04 (s, 2H), 2.82-2.72 (m, 4H), 2.03-1.98 (m, 2H). LCMS (m/z): 293.7 [M+H]$^+$.

In a 50 mL resealable reaction tube, a solution of 7-chloro-5-iodo-2,3-dihydro-1 H-inden-4-amine, (0.35 g, 1.19 mmol) and cyclopropyl boronic acid (0.41 g, 4.77 mmol) in 1,4-dioxane (14 mL) and water (4 mL) was treated with Cs$_2$CO$_3$ (1.16 g, 3.57 mmol) at RT under nitrogen atmosphere. Nitrogen gas was purged through the solution for 5 minutes and treated with Pd(OAc)$_2$ (26 mg, 0.119 mmol) and Catacxium-A (42 mg, 0.119 mmol) under nitrogen atmosphere. The resulting mixture was again degassed with nitrogen gas for another 5 minutes. The resulting mixture was stirred at 100° C. for 24 h. Upon completion the reaction mixture was diluted with water and extracted with EtOAc (2×25 mL). The combined organic extract was washed with water, brine, dried (Na$_2$SO$_4$) and concentrated in vacuo. The crude product was purified by column chromatography on silica gel (60-120 mesh) using 5% EtOAc-hexanes eluant to give 7-chloro-5-cyclopropyl-2,3-dihydro-1H-inden-4-amine (70 mg, 28%) as a light brown solid. $^1$H NMR (300 MHz, CDCl$_3$): δ=6.86 (s, 1H), 2.94 (t, J=7.5 Hz, 2H), 2.80 (t, J=7.5 Hz, 2H), 2.15-2.10 (m, 2H), 1.44-1.43 (m, 1H), 0.91-0.88 (m, 2H), 0.58-0.55 (m, 2H). LCMS (m/z): 208.3 [M+H]$^+$.

Synthesis of R2 Acid Intermediates 2,3,6,7-tetrahydrobenzo[1,2-b:4,5-b']difuran-4-carboxylic acid

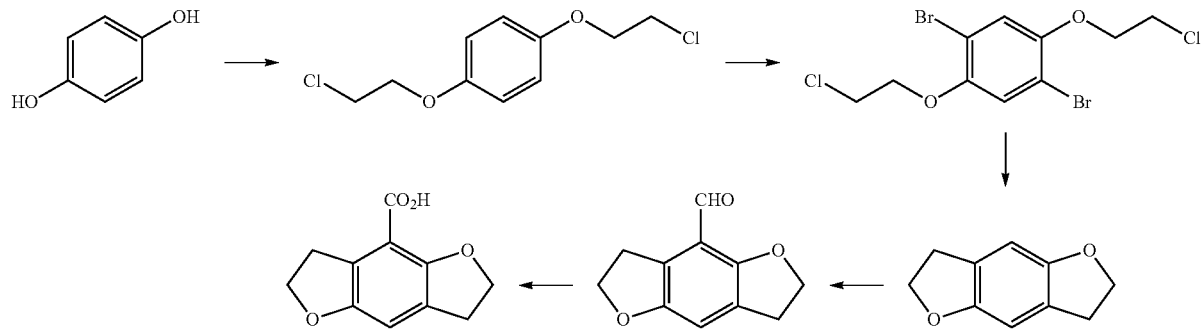

Synthesis of 2,3,6,7-tetrahydrobenzo[1,2-b:4,5-b']difuran-4-carboxylic acid was carried out from hydroquinone using procedures detailed by Monte et. al. *J. Med. Chem.* 1996, 39, 2953-2961 to give the 2,3,6,7-tetrahydrobenzo[1,2-b:4,5-b']difuran-4-carbaldehyde as a bright yellow solid; $^1$H NMR (400 MHz, CDCl$_3$): δ=10.27 (s, 1H), 6.87 (s, 1H), 4.67 (t, J=8.8 Hz, 2H), 4.59 (t, J=8.8 Hz, 2H), 4.59 (t, J=8.8 Hz, 2H), 3.46 (t, J=8.8 Hz, 2H), 3.18 (t, J=8.8 Hz, 2H).

The aldehyde (0.68 g, 3.58 mmol) was oxidized using silver (I) oxide (1.5 eq.) in 5% aqueous sodium hydroxide at rt for 20 days. The crude reaction mixture was filtered through celite, extracted using diethyl ether (2×50 mL) to remove unreacted aldehyde then the aqueous phase was acidified to pH 1 using 3.0 M aqueous HCl drop-wise at 0° C. The product was extracted using dichloromethane (2×50 mL) and the combined organics washed using brine (50 mL), dried (MgSO$_4$) and concentrated in vacuo to give 2,3,6,7-tetrahydrobenzo[1,2-b:4,5-b']difuran-4-carboxylic acid as a white solid (0.44 g; 60%).

Alternatively, the aldehyde (0.5 g, 2.77 mmol) in acetone (5.0 mL) was treated with sulfamic acid (0.4 g, 4.17 mmol) in two portions at 0° C. After 2 min a solution of sodium chlorite (0.32 g, 3.6 mmol) in water (1.0 mL) was added drop-wise and stirring continued at 0° C. for 4 h. The reaction mixture was diluted with water (20 mL) and extracted using 10% IPA/chloroform (2×20 mL). The combined organics were washed with water (25 mL), brine (25 mL), dried (Na$_2$SO$_4$) and concentrated in vacuo. The crude solid was triturated with diethyl ether to give 2,3,6,7-tetrahydrobenzo[1,2-b:4,5-b']difuran-4-carboxylic acid (0.4 g; 70%). $^1$H NMR (400 MHz, DMSO-d$_6$): δ=6.86 (s, 1H), 4.52 (t, J=8.8 Hz, 2H), 4.47 (t, J=8.8 Hz, 2H), 3.30 (t, J=8.8 Hz, 2H), 3.10 (t, J=8.8 Hz, 2H). $^{13}$C (100 MHz, DMSO-d$_6$): δ=166.4, 154.2, 153.9, 128.9, 127.2, 111.4, 110.43, 71.9, 71.6, 31.5, 29.5.

Benzo[d][1,3]dioxole-4-carboxylic acid

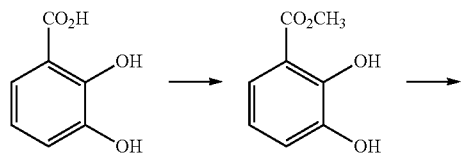

Synthesised using procedures modified from Plé et. al. *J. Med. Chem.* 2004, 47, 871-887 as follows:

2,3-Dihydroxybenzoic acid (5.0 g, 32.4 mmol) in anhydrous methanol (50 mL) was treated with concentrated sulfuric acid (10 drops) and heated at reflux overnight. The reaction mixture was concentrated in vacuo, diluted using EtOAc (100 mL) washed using sat. aqueous NaHCO$_3$ (2×50 mL), brine (50 mL) then dried (MgSO$_4$) and concentrated in vacuo to give methyl 2,3-dihydroxybenzoate (2.92 g; 54%). $^1$H NMR (400 MHz, CDCl$_3$): δ=10.9 (s, 1H), 7.32 (dd, J=8.0, 1.2 Hz, 1H), 7.09 (m, 1H), 6.78 (t, J=8.0 Hz, 1H), 5.65 (s, 3H). $^{13}$C NMR (100 Hz, CDCl$_3$) 170.7, 148.8, 145.0, 120.5, 119.8, 119.2, 112.4, 52.4.

Methyl 2,3-dihydroxybenzoate (1.0 g, 5.95 mmol) in DMF (16 mL) was treated with KF (1.79 g, 30.9 mmol) and stirred at ambient temperature for 30 minutes. Diiodomethane (1.79 g, 6.7 mmol) was added and the reaction heated at 100° C. for 5 hours. The reaction mixture was cooled to rt, poured onto water (100 mL) and extracted using diethyl ether (2×50 mL). The combined organics were washed with water (50 mL), brine (50 mL), dried (MgSO$_4$) and concentrated in vacuo. The crude product was purified by column chromatography on silica gel using 10% EtOAc-petroleum ether eluent to give methyl benzo[d][1,3]dioxole-4-carboxylate as a white crystalline solid (0.56 g; 52%); $^1$H NMR (400 MHz, CDCl$_3$): δ=7.41 (dd, J=8.0, 1.2 Hz, 1H), 6.97 (dd, J=8.0, 1.2 Hz, 1H), 6.86 (t, J=8.0 Hz, 1H), 6.1 (s, 2H), 3.93 (s, 3H).

A solution of methyl benzo[d][1,3]dioxole-4-carboxylate (0.4 g, 2.22 mmol) in methanol (8.0 mL) was treated with 2.0 M aqueous KOH (2.2 mL) and the solution stirred at rt for 3 hours. The mixture was concentrated to ~3 mL volume, diluted with water (5 mL) and acidified to pH ~3 using 2.0 M HCl. The resulting precipitate was removed by filtration, washed with water then diethyl ether and dried in vacuo to give benzo[d][1,3]dioxole-4-carboxylic acid as a beige solid (0.38 g, 97%). $^1$H NMR (400 MHz, DMSO-d$_6$): δ=7.28 (dd, J=8.0, 1.2 Hz, 1H), 6.97 (dd, J=8.0, 1.2 Hz, 1H), 6.89 (t, J=8.0 Hz, 1H), 6.12 (s, 2H); $^{13}$C NMR (100 Hz, DMSO-d$_6$) 165.5, 148.9, 148.5, 122.9, 121.6, 113.8, 112.5, 102.1.

Synthesised Compounds by Substituent Class

ALIPHATICS

N-((1,2,3,5,6,7-hexahydro-s-indacen-4-yl)carbamoyl)cyclohexanesulfonamide

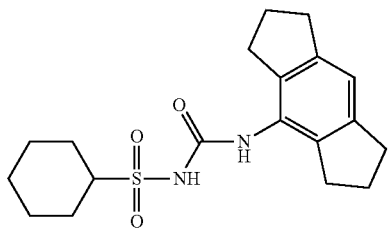 [SMILES: O=C(Nc1c2c(cc3c1CCC3)CCC2)NS(=O)(=O)C1CCCCC1]

4-Isocyanato-1,2,3,5,6,7-hexahydro-s-indacene (prepared using general method A2) and cyclohexanesulfonamide were used in general method C3 to give the titled compound as a white solid (12 mg, 41%). $^1$H NMR (400 MHz, CD$_3$OD): δ=6.97 (s, 1H), 3.50-3.43 (m, 1H), 2.87 (t, 4H, J=8.0 Hz), 2.78 (t, 4H, J=8.0 Hz), 2.22-2.18 (m, 2H), 2.10-2.02 (m, 4H), 1.94-1.71 (m, 2H), 1.63-1.59 (m, 1H), 1.64-1.53 (m, 2H); 1.41-1.21 (m, 3H); $^{13}$C NMR (100 MHz, CD$_3$OD): δ=143.7, 137.8, 126.4, 118.4, 110.2, 59.9, 35.5, 30.0, 28.5, 25.8, 25.1, 24.8; LCMS Purity: >95%; LCMS (m/z): 363 [M+H]; HRMS calculated for C$_{19}$H$_{26}$N$_2$O$_3$S [M+H]$^+$:363.1737, found 363.1729.

N-((1,2,3,5,6,7-hexahydro-s-indacen-4-yl)carbamoyl)cyclopentanesulfonamide

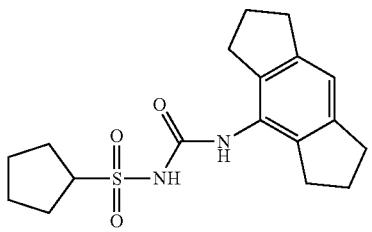 [SMILES: O=C(Nc1c2c(cc3c1CCC3)CCC2)NS(=O)(=O)C1CCCC1]

4-Isocyanato-1,2,3,5,6,7-hexahydro-s-indacene (prepared using general method A2) and cyclopentanesulfonamide were used in general method C3 to give the titled compound as a white solid (26 mg, 42%) $^1$H NMR (400 MHz, CD$_3$OD): δ=6.97 (s, 1H), 4.08-4.02 (m, 1H), 2.83 (t, J=8.0 Hz, 4H), 2.80 (t, J=8.0 Hz, 4H), 2.13-2.01 (m, 8H), 1.84-1.77 (m, 2H), 1.71-1.65 (m, 2H); $^{13}$C NMR (100 MHz, CD$_3$OD): δ=145.1, 139.2, 127.8, 119.8, 111.7, 62.2, 33.9, 31.4, 29.9, 28.6, 26.9; LCMS Purity: >95%; LCMS (m/z): 349 [M+H]$^+$; HRMS calculated for C$_{18}$H$_{24}$N$_2$O$_3$S: 349.1580, found 349.1588.

N-((1,2,3,5,6,7-hexahydro-s-indacen-4-yl)carbamoyl)tetrahydro-2H-pyran-4-sulfonamide

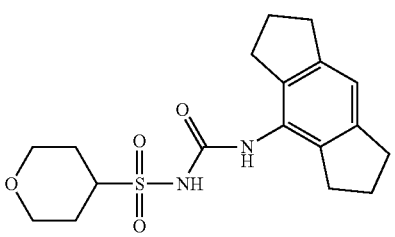 [SMILES: O=C(Nc1c2c(cc3c1CCC3)CCC2)NS(=O)(=O)C1CCOCC1]

4-Isocyanato-1,2,3,5,6,7-hexahydro-s-indacene (prepared using general method A2) and tetrahydro-2H-pyran-4-sulfonamide were used in general method C2 to give the titled compound as a white solid (12 mg, 57%). $^1$H NMR (400 MHz, CD$_3$OD): δ=7.00 (s, 1H), 4.09 (dd, J$_1$=4 Hz, J$_2$=12 Hz, 2H), 3.82-3.76 (m, 1H), 3.49-3.43, (m, 2H), 2.89 (t, J=8 Hz, 4H), 2.81 (t, J=8 Hz, 4H), 2.12-2.05 (m, 6H), 1.98-1.87 (m, 2H); $^{13}$C NMR (100 MHz, CD$_3$OD): δ=154.0, 143.1, 137.7, 126.5, 110.4, 66.0, 57.0, 32.5, 28.5, 25.9, 25.1; LCMS Purity: >95%; LCMS (m/z): 365 [M+H]$^+$; HRMS calculated for C$_{18}$H$_{24}$N$_2$O$_4$S, 365.1530, found 365.1541.

N-((1,2,3,5,6,7-hexahydro-s-indacen-4-yl)carbamoyl)tetrahydrofuran-3-sulfonamide

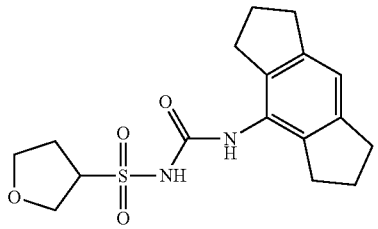 [SMILES: O=C(Nc1c2c(cc3c1CCC3)CCC2)NS(=O)(=O)C1CCOC1]

4-Isocyanato-1,2,3,5,6,7-hexahydro-s-indacene (prepared using general method A2) and tetrahydrofuran-3-sulfonamide were used in general method C2 to give the titled compound as a white solid (12 mg, 60%). $^1$H NMR (400 MHz, DMSO-d$_6$): δ=8.04 (s, 1H), 6.93 (s, 1H), 4.33-4.27 (m, 1H), 4.04-4.00 (m, 1H), 3.91-3.89 (m, 1H), 3.85-3.79 (m, 1H), 3.72-3.66 (m, 1H), 2.80 (t, J=16.0 Hz, 4H), 2.70 (t, J=16.0 Hz, 4H), 2.24-2.17 (m, 2H), 1.99-1.95 (m, 4H). $^{13}$C NMR (100 MHz, DMSO-d$_6$): δ=142.4, 139.6, 136.6, 124.7, 108.2, 68.7, 61.7, 32.5, 30.3, 28.8, 28.1, 24.9; LCMS Purity: >95%; LCMS (m/z): 351 [M+H]$^+$; HRMS calculated for C$_{17}$H$_{22}$N$_2$O$_4$S 351.1373, found 351.1389.

Furans

N-((1,2,3,5,6,7-hexahydro-s-indacen-4-yl)carbamoyl)furan-2-sulfonamide

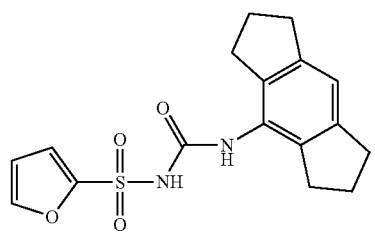 [SMILES: O=C(Nc1c2c(cc3c1CCC3)CCC2)NS(=O)(=O)c1ccco1]

4-Isocyanato-1,2,3,5,6,7-hexahydro-s-indacene (prepared using general method A1) and furan-2-sulfonamide were used in general method C4 to give the titled compound as a white solid (75 mg, 16%). $^1$H NMR (400 MHz, DMSO-d$_6$): δ=11.08 (br.s, 1H), 8.08 (s, 1H), 8.02 (s, 1H), 7.22 (q, J=2.0 Hz, 1H), 6.94 (s, 1H), 6.71 (q, J=2.0 Hz, 1H), 2.78 (t, J=7.2 Hz, 4H), 2.59 (t, J=7.2 Hz, 4H), 1.94 (quin, J=7.2 Hz, 4H). $^{13}$C NMR (100 MHz, DMSO-d$_6$): δ=148.9, 147.9, 147.3, 143.1, 137.3, 128.7, 118.0, 117.5, 111.7, 54.9, 32.5, 30.1, 25.1. LCMS, Purity: 96.26%; m/z 345.1 (M−H$^+$). HRMS (FAB$^-$) calcd for C$_{17}$H$_{18}$N$_2$O$_4$S [M−H]$^-$: 345.0987, found: 345.0866.

145
N-((1,2,3,5,6,7-hexahydro-s-indacen-4-yl)carbamoyl)-5-methylfuran-2-sulfonamide

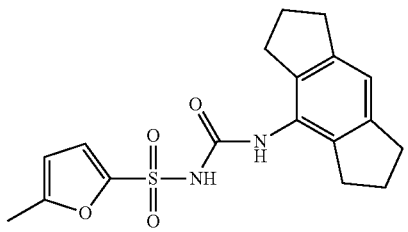 [SMILES: Cc1ccc(S(=O)(=O)NC(=O)Nc2c3c(cc4c2CCC4)CCC3)o1]

4-Isocyanato-1,2,3,5,6,7-hexahydro-s-indacene (prepared using general method A2) and 5-methylfuran-2-sulfonamide were used in general method C2 to give the titled compound as a white solid (28 mg, 53%). $^1$H NMR (400 MHz, DMSO-d$_6$): δ=7.96 (s, 1H), 7.00-6.99 (d, J=4.0 Hz, 1H), 6.91 (s, 1H), 6.29-6.28 (d, J=4.0 Hz, 1H), 1H), 2.78 (t, J=8.0 Hz, 4H), 2.61 (t, J=8.0 Hz, 4H), 2.34 (s, 3H), 2 (t, J=8.0 Hz, 4H), 1.98-1.90 (m, 4H); $^{13}$C NMR (100 MHz, DMSO-d$_6$): δ=143.3, 137.6, 129.9, 125.2, 118.0, 114.6, 108.7, 108.2, 107.8, 32.9, 30.6, 25.4, 13.8; LCMS Purity: >95%; LCMS (m/z): 361 [M+H]$^+$; HRMS calculated for C$_{18}$H$_{20}$N$_2$O$_4$S [M+H]$^+$361.1216, found 361.1217.

5-ethyl-N-((1,2,3,5,6,7-hexahydro-s-indacen-4-yl)carbamoyl)furan-2-sulfonamide

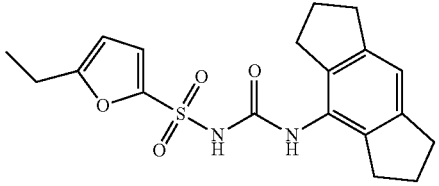 [SMILES: CCc1ccc(S(=O)(=O)NC(=O)Nc2c3c(cc4c2CCC4)CCC3)o1]

4-Isocyanato-1,2,3,5,6,7-hexahydro-s-indacene (prepared using general method A2) and 5-ethylfuran-2-sulfonamide were used in general method C2 to give the titled compound as a white solid (51 mg, 47%). $^1$H NMR (400 MHz, DMSO-d$_6$): δ=7.97 (bs, 1H), 7.02 (s, 1H), 6.91 (d, J=4.0 Hz, 1H), 6.31 (d, J=4.0 Hz, 1H), 2.78 (t, J=8.0 Hz, 4H), 2.68 (q, J=8.0 Hz, 2H), 2.59 (t, J=6.0 Hz, 4H), 1.97-1.90 (m, 4H), 1.19 (t, J=8.0 Hz, 3H). $^{13}$C NMR (150 MHz, DMSO-d$_6$): δ=143.5, 143.3, 142.9, 137.6, 129.8, 118.0, 108.7, 106.8, 106.3, 32.9, 30.5, 25.4, 21.3, 12.1; LCMS Purity: >95%; LCMS (m/z): 375 [M+H]$^+$; HRMS calculated for C$_{19}$H$_{22}$N$_2$O$_4$S [M+H]$^+$375.13730, found 375.13910.

146
5-((dimethylamino)methyl)-N-((1,2,3,5,6,7-hexahydro-s-indacen-4-yl)carbamoyl)furan-2-sulfonamide

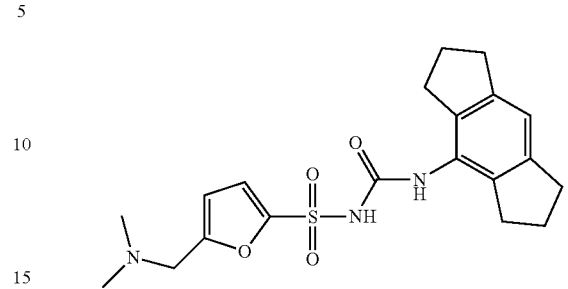

4-Isocyanato-1,2,3,5,6,7-hexahydro-s-indacene (prepared using general method A1) and 5-((dimethylamino)methyl)furan-2-sulfonamide were used in general method C2 to give the titled compound as a white solid (25 mg, 6%). $^1$H NMR (400 MHz, CD$_3$OD) δ=7.17 (d, J=3.5 Hz, 1H), 6.96 (s, 1H), 6.86 (d, J=3.5 Hz, 1H), 4.43 (s, 2H), 2.86 (s, 3H), 2.86 (t, J=7.4 Hz, 4H), 2.73 (t, J=7.4 Hz, 4H), 2.04 (p, J=7.4 Hz, 4H).

N-((1,2,3,5,6,7-hexahydro-s-indacen-4-yl)carbamoyl)-4-(2-hydroxypropan-2-yl)furan-2-sulfonamide

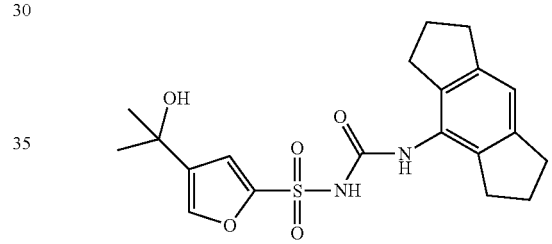

4-Isocyanato-1,2,3,5,6,7-hexahydro-s-indacene (prepared using general method A2) and 4-(2-hydroxypropan-2-yl)furan-2-sulfonamide were used in general method C5 to give the titled compound as a white solid (2.5 g, 63%). $^1$H NMR (600 MHz, DMSO-d$_6$): δ=7.61 (br.s., 1H), 7.37 (d, J=0.9 Hz, 1H), 6.77 (s, 1H), 6.58 (d, J=0.9 Hz, 1H), 2.74 (t, J=7.3 Hz, 4H), 2.65 (t, J=7.3 Hz, 4H), 1.89 (tt, J=7.3, 7.3 Hz, 4H), 1.34 (s, 6H). $^{13}$C NMR (101 Hz, DMSO-d$_6$): δ=157.4, 155.7, 142.2, 137.3, 136.7, 135.7, 132.4, 115.7, 109.3, 66.6, 32.6, 31.1, 30.6, 25.1.

N-((8-bromo-1,2,3,5,6,7-hexahydro-s-indacen-4-yl)carbamoyl)-4-(2-hydroxypropan-2-yl)furan-2-sulfonamide

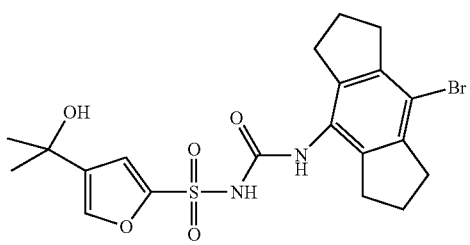 [SMILES: CC(C)(O)c1coc(S(=O)(=O)NC(=O)Nc2c3c(c(Br)c4c2CCC4)CCC3)c1]

4-Bromo-8-isocyanato-1,2,3,5,6,7-hexahydro-s-indacene (prepared using general method A1) and 4-(2-hydroxypropan-2-yl)furan-2-sulfonamide were used in general method C1 to give the titled compound as a white solid (40 mg, 7%). ¹H NMR (400 MHz, CD₃OD): δ=7.68 (s, 1H), 7.23 (s, 1H), 2.91 (t, J=7.6 Hz, 4H), 2.85 (t, J=7.6 Hz, 4H), 2.11 (m, 4H), 1.51 (s, 6H). LCMS (m/z): 482.9 [M−H]⁻; 97.64% (210 nm), 99% (254 nm). HPLC: 96.70% (210 nm), 97.22% (254 nm).

N-((8-chloro-1,2,3,5,6,7-hexahydro-s-indacen-4-yl)carbamoyl)-4-(2-hydroxypropan-2-yl)furan-2-sulfonamide

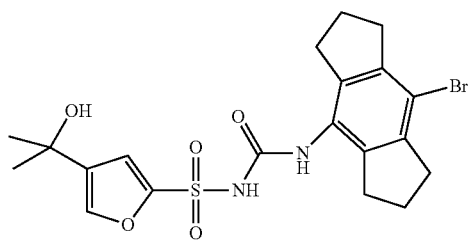 [SMILES: CC(C)(O)c1coc(S(=O)(=O)NC(=O)Nc2c3c(c(Br)c4c2CCC4)CCC3)c1]

4-Chloro-8-isocyanato-1,2,3,5,6,7-hexahydro-s-indacene (prepared using general method A1) and 4-(2-hydroxypropan-2-yl)furan-2-sulfonamide were used in general method C1 to give the titled compound as a white solid (50 mg, 16%). ¹H NMR (400 MHz, CD₃OD) δ=7.55 (s, 1H), 7.02 (s, 1H), 2.91 (t, J=7.2 Hz, 4H), 2.85 (t, J=7.2 Hz, 4H), 2.09 (m, 4H), 1.5 (s, 6H). LCMS (m/z): 460.9 (M+Na)⁻; 95.16% (210 nm), 95.07% (254 nm). HPLC: 97.91% (210 nm), 98.04% (254 nm).

4-(2-hydroxypropan-2-yl)-N-((8-methyl-1,2,3,5,6,7-hexahydro-s-indacen-4-yl)carbamoyl)furan-2-sulfonamide

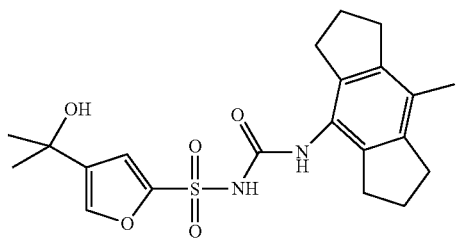 [SMILES: Cc1c2c(c(NC(=O)NS(=O)(=O)c3cc(C(C)(C)O)co3)c3c1CCC3)CCC2]

4-Isocyanato-8-methyl-1,2,3,5,6,7-hexahydro-s-indacene (prepared using general method A1) and 4-(2-hydroxypropan-2-yl)furan-2-sulfonamide were used in general method C1 to give the titled compound as a white solid (15 mg, 3%). ¹H NMR (400 MHz, CD₃OD): δ=7.58 (s, 1H), 7.07 (s, 1H), 6.46 (s, 1H), 2.82-2.73 (m, J=7.5 Hz, 8H), 2.12 (s, 3H), 2.05-2.02 (m, 4H), 1.508 (s, 6H). LCMS (m/z): 417.10 (M −1)⁻; 99.59% (210 nm), 99.33% (254 nm). HPLC: 97.92% (210 nm), 97.53% (254 nm).

5-(N-((1,2,3,5,6,7-hexahydro-s-indacen-4-yl)carbamoyl)sulfamoyl)furan-3-carboxylic acid

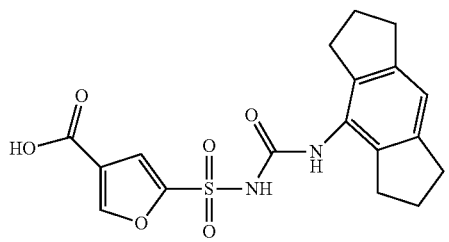 [SMILES: O=C(Nc1c2c(cc3c1CCC3)CCC2)NS(=O)(=O)c1cc(C(=O)O)co1]

Ethyl 5-(N-((1,2,3,5,6,7-hexahydro-s-indacen-4-yl)carbamoyl)sulfamoyl)furan-3-carboxylate (0.1 g, 0.24 mmol) in THF (8 mL) at 0° C. was treated with a solution of LiOH (0.1 g, 2.4 mmol) in water (2 mL). The cooling bath was removed and the reaction mixture stirred for 3 h. The solution was acidified using 10% citric acid and immediately extracted using ethyl acetate (2×25 mL). The organics were washed using water (20 mL), brine (20 mL), dried (Na₂SO₄) and concentrated in vacuo. The crude product was purified by reversed phase HPLC to give the titled compound as a white solid (5.0 mg, 5%). ¹H NMR (400 MHz, CD₃OD): δ=8.14 (s, 1H), 7.28 (s, 1H), 6.93 (s, 1H), 2.85 (t, J=7.6 Hz, 4H), 2.74 (t, J=7.6 Hz, 4H), 2.04 (quin, J=7.6 Hz, 4H).

Ethyl 5-(N-((1,2,3,5,6,7-hexahydro-s-indacen-4-yl)carbamoyl)sulfamoyl)furan-3-carboxylate

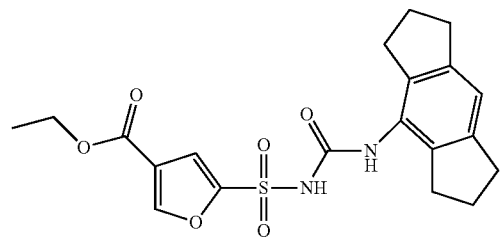 [SMILES: CCOC(=O)c1coc(S(=O)(=O)NC(=O)Nc2c3c(cc4c2CCC4)CCC3)c1]

4-Isocyanato-1,2,3,5,6,7-hexahydro-s-indacene (prepared using general method A2) and ethyl 5-sulfamoylfuran-3-carboxylate were used in general method C3. The reaction mixture was quenched using water (50 mL), extracted using ethyl acetate (2×25 mL) and the organics washed with brine (25 mL), dried (Na₂SO₄) and concentrated in vacuo. The crude product was purified by column chromatography on silica gel using 50% EtOAc-hexanes eluent to give the titled compound as a white solid (0.45 g, 63%). ¹H NMR (300 MHz, DMSO-d₆) δ=8.31 (s, 1H), 7.59 (s, 1H), 6.77 (s, 1H), 4.22 (q, J=7.2 Hz, 2H), 2.75 (t, J=7.3 Hz, 4H), 2.65 (t, J=7.3 Hz, 4H) 1.90 (pent, J=7.6 Hz, 4H), 1.26 (t, J=7.2 Hz, 3H).

N-((1,2,3,5,6,7-hexahydro-s-indacen-4-yl)carbamoyl)-4-(prop-1-en-2-yl)furan-2-sulfonamide

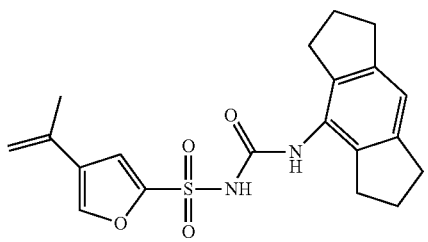 [SMILES: C=C(C)c1coc(S(=O)(=O)NC(=O)Nc2c3c(cc4c2CCC4)CCC3)c1]

4-Isocyanato-1,2,3,5,6,7-hexahydro-s-indacene (prepared using general method A2) and 4-(prop-1-en-2-yl)furan-2-sulfonamide were used in general method C6 to give the titled compound as a white solid (85 mg, 51%). $^1$H NMR (400 MHz, CDCl$_3$) δ 7.54 (s, 1H), 7.28 (s, 1H), 7.00 (s, 1H), 5.26 (s, 1H), 5.05 (s, 1H), 2.86 (t, J=7.4 Hz, 4H), 2.69 (t, J=7.5 Hz, 4H), 2.09-1.98 (m, 7H). $^{13}$C NMR (101 MHz, CDCl$_3$) δ 144.4, 142.8, 137.8, 132.8, 129.2, 127.2, 119.4, 115.4, 113.6, 32.9, 30.5, 25.5, 20.9. HRMS (ESI) calcd. for C20H23N2O4S [M+H] 387.1373, found 387.1379.

4-(2-hydroxypropan-2-yl)-N-((3,5,6,7-tetrahydro-2H-indeno[5,6-b]furan-8-yl)carbamoyl)furan-2-sulfonamide

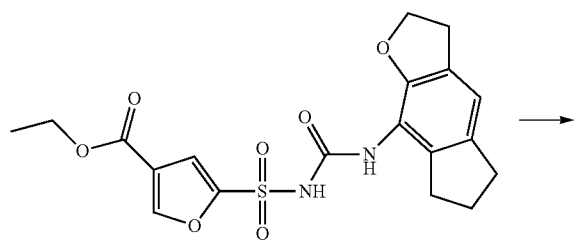

8-isocyanato-3,5,6,7-tetrahydro-2H-indeno[5,6-b]furan (prepared using general method A1) and ethyl 5-sulfamoyl-furan-3-carboxylate were used in general method C3 to give ethyl 5-(N-((3,5,6,7-tetrahydro-2H-indeno[5,6-b]furan-8-yl)carbamoyl)sulfamoyl)furan-3-carboxylate as a pale-brown solid (0.25 g, 50%). $^1$H NMR (300 MHz, DMSO-d$_6$) δ 8.32 (s, 1H), 7.17 (s, 1H), 6.77 (d, J=5.2 Hz, 1H), 4.43 (t, J=8.6 Hz, 2H), 4.23 (q, J=7.1 Hz, 2H), 3.07 (t, J=8.6 Hz, 2H), 2.71 (t, J=7.3 Hz, 2H), 2.63 (t, J=7.3 Hz, 2H), 1.89 (p, J=7.4 Hz, 2H), 1.26 (t, J=7.1 Hz, 3H).

Ethyl 5-(N-((3,5,6,7-tetrahydro-2H-indeno[5,6-b]furan-8-yl)carbamoyl)sulfamoyl)furan-3-carboxylate (0.25 g, 0.6 mmol) in anhydrous THF (10 mL) at 0° C. was treated with methyl magnesium chloride solution (3.0 M in Et$_2$O, 6 eq.) drop-wise over 5 minutes with vigorous stirring. The solution was then stirred at 0° C. for 30 min then at ambient temperature for 4 h before being quenched drop-wise with a solution of sat. ammonium chloride. The aqueous solution was extracted using EtOAc (2×25 mL), the combined organics washed with brine (20 mL), dried (Na$_2$SO$_4$) and concentrated in vacuo.

The crude product was triturated with diethyl ether then purified by reverse phase preparative HPLC to give the titled compound as a white solid (32 mg, 13%). $^1$H NMR (400 MHz, DMSO-d$_6$) δ 7.58 (s, 1H), 7.08 (s, 1H), 6.84 (s, 1H), 5.02 (s, 1H), 4.47 (t, J=8.6 Hz, 2H), 3.10 (t, J=8.6 Hz, 2H), 2.73 (t, J=7.3 Hz, 2H), 2.59 (t, J=7.5 Hz, 2H), 1.90 (d, J=7.4 Hz, 2H), 1.36 (s, 6H).

N-((4-bromo-3,5,6,7-tetrahydro-2H-indeno[5,6-b]furan-8-yl)carbamoyl)-4-(2-hydroxypropan-2-yl)furan-2-sulfonamide

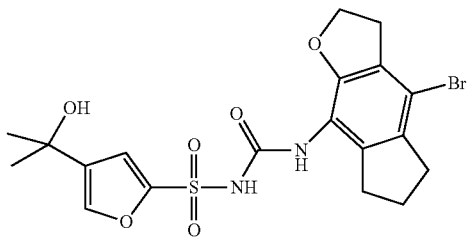

4-bromo-8-isocyanato-3,5,6,7-tetrahydro-2H-indeno[5,6-b]furan (prepared using general method A1) and 4-(prop-1-en-2-yl)furan-2-sulfonamide were used in general method C1 to give the titled compound as a white solid (20 mg, 9%). $^1$H NMR (400 MHz, CD$_3$OD) δ=7.48 (d, J=1.2 Hz, 1H), 6.93 (d, J=1.2 Hz, 1H), 4.60 (t, J=8.7 Hz, 2H), 3.16 (t, J=8.6 Hz, 2H), 2.85 (m, 4H), 2.03 (p, J=7.5 Hz, 2H), 1.50 (s, 6H).

4-(2-hydroxypropan-2-yl)-N-((3,5,6,7-tetrahydro-2H-indeno[5,6-b]furan-4-yl)carbamoyl)furan-2-sulfonamide

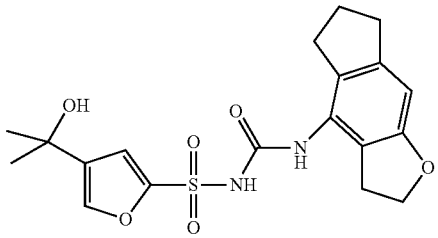 [SMILES: CC(C)(O)c1coc(S(=O)(=O)NC(=O)Nc2c3c(cc4c2CCO4)CCC3)c1]

4-isocyanato-3,5,6,7-tetrahydro-2H-indeno[5,6-b]furan (prepared using general method A1) and 4-(prop-1-en-2-yl)furan-2-sulfonamide were used in general method C1 to give the titled compound as a white solid (20 mg, 9%). $^1$H NMR (400 MHz, CD$_3$OD) δ=7.58 (s, 1H), 7.07 (s, 1H), 6.46 (s, 1H), 4.49 (d, J=8.9 Hz, 2H), 3.05 (t, J=8.7 Hz, 2H), 2.82 (t, J=7.4 Hz, 2H), 2.70 (t, J=7.4 Hz, 2H), 2.04 (p, J=7.4 Hz, 2H), 1.51 (d, J=1.9 Hz, 6H).

4-(2-hydroxypropan-2-yl)-N-((2,3,6,7-tetrahydrobenzo[1,2-b:4,5-b']difuran-4-yl)carbamoyl)furan-2-sulfonamide

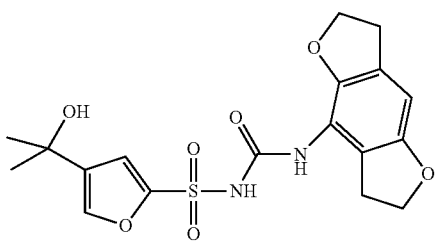 [SMILES: CC(C)(O)c1coc(S(=O)(=O)NC(=O)Nc2c3c(cc4c2OCC4)OCC3)c1]

4-isocyanato-2,3,6,7-tetrahydrobenzo[1,2-b:4,5-b']difuran (prepared using general method A1) and 4-(2-hydroxypropan-2-yl)furan-2-sulfonamide were used in general method C6 to give the titled compound as a white solid (285 mg, 96%). $^1$H NMR (600 MHz, DMSO-$d_6$) δ 7.76 (s, 1H), 7.66 (s, 1H), 7.01 (s, 1H), 6.45 (s, 1H), 5.04 (s, 1H), 4.46 (t, J=8.6 Hz, 2H), 4.39 (t, J=8.6 Hz, 2H), 3.08 (t, J=8.6 Hz, 2H), 2.94 (t, J=8.6 Hz, 2H), 1.37 (s, 6H).

N-(benzo[1,2-b:4,5-b']difuran-4-ylcarbamoyl)-4-(2-hydroxypropan-2-yl)furan-2-sulfonamide

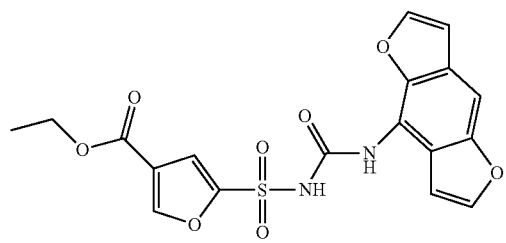

4-isocyanatobenzo[1,2-b:4,5-b']difuran (prepared using general method A1) and ethyl 5-sulfamoylfuran-3-carboxylate were used in general method C3 to give ethyl 5-(N-(benzo[1,2-b:4,5-b']difuran-4-ylcarbamoyl)sulfamoyl)furan-3-carboxylate as a white solid (0.05 g, 53%). $^1$H NMR (300 MHz, CD$_3$OD) δ=8.25 (s, 1H), 7.72 (d, J2.1 Hz, 1H), 7.63 (d, J2.1 Hz, 1H), 7.46 (s, 1H), 7.27 (s, 1H), 6.93 (s, 1H), 6.89 (d, J2.1 Hz, 1H), 6.86 (d, J2.1 Hz, 1H), 4.30 (q, J6.9 Hz, 2H), 1.4 (t, J6.9 Hz, 3H).

Ethyl 5-(N-(benzo[1,2-b:4,5-b']difuran-4-ylcarbamoyl)sulfamoyl)furan-3-carboxylate (0.25 g, 0.6 mmol) in anhydrous THF (10 mL) at 0° C. was treated with methyl magnesium chloride solution (3.0 M in Et$_2$O, 10 eq.) drop-wise over 10 minutes with vigorous stirring. The solution was then stirred at 0-10° C. for 3 h then quenched drop-wise with a solution of sat. ammonium chloride. The aqueous solution was extracted using EtOAc (2×20 mL), the combined organics washed with brine (20 mL), dried (Na$_2$SO$_4$) and concentrated in vacuo. The crude product was triturated with diethyl ether then purified by reverse phase preparative HPLC to give the titled compound as a white solid (15 mg, 6%). $^1$H NMR (400 MHz, CD$_3$OD) δ=7.76 (d, J2.0 Hz, 1H), 7.65 (d, J2.4 Hz, 1H), 7.55 (s, 1H), 7.47 (s, 1H), 7.05 (s, 1H), 6.93 (d, J2.0 Hz, 1H), 6.89 (d, J 2.4 Hz, 1H), 1.5 (s, 6H).

N-(anthracen-9-ylcarbamoyl)-4-(2-hydroxypropan-2-yl)furan-2-sulfonamide

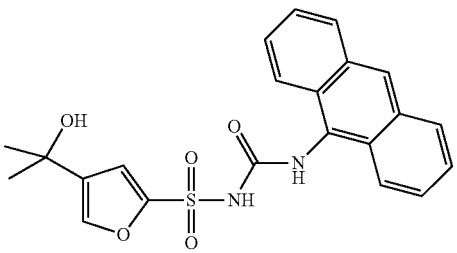 [SMILES: CC(C)(O)c1coc(S(=O)(=O)NC(=O)Nc2c3ccccc3cc3ccccc23)c1]

9-isocyanatoanthracene (prepared using general method B2) and 4-(2-hydroxypropan-2-yl)furan-2-sulfonamide were used in general method C6 to give the titled compound as a white solid (24 mg, 23%). $^1$H NMR (400 MHz, CD$_3$OD) δ=8.49 (s, 1H), 8.07-7.98 (m, 4H), 7.75 (s, 1H), 7.55-7.44 (m, 4H), 7.27-7.22 (m, 1H), 1.49 (s, 6H). $^{13}$C NMR (101 MHz, CD$_3$OD) δ=153.8, 149.4, 141.4, 136.6, 131.7, 128.8, 128.2, 127.4, 126.4, 125.9, 124.9, 122.8, 115.2, 111.1, 67.2, 29.6.

4-(2-hydroxypropan-2-yl)-N-(quinolin-8-ylcarbamoyl)furan-2-sulfonamide

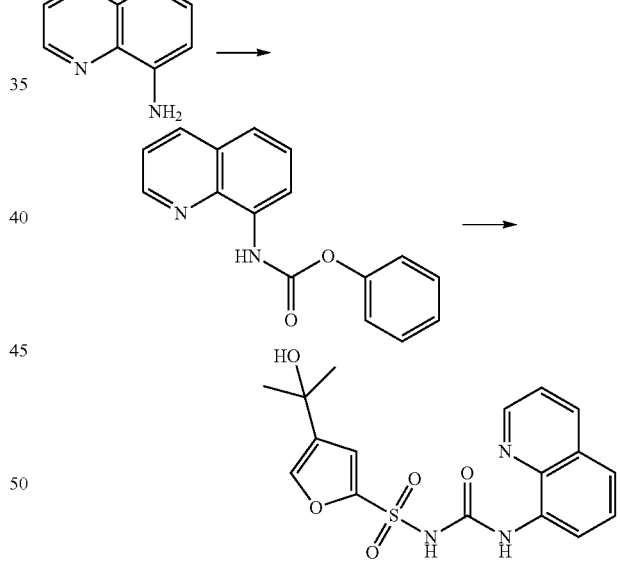

Phenyl chloroformate (1.5 eq) was added slowly to a solution of quinolin-8-amine (1 g, 6.9 mmol) in THF (10 mL) and triethylamine (2 eq.) to 0° C. The solution was stirred at room temperature for 2 h or until completion. The solution was diluted using sat.aq. NaHCO3 solution, extracted using ethyl acetate (2×50 mL), washed with water, brine then dried (Na$_2$SO$_4$) and concentrated in vacuo. The crude product was purified by column chromatography on silica using 10% EtOAc-hexanes to give phenyl quinolin-8-ylcarbamate (1.5 g, 83%) as α-white solid which was used directly in the next reaction step.

4-(2-hydroxypropan-2-yl)furan-2-sulfonamide (0.2 g, 0.98 mmol) in THF (5 mL) at 0° C. was treated portion-wise with sodium hydride (3 eq.) and the suspension stirred at ambient temperature for 45 minutes (until effervescence ceased). The crude phenyl quinolin-8-ylcarbamate was dissolved in THF (5 mL) then added slowly to the reaction and the solution stirred at ambient temperature until completion, typically 4 h. The reaction was quenched with sat.aq. NH$_4$Cl, extracted with ethyl acetate (×2), washed with water, brine, dried (Na$_2$SO$_4$) and concentrated in vacuo. The crude product was purified using reverse phase HPLC to give the titled compound, 4-(2-hydroxypropan-2-yl)-N-(quinolin-8-ylcarbamoyl)furan-2-sulfonamide as a white solid (40 mg, 11%). $^1$H NMR (400 MHz, DMSO-d$_6$) δ 9.63 (s, 1H), 8.89 (d, J=4.3 Hz, 1H), 8.37 (m, 2H), 7.80-6.76 (m, 5H), 5.09 (s, 1H), 1.38 (s, 6H).

4-(2-hydroxypropan-2-yl)-N-((6-methoxyquinolin-8-yl)carbamoyl)furan-2-sulfonamide

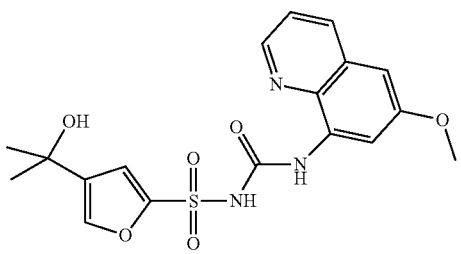 [SMILES: COc1cc(NC(=O)NS(=O)(=O)c2cc(C(C)(C)O)co2)c2ncccc2c1]

4-(2-hydroxypropan-2-yl)-N-((6-methoxyquinolin-8-yl)carbamoyl)furan-2-sulfonamide was synthesised using modification of the procedures used to make 4-(2-hydroxypropan-2-yl)-N-(quinolin-8-ylcarbamoyl)furan-2-sulfonamide but using 6-methoxyquinolin-8-amine in place of quinolin-8-amine. The titled compound was obtained as an off-white solid (75 mg, 38%). $^1$H NMR (400 MHz, DMSO-d$_6$) δ 8.79 (s, 1H), 8.63 (m, 1H), 8.17 (m, 1H), 8.09 (d, J=2.7 Hz, 1H), 7.49 (dd, J=8.3, 4.2 Hz, 1H), 7.40 (s, 1H), 6.79 (d, J=2.8 Hz, 1H), 6.69 (s, 1H), 4.96 (s, 1H), 3.84 (s, 3H), 1.36 (s, 6H).

N-((2,3-dihydrobenzo[b][1,4]dioxin-5-yl)carbamoyl)-4-(2-hydroxypropan-2-yl)furan-2-sulfonamide

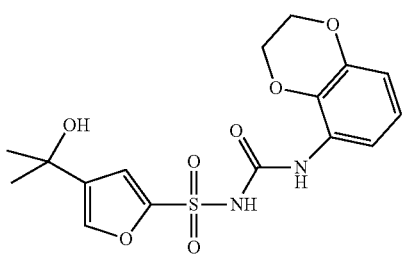 [SMILES: CC(C)(O)c1coc(S(=O)(=O)NC(=O)Nc2cccc3c2OCCO3)c1]

5-Isocyanato-2,3-dihydrobenzo[b][1,4]dioxine (prepared using general method A1) and 4-(2-hydroxypropan-2-yl)furan-2-sulfonamide were used in general method C6 to give the titled compound as a white solid (49 mg, 39%). $^1$H NMR (600 MHz, Acetonitrile-d$_3$) δ=7.56 (dd, J=8.4, 1.5 Hz, 1H), 7.45 (d, J=1.0 Hz, 1H), 6.98 (d, J=1.0 Hz, 1H), 6.7 (t, J=8.4 Hz, 1H), 6.48 (dd, J=8.4, 1.5 Hz, 1H), 4.22 (m, 4H), 1.43 (s, 6H).

N-((2,3-dihydrobenzofuran-7-yl)carbamoyl)-4-(2-hydroxypropan-2-yl)furan-2-sulfonamide

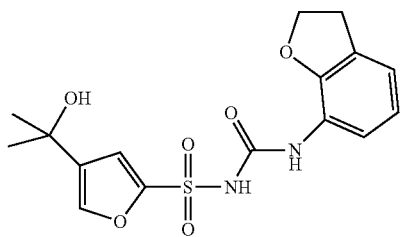 [SMILES: CC(C)(O)c1coc(S(=O)(=O)NC(=O)Nc2cccc3c2OCC3)c1]

7-Isocyanato-2,3-dihydrobenzofuran (prepared using general method A1) and 4-(2-hydroxypropan-2-yl)furan-2-sulfonamide were used in general method C6 to give the titled compound as a white solid (32 mg, 39%). $^1$H NMR (600 MHz, Acetonitrile-d$_3$) δ 7.64 (d, J=7.7 Hz, 1H), 7.48 (d, J=1.1 Hz, 1H), 7.00 (d, J=1.1 Hz, 1H), 6.89 (m, 1H), 6.74 (t, J=7.7 Hz, 1H), 4.56 (t, J=8.7 Hz, 1H), 3.2 (t, J=8.7 Hz, 1H), 1.43 (s, 6H).

N-((2,4-bis(trifluoromethyl)phenyl)carbamoyl)-4-(2-hydroxypropan-2-yl)furan-2-sulfonamide

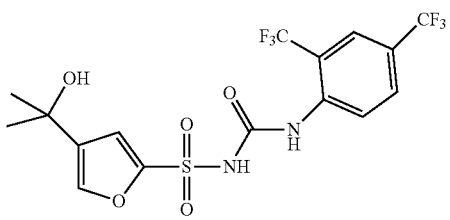 [SMILES: CC(C)(O)c1coc(S(=O)(=O)NC(=O)Nc2ccc(C(F)(F)F)cc2C(F)(F)F)c1]

1-Isocyanato-2,4-bis(trifluoromethyl)benzene (prepared using general method A1) and 4-(2-hydroxypropan-2-yl)furan-2-sulfonamide were used in general method C4 to give the titled compound as an off white solid (0.12 g, 33%). $^1$H NMR (400 MHz, DMSO-d$_6$): δ=8.59 (d, J=8.8 Hz, 1H), 7.87 (d, J=9.2 Hz, 1H), 7.81 (s, 1H), 7.67 (s, 1H), 7.43 (s, 1H), 6.68 (s, 1H), 4.94 (s, 1H), 1.36 (s, 6H). $^{13}$C NMR (100 MHz, DMSO-d$_6$): δ=156.0, 154.4, 142.5, 138.1, 135.8, 129.9, 125.2, 124.9, 123.0, 122.5, 121.3, 120.7, 120.4, 115.5, 115.2, 110.2, 66.5, 31.0. LCMS, Purity: 90.47%, tr=3.84 min, m/z 459.25 (M-H$^+$). HRMS (FAB$^-$) calcd for C$_{16}$H$_{14}$F$_6$N$_2$O$_5$S [M-H]$^-$: 459.0528, found: 459.0512.

N-((2,5-bis(trifluoromethyl)phenyl)carbamoyl)-4-(2-hydroxypropan-2-yl)furan-2-sulfonamide

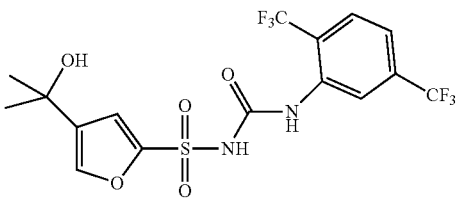 [SMILES: CC(C)(O)c1coc(S(=O)(=O)NC(=O)Nc2cc(C(F)(F)F)ccc2C(F)(F)F)c1]

2-Isocyanato-1,4-bis(trifluoromethyl)benzene (prepared using general method A1) and 4-(2-hydroxypropan-2-yl)furan-2-sulfonamide were used in general method C4 to give the titled compound as an off white solid (55 mg, 12%). $^1$H NMR (400 MHz, CD$_3$OD): δ=8.61 (s, 1H), 7.75 (d, J=7.6

Hz, 1H), 7.48 (s, 1H), 7.37 (d, J=8.4 Hz, 1H), 6.95 (s, 1H), 1.41 (s, 6H). $^{13}$C NMR (100 MHz, DMSO-$d_6$): δ 156.4, 154.5, 139.7, 138.1, 132.9, 127.2, 124.9, 122.3, 118.9, 117.6, 117.0, 110.0, 66.5, 31.0. LCMS, Purity: 95.02%, tr=2.09 min, m/z 558.94 (M−H$^+$). HRMS (FAB$^-$) calcd for $C_{16}H_{14}F_6N_2O_5S$ [M−H]$^-$: 459.0528, found: 459.0224.

4-(2-hydroxypropan-2-yl)-N-((2-methoxyphenyl) carbamoyl)furan-2-sulfonamide

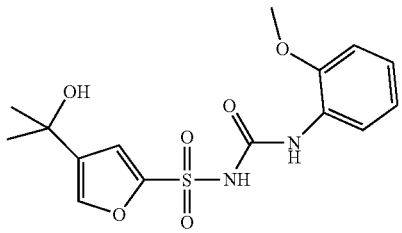 [SMILES: COc1ccccc1NC(=O)NS(=O)(=O)c1cc(C(C)(C)O)co1]

1-isocyanato-2-methoxybenzene (prepared using general method A2) and 4-(2-hydroxypropan-2-yl)furan-2-sulfonamide were used in general method C2 to give the titled compound as an off white solid (30 mg, 38%).

N-((2,5-dimethoxyphenyl)carbamoyl)-4-(2-hydroxypropan-2-yl)furan-2-sulfonamide

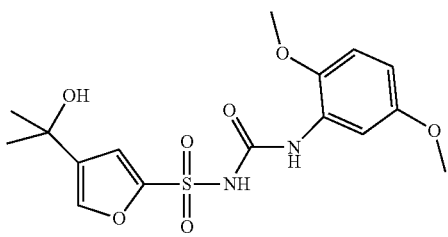 [SMILES: COc1ccc(OC)c(NC(=O)NS(=O)(=O)c2cc(C(C)(C)O)co2)c1]

2-isocyanato-1,4-dimethoxybenzene and 4-(2-hydroxypropan-2-yl)furan-2-sulfonamide were used in general method C2 to give the titled compound as an off white solid (52 mg, 55%).

N-((4-chloro-2,6-dimethylphenyl)carbamoyl)-4-(2-hydroxypropan-2-yl)furan-2-sulfonamide

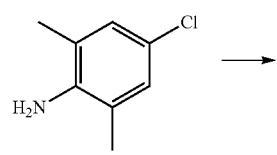

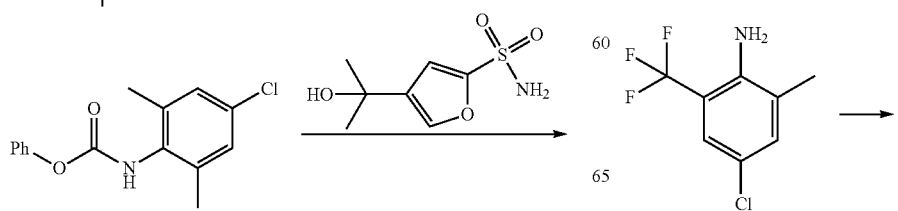

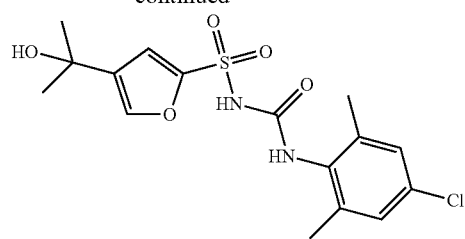

4-chloro-2,6-dimethylaniline, 1 (300 mg, 1.92 mmol) was dissolved in THF (50 mL) and cooled to 0° C. NaH (100 mg, 2.49 mmol) was added in portions to the aforementioned solution under nitrogen atmosphere and stirred the mixture for 15 min. Phenyl chloroformate (0.33 mL, 0.72 mmol) was added dropwise to the aforementioned solution at 0° C. The reaction mixture was warmed to RT and stirred for 12 h. Upon completion, the reaction mixture was diluted with EtOAc, filtered through celite and concentrated in vacuo. The crude product was purified by column chromatography on silica gel (60-120 mesh) using 30% EtOAc-hexanes eluant to give phenyl (4-chloro-2,6-dimethylphenyl)carbamate (0.2 g, 85%) as a white solid. $^1$H NMR (300 MHz, CDCl$_3$): δ=7.41-7.36 (m, 2H), 7.21-7.19 (m, 2H), 7.11-7.10 (m, 3H), 6.30 (bs, 1H), 2.33 (s, 6H).

4-(2-hydroxypropan-2-yl)furan-2-sulfonamide (133 mg, 0.64 mmol) was dissolved in anhydrous THF (5 mL) and treated carefully with NaH (65 mg, 1.63 mmol) at 0° C. under nitrogen atmosphere. The resulting mixture was stirred at RT for 45 min then treated with a solution of phenyl (4-chloro-2,6-dimethylphenyl)carbamate (200 mg, 0.73 mmol) in THF (3 mL) under nitrogen atmosphere at 0° C. The resulting reaction mixture was warmed to RT and stirred for 2 h. Upon completion, the reaction mixture was diluted with saturated NH$_4$Cl solution, extracted with EtOAc (2×50 mL) and the combined organic extract washed with water, brine, dried (Na$_2$SO$_4$) and concentrated in vacuo.

The crude product was purified by column chromatography on silica gel (60-120 mesh) using 40% EtOAc-hexanes eluant to give N-((4-chloro-2,6-dimethylphenyl)carbamoyl)-4-(2-hydroxypropan-2-yl)furan-2-sulfonamide (20 mg, 31%) as a white solid. $^1$H NMR (400 MHz, CDCl$_3$): δ=7.83 (s, 1H), 7.56 (s, 1H), 7.19 (s, 1H), 7.10-7.05 (m, 2H), 2.16 (s, 6H), 1.55 (s, 6H). LCMS (m/z): 385.05 [M−H]$^-$, 94.12% (210 nm). HPLC: 92.60% (210 nm). HRMS calculated for $C_{16}H_{18}Cl_1N_2O_5S_1$ [M−H]$^-$ 385.0630, found 365.0621.

N-((2,4-dimethyl-6-(trifluoromethyl) phenyl)carbamoyl)-4-(2-hydroxypropan-2-yl)furan-2-sulfonamide

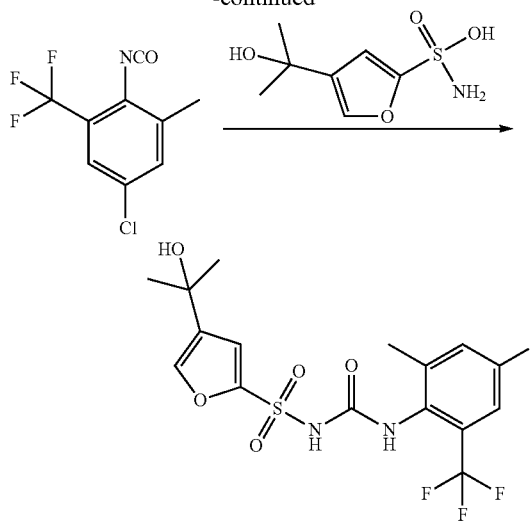

4-Chloro-2-methyl-6-(trifluoromethyl)aniline (230 mg, 1.1 mmol) was dissolved in anhydrous THF (20 mL) and treated with Et₃N (0.17 mL, 1.32 mmol) at RT. The solution was treated with triphosgene (130 mg, 0.44 mmol) and the resulting mixture stirred at 60° C. for 4 h then concentrated in vacuo. The residue obtained was stirred with n-pentane (20 mL) for 10 min, filtered through a Celite pad and concentrated in vacuo to give 5-chloro-2-isocyanato-1-methyl-3-(trifluoromethyl)benzene (0.2 g) as a white solid. The product was used in the next step without further purification.

4-(2-hydroxypropan-2-yl)furan-2-sulfonamide, 3 (150 mg, 0.731 mmol) was dissolved in anhydrous THF (50 mL) and treated carefully with NaH (44 mg, 1.096 mmol) at 0° C. under nitrogen atmosphere. The resulting reaction mixture was stirred at RT for 30 minutes and treated with solution of 5-chloro-2-isocyanato-1-methyl-3-(trifluoromethyl)benzene (0.2 g) in THF (30 mL) under nitrogen atmosphere. The resulting reaction mixture was stirred at RT for 2 h. Upon completion, the reaction mixture was diluted with saturated NH₄Cl solution, extracted with EtOAc (2×50 mL) and the combined organic extract washed with water, brine, dried (Na₂SO₄) and concentrated in vacuo. The crude product was purified by column chromatography on silica gel (60-120 mesh) using 40% EtOAc-hexanes eluent. The product was then triturated with diethyl ether and n-pentane to give N-((2,4-dimethyl-6-(trifluoromethyl) phenyl)carbamoyl)-4-(2-hydroxypropan-2-yl)furan-2-sulfonamide (15 mg, 5%) as a white solid. ¹H NMR (400 MHz, CD₃OD): δ=7.52-7.48 (m, 3H), 6.99 (s, 1H), 2.19 (s, 3H), 1.47 (s, 6H). 19F NMR (400 MHz, CD₃OD): δ=−63.09. LCMS (m/z): 439.05 [M−H]⁻; 94.86% (210 nm), 96.92% (254 nm). HPLC: 98.90% (210 nm). HRMS calculated for C₁₆H₁₅Cl₁F₃N₂O₅S₁ [M−H]⁻ 439.0348, found 439.0339.

N-((4-chloro-2,6-diisopropylphenyl)carbamoyl)-4-(2-hydroxypropan-2-yl)furan-2-sulfonamide

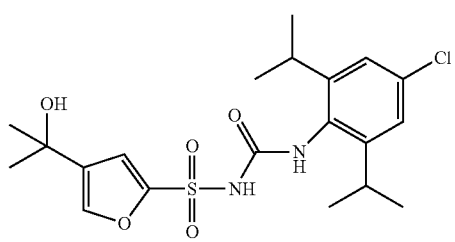 [SMILES: CC(C)c1cc(Cl)cc(C(C)C)c1NC(=O)NS(=O)(=O)c1cc(C(C)(C)O)co1]

5-chloro-2-isocyanato-1,3-diisopropylbenzene (prepared using general method A2) and 4-(2-hydroxypropan-2-yl)furan-2-sulfonamide were used in general method C2 to give the titled compound as a white solid (161 mg, 34%). ¹H NMR (600 MHz, DMSO-d₆) δ=7.82 (s, 1H), 7.61 (s, 1H), 7.09 (s, 2H), 6.93 (s, 1H), 5.04 (s, 1H), 3.05-2.99 (m, 2H), 1.35 (s, 6H), 1.05 (d, J=6.9 Hz, 12H). HRMS calculated for C₂₀H₂₆Cl₁N₂O₅S₁ [M−H]⁻ 441.1256, found 441.1264.

N-((4-chloro-2,6-dicyclopropylphenyl)carbamoyl)-4-(2-hydroxypropan-2-yl)furan-2-sulfonamide

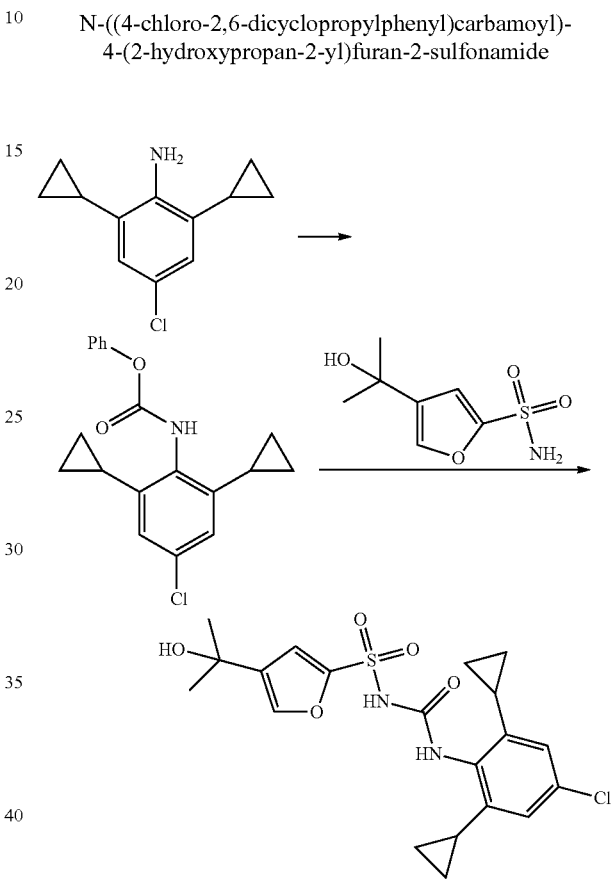

4-Chloro-2,6-dicyclopropylaniline, 1 (250 mg, 1.20 mmol) was dissolved in THF (50 mL) and cooled to 0° C. NaH (72 mg, 1.80 mmol) was added in portions and the resulting mixture stirred for 20 min under nitrogen atmosphere. Phenyl chloroformate (370 mg, 2.40 mmol) was added dropwise at 0° C. then the reaction mixture was warmed to RT and stirred for 12 h. Upon completion the reaction mixture was diluted with EtOAc, filtered through celite and concentrated in vacuo. The crude product was purified by column chromatography on silica gel (60-120 mesh) using 8% EtOAc-hexanes eluent to give phenyl (4-chloro-2,6-dicyclopropyl phenyl)carbamate (0.2 g, 51%) as a white solid. ¹H NMR (300 MHz, CDCl₃): δ=7.38-7.35 (m, 2H), 7.21-7.19 (m, 3H), 6.84-6.83 (m, 2H), 2.06-2.04 (m, 2H), 1.04-1.02 (m, 4H), 0.69-0.68 (m, 4H).

4-(2-hydroxypropan-2-yl)furan-2-sulfonamide (75 mg, 0.365 mmol) was dissolved in anhydrous THF (50 mL) and treated carefully with NaH (36 mg, 0.914 mmol) at 0° C. under nitrogen atmosphere. The resulting mixture was stirred at RT for 30 min then treated with a solution of phenyl (4-chloro-2,6-dicyclopropyl phenyl)carbamate (135 mg, 0.402 mmol) in THF (3 mL) under nitrogen atmosphere at 0° C. The resulting reaction mixture was warmed to RT and stirred for 4 h. Upon completion the reaction mixture was diluted with saturated NH₄Cl solution, extracted with EtOAc (2×50 mL) and the combined organic extract washed with water, brine, dried (Na₂SO₄) and concentrated in vacuo. The crude product was purified by column chromatography on silica gel (60-120 mesh) using 50-100% EtOAc-hexanes to give N-((4-chloro-2,6-dicyclopropylphenyl)carbamoyl)-4-(2-hydroxypropan-2-yl)furan-2-sulfonamide (10 mg, 6%) as a white solid. $^1$H NMR (400 MHz, CD₃OD): δ=7.59 (s, 1H), 7.13 (s, 1H), 6.76 (s, 2H), 1.88-1.86 (m, 2H), 1.47 (s, 6H), 0.89-0.84 (m, 4H), 0.55-0.54 (m, 4H). LCMS (m/z): 436.95 [M–H]⁻; 96.29% (210 nm). HPLC: 98.29% (210 nm). HRMS calculated for $C_{20}H_{22}Cl_1N_2O_5S_1$ [M–H]⁻ 437.0943, found 437.0945. HRMS calculated for $C_{20}H_{22}Cl_1N_2O_5S_1$ [M–H]⁻ 437.0943, found 437.0945.

4-(2-hydroxypropan-2-yl)-N-((5-methoxy-2,3-dihydro-1H-inden-4-yl)carbamoyl)furan-2-sulfonamide

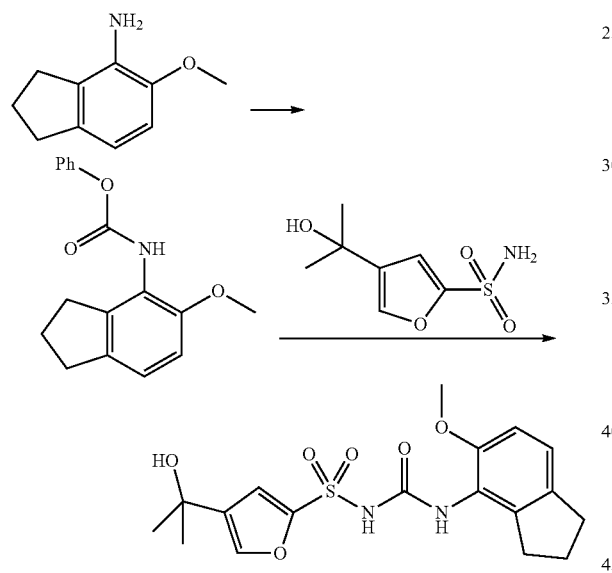

5-methoxy-2,3-dihydro-1H-inden-4-amine (150 mg, 0.59 mmol) was dissolved in THF (15 mL) and cooled to 0° C. NaH (35 mg, 0.89 mmol) was added to the aforementioned solution and stirred for 20 min. Phenyl chloroformate (150 mg, 0.932 mmol) was added dropwise at 0° C. then the solution allowed to warm to RT overnight. Upon completion, the reaction mixture was diluted with saturated NaHCO₃ and extracted with EtOAc (30 mL) The organic extract was washed with water, brine dried (Na₂SO₄) and concentrated in vacuo to give phenyl (5-methoxy-2,3-dihydro-1H-inden-4-yl)carbamate (100 mg, 59%) as a white solid. $^1$H NMR (300 MHz, CDCl₃): δ=7.40-7.35 (m, 2H), 7.22-7.18 (m, 3H), 7.06 (d, J=8.1 Hz, 1H), 6.73 (d, J=8.4 Hz, 1H), 3.86 (s, 3H), 2.98-2.84 (m, 4H), 2.08 (t, J=7.5 Hz, 2H). LCMS (m/z): 284.3 [M+H]⁺

4-(2-hydroxypropan-2-yl)furan-2-sulfonamide (87 mg, 0.424 mmol) was dissolved in anhydrous THF (5 mL) and treated carefully with NaH (44 mg, 1.097 mmol) at 0° C. under nitrogen atmosphere. The resulting mixture was stirred at RT for 1 h then treated with a solution of phenyl (5-methoxy-2,3-dihydro-1H-inden-4-yl)carbamate (120 mg, 0.424 mmol) in THF (5 mL) under nitrogen atmosphere at 0° C. The resulting reaction mixture was warmed to RT and stirred for 6 h. Upon completion, the reaction mixture was diluted with saturated NH₄Cl solution and extracted with EtOAc (2×30 mL). The combined organic extract was washed with water, brine dried (Na₂SO₄) and concentrated in vacuo. The crude product was purified by reverse phase preparative HPLC [column: X bridge (150 mm×19 mm particle size 5 µm); flow: 15 mL/min; eluent: 10 mM ammonium bicarbonate in water (A) & MeCN (B); gradient: T/% B=0/10, 2/10, 9/70]. The fractions were lyophilized to give 4-(2-hydroxypropan-2-yl)-N-((5-methoxy-2,3-dihydro-1H-inden-4-yl)carbamoyl) furan-2-sulfonamide (45 mg, 17%) as a white solid. $^1$H NMR (400 MHz, CD₃OD): δ=7.67 (s, 1H), 7.21 (s, 1H), 7.04 (d, J=8 Hz, 1H), 6.77 (d, J=8 Hz, 1H), 3.79 (s, 3H), 2.84 (t, J=7.2 Hz, 2H), 2.69 (t, J=7.2 Hz, 2H), 2.01-1.97 (m, 2H), 1.49 (s, 6H). LCMS (m/z): 393.10 [M–H]⁻; 98.97% (210 nm), 99.47% (254 nm). HPLC: 92.07% (210 nm), 93.87% (254 nm). HRMS calculated for $C_{18}H_{21}N_2O_6S_1$ [M–H]⁺ 393.1126, found 392.1113.

N-((7-chloro-5-cyclopropyl-2,3-dihydro-1H-inden-4-yl)carbamoyl)-4-(2-hydroxypropan-2-yl)furan-2-sulfonamide

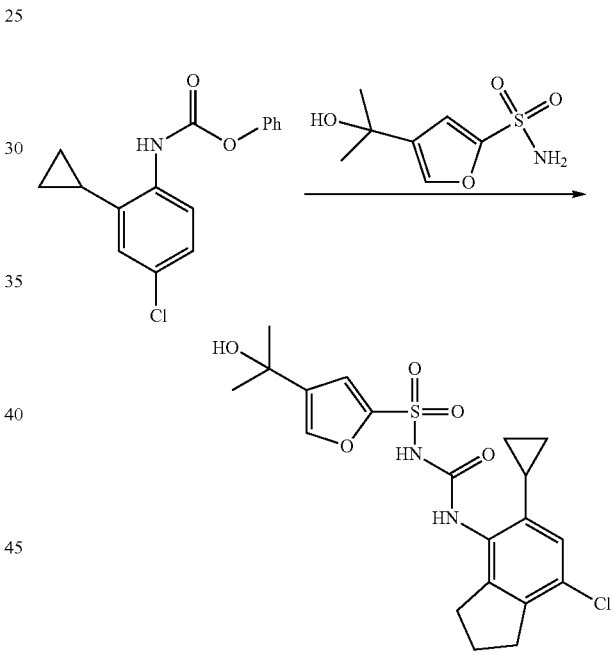

7-chloro-5-cyclopropyl-2,3-dihydro-1H-inden-4-amine, 6 (70 mg, 0.33 mmol) was dissolved in THF (5 mL) and cooled to 0° C. NaH (20 mg, 0.505 mmol) was added to the aforementioned solution under nitrogen atmosphere and stirred for 15 min before phenyl chloroformate (100 mg, 0.674 mmol) was added dropwise at 0° C. The reaction mixture was warmed to RT and stirred for 12 h. Upon completion the reaction mixture was diluted with EtOAc, filtered through celite and concentrated in vacuo. The crude product was purified by column chromatography on silica gel (60-120 mesh) using, 10% EtOAc-hexanes eluent to give phenyl (7-chloro-5-cyclopropyl-2,3-dihydro-1H-inden-4-yl) carbamate (80 mg, 73%) as a brown solid. $^1$H NMR (300 MHz, CDCl₃): δ=7.39-7.37 (m, 3H), 7.25-7.24 (m, 2H), 6.85 (s, 1H), 3.0-2.94 (m, 4H), 2.12-2.10 (m, 2H), 1.34 (m, 1H), 0.96-0.95 (m, 2H), 0.59-0.57 (m, 2H). LCMS (m/z): 328.30 [M+H]⁺.

4-(2-hydroxypropan-2-yl)furan-2-sulfonamide (56 mg, 0.274 mmol) was dissolved in anhydrous THF (5 mL) and treated carefully with NaH (27 mg, 0.685 mmol) at 0° C. under nitrogen atmosphere. The resulting mixture was stirred at RT for 15 min and was treated with a solution of phenyl (7-chloro-5-cyclopropyl-2,3-dihydro-1H-inden-4-yl) carbamate (100 mg, 0.244 mmol) in THF (2 mL) under nitrogen atmosphere at 0° C. The resulting reaction mixture was warmed to RT and stirred for 3 h. Upon completion the reaction mixture was diluted with saturated NH$_4$Cl solution, extracted with EtOAc (2×30 mL) and the combined organic extract washed with water, brine dried (Na$_2$SO$_4$) and concentrated in vacuo. The crude product was purified by reverse phase preparative HPLC [column: Gemini NX C18 (21.2 mm×150 mm particle size 5 μm); flow: 18 mL/min; eluent: 10 mM ammonium bicarbonate in water (A) & MeCN (B); gradient: T/% B=0/20, 2/30, 10/50]. The fractions were lyophilized to give N-((7-chloro-5-cyclopropyl-2,3-dihydro-1H-inden-4-yl)carbamoyl)-4-(2-hydroxypropan-2-yl)furan-2-sulfonamide (45 mg, 38%) as a white solid. $^1$H NMR (400 MHz, DMSO-d$_6$): δ=7.95 (d, J=2.4 Hz, 1H), 6.74 (s, 1H), 6.69 (d, J=2.4 Hz, 1H), 4.49 (m, 1H), 2.84 (t, J=7.6 Hz, 2H), 2.66 (t, J=7.6 Hz, 2H), 1.95 (m, 2H), 1.78 (m, 1H), 1.41 (d, J=6.4 Hz, 6H), 0.82 (m, 2H), 0.54 (m, 2H). LCMS (m/z): 437.0 [M−H]$^-$, 97.99% (210 nm). HPLC: 98.26% (210 nm). HRMS calculated for C$_{20}$H$_{22}$Cl$_1$N$_2$O$_5$S$_1$ [M−H]$^+$437.0943, found 437.0927.

4-(2-hydroxypropan-2-yl)-N-((3-oxo-1,2,3,5,6,7-hexahydro-s-indacen-4-yl)carbamoyl)furan-2-sulfonamide

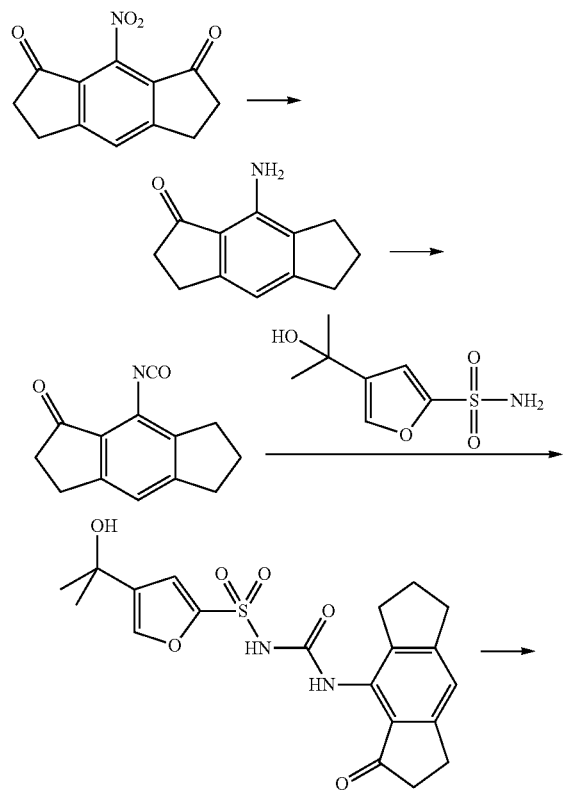

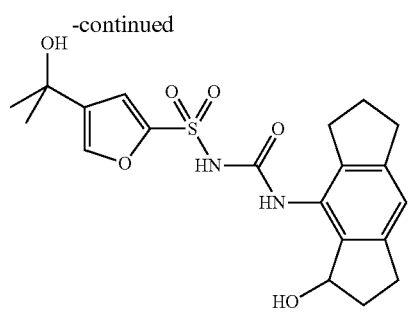

A solution of 8-nitro-3,5,6,7-tetrahydro-s-indacen-1(2H)-one (200 mg, 0.92 mmol) in MeOH (5 mL) was degassed with nitrogen for 5 minutes, 10% Pd/C (20 mg, 10% wt/wt) was added and the mixture stirred under hydrogen atmosphere at room temperature for 2 h. The reaction mixture was filtered through Celite and the filtrate was concentrated in vacuo to give 8-amino-3,5,6,7-tetrahydro-s-indacen-1(2H)-one as off an white solid (160 mg, 93%). $^1$H NMR (600 MHz, DMSO-d$_6$) δ 6.49 (s, 1H), 6.34 (s, 2H), 2.90-2.84 (m, 2H), 2.80 (t, J=7.5 Hz, 2H), 2.62 (t, J=7.4 Hz, 2H), 2.56-2.51 (m, 2H), 2.04-1.99 (m, 2H). $^{13}$C NMR (150 MHz, DMSO-d$_6$): 206.6, 155.4, 153.7, 144.1, 125.3, 118.6, 109.4, 36.8, 33.7, 28.6, 25.0, 24.9. LCMS (m/z): 188 [M+H]$^+$. HRMS calculated for C$_2$H$_{14}$N$_1$O$_1$ [M+H]$^+$188.1070, found 188.1077.

To di-t-butyldicarbonate (163 mg, 0.74 mmol) in anhydrous acetonitrile (1 mL) was added DMAP (26.1 mg, 0.21 mmol) at room temperature, stirred for 5 minutes, a solution of 8-amino-3,5,6,7-tetrahydro-s-indacen-1(2H)-one (100 mg, 0.53 mmol) in acetonitrile was added. The reaction mixture was stirred for 30 minutes at room temperature. Reaction mixture was used directly in the next step without workup.

To 4-(2-hydroxypropan-2-yl) furan-2-sulfonamide intermediate (100 mg, 0.48 mmol) in anhydrous THF (1 mL) was added NaH (18.3 mg, 0.48 mmol) at 0° C. and stirred for 30 minutes at ambient temperature under nitrogen atmosphere. Again cooled to 0° C., 8-isocyanato-3,5,6,7-tetrahydro-s-indacen-1(2H)-one (previous step reaction mixture) was added and stirred at ambient temperature for 16 h. To the reaction mixture added 0.5 mL of H$_2$O, loaded directly on C18 column for purification using aqueous 10 mM (NH$_4$)HCO$_3$ solution and acetonitrile as mobile phase, to give 4-(2-hydroxypropan-2-yl)-N-((3-oxo-1,2,3,5,6,7-hexahydro-s-indacen-4-yl)carbamoyl) furan-2-sulfonamide as a white solid (150 mg, 67%). $^1$H NMR (600 MHz, DMSO-d$_6$): δ 8.79 (s, 1H), 7.37 (s, 1H), 6.94 (s, 1H), 6.61 (s, 1H), 4.92 (s, 1H), 2.92 (t, J=5.6 Hz, 2H), 2.82 (t, J=7.5 Hz, 2H), 2.75 (t, J=7.5 Hz, 2H), 2.63-2.57 (m, 2H), 1.97-1.80 (m, 2H), 1.34 (s, 6H); LCMS (m/z): 417 [M−H]$^-$. HRMS calculated for C$_{20}$H$_{23}$N$_2$O$_6$S$_1$ [M+H]$^+$419.1271, found 419.1291.

To a solution of 4-(2-hydroxypropan-2-yl)-N-((3-oxo-1,2,3,5,6,7-hexahydro-s-indacen-4-yl)carbamoyl)furan-2-sulfonamide (70 mg, 0.16 mmol) in MeOH (2 mL) was added NaBH$_4$(63 mg, 1.67 mmol) at 0° C. under nitrogen atmosphere, resulting reaction mixture was stirred at room temperature for 3 h. Reaction mixture was quenched with H$_2$O (2 mL, distilled out MeOH, aqueous layer was directly loaded on C18 column for purification using aqueous 10 mM (NH$_4$)HCO$_3$ solution and acetonitrile as mobile phase, to give N-((3-hydroxy-1,2,3,5,6,7-hexahydro-s-indacen-4-yl)carbamoyl)-4-(2-hydroxypropan-2-yl)furan-2-sulfonamide as off-white solid (60 mg, 86%). $^1$H NMR (600 MHz, DMSO-d$_6$) δ 7.73 (bs, 1H), 7.38 (s, 1H), 6.81 (s, 1H), 6.60

(s, 1H), 5.63 (bs, 1H), 4.92 (bs, 1H), 4.87 (d, J=6.0 Hz, 1H), 3.00-2.84 (m, 2H), 2.77 (t, J=7.4 Hz, 2H), 2.64-2.53 (m, 2H), 2.07-2.00 (m, 1H), 1.97-1.92 (m, 1H), 1.91-1.81 (m, 2H), 1.35 (s, 6H); $^{13}$C NMR (150 MHz, DMSO-d$_6$): 159.5, 156.0, 144.9, 143.3, 138.3, 137.7, 136.8, 136.0, 133.0, 72.6, 67.0, 35.4, 33.1, 31.5, 31.4, 31.0, 30.4, 25.5; LCMS (m/z): 419 [M–H]$^−$; HRMS calculated for C$_{20}$H$_{23}$N$_2$O$_6$S$_1$ [M–H]$^−$ 419.1282, found 419.1263.

N-((1-hydroxy-1,2,3,5,6,7-hexahydro-s-indacen-4-yl)carbamoyl)-4-(2-hydroxypropan-2-yl) furan-2-sulfonamide

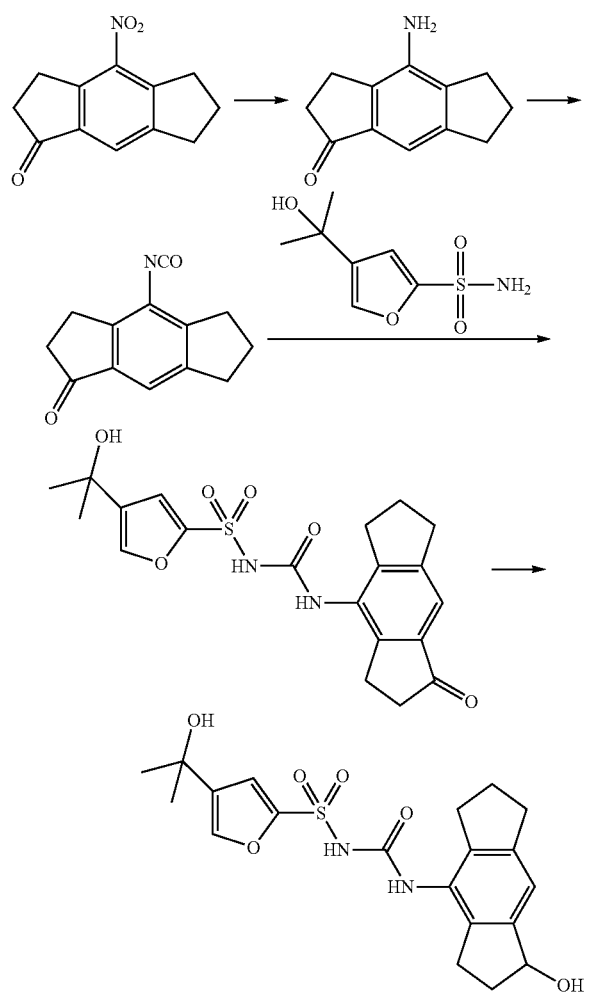

A solution of 4-nitro-3,5,6,7-tetrahydro-s-indacen-1(2H)-one (110 mg, 0.50 mmol) in MeOH (5 mL) was degassed with nitrogen for 5 minutes, added 10% Pd/C (11 mg, 10% wt/wt), stirred under hydrogen atmosphere at room temperature for about 2 h. Reaction mixture was filtered through Celite pad, filtrate was concentrated to give 4-amino-3,5,6,7-tetrahydro-s-indacen-1 (2H)-one as an off white solid (75 mg, 80%). $^1$H NMR (600 MHz, DMSO-d$_6$) δ 6.72 (s, 1H), 5.11 (s, 2H), 2.87-2.74 (m, 4H), 2.70 (t, J=7.4 Hz, 2H), 2.62-2.54 (m, 2H), 2.06-1.99 (m, 2H); $^{13}$C NMR (150 MHz, DMSO-d$_6$) 206.7, 144.6, 141.7, 139.9, 136.9, 136.8, 104.2, 39.9, 36.7, 30.6, 30.4, 24.5, 23.7. LCMS (m/z): 188 [M+H]$^+$; HRMS calculated for C$_{12}$H$_{14}$N$_1$O$_1$ [M+H]$^+$ 188.1070, found 188.1074.

To di-t-butyldicarbonate (81.6 mg, 0.37 mmol) in anhydrous acetonitrile (1 mL) was added DMAP (13.0 mg, 0.04 mmol) at room temperature, stirred for 5 minutes, a solution of 4-amino-3,5,6,7-tetrahydro-s-indacen-1 (2H)-one (50 mg, 0.26 mmol) in acetonitrile (1 mL) was added. The reaction mixture was stirred for 30 minutes at room temperature. Reaction mixture was used directly in the next step without workup.

To 4-(2-hydroxypropan-2-yl) furan-2-sulfonamide intermediate (50 mg, 0.24 mmol) in anhydrous THF (1 mL) was added NaH (9.3 mg, 0.24 mmol) at 0° C. and stirred for 30 minutes at ambient temperature under nitrogen atmosphere. Again cooled to 0° C., 4-isocyanato-3,5,6,7-tetrahydro-s-indacen-1(2H)-one (previous step reaction mixture) was added and stirred at ambient temperature for 16 h. To the reaction mixture added 0.5 mL of H$_2$O, loaded directly on C18 column for purification using aqueous 10 mM (NH$_4$) HCO$_3$ solution and acetonitrile as mobile phase, to give 4-(2-hydroxypropan-2-yl)-N-((1-oxo-1,2,3,5,6,7-hexahydro-s-indacen-4-yl) carbamoyl) furan-2-sulfonamide (70 mg, 63%). $^1$H NMR (600 MHz, DMSO-d$_6$) δ 7.94 (s, 1H), 7.38 (s, 1H), 7.17 (s, 1H), 6.60 (s, 1H), 4.92 (s, 1H), 2.94-2.89 (m, 2H), 2.85 (t, J=7.4 Hz, 2H), 2.80 (t, J=7.4 Hz, 2H), 2.56-2.52 (m, 2H), 2.00-1.94 (m, 2H), 1.35 (s, 6H); LCMS (m/z): 417 [M–H]$^−$; HRMS calculated for C$_{20}$H$_{21}$N$_2$O$_6$S$_1$ [M–H]$^−$ 417.1126, found 417.1113.

To a solution of 4-(2-hydroxypropan-2-yl)-N-((1-oxo-1,2,3,5,6,7-hexahydro-s-indacen-4-yl)carbamoyl)furan-2-sulfonamide (50 mg, 0.11 mmol) in MeOH (2 mL) was added NaBH$_4$ (45 mg, 1.19 mmol) at 0° C. under nitrogen atmosphere, resulting reaction mixture was stirred at room temperature for 3 h. Reaction mixture was quenched with H$_2$O (1 mL), distilled out MeOH, aqueous layer was loaded directly on C18 column for purification using aqueous 10 mM (NH$_4$)HCO$_3$ solution and acetonitrile as mobile phase, to give N-((1-hydroxy-1,2,3,5,6,7-hexahydro-s-indacen-4-yl)carbamoyl)-4-(2-hydroxypropan-2-yl)furan-2-sulfonamide (20 mg, 40%). $^1$H NMR (600 MHz, DMSO-d$_6$) δ 7.77 (s, 1H), 7.51 (s, 1H), 6.93 (s, 1H), 6.79 (s, 1H), 6.55 (s, 1H), 5.05 (d, J=5.8 Hz, 1H), 4.99 (s, 1H), 4.94 (q, J=6.4 Hz, 1H), 2.79 (t, J=7.5 Hz, 2H), 2.70-2.61 (m, 3H), 2.52-2.49 (m, 1H), 2.2-2.21 (m, 1H), 1.95-1.90 (m, 2H), 1.74-1.59 (m, 1H), 1.36 (s, 6H); $^{13}$C NMR (150 MHz, DMSO-d$_6$):163.5, 146.0, 143.1, 140.6, 138.5, 136.5, 136.2, 122.0, 116.5, 112.5, 108.5, 74.9, 67.0, 36.0, 33.0, 31.5, 30.9, 27.8, 25.6; LCMS (m/z): 419 [M–H]$^−$. HRMS calculated for C$_{20}$H$_{23}$N$_2$O$_6$S$_1$ [M–H]$^−$ 419.1282, found 419.1265.

N-((4,6-dimethylpyrimidin-2-yl)carbamoyl)-4-(2-hydroxypropan-2-yl)furan-2-sulfonamide

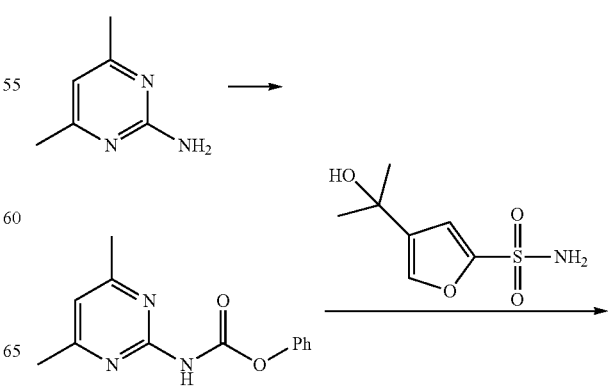

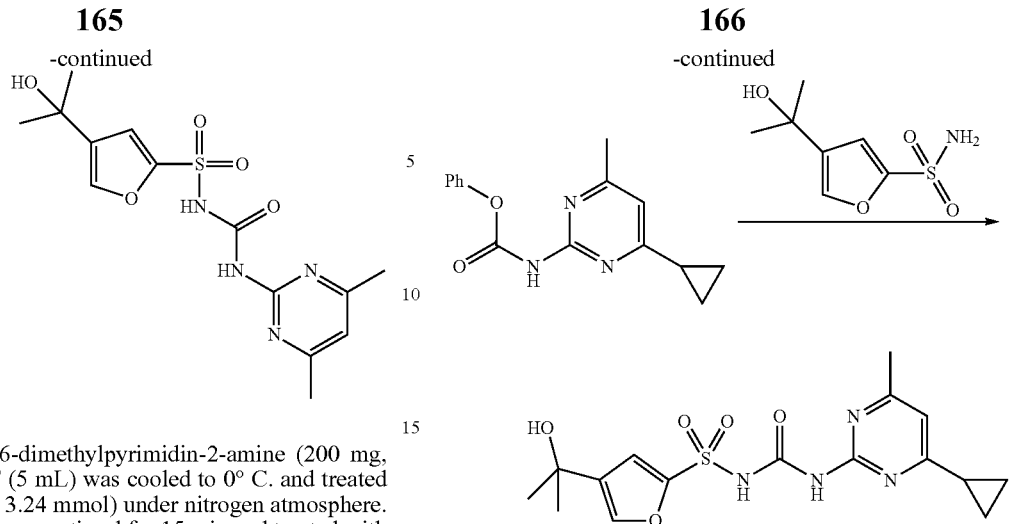

A solution of 4,6-dimethylpyrimidin-2-amine (200 mg, 1.62 mmol) in THF (5 mL) was cooled to 0° C. and treated with NaH (130 mg, 3.24 mmol) under nitrogen atmosphere. The reaction mixture was stirred for 15 min and treated with phenyl chloroformate (380 mg, 2.43 mmol) at 0° C. under nitrogen atmosphere. The reaction mixture was warmed to RT and stirred for 12 h. Upon completion the reaction mixture was diluted with EtOAc, filtered through celite and concentrated in vacuo. The crude product was purified by column chromatography on silica gel (60-120 mesh) using 40% EtOAc-hexanes eluant to give phenyl (4,6-dimethylpyrimidin-2-yl)carbamate (200 mg, 51%) as a white solid. $^1$H NMR (300 MHz, CDCl$_3$): δ=7.91 (s, 1H), 7.40-7.35 (m, 2H), 7.24-7.19 (m, 3H), 6.78 (s, 1H), 2.41 (s, 6H). LCMS (m/z): 244.20 [M+H]$^+$. 4-(2-hydroxypropan-2-yl)furan-2-sulfonamide (150 mg, 0.731 mmol) was dissolved in anhydrous THF (5 mL) and treated carefully with NaH (75 mg, 1.83 mmol) at 0° C. under nitrogen atmosphere. The resulting mixture was warmed to 60° C. and stirred for 2 h. The solution was cooled to 0° C. and treated with a solution of phenyl (4,6-dimethylpyrimidin-2-yl)carbamate (195 mg, 0.804 mmol) in THF (5 mL) under nitrogen atmosphere at 0° C. The reaction mixture was warmed to 50° C. for 4 h and then stirred at RT for 4 h. Upon completion the reaction mixture was diluted with saturated NH$_4$Cl solution, extracted with EtOAc (2×30 mL) and the combined organic extract washed with water, brine, dried (Na$_2$SO$_4$) and concentrated in vacuo. The crude product was purified by reverse phase preparative HPLC [column: X-bridge (150 mm×19 mm particle size 5 μm); flow: 15 mL/min; eluent: 10 mM ammonium acetate in 0.1% AcOH in water (A) & MeCN (B); gradient: T/% B=0/15, 2/25, 8/40]. The fractions were lyophilized to give N-((4,6-dimethylpyrimidin-2-yl)carbamoyl)-4-(2-hydroxypropan-2-yl)furan-2-sulfonamide (25 mg, 7%) as a white solid. $^1$H NMR (400 MHz, CDCl$_3$): δ=8.18 (s, 1H), 7.51 (d, J=0.8 Hz, 1H), 7.40 (d, J=1.2 Hz, 1H), 6.78 (s, 1H), 2.48 (s, 6H), 1.57 (s, 6H). LCMS (m/z): 355.0 [M+H]+, 100% (210 nm), 100% (254 nm). HPLC: 96.49% (210 nm), 98.76% (254 nm). HRMS calculated for C$_{14}$H$_{17}$N$_4$O$_5$S$_1$ [M−H]$^-$ 353.0925, found 353.0921.

N-((4-cyclopropyl-6-methylpyrimidin-2-yl)carbamoyl)-4-(2-hydroxypropan-2-yl)furan-2-sulfonamide

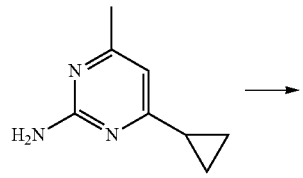

1e;2q4-cyclopropyl-6-methylpyrimidin-2-amine (50 mg, 0.33 mmol) was dissolved in THF (2 mL) and cooled to 0° C. NaH (16 mg, 0.40 mmol) was added carefully to aforementioned solution and stirred for 20 min. Phenyl chloroformate (80 mg, 0.503 mmol) was added dropwise at 0° C. The reaction mixture was warmed to RT and stirred at RT for 12 h. Upon completion of reaction (TLC, 50% ethyl acetate-hexanes, R$_f$, 0.4), the reaction mixture was diluted with EtOAc and filtered through a celite pad. The filtrate was concentrated in vacuo and crude product was purified by column chromatography on silica gel (60-120 mesh) using 30% EtOAc-hexanes eluant to give phenyl (4-cyclopropyl-6-methylpyrimidin-2-yl)carbamate (40 mg, 44%) as an off white solid. $^1$H NMR (300 MHz, CDCl$_3$): δ=8.06 (s, 1H), 7.40-7.37 (m, 2H), 7.24-7.15 (m, 3H), 6.73 (s, 1H), 2.4 (s, 3H), 1.94-1.86 (m, 1H), 1.15-1.1 (m, 2H), 1.0-0.99 (m, 2H). LCMS (m/z): 270.3 [M+H]$^+$ 4-(2-hydroxypropan-2-yl)furan-2-sulfonamide (150 mg, 0.731 mmol) was dissolved in anhydrous THF (5 mL) and treated carefully with NaH (73 mg, 1.829 mmol) at 0° C. under nitrogen atmosphere. The resulting mixture was stirred at RT for 1 h and treated with a solution of phenyl (4-cyclopropyl-6-methylpyrimidin-2-yl)carbamate (190 mg, 0.731 mmol) in THF (5 mL) under nitrogen atmosphere at 0° C. The resulting reaction mixture was warmed to RT and stirred at RT for 6 h. Upon completion, the reaction mixture was diluted with saturated NH$_4$Cl solution and extracted with EtOAc (2×30 mL). The combined organic extract was washed with water, brine dried (Na$_2$SO$_4$) and concentrated in vacuo. The crude product was purified by reverse phase preparative HPLC [column: X bridge (150 mm×19 mm particle size 5 μm); flow: 15 mL/min; eluent: 10 mM ammonium bicarbonate in water (A) & MeCN (B); gradient: T/% B=0/15, 2/25, 8/40]. The fractions were lyophilized to give N-((4-cyclopropyl-6-methylpyrimidin-2-yl)carbamoyl)-4-(2-hydroxypropan-2-yl)furan-2-su fonamide (30 mg, 11%) as a white solid. $^1$H NMR (400 MHz, CD$_3$OD): δ=7.53 (s, 1H), 7.07 (s, 1H), 6.80 (s, 1H), 2.35 (s, 3H), 1.97-1.93 (m, 1H), 1.42 (s, 6H), 1.08-1.02 (m, 4H). LCMS (m/z): 381.00 [M+H]$^+$; 98.60% (210 nm), 99.49% (254 nm). HPLC: 98.05% (210 nm), 99.01% (254 nm). HRMS calculated for C$_{16}$H$_{19}$N$_4$O$_5$S$_1$ [M−H]$^+$379.1082, found 379.1082.

N-((4,6-di-tert-butylpyrimidin-2-yl)carbamoyl)-4-(2-hydroxypropan-2-yl)furan-2-sulfonamide

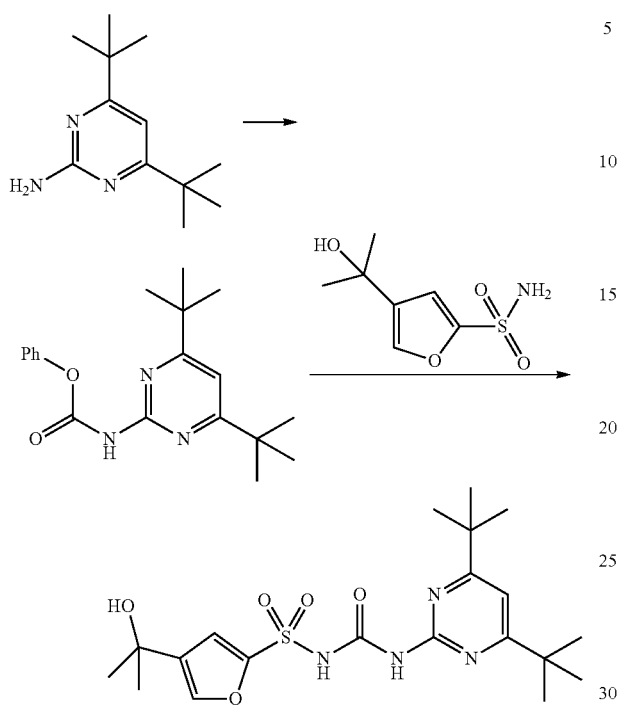

4,6-di-tert-butylpyrimidin-2-amine (0.15 g, 0.72 mmol) was dissolved in THF (5 mL) and cooled to 0° C. NaH (37 mg, 0.93 mmol) was added to aforementioned solution and resulting mixture was stirred at 15 min under nitrogen atmosphere. Phenyl chloroformate (0.16 g, 1.08 mmol) was added dropwise to the aforementioned solution at 0° C. The reaction mixture was warmed to RT and stirred for 12 h. Upon completion of reaction (TLC, 10% ethyl acetate-hexanes, $R_f$ 0.5), the reaction mixture was concentrated in vacuo. The residue obtained was diluted with 10% IPA/CHCl$_3$, filtered through a celite pad and concentrated in vacuo. The crude product was purified by column chromatography on silica gel (60-120 mesh) using 4% EtOAc-hexanes eluant to give phenyl (4,6-di-tert-butylpyrimidin-2-yl)carbamate (0.1 g, 43%) as a white solid. $^1$H NMR (300 MHz, CDCl$_3$): δ=7.65 (s, 1H), 7.38 (m, 2H), 7.22 (m, 3H), 7.01 (s, 1H), 1.32 (s, 18H). LCMS (m/z): 327.80 [M+H]$^+$ 4-(2-hydroxypropan-2-yl)furan-2-sulfonamide (65 mg, 0.305 mmol) was dissolved in anhydrous THF (8 mL) and treated carefully with NaH (30 mg, 0.764 mmol) at 0° C. under nitrogen atmosphere. The resulting mixture was stirred at RT for 45 minutes and treated with a solution of phenyl (4,6-di-tert-butylpyrimidin-2-yl)carbamate (100 mg, 0.305 mmol) in THF (5 mL) dropwise under nitrogen atmosphere at 0° C. The resulting reaction mixture was warmed to RT and stirred for 3 h. Upon completion of reaction, (TLC, 50% ethyl acetate-hexanes, $R_f$ 0.5), the reaction mixture was diluted with saturated NH$_4$Cl solution and extracted with EtOAc (2×20 mL). The combined organic extract was washed with water, brine dried (Na$_2$SO$_4$) and concentrated in vacuo. The crude product was purified by column chromatography on silica gel (60-120 mesh) using 40% EtOAc-hexanes eluant to give N-((4,6-di-tert-butylpyrimidin-2-yl)carbamoyl)-4-(2-hydroxypropan-2-yl)furan-2-sulfonamide (0.07 g, 52%) as a white solid. $^1$H NMR (400 MHz, DMSO-d$_6$): δ=13.75 (s, 1H), 10.71 (s, 1H), 7.83 (s, 1H), 7.37 (s, 1H), 7.20 (s, 1H), 5.17 (s, 1H), 1.39 (s, 6H), 1.31 (s, 18H). LCMS (m/z): 439.55 [M+H]$^+$; 94.58% (210 nm), 97.94% (254 nm). HPLC: 98.51% (210 nm), 99.27% (254 nm). HRMS calculated for C$_{20}$H$_{29}$N$_4$O$_5$S$_1$ [M−H]$^+$ 437.1864, found 437.1846.

Methyl Furans

N-((1,2,3,5,6,7-hexahydro-s-indacen-4-yl)carbamoyl)-4-(2-hydroxypropan-2-yl)-5-methylfuran-2-sulfonamide

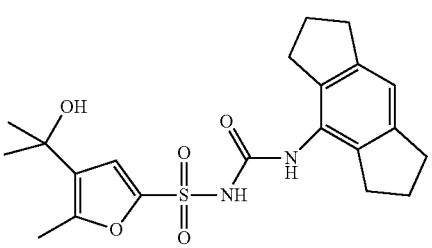 [SMILES: Cc1oc(S(=O)(=O)NC(=O)Nc2c3c(cc4c2CCC4)CCC3)cc1C(C)(C)O]

4-isocyanato-1,2,3,5,6,7-hexahydro-s-indacene (prepared using general method A2) and 4-(2-hydroxypropan-2-yl)-5-methylfuran-2-sulfonamide were used in general method C2 to give the titled compound as a white solid (52 mg, 51%).

N-((2,6-diisopropyl phenyl)carbamoyl)-4-(2-hydroxypropan-2-yl)-5-methylfuran-2-sulfonamide

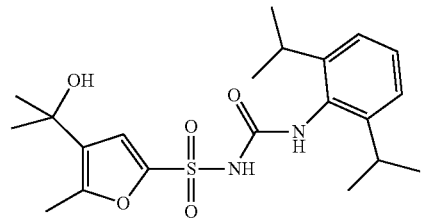 [SMILES: Cc1oc(S(=O)(=O)NC(=O)Nc2c(C(C)C)cccc2C(C)C)cc1C(C)(C)O]

2-Isocyanato-1,3-diisopropylbenzene (prepared using general method A1) and 4-(2-hydroxypropan-2-yl)-5-methylfuran-2-sulfonamide were used in general method C1 to give the titled compound as an off white solid (14 mg, 4%). $^1$H NMR (400 MHz, CD$_3$OD): δ=7.24 (t, J=7.6 Hz, 1H), 7.15 (d, J=7.6 Hz, 2H), 7.04 (s, 1H), 3.10 (sept., J=6.8 Hz, 2H), 2.50 (s, 3H), 1.50 (s, 6H), 1.17 (d, J=6.8 Hz, 12H).

Deuterated Furans

N-((1,2,3,5,6,7-hexahydro-s-indacen-4-yl)carbamoyl)-4-(2-hydroxypropan-2-yl-1,1,1,3,3,3-d$_6$)furan-2-sulfonamide

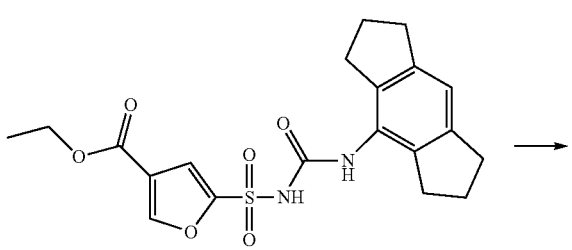

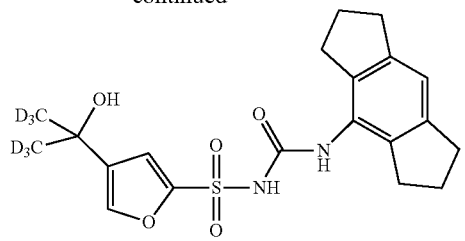

N-((1,2,3,5,6,7-hexahydro-s-indacen-4-yl)carbamoyl)-4-(2-hydroxypropan-2-yl)furan-2-sulfonamide can be synthesized using 4-isocyanato-1,2,3,5,6,7-hexahydro-s-indacene (prepared using general method A1) and $d_6$-4-(2-hydroxypropan-2-yl)-5-methylfuran-2-sulfonamide in general method C1.

Alternatively, ethyl 2-methyl-5-sulfamoylfuran-3-carboxylate (0.4 g, 0.96 mmol) in anhydrous THF (30 mL) at −10° C. was treated with $d_3$-methyl magnesium iodide solution (1.0 M in $Et_2O$, 10 eq.) drop-wise over 10 minutes with vigorous stirring. The solution was then stirred at ambient temperature for 12 h then cooled to 0° C. and quenched drop-wise with a solution of sat. ammonium chloride. The aqueous solution was extracted using EtOAc (2×20 mL), the combined organics washed with brine (20 mL), dried ($Na_2SO_4$) and concentrated in vacuo. The crude product was purified by reverse phase preparative HPLC to give the titled compound as a white solid (5 mg, 1%). $^1$H NMR (300 MHz, $CD_3OD$): δ=7.50 (d, J=1.2 Hz, 1H), 6.95 (d, J=1.2 Hz, 1H), 6.89 (s, 1H), 2.83 (t, J=7.2 Hz, 4H), 2.75 (t, J=7.2 Hz, 4H), 2.02 (quin, J=7.2 Hz, 4H).

N-((1,2,3,5,6,7-hexahydro-s-indacen-4-yl)carbamoyl)-4-(2-hydroxypropan-2-yl-1,1,1,3,3,3-$d_6$)-5-methylfuran-2-sulfonamide

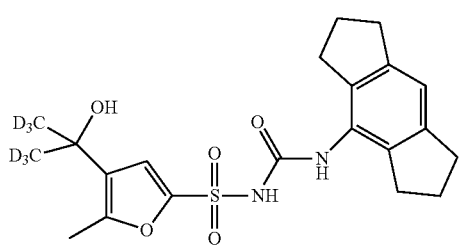 [SMILES: [2H]C([2H])([2H])C(O)(c1cc(S(=O)(=O)NC(=O)Nc2c3c(cc4c2CCC4)CCC3)oc1C)C([2H])([2H])[2H]]

4-Isocyanato-1,2,3,5,6,7-hexahydro-s-indacene (prepared using general method A1) and $d_6$-4-(2-hydroxypropan-2-yl)-5-methylfuran-2-sulfonamide were used in general method C1 to give the titled compound as a white solid (10 mg, 3%). $^1$H NMR (400 MHz, $CD_3OD$) δ=7.03 (s, 1H), 6.95 (s, 1H), 2.86 (t, J=7.4 Hz, 4H), 2.73 (t, J=7.4 Hz, 4H), 2.48 (s, 3H), 2.04 (p, J=7.4 Hz, 4H).

4-(2-hydroxypropan-2-yl-1,1,1,3,3,3-$d_6$)-5-methyl-N-((3,5,6,7-tetrahydro-2H-indeno[5,6-b]furan-4-yl)carbamoyl)furan-2-sulfonamide

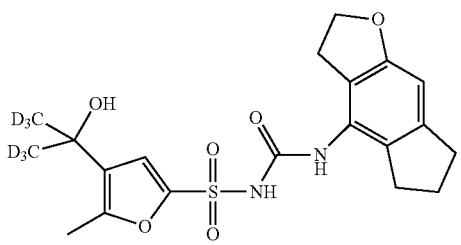 [SMILES: [2H]C([2H])([2H])C(O)(c1cc(S(=O)(=O)NC(=O)Nc2c3c(cc4c2CCO4)CCC3)oc1C)C([2H])([2H])[2H]]

4-isocyanato-3,5,6,7-tetrahydro-2H-indeno[5,6-b]furan (prepared using general method A1) and $d_6$-4-(2-hydroxypropan-2-yl)-5-methylfuran-2-sulfonamide were used in general method C1 to give the titled compound as a white solid (20 mg, 5%). $^1$H NMR (400 MHz, $CD_3OD$) δ=7.13 (s, 1H), 6.52 (s, 1H), 4.51 (t, J=8.6 Hz, 2H), 3.03 (t, J=8.6 Hz, 2H), 2.84 (t, J=7.4 Hz, 2H), 2.68 (t, J=7.4 Hz, 2H), 2.50 (s, 3H), 2.05 (p, J=7.4 Hz, 2H).

N-((4-bromo-3,5,6,7-tetrahydro-2H-indeno[5,6-b]furan-8-yl)carbamoyl)-4-(2-hydroxypropan-2-yl-1,1,1,3,3,3-$d_6$)-5-methylfuran-2-sulfonamide

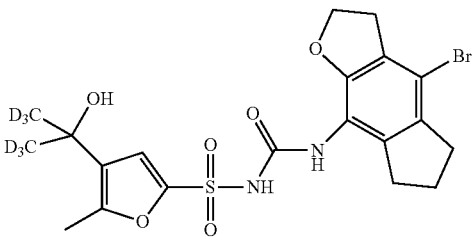 [SMILES: [2H]C([2H])([2H])C(O)(c1cc(S(=O)(=O)NC(=O)Nc2c3c(c(Br)c4c2OCC4)CCC3)oc1C)C([2H])([2H])[2H]]

4-Bromo-8-isocyanato-3,5,6,7-tetrahydro-2H-indeno[5,6-b]furan (prepared using general method A1) and $d_6$-4-(2-hydroxypropan-2-yl)-5-methylfuran-2-sulfonamide were used in general method C1 to give the titled compound as a white solid (32 mg, 39%). 1H NMR (400 MHz, DMSO-$d_6$) δ=8.01 (s, 1H), 7.07 (s, 1H), 5.04 (s, 1H), 4.59 (t, J=8.7 Hz, 2H), 3.14 (t, J=8.7 Hz, 2H), 2.77 (t, J=7.4 Hz, 2H), 2.69 (t, J=7.4 Hz, 2H), 2.43 (s, 3H), 1.98 (q, J=7.4 Hz, 2H).

Thiophenes

N-((1,2,3,5,6,7-hexahydro-s-indacen-4-yl)carbamoyl)thiophene-2-sulfonamide

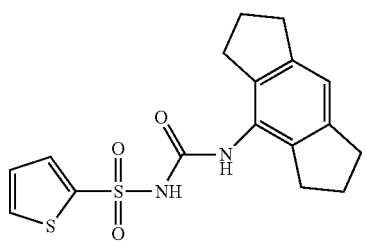 [SMILES: O=C(Nc1c2c(cc3c1CCC3)CCC2)NS(=O)(=O)c1cccs1]

4-Isocyanato-1,2,3,5,6,7-hexahydro-s-indacene (prepared using general method A2) and thiophene-2-sulfonamide were used in general method C2 to give the titled compound as a white solid (11 mg, 11%). $^1$H NMR (400 MHz, CD$_3$OD): δ=7.79 (d, J=4.0 Hz, 1H), 7.76 (d, J=4.0 Hz, 1H), 7.73 (t, J=4.0 Hz, 1H), 6.93 (s, 1H), 2.83 (t, J=12 Hz, 4H), 2.66 (t, J=12 Hz, 4H), 2.04-1.96 (m, 4H). $^{13}$C NMR (100 MHz, CD$_3$OD): δ 143.5, 143.2, 137.8, 132.7, 132.2, 126.6, 126.4, 118.2, 110.3, 32.5, 29.9, 25.1; LCMS Purity: >95%; LCMS (m/z): 363 [M+H]$^+$; HRMS calculated for C$_{17}$H$_{18}$N$_2$O$_3$S$_2$(M+H)$^+$, 363.0832, found 363.0819.

N-((1,2,3,5,6,7-hexahydro-s-indacen-4-yl)carbamoyl)-5-methylthiophene-2-sulfonamide

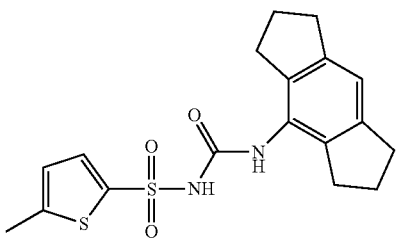 [SMILES: Cc1ccc(S(=O)(=O)NC(=O)Nc2c3c(cc4c2CCC4)CCC3)s1]

4-Isocyanato-1,2,3,5,6,7-hexahydro-s-indacene (prepared using general method A2) 5-methylthiophene-2-sulfonamide were used in general method C2 to give the titled compound as a white solid (12 mg, 18%). $^1$H NMR (400 MHz, DMSO-d$_6$): δ=7.88 (s, 1H), 7.43 (d, J=4.0 Hz, 1H), 6.89 (s, 1H), 6.82 (d, J=4.0 Hz, 1H), 2.78 (t, J=12 Hz, 4H), 2.61 (t, J=12 Hz, 4H), 2.47 (s, 3H), 1.97-1.89 (m, 4H). $^{13}$C NMR (100 MHz, DMSO-d$_6$): δ=143.2, 142.9, 137.3, 130.6, 126.0, 125.6, 125.2, 117.5, 108.7, 32.69, 30.7, 25.5, 15.4; LCMS Purity: >95%; LCMS (m/z): 377 [M+H]$^+$; HRMS calculated for C$_{18}$H$_{20}$N$_2$O$_3$S$_2$, (M+H)$^+$ 377.0988, found 377.0994.

Thiazoles

N-((1,2,3,5,6,7-hexahydro-s-indacen-4-yl)carbamoyl)thiazole-2-sulfonamide

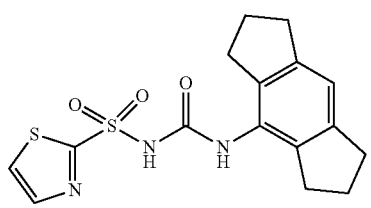 [SMILES: O=C(Nc1c2c(cc3c1CCC3)CCC2)NS(=O)(=O)c1nccs1]

4-Isocyanato-1,2,3,5,6,7-hexahydro-s-indacene (prepared using general method A2) and thiazole-2-sulfonamide were used in general method C2 to give the titled compound as a white solid (8 mg, 20%). $^1$H NMR (400 MHz, CD$_3$OD): δ=7.02 (d, 1H, J=4.0 Hz), 6.99 (s, 1H), 6.60 (d, 1H, J=4.0 Hz), 2.88 (t, 4H, J=8.0 Hz), 2.76 (t, 4H, J=8.0 Hz), 2.08-2.02 (m, 4H); $^{13}$C NMR (100 MHz, CD$_3$OD): δ=169.6, 144.2, 144.1, 137.7, 137.5, 132.4, 118.1, 106.9, 32.4, 29.9, 25.2.

N-((1,2,3,5,6,7-hexahydro-s-indacen-4-yl)carbamoyl)-2-methylthiazole-5-sulfonamide

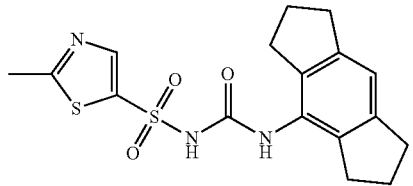 [SMILES: Cc1ncc(S(=O)(=O)NC(=O)Nc2c3c(cc4c2CCC4)CCC3)s1]

4-Isocyanato-1,2,3,5,6,7-hexahydro-s-indacene (prepared using general method A2) and 2-methylthiazole-5-sulfonamide were used in general method C3 to give the titled compound as a white solid (35 mg, 65%); $^1$H NMR (600 MHz, DMSO-d$_6$) δ=7.73 (s, 1H), 7.53 (s, 1H), 6.78 (s, 1H), 2.75 (t, J=7.4 Hz, 4H), 2.66 (t, J=7.4 Hz, 4H), 2.59 (s, 3H), 1.93-1.88 (m, 4H); $^{13}$C NMR (150 MHz, DMSO-d$_6$): 166.8, 158.3, 143.9, 142.0, 141.4, 136.6, 132.3, 115.5, 32.5, 30.4, 25.0, 18.6; LCMS Purity: >95%; LCMS (m/z): 378 [M+H]$^+$; HRMS calculated for C$_{17}$H$_{18}$N$_3$O$_3$S$_2$[M–H]$^+$ 376.0795, found 376.0791.

Triazoles 1-benzyl-N-((1,2,3,5,6,7-hexahydro-s-indacen-4-yl)carbamoyl)-1H-1,2,4-triazole-3-sulfonamide

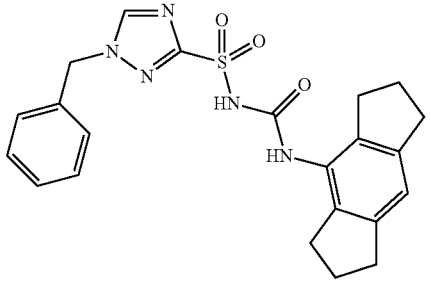 [SMILES: O=C(Nc1c2c(cc3c1CCC3)CCC2)NS(=O)(=O)c1ncn(Cc2ccccc2)n1]

4-Isocyanato-8-methyl-1,2,3,5,6,7-hexahydro-s-indacene (prepared using general method A1) and 1-benzyl-1H-1,2,4-triazole-3-sulfonamide were used in general method C3 to give the titled compound as a white solid (40 mg, 15%) $^1$H NMR (400 MHz, DMSO-d$_6$): δ=8.9 (s, 1H), 8.0 (s, 1H), 7.35-7.28 (m, 5H), 6.90 (s, 1H), 5.48 (s, 2H), 2.77 (t, J=7.2 Hz, 4H), 2.59 (t, J=7.2 Hz, 4H), 1.95-1.90 (m, 4H). LCMS (m/z): 438.10 (M+1)$^+$ 95.84% (210 nm), 97.84% (254 nm). HPLC: 95.99% (210 nm), 95.31% (254 nm).

N-((1,2,3,5,6,7-hexahydro-s-indacen-4-yl)carbamoyl)-4H-1,2,4-triazole-3-sulfonamide

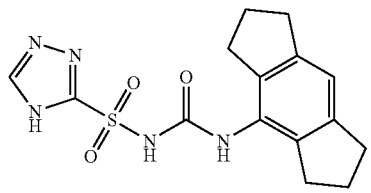 [SMILES: O=C(Nc1c2c(cc3c1CCC3)CCC2)NS(=O)(=O)c1nnc[nH]1]

4-Isocyanato-1,2,3,5,6,7-hexahydro-s-indacene (prepared using general method A2) and 4H-1,2,4-triazole-3-sulfonamide were used in general method C3 to give the titled compound as a white solid (31 mg, 62%); $^1$H NMR (600 MHz, DMSO-d$_6$) δ=9.83 (bs, 1H), 7.99 (s, 1H), 7.62 (s, 1H), 6.77 (s, 1H), 2.73 (t, J=7.4 Hz, 4H), 2.64 (t, J=7.4 Hz, 4H), 1.91-1.86 (m, 4H); $^{13}$C NMR (150 MHz, DMSO-d$_6$): 159.2, 149.8, 148.7, 142.5, 137.2, 132.8, 116.1, 33.0, 30.9, 25.6; LCMS Purity: >95%; LCMS (m/z): 348 [M+H]$^+$; HRMS calculated for C$_{15}$H$_{16}$N$_5$O$_3$S$_1$ [M−H]$^-$ 346.0979, found 346.0983.

N-((1,2,3,5,6,7-hexahydro-s-indacen-4-yl)carbamoyl)-1-isopropyl-1H-1,2,3-triazole-4-sulfonamide

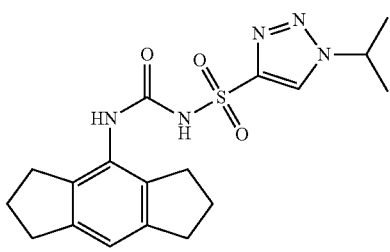 [SMILES: CC(C)n1cc(S(=O)(=O)NC(=O)Nc2c3c(cc4c2CCC4)CCC3)nn1]

1,2,3,5,6,7-hexahydro-s-indacen-4-amine, 7 (100 mg, 0.578 mmol) was dissolved in anhydrous THF (5 mL) and treated with Et$_3$N (70 mg, 0.693 mmol) at RT. The solution was treated with triphosgene (70 mg, 0.231 mmol) and resulting mixture was stirred at 70° C. for 3 h. The reaction mixture was concentrated in vacuo. The residue obtained was stirred with n-pentane (20 mL) for 10 min and filtered through celite. The filtrate was concentrated in vacuo to give isocyanate as a white solid. In another 50 mL round bottom flask, 1-isopropyl-1H-1,2,3-triazole-4-sulfonamide (95 mg, 0.50 mmol) was dissolved in anhydrous THF (5 mL) and treated carefully with NaH (42 mg, 1.05 mmol) at 0° C. under nitrogen. It was stirred at RT for 45 minutes and treated with aforementioned solution of isocyanate in THF under nitrogen. The resulting reaction mixture was stirred at RT for 5 h. Upon completion (TLC, 70% ethyl acetate-hexanes, R$_f$ 0.3), the reaction mixture was diluted with saturated NH$_4$Cl solution and extracted with EtOAc (2×25 mL). The combined organic extract was washed with water, brine, dried (Na$_2$SO$_4$) and concentrated in vacuo. The crude product was purified by reverse phase preparative HPLC [column: Gemini NX C18 (21.5 mm×150 mm particle size 5 μm); flow: 15 mL/min; eluent: 10 mM ammonium bicarbonate in water (A) & MeCN (B); gradient: T/% B=0/10, 2/20, 8/65]. The fractions were lyophilized to give N-((1,2,3,5,6,7-hexahydro-s-indacen-4-yl)carbamoyl)-1-isopropyl-1H-1,2,3-triazole-4-sulfonamide (25 mg, 12%), as a white solid. $^1$H NMR (400 MHz, DMSO-d$_6$): δ=8.75 (s, 1H), 7.91 (s, 1H), 6.89 (s, 1H), 4.9 (m, 1H), 2.79 (t, J=7.2 Hz, 4H), 2.60 (t, J=7.2 Hz, 4H), 1.96-1.89 (m, 4H), 1.5 (d, J=6.8 Hz, 6H). LCMS (m/z): 390.10 [M+H]$^+$; 100% (210 nm), 100% (254 nm). HPLC: 96.05% (210 nm), 96.13% (254 nm). HRMS calculated for C$_{18}$H$_{22}$N$_5$O$_3$S$_1$ [M−H]$^-$ 388.1449, found 388.1457.

Pyrazoles

N-((1,2,3,5,6,7-hexahydro-s-indacen-4-yl)carbamoyl)-1-methyl-1H-pyrazole-5-sulfonamide

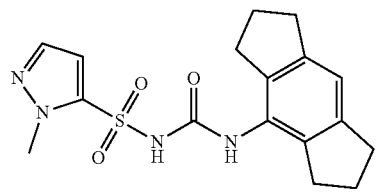 [SMILES: Cn1nccc1S(=O)(=O)NC(=O)Nc1c2c(cc3c1CCC3)CCC2]

4-Isocyanato-8-methyl-1,2,3,5,6,7-hexahydro-s-indacene (prepared using general method A2) and 1-methyl-1H-pyrazole-5-sulfonamide were used in general method C2 to give the titled compound as a white solid (8 mg) 20%. $^1$H NMR (400 MHz, DMSO-d$_6$): δ=7.95 (bs, 1H), 7.45 (s, 1H), 6.88 (s, 1H), 6.66 (s, 1H), 4.02 (s, 3H), 2.77 (t, J=16 Hz, 4H), 2.60 (t, J=16 Hz, 4H), 1.96-1.88 (m, 4H). $^{13}$C NMR (150 MHz, DMSO-d6): δ=143.1, 142.9, 137.2, 125.2, 117.4, 110.0, 109.0, 108.7, 38.6, 33.0, 30.7, 25.5; LCMS Purity: >95%; LCMS (m/z): 361 [M+H]$^+$; HRMS calculated for C$_{17}$H$_{20}$N$_4$O$_3$S (M+H)$^+$, 361.13289, found 361.13213.

N-((1,2,3,5,6,7-hexahydro-s-indacen-4-yl)carbamoyl)-1-methyl-1H-pyrazole-3-sulfonamide

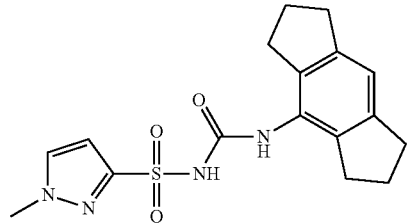 [SMILES: Cn1ccc(S(=O)(=O)NC(=O)Nc2c3c(cc4c2CCC4)CCC3)n1]

4-Isocyanato-8-methyl-1,2,3,5,6,7-hexahydro-s-indacene (prepared using general method A1) and 1-methyl-1H-pyrazole-3-sulfonamide were used in general method C1 to give the titled compound as a white solid (40 mg, 8%). $^1$H NMR (400 MHz, DMSO-d$_6$): δ=10.8 (brs, 1H), 8.02 (s, 1H), 7.86 (s, 1H), 6.92 (s, 1H), 6.69 (s, 1H), 3.91 (s, 3H), 2.80 (t, J=7.2 Hz, 4H), 2.62 (t, J=7.2 Hz, 4H), 1.96 (t, J=7.2 Hz, 4H). LCMS (m/z): 383.10 (M+Na)$^+$; 96.00% (210 nm), 93.44% (254 nm). HPLC: 97.86% (210 nm), 97.44% (254 nm).

N-((1,2,3,5,6,7-hexahydro-s-indacen-4-yl)carbamoyl)-1-(trifluoromethyl)-1H-pyrazole-3-sulfonamide

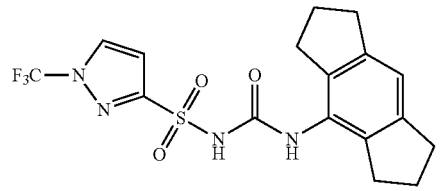 [SMILES: O=C(Nc1c2c(cc3c1CCC3)CCC2)NS(=O)(=O)c1ccn(C(F)(F)F)n1]

4-Isocyanato-1,2,3,5,6,7-hexahydro-s-indacene (prepared using general method A1) and 1-(trifluoromethyl)-1H-pyrazole-3-sulfonamide were used in general method C2 to give the titled compound as a white solid (5 mg, 1%). $^1$H NMR (400 MHz, CD$_3$OD) δ=8.28 (d, J=2.8 Hz, 1H), 6.96 (d, J=2.8, 1H), 6.91 (s, 1H), 2.84 (t, J=7.4 Hz, 4H), 2.75 (t, J=7.4 Hz, 4H), 2.03 (m, J=7.4 Hz, 4H).

N-((1,2,3,5,6,7-hexahydro-s-indacen-4-yl)carbamoyl)-1-isopropyl-1H-pyrazole-3-sulfonamide

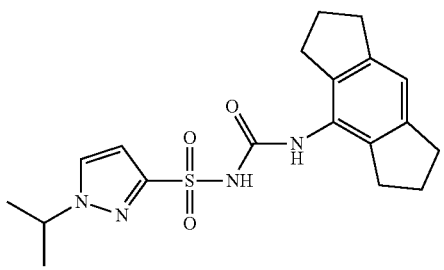 [SMILES: CC(C)n1ccc(S(=O)(=O)NC(=O)Nc2c3c(cc4c2CCC4)CCC3)n1]

4-Isocyanato-8-methyl-1,2,3,5,6,7-hexahydro-s-indacene (prepared using general method A1) and 1-isopropyl-1H-pyrazole-3-sulfonamide were used in general method C1 to give the titled compound as an off-white solid (40 mg, 9%). $^1$H NMR (400 MHz, DMSO-d$_6$): δ=10.92 (s, 1H), 8.02 (s, 1H), 8.0 (s, 1H), 6.94 (s, 1H), 6.74 (s, 1H), 4.67-4.59 (m, 1H), 2.78 (t, J=7.2 Hz, 4H), 2.58 (t, J=7.2 Hz, 4H), 1.95-1.91 (m, 4H), 1.44 (d, J=6.8 Hz, 6H). LCMS (m/z): 387.1 (M−1)$^-$; 97.14% (210 nm), 95.11% (254 nm). HPLC: 95.57% (210 nm), 93.53% (254 nm).

N-((1,2,3,5,6,7-hexahydro-s-indacen-4-yl)carbamoyl)-1-isopropyl-1H-pyrazole-4-sulfonamide

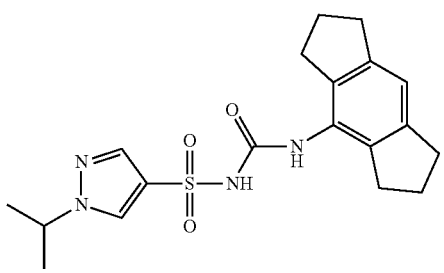 [SMILES: CC(C)n1cc(S(=O)(=O)NC(=O)Nc2c3c(cc4c2CCC4)CCC3)cn1]

4-Isocyanato-8-methyl-1,2,3,5,6,7-hexahydro-s-indacene (prepared using general method A1) and 1-isopropyl-1H-pyrazole-4-sulfonamide were used in general method C3 to give the titled compound as a white solid (40 mg, 10%) $^1$H NMR (400 MHz, DMSO-d$_6$): δ=10.6 (s, 1H), 8.44 (s, 1H), 8.05 (s, 1H), 7.86 (s, 1H), 6.94 (s, 1H), 4.63-4.57 (m, 1H), 2.80 (t, J=7.2 Hz, 4H), 2.57 (t, J=7.6 Hz, 4H), 1.94-1.89 (m, 4H), 1.42 (d, J=6.8 Hz 6H). LCMS (m/z): 389.20 (M+1)$^+$; 97.25% (210 nm), 94.22% (254 nm). HPLC: 97.13% (210 nm), 95.06% (254 nm).

1-cyclopropyl-N-((1,2,3,5,6,7-hexahydro-s-indacen-4-yl)carbamoyl)-1H-pyrazole-3-sulfonamide

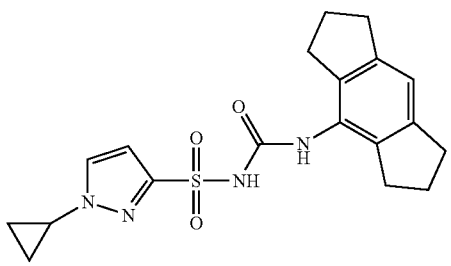 [SMILES: O=C(Nc1c2c(cc3c1CCC3)CCC2)NS(=O)(=O)c1ccn(C2CC2)n1]

4-Isocyanato-8-methyl-1,2,3,5,6,7-hexahydro-s-indacene (prepared using general method A1) and 1-cyclopropyl-1H-pyrazole-3-sulfonamide were used in general method C3 to give the titled compound as a white solid (20 mg, 6%). $^1$H NMR (400 MHz, DMSO-d$_6$) δ=7.83 (s, 1H), 7.8 (s, 1H), 6.84 (s, 1H), 6.48 (s, 1H), 3.81-3.71 (m, 1H), 2.77 (t, J=7.4 Hz, 4H), 2.64 (t, J=7.4 Hz, 4H), 2.02-1.86 (m, 4H), 1.09-0.93 (m, 4H).

1-(tert-butyl)-N-((1,2,3,5,6,7-hexahydro-s-indacen-4-yl)carbamoyl)-1H-pyrazole-3-sulfonamide

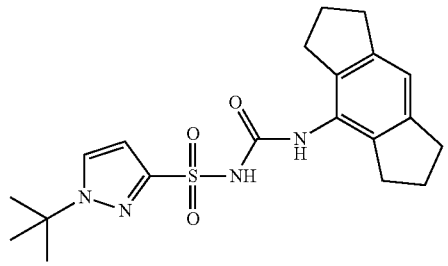 [SMILES: CC(C)(C)n1ccc(S(=O)(=O)NC(=O)Nc2c3c(cc4c2CCC4)CCC3)n1]

4-Isocyanato-8-methyl-1,2,3,5,6,7-hexahydro-s-indacene (prepared using general method A1) and 1-(tert-butyl)-1H-pyrazole-3-sulfonamide were used in general method C3 to give the titled compound as a pale yellow solid (120 mg, 51%). $^1$H NMR (400 MHz, DMSO-d$_6$): δ=10.85 (br.s., 1H), 7.95 (s, 1H), 7.88 (br.s., 1H), 6.88 (s, 1H), 6.63 (s, 1H), 2.79 (t, J=7.2 Hz, 4H), 2.61 (t, J=7.2 Hz, 4H), 1.96 (m, 4H), 1.55 (s, 9H). LCMS (m/z): 403.15 (M+1)$^+$; 97.86% (210 nm), 96.50% (254 nm). HPLC: 96.45% (210 nm), 95.89% (254 nm).

N-((1,2,3,5,6,7-hexahydro-s-indacen-4-yl)carbamoyl)-1-(1-methylpiperidin-4-yl)-1H-pyrazole-3-sulfonamide

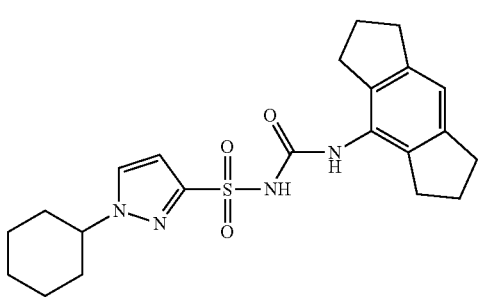 [SMILES: O=C(Nc1c2c(cc3c1CCC3)CCC2)NS(=O)(=O)c1ccn(C2CCCCC2)n1]

4-Isocyanato-8-methyl-1,2,3,5,6,7-hexahydro-s-indacene (prepared using general method A1) and 1-cyclohexyl-1H-pyrazole-3-sulfonamide were used in general method C3 to give the titled compound as a white solid (20 mg, 6%). $^1$H NMR (400 MHz, DMSO-d$_6$) δ=10.8 (s, 1H), 8.03 (s, 1H), 7.99 (d, J=2.4, 1H), 6.95 (s, 1H), 6.75 (d, J=2.4 Hz, 1H), 4.33-4.20 (m, 1H), 2.79 (t, J=7.4 Hz, 4H), 2.58 (t, J=7.4 Hz, 4H), 2.05-1.88 (m, 6H), 1.86-1.63 (m, 6H), 1.48-1.33 (m, 2H).

N-((1,2,3,5,6,7-hexahydro-s-indacen-4-yl)carbamoyl)-1-phenyl-1H-pyrazole-3-sulfonamide

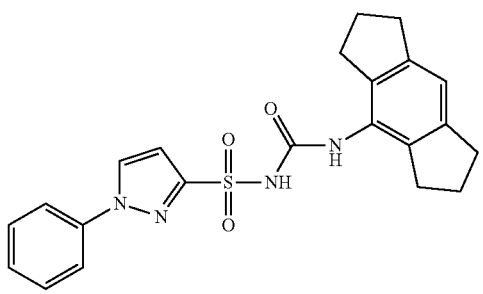 [SMILES: O=C(Nc1c2c(cc3c1CCC3)CCC2)NS(=O)(=O)c1ccn(-c2ccccc2)n1]

4-Isocyanato-8-methyl-1,2,3,5,6,7-hexahydro-s-indacene (prepared using general method A1) and 1-phenyl-1H-pyrazole-3-sulfonamide were used in general method C1 to give the titled compound as an off-white solid (110 mg, 27%). $^1$H NMR (400 MHz, DMSO-d$_6$): δ=10.92 (s, 1H), 8.61 (d, J=2.4 Hz, 1H), 7.95 (br.s., 1H), 7.86 (d, J=8.4 Hz, 2H), 7.56 (t, J=7.6 Hz, 2H), 7.41 (t, J=7.2 Hz, 1H), 6.9 (d, J=2.0 Hz, 1H), 6.86 (s, 1H), 2.77 (t, J=7.2 Hz, 4H), 2.62 (t, J=7.2 Hz, 4H), 1.91-1.83 (m, 4H). LCMS (m/z): 421.05 (M−1)$^-$; 96.62% (210 nm), 95.12% (254 nm). HPLC: 95.2% (210 nm), 95.77% (254 nm).

1-benzyl-N-((1,2,3,5,6,7-hexahydro-s-indacen-4-yl)carbamoyl)-1H-pyrazole-3-sulfonamide

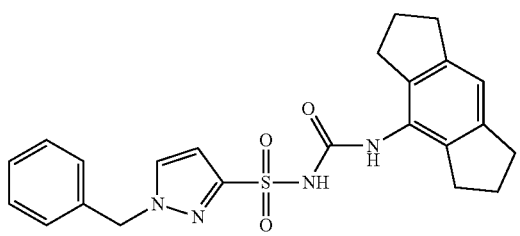 [SMILES: O=C(Nc1c2c(cc3c1CCC3)CCC2)NS(=O)(=O)c1ccn(Cc2ccccc2)n1]

4-Isocyanato-8-methyl-1,2,3,5,6,7-hexahydro-s-indacene (prepared using general method A1) and, 1-benzyl-1H-pyrazole-3-sulfonamide were used in general method C3 to give the titled compound as a white solid (85 mg, 34%). 1H NMR (400 MHz, DMSO-d$_6$): δ=10.85 (s, 1H), 8.05 (d, J=2.4 Hz, 1H), 7.99 (s, 1H), 7.32-7.31 (m, 3H), 7.24-7.22 (m, 2H), 6.93 (s, 1H), 6.78 (d, J=2.4 Hz, 1H), 5.44 (s, 2H), 2.80 (t, J=7.6 Hz, 4H), 2.57 (t, J=7.2 Hz, 4H), 1.96 (m, 4H). LCMS (m/z): 437.15 (M+1)$^+$; 97.70% (210 nm), 96.86% (254 nm). HPLC: 98.05% (210 nm), 97.56% (254 nm).

N-((1,2,3,5,6,7-hexahydro-s-indacen-4-yl)carbamoyl)-1-(1-phenylethyl)-1H-pyrazole-3-sulfonamide

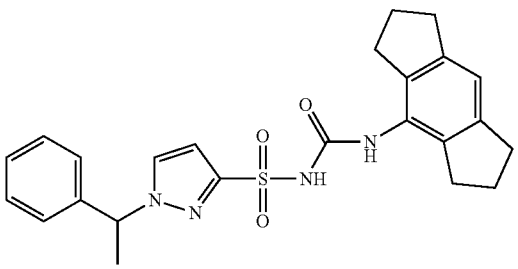 [SMILES: CC(c1ccccc1)n1ccc(S(=O)(=O)NC(=O)Nc2c3c(cc4c2CCC4)CCC3)n1]

4-Isocyanato-8-methyl-1,2,3,5,6,7-hexahydro-s-indacene (prepared using general method A1) and, 1-(1-phenylethyl)-1H-pyrazole-3-sulfonamide were used in general method C3 to give the titled compound as a white solid (0.13 g, 38%). $^1$H NMR (400 MHz, DMSO-d$_6$) δ=7.94 (d, J=2.4 Hz, 1H), 7.80 (s, 1H), 7.34-7.18 (m, 5H), 6.85 (s, 1H), 6.62 (d, J=2.3 Hz, 1H), 5.68 (q, J=7.0 Hz, 1H), 2.76 (t, J=7.4 Hz, 4H), 2.58 (t, J=7.4 Hz, 4H), 1.90 (p, J=7.4 Hz, 4H), 1.8 (d, J7.1 Hz, 3H).

N-((1,2,3,5,6,7-hexahydro-s-indacen-4-yl)carbamoyl)-1-(2-(piperidin-1-yl)ethyl)-1H-pyrazole-3-sulfonamide

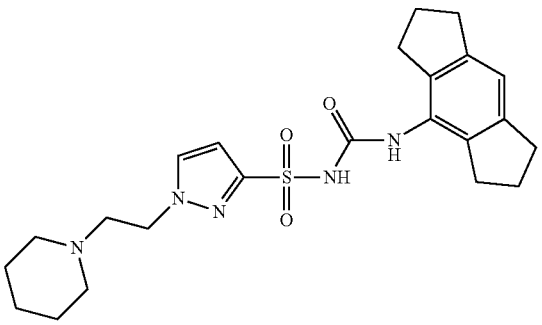 [SMILES: O=C(Nc1c2c(cc3c1CCC3)CCC2)NS(=O)(=O)c1ccn(CCN2CCCCC2)n1]

4-Isocyanato-8-methyl-1,2,3,5,6,7-hexahydro-s-indacene (prepared using general method A1) and, 1-(2-(piperidin-1-yl)ethyl)-1H-pyrazole-3-sulfonamide were used in general method C3 to give the titled compound as a white solid (110 mg, 25%). $^1$H NMR (400 MHz, CD$_3$OD): δ=7.76 (d, J=2.4 Hz, 1H), 6.91 (s, 1H), 6.73 (d, J=2.4 Hz 1H), 4.55 (t, J=6.4 Hz, 2H), 3.41 (t, J=6.0 Hz, 2H), 3.02 (s, 4H), 2.86 (t, J=7.2 Hz, 4H), 2.78 (t, J=7.2 Hz, 4H), 2.06-1.99 (m, 4H), 1.74-1.70 (m, 4H), 1.51 (d, J=5.2 Hz, 2H). LCMS (m/z): 458.20 (M+1)$^+$; 100% (210 nm), 100% (254 nm). HPLC: 98.70% (210 nm), 98.31% (254 nm).

N-((1,2,3,5,6,7-hexahydro-s-indacen-4-yl)carbamoyl)-1,5-dimethyl-1H-pyrazole-3-sulfonamide

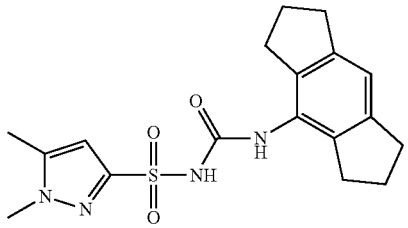 [SMILES: Cc1cc(S(=O)(=O)NC(=O)Nc2c3c(cc4c2CCC4)CCC3)nn1C]

4-Isocyanato-8-methyl-1,2,3,5,6,7-hexahydro-s-indacene (prepared using general method A1) and 1,5-dimethyl-1H-pyrazole-3-sulfonamide were used in general method C1 to give the titled compound as a white solid (15 mg, 4%). $^1$H NMR (400 MHz, DMSO-d$_6$): δ=10.7 (br.s., 1H), 7.98 (s, 1H), 6.93 (s, 1H), 6.52 (s, 1H), 3.79 (s, 3H), 2.80 (t, J=7.2 Hz, 4H), 2.62 (t, J=7.6 Hz, 4H), 2.28 (s, 3H), 1.98-1.93 (m, 4H). LCMS (m/z): 397.10 (M+Na)$^+$; 97.75% (210 nm), 88.23% (254 nm). HPLC: 94.42% (210 nm), 95.19% (254 nm).

N-((1,2,3,5,6,7-hexahydro-s-indacen-4-yl)carbamoyl)-1-methyl-5-(trifluoromethyl)-1H-pyrazole-3-sulfonamide

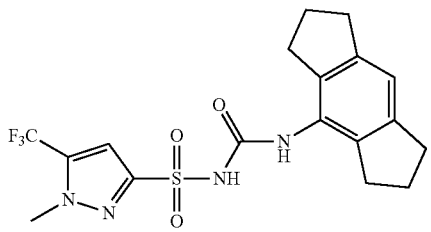 [SMILES: Cn1nc(S(=O)(=O)NC(=O)Nc2c3c(cc4c2CCC4)CCC3)cc1C(F)(F)F]

4-Isocyanato-8-methyl-1,2,3,5,6,7-hexahydro-s-indacene (prepared using general method A1) and 1-methyl-5-(trifluoromethyl)-1H-pyrazole-3-sulfonamide were used in general method C3 to give the titled compound as a white solid (200 mg, 48%). $^1$H NMR (400 MHz, CD$_3$OD): δ=7.10 (s, 1H), 6.87 (s, 1H), 4.03 (s, 3H), 2.83 (t, J=7.2 Hz, 4H), 2.74-(t, J=7.2 Hz, 4H), 2.03-1.99 (m, 4H). LCMS (m/z): 429.10 (M+1)$^+$; 97.73% (210 nm), 95.71% (254 nm). HPLC: 94.95% (210 nm), 93.52% (254 nm).

N-((2,6-diisopropylphenyl)carbamoyl)-1-methyl-5-(trifluoromethyl)-1H-pyrazole-3-sulfonamide

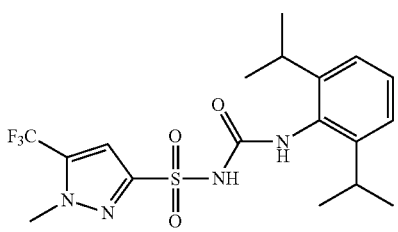 [SMILES: CC(C)c1cccc(C(C)C)c1NC(=O)NS(=O)(=O)c1cc(C(F)(F)F)n(C)n1]

2-Isocyanato-1,3-diisopropylbenzene (prepared using general method A1) and 1-methyl-5-(trifluoromethyl)-1H-pyrazole-3-sulfonamide were used in general method C3 to give the titled compound as a white solid (70 mg, 39%). $^1$H NMR (400 MHz, CD$_3$OD): δ=7.18-7.16 (m, 1H), 7.10-7.08 (m, 3H), 4.03 (s, 3H), 3.17-3.13 (m, 2H), 1.03 (d, J=6.0 Hz, 12H). LCMS (m/z): 433.15 (M+1)$^+$; 99.73% (210 nm), 98.16% (254 nm). HPLC: 97.51% (210 nm), 95.47% (254 nm).

N-((1,2,3,5,6,7-hexahydro-s-indacen-4-yl)carbamoyl)-1-isopropyl-5-(trifluoromethyl)-1H-pyrazole-3-sulfonamide

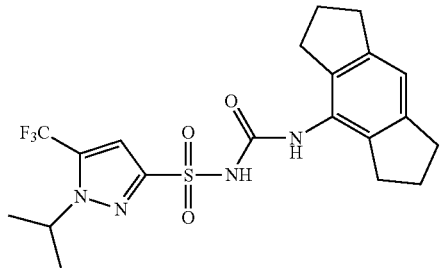 [SMILES: CC(C)n1nc(S(=O)(=O)NC(=O)Nc2c3c(cc4c2CCC4)CCC3)cc1C(F)(F)F]

4-Isocyanato-8-methyl-1,2,3,5,6,7-hexahydro-s-indacene (prepared using general method A1) and 1-isopropyl-5-(trifluoromethyl)-1H-pyrazole-3-sulfonamide were used in general method C3 to give the titled compound as a white solid (15 mg, 12%). $^1$H NMR (400 MHz, DMSO-d$_6$): δ=8.54 (s, 1H), 6.90 (s, 1H), 6.77 (s, 1H), 4.62-4.56 (m, 1H), 2.76 (t, J=7.2 Hz, 4H), 2.67 (t, J=7.6 Hz, 4H), 1.92-1.84 (m, 4H), 1.44 (d, J=6.4 Hz, 6H). LCMS (m/z): 455.05 (M−1)$^-$; 96.13% (210 nm), 95.41% (254 nm). HPLC: 95.71% (210 nm), 95.12% (254 nm).

N-((1,2,3,5,6,7-hexahydro-s-indacen-4-yl)carbamoyl)-5-isopropyl-1-methyl-1H-pyrazole-3-sulfonamide

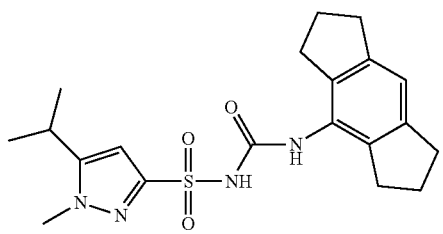 [SMILES: CC(C)c1cc(S(=O)(=O)NC(=O)Nc2c3c(cc4c2CCC4)CCC3)nn1C]

4-Isocyanato-8-methyl-1,2,3,5,6,7-hexahydro-s-indacene (prepared using general method A1) and 5-isopropyl-1-methyl-1H-pyrazole-3-sulfonamide were used in general method C3 to give the titled compound as a white solid (10 mg, 17%). $^1$H NMR (400 MHz, CD$_3$OD): δ=6.88 (s, 1H), 6.50 (s, 1H), 3.82 (s, 3H), 3.08-3.03 (m, 1H), 2.83 (t, J=7.2 Hz, 4H), 2.71 (t, J=7.2 Hz, 4H), 2.04-1.96 (m, 4H), 1.21 (d, J=6.8 Hz, 6H). LCMS (m/z): 403.20 (M+1)$^+$; 98.39% (210 nm), 94.19% (254 nm). HPLC: 95.62% (210 nm), 93.00% (254 nm).

N-((2,6-diisopropylphenyl)carbamoyl)-5-(2-hydroxypropan-2-yl)-1-methyl-1H-pyrazole-3-sulfonamide

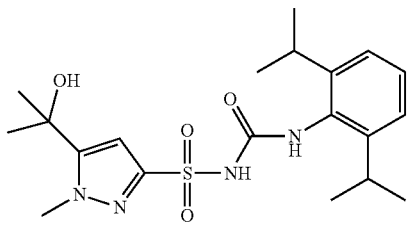 [SMILES: CC(C)c1cccc(C(C)C)c1NC(=O)NS(=O)(=O)c1cc(C(C)(C)O)n(C)n1]

2-Isocyanato-1,3-diisopropylbenzene (prepared using general method A1) and 5-(2-hydroxypropan-2-yl)-1-methyl-1H-pyrazole-3-sulfonamide were used in general method C1 to give the titled compound as a white solid (90 mg, 26%). $^1$H NMR (400 MHz, CD$_3$OD): δ=7.25-7.24 (m, 1H), 7.16-7.14 (m, 2H), 6.67 (s, 1H), 4.13 (s, 3H), 3.11-3.08 (m, 2H), 1.61 (s, 6H), 1.16 (d, J=6.8 Hz, 12H). LCMS (m/z): 423.20 (M+1)$^+$; 99.16% (210 nm), 97.19% (254 nm). HPLC: 98.16% (210 nm), 97.09% (254 nm).

N-((1,2,3,5,6,7-hexahydro-s-indacen-4-yl)carbamoyl)-5-(2-hydroxypropan-2-yl)-1-methyl-1H-pyrazole-3-sulfonamide

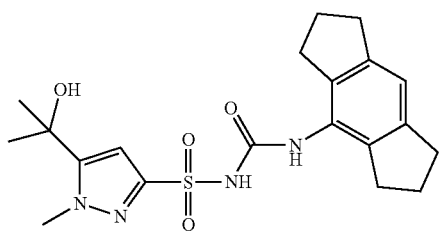 [SMILES: Cn1nc(S(=O)(=O)NC(=O)Nc2c3c(cc4c2CCC4)CCC3)cc1C(C)(C)O]

4-Isocyanato-8-methyl-1,2,3,5,6,7-hexahydro-s-indacene (prepared using general method A1) and 5-(2-hydroxypropan-2-yl)-1-methyl-1H-pyrazole-3-sulfonamide were used in general method C1 to give the titled compound as a white solid (70 mg, 15%). $^1$H NMR (400 MHz, DMSO-d$_6$) δ 8.01 (s, 1H), 6.92 (s, 1H), 6.53 (s, 1H), 5.51 (s, 1H), 4.02 (s, 3H), 2.79 (t, J=7.4 Hz, 4H), 2.62 (t, J=7.4 Hz, 4H), 1.95 (p, J=7.4 Hz, 4H), 1.50 (s, 6H).

N-((1,2,3,5,6,7-hexahydro-s-indacen-4-yl)carbamoyl)-5-(2-hydroxypropan-2-yl)-1-phenyl-1H-pyrazole-3-sulfonamide

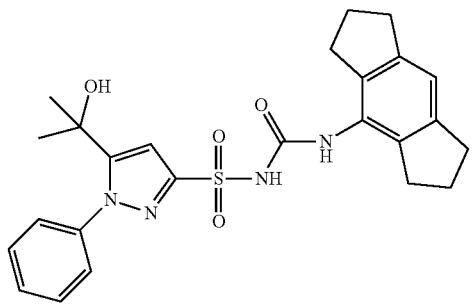 [SMILES: CC(C)(O)c1cc(S(=O)(=O)NC(=O)Nc2c3c(cc4c2CCC4)CCC3)nn1-c1ccccc1]

4-Isocyanato-8-methyl-1,2,3,5,6,7-hexahydro-s-indacene (prepared using general method A1) and 5-(2-hydroxypropan-2-yl)-1-phenyl-1H-pyrazole-3-sulfonamide were used in general method C1 to give the titled compound as a white solid (10 mg, 2%). $^1$H NMR (400 MHz, CD$_3$OD): δ=7.54 (s, 5H), 6.59 (s, 1H), 6.91 (s, 1H), 2.86 (t, J=7.2 Hz, 4H), 2.69 (t, J=7.2 Hz, 4H), 2.05-1.96 (m, 4H), 1.44 (s, 6H). LCMS (m/z): 481.20 (M−1)$^-$; 93.76% (210 nm), 93.24% (254 nm). HPLC: 95.86% (210 nm), 93.93% (254 nm).

1-benzyl-N-((1,2,3,5,6,7-hexahydro-s-indacen-4-yl)carbamoyl)-5-(2-hydroxypropan-2-yl)-1H-pyrazole-3-sulfonamide

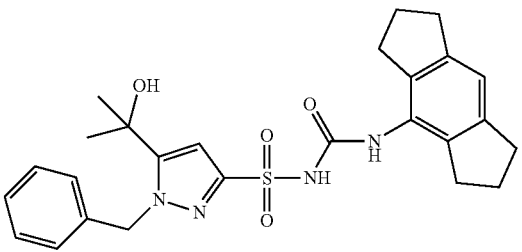 [SMILES: CC(C)(O)c1cc(S(=O)(=O)NC(=O)Nc2c3c(cc4c2CCC4)CCC3)nn1Cc1ccccc1]

4-Isocyanato-8-methyl-1,2,3,5,6,7-hexahydro-s-indacene (prepared using general method A1) and 1-benzyl-5-(2-hydroxypropan-2-yl)-1H-pyrazole-3-sulfonamide were used in general method C1 to give the titled compound as a white solid (40 mg, 7%). $^1$H NMR (400 MHz, CD$_3$OD): δ=7.20-7.14 (m, 5H), 6.95 (s 2H), 6.73 (s, 1H), 5.77 (s, 2H), 2.86 (t, J=7.2 Hz, 4H), 2.68 (t, J=7.6 Hz, 4H), 2.01-1.94 (m, 4H), 1.51 (s, 6H). LCMS (m/z): 494.7 (M+1)$^+$; 98.74% (210 nm), 96.05% (254 nm). HPLC: 95.11% (210 nm), 95.08% (254 nm).

N-((4-chloro-2,6-diisopropyl phenyl)carbamoyl)-5-(2-hydroxypropan-2-yl)-1-methyl-1H-pyrazole-3-sulfonamide

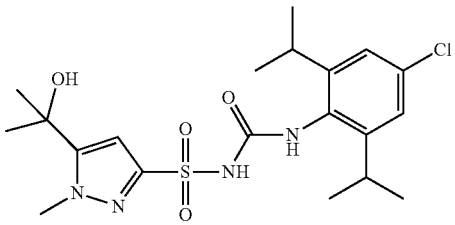 [SMILES: CC(C)c1cc(Cl)cc(C(C)C)c1NC(=O)NS(=O)(=O)c1cc(C(C)(C)O)n(C)n1]

5-chloro-2-isocyanato-1,3-diisopropylbenzene (prepared using general method A2) and 5-(2-hydroxypropan-2-yl)-1-methyl-1H-pyrazole-3-sulfonamide were used in general method C2 to give the titled compound as a white solid (83 mg, 17%). $^1$H NMR (600 MHz, DMSO-d$_6$) δ=7.81 (s, 1H), 7.10 (s, 2H), 6.42 (s, 1H), 5.45 (s, 1H), 3.99 (s, 3H), 3.03 (hept, J=7.0 Hz, 2H), 1.47 (s, 6H), 1.05 (d, J=1.8 Hz, 12H). HRMS calculated for C$_{20}$H$_{28}$Cl$_1$N$_4$O$_4$S$_1$ [M−H]$^-$ 455.1525, found 455.1515.

N-((4-chloro-2,6-diisopropyl phenyl)carbamoyl)-5-(2-hydroxypropan-2-yl)-1-phenyl-1H-pyrazole-3-sulfonamide

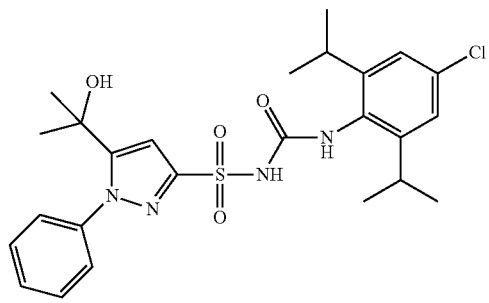 [SMILES: CC(C)c1cc(Cl)cc(C(C)C)c1NC(=O)NS(=O)(=O)c1cc(C(C)(C)O)n(-c2ccccc2)n1]

5-chloro-2-isocyanato-1,3-diisopropylbenzene (prepared using general method A2) and 5-(2-hydroxypropan-2-yl)-1-phenyl-1H-pyrazole-3-sulfonamide were used in general method C2 to give the titled compound as a white solid (168 mg, 31%). $^1$H NMR (600 MHz, DMSO-d$_6$) δ=7.87 (s, 1H), 7.52 (s, 5H), 7.10 (s, 2H), 6.71 (s, 1H), 5.42 (s, 1H), 3.10-2.92 (m, 2H), 1.31 (s, 6H), 1.02 (d, J=7.0 Hz, 12H). HRMS calculated for C$_{25}$H$_{30}$Cl$_1$N$_4$O$_4$S$_1$ [M−H]$^−$ 517.1682, found 517.1671.

N-((4-chloro-2,6-dimethylphenyl)carbamoyl)-1-isopropyl-1H-pyrazole-3-sulfonamide

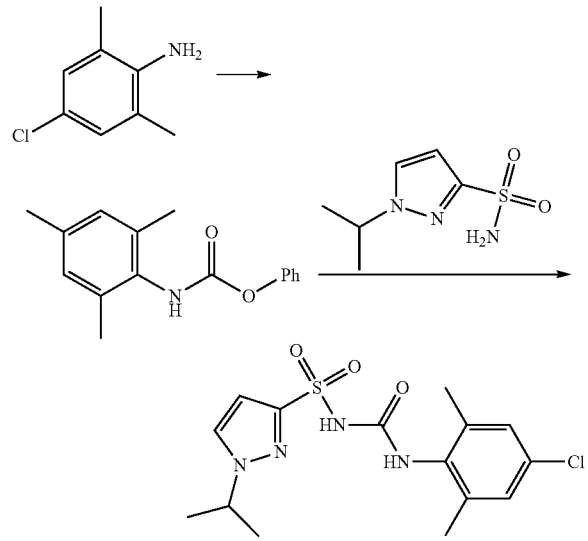

A solution of 4-chloro-2,6-dimethylaniline (50 mg, 0.321 mmol) in DCM (5 mL) was treated with Et$_3$N (50 mg, 0.48 mmol) and cooled to 0° C., Phenyl chloroformate (60 mg, 0.39 mmol) was added dropwise at 0° C. The reaction mixture was warmed to RT and stirred for 12 h. Upon completion the reaction mixture was diluted with saturated NaHCO$_3$ solution, extracted with DCM (2×20 mL) and the combined organic extract washed with water, brine dried (Na$_2$SO$_4$) and concentrated in vacuo. The residue obtained was washed with n-pentane and dried in vacuo to give phenyl (4-chloro-2,6-dimethylphenyl)carbamate (75 mg, 85%) as a brown solid. 1H NMR (300 MHz, CDCl$_3$): δ=7.46-7.37 (m, 4H), 7.26-7.20 (m, 2H), 7.12-7.11 (m, 2H), 2.33 (s, 6H). LCMS (m/z): 275.9 [M+H]$^+$.

1-isopropyl-1H-pyrazole-3-sulfonamide (150 mg, 0.79 mmol) was dissolved in anhydrous THF (5 mL) and treated carefully with NaH (80 mg, 1.98 mmol) at 0° C. under nitrogen atmosphere. The resulting mixture was stirred at RT for 30 min then treated with a solution of phenyl (4-chloro-2,6-dimethylphenyl)carbamate (240 mg, 0.87 mmol) in THF (3 mL) under nitrogen atmosphere at 0° C. The resulting reaction mixture was warmed to RT and stirred for 3 h. Upon completion the reaction mixture was diluted with saturated NH$_4$Cl solution, extracted with EtOAc (2×30 mL) and the combined organic extract was washed with water, brine dried (Na$_2$SO$_4$) and concentrated in vacuo. The crude product was purified by column chromatography on silica gel (60-120 mesh) using 40% EtOAc-hexanes eluant to give N-((4-chloro-2,6-dimethylphenyl)carbamoyl)-1-isopropyl-1H-pyrazole-3-sulfonamide (90 mg, 31%) as a white solid.

$^1$H NMR (400 MHz, DMSO-d$_6$): δ=11.05 (s, 1H), 7.99 (d, J=2.8 Hz, 1H), 7.93 (s, 1H), 7.13 (s, 2H), 6.73 (d, J=2.4 Hz, 1H), 4.64-4.57 (m, 1H), 2.03 (s, 6H), 1.43 (d, J=6.8 Hz, 6H). LCMS (m/z): 370.95 [M+H]+; 97.62% (210 nm), 97.48% (254 nm). HPLC: 97.20% (210 nm). HRMS calculated for C$_{15}$H$_{18}$Cl$_1$N$_4$O$_3$S$_1$ [M−H]$^−$ 369.0794, found 369.0785.

N-((4-chloro-2,6-dimethoxyphenyl)carbamoyl)-1-isopropyl-1H-pyrazole-3-sulfonamide

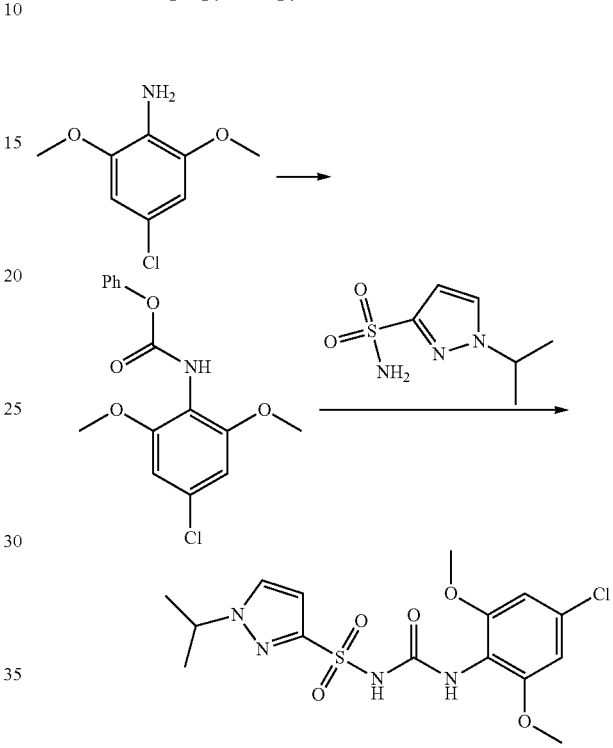

A solution of 4-chloro-2,6-dimethoxyaniline (200 mg, 1.06 mmol) in THF (8 mL) was cooled to 0° C. and treated with NaH (62 mg, 1.59 mmol) under nitrogen atmosphere. The resulting mixture was stirred for 15 min. before phenylchloroformate (330 mg, 2.13 mmol) was added dropwise at 0° C. The reaction mixture was warmed to RT and stirred for 12 h. Upon completion, the reaction mixture was diluted with EtOAc and filtered through a celite pad and concentrated in vacuo. The crude product was purified by column chromatography on silica gel (60-120 mesh) using 10% EtOAc-hexanes eluant to give phenyl (4-chloro-2,6-dimethoxyphenyl)carbamate (0.2 g, 61%) as a white solid. 1H NMR (300 MHz, CDCl$_3$): δ=7.35-7.33 (m, 2H), 7.20-7.19 (m, 3H), 6.61 (s, 2H), 3.83 (s, 6H).

1-isopropyl-1H-pyrazole-3-sulfonamide (100 mg, 0.53 mmol) was dissolved in anhydrous THF (5 mL) and treated carefully with NaH (52 mg, 1.32 mmol) at 0° C. under nitrogen atmosphere). The resulting mixture was stirred at RT for 40 min then treated with a solution of phenyl (4-chloro-2,6-dimethoxyphenyl)carbamate (180 mg, 0.58 mmol) in THF (3 mL) under nitrogen atmosphere at 0° C. The resulting reaction mixture was warmed to RT and stirred for 12 h. Upon completion the reaction mixture was diluted with saturated NH$_4$Cl solution, extracted with EtOAc (2×50 mL) and the combined organic extract washed with water, brine, dried (Na$_2$SO$_4$) and concentrated in vacuo. The combined organic extract was washed with water, brine, dried over anhydrous Na$_2$SO$_4$ and concentrated in vacuo. The crude product was purified by reverse phase preparative HPLC [column: Gemini NX C18 (21.2 mm×150 mm particle size 5 μm); flow: 20 mL/min; eluent: 10 mM ammonium bicarbonate in water (A) & MeCN (B); gradient: T/% B=0/20, 2/20, 8/70]. The fractions were lyophilized to give N-((4-chloro-2,6-dimethoxyphenyl)carbamoyl)-1-isopropyl-1H-pyrazole-3-sulfonamide (20 mg, 9%) as a white solid. $^1$H NMR (400 MHz, DMSO-$d_6$): δ=7.90 (d, J=2.0 Hz, 1H), 7.28 (s, 1H), 6.72 (s, 2H), 6.63 (d, J=2.0 Hz, 1H), 4.60-4.54 (m, 1H), 3.70 (s, 6H), 1.43 (d, J=6.8 Hz, 6H). LCMS (m/z): 403.0 [M+H]$^+$; 90.61% (210 nm). HPLC: 91.63% (210 nm). HRMS calculated for $C_{15}H_{18}Cl_1N_4O_5S_1$ [M–H]$^-$ 401.0692, found 401.0684.

N-((4-chloro-2-methyl-6-(trifluoromethyl)phenyl)carbamoyl)-1-isopropyl-1H-pyrazole-3-sulfonamide

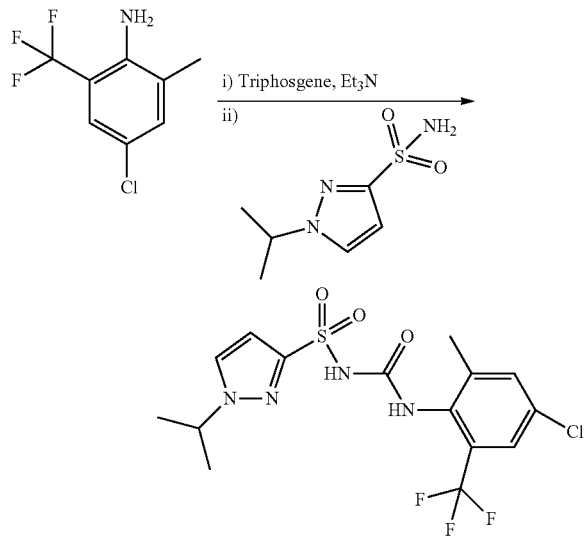

4-Chloro-2-methyl-6-(trifluoromethyl)aniline (50 mg, 0.24 mmol) was dissolved in anhydrous THF (5 mL) and treated with Et$_3$N (30 mg, 0.29 mmol) at RT. The solution was treated with triphosgene (30 mg, 0.095 mmol) and resulting mixture was stirred at 60° C. for 4 h. The reaction mixture was concentrated in vacuo. The residue obtained was stirred with n-pentane (20 mL) for 10 min, filtered through a celite pad and concentrated in vacuo to give the corresponding isocyanate as a white solid. In another 50 mL round bottom flask, 1-isopropyl-1H-pyrazole-3-sulfonamide (40 mg, 0.212 mmol) was dissolved in anhydrous THF (5 mL) and treated carefully with NaH (22 mg, 0.529 mmol) at 0° C. under nitrogen atmosphere. It was stirred at RT for 30 minutes. The aforementioned solution of isocyanate was added in THF under nitrogen atmosphere. The resulting reaction mixture was stirred at RT for 2 h. Upon completion of reaction the reaction mixture was diluted with saturated NH$_4$Cl solution, extracted with EtOAc (2×25 mL) and the combined organic extract washed with water, brine, dried (Na$_2$SO$_4$) and concentrated in vacuo. The crude product was purified by column chromatography on silica gel (60-120 mesh) using 40% EtOAc-hexanes eluant to give N-((4-chloro-2-methyl-6-(trifluoromethyl)phenyl)carbamoyl)-1-isopropyl-1H-pyrazole-3-sulfonamide. This was triturated with diethyl ether and n-pentane to give N-((4-chloro-2-methyl-6-(trifluoromethyl)phenyl)carbamoyl)-1-isopropyl-1H-pyrazole-3-sulfonamide (35 mg, 35%) as a white solid. $^1$H NMR (400 MHz, DMSO-$d_6$): δ=11.05 (s, 1H), 8.09 (s, 1H), 7.96 (s, 1H), 7.70 (s, 1H), 7.61 (s, 1H), 6.67 (d, J=0.4 Hz, 1H), 4.62 (m, 1H), 2.05 (s, 3H), 1.43 (d, J=6.8 Hz, 6H). 19F NMR (400 MHz, DMSO-d6): δ=–60.82. LCMS (m/z): 425.00 [M+H]$^+$; 94.05% (210 nm). HPLC: 98.03% (210 nm). HRMS calculated for $C_{15}H_{15}Cl_1F_3N_4O_3S_1$ [M–H]$^-$ 423.0511, found 423.0513.

N-((4-chloro-2-methoxy-6-(trifluoromethyl)phenyl)carbamoyl)-1-isopropyl-1H-pyrazole-3-sulfonamide

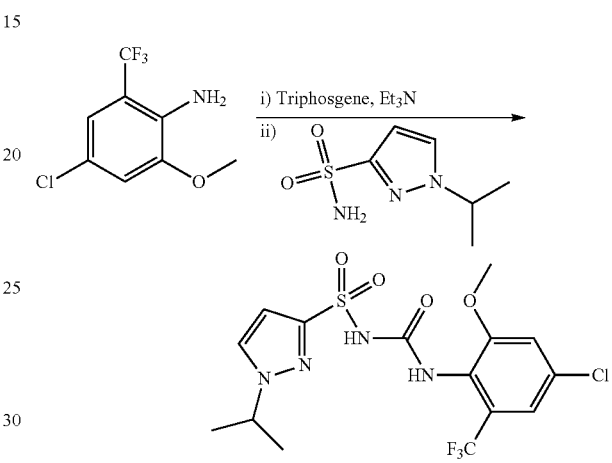

4-Chloro-2-methoxy-6-(trifluoromethyl)aniline (50 mg, 0.22 mmol) was dissolved in anhydrous THF (2 mL) and treated with Et$_3$N (27 mg, 0.27 mmol) at RT. The solution was treated with triphosgene (32 mg, 0.11 mmol) and resulting mixture was stirred at 70° C. for 3 h. The reaction mixture was concentrated in vacuo and the residue obtained stirred with 5% EtOAc-hexanes (20 mL) for 10 min, filtered through celite and concentrated in vacuo to give the desired isocyanate as a white solid. In another 50 mL round bottom flask, 1-isopropyl-1H-pyrazole-3-sulfonamide (42 mg, 0.22 mmol) was dissolved in anhydrous THF (5 mL) and treated carefully with NaH (18 mg, 0.44 mmol) at 0° C. under nitrogen atmosphere. The mixture was stirred at 0° C. for 20 minutes and treated with aforementioned solution of isocyanate in THF under nitrogen atmosphere. The resulting reaction mixture was stirred at 0-10° C. for 2 h. Upon completion, the reaction mixture was diluted with saturated NH$_4$Cl solution, extracted with EtOAc (2×50 mL) and the combined organic extract washed with water, brine, dried (Na$_2$SO$_4$) and concentrated in vacuo. The crude product was purified by column chromatography on silica gel (60-120 mesh) using 50% EtOAc-hexanes eluant to give N-((4-chloro-2-methoxy-6-(trifluoromethyl)phenyl)carbamoyl)-1-isopropyl-1H-pyrazole-3-sulfonamide (10 mg, 10%) as a white solid. $^1$H NMR (400 MHz, CDCl$_3$): δ=7.81 (s, 1H), 7.53 (d, J=2.4 Hz, 1H), 7.22 (d, J=1.6 Hz, 1H), 7.10 (s, 1H), 6.82 (d, J=2.0 Hz, 1H), 4.64-4.57 (m, 1H), 3.84 (s, 3H), 1.54 (d, J=6.8 Hz, 6H). 19F NMR (400 MHz, CDCl$_3$): δ=–61.55. LCMS (m/z): 441.05 [M+H]$^+$; 94.58% (210 nm). HPLC: 92.16% (210 nm). HRMS calculated for $C_{15}H_{15}Cl_1F_3N_4O_4S_1$ [M–H]$^-$ 439.0460, found 439.0478.

N-((4-chloro-2,6-diethylphenyl)carbamoyl)-1-isopropyl-1H-pyrazole-3-sulfonamide

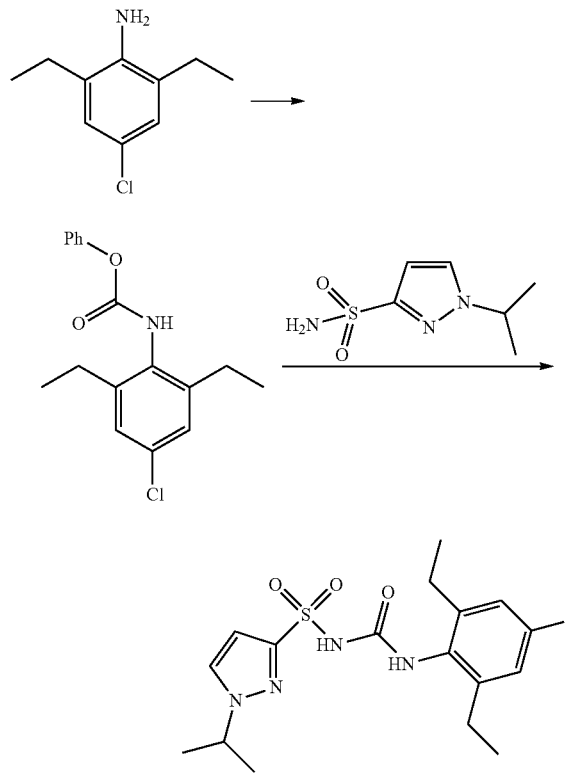

A solution of 4-chloro-2,6-dicyclopropylaniline (100 mg, 0.546 mmol) in THF (5 mL) was cooled to 0° C. and treated with NaH (30 mg, 0.66 mmol) under nitrogen atmosphere and stirred for 15 min. Phenyl chloroformate (130 mg, 0.819 mmol) was added dropwise to the aforementioned solution at 0° C. The reaction mixture was warmed to RT and stirred for 12 h. Upon completion the mixture was diluted with EtOAc, filtered through a celite pad and concentrated in vacuo. The crude product was was purified by column chromatography on silica gel (60-120 mesh) using 10% EtOAc-hexanes to give phenyl (4-chloro-2,6-diethylphenyl)carbamate (0.15 g, 91%) as a white solid. $^1$H NMR (300 MHz, CDCl$_3$): δ=7.38-7.33 (m, 2H), 7.23-7.18 (m, 3H), 7.13 (m, 2H), 6.27 (s, 1H), 2.75-2.64 (m, 4H), 1.28-1.22 (m, 6H).

1-isopropyl-1H-pyrazole-3-sulfonamide (75 mg, 0.40 mmol) was dissolved in anhydrous THF (5 mL) and treated carefully with NaH (40 mg, 0.99 mmol) at 0° C. under nitrogen atmosphere. The resulting mixture was stirred at RT for 30 min then treated with a solution of give phenyl (4-chloro-2,6-diethylphenyl)carbamate (130 mg, 0.44 mmol) in THF (3 mL) under nitrogen atmosphere at 0° C. The resulting reaction mixture was warmed to RT and stirred for 4 h. Upon completion, the reaction mixture was diluted with saturated NH$_4$Cl solution, extracted with EtOAc (2×30 mL) and the combined organic extract was washed with water, brine, dried (Na$_2$SO$_4$) and concentrated in vacuo. The crude product was was purified by column chromatography on silica gel (60-120 mesh) using 30-40% EtOAc-hexanes eluant followed by trituration with diethyl ether and n-pentane to give N-((4-chloro-2,6-diethylphenyl)carbamoyl)-1-isopropyl-1H-pyrazole-3-sulfonamide (40 mg, 24%) as a white solid. $^1$H NMR (400 MHz, DMSO-d$_6$): δ=11.05 (s, 1H), 7.99 (d, J=2.4 Hz, 1H), 7.89 (s, 1H), 7.12 (s, 2H), 6.72 (d, J=2.4 Hz, 1H), 4.62-4.59 (m, 1H), 2.42 (q, J=7.6 Hz, 4H), 1.43 (d, J=6.8 Hz, 6H), 1.02 (t, J=7.6 Hz, 6H). LCMS (m/z): 399.0 [M+H]$^+$, 96.72% (210 nm). HPLC: 97.13% (210 nm). HRMS calculated for C$_{17}$H$_{22}$Cl$_1$N$_4$O$_3$S$_1$ [M–H]$^-$ 397.1107, found 397.1090.

N-((4-chloro-2,6-diisopropyl phenyl)carbamoyl)-1-isopropyl-1H-pyrazole-3-sulfonamide

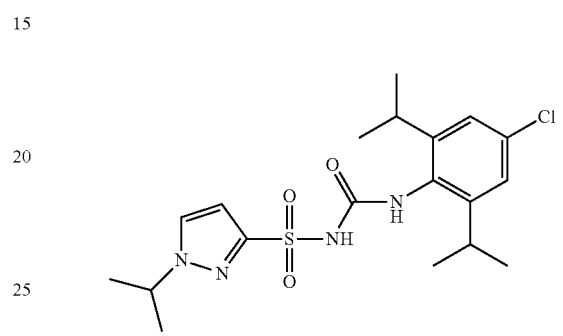

5-Chloro-2-isocyanato-1,3-diisopropylbenzene (prepared using general method A2) and 1-isopropyl-1H-pyrazole-3-sulfonamide were used in general method C2 to give the titled compound as a white solid (221 mg, 49%). $^1$H NMR (600 MHz, DMSO-d6) δ=7.70 (d, J=2.3 Hz, 1H), 7.49 (s, 1H), 7.00 (s, 2H), 6.36 (s, 1H), 4.62-4.29 (m, 1H), 3.11 (d, J=6.4 Hz, 2H), 1.38 (d, J=6.8 Hz, 6H), 1.01 (d, J=6.8 Hz, 12H). $^{13}$C NMR (151 MHz, DMSO) δ=160.96, 156.43, 150.19, 135.25, 131.49, 128.53, 123.27, 105.21, 54.23, 28.80, 24.15, 23.55. HRMS calculated for C$_{19}$H$_{26}$Cl$_1$N$_4$O$_3$S$_1$ [M–H]$^-$ 425.1420, found 425.1409.

N-((4-chloro-2,6-dicyclo propylphenyl)carbamoyl)-1-isopropyl-1H-pyrazole-3-sulfonamide

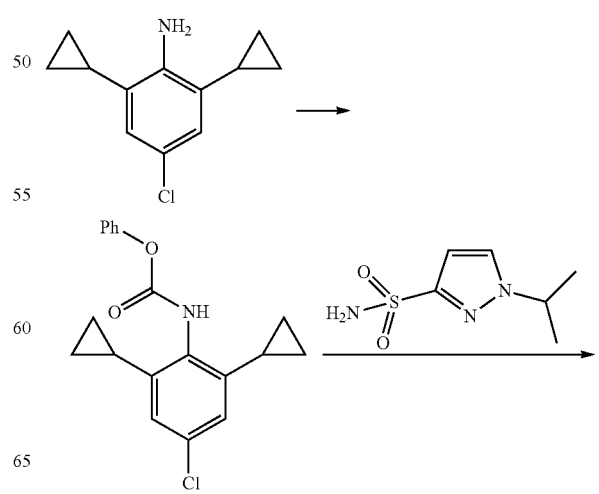

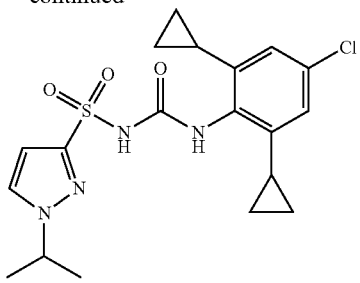

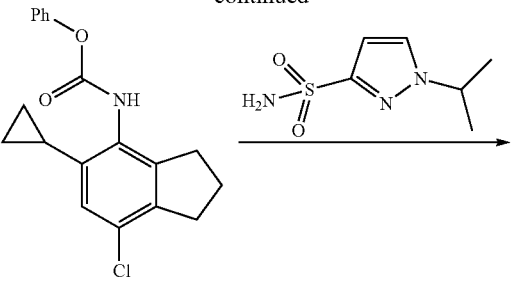

A solution of 4-chloro-2,6-dicyclopropylaniline (150 mg, 0.724 mmol) in THF (5 mL) was cooled to 0° C. NaH (35 mg, 0.87 mmol) was added in portions to aforementioned solution and stirred for 20 min. Phenyl chloroformate (170 mg, 1.08 mmol) was added dropwise to the aforementioned solution at 0° C. The reaction mixture was warmed to RT and stirred for 12 h. Upon completion, the mixture was diluted with EtOAc, filtered through celite and concentrated in vacuo. The crude product was purified by column chromatography on silica gel (60-120 mesh) using 15% EtOAc-hexanes eluant to give phenyl (4-chloro-2,6-dicyclopropylphenyl)carbamate (195 mg, 83%) as a white solid. $^1$H NMR (300 MHz, CDCl$_3$): δ=7.37-7.35 (m, 2H), 7.21-7.19 (m, 3H), 6.84-6.83 (m, 2H), 2.08-2.04 (m, 2H), 1.04-1.02 (m, 4H), 0.69-0.68 (m, 4H). LCMS (m/z): 328.2 [M+H]$^+$.

1-isopropyl-1H-pyrazole-3-sulfonamide (100 mg, 0.53 mmol) was dissolved in anhydrous THF (5 mL) and treated carefully with NaH (53 mg, 1.32 mmol) at 0° C. under nitrogen atmosphere. The resulting mixture was stirred at RT for 30 min then treated with a solution of phenyl (4-chloro-2,6-dicyclopropylphenyl)carbamate (190 mg, 0.582 mmol) in THF (3 mL) under nitrogen atmosphere at 0° C. The reaction mixture was warmed to RT and stirred for 4 h. Upon completion of reaction the reaction mixture was diluted with saturated NH$_4$Cl solution, extracted with EtOAc (2×30 mL) and the combined organic extract washed with water, brine, dried (Na$_2$SO$_4$) and concentrated in vacuo. The crude product was purified by column chromatography on silica gel (60-120 mesh) using 40% EtOAc-hexanes eluant to give N-((4-chloro-2,6-dicyclo propylphenyl)carbamoyl)-1-isopropyl-1H-pyrazole-3-sulfonamide. This was triturated with diethyl ether and n-pentane to give (25 mg, 11%) as a white solid. $^1$H NMR (400 MHz, DMSO-d$_6$): δ=11.05 (s, 1H), 8.01-7.98 (m, 2H), 6.74 (s, 3H), 4.59-4.56 (m, 1H), 1.77-1.76 (m, 2H), 1.41 (d, J=6.8 Hz, 6H), 0.77-0.75 (m, 4H), 0.56-0.55 (m, 4H). LCMS (m/z): 423.00 [M+H]+; 93.58% (210 nm). HPLC: 92.87% (210 nm). HRMS calculated for C$_{19}$H$_{22}$Cl$_1$N$_4$O$_3$S$_1$ [M−H]$^-$ 421.1107, found 421.1107.

N-((7-chloro-5-cyclopropyl-2,3-dihydro-1H-inden-4-yl)carbamoyl)-1-isopropyl-1H-pyrazole-3-sulfonamide

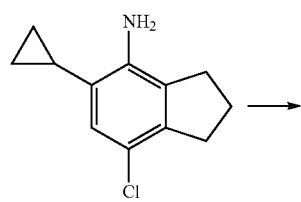

7-chloro-5-cyclopropyl-2,3-dihydro-1H-inden-4-amine, 6 (70 mg, 0.33 mmol) was dissolved in THF (5 mL) and cooled to 0° C. NaH (20 mg, 0.505 mmol) was added to the aforementioned solution under nitrogen atmosphere and stirred for 15 min before phenyl chloroformate (100 mg, 0.674 mmol) was added dropwise at 0° C. The reaction mixture was warmed to RT and stirred for 12 h. Upon completion the reaction mixture was diluted with EtOAc, filtered through celite and concentrated in vacuo. The crude product was purified by column chromatography on silica gel (60-120 mesh) using, 10% EtOAc-hexanes eluent to give phenyl (7-chloro-5-cyclopropyl-2,3-dihydro-1H-inden-4-yl) carbamate (80 mg, 73%) as a brown solid. $^1$H NMR (300 MHz, CDCl$_3$): δ=7.39-7.37 (m, 3H), 7.25-7.24 (m, 2H), 6.85 (s, 1H), 3.0-2.94 (m, 4H), 2.12-2.10 (m, 2H), 1.34 (m, 1H), 0.96-0.95 (m, 2H), 0.59-0.57 (m, 2H). LCMS (m/z): 328.30 [M+H]$^+$.

1-isopropyl-1H-pyrazole-3-sulfonamide (41 mg, 0.219 mmol) was dissolved in anhydrous THF (3 mL) and treated carefully with NaH (21 mg, 0.549 mmol) at 0° C. under nitrogen atmosphere. The resulting mixture was stirred at RT for 30 min and was treated with a solution of phenyl (7-chloro-5-cyclopropyl-2,3-dihydro-1H-inden-4-yl)carbamate (80 mg, 0.244 mmol) in THF (2 mL) under nitrogen atmosphere at 0° C. The resulting reaction mixture was warmed to RT and stirred for 4 h. Upon completion the reaction mixture was diluted with saturated NH$_4$Cl solution, extracted with EtOAc (2×30 mL) and the combined organic extract was washed with water, brine, dried (Na$_2$SO$_4$) and concentrated in vacuo. The crude product was purified by reverse phase preparative HPLC [column: Gemini NX C18 (21.2 mm×150 mm particle size 5 μm); flow: 20 mL/min; eluent: 10 mM ammonium bicarbonate in water (A) & MeCN (B); gradient: T/% B=0/20, 2/30, 8/70]. The fractions were lyophilized to give N-((7-chloro-5-cyclopropyl-2,3-dihydro-1H-inden-4-yl)carbamoyl)-1-isopropyl-1H-pyrazole-3-sulfonamide (20 mg, 20%) as a white solid. $^1$H NMR (400 MHz, DMSO-d$_6$): δ=7.95 (d, J=2.4 Hz, 1H), 6.74 (s, 1H), 6.69 (d, J=2.4 Hz, 1H), 4.60-4.55 (m, 1H), 2.84 (t, J=7.6 Hz, 2H), 2.66 (t, J=7.6 Hz, 2H), 1.95-1.92 (m, 2H), 1.79-1.76 (m, 1H), 1.41 (d, J=6.4 Hz, 6H), 0.82-0.78 (m, 2H), 0.54-0.50 (m, 2H). LCMS (m/z): 421.15 [M−H]$^-$;

94.19% (210 nm). HPLC: 95.46% (210 nm). HRMS calculated for $C_{19}H_{22}Cl_1N_4O_3S_1$ [M−H]⁻ 421.1107, found 421.1110.

5-chloro-3-cyclopropyl-2-(3-((1-isopropyl-1H-pyrazol-3-yl)sulfonyl)ureido)-N,N-dimethylbenzamide

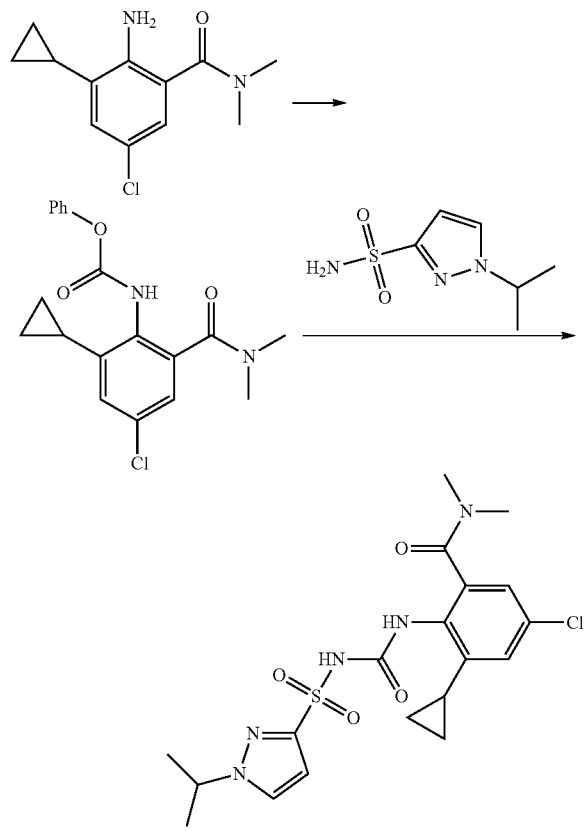

2-amino-5-chloro-3-cyclopropyl-N,N-dimethylbenzamide (200 mg, 0.84 mmol) was dissolved in anhydrous THF (5 mL) and treated carefully with NaH (50 mg, 1.26 mmol) at 0° C. under nitrogen atmosphere. The resulting reaction mixture was stirred for 15 min. then phenyl chloroformate (262 mg, 1.68 mmol) was added dropwise at 0° C. The reaction mixture was warmed to RT and stirred for 12 h. Upon completion the reaction mixture was diluted with EtOAc, filtered through celite and concentrated in vacuo. The crude product was purified by column chromatography on silica gel (60-120 mesh) using 15% EtOAc-hexanes eluant to give phenyl (4-chloro-2-cyclopropyl-6-(dimethylcarbamoyl) phenyl)carbamate (0.14, 47%) as dark brown liquid. ¹H NMR (300 MHz, CDCl₃): δ=7.39-7.34 (m, 2H), 7.23-7.15 (m, 3H), 7.08-7.02 (m, 2H), 3.09 (s, 3H), 2.96 (s, 3H), 2.05-2.0 (m, 1H), 1.05-1.02 (m, 2H), 0.71-0.69 (m, 2H). LCMS (m/z): 358.60 [M+H]⁺.

1-isopropyl-1H-pyrazole-3-sulfonamide (57 mg, 0.30 mmol) was dissolved in anhydrous THF (5 mL) and treated carefully with NaH (18 mg, 0.451 mmol) at 0° C. under nitrogen atmosphere. The resulting mixture was stirred at RT for 45 min then treated with a solution of phenyl (4-chloro-2-cyclopropyl-6-(dimethylcarbamoyl) phenyl)carbamate (120 mg, 0.335 mmol) in THF (3 mL) under nitrogen atmosphere at 0° C. The resulting reaction mixture was warmed to RT and stirred for 2 h. Upon completion, the reaction mixture was diluted with saturated NH₄Cl solution, extracted with EtOAc (2×30 mL) and the combined organic extract washed with water, brine, dried (Na₂SO₄) and concentrated in vacuo. The crude product was purified by reverse phase preparative HPLC [column: Gemini NX C18 110AAXIA (21.2 mm×150 mm particle size 5 μm); flow: 18 mL/min; eluent: 10 mM ammonium bicarbonate in water (A) & MeCN (B); gradient: T/% B=0/20, 2/20, 10/60]. The fractions were lyophilized to give 5-chloro-3-cyclopropyl-2-(3-((1-isopropyl-1H-pyrazol-3-yl)sulfonyl)ureido)-N,N-dimethylbenzamide (10 mg, 7%) as a white solid. ¹H NMR (400 MHz, CD₃OD): δ=7.77 (s, 1H), 7.11 (d, J=2.4 Hz, 1H), 7.05 (d, J=2.0 Hz, 1H), 6.76 (s, 1H), 4.62-4.53 (m, 1H), 2.96 (s, 3H), 2.84 (s, 3H), 1.88-1.87 (m, 1H), 1.50 (d, J=6.8 Hz, 6H), 0.90-0.88 (m, 2H), 0.63-0.61 (m, 2H). LCMS (m/z): 454.0 [M+H]⁺; 97.52% (210 nm). HPLC: 92.05% (210 nm). HRMS calculated for $C_{19}H_{23}Cl_1N_5O_4S_1$ [M−H]⁻ 452.1165, found 452.1180.

N-((4,6-dimethylpyrimidin-2-yl)carbamoyl)-1-isopropyl-1H-pyrazole-3-sulfonamide

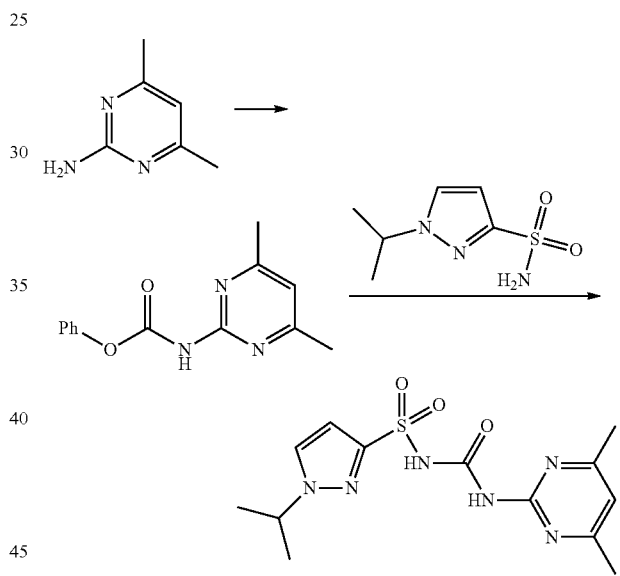

A solution of 4,6-dimethylpyrimidin-2-amine (300 mg, 2.43 mmol) in THF (10 mL) was cooled to 0° C. and treated with NaH (140 mg, 3.64 mmol) under nitrogen atmosphere. The resulting mixture was stirred for 15 min then treated with phenyl chloroformate (0.6 mL, 4.87 mmol) at 0° C. The reaction mixture was warmed to RT and stirred for 12 h. Upon completion, the reaction mixture was diluted with EtOAc (30 mL) filtered through celite and concentrated in vacuo. The crude product was purified by column chromatography on silica gel (60-120 mesh) using 30% EtOAc-hexanes eluant to give phenyl (4,6-dimethylpyrimidin-2-yl) carbamate (250 mg, 42%) as a white solid. ¹H NMR (300 MHz, CDCl₃): δ=8.14 (s, 1H), 7.45-7.34 (m, 2H), 7.25-7.18 (m, 3H), 6.78 (s, 1H), 2.46 (s, 6H). LCMS (m/z): 244.30 [M+H]⁺.

1-isopropyl-1H-pyrazole-3-sulfonamide (75 mg, 0.396 mmol) was dissolved in anhydrous THF (50 mL) and treated carefully with NaH (40 mg, 0.99 mmol) at 0° C. under nitrogen atmosphere. The resulting mixture was warmed to RT and stirred for 30 min. The reaction mixture was cooled to 0° C. then treated with a solution of phenyl (4,6-dimethylpyrimidin-2-yl)carbamate (100 mg, 0.436 mmol) in THF (5 mL) under nitrogen atmosphere at 0° C. The reaction mixture was warmed to RT and stirred for 3 h. Upon completion, the reaction mixture was diluted with saturated NH$_4$Cl solution, extracted with EtOAc (2×50 mL) and the combined organic extract washed with water, brine, dried (Na$_2$SO$_4$) and concentrated in vacuo. The crude product was purified by reverse phase preparative HPLC [column: Gemini NX-bridge (150 mm×21.2 mm particle size 5 μm); flow: 15 mL/min; eluent: 10 mM ammonium bicarbonate in water (A) & MeCN (B); gradient: T/% B=0/10, 2/20, 10/60]. The fractions were lyophilized to give N-((4,6-dimethylpyrimidin-2-yl)carbamoyl)-1-isopropyl-1H-pyrazole-3-sulfonamide (10 mg, 13%) as a white solid. $^1$H NMR (400 MHz, CDCl$_3$): δ=13.0 (s, 1H), 7.49-7.46 (m, 2H), 7.02 (d, J=2.4 Hz, 1H), 6.74 (s, 1H), 4.62-4.57 (m, 1H), 2.45 (s, 6H), 1.53 (d, J=6.8 Hz, 6H). LCMS (m/z): 339.10 [M+H]$^+$. 99.70% (210 nm), 100% (254 nm). HPLC: 97.22% (210 nm). HRMS calculated for C$_{13}$H$_{17}$N$_6$O$_3$S$_1$ [M-H]$^-$ 337.1088, found 337.1099.

N-((4,6-di-tert-butylpyrimidin-2-yl)carbamoyl)-1-isopropyl-1H-pyrazole-3-sulfonamide

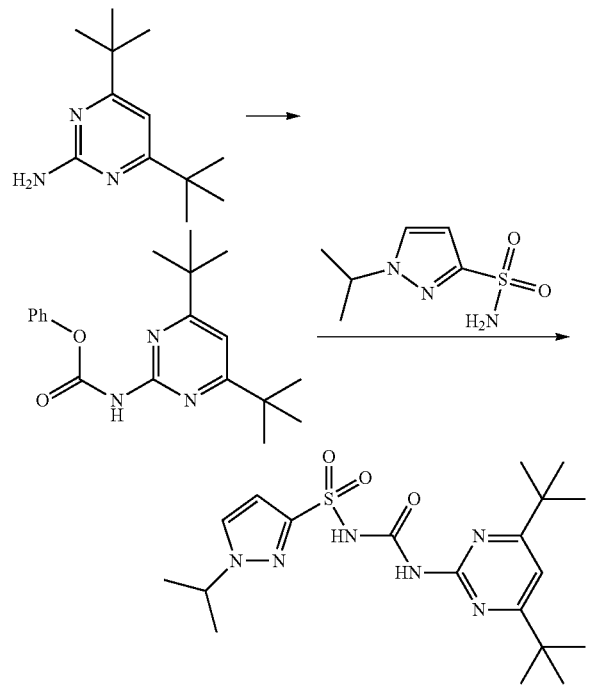

A solution of 4,6-di-tert-butylpyrimidin-2-amine (0.15 g, 0.72 mmol) in THF (5 mL) was cooled to 0° C. and treated with NaH (35 mg, 0.86 mmol) under nitrogen atmosphere. The resulting mixture was stirred for 15 min and phenyl chloroformate (0.17 g, 1.08 mmol) was added dropwise to the aforementioned solution at 0° C. The reaction mixture was warmed to RT and stirred for 12 h. Upon completion, the reaction mixture was concentrated in vacuo and the residue obtained diluted with ethyl acetate, filtered through celite and concentrated in vacuo. The crude product was purified by column chromatography on silica gel (60-120 mesh) using 15% EtOAc-hexanes eluant to give phenyl (4,6-di-tert-butylpyrimidin-2-yl)carbamate (140 mg, 59%) as a white solid. $^1$H NMR (400 MHz, CDCl$_3$): δ=7.95 (s, 1H), 7.65-7.61 (m, 2H), 7.50-7.45 (m, 4H), 1.32 (s, 18H). LCMS (m/z): 328.40 [M+H]$^+$;

1-Isopropyl-1H-pyrazole-3-sulfonamide (50 mg, 0.264 mmol) was dissolved in anhydrous THF (40 mL) and treated carefully with NaH (27 mg, 0.661 mmol) at 0° C. under nitrogen atmosphere. The resulting mixture was stirred for 30 minutes then treated with a solution of phenyl (4,6-di-tert-butylpyrimidin-2-yl)carbamate (95 mg, 0.29 mmol) in THF (5 mL) under nitrogen atmosphere at 0° C. The resulting reaction mixture was warmed to RT and stirred for 4 h. Upon completion, the reaction mixture was diluted with saturated NH$_4$Cl solution, extracted with EtOAc (2×50 mL) and the combined organic extract washed with water, brine, dried (Na$_2$SO$_4$) and concentrated in vacuo. The crude product was purified by column chromatography on silica gel (60-120 mesh) using 40% EtOAc-hexanes eluant to give N-((4,6-di-tert-butylpyrimidin-2-yl)carbamoyl)-1-isopropyl-1H-pyrazole-3-sulfonamide (38 mg, 25%) as a white solid. $^1$H NMR (400 MHz, DMSO-d$_6$): δ=13.75 (s, 1H), 10.71 (s, 1H), 8.01 (d, J=2.4 Hz, 1H), 7.18 (s, 1H), 6.81 (d, J=2.4 Hz, 1H), 4.61-4.54 (m, 1H), 1.38 (d, J=6.8 Hz, 6H), 1.31 (s, 18H). LCMS (m/z): 423.50 [M+H]$^+$; 99.88% (210 nm). HPLC: 98.49% (210 nm). HRMS calculated for C$_{19}$H$_{29}$N$_6$O$_3$S$_1$ [M-H]$^-$ 421.2027, found 421.2008.

Phenyl/Bicyclics

N-((1,2,3,5,6,7-hexahydro-s-indacen-4-yl)carbamoyl)benzenesulfonamide

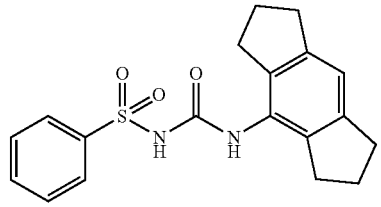 [SMILES: O=C(Nc1c2c(cc3c1CCC3)CCC2)NS(=O)(=O)c1ccccc1]

4-Isocyanato-8-methyl-1,2,3,5,6,7-hexahydro-s-indacene (prepared using general method A1) and phenylsulfonamide were used in general method C1 to give the titled compound as a white solid (50 mg, 13%). $^1$H NMR (400 MHz, CD$_3$OD): δ=8.05 (d, J=7.6 Hz, 2H), 7.72 (t, J=7.6 Hz, 1H), 7.63 (t, J=7.6 Hz, 2H), 6.96 (s, 1H), 2.84 (t, J=7.2 Hz, 4H), 2.59 (t, J=7.2 Hz, 4H), 2.00 (quin, J=7.2 Hz, 4H).

5-(Dimethylamino)-N-((1,2,3,5,6,7-hexahydro-s-indacen-4-yl)carbamoyl)naphthalene-1-sulfonamide

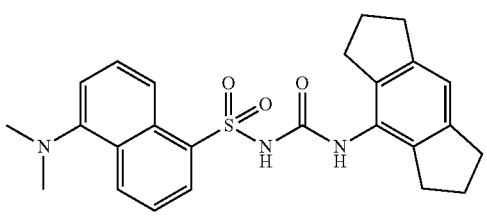 [SMILES: CN(C)c1cccc2c(S(=O)(=O)NC(=O)Nc3c4c(cc5c3CCC5)CCC4)cccc12]

A solution of 5-(dimethylamino)naphthalene-1-sulfonamide (20 mg, 0.08 mmol) in THF (5.0 mL) was treated with DIPEA (17 µL, 0.09 mmol), stirred at ambient temperature for 15 min, then a solution of 4-isocyanato-1,2,3,5,6,7-hexahydro-s-indacene (prepared using general method A2) (19 mg, 0.09 mmol) in THF (1.0 mL) was added drop wise. The reaction mixture was stirred at ambient temperature overnight then concentrated in vacuo. The crude product was purified by HPLC to give the titled compound as a pale-yellow solid (24 mg, 66%). $^1$H NMR (400 MHz, CD$_3$OD) δ=8.62 (d, J=8.4 Hz, 1H), 8.36 (dd, J=9.5, 8.1 Hz, 2H), 7.67-7.56 (m, 2H), 7.26 (d, J=7.8 Hz, 1H), 6.91 (s, 1H), 2.91 (s, 6H), 2.79 (t, J=7.4 Hz, 4H), 2.40 (t, J=7.4 Hz, 4H), 1.92 (quin, J=7.4 Hz, 4H). $^{13}$C NMR (101 MHz, CD$_3$OD) δ=152.5, 150.3, 144.4, 138.3, 131.9, 131.7, 131.1, 130.3, 130.1, 129.9, 128.9, 127.2, 123.6, 119.4, 119.1, 118.9, 115.7, 78.4, 78.0, 77.7, 49.6, 48.3, 45.6, 33.4, 33.2, 30.5, 29.3, 25.9, 25.8; HRMS (ESI) calcd. for C$_{25}$H$_{27}$N$_3$O$_3$S [M+H] 450.1846, found 450.1859.

N-((1,2,3,5,6,7-hexahydro-s-indacen-4-yl)carbamoyl)-2,3-dihydro benzo[b]thiophene-6-sulfonamide 1,1-dioxide

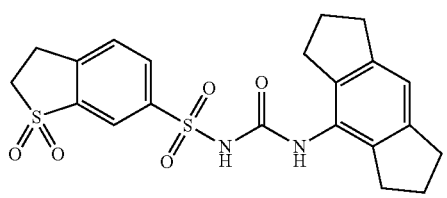 [SMILES: O=C(Nc1c2c(cc3c1CCC3)CCC2)NS(=O)(=O)c1ccc2c(c1)S(=O)(=O)CC2]

4-Isocyanato-1,2,3,5,6,7-hexahydro-s-indacene (prepared using general method A2) and 2,3-dihydrobenzo[b]thiophene-6-sulfonamide 1,1-dioxide were used in general method C2 to give the titled compound as a white solid (33 mg, 28%). $^1$H NMR (600 MHz, DMSO-d$_6$): δ=8.17 (bs, 1H), 8.15 (s, 1H), 8.13 (d, J=9 Hz, 1H), 7.73 (d, J=12 Hz, 1H), 6.89 (s, 1H), 3.68 (t, J=9 Hz, 2H), 3.43 (t, J=6 Hz, 2H), 2.75 (t, J=6 Hz, 4H), 2.55 (t, J=6 Hz, 4H), 1.93-1.88 (m, 4H). $^{13}$C NMR (150 MHz, DMSO-d$_6$): δ=151.6, 143.3, 143.0, 142.7, 139.6, 137.6, 137.5, 132.2, 128.9, 120.1, 117.9, 50.9, 32.9, 30.6, 25.6, 25.4 LCMS (m/z): 447 [M+H]$^+$ N-((1,2,3,5,6,7-hexahydro-s-indacen-4-yl)carbamoyl)-2-methoxybenzenesulfonamide

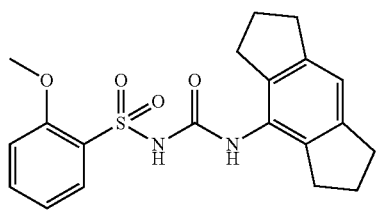 [SMILES: COc1ccccc1S(=O)(=O)NC(=O)Nc1c2c(cc3c1CCC3)CCC2]

4-Isocyanato-1,2,3,5,6,7-hexahydro-s-indacene (prepared using general method A2) and 2-methoxybenzenesulfonamide were used in general method C6 to give the titled compound as a white solid (30 mg, 48%). $^1$H NMR (400 MHz, CD$_3$OD) δ 7.96 (d, J=7.9 Hz, 1H), 7.62 (t, J=8.3 Hz, 1H), 7.14-7.05 (m, 2H), 6.97 (s, 1H), 4.00 (s, 3H), 2.83 (t, J=7.3 Hz, 4H), 2.56 (t, J=7.3 Hz, 4H), 2.09-1.90 (m, 4H). $^{13}$C NMR (101 MHz, CD$_3$OD) δ 155.9, 143.2, 136.6, 134.7, 129.5, 127.2, 126.6, 125.9, 119.5, 118.0, 111.6, 111.2, 55.3, 31.9, 29.3, 24.5. HRMS (ESI) calcd. for C$_{20}$H$_{23}$N$_2$O$_4$S [M+H] 387.1373, found 387.1378.

N-(1,2,3,5,6,7-Hexahydros-indacen-4-ylcarbamoyl)-3-(trifluoromethyl)benzenesulfonamide

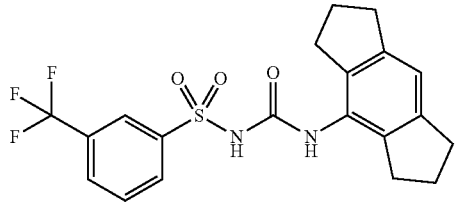 [SMILES: O=C(Nc1c2c(cc3c1CCC3)CCC2)NS(=O)(=O)c1cccc(C(F)(F)F)c1]

4-Isocyanato-1,2,3,5,6,7-hexahydro-s-indacene (prepared using general method A1) and 3-(trifluoromethyl)benzenesulfonamide were used in general method C4 to give the titled compound as a white solid (0.015 g, 12%); Off white sticky. $^1$H NMR (400 MHz, DMSO-d$_6$): δ=11.01 (bs, 1H), 8.34 (s, 1H), 8.25-8.23 (m, 2H), 8.11 (d, J=7.6 Hz, 1H), 7.90 (t, J=8.0 Hz, 1H), 6.93 (s, 1H), 2.77 (t, J=7.2 Hz, 4H), 2.50 (m, 4H), 1.90 (quin, J=7.6 Hz, 4H). LCMS, Purity: 96.69%, m/z 425.1 (M+H$^+$). HRMS (FAB$^+$) calcd for C$_{20}$H$_{19}$F$_3$N$_2$O$_3$S [M+H]$^+$: 425.1068, found: 425.1009.

N-(1,2,3,5,6,7-Hexahydros-indacen-4-ylcarbamoyl)-3-methoxybenzenesulfonamide

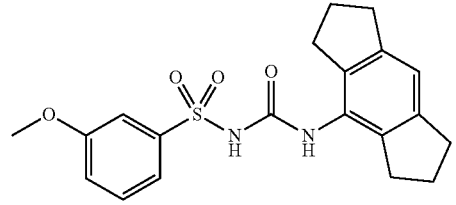 [SMILES: COc1cccc(S(=O)(=O)NC(=O)Nc2c3c(cc4c2CCC4)CCC3)c1]

4-Isocyanato-1,2,3,5,6,7-hexahydro-s-indacene (prepared using general method A1) and 3-methoxybenzenesulfonamide were used in general method C4 to give the titled compound as an off-white solid (0.025 g, 23%). $^1$H NMR (400 MHz, DMSO-d$_6$): δ=10.77 (bs, 1H), 8.15 (s, 1H), 7.56-7.45 (m, 3H), 7.27 (d, J=8.0 Hz, 1H), 6.93 (s, 1H), 3.82 (s, 3H), 2.77 (t, J=7.2 Hz, 4H), 2.53 (t, J=7.6 Hz, 4H), 1.92 (quin, J=7.2 Hz, 4H). LCMS, Purity: 95.02%, tr=3.77 min, m/z 387.28 (M+H$^+$). HRMS (FAB$^+$) calcd for C$_{20}$H$_{22}$N$_2$O$_4$S [M+H]$^+$: 387.1300, found: 387.1301.

N-(1,2,3,5,6,7-Hexahydros-indacen-4-ylcarbamoyl)-3-(trifluoromethoxy)benzenesulfonamide

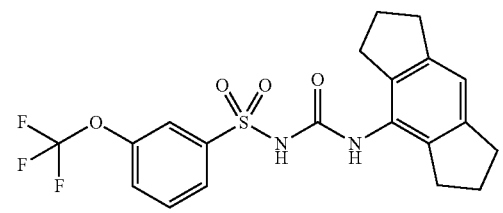 [SMILES: O=C(Nc1c2c(cc3c1CCC3)CCC2)NS(=O)(=O)c1cccc(OC(F)(F)F)c1]

4-Isocyanato-1,2,3,5,6,7-hexahydro-s-indacene (prepared using general method A1) and 3-(trifluoromethoxy)benzenesulfonamide were used in general method C4 to give the titled compound as an off-white solid (0.045 g, 43%). $^1$H NMR (400 MHz, DMSO-d$_6$): δ=8.04 (d, J=8.0 Hz, 1H), 7.95 (s, 1H), 7.72 (t, J=8.4 HZ, 1H), 7.62 (d, J=8.4 Hz, 1H), 6.95 (s, 1H), 2.82 (t, J=7.6 Hz, 4H), 2.59 (t, J=7.6 Hz, 4H), 1.99 (quin, J=7.6 Hz, 4H). $^{13}$C NMR (100 MHz, DMSO-d6): δ=149.2, 147.9, 143.1, 142.2, 137.3, 131.5, 128.5, 126.4, 125.9, 121.2, 119.7, 118.6, 118.1, 32.5, 29.4, 25.0. $^{19}$F NMR (233.33 MHz, DMSO-d$_6$): −57.10 (s, 3F). LCMS, Purity: 95.56%, m/z 441.20 (M+H$^+$). HRMS (FAB$^+$) calcd for C$_{20}$H$_{19}$F3N$_2$O$_4$S [M+H]: 441.1018, found: 441.1015.

3-(difluoromethoxy)-N-((1,2,3,5,6,7-hexahydro-s-indacen-4-yl)carbamoyl)benzenesulfonamide

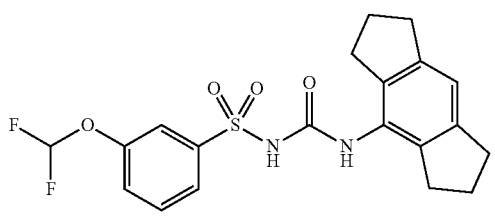 [SMILES: O=C(Nc1c2c(cc3c1CCC3)CCC2)NS(=O)(=O)c1cccc(OC(F)F)c1]

4-Isocyanato-1,2,3,5,6,7-hexahydro-s-indacene (prepared using general method A2) and 3-(difluoromethoxy)benzenesulfonamide were used in general method C5 to give the titled compound as an off-white solid (0.056 g, 50%). $^1$H NMR (600 MHz, Acetonitrile-d$_3$) δ=7.85 (d, J=8.0 Hz, 1H), 7.75 (t, J=2.1 Hz, 1H), 7.60 (t, J=8.0 Hz, 1H), 7.53 (s, 1H), 7.43 (dd, J=8.0, 2.1 Hz, 1H), 6.95 (s, 1H), 2.81 (t, J=7.5 Hz, 4H), 2.55 (t, J=7.5 Hz, 4H), 1.95 (quin, J=7.5 Hz, 4H).

N$^1$-(1,2,3,5,6,7-Hexahydros-indacen-4-ylcarbamoyl)benzene-1,3-disulfonamide

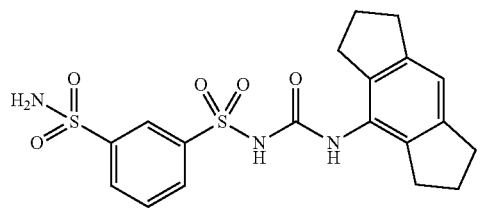 [SMILES: NS(=O)(=O)c1cccc(S(=O)(=O)NC(=O)Nc2c3c(cc4c2CCC4)CCC3)c1]

4-Isocyanato-1,2,3,5,6,7-hexahydro-s-indacene (prepared using general method A1) and benzene-1,3-disulfonamide were used in general method C4 to give the titled compound as a white solid (0.080 g, 12%). $^1$H NMR (400 MHz, DMSO-d$_6$): δ=11.02 (bs, 1H), 8.36 (s, 1H), 8.24 (s, 1H), 8.15 (d, J=7.8 Hz, 1H), 8.11 (d, J=8.0 Hz, 1H), 7.84 (t, J=8.0 Hz, 1H), 7.63 (s, 2H), 6.93 (s, 1H), 2.77 (t, J=7.2 Hz, 4H), 2.54 (t, J=7.6 Hz, 4H), 1.92 (quin, J=7.2 Hz, 4H). $^{13}$C NMR (100 MHz, DMSO-d$_6$): δ=149.0, 144.9, 143.1, 140.9, 137.3, 130.4, 130.2, 128.5, 124.4, 118.1, 32.4, 30.0, 25.0. LCMS, Purity: 98.63%, m/z 436.03 (M+H$^+$). HRMS (FAB$^+$) calcd for C$_{19}$H$_{21}$N$_3$O$_5$S$_2$[M+H]$^+$: 436.0923, found: 436.0919.

N$^1$-((1,2,3,5,6,7-hexahydro-s-indacen-4-yl)carbamoyl)-N$^3$,N$^3$-dimethylbenzene-1,3-disulfonamide

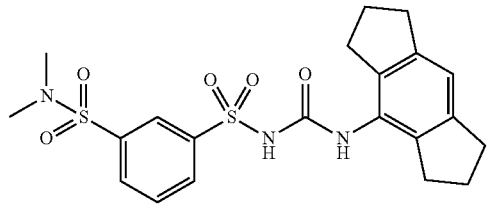 [SMILES: CN(C)S(=O)(=O)c1cccc(S(=O)(=O)NC(=O)Nc2c3c(cc4c2CCC4)CCC3)c1]

4-Isocyanato-1,2,3,5,6,7-hexahydro-s-indacene (prepared using general method A1) and N$^1$,N$^1$-dimethylbenzene-1,3-disulfonamide were used in general method C1 to give the titled compound as a white solid (0.019 g, 5%). $^1$H NMR (400 MHz, CD30D) δ 8.41 (t, J=1.4 Hz, 1H), 8.32 (dt, J=7.9, 1.4 Hz, 1H), 8.08 (dt, J=7.9, 1.4 Hz, 1H), 7.87 (t, J=7.9 Hz, 1H), 6.95 (s, 1H), 2.84 (t, J=7.4 Hz, 4H), 2.73 (s, 6H), 2.61 (t, J=7.4 Hz, 4H), 2.00 (p, J=7.4 Hz, 4H).

3-(N-((1,2,3,5,6,7-hexahydro-s-indacen-4-yl)carbamoyl)sulfamoyl)benzoic acid

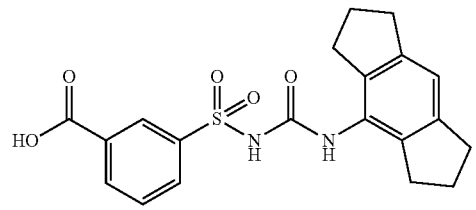 [SMILES: O=C(Nc1c2c(cc3c1CCC3)CCC2)NS(=O)(=O)c1cccc(C(=O)O)c1]

Methyl 3-(N-(1,2,3,5,6,7-hexahydro-s-indacen-4-ylcarbamoyl)sulfamoyl)benzoate (0.25 g, 0.603 mmol) was dissolved in a mixture of tetrahydrofuran:methanol:water (9 mL, 1:1:1) and the mixture was cooled to 0° C. Lithium hydroxide monohydrate (0.75 g, 1.81 mmol, 3 eq) was added and the mixture stirred at ambient temperature for 3 h. Upon completion, the reaction mixture was poured into chilled water and extracted with ethyl acetate. The combined organic extracts were washed with brine, dried (Na$_2$SO$_4$) and concentrated in vacuo. The product was purified by reverse phase preparative HPLC to afford the titled compound as a white solid (0.017 g, 3%). $^1$H NMR (400 MHz, DMSO-d$_6$): δ=13.26 (bs, 1H), 8.43 (s, 1H), 8.13-8.08 (m, 2H), 7.99 (bs, 1H), 7.67 (t, J=8.0 Hz, 1H), 6.87 (s, 1H), 6.52 (s, 1H), 2.75 (t, J=7.2 Hz, 4H), 2.55 (t, J=7.6 Hz, 4H), 1.89 (quin, J=7.6 Hz, 4H). LCMS, Purity: 96%, m/z 400.98 (M+H$^+$). HRMS (FAB$^+$) calcd for C$_{20}$H$_{20}$N$_2$O$_5$S [M+H]$^+$: 401.1093, found: 401.4514.

3-(N-(1,2,3,5,6,7-Hexahydro-s-indacen-4-ylcarbamoyl)sulfamoyl)benzamide

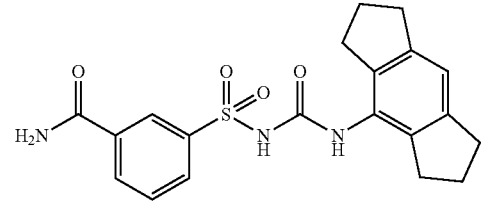 [SMILES: NC(=O)c1cccc(S(=O)(=O)NC(=O)Nc2c3c(cc4c2CCC4)CCC3)c1]

3-(N-((1,2,3,5,6,7-hexahydro-s-indacen-4-yl)carbamoyl) sulfamoyl)benzoic acid (0.06 g, 0.074 mmol) was dissolved in anhydrous N,N-dimethylformamide (4 mL) and the solution cooled to 0° C. Diisopropylethylamine (3.0 eq) and HATU (2.0 eq) were added and the mixture stirred at 0° C. for 15 min. Ammonium chloride (3.0 eq) was added and the mixture stirred at ambient temperature for 5 h. Upon completion the reaction mixture was poured into brine (20 mL) and extracted with ethyl acetate (2×10 mL). The combined organic extracts were washed with brine (10 mL), dried ($Na_2SO_4$) and concentrated in vacuo. The crude residue was purified by reverse phase preparative HPLC to afford the titled compound as a white solid (0.011 g, 37%). $^1$H NMR (400 MHz, DMSO-$d_6$): δ=8.23 (d, J=9.2 Hz, 2H), 8.02 (s, 1H), 7.89 (d, J=7.6 Hz, 1H), 7.84 (d, J=7.6 Hz, 1H), 7.42 (t, J=8.0 Hz, 1H), 7.38 (s, 1H), 7.33 (s, 1H). 6.74 (s, 1H), 2.73 (t, J=6.8 Hz, 4H), 2.62 (t, J=6.8 Hz, 4H), 1.87 (quin, J=7.6 Hz, 4H). LCMS, Purity: 93%, m/z 400.05 (M+H$^+$). HRMS (FAB$^+$) calcd for $C_{20}H_{21}N_3O_4S$ [M+H]$^+$: 400.1253, found: 400.1378.

N-((1,2,3,5,6,7-hexahydro-s-indacen-4-yl)carbamoyl)-3-(2-hydroxypropan-2-yl)benzenesulfonamide

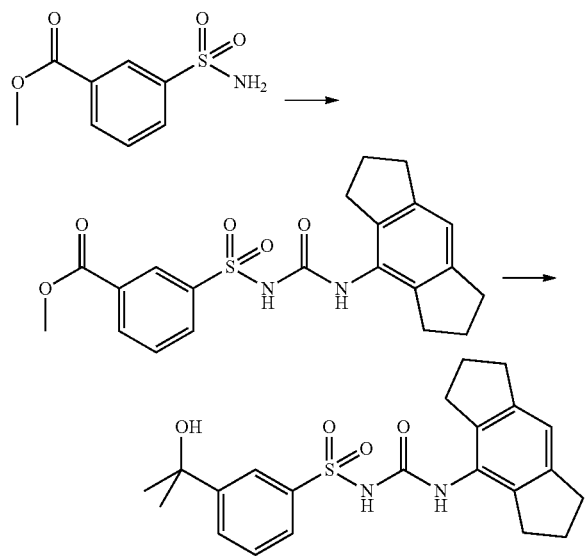

4-Isocyanato-1,2,3,5,6,7-hexahydro-s-indacene (prepared using general method A1) was added directly to methyl 3-sulfamoylbenzoate (0.447 g, 2.07 mmol, 1.20 equiv) at ambient temperature and the mixture was stirred overnight. The reaction mixture was poured into chilled water and extracted with ethyl acetate. The combined organic extracts were washed with brine, dried ($Na_2SO_4$) and concentrated in vacuo. The residue obtained was purified by column chromatography on silica gel using 0-10% gradient of methanol in dichloromethane to give methyl 3-(N-((1,2,3,5,6,7-hexahydro-s-indacen-4-yl)carbamoyl)sulfamoyl)benzoate as a light-brown solid (0.36 g, 50%).

Methyl 3-(N-((1,2,3,5,6,7-hexahydro-s-indacen-4-yl)carbamoyl)sulfamoyl)benzoate (0.06 g, 0.144 mmol) was dissolved in anhydrous THF and the solution cooled to 0° C. Methyl magnesium bromide (3 M solution in diethyl ether, 0.14 mL, 0.42 mmol, 3.0 eq) was added and the mixture stirred at ambient temperature for 4 h. Upon completion, saturated aqueous ammonium chloride was added to the reaction mixture and extracted with ethyl acetate. The combined organic extracts were washed with brine, dried ($Na_2SO_4$) and concentrated in vacuo. Purification of the crude residue by reverse phase preparative HPLC gave the titled compound as an off-white solid (0.015 g, 25%). $^1$H NMR (400 MHz, DMSO-$d_6$): δ=8.16 (s, 1H), 7.91 (s, 1H), 7.62 (d, J=7.2 Hz, 1H), 7.59-7.48 (m, 2H), 7.32 (t, J=7.6 Hz, 1H), 6.78 (s, 1H), 5.10 (s, 1H), 2.74 (t, J=7.2 Hz, 4H), 2.60 (t, J=6.8 Hz, 4H), 1.88 (quin, J=7.6 Hz, 4H), 1.42 (s, 6H). LCMS, Purity: 91%, m/z 415.05 (M+H$^+$).

3-Azido-N-((1,2,3,5,6,7-hexahydro-s-indacen-4-yl)carbamoyl)benzenesulfonamide

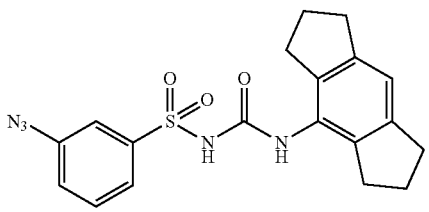 [SMILES: [N-]=[N+]=Nc1cccc(S(=O)(=O)NC(=O)Nc2c3c(cc4c2CCC4)CCC3)c1]

4-Isocyanato-1,2,3,5,6,7-hexahydro-s-indacene (prepared using general method A2) and 3-azidobenzenesulfonamide were used in general method C6 to give the titled compound as an off white solid (70 mg, 50%). $^1$H NMR (600 MHz, DMSO-$d_6$) δ=8.22 (s, 1H), 7.72 (m, J=5.2 Hz, H), 7.65 (t, J=8.0 Hz, 1H), 7.59 (s, 1H), 7.46-7.42 (m, 1H), 6.93 (s, 1H), 2.77 (t, J=7.4 Hz, 4H), 2.53 (t, J=7.4 Hz, 4H), 1.92 (m, 4H). $^{13}$C NMR (101 MHz, $CD_3OD$) δ 151.2, 144.9, 144.6, 142.9, 142.5, 138.9, 131.5, 131.4, 128.6, 124.9, 124.6, 124.6, 119.8, 119.2, 118.9, 111.9, 33.7, 33.6, 31.1, 29.7, 26.3. HRMS (ESI) calcd. for $C_{19}H_{20}N_5O_3S$ [M+H] 398.1281, found 398.1272.

N-((1,2,3,5,6,7-Hexahydro-s-indacen-4-yl)carbamoyl)-3-(4-phenyl-1H-1,2,3-triazol-1-yl) benzenesulfonamide

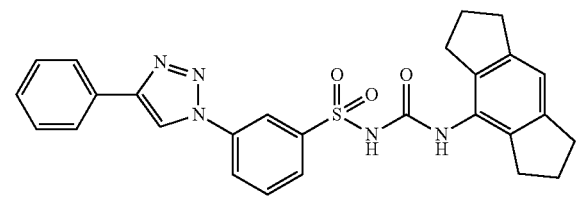 [SMILES: O=C(Nc1c2c(cc3c1CCC3)CCC2)NS(=O)(=O)c1cccc(-n2cc(-c3ccccc3)nn2)c1]

4-Isocyanato-1,2,3,5,6,7-hexahydro-s-indacene (prepared using general method A2) and 3-(4-phenyl-1H-1,2,3-triazol-1-yl)benzenesulfonamide were used in general method C6 to give the titled compound as a pale yellow solid (10 mg, 49%). $^1$H NMR (400 MHz, $CD_3OD$) δ=8.89 (s, 1H), 8.55 (s, 1H), 8.21 (d, J=8.2 Hz, 1H), 8.13 (d, J=7.8 Hz, 1H), 7.92 (d, J=7.6 Hz, 2H), 7.79 (t, J=8.0 Hz, 1H), 7.68 (s, 1H), 7.48 (t, J=7.6 Hz, 2H), 7.39 (t, J=7.4 Hz, 1H), 6.92 (s, 1H), 2.82 (t, J=7.4 Hz, 4H), 2.70-2.63 (m, 4H), 1.98 (m, 4H). $^{13}$C NMR (151 MHz, $CD_3OD$) δ=148.8, 143.9, 143.6, 137.7, 137.2, 137.0, 130.6, 130.3, 129.7, 129.6, 128.8, 128.5, 127.6, 127.4, 126.7, 125.6, 124.5, 124.0, 119.3, 118.7, 110.8, 32.7, 32.6, 30.2, 28.7, 25.3. HRMS (ESI) calcd. for $C_{27}H_{26}N_5O_3S$ [M+H] 500.1751, found 500.1735.

N-(3-(N-((1,2,3,5,6,7-hexahydro-s-indacen-4-yl)carbamoyl)sulfamoyl)phenyl)pent-4-ynamide

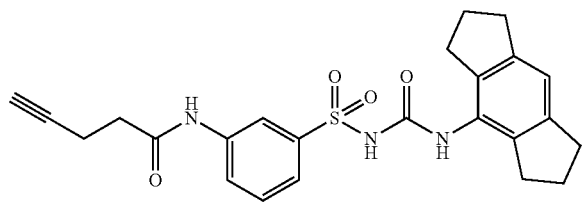 [SMILES: C#CCCC(=O)Nc1cccc(S(=O)(=O)NC(=O)Nc2c3c(cc4c2CCC4)CCC3)c1]

4-Isocyanato-1,2,3,5,6,7-hexahydro-s-indacene (prepared using general method A2) and N-(3-sulfamoylphenyl)pent-4-ynamide were used in general method C6 to give the titled compound as a white solid (116 mg, 61%). $^1$H NMR (400 MHz, CD$_3$OD) δ=8.18 (s, 1H), 7.81 (d, J=8.3 Hz, 1H), 7.68 (d, J=8.3 Hz, 1H), 7.43 (dd, J=8.3, 7.8 Hz, 1H), 6.87 (s, 1H), 2.79 (t, J=7.2 Hz, 4H), 2.67-2.60 (m, 4H), 2.60-2.48 (m, 4H), 2.28-2.22 (m, 1H), 2.04-1.89 (m, 4H). $^{13}$C NMR (101 MHz, CD$_3$OD)=170.9, 143.3, 143.0, 138.8, 137.7, 128.7, 128.3, 126.4, 122.8, 122.0, 117.9, 117.7, 82.0, 68.9, 35.4, 32.4, 29.9, 25.1, 13.9. HRMS (ESI) calcd. for C$_{24}$H$_{26}$N$_3$O$_4$S [M+H] 452.1639, found 452.1658.

3-(1-(3-aminopropyl)-1H-1,2,3-triazol-4-yl)-N-(3-(N-((1,2,3,5,6,7-hexahydro-s-indacen-4-yl)carbamoyl)sulfamoyl)phenyl)propanamide

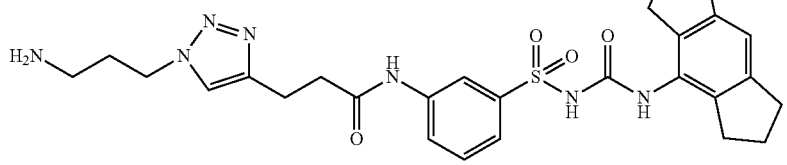

N-(3-(N-((1,2,3,5,6,7-hexahydro-s-indacen-4-yl)carbamoyl)sulfamoyl)phenyl)pent-4-ynamide and 3-azidopropan-1-amine were used in general method F to give the titled compound as a white solid (6 mg, 43%). $^1$H NMR (600 MHz, CD$_3$OD) δ=7.85 (s, 1H), 7.55 (t, J=3.8 Hz, 2H), 7.50 (d, J=8.0 Hz, 2H), 7.29 (t, J=7.9 Hz, 1H), 6.78 (s, 1H), 4.26 (t, J=6.4 Hz, 2H), 3.00 (t, J=6.6 Hz, 2H), 2.71 (t, J=7.3 Hz, 4H), 2.64-2.50 (m, 8H), 1.94-2.02 (m, 2H), 1.92-1.83 (m, 4H). $^{13}$C NMR (151 MHz, CD$_3$OD) δ=173.0, 147.4, 146.8, 144.7, 144.6, 139.5, 139.2, 131.6, 130.0, 129.8, 129.2, 124.2, 123.9, 123.2, 119.5, 118.6, 48.3, 37.7, 34.0, 31.6, 26.7, 26.6, 22.9. HRMS (ESI) calcd. for C$_{27}$H$_{34}$N$_7$O$_4$S [M+H] 552.2387, found 552.2368.

N-(3-(N-((1,2,3,5,6,7-hexahydro-s-indacen-4-yl)carbamoyl)sulfamoyl)phenyl)-3-(1-(3-((7-nitrobenzo[c][1,2,5]oxadiazol-4-yl)amino)propyl)-1H-1,2,3-triazol-4-yl)propanamide

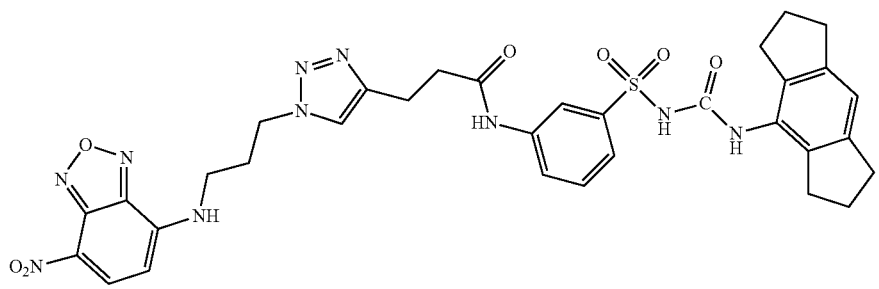 [SMILES: O=C(CCc1cn(CCCNc2ccc([N+](=O)[O-])c3nonc23)nn1)Nc1cccc(S(=O)(=O)NC(=O)Nc2c3c(cc4c2CCC4)CCC3)c1]

N-(2-Azidopropyl)-7-nitrobenzo[c][1,2,5]oxadiazol-4-amine was synthesized by the methods contained in Chun Li, Etienne Henry, Naresh Kumar Mani, Jie Tang, Jean-Claude Brochon, Eric Deprez, and Juan Xie *Eur. J. Org. Chem.* 2010, 2395-2405. To a solution of 4-chloro-7-nitrobenzo[c][1,2,5]oxadiazole (300 mg, 1.5 mmol) in THF (10 mL) was added 3-azidopropyl amine (160 mg, 1.65 mmol) and Cs$_2$CO$_3$ (480 mg, 1.5 mmol). The reaction mixture was stirred at 50° C. for 4 h. The reaction mixture was partitioned between EtOAc (50 mL) concentrated in vacuo. The residue was purified by column chromatography on silica gel using 30% EtOAc-petroleum ether eluent to afford N-(2-Azidopropyl)-7-nitrobenzo[c][1,2,5]oxadiazol-4-amine (240 mg, 76%). $^1$H NMR (400 MHz, CDCl$_3$): δ=8.50 (d, J=8.8 Hz, 1H), 6.57 (s, 1H, NH), 6.23 (d, J=8.8 Hz, 1H), 3.66 (q, J=6.8 Hz, 2H), 3.59 (J=6.0 Hz, 2H), 2.00-2.16 (m, 2H). $^{13}$C NMR (101 MHz, CDCl$_3$) δ 144.2, 144.0, 143.8, 136.7, 123.7, 98.8, 49.1, 41.6, 27.6. HRMS (ESI): calcd. for C$_9$H$_{10}$N$_7$O$_3$ 264.0840; found 264.0711.

N-(3-(N-((1,2,3,5,6,7-Hexahydro-s-indacen-4-yl)carbamoyl)sulfamoyl)phenyl)pent-4-ynamide (10 mg, 0.022 mmol) and N-(2-azidopropyl)-7-nitrobenzo[c][1,2,5]oxadiazol-4-amine (7.0 mg, 0.026 mmol), 10 mol % THPTA, 5 mol % CuSO$_4$, 10 mol % sodium ascorbate in DMSO (500 uL) were stirred at room temperature for 12 h. The reaction mixture was subjected to purification using reverse phase (Reveleris flash column chromatography, 4 g, 18 mL/min., mobile phase; 10 mmol aqu. NH$_4$CO$_3$, MeCN) and freeze dried to give the product as a white solid (7.0 mg, 44%). $^1$H NMR (600 MHz, CD$_3$OD) δ=8.46 (d, J=8.7 Hz, 1H), 8.18 (s, 1H), 7.79 (d, J=8.4 Hz, 1H), 7.67 (d, J=7.9 Hz, 1H), 7.61 (s, 1H), 6.94 (s, 1H), 6.15 (d, J=9.0 Hz, 1H), 4.46 (t, J=6.7 Hz, 2H), 3.09 (t, J=7.0 Hz, 2H), 2.82 (t, J=7.4 Hz, 4H), 2.77 (t, J=7.0 Hz, 2H), 2.70-2.56 (m, 6H), 2.37-2.26 (m, 2H), 1.99 (q, J=7.3 Hz, 4H). $^{13}$C NMR (151 MHz, CD$_3$OD) δ=172.9, 147.9, 145.4, 140.5, 139.0, 138.4, 130.6, 129.1, 128.0, 125.6, 124.2, 123.6, 120.3, 119.6, 112.4, 70.6, 48.9, 37.2, 34.3, 34.2, 31.7, 30.2, 26.8, 22.3; HRMS (ESI) calcd. for C$_{33}$H$_{34}$N$_{10}$O$_7$S [M–H] 713.2260, found 713.2290.

N-(3-(4-(3-((3-(N-((1,2,3,5,6,7-hexahydro-s-in-dacen-4-yl)carbamoyl)sulfamoyl)phenyl) amino)-3-oxopropyl)-1H-1,2,3-triazol-1-yl)propyl)-5-((3aS,4S,6aR)-2-oxohexahydro-1H-thieno[3,4-d]imidazol-4-yl)pentanamide

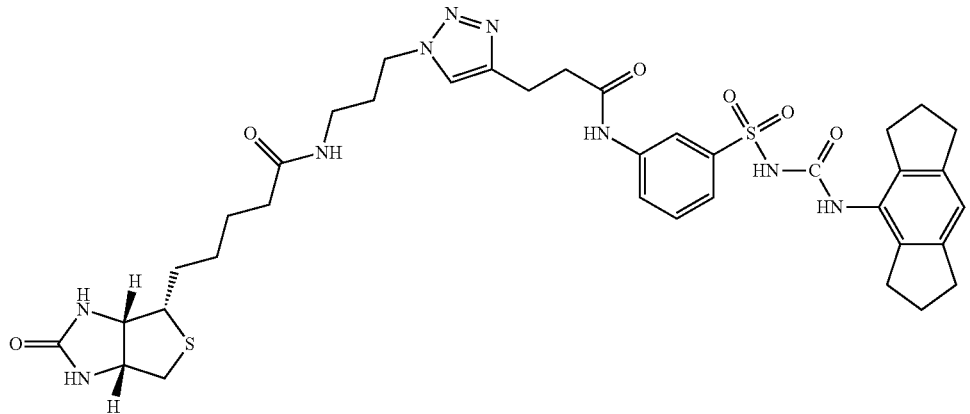 [SMILES: O=C(CCCC[C@@H]1SC[C@@H]2NC(=O)N[C@@H]21)NCCCn1cc(CCC(=O)Nc2cccc(S(=O)(=O)NC(=O)Nc3c4c(cc5c3CCC5)CCC4)c2)nn1]

To a solution of biotin (0.4 g, 1.63 mmol) and 3-azidopropylamine (0.2 g, 1.96 mmol) in dry DMF (10.0 ml) was added HBTU (0.93 g, 2.45 mmol) followed by DIPEA (428 uL, 2.45 mmol). The reaction mixture was stirred at RT for 12 h. The reaction was monitored by LCMS and after the completion of reaction, it was diluted with EtOAc (50 mL) washed with $H_2O$ (25 mL), brine (25 mL). The organic layer was separated; dried ($MgSO_4$) and evaporated to give the crude product. The crude product was purified by column chromatography on silica gel using 50% EtOAc-Hexane eluent to isolate N-(3-azidopropyl)-5-((3aS,4S,6aR)-2-oxo-hexahydro-1H-thieno[3,4-d]imidazol-4-yl)pentanamide as a white solid (0.13 g, 24%). H NMR (400 MHz, $CD_3OD$) δ=4.52 (dd, J=7.9, 5.0 Hz, 1H), 4.32 (dd, J=7.9, 4.5 Hz, 1H), 3.36 (t, J=6.7 Hz, 2H), 3.28 (d, J=6.8 Hz, 2H), 3.21-3.14 (m, 1H), 2.93 (dd, J=12.8, 5.0 Hz, 1H), 2.75 (d, J=12.8 Hz, 1H), 2.20 (t, J=7.3 Hz, 2H), 1.78 (q, J=6.8 Hz, 2H), 1.74-1.57 (m, 4H), 1.45 (q, J=7.5 Hz, 2H). $^{13}C$ NMR (101 MHz, $CD_3OD$) δ=173.5, 163.4, 61.0, 59.3, 54.7, 48.2, 39.4, 35.8, 34.8, 27.7, 27.5, 27.2, 24.6.

N-(3-(N-((1,2,3,5,6,7-hexahydro-s-indacen-4-yl)carbamoyl)sulfamoyl)phenyl)pent-4-ynamide (1.0 mmol) and N-(3-azidopropyl)-5-((3aS,4S,6aR)-2-oxohexahydro-1H-thieno[3,4-d]imidazol-4-yl)pentanamide (2.0 mmol), 10 mol % THPTA, 5 mol % $CuSO_4$, 10 mol % sodium ascorbate in DMSO were stirred at room temperature for 12 h. The reaction mixture was purified using reverse phase column chromatography to give the titled compound as a white solid (8.0 mg, 31%); $^1H$ NMR (600 MHz, $CD_3OD$) δ=8.26 (s, 1H), 7.83-7.68 (m, 3H), 7.50-7.43 (m, 1H), 6.92 (s, 1H), 4.48 (dd, J=8.0, 4.8 Hz, 1H), 4.41-4.22 (m, 3H), 3.18 (dd, J=6.9, 3.5 Hz, 1H), 3.14 (td, J=6.7, 1.7 Hz, 2H), 3.12-3.06 (m, 2H), 2.90 (dd, J=12.8, 4.9 Hz, 1H), 2.81 (t, J=7.7 Hz, 4H), 2.77 (d, J=7.1 Hz, 1H), 2.71 (s, 1H), 2.62 (t, J=7.3 Hz, 4H), 2.19 (td, J=7.4, 1.7 Hz, 2H), 2.05-2.01 (m, 2H), 2.00-1.95 (m, 4H), 1.76-1.57 (m, 4H), 1.43 (q, J=7.6, 7.1 Hz, 2H). $^{13}C$ NMR (151 MHz, $CD_3OD$) δ=174.8, 174.8, 171.6, 171.5, 164.5, 146.2, 143.6, 139.1, 137.7, 129.1, 129.1, 128.7, 128.1, 126.5, 123.7, 122.9, 122.4, 122.2, 120.9, 118.4, 118.4, 118.3, 118.2, 118.2, 117.2, 110.5, 69.0, 61.9, 60.2, 55.6, 39.8, 36.1, 36.0, 35.8, 35.4, 35.4, 32.6, 32.6, 30.0, 29.7, 29.7, 28.6, 28.3, 28.0, 25.3, 25.2, 25.2, 20.9. HRMS (ESI) calcd. for $C_{37}H_{48}N_9O_6S_2$[M+H] 778.3163, found 778.3145.

N-((1-(3-(N-((1,2,3,5,6,7-hexahydro-s-indacen-4-yl) carbamoyl)sulfamoyl)phenyl)-1H-1,2,3-triazol-4-yl) methyl)-5-((3aS,4S,6aR)-2-oxohexahydro-1H-thieno [3,4-d]imidazol-4-yl)pentanamide

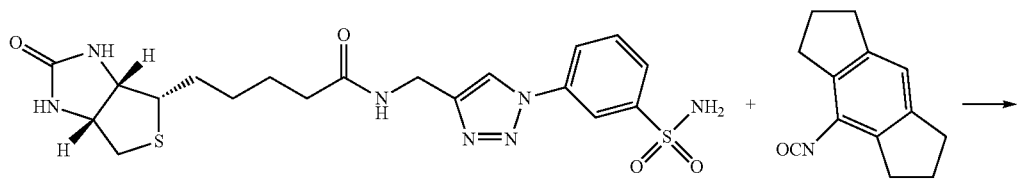

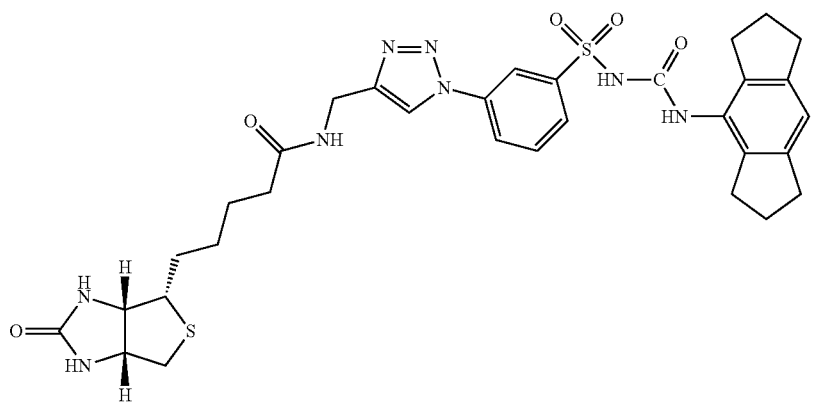

5-((3aS,4S,6aR)-2-oxohexahydro-1H-thieno[3,4-d]imidazol-4-yl)-N-((1-(3-sulfamoylphenyl)-1H-1,2,3-triazol-4-yl)methyl)pentanamide was synthesized using 5-((3aS,4S,6aR)-2-oxohexahydro-1H-thieno[3,4-d]imidazol-4-yl)-N-(prop-2-yn-1-yl)pentanamide (1.0 mmol) and 3-azidobenzenesulfonamide (2.0 mmol), 10 mol % THPTA, 5 mol % CuSO$_4$, 10 mol % NaAsc in DMSO were stirred at room temperature for 12 h. The formation of product was observed in LCMS. After completion of the reaction, the reaction mixture was subjected to HPLC purification (Reveleris flash column chromatography, 4 g, 18 mL/min., mobile phase; 10 mmol aq. NH$_4$CO$_3$, MeCN) to isolate 5-((3aS,4S,6aR)-2-oxohexahydro-1H-thieno[3,4-d]imidazol-4-yl)-N-((1-(3-sulfamoylphenyl)-1H-1,2,3-triazol-4-yl)methyl)pentanamid as a white solid (24 mg, 47%) which was used directly.

To a solution of 5-((3aS,4S,6aR)-2-oxohexahydro-1H-thieno[3,4-d]imidazol-4-yl)-N-((1-(3-sulfamoylphenyl)-1H-1,2,3-triazol-4-yl)methyl)pentanamide (15 mg, 0.031 mmol) in THF (5.0 mL) under a nitrogen atmosphere was added DIPEA (605 µL, 0.037 mmol). This mixture was stirred at room temperature for 15 min. A solution of 4-isocyanato-1,2,3,5,6,7-hexahydro-s-indacene (prepared using general method A2) (705 mg, 0.037 mmol) in THF was added drop-wise. The reaction mixture was stirred at room temperature overnight then the solvent was removed in vacuo to give crude compound which was purified by reversed phase column chromatography using 10 mM aq. (NH$_4$)$_2$CO$_3$ and MeCN mobile phase to isolate the titled compound as a white solid (5.2 mg, 24%). $^1$H NMR (600 MHz, CD$_3$OD) δ=8.53 (d, J=2.4 Hz, 1H), 8.50 (d, J=7.5 Hz, 1H), 8.22-8.11 (m, 2H), 7.86-7.78 (m, 1H), 6.99 (s, 1H), 4.62 (s, 2H), 4.57-4.49 (m, 1H), 4.38-4.31 (m, 1H), 3.27-3.20 (m, 1H), 3.00-2.84 (m, 4H), 2.78-2.70 (m, 4H), 2.36 (t, J=7.2 Hz, 2H), 2.06 (q, J=7.4 Hz, 4H), 1.83-1.73 (m, 3H), 1.71-1.63 (m, 1H), 1.54-1.43 (m, 3H). $^{13}$C NMR (151 MHz, CD$_3$OD) δ=174.6, 164.5, 146.1, 145.4, 143.6, 137.7, 137.2, 130.5, 125.9, 123.4, 121.1, 117.8, 110.6, 61.8, 60.2, 55.5, 47.7, 47.6, 39.8, 3.2, 34.3, 32.6, 30.14, 28.2, 27.9, 25.3, 25.2. HRMS (ESI) calcd. for C$_{32}$H$_{39}$N$_8$O$_5$S$_2$[M+H] 679.2479, found 679.2456.

N-(quinolin-6-ylcarbamoyl)-3-(3-(trifluoromethyl)-3H-diazirin-3-yl)benzenesulfonamide

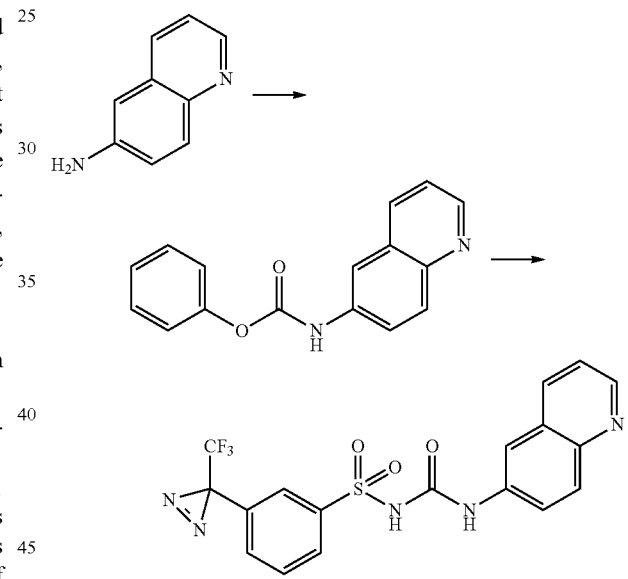

Phenyl chloroformate (1 eq) was added to a solution of quinolin-6-amine (0.1 g, 0.69 mmol) in THF (50 mL) and triethylamine (1.5 eq.) to 0° C. The solution was diluted using water, extracted using ethyl acetate (×2), washed with water, brine then dried (Na$_2$SO$_4$) and concentrated in vacuo. The crude product was triturated with pentane to give phenyl quinolin-6-ylcarbamate as an off-white solid which was used directly in the next reaction step.

3-(3-(trifluoromethyl)-3H-diazirin-3-yl)benzenesulfonamide (0.185 g, 0.69 mmol) in THF (30 mL) at 0° C. was treated portion-wise with sodium hydride (3 eq.) and the suspension stirred for 30 minutes (until effervescence ceased). The crude phenyl quinolin-6-ylcarbamate was dissolved in THF (20 mL) then added slowly to the reaction and stirring continued at ambient temperature until completion, typically 2 h. The reaction was quenched with sat.aq. NH$_4$Cl, extracted with ethyl acetate (×2), washed with water (100 mL), brine (100 mL), dried (Na$_2$SO$_4$) and concentrated in vacuo. The crude product was triturated using diethyl ether then pentane to give the titled compound, N-(quinolin- 6-ylcarbamoyl)-3-(3-(trifluoromethyl)-3H-diazirin-3-yl)benzenesulfonamide as a white solid (10 mg, 3%). $^1$H NMR (400 MHz, DMSO-$d_6$) δ=8.88 (s, 1H), 8.59 (d, J=3.5 Hz, 1H), 8.11 (s, 1H), 8.04 (d, J=8.3 Hz, 1H), 7.96 (d, J=7.9 Hz, 1H), 7.74 (d, J=9.1 Hz, 1H), 7.70-7.60 (m, 2H), 7.56 (t, J=7.8 Hz, 1H), 7.34 (dd, J=8.3, 4.2 Hz, 1H), 7.30 (d, J=8.0 Hz, 1H). 19F NMR (376 MHz, DMSO-$d_6$) δ −64.49.

N-(quinolin-5-ylcarbamoyl)-3-(3-(trifluoromethyl)-3H-diazirin-3-yl)benzenesulfonamide

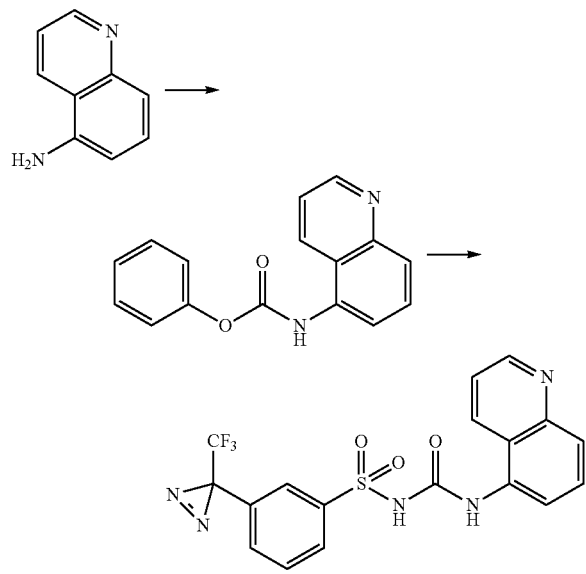

N-(quinolin-5-ylcarbamoyl)-3-(3-(trifluoromethyl)-3H-diazirin-3-yl)benzenesulfonamide was synthesised using modification of the procedures used to make N-(quinolin-6-ylcarbamoyl)-3-(3-(trifluoromethyl)-3H-diazirin-3-yl)benzenesulfonamide but using quinolin-5-amine in place of quinolin-6-amine.

The titled compound was obtained as an off-white solid (10 mg, 3%). $^1$H NMR (400 MHz, DMSO-$d_6$) δ=8.79 (d, J=4.1 Hz, 1H), 8.61 (s, 1H), 8.57 (d, J=8.7 Hz, 1H), 7.95 (d, J=7.8 Hz, 1H), 7.88 (d, J=7.2 Hz, 1H), 7.70 (s, 1H), 7.59-7.50 (m, 2H), 7.40 (dd, J=8.7, 4.1 Hz, 1H), 7.29 (d, J=7.9 Hz, 1H). $^{19}$F NMR (376 MHz, DMSO-$d_6$) δ−64.51.

N-((6-methoxyquinolin-8-yl)carbamoyl)-3-(3-(trifluoromethyl)-3H-diazirin-3-yl)benzenesulfonamide

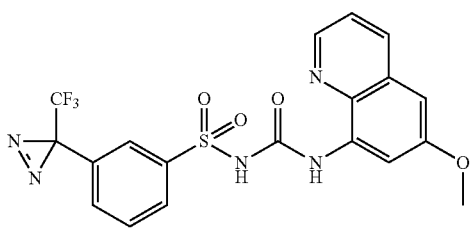 [SMILES: COc1cc(NC(=O)NS(=O)(=O)c2cccc(C3(C(F)(F)F)N=N3)c2)c2ncccc2c1]

N-((6-methoxyquinolin-8-yl)carbamoyl)-3-(3-(trifluoromethyl)-3H-diazirin-3-yl)benzenesulfonamide was synthesised using modification of the procedures used to make N-(quinolin-6-ylcarbamoyl)-3-(3-(trifluoromethyl)-3H-diazirin-3-yl)benzenesulfonamide but using 6-methoxyquinolin-8-amine in place of quinolin-6-amine. The titled compound was obtained as an off-white solid (35 mg, 20%). $^1$H NMR (400 MHz, CD$_3$OD) δ 8.64 (dd, J=4.2, 1.6 Hz, 1H), 8.18-8.02 (m, 3H), 7.88 (s, 1H), 7.60 (t, J=7.9 Hz, 1H), 7.50-7.36 (m, 2H), 6.79 (d, J=2.6 Hz, 1H), 3.88 (s, 3H). $^{19}$F NMR (376 MHz, CD$_3$OD) δ −67.04.

N-(quinolin-8-ylcarbamoyl)-3-(3-(trifluoromethyl)-3H-diazirin-3-yl)benzenesulfonamide

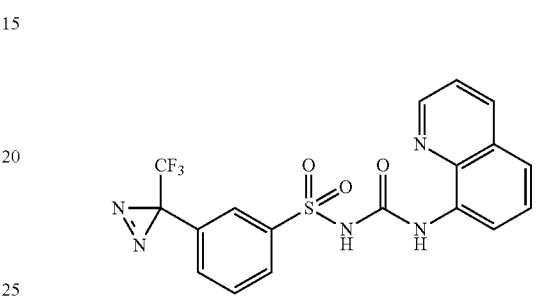

N-(Quinolin-8-ylcarbamoyl)-3-(3-(trifluoromethyl)-3H-diazirin-3-yl)benzenesulfonamide was synthesised using modification of the procedures used to make N-(quinolin-6-ylcarbamoyl)-3-(3-(trifluoromethyl)-3H-diazirin-3-yl) benzenesulfonamide but using quinolin-8-amine in place of quinolin-6-amine. The titled compound was obtained as a white solid (20 mg, 16%). $^1$H NMR (400 MHz, CD$_3$OD) δ=8.82 (dd, J=4.3, 1.6 Hz, 1H), 8.35 (dd, J=7.4, 1.8 Hz, 1H), 8.21 (dd, J=8.3, 1.7 Hz, 1H), 8.12 (d, J=7.9 Hz, 1H), 7.88 (s, 1H), 7.59 (t, J=7.9 Hz, 1H), 7.52-7.38 (m, 4H).

N-((2,3,6,7-tetrahydrobenzo[1,2-b:4,5-b']difuran-4-yl)carbamoyl)-3-(3-(trifluoromethyl)-3H-diazirin-3-yl)benzenesulfonamide

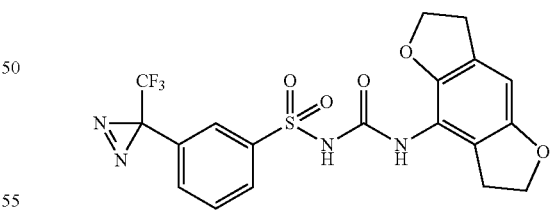

4-isocyanato-2,3,6,7-tetrahydrobenzo[1,2-b:4,5-b']difuran (prepared using general method A1) and 3-(3-(trifluoromethyl)-3H-diazirin-3-yl)benzenesulfonamide were used in general method C1 to give the titled compound as a white solid (0.01 g, 2%). $^1$H NMR (400 MHz, CD$_3$OD) δ=8.06 (dt, J=7.9, 1.3 Hz, 1H), 7.80 (s, 1H), 7.57 (t, J=7.9 Hz, 1H), 7.44 (d, J=7.9 Hz, 1H), 6.39 (s, 1H), 4.49 (t, J=8.6 Hz, 2H), 4.42 (t, J=8.6 Hz, 2H), 3.09 (t, J=8.4 Hz, 2H), 3.02 (t, J=8.6 Hz, 2H). $^{19}$F NMR (376 MHz, CD$_3$OD) δ −67.06.

4-chloro-N-((1,2,3,5,6,7-hexahydro-s-indacen-4-yl)carbamoyl)benzenesulfonamide

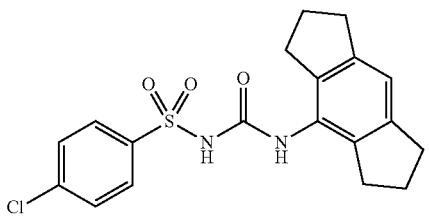 [SMILES: O=C(Nc1c2c(cc3c1CCC3)CCC2)NS(=O)(=O)c1ccc(Cl)cc1]

4-Isocyanato-1,2,3,5,6,7-hexahydro-s-indacene (prepared using general method A2) and 4-chlorobenzenesulfonamide were used in general method C2 to give the titled compound as a white solid (48 mg, 43%). $^1$H NMR (400 MHz, DMSO-d$_6$): δ=8.13 (s, 1H), 7.93 (d, J=8.0 Hz, 2H), 7.68 (d, J=12 Hz, 2H), 6.92 (s, 1H), 2.77 (t, J=8.0 Hz, 4H), 2.54 (t, J=8.0 Hz, 4H), 1.95-1.88 (m, 4H); $^{13}$C NMR (100 MHz, DMSO-d$_6$): δ=150.1, 143.4, 139.9, 138.1, 137.6, 129.6, 129.4, 129.2, 32.8, 30.5, 25.9; LCMS purity: >95%; LCMS (m/z): 391 [M+H]$^+$; HRMS calculated for C$_{19}$H$_{19}$ClN$_2$O$_3$S [M+H]$^+$: 391.0878, found: 391.0895.

N-(1,2,3,5,6,7-hexahydro-s-indacen-4-ylcarbamoyl)-4-methylbenzenesulfonamide

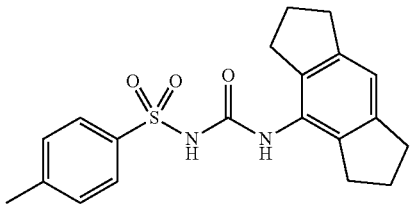 [SMILES: Cc1ccc(S(=O)(=O)NC(=O)Nc2c3c(cc4c2CCC4)CCC3)cc1]

4-Isocyanato-1,2,3,5,6,7-hexahydro-s-indacene (prepared using general method A1) and 4-methylbenzenesulfonamide were used in general method C4 to give the titled compound as a white solid (0.045 g, 27%). $^1$H NMR (400 MHz, DMSO-d$_6$): δ=10.70 (br.s, 1H), 8.08 (s, 1H), 7.82 (d, J=8 Hz, 2H), 7.41 (d, J=8.0 Hz, 2H), 6.92 (s, 1H), 2.79-2.68 (m, 4H), 2.58-2.50 (m, 4H), 2.39 (s, 3H), 1.97-1.87 (m, 4H). $^{13}$C NMR (100 MHz, DMSO-d$_6$): δ=149.0, 143.6, 143.0, 137.1, 129.4, 128.6, 127.3, 117.9, 32.4, 30.0, 25.0, 21.0. LCMS, Purity: 95.08%, m/z 371.07 (M+H$^+$). HRMS (FAB$^+$) calcd for C$_{20}$H$_{22}$N$_2$O$_3$S [M+H]: 371.1351, found: 371.1419.

5-Chloro-N-(4-(N-(1,2,3,5,6,7-hexahydro-s-indacen-4-ylcarbamoyl)sulfamoyl)phenethyl)-2-methoxybenzamide

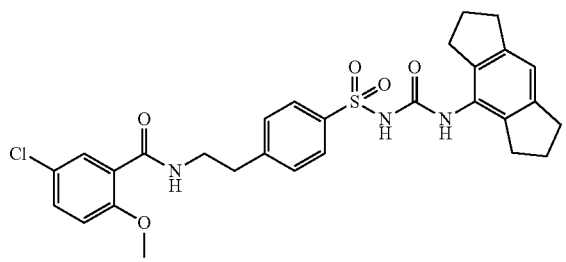 [SMILES: COc1ccc(Cl)cc1C(=O)NCCc1ccc(S(=O)(=O)NC(=O)Nc2c3c(cc4c2CCC4)CCC3)cc1]

4-Isocyanato-1,2,3,5,6,7-hexahydro-s-indacene (prepared using general method A1) and 5-chloro-2-methoxy-N-(4-sulfamoylphenethyl)benzamide were used in general method C4 to give the titled compound as a white solid (45 mg, 10%). $^1$H NMR (400 MHz, DMSO-d$_6$): δ=10.73 (s, 1H), 8.27 (t, J=5.2 Hz, 1H), 8.09 (s, 1H), 7.89 (d, J=8.4 Hz, 2H), 7.65 (d, J=2.4 Hz, 1H), 7.50 (d, J=8.4 Hz, 2H), 7.49 (d, J=2.4 Hz, 1H), 7.13 (d, J=9.2 Hz, 1H), 6.92 (s, 1H), 3.78 (s, 3H), 3.54 (q, J=6.4 Hz, 2H), 2.94 (t, J=6.8 Hz, 2H), 2.75 (t, J=7.2 Hz, 4H), 2.50 (m, 4H), 1.89 (quin, J=7.6 Hz, 4H). $^{13}$C NMR (100 MHz, DMSO-d$_6$): δ=163.6, 155.7, 145.3, 143.6, 143.0, 142.4, 142.1, 139.6, 137.1, 131.5, 129.5, 129.2, 127.4, 125.7, 124.8, 124.3, 117.9, 114.1, 108.3, 56.2, 34.7, 32.6, 32.4, 30.0, 28.9, 24.9. LCMS, Purity: 90.06%, tr=3.38 min, m/z 566.37 (M-H$^+$). HRMS (FAB$^+$) calcd for C$_{29}$H$_{30}$ClN$_3$O$_5$S [M+H]$^+$: 568.1595, found: 568.1589.

N-(4-(N-(1,2,3,5,6,7-Hexahydros-indacen-4-ylcarbamoyl)sulfamoyl)phenethyl)-5-methylpyrazine-2-carboxamide

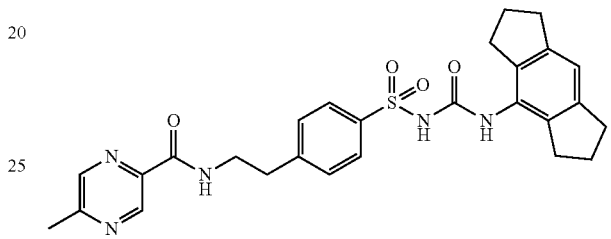

4-Isocyanato-1,2,3,5,6,7-hexahydro-s-indacene (prepared using general method A1) and 5-methyl-N-(4-sulfamoylphenethyl)pyrazine-2-carboxamide were used in general method C4 to give the titled compound as an off-white solid (0.02 g, 4%). $^1$H NMR (400 MHz, DMSO-d$_6$): δ=10.71 (s, 1H), 9.02 (s, 1H), 8.96 (t, J=6 Hz, 1H), 8.59 (s, 1H), 8.07 (s, 1H), 7.85 (d, J=8.4 Hz, 2H), 7.47 (d, J=8.0 Hz, 2H), 6.92 (s, 1H), 3.57 (q, J=6.8 Hz, 2H), 2.97 (t, J=7.4 Hz, 2H), 2.82-2.73 (m, 4H), 2.53 (s, 3H), 2.57-2.50 (m, 4H), 1.97-1.84 (m, 4H). LCMS, Purity: 88.15%, m/z 520.28 (M+H$^+$). HRMS (FAB$^+$) calcd for C$_{27}$H$_{29}$N$_5$O$_4$S [M+H]$^+$: 520.1940, found: 520.1977.

3-(4-(N-((1,2,3,5,6,7-Hexahydro-s-indacen-4-yl)carbamoyl)sulfamoyl)phenyl)-N-(prop-2-yn-1-yl)propanamide

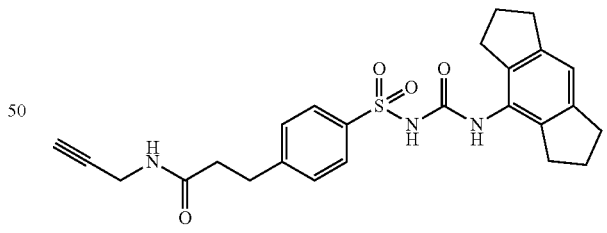

4-Isocyanato-1,2,3,5,6,7-hexahydro-s-indacene (prepared using general method A2) and N-(prop-2-yn-1-yl)-3-(4-sulfamoylphenyl)propanamide were used in general method C6 to give the titled compound as a white solid (120 mg, 68%). $^1$H NMR (400 MHz, CD$_3$OD) δ=7.91 (d, J=7.8 Hz, 2H), 7.39 (d, J=7.8 Hz, 2H), 6.98 (s, 1H), 3.95 (d, J=2.9 Hz, 2H), 3.03 (t, J=7.7 Hz, 2H), 2.85 (t, J=7.4 Hz, 4H), 2.62 (t, J=6.9 Hz, 4H), 2.55-2.46 (m, 2H), 2.25 (t, J=2.6 Hz, 1H), 2.02 (m, 4H). $^{13}$C NMR (101 MHz, CD$_3$OD) δ=172.0, 147.2, 144.1, 143.8, 137.5, 129.0, 128.8, 128.1, 127.4, 126.5, 118.9, 79.2, 71.0, 36.8, 32.8, 32.8, 31.2, 30.7, 28.8, 28.7, 25.4, 25.3. HRMS (ESI) calcd. for C$_{25}$H$_{28}$N$_3$O$_4$S [M+H] 466.1795, found 466.1794.

N-(4-(N-(1,2,3,5,6,7-Hexahydros-indacen-4-ylcarbamoyl)sulfamoyl)phenethyl)-2-(methyl(7-nitrobenzo[c][1,2,5]oxadiazol-4-yl)amino)acetamide

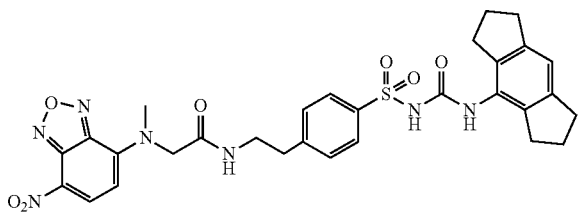 [SMILES: CN(CC(=O)NCCc1ccc(S(=O)(=O)NC(=O)Nc2c3c(cc4c2CCC4)CCC3)cc1)c1ccc([N+](=O)[O-])c2nonc12]

4-Isocyanato-1,2,3,5,6,7-hexahydro-s-indacene (prepared using general method A1) and 2-(methyl(7-nitrobenzo[c][1,2,5]oxadiazol-4-yl)amino)-N-(4-sulfamoylphenethyl)acetamide were used in general method C4 to give the titled compound as an orange solid (0.003 g, 1%). $^1$H NMR (400 MHz, DMSO-d$_6$): δ=10.74 (s, 1H), 8.51 (d, J=8.8 Hz, 1H), 8.31 (t, J=7.6 Hz, 1H), 8.09-7.96 (m, 1H), 7.82 (d, J=8.4 Hz, 2H), 7.41 (d, J=7.6 Hz, 2H), 6.89 (s, 1H), 6.42-6.32 (m, 1H), 4.74 (bs, 2H), 3.44-3.30 (m, 5H), 2.80 (t, J=7.6 Hz, 2H), 2.73-2.69 (m, 4H), 2.61-2.50 (m, 4H), 1.92-1.88 (m, 4H). LCMS, Purity: 92.20%, m/z 632.35 (M−H$^+$).

N-((1,2,3,5,6,7-hexahydro-s-indacen-4-yl)carbamoyl)-4-(2-((7-nitrobenzo[c][1,2,5]oxadiazol-4-yl)amino)ethyl)benzenesulfonamide

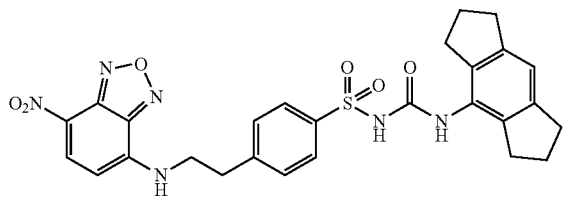 [SMILES: O=C(Nc1c2c(cc3c1CCC3)CCC2)NS(=O)(=O)c1ccc(CCNc2ccc([N+](=O)[O-])c3nonc23)cc1]

4-Isocyanato-1,2,3,5,6,7-hexahydro-s-indacene (prepared using general method A1) and 4-(2-((7-nitrobenzo[c][1,2,5]oxadiazol-4-yl)amino)ethyl)benzenesulfonamide were used in general method C4 to give the titled compound as a yellow solid (0.047 g, 15%). $^1$H NMR (400 MHz, DMSO-d$_6$): δ=10.69 (bs, 1H), 9.55 (s, 1H), 8.50 (d, J=8.8 Hz, 1H), 8.09 (s, 1H), 7.87 (d, J=8.0 Hz, 2H), 7.56 (d, J=8.0 Hz, 2H), 6.92 (s, 1H), 6.50 (d, J=8.8 Hz, 1H), 3.76 (bs, 2H), 3.11 (t, J=6.8 Hz, 2H), 2.76 (t, J=7.6 Hz, 4H), 2.53 (t, J=6.8 Hz, 4H), 1.90 (quin, J=7.6 Hz, 4H). $^{13}$C NMR (100 MHz, DMSO-d$_6$): δ=149.1, 144.8, 144.3, 142.4, 138.3, 137.8, 137.1, 129.3, 128.6, 127.3, 125.7, 121.0, 117.9, 108.3, 99.5, 44.1, 33.2, 32.5, 30.1, 28.9, 25.0. LCMS, Purity: 96.50%, tr=2.29 min, m/z 563.20 (M+H$^+$). HRMS (FAB$^+$) calcd for C$_{27}$H$_{26}$N$_6$O$_6$S [M+H]$^+$: 563.1635, found: 563.1641.

2-(7-(Dimethylamino)-2-oxo-2H-chromen-4-yl)-N-(4-(N-(1,2,3,5,6,7-hexahydro-s-indacen-4-ylcarbamoyl)sulfamoyl)phenethyl)acetamide

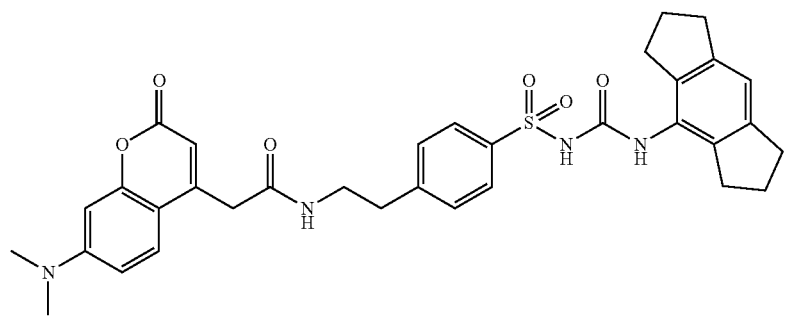 [SMILES: CN(C)c1ccc2c(CC(=O)NCCc3ccc(S(=O)(=O)NC(=O)Nc4c5c(cc6c4CCC6)CCC5)cc3)cc(=O)oc2c1]

4-Isocyanato-1,2,3,5,6,7-hexahydro-s-indacene (prepared using general method A1) and 2-(7-(dimethylamino)-2-oxo-2H-chromen-4-yl)-N-(4-sulfamoylphenethyl)acetamide were used in general method C4 to give the titled compound as a pale-yellow solid (0.008 g, 0.44%). $^1$H NMR (400 MHz, DMSO-d$_6$): δ=9.53 (s, 1H), 8.29 (t, J=4.8 Hz, 1H), 8.22 (s, 1H), 7.68 (d, J=8.0 Hz, 2H), 7.46 (d, J=8.8 Hz, 1H), 8.42 (s, 1H), 7.16 (d, J=8.0 Hz, 2H), 6.74-6.70 (m, 2H), 6.54 (d J=2.4 Hz, 1H), 5.99 (s, 1H), 3.56-3.52 (m, 2H), 3.48 (t, J=6.0 Hz, 2H), 3.31-3.24 (m, 2H), 2.76-2.70 (m, 4H), 3.02 (s, 6H), 2.63 (t, J=7.2 Hz, 4H), 1.88 (quin, J=7.6 Hz, 4H). LCMS, Purity: 92.26%, m/z 629.40 (MH$^+$).

N-((1,2,3,5,6,7-hexahydro-s-indacen-4-yl)carbamoyl)benzo[d][1,3]dioxole-5-sulfonamide

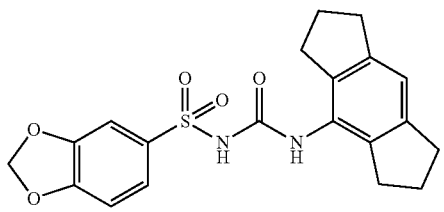 [SMILES: O=C(Nc1c2c(cc3c1CCC3)CCC2)NS(=O)(=O)c1ccc2c(c1)OCO2]

4-Isocyanato-1,2,3,5,6,7-hexahydro-s-indacene (prepared using general method A2) and benzo[d][1,3]dioxole-5-sulfonamide were used in general method C2 to give the titled compound as a white solid (28 mg, 27%). $^1$H NMR (400 MHz, DMSO-d$_6$): δ=8.04 (br.s., 1H), 7.47 (d, J=8.0 Hz, 1H), 7.38 (s, 1H), 7.09 (d, J=4.0 Hz, 1H), 6.91 (s, 1H), 6.16 (s, 2H) 2.77 (t, J=8.0 Hz, 4H), 2.56 (t, J=8.0 Hz, 4H), 1.96-1.89 (m, 4H); LCMS Purity: >95%; LCMS (m/z): 401 [M+H]$^+$; HRMS calculated for C$_{20}$H$_{20}$N$_2$O$_5$S [M+H]$^+$ 401.1166, found 401.1182.

N-((1,2,3,5,6,7-hexahydro-s-indacen-4-yl)carbamoyl)-6,7-dihydro-5H-pyrrolo[1,2-a]imidazole-2-sulfonamide

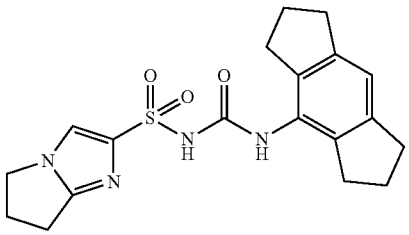 [SMILES: O=C(Nc1c2c(cc3c1CCC3)CCC2)NS(=O)(=O)c1cn2c(n1)CCC2]

1,2,3,5,6,7-Hexahydro-s-indacen-4-amine (70 mg, 0.40 mmol) was dissolved in anhydrous THF (5 mL) and treated with Et$_3$N (49 mg, 0.49 mmol) at RT. The solution was treated with triphosgene (48 mg, 0.161 mmol) and resulting mixture was stirred at 70° C. for 2 h. The reaction mixture was concentrated in vacuo. The residue obtained was stirred with 5% EtOAc-hexanes (20 mL) for 10 min, filtered through a celite pad and concentrated in vacuo to give the corresponding isocyanate as a white solid. In a separate flask, 6,7-dihydro-5H-pyrrolo[1,2-a]imidazole-2-sulfonamide (115 mg, 0.61 mmol) was dissolved in anhydrous THF (5 mL) and treated carefully with NaH (25 mg, 0.61 mmol) at 0° C. under nitrogen atmosphere and stirred for 20 minutes. The aforementioned isocyanate in THF was added to reaction mixture under nitrogen atmosphere. The reaction mixture was warmed to RT, stirred for 4 h then concentrated in vacuo. The residue obtained was diluted with 10 mM ammonium bicarbonate in water (20 mL), acetonitrile (20 mL), ethyl acetate (10 mL) and solid formed was removed by filtration and washed with diethyl ether to give N-((1,2,3,5,6,7-hexahydro-s-indacen-4-yl)carbamoyl)-6,7-dihydro-5H-pyrrolo[1,2-a]imidazole-2-sulfonamide (50 mg, 32%) as a white solid. $^1$H NMR (400 MHz, CD$_3$OD): δ=7.29 (s, 1H), 6.85 (s, 1H), 4.23 (t, J=7.2 Hz, 1H), 2.86-2.79 (m, 6H), 2.72 (t, J=7.2 Hz, 4H), 2.65-2.60 (m, 2H), 2.02-1.95 (m, 4H). LCMS (m/z): 387.10 [M+H]; 95.53% (210 nm). HPLC: 94.43% (210 nm). HRMS calculated for C$_{19}$H$_{21}$N$_4$O$_3$S$_1$ [M-H]$^-$ 385.1340, found 385.1331.

4-Acetyl-N-((1,2,3,5,6,7-hexahydro-s-indacen-4-yl)carbamoyl)benzenesulfonamide

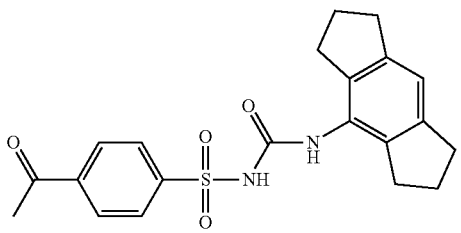 [SMILES: CC(=O)c1ccc(S(=O)(=O)NC(=O)Nc2c3c(cc4c2CCC4)CCC3)cc1]

4-Isocyanato-1,2,3,5,6,7-hexahydro-s-indacene (prepared using general method A2) and 4-acetylbenzenesulfonamide were used in general method C2 to give the titled compound as a white solid (31 mg, 16%). $^1$H NMR (600 MHz, DMSO-d$_6$) δ=11.03 (bs, 1H) 8.08 (d, J=8.5 Hz, 2H), 7.99 (d, J=8.5 Hz, 2H), 7.03 (bs, 1H), 6.87 (s, 1H), 2.75 (t, J=7.4 Hz, 4H), 2.62 (s, 3H), 2.56 (t, J=7.4 Hz, 4H), 1.90 (p, J=7.4 Hz, 4H). HRMS calculated for C$_{21}$H$_{21}$N$_2$O$_4$S$_1$ [M-H]$^-$ 397.1128, found 397.1225.

N-((1,2,3,5,6,7-hexahydro-s-indacen-4-yl)carbamoyl)-4-nitrobenzenesulfonamide

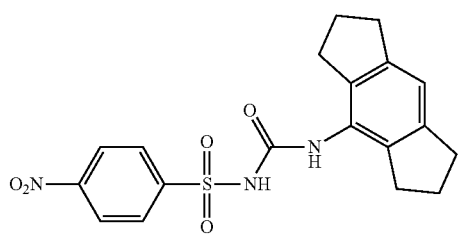

4-Isocyanato-1,2,3,5,6,7-hexahydro-s-indacene (prepared using general method A2) and 4-nitrobenzenesulfonamide were used in general method C2 to give the titled compound as a pale yellow solid (148 mg, 60%). 1H NMR (600 MHz, DMSO-d$_6$) δ=10.00 (bs, 1H), 8.21 (d, J=9.0 Hz, 2H), 7.97 (d, J=9.0 Hz, 2H), 7.45 (s, 1H), 6.75 (s, 1H), 2.73 (t, J=7.4 Hz, 4H), 2.61 (t, J=7.4 Hz, 4H), 1.87 (p, J=7.4 Hz, 4H). HRMS calculated for C$_{19}$H$_{18}$N$_3$O$_5$S$_1$ [M-H]$^-$ 400.0973, found 400.0979.

4-Amino-N-((1,2,3,5,6,7-hexahydro-s-indacen-4-yl)carbamoyl)benzenesulfonamide

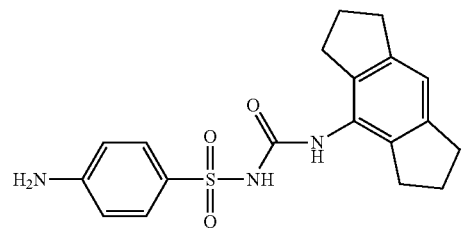 [SMILES: O=C(Nc1c2c(cc3c1CCC3)CCC2)NS(=O)(=O)c1ccc([N+](=O)[O-])cc1]

N-((1,2,3,5,6,7-hexahydro-s-indacen-4-yl)carbamoyl)-4-nitrobenzenesulfonamide dissolved in a solution of ethyl acetate/DMF (4:1, 25 mL/mmol) was stirred at room temperature for 1 h under hydrogen atmosphere with a catalytic amount of Pd/C (0.1 mol %) to afford the titled compound as a white solid (16 mg, 43%). $^1$H NMR (600 MHz, DMSO-d$_6$) δ=7.95 (s, 1H), 7.54 (d, J=8.8 Hz, 2H), 6.91 (s, 1H), 6.59 (d, J=8.8 Hz, 2H), 6.05 (s, 2H), 2.77 (t, J=7.4 Hz, 4H), 2.55 (t, J=7.4 Hz, 4H), 1.93 (q, J=7.4 Hz, 4H). HRMS calculated for C$_{19}$H$_{20}$N$_3$O$_3$S$_1$ [M-H]$^-$ 370.1231, found 370.1225.

N-((1,2,3,5,6,7-hexahydro-s-indacen-4-yl)carbamoyl)-2,3-dihydro-1H-indene-5-sulfonamide

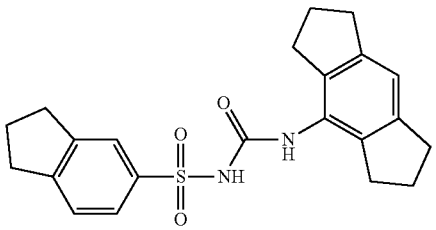 [SMILES: O=C(Nc1c2c(cc3c1CCC3)CCC2)NS(=O)(=O)c1ccc2c(c1)CCC2]

4-Isocyanato-1,2,3,5,6,7-hexahydro-s-indacene (prepared using general method A2) and 2,3-dihydro-1H-indene-5-sulfonamide were used in general method C2 to give the titled compound as a white solid (48 mg, 12%). 1H NMR (600 MHz, DMSO-d$_6$) δ=10.68 (bs, 1H), 8.02 (s, 1H), 7.75 (d, J=1.7 Hz, 1H), 7.68 (dd, J=7.9, 1.7 Hz, 1H), 7.41 (d, J=7.9 Hz, 1H), 6.90 (s, 1H), 2.91 (t, J=7.5 Hz, 4H), 2.76 (t, J=7.4 Hz, 4H), 2.53 (t, J=7.4 Hz, 4H), 2.05 (p, J=7.5 Hz, 2H), 1.91 (p, J=7.4 Hz, 4H). HRMS calculated for C$_{22}$H$_{23}$N$_2$O$_3$S$_1$ [M-H]$^-$ 395.1435, found 395.1430.

N-((4-chlorophenyl)carbamoyl)-2,3-dihydro-1H-indene-5-sulfonamide

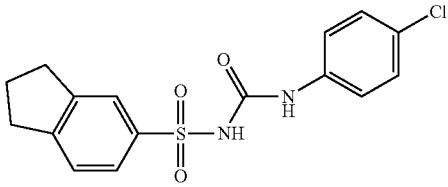 [SMILES: O=C(Nc1ccc(Cl)cc1)NS(=O)(=O)c1ccc2c(c1)CCC2]

1-Chloro-4-isocyanatobenzene (prepared using general method B1) and 2,3-dihydro-1H-indene-5-sulfonamide were used in general method C2 to give the titled compound as a white solid (60 mg, 32%). $^1$H NMR (600 MHz, DMSO-d$_6$) δ 10.90 (bs, 1H), 8.90 (s, 1H), 7.74 (d, J=1.8 Hz, 1H) 7.68 (dd, J=7.9, 1.7 Hz, 1H), 7.41-7.35 (m, 3H), 7.26 (dt, 2H), 2.91 (m, 4H), 2.05 (p, J=7.5 Hz, 2H). HRMS calculated for $C_{16}H_{14}Cl_1N_2O_3S_1$ [M–H]$^-$ 349.0419, found HRMS 349.0418.

N-((4-chloro-2,6-diisopropylphenyl)carbamoyl)quinoline-8-sulfonamide

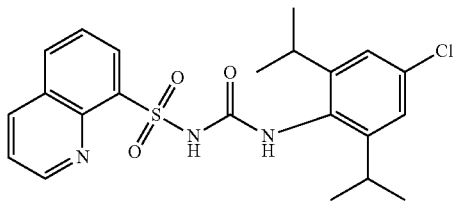 [SMILES: CC(C)c1cc(Cl)cc(C(C)C)c1NC(=O)NS(=O)(=O)c1cccc2cccnc12]

5-Chloro-2-isocyanato-1,3-diisopropylbenzene (prepared using general method A2) and quinoline-8-sulfonamide were used in general method C3 to give the titled compound as a white solid (75 mg, 71%). $^1$H NMR (600 MHz, CD$_3$OD): δ=9.13 (dd, J=4.2, 1.6 Hz, 1H), 8.57-8.49 (m, 2H), 8.26 (d, J=8.2 Hz, 1H), 7.77-7.67 (m, 2H), 6.99 (s, 2H), 2.65-2.60, (m, 2H), 0.85 (d, 12H); $^{13}$C NMR (150 MHz, CD$_3$OD) δ=151.2, 149.0, 143.3, 136.8, 136.7, 133.8, 133.5, 132.3, 129.4, 129.1, 125.3, 123.0, 122.1, 109.1, 28.3, 22.5; LCMS Purity: >95%; LCMS (m/z): 446 [M+H]$^+$; HRMS calculated for $C_{22}H_{25}Cl_1N_3O_3S_1$ [M+H]$^+$ 446.1300, found 446.1314.

N-((4-chloro-2,6-diisopropylphenyl)carbamoyl)isoquinoline-5-sulfonamide

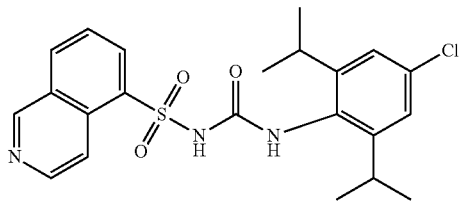 [SMILES: CC(C)c1cc(Cl)cc(C(C)C)c1NC(=O)NS(=O)(=O)c1cccc2cnccc12]

5-Chloro-2-isocyanato-1,3-diisopropylbenzene (prepared using general method A2) and isoquinoline-5-sulfonamide (prepared using general method E3) were used in general method C3 to give the titled compound as a white solid (70 mg, 67%). $^1$H NMR (600 MHz, CD$_3$OD): δ=9.41 (s, 1H), 8.82 (s, 1H), 8.59 (d, J=7.3 Hz, 2H), 8.35 (d, J=8.2 Hz, 1H), 7.79 (t, J=7.6 Hz, 1H), 6.96 (s, 2H), 2.74-2.70 (m, 2H), 0.96 (s, 6H), 0.85 (d, 12H); $^{13}$C NMR (150 MHz, CD$_3$OD) δ=156.3, 152.5, 149.1, 143.8, 137.2, 133.9, 133.1, 132.6, 131.5, 130.4, 126.3, 124.8, 122.8, 122.1, 28.3, 22.4; LCMS Purity: >95%; LCMS (m/z): 446 [M+H]$^+$; HRMS calculated for $C_{22}H_{25}Cl_1N_3O_3S_1$ [M+H]$^+$ 446.1300, found 446.1319.

N-((4-chloro-2,6-diisopropylphenyl)carbamoyl)quinoline-5-sulfonamide

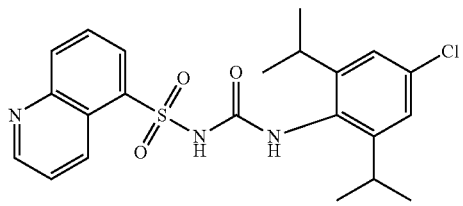 [SMILES: CC(C)c1cc(Cl)cc(C(C)C)c1NC(=O)NS(=O)(=O)c1cccc2ncccc12]

5-Chloro-2-isocyanato-1,3-diisopropylbenzene (prepared using general method A2) and quinoline-5-sulfonamide (prepared using general method E3) were used in general method C3 to give the titled compound as a white solid (31 mg, 60%). $^1$H NMR (600 MHz, CD$_3$OD): δ=9.53 (d, J=8.9 Hz, 1H), 8.94 (d, J=3.8 Hz, 1H), 8.35 (dd, J=7.3, 1.2 Hz, 1H), 8.15 (d, J=8.5 Hz, 1H), 7.79 (dd, J=8.5, 7.3 Hz, 1H), 7.69 (dd, J=8.7, 4.3 Hz, 1H), 2.81-2.76 (m, 2H), 0.85 (d, 12H); $^{13}$C NMR (150 MHz, CD$_3$OD)=161.4, 151.3, 150.7, 149.1, 142.2, 137.4, 134.0, 133.0, 132.8, 129.9, 129.4, 126.0, 124.1, 122.9, 29.6, 24.0; LCMS Purity: >95%; LCMS (m/z): 446 [M+H]$^+$; HRMS calculated for $C_{22}H_{25}Cl_1N_3O_3S_1$ [M+H]$^+$ 446.1300, found 446.1317.

N-((1,2,3,5,6,7-hexahydro-s-indacen-4-yl)carbamoyl)quinoline-8-sulfonamide

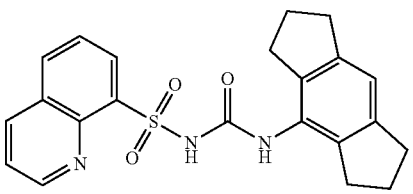 [SMILES: O=C(Nc1c2c(cc3c1CCC3)CCC2)NS(=O)(=O)c1cccc2cccnc12]

4-Isocyanato-1,2,3,5,6,7-hexahydro-s-indacene (prepared using general method A2) and 4H-quinoline-8-sulfonamide were used in general method C3 to give the titled compound as a white solid (60 mg, 51%); $^1$H NMR (600 MHz, DMSO-d$_6$) δ=9.11 (d, J=2.7 Hz, 1H), 8.56 (d, J=8.3 Hz, 1H), 8.40 (d, J=7.4 Hz, 1H), 8.32 (d, J=8.2 Hz, 1H), 8.17 (s, 1H), 7.76 (t, J=7.7 Hz, 1H), 7.73 (dd, J=8.4, 4.2 Hz, 1H), 6.82 (s, 1H), 2.67 (t, J=7.4 Hz, 4H), 2.26 (t, J=7.4 Hz, 4H), 1.79 (p, J=7.5 Hz, 4H); $^{13}$C NMR (150 MHz, DMSO-d$_6$): δ=151.8, 151.7, 143.3, 143.2, 137.5, 137.1, 134.5, 133.4, 132.8, 129.9, 126.0, 122.8, 118.0, 108.7, 32.7, 30.2, 25.3. LCMS (m/z): 408 [M+H]$^+$. HRMS calculated for $C_{22}H_{22}N_3O_3S_1$ [M+H]$^+$ 408.1376, found 408.1371.

N-((4-chloro-2,6-diisopropylphenyl)carbamoyl)quinoline-3-sulfonamide

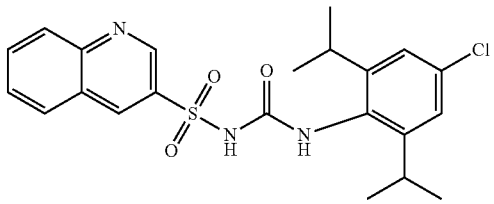 [SMILES: CC(C)c1cc(Cl)cc(C(C)C)c1NC(=O)NS(=O)(=O)c1cnc2ccccc2c1]

5-Chloro-2-isocyanato-1,3-diisopropylbenzene (prepared using general method A2) and quinoline-3-sulfonamide (prepared using general method E3) were used in general method C3 to give the titled compound as a white solid (30 mg, 57%). $^1$H NMR (600 MHz, DMSO-$d_6$): ($^1$H NMR (600 MHz, DMSO-$d_6$) δ=9.24 (s, 1H), 8.92 (s, 1H), 8.20 (d, J=8.3 Hz, 1H), 8.12 (d, J=8.5 Hz, 1H), 7.98 (s, 1H), 7.93 (t, J=7.7 Hz, 1H), 7.74 (t, J=7.6 Hz, 1H), 7.02 (s, 2H), 2.81-2.78 (m, 2H), 0.84 (d, 12H); $^{13}$C NMR (150 MHz, DMSO-$d_6$): δ=153.7, 149.3, 148.7, 147.6, 141.5, 136.8, 132.6, 132.4, 131.5, 129.9, 129.2, 128.4, 126.4, 123.3, 28.5, 23.5; LCMS Purity: >95%; LCMS (m/z): 446 [M+H]$^+$; HRMS calculated for $C_{22}H_{25}Cl_1N_3O_3S_1$ [M+H]$^+$ 446.1300, found 446.1315.

N-((4-chloro-2,6-diisopropylphenyl)carbamoyl)quinoxaline-5-sulfonamide

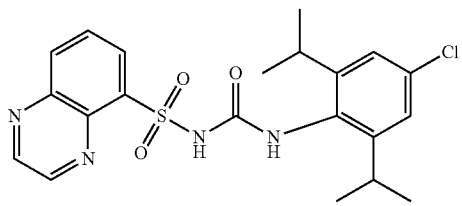 [SMILES: CC(C)c1cc(Cl)cc(C(C)C)c1NC(=O)NS(=O)(=O)c1cccc2nccnc12]

5-Chloro-2-isocyanato-1,3-diisopropylbenzene (prepared using general method A2) and quinoxaline-5-sulfonamide (prepared using general method E3) were used in general method C3 to give the titled compound as a white solid (39 mg, 75%); $^1$H NMR (600 MHz, DMSO-$d_6$) δ=9.18 (d, J=3.7 Hz, 2H), 8.46 (d, J=7.3 Hz, 1H), 8.38 (dd, J=8.1, 2.7 Hz, 1H), 8.04-7.95 (m, 1H), 7.83 (s, 1H), 6.99 (s, 2H), 2.55-2.49 (m, 2H), 0.74 (d, 12H); $^{13}$C NMR (150 MHz, DMSO-$d_6$): 149.2, 147.1, 146.8, 146.2, 142.7, 140.5, 138.5, 138.2, 134.2, 133.4, 132.6, 129.6, 123.4, 28.4, 22.7; LCMS Purity: >95%; LCMS (m/z): 447 [M+H]$^+$; HRMS calculated for $C_{21}H_{24}Cl_1N_4O_3S_1$ [M+H]$^+$ 447.1252, found 447.1266.

N-((4-chloro-2,6-diisopropylphenyl)carbamoyl)naphthalene-2-sulfonamide

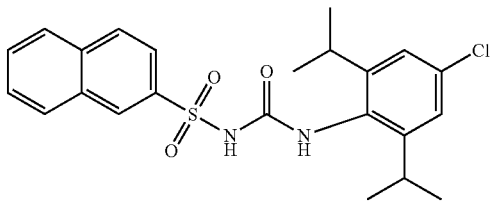 [SMILES: CC(C)c1cc(Cl)cc(C(C)C)c1NC(=O)NS(=O)(=O)c1ccc2ccccc2c1]

5-chloro-2-isocyanato-1,3-diisopropylbenzene (prepared using general method A2) and naphthalene-2-sulfonamide (prepared using general method E3) were used in general method C3 to give the titled compound as a white solid (35 mg, 67%). $^1$H NMR (600 MHz, CD$_3$OD): δ=8.55 (s, 1H), 8.05-7.92 (m, 4H), 7.64-7.58 (m 2H), 6.99 (s, 2H), 2.94-2.89 (m, 2H), 0.94 (bs, 12H); $^{13}$C NMR (150 MHz, CD$_3$OD) δ 159.9, 150.6, 142.2, 135.9, 134.0, 133.7, 132.6, 130.2, 129.5, 129.1, 128.8, 128.6, 128.1, 124.3, 124.2, 29.7, 24.0; LCMS Purity: >95%; LCMS (m/z): 445 [M+H]$^+$; HRMS calculated for $C_{23}H26Cl_1N_2O_3S_1$ [M+H]$^+$ 445.1347, found 445.1349.

N-((4-chloro-2,6-diisopropylphenyl)carbamoyl)-6-methoxynaphthalene-2-sulfonamide

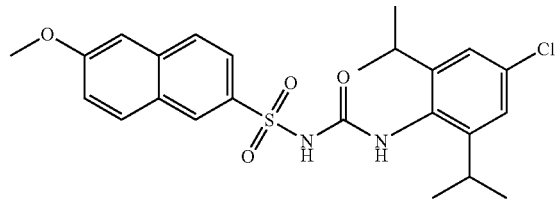 [SMILES: COc1ccc2cc(S(=O)(=O)NC(=O)Nc3c(C(C)C)cc(Cl)cc3C(C)C)ccc2c1]

5-chloro-2-isocyanato-1,3-diisopropylbenzene (prepared using general method A2) and 6-methoxynaphthalene-2-sulfonamide (prepared using general method E3) were used in general method C3 to give the titled compound as a white solid (39 mg, 70%); $^1$H NMR (600 MHz, DMSO-$d_6$) δ=8.23 (s, 1H), 7.86 (d, J=9.0 Hz, 1H), 7.78 (dd, J=9.1, 6.4 Hz, 2H), 7.49 (s, 1H), 7.35 (d, J=2.6 Hz, 1H), 7.20 (dd, J=8.9, 2.6 Hz, 1H), 6.96 (s, 2H), 3.08-2.98 (m, 2H), 0.93 (bs, 12H); $^{13}$C NMR (150 MHz, DMSO-$d_6$): δ=158.0, 149.6, 135.2, 134.4, 131.0, 130.5, 128.1, 127.5, 127.3, 126.5, 124.7, 124.6, 122.7, 119.4, 106.2, 55.7, 28.3, 23.4; LCMS Purity: >95%; LCMS (m/z): 475 [M+H]$^+$; HRMS calculated for $C_{24}H_{28}Cl_1N_2O_4S_1$ [M+H]$^+$475.1453, found 475.1474.

6-chloro-N-((4-chloro-2,6-diisopropylphenyl)carbamoyl)naphthalene-2-sulfonamide

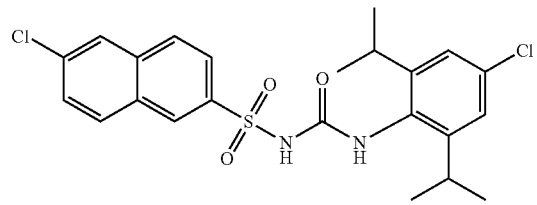 [SMILES: CC(C)c1cc(Cl)cc(C(C)C)c1NC(=O)NS(=O)(=O)c1ccc2cc(Cl)ccc2c1]

5-Chloro-2-isocyanato-1,3-diisopropylbenzene (prepared using general method A2) and 6-chloronaphthalene-2-sulfonamide (prepared using general method E3) were used in general method C3 to give the titled compound as a white solid (34 mg, 61%); $^1$H NMR (600 MHz, DMSO-$d_6$) δ=8.30 (s, 1H), 8.06 (d, J=2.2 Hz, 1H), 8.01 (d, J=8.8 Hz, 1H), 7.93-7.85 (m, 2H), 7.55 (dd, J=8.7, 2.2 Hz, 1H), 7.40 (s, 1H), 6.95 (s, 2H), 3.09-2.97 (m, 2H), 0.92 (bs, 12H); $^{13}$C NMR (150 MHz, DMSO-$d_6$): δ=160.2, 149.6, 145.8, 134.8, 134.2, 131.7, 131.1, 130.8, 130.7, 127.2, 126.8, 126.6, 125.8, 125.7, 122.7, 28.3, 23.6; LCMS Purity: >95%; LCMS (m/z): 479 [M+H]$^+$; HRMS calculated for $C_{23}H_{25}Cl_2N_2O_3S_1$ [M+H]$^+$ 479.0957, found 479.0937.

N-((4-chloro-2,6-diisopropylphenyl)carbamoyl)-5,6,7,8-tetrahydronaphthalene-2-sulfonamide

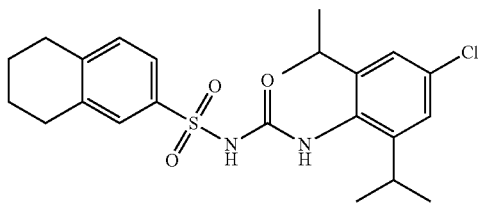 [SMILES: CC(C)c1cc(Cl)cc(C(C)C)c1NC(=O)NS(=O)(=O)c1ccc2c(c1)CCCC2]

5-chloro-2-isocyanato-1,3-diisopropylbenzene (prepared using general method A2) and 5,6,7,8-tetrahydronaphthalene-2-sulfonamide (prepared using general method E3) were used in general method C1 to give the titled compound as a white solid (8 mg, 38%); $^1$H NMR (600 MHz, DMSO-$d_6$) δ=7.85 (s, 1H), 7.58 (s, 1H), 7.57 (d, J=8.0 Hz, 1H), 7.22 (d, J=7.2 Hz, 1H), 7.08 (s, 2H), 2.85-2.81 (m, 2H), 2.78-2.74 (m, 4H), 1.74 (t, J=3.3 Hz, 4H), 0.98 (bs, 12H); $^{13}$C NMR (150 MHz, DMSO-$d_6$): δ=149.3, 137.7, 137.5, 132.4, 129.8, 129.5, 129.7, 126.3, 124.3, 123.4, 122.9, 29.3, 29.2, 28.5, 23.4, 22.8, 22.7; LCMS Purity: >95%; LCMS (m/z): 449 [M+H]$^+$; HRMS calculated for $C_{23}H_{30}Cl_1N_2O_3S_1$ [M+H]$^+$ 449.1660, found 449.1664.

N-((4-chloro-2,6-diisopropylphenyl)carbamoyl)thieno[3,2-b]pyridine-6-sulfonamide

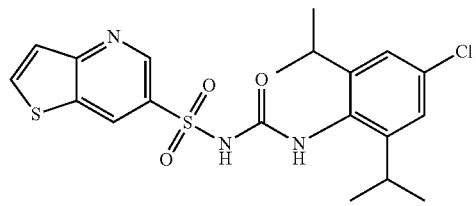 [SMILES: CC(C)c1cc(Cl)cc(C(C)C)c1NC(=O)NS(=O)(=O)c1cnc2ccsc2c1]

5-chloro-2-isocyanato-1,3-diisopropylbenzene (prepared using general method A2) and thieno[3,2-b]pyridine-6-sulfonamide were used in general method C3 to give the titled compound as a white solid (35 mg, 66%); $^1$H NMR (600 MHz, DMSO-$d_6$) δ=9.07 (d, J=2.0 Hz, 1H), 9.05 (s, 1H), 8.45 (d, J=5.5 Hz, 1H), 8.01 (s, 1H), 7.70 (d, J=5.5 Hz, 1H), 7.05 (s, 2H), 2.79-2.75 (m, 2H), 0.87 (d, 12H); $^{13}$C NMR (150 MHz, DMSO-$d_6$): δ=158.2, 152.7, 149.3, 145.8, 138.2, 132.7, 132.3, 132.2, 131.6, 131.1, 124.7, 123.4, 28.5, 22.9; LCMS Purity: >95%; LCMS (m/z): 452 [M+H]$^+$; HRMS calculated for $C_{20}H_{23}Cl_1N_3O_3S_2$[M+H]$^+$ 452.0864, found 452.0884.

N-((4-chloro-2,6-diisopropylphenyl)carbamoyl)-3-ethylisoxazolo[5,4-b]pyridine-5-sulfonamide

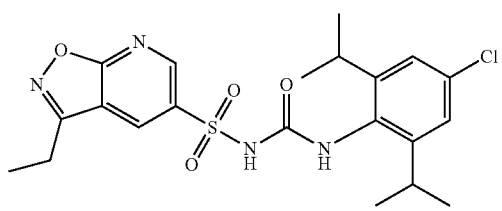 [SMILES: CCc1noc2ncc(S(=O)(=O)NC(=O)Nc3c(C(C)C)cc(Cl)cc3C(C)C)cc12]

5-Chloro-2-isocyanato-1,3-diisopropylbenzene (prepared using general method A2) and thieno[3,2-b]pyridine-6-sulfonamide were used in general method C3 to give the titled compound as a white solid (38 mg, 64%); $^1$H NMR (600 MHz, DMSO-$d_6$) δ=9.11 (s, 1H), 8.98 (s, 1H), 8.14 (s, 1H), 7.08 (s, 2H), 3.09 (q, J=7.5 Hz, 2H), 2.82-2.77 (m, 2H), 1.34 (t, J=7.5 Hz, 3H), 1.02-0.90 (d, 12H). $^{13}$C NMR (150 MHz, DMSO-$d_6$): δ=170.2, 161.9, 150.5, 149.3, 134.3, 134.2, 132.8, 131.0, 123.5, 112.7, 109.9, 28.5, 23.0, 19.2, 11.9; LCMS Purity: >95%; LCMS (m/z): 465 [M+H]$^+$; HRMS calculated for $C_{21}H_{26}Cl_1N_4O_4S_1$ [M+H]465.1358, found 465.1354.

N-((1,2,3,5,6,7-hexahydro-s-indacen-4-yl)carbamoyl)benzofuran-2-sulfonamide

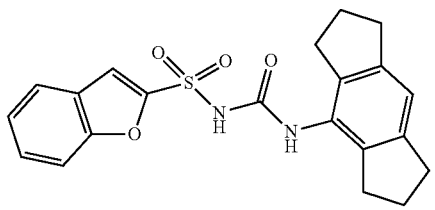 [SMILES: O=C(Nc1c2c(cc3c1CCC3)CCC2)NS(=O)(=O)c1cc2ccccc2o1]

4-Isocyanato-1,2,3,5,6,7-hexahydro-s-indacene (prepared using general method A2) and benzofuran-2-sulfonamide were used in general method C3 to give the titled compound as a white solid (60 mg, 52%); $^1$H NMR (400 MHz, DMSO-$d_6$): δ=8.00 (bs, 1H), 7.77 (d, J=8 Hz, 1H), 7.69 (d, J=8 Hz, 1H), 7.51 (s, 1H), 7.49 (d, J=8 Hz, 1H), 7.36 (t, J=8 Hz, 1H), 7.08 (bs, 1H), 6.87 (s, 1H), 2.75 (t, J=8 Hz, 4H), 2.59 (t, J=8 Hz, 4H), 1.92-1.85 (m, 4H). $^{13}$C NMR (150 MHz, DMSO-$d_6$): δ=154.9, 143.2, 137.6, 130.3, 127.5, 126.7, 124.4, 123.3, 117.7, 112.3, 110.0, 109.4, 107.4, 32.9, 30.6, 25.5. LCMS (m/z): 397 [M+H]$^+$. HRMS calculated for $C_{21}H_{21}N_2O_4S_1$ [M+H]$^+$397.1217, found 397.1215.

N-((4-chloro-2,6-diisopropylphenyl)carbamoyl)benzofuran-2-sulfonamide

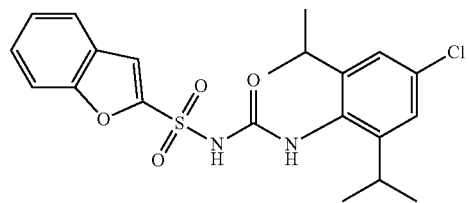 [SMILES: CC(C)c1cc(Cl)cc(C(C)C)c1NC(=O)NS(=O)(=O)c1cc2ccccc2o1]

5-chloro-2-isocyanato-1,3-diisopropylbenzene (prepared using general method A2) and benzofuran-2-sulfonamide (prepared using general method E3) were used in general method C3 to give the titled compound as a white solid (25 mg, 49%). 1H NMR (600 MHz, DMSO-$d_6$) δ=7.85 (s, 1H), 7.73 (d, J=7.8 Hz, 1H), 7.66 (d, J=8.4 Hz, 1H), 7.47 (s, 1H), 7.34 (t, J=7.5 Hz, 1H), 7.17 (s, 1H), 7.04 (s, 2H), 2.99-2.95 (m, 2H), 0.94 (bs, 12H); $^{13}$C NMR (150 MHz, DMSO-$d_6$): δ=154.9, 149.5, 132.6, 132.3, 132.0, 127.2, 126.9, 126.8, 123.3, 123.2, 112.1, 112.0, 109.8, 28.5, 23.3; LCMS Purity: >95%; LCMS (m/z): 435 [M+H]$^+$; HRMS calculated for $C_{21}H_{24}Cl_1N_2O_4S_1$ [M+H]$^+$435.1140, found 435.1140.

N-((4-chloro-2,6-diisopropylphenyl)carbamoyl)benzo[b]thiophene-2-sulfonamide

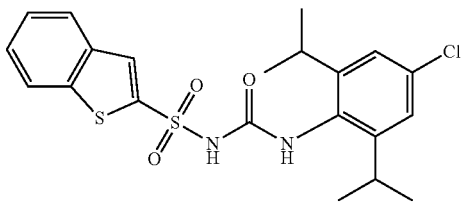 [SMILES: CC(C)c1cc(Cl)cc(C(C)C)c1NC(=O)NS(=O)(=O)c1cc2ccccc2s1]

5-chloro-2-isocyanato-1,3-diisopropylbenzene (prepared using general method A2) and benzo[b]thiophene-2-sulfonamide (prepared using general method E3) were used in general method C3 to give the titled compound as a white solid (38 mg, 72%); $^1$H NMR (600 MHz, DMSO-$d_6$) δ 8.03 (d, J=7.9 Hz, 1H), 7.93 (d, J=8.0 Hz, 2H), 7.80 (s, 1H), 7.46 (dt, J=15.4, 7.0 Hz, 2H), 7.04 (s, 2H), 3.05-2.83 (m, 2H), 0.94 (bs, 12H); $^{13}$C NMR (150 MHz, DMSO-$d_6$): δ 155.3, 149.5, 141.1, 138.0, 132.4, 132.0, 126.8, 125.7, 125.4, 123.1, 123.0, 122.9, 109.7, 28.5, 23.3; LCMS Purity: >95%; LCMS (m/z): 451 [M+H]$^+$; HRMS calculated for $C_{21}H_{24}Cl_1N_2O_3S_2$ [M+H]$^+$ 451.0911, found. 451.0900.

N-((1,2,3,5,6,7-hexahydro-s-indacen-4-yl)carbamoyl)-4-(2-(7-methoxy-4,4-dimethyl-1,3-dioxo-3,4-dihydroisoquinolin-2(1H)-yl)ethyl)benzenesulfonamide

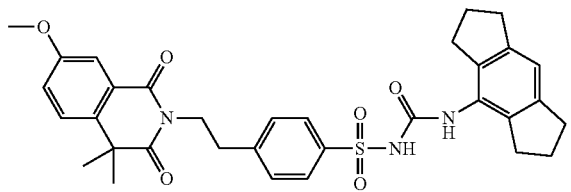 [SMILES: COc1ccc2c(c1)C(=O)N(CCc1ccc(S(=O)(=O)NC(=O)Nc3c4c(cc5c3CCC5)CCC4)cc1)C(=O)C2(C)C]

4-Isocyanato-1,2,3,5,6,7-hexahydro-s-indacene (prepared using general method A2) and 4-(2-(7-methoxy-4,4-dimethyl-1,3-dioxo-3,4-dihydroisoquinolin-2(1H)-yl)ethyl)benzenesulfonamide were used in general method C2 to give the titled compound as a white solid (85 mg, 52%). 1H NMR (600 MHz, DMSO-$d_6$) δ=10.72 (bs, 1H), 7.91 (s, 1H), 7.80 (d, J=8.1 Hz, 2H), 7.58 (d, J=8.7 Hz, 1H), 7.53 (d, J=2.9 Hz, 1H), 7.39 (d, J=7.9 Hz, 2H), 7.29 (dd, J=8.7, 2.9 Hz, 1H), 6.88 (s, 1H), 4.13 (t, J=7.5 Hz, 2H), 3.83 (s, 3H), 2.93 (t, J=7.5 Hz, 2H), 2.76 (t, J=7.4 Hz, 4H), 2.55 (t, J=7.4 Hz, 4H), 1.90 (p, J=7.4 Hz, 4H), 1.42 (s, 6H). HRMS calculated for $C_{33}H_{34}N_3O_6S_1$ [M–H]$^-$ 600.2174, found 600.2183.

N-(4-(N-((1,2,3,5,6,7-hexahydro-s-indacen-4-yl)carbamoyl)sulfamoyl)phenethyl)-5-methylisoxazole-3-carboxamide

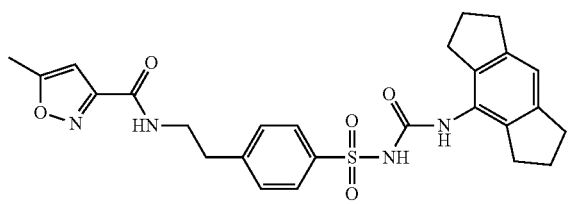 [SMILES: Cc1cc(C(=O)NCCc2ccc(S(=O)(=O)NC(=O)Nc3c4c(cc5c3CCC5)CCC4)cc2)no1]

4-Isocyanato-1,2,3,5,6,7-hexahydro-s-indacene (prepared using general method A2) and 5-methyl-N-(4-sulfamoylphenethyl)isoxazole-3-carboxamide were used in general method C2 to give the titled compound as a white solid (14 mg, 62%). $^1$H NMR (600 MHz, DMSO-$d_6$) δ 8.78 (t, J=5.8 Hz, 1H), 7.80 (s, 1H), 7.74 (d, J=8.3 Hz, 2H), 7.41 (d, J=8.3 Hz, 2H), 6.85 (s, 1H), 6.50 (q, J=1.0 Hz, 1H), 3.49 (m, 2H), 2.91 (t, J=7.0 Hz, 2H), 2.75 (t, J=7.4 Hz, 4H), 2.56 (t, J=7.4 Hz, 4H), 2.45 (d, J=0.9 Hz, 3H), 1.89 (p, J=7.4 Hz, 4H). HRMS calculated for $C_{26}H_{27}N_4O_5S_1$ [M–H]$^-$ 507.1708, found 507.1709.

3-Ethyl-N-(4-(N-((1,2,3,5,6,7-hexahydro-s-indacen-4-yl)carbamoyl)sulfamoyl)phenethyl)-4-methyl-2-oxo-2,5-dihydro-1H-pyrrole-1-carboxamide

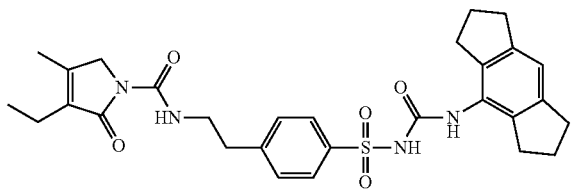 [SMILES: CCC1=C(C)CN(C(=O)NCCc2ccc(S(=O)(=O)NC(=O)Nc3c4c(cc5c3CCC5)CCC4)cc2)C1=O]

4-Isocyanato-1,2,3,5,6,7-hexahydro-s-indacene (prepared using general method A2) and 3-ethyl-4-methyl-2-oxo-N-(4-sulfamoylphenethyl)-2,5-dihydro-1H-pyrrole-1-carboxamide were used in general method C2 to give the titled compound as a white solid (78 mg, 50%). $^1$H NMR (600 MHz, DMSO-$d_6$) δ=10.78 (bs, 1H), 8.38 (t, J=7.6 Hz, 1H), 7.97 (s, 1H), 7.82 (d, J=8.2 Hz, 2H), 7.42 (d, J=8.2 Hz, 2H), 6.88 (s, 1H), 4.16 (s, 2H), 3.48 (q, J=6.7 Hz, 2H), 2.88 (t, J=7.2 Hz, 2H), 2.75 (t, J=7.4 Hz, 4H), 2.53 (t, J=7.4 Hz, 4H), 2.18 (q, J=7.5 Hz, 2H), 2.01 (s, 3H), 1.90 (p, J=7.4 Hz, 4H), 0.97 (t, J=7.5 Hz, 3H). HRMS calculated for $C_{29}H_{33}N_4O_5S_1$ [M–H]$^-$ 549.2177, found 549.2169.

5-Chloro-N-(4-(N-((1,2,3,5,6,7-hexahydro-s-indacen-4-yl)carbamoyl)sulfamoyl)phenethyl)-2-methoxybenzamide

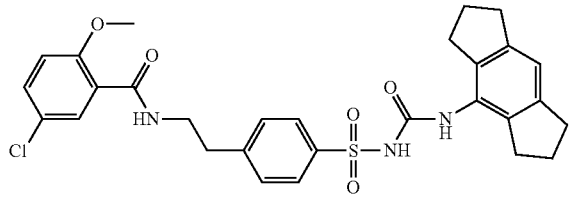 [SMILES: COc1ccc(Cl)cc1C(=O)NCCc1ccc(S(=O)(=O)NC(=O)Nc2c3c(cc4c2CCC4)CCC3)cc1]

4-Isocyanato-1,2,3,5,6,7-hexahydro-s-indacene (prepared using general method A2) and 5-chloro-2-methoxy-N-(4-sulfamoylphenethyl)benzamide were used in general method C2 to give the titled compound as a white solid (325 mg, 70%). $^1$H NMR (600 MHz, DMSO-$d_6$) δ=10.83 (bs, 1H), 8.27 (t, J=6.0 Hz, 1H), 7.96 (s, 1H), 7.84 (d, J=8.0 Hz, 2H), 7.66 (d, J=2.8 Hz, 1H), 7.50 (dd, J=8.9 Hz, 2.8 Hz, 1H), 7.44 (t, J=8.0 Hz, 2H), 7.13 (d, J=8.9 Hz, 1H), 6.87 (s, 1H), 3.78 (s, 3H), 3.53 (q, J=6.6 Hz, 2H), 2.91 (t, J=7.2 Hz, 2H), 2.74 (t, J=7.4 Hz, 4H), 2.53 (t, J=7.4 Hz, 4H), 1.88 (p, J=7.3 Hz, 4H). HRMS calculated for $C_{29}H_{29}Cl_1N_3O_5S_1$ [M–H]$^-$ 566.1522, found 566.1543.

¹³C NMR (100 MHz, DMSO-d₆): δ=163.6, 155.7, 145.3, 143.6, 143.0, 142.4, 142.1, 139.6, 137.1, 131.5, 129.5, 129.2, 127.4, 125.7, 124.8, 124.3, 117.9, 114.1, 108.3, 56.2, 34.7, 32.6, 32.4, 30.0, 28.9, 24.9. LCMS, Purity: 90.06%, tr=3.38 min, m/z 566.37 (M−H⁺). HRMS (FAB⁺) calcd for C₂₉H₃₀ClN₃O₅S [M+H]⁺: 568.1595, found: 568.1589.

Pyridines

N-(1,2,3,5,6,7-hexahydro-s-indacen-4-ylcarbamoyl)-4-(2-hydroxypropan-2-yl)pyridine-2-sulfonamide

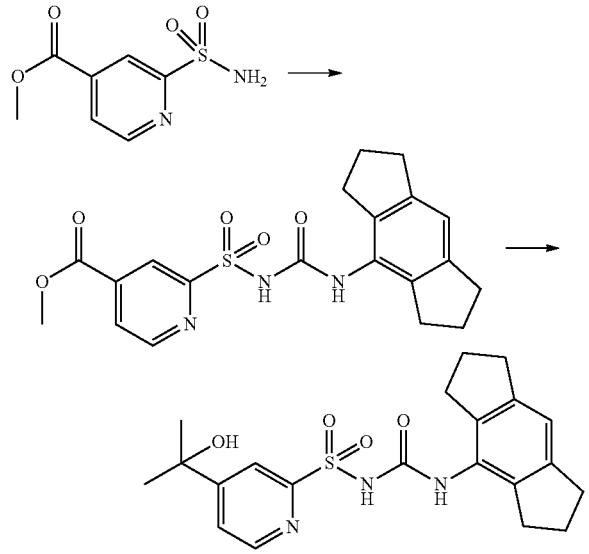

To a solution of 1,2,3,5,6,7-hexahydros-indacen-4-amine (0.20 g, 1.15 mmol) in anhydrous THF (5 mL), triethylamine (0.35 g, 3.47 mmol, 3.0 eq) was added followed by triphosgene (0.265 g, 0.86 mmol, 0.5 eq) at 0° C. and the mixture was stirred at ambient temperature for 3 h. The mixture was cooled to 0° C., methyl 2-sulfamoylisonicotinate (0.27 g, 1.27 mmol, 1.1 eq) added and stirring continued at ambient temperature overnight. Upon completion the reaction mixture was poured into brine and extracted with ethyl acetate. The combined organic extracts were washed with brine, dried (Na₂SO₄) and concentrated in vacuo. The crude product was purified by column chromatography on silica gel using 20-50% gradient of EtOAc-hexanes eluent to give methyl 2-(N-(1, 2, 3, 5, 6, 7-hexahydro-s-indacen-4-ylcarbamoyl)sulfamoyl)isonicotinate as a light brown solid (0.31 g, 65%).

Methyl 2-(N-(1,2,3,5,6,7-hexahydro-s-indacen-4-ylcarbamoyl)sulfamoyl)isonicotinate (0.30 g, 0.72 mmol) was dissolved in anhydrous THF (8 mL) and the solution cooled to 0° C. Methyl magnesium bromide (3 M solution in diethyl ether, 0.96 mL, 2.88 mmol, 4.0 eq) was added at 0° C. under nitrogen atmosphere and stirring continued at ambient temperature for 3 h. Upon completion the reaction mixture was poured into saturated aqueous ammonium chloride and extracted with ethyl acetate. The combined organic extracts were washed with brine, dried (Na₂SO₄) and concentrated in vacuo. The crude residue was purified by reverse phase prep HPLC to afford the titled compound as a white solid (0.016 g, 5%). ¹H NMR (400 MHz, CD₃OD): δ=8.45 (br.s, 1H), 8.16 (s, 1H), 7.55 (br.s, 1H), 6.87 (s, 1H), 2.80 (t, J=7.2 Hz, 4H), 2.66 (t, J=7.2 Hz, 4H), 1.96 (quin, J=7.6 Hz, 4H), 1.53 (s, 6H). LCMS, Purity: 98%, m/z 416.09 (M+H⁺). HRMS (FAB⁺) calcd for C₂₁H₂₅N₃O₄S [M+H]: 416.1566, found: 416.1556.

N-((1,2,3,5,6,7-hexahydro-s-indacen-4-yl)carbamoyl)-6,7-dihydro-5H-cyclopenta[b]pyridine-3-sulfonamide

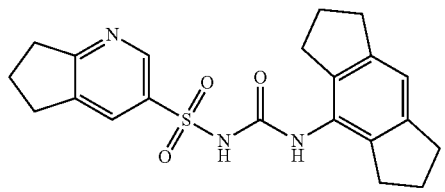 [SMILES: O=C(Nc1c2c(cc3c1CCC3)CCC2)NS(=O)(=O)c1cnc2c(c1)CCC2]

4-Isocyanato-1,2,3,5,6,7-hexahydro-s-indacene (prepared using general method A2) and 6,7-dihydro-5H-cyclopenta[b]pyridine-3-sulfonamide were used in general method C2 to give the titled compound as a white solid (12 mg, 27%). ¹H NMR (600 MHz, DMSO-d₆): δ=8.71 (s, 1H), 8.01 (s, 1H), 7.96 (bs, 1H), 6.87 (s, 1H), 2.97-2.93 (m, 4H), 2.75 (t, J=6 Hz, 4H), 2.55 (t, J=6 Hz, 4H), 2.11-2.07 (m, 2H), 1.93-1.88 (m, 4H). ¹³C NMR (150 MHz, DMSO-d₆): δ 169.6, 146.4, 144.9, 143.2, 137.4, 137.2, 131.0, 129.6, 117.7, 108.7, 34.0, 32.9, 30.6, 30.3, 25.4, 23.2. LCMS (m/z): 398 [M+H]⁺.

N-((1,2,3,5,6,7-hexahydro-s-indacen-4-yl)carbamoyl)pyridine-2-sulfonamide

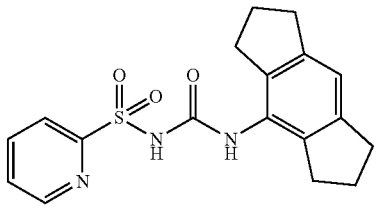 [SMILES: O=C(Nc1c2c(cc3c1CCC3)CCC2)NS(=O)(=O)c1ccccn1]

4-Isocyanato-8-methyl-1,2,3,5,6,7-hexahydro-s-indacene (prepared using general method A1) and pyridine-2-sulfonamide were used in general method C1 to give the titled compound as a white solid (40 mg, 10%). ¹H NMR (400 MHz, DMSO-d₆): δ=8.5 (d, J=4.0 Hz, 1H), 7.88 (t, J=7.6 Hz, 1H), 7.81 (t, J=7.6 Hz, 1H), 7.59 (s, 1H), 7.4 (t, J=5.8 Hz, 1H), 6.76 (s, 1H), 2.73 (t, J=7.2 Hz, 4H), 2.61 (t, J=7.2 Hz, 4H), 1.88 (quin, J=7.2 Hz, 4H).

N-((1,2,3,5,6,7-hexahydro-s-indacen-4-yl)carbamoyl)pyridine-3-sulfonamide

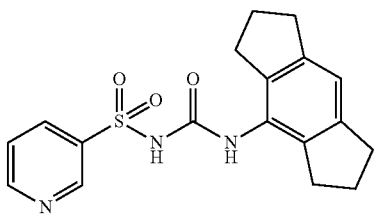 [SMILES: O=C(Nc1c2c(cc3c1CCC3)CCC2)NS(=O)(=O)c1cccnc1]

4-Isocyanato-8-methyl-1,2,3,5,6,7-hexahydro-s-indacene (prepared using general method A1) and pyridine-3-sulfonamide were used in general method C1 to give the titled compound as a white solid (12 mg, 3%). ¹H NMR (400 MHz, CD3OD): δ=9.08 (s, 1H), 8.65 (d, J=4.4 Hz, 1H), 8.36 (d, J=8.0 Hz, 1H), 7.56 (dd, J=8.0, 4.8 Hz, 1H), 6.88 (s, 1H), 2.82 (t, J=7.2 Hz, 4H), 2.69 (t, J=7.2 Hz, 4H), 2.0 (quin, J=7.2 Hz, 4H).

N-((1,2,3,5,6,7-hexahydro-s-indacen-4-yl)carbamoyl)-4-(trifluoromethyl)pyridine-2-sulfonamide

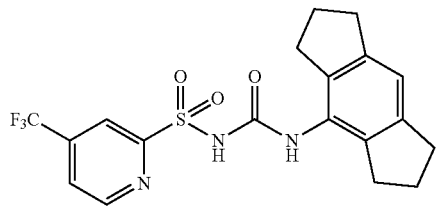 [SMILES: O=C(Nc1c2c(cc3c1CCC3)CCC2)NS(=O)(=O)c1cc(C(F)(F)F)ccn1]

4-Isocyanato-8-methyl-1,2,3,5,6,7-hexahydro-s-indacene (prepared using general method A1) and 4-(trifluoromethyl)pyridine-2-sulfonamide were used in general method C1 to give the titled compound as a white solid (16 mg, 3%). $^1$H NMR (400 MHz, CD$_3$OD): δ=8.47 (s, 1H), 8.22 (s, 1H), 7.42 (s, 1H), 6.98 (s, 1H), 2.82 (t, J=7.2 Hz, 4H), 2.66 (t, J=7.2 Hz, 4H), 1.95 (quin, J=7.2 Hz, 4H); 19F NMR (233.33 MHz, DMSO-d$_6$): −63.48 (s, 3F).

Linker

N-((1,2,3,5,6,7-hexahydro-s-indacen-4-yl)carbamothioyl)-4-(2-hydroxypropan-2-yl)furan-2-sulfonamide

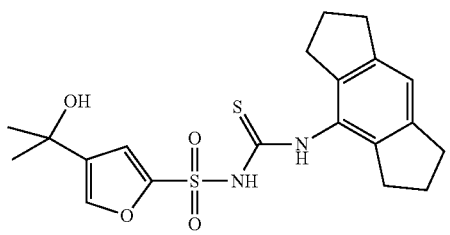 [SMILES: CC(C)(O)c1coc(S(=O)(=O)NC(=S)Nc2c3c(cc4c2CCC4)CCC3)c1]

To s solution of 1,2,3,5,6,7-hexahydro-s-indacen-4-amine (0.10 g, 0.58 mmol) in anhydrous DCM (2.0 mL) was added 1,1'-thiocarbonyldiimidazole (1.1 eq) and the reaction stirred for 4 h at ambient temperature. The solvent was removed in vacuo then the residue taken up in acetone (2.0 mL) and potassium carbonate (2.5 eq) was added followed by 4-(2-hydroxypropan-2-yl)furan-2-sulfonamide (1.2 eq). The reaction mixture was heated at reflux overnight, concentrated in vacuo then neutralized using 10% citric acid (10 mL) and immediately extracted using ethyl acetate (2×10 mL), dried (MgSO4) and concentrated in vacuo. The crude product was purified using column chromatography on silica with MeOH/DCM eluent followed by HPLC to give the titled compound as an off white solid (13 mg, 4%). $^1$H NMR (400 MHz, DMSO-d$_6$): δ=12.0 (bs, 1H), 9.72 (s, 1H), 7.88 (s, 1H), 7.43 (s, 1H), 7.01 (s, 1H), 5.15 (br.s., 1H), 2.81 (t, J=6.8 Hz, 4H), 2.59 (t, J=6.8 Hz, 4H), 1.95 (quin, J=7.6 Hz, 4H), 1.39 (s, 6H). $^{13}$C NMR (100 MHz, DMSO-d$_6$): δ=176.9, 143.1, 142.7, 138.7, 137.1, 130.4, 119.3, 117.7, 66.6, 32.4, 30.9, 29.9, 24.9. LCMS: Purity=95.08%, tr=3.45 min, m/z 421.30 (M+H$^+$).

Biological Testing Methodology

NLRP3 Inhibition Assays

The following assays can be used to determine inhibitory activity of test compounds on the NLRP3 inflammasome using common stimuli such as adenosine triphosphate, nigericin, LeuLeu-OMe or monosodium urate crystals (MSU).

Cell Culture

To generate HMDM, human monocytes are isolated from buffy coat blood using Ficoll-Plaque Plus (GE Healthcare) and density centrifugation. CD14$^+$ cell selection is performed using MACS magnetic beads (Miltenyl Biotec). Isolated CD14$^+$ monocytes are differentiated in culture for 7 days with 10 ng/ml human CSF-1 (Miltenyl Biotec) in Iscove's modified Dulbecco's medium (IMDM) containing L-glutamine supplemented with 10% FBS and 1% penicillin/streptomycin (Life Technologies) as described by Croker et al 2013 *Immunol Cell Biol* 91:625.

Mouse bone marrow-derived macrophages (BMDM) were derived from bone marrow progenitors isolated from the femurs and tibias of C57BL/6 mice. Bones were flushed with medium, and bone marrow cells were cultured for 7 days in RPMI 1640 medium supplemented with 10% heat inactivated FCS, 2 mM GlutaMAX (Life Technologies), 50 U/ml penicillin-streptomycin (Life Technologies) and 150 ng/ml recombinant human M-CSF (endotoxin-free, expressed and purified by The University of Queensland Protein Expression Facility).

NLRP3 Inflammasome Activation Assays

HMDM are seeded at 1×10$^5$/ml. The following day the overnight medium is replaced and cells are stimulated with *Escherichia coli* serotype 0111:B4 (Sigma Aldrich) for 3 h. Medium is removed and replaced with serum free medium (SFM) containing test compound 30 min prior to NLRP3 stimulation. Cells are then stimulated with: adenosine 5'-triphosphate disodium salt hydrate (5 mM 1 h), nigericin (10 μM 1 h), LeuLeu-OMe (1 mM 2 h) or MSU (200 μg/ml 15 h). ATP can be sourced from Sigma Aldrich, nigericin and MSU from Invivogen and LeuLeu-Ome from Chem-Impex International.

BMDM are seeded at 1×10$^5$/ml. The following day the overnight medium is replaced and cells are stimulated with Ultrapure lipopolysaccharide from *Escherichia coli* K12 strain (InvivoGen) for 3 h. Medium is removed and replaced with serum free medium (SFM) containing test compound 30 min prior to NLRP3 stimulation. Cells are then stimulated with: adenosine 5'-triphosphate disodium salt hydrate (1.25-5 mM 1 h), nigericin (5 μM 1 h), LeuLeu-OMe (1 mM 2 h) or MSU (200 μg/ml 15 h). ATP can be sourced from Sigma Aldrich, nigericin and MSU from Invivogen and LeuLeu-Ome from Chem-Impex International.

Measurement of IL-1β, IL-18, TNFα and Cell Death

For ELISA and cell death assays cells are seeded in 96 well plates. Supernatants are removed and analysed using ELISA kits according to the manufacturer's instructions (DuoSet® R&D Systems, ReadySetGo!® eBioscience, BD OptEIA™, or Perkin Elmer AlphaLISA®). Cell death is assessed by measurement of LDH release relative to a 100% cell lysis control using the CytoTox96® non-radioactive cytotoxicity assay (Promega).

Murine Studies on Compound Levels in Blood Plasma and Brain

General experimental: Carbutamide was purchased from Sigma Aldrich (Catalogue No. 381578). Acetonitrile was Chromasolv® HPLC grade (Sigma Aldrich, Sydney, Australia), the formic acid was AR grade 99%-100% Normapur (VWR International Pty Ltd, Brisbane, Australia), DMSO was ReagentPlus® grade (D5879, Sigma Aldrich, Sydney, Australia) and the H$_2$O Milli-Q was filtered. The HPLC vial and polypropylene inserts from Agilent Technologies (Melbourne, Australia), while the 1.5 mL Eppendorf tubes Protein LoBind Tubes were from VWR International Pty Ltd (Brisbane, Australia).

Preparation of Precipitation Solution:

100 mL ACN and 5 µL of 10 mM carbutamide in DMSO (ACN with 135 ng/mL carbutamide MS internal standard).

Preparation of Standard Curve in Plasma:

A 1 mg/mL of test compound in 10 mM $NH_4HCO_3$ was prepared and diluted 10-fold to give a 100,000 ng/mL stock solution. A series of 10-fold dilutions of the 100,000 ng/mL stock solution with 10 mM $NH_4HCO_3$ gave concentrations of 10,000, 1,000, 100 and 10 ng/mL. The 100,000 ng/mL stock solution was diluted to 3:7 with 10 mM $NH_4HCO_3$ to give a concentration of 30,000 ng/mL and a series of 10-fold dilutions gave concentrations of 3,000, 300, 30 and 3 ng/mL.

20 µL of test compound-containing solution and 160 µL precipitation solution were added to 20 µL of mouse plasma in a low binding Eppendorf tube. The samples were vortexed, allowed to stand at 4° C. for 10 mins and centrifuged at 14,000×g for 8 min. 150 µL of the supernatant was transferred to an HPLC vial insert. The samples were stored at 4° C. until analysis.

Preparation of Standard Curve in Brain Homogenate:

The sample solutions prepared for the plasma standard curve were used for the brain homogenate standard curve.

The mouse brain homogenate from the saline control was thawed and vortexed for 3 min or until homogenous, sonicated for 1 min. When the foam settled, 50 µL of mouse brain homogenate was transferred into an Eppendorf tube, followed by 50 µL of test compound in 10 mM $NH_4HCO_3$, 150 µL of $H_2O$ and 500 µL of ice cold precipitation solution with vortexing after every addition. The standards were allowed to stand at 4° C. for 10 mins and then centrifuged at 14,000×g for 8 min. 200 µL of the supernatant was transferred to HPLC vial insert ensuring that no air bubbles were present and the samples stored at 4° C. until analysis.

Dosing of Mice and Transcardial Perfusion

Dosing: Oral gavage at 20 mg/kg

Time point: 2 hour

Prepare stock compounds for dosing at 4 mg/ml in sterile PBS. Mice were weighed and dosed by oral gavage at 20 mg/kg for each compound. After 2 hours mice were anesthetized using a combination of Zoletil (50 mg/kg) and Xylazine (10 mg/kg) and blood was collected by cardiac puncture into tubes containing 20 µL of 100 mM EDTA. The blood was centrifuged at 2000×g for 15 minutes at 4° C. to collect plasma.

Preparation of Plasma Samples for Analysis:

20 µL of $NH_4HCO_3$ and 160 µL precipitation solution were added to 20 µL of mouse plasma in a low binding Eppendorf tube. The samples were vortexed, allowed to stand at 4° C. for 10 mins and centrifuged at 14,000×g for 8 min. 150 µL of the supernatant was transferred to an HPLC vial insert ensuring that no air bubbles were present. The samples were stored at 4° C. until analysis.

Brain Homogenate Preparation:

The brains of mice were perfused with PBS for 5 minutes then dissected and weighed. Brain homogenate was prepared by homogenizing total brain (0.5 g) with 4 volumes (2 ml) of deionized water and stored at −20° C. before analysis. The homogenate was thawed, vortexed for 3 min or until homogenous, and sonicated for 1 min. When the foam settled, 50 µL of mouse brain homogenate was transferred into an Eppendorf tube, followed by 50 µL of 10 mM $NH_4HCO_3$, 150 µL of $H_2O$ and 500 µL of ice cold precipitation solution with vortexing after every addition. 200 µL of the supernatant was transferred to HPLC vial insert ensuring that no air bubbles were present and the samples stored at 4° C. until analysis.

Preparation of Brain Samples for Analysis:

50 µL of mouse brain was transferred into an Eppendorf tube, followed by 50 µL of 10 mM $NH_4HCO_3$, 150 µL of $H_2O$ and 500 µL of ice cold precipitation solution with vortexing after every addition. The solutions were allowed to stand at 4° C. for 10 mins and then centrifuged at 14,000×g for 8 min. 200 µL of the supernatant was transferred to HPLC vial insert ensuring that no air bubbles were present and the samples stored at 4° C. until analysis.

LC-MS/MS:

The samples were analysed on an AB Sciex 4000QTrap MS with 2 Shimadzu Nexera LC-30AD Solvent Delivery Units, Shimadzu Nexera SIL-30AC Auto-Sampler, Shimadzu Prominence DGU-20A$_5$ Degasser, Shimadzu Prominence CBM-20A System Controller and Shimadzu Prominence CTO-20A Column Oven. The column oven was set to 40° C., while the Autosampler was set to 15° C. 2 µL injections were made and MS analyses were undertaken in Selected Reaction Monitoring (SRM) mode using Turbo Spray (−)-ESI with Low Resolution Q1 and Low Resolution Q3. MS parameters: CUR: 30.00, IS: −4300.00, TEM: 500.00, GS1: 50.00, GS2: 50.00, ihe: ON, CAD: High, DP −60.00, EP −10.00, CXP −15.00. MCC950 SRM: Q1 403.2 to Q3 204.3 Da, dwell 150 msec, CE −27 and carbutamide (IS) SRM: Q1 270.0 to Q3 171.0 Da, dwell 100 msec, CE −25. HPLC Column: Waters Atlantis® T3 5 µm 2.1×50 mm with Atlantis® T3 5 µm 2.1×10 mm guard column. Flow rates and solvent: 0.35 ml/min, solvent A: 0.1% formic acid in $H_2O$, solvent B: 0.1% formic acid in ACN; isocratic 2% B from 0→2 mins, gradient 2%→100% B from 2→5 mins, isocratic 100% from 5→9 mins, gradient 100%→2% B from 9→9.1 mins and isocratic 2% B from 9.1→13 mins. The peak areas from the SRM data for carbutamide and test compound were analysed using the AB Sciex's Analyst software using the Quantitation Wizard. The peak area was plotted against the ng/mL concentration in 20 µL 3 to 30,000 ng/mL test compound solutions and the lower and upper range of linear response was determined. These data were then plotted in Microsoft Excel and the linear response equation used to determine the test compound concentration in the 20 µL plasma solutions. Similarly, for the brain homogenate samples, the peak areas of the 50 µL 3 to 3,000 ng/mL test compound solutions were used to determine the test compound concentration in the 50 µL brain homogenate solutions.

Results

The full series of tPSA and biological results are provided in the tables below, however select data is presented below for certain compounds of the invention.

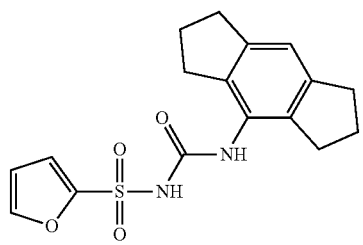

MCC7401
IC$_{50}$ 108 nM

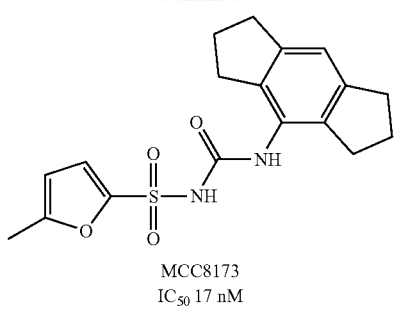
MCC8173
IC$_{50}$ 17 nM
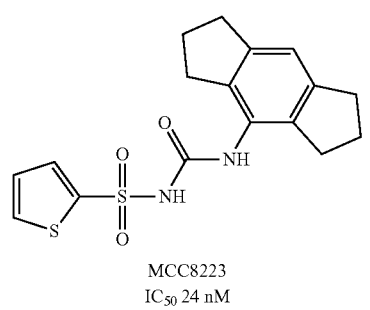
MCC8223
IC$_{50}$ 24 nM
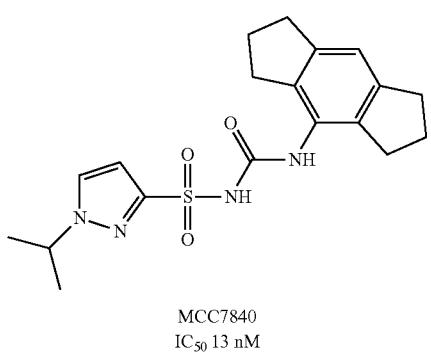
MCC7840
IC$_{50}$ 13 nM
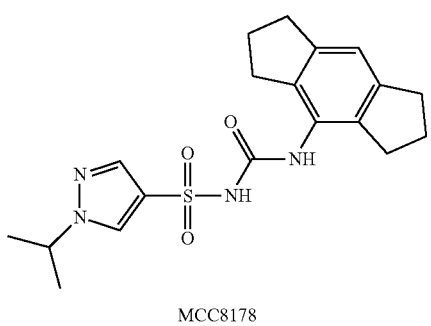
MCC8178
IC$_{50}$ 11 nM
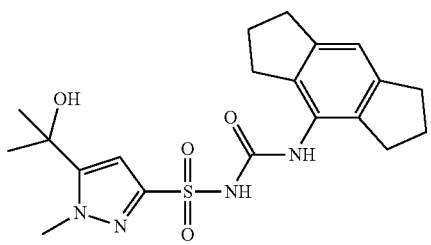
MCC7441
IC$_{50}$ 40 nM
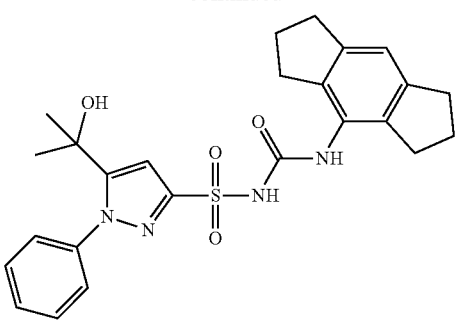
MCC7838
IC$_{50}$ 15 nM
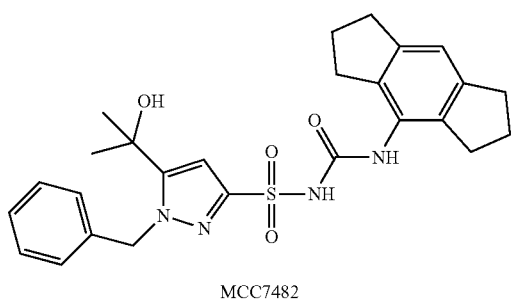
MCC7482
IC$_{50}$ 26 nM
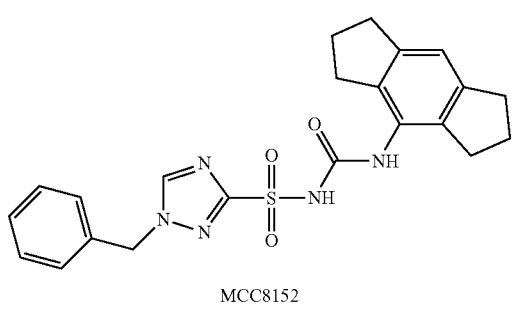
MCC8152
IC$_{50}$ 28 nM
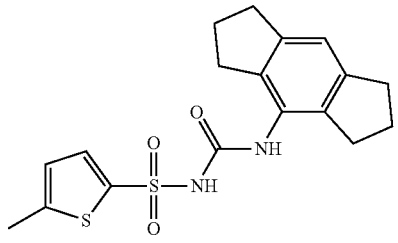
MCC8219
IC$_{50}$ 50 nM
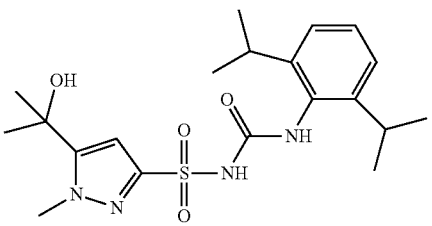
MCC7831
IC$_{50}$ 25 nM

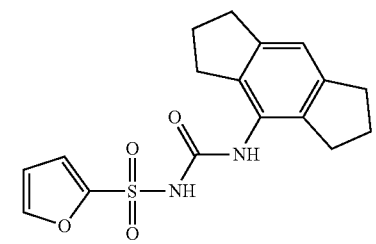
MCC7401
IC$_{50}$ 108 nM
PSA 84
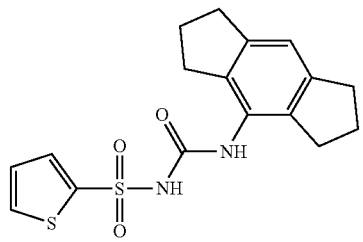
MCC8223
IC$_{50}$ 24 nM
PSA 75
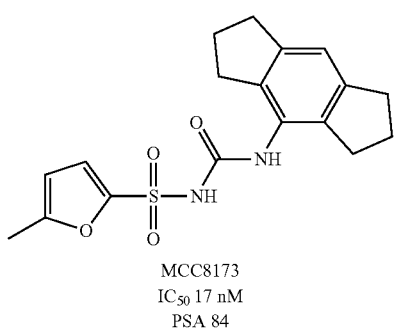
MCC8173
IC$_{50}$ 17 nM
PSA 84
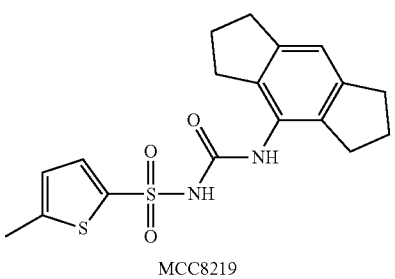
MCC8219
IC$_{50}$ 50 nM
PSA 75
TABLE 1
Topological Polar Surface Area (tPSA) and molecular weight of select compounds.
| SMILES | NAME | tPSA | MV |
|---|---|---|---|
| O=C(NC1=C2C(CCC2)=CC3=C1CCC3)NS(C4CCCCC4)(=O)=O | N-((1,2,3,5,6,7-hexahydro-s-indacen-4-yl)carbamoyl)cyclohexanesulfonamide | 75 | 362 |
| O=C(NC1=C2CCCC2=CC3=C1CCC3)NS(C4CCCC4)(=O)=O | N-((1,2,3,5,6,7-hexahydro-s-indacen-4-yl)carbamoyl)cyclopentanesulfonamide | 75 | 348 |

TABLE 1-continued

Topological Polar Surface Area (tPSA) and molecular weight of select compounds.

| SMILES | NAME | tPSA | MV |
|---|---|---|---|
| 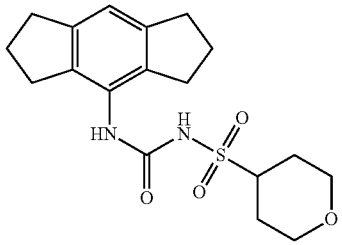 [SMILES: O=C(Nc1c2c(cc3c1CCC3)CCC2)NS(=O)(=O)C1CCOCC1]<br>O=S(C1CCOCC1)(NC2=C3CCCC3=C<br>C4=C2CCC4)=O)=O | N-((1,2,3,5,6,7-hexahydro-s-indacen-4-yl)carbamoyl)tetrahydro-2H-pyran-4-sulfonamide | 85 | 364 |
| 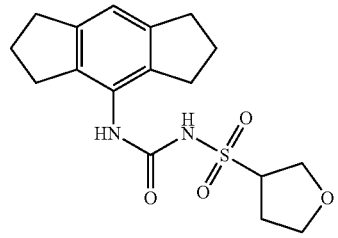 [SMILES: O=C(Nc1c2c(cc3c1CCC3)CCC2)NS(=O)(=O)C1CCOC1]<br>O=C(NC1=C2CCCC2=CC3=C1CCC3)NS(<br>C4COCC4)(=O)=O | N-((1,2,3,5,6,7-hexahydro-s-indacen-4-yl)carbamoyl)tetrahydrofuran-3-sulfonamide | 85 | 350 |
| 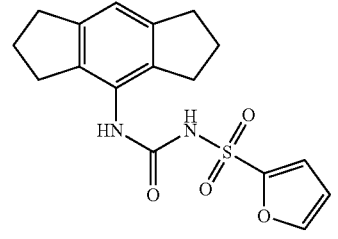 [SMILES: O=C(Nc1c2c(cc3c1CCC3)CCC2)NS(=O)(=O)c1ccco1]<br>O=C(NC1=C2C(CCC2)=CC3=C1CCC3)NS<br>(C4=CC=CO4)(=O)=O | N-((1,2,3,5,6,7-hexahydro-s-indacen-4-yl)carbamoyl)furan-2-sulfonamide | 85 | 346 |
| 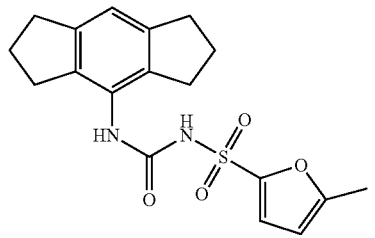 [SMILES: Cc1ccc(S(=O)(=O)NC(=O)Nc2c3c(cc4c2CCC4)CCC3)o1]<br>CC1=CC=C(S(NC(NC2=C3CCCC3=CC4=<br>C2CCC4)=O)(=O)=O)O1 | N-((1,2,3,5,6,7-hexahydro-s-indacen-4-yl)carbamoyl)-5-methylfuran-2-sulfonamide | 85 | 360 |
| 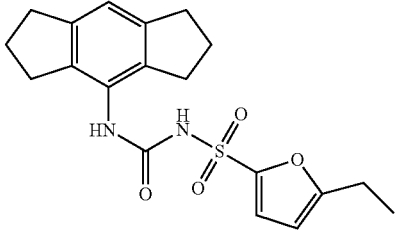 [SMILES: CCc1ccc(S(=O)(=O)NC(=O)Nc2c3c(cc4c2CCC4)CCC3)o1]<br>CCC1=CC=C(S(NC(NC2=C3CCCC3=CC4<br>=C2CCC4)=O)(=O)=O)O1 | 5-ethyl-N-((1,2,3,5,6,7-hexahydro-s-indacen-4-yl)carbamoyl)furan-2-sulfonamide | 85 | 374 |

TABLE 1-continued

Topological Polar Surface Area (tPSA) and molecular weight of select compounds.

| SMILES | NAME | tPSA | MV |
|---|---|---|---|
| 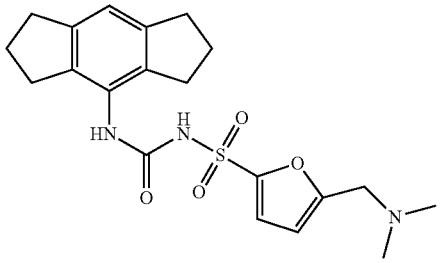 [SMILES: CN(C)Cc1ccc(S(=O)(=O)NC(=O)Nc2c3c(cc4c2CCC4)CCC3)o1]<br>O=S(NC(NC1=C2C(CCC2)=CC3=C1CCC3)=O)(C4=CC=C(CN(C)C)O4)=O | 5-((dimethylamino)methyl)-N-((1,2,3,5,6,7-hexahydro-s-indacen-4-yl)carbamoyl)furan-2-sulfonamide | 88 | 403 |
| 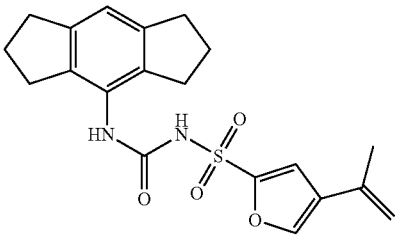 [SMILES: C=C(C)c1coc(S(=O)(=O)NC(=O)Nc2c3c(cc4c2CCC4)CCC3)c1]<br>O=S(C1=CC(C(C)=C)=CO1)(NC(NC2=C(CCC3)C3=CC4=C2CCC4)=O)=O | N-((1,2,3,5,6,7-hexahydro-s-indacen-4-yl)carbamoyl)-4-(prop-1-en-2-yl)furan-2-sulfonamide | 85 | 386 |
| 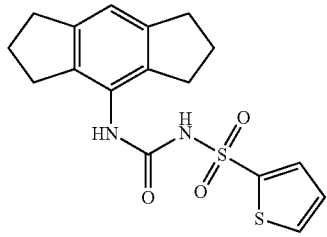 [SMILES: O=C(Nc1c2c(cc3c1CCC3)CCC2)NS(=O)(=O)c1cccs1]<br>O=C(NC1=C2CCCC2=CC3=C1CCC3)NS(C4=CC=CS4)(=O)=O | N-((1,2,3,5,6,7-hexahydro-s-indacen-4-yl)carbamoyl)thiophene-2-sulfonamide | 75 | 362 |
| 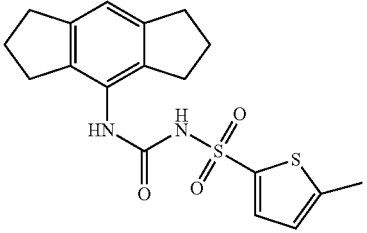 [SMILES: Cc1ccc(S(=O)(=O)NC(=O)Nc2c3c(cc4c2CCC4)CCC3)s1]<br>O=S(NC(NC1=C2C(CCC2)=CC3=C1CCC3)=O)(C4=CC=C(C)S4)=O | N-((1,2,3,5,6,7-hexahydro-s-indacen-4-yl)carbamoyl)-5-methylthiophene-2-sulfonamide | 75 | 376 |
| 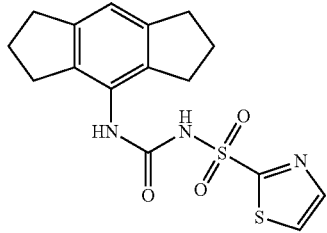 [SMILES: O=C(Nc1c2c(cc3c1CCC3)CCC2)NS(=O)(=O)c1nccs1]<br>O=C(NC1=C2C(CCC2)=CC3=C1CCC3)NS(C4=NC=CS4)(=O)=O | N-((1,2,3,5,6,7-hexahydro-s-indacen-4-yl)carbamoyl)thiazole-2-sulfonamide | 88 | 363 |

TABLE 1-continued

Topological Polar Surface Area (tPSA) and molecular weight of select compounds.

| SMILES | NAME | tPSA | MV |
|---|---|---|---|
| 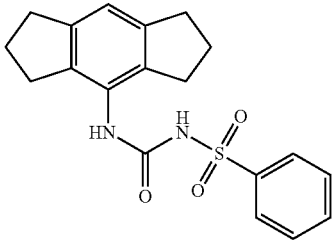 [SMILES: O=C(Nc1c2c(cc3c1CCC3)CCC2)NS(=O)(=O)c1ccccc1]<br>O=S(C1=CC=CC=C1)(NC(NC2=C(CCC3)C3=CC4=C2CCC4)=O)=O | N-((1,2,3,5,6,7-hexahydro-s-indacen-4-yl)carbamoyl)benzenesulfonamide | 75 | 356 |
| 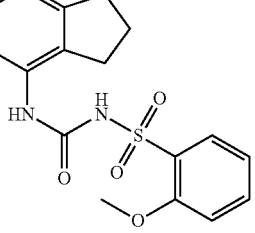<br>O=C(NC1=C2C(CCC2)=CC3=C1CCC3)NS(C4=C(OC)C=CC=C4)(=O)=O | N-((1,2,3,5,6,7-hexahydro-s-indacen-4-yl)carbamoyl)-2-methoxybenzenesulfonamide | 85 | 386 |
| 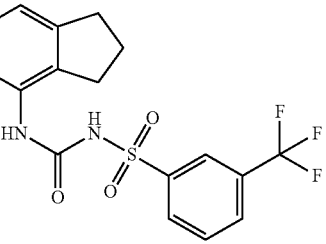<br>FC(F)(F)C1=CC=CC(S(=O)(NC(NC2=C3CCCC3=CC4=C2CCC4)=O)=O)=C1 | N-((1,2,3,5,6,7-hexahydro-s-indacen-4-yl)carbamoyl)-3-(trifluoromethyl)benzenesulfonamide | 75 | 424 |
| 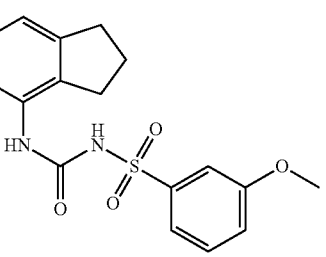<br>O=S(C1=CC(OC)=CC=C1)(NC(NC2=C(CCC3)C3=CC4=C2CCC4)=O)=O | N-((1,2,3,5,6,7-hexahydro-s-indacen-4-yl)carbamoyl)-3-methoxybenzenesulfonamide | 85 | 386 |

TABLE 1-continued

Topological Polar Surface Area (tPSA) and molecular weight of select compounds.

| SMILES | NAME | tPSA | MV |
|---|---|---|---|
| O=S(C1=CC(OC(F)(F)F)=CC=C1)(NC(NC2=C(CCC3)C3=CC4=C2CCC4)=O)=O | N-((1,2,3,5,6,7-hexahydro-s-indacen-4-yl)carbamoyl)-3-(trifluoromethoxy)benzenesulfonamide | 85 | 440 |
| O=S(C1=CC(OC(F)F)=CC=C1)(NC(NC2=C(CCC3)C3=CC4=C2CCC4)=O)=O | 3-(difluoromethoxy)-N-((1,2,3,5,6,7-hexahydro-s-indacen-4-yl)carbamoyl)benzenesulfonamide | 85 | 422 |
| O=C(NC1=C2C(CCC2)=CC3=C1CCC3)NS(C4=CC=C(Cl)C=C4)(=O)=O | 4-chloro-N-((1,2,3,5,6,7-hexahydro-s-indacen-4-yl)carbamoyl)benzenesulfonamide | 75 | 391 |
| O=C(NC1=C2C(CCC2)=CC3=C1CCC3)NS(C4=CC=C(C)C=C4)(=O)=O | N-((1,2,3,5,6,7-hexahydro-s-indacen-4-yl)carbamoyl)-4-methylbenzenesulfonamide | 75 | 370 |

TABLE 1-continued

Topological Polar Surface Area (tPSA) and molecular weight of select compounds.

| SMILES | NAME | tPSA | MV |
|---|---|---|---|
| 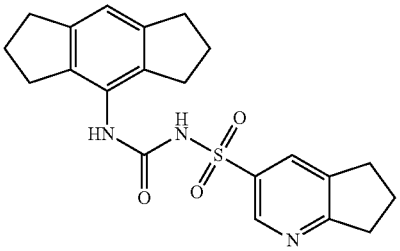 [SMILES: O=C(Nc1c2c(cc3c1CCC3)CCC2)NS(=O)(=O)c1cnc2c(c1)CCC2]<br>O=C(NC1=C2CCCC2=CC3=C1CCC3)NS(C4=CN=C5CCCC5=C4)(=O)=O | N-((1,2,3,5,6,7-hexahydro-s-indacen-4-yl)carbamoyl)-6,7-dihydro-5H-cyclopenta[b]pyridine-3-sulfonamide | 88 | 397 |
| 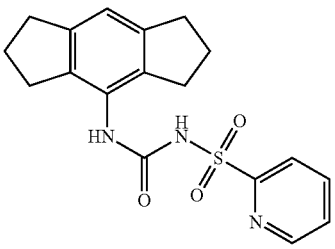 [SMILES: O=C(Nc1c2c(cc3c1CCC3)CCC2)NS(=O)(=O)c1ccccn1]<br>O=S(C1=CC=CC=N1)(NC(NC2=C(CCC3)C3=CC4=C2CCC4)=O)=O | N-((1,2,3,5,6,7-hexahydro-s-indacen-4-yl)carbamoyl)pyridine-2-sulfonamide | 88 | 357 |
| 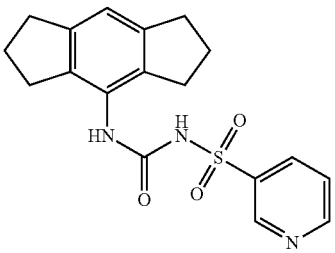 [SMILES: O=C(Nc1c2c(cc3c1CCC3)CCC2)NS(=O)(=O)c1cccnc1]<br>O=S(C1=CC=CN=C1)(NC(NC2=C(CCC3)C3=CC4=C2CCC4)=O)=O | N-((1,2,3,5,6,7-hexahydro-s-indacen-4-yl)carbamoyl)pyridine-3-sulfonamide | 88 | 357 |
| 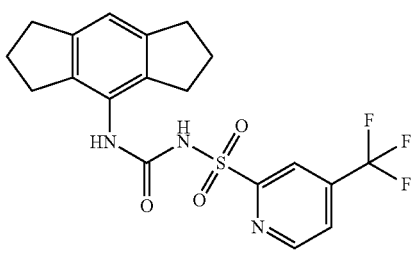 [SMILES: O=C(Nc1c2c(cc3c1CCC3)CCC2)NS(=O)(=O)c1cc(C(F)(F)F)ccn1]<br>O=S(C1=CC(C(F)(F)F)=CC=N1)(NC(NC2=C(CCC3)C3=CC4=C2CCC4)=O)=O | N-((1,2,3,5,6,7-hexahydro-s-indacen-4-yl)carbamoyl)-4-(trifluoromethyl)pyridine-2-sulfonamide | 88 | 425 |

TABLE 2

Compound HRMS characterisation data; Inhibition of IL-1β release IC50 in nM cell based assay using either HMDM or BMDM (<100 nM = '++++'/ <1 μM = '+++'/<10 μM = '++'/<50 μM = '+'); Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-((1,2,3,5,6,7-hexahydro-s-indacen-4-yl)carbamoyl)cyclohexanesulfonamide | C19H26N2O3S | C19H27N2O3S | ESI+ | 363.1737 | 363.1729 | ND | ++ | ND |
| N-((1,2,3,5,6,7-hexahydro-s-indacen-4-yl)carbamoyl)cyclopentanesulfonamide | C18H24N2O3S | C18H25N2O3S | ESI+ | 349.158 | 349.1588 | ND | ++ | ND |
| N-((1,2,3,5,6,7-hexahydro-s-indacen-4-yl)carbamoyl)tetrahydro-2H-pyran-4-sulfonamide | C18H24N2O4S | C18H25N2O4S | ESI+ | 365.153 | 365.1541 | ND | +++ | ND |
| N-((1,2,3,5,6,7-hexahydro-s-indacen-4-yl)carbamoyl)tetrahydrofuran-3-sulfonamide | C17H22N2O4S | C17H23N2O4S | ESI+ | 351.1373 | 351.1389 | ND | ++ | ND |
| N-((1,2,3,5,6,7-hexahydro-s-indacen-4-yl)carbamoyl)morpholine-4-sulfonamide | C17H23N3O4S | C 17 H 24 N 3 O 4 S 1 | ESI+ | 366.1482 | 366.14956 | ND | ++ | ND |
| N-[1,2,3,5,6,7-hexahydro-s-indacen-4-yl]-N'-[(dimethylamino)sulfonyl]urea | C15H21N3O3S | C 15 H 22 N 3 O 3 S 1 | ESI+ | 324.13764 | 324.13891 | ND | ++ | ND |
| N-((1,2,3,5,6,7-hexahydro-s-indacen-4-yl)carbamoyl)furan-2-sulfonamide | C17H18N2O4S | C 17 H 17 N 2 O 4 S 1 | ESI− | 345.0915 | 345.0906 | +++ | +++ | ND |
| N-((1,2,3,5,6,7-hexahydro-s-indacen-4-yl)carbamoyl)-5-methylfuran-2-sulfonamide | C18H20N2O4S | C18H21N2O4S | ESI+ | 361.1216 | 361.1217 | ND | ++++ | ++++ |
| 5-ethyl-N-((1,2,3,5,6,7-hexahydro-s-indacen-4-yl)carbamoyl)furan-2-sulfonamide | C19H22N2O4S | C19H22N2O4S | ESI+ | 375.1373 | 375.1391 | ND | +++ | ND |
| 5-((dimethylamino)methyl)-N-((1,2,3,5,6,7-hexahydro-s-indacen-4-yl)carbamoyl)furan-2-sulfonamide | C20H25N3O4S | C 20 H 26 N 3 O 4 S 1 | ESI+ | 404.1639 | 404.1653 | ND | ++++ | ND |
| N-((1,2,3,5,6,7-hexahydro-s-indacen-4-yl)carbamoyl)-4-(2-hydroxypropan-2-yl)furan-2-sulfonamide | C20H24N2O5S | C 20 H 23 N 2 O 5 S 1 | ESI− | 403.1333 | 403.1351 | ND | ++++ | ++++ |

TABLE 2-continued

Compound HRMS characterisation data; Inhibition of IL-1β release IC50 in nM cell based assay using either HMDM or BMDM (<100 nM = '++++'/ <1 μM = '+++'/<10 μM = '++'/<50 μM = '+'). Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-((8-bromo-1,2,3,5,6,7-hexahydro-s-indacen-4-yl)carbamoyl)-4-(2-hydroxypropan-2-yl)furan-2-sulfonamide | C20H23BrN2O5S | C 20 H 22 Br 1 N 2 O 5 S 1 | ESI− | 481.0438 | 481.043 and 483.0392 | ++++ | +++ | ND |
| N-((8-chloro-1,2,3,5,6,7-hexahydro-s-indacen-4-yl)carbamoyl)-4-(2-hydroxypropan-2-yl)furan-2-sulfonamide | C20H23ClN2O5S | C 20 H 22 Cl 1 N 2 O 5 S 1 | ESI− | 437.0943 | 437.0941 | ++++ | ++++ | ND |
| 4-(2-hydroxypropan-2-yl)-N-((8-methyl-1,2,3,5,6,7-hexahydro-s-indacen-4-yl)carbamoyl)furan-2-sulfonamide | C21H26N2O5S | C 21 H 25 N 2 O 5 S 1 | ESI− | 417.149 | 417.1499 | ++++ | ++++ | ND |
| 5-(N-((1,2,3,5,6,7-hexahydro-s-indacen-4-yl)carbamoyl)sulfamoyl)furan-3-carboxylic acid | C18H18N2O6S | C 18 H 17 N 2 O 6 S 1 | ESI− | 389.0813 | 389.0796 | ++ | ND | ND |
| ethyl 5-(N-((1,2,3,5,6,7-hexahydro-s-indacen-4-yl)carbamoyl)sulfamoyl)furan-3-carboxylate | C20H22N2O6S | C 20 H 21 N 2 O 6 S 1 | ESI− | 417.1126 | 417.1117 | +++ | ND | ND |
| N-((1,2,3,5,6,7-hexahydro-s-indacen-4-yl)carbamoyl)-4-(prop-1-en-2-yl)furan-2-sulfonamide | C20H22N2O4S | C 20 H 23 N 2 O 4 S 1 | ESI+ | 387.1373 | 387.1379 | +++ | +++ | ND |
| 4-(2-hydroxypropan-2-yl)-N-((3,5,6,7-tetrahydro-2H-indeno[5,6-b]furan-8-yl)carbamoyl)furan-2-sulfonamide | C19H22N2O6S | C 19 H 21 N 2 O 6 S 1 | ESI− | 405.1126 | 405.1113 | ++++ | ND | ND |
| N-((4-bromo-3,5,6,7-tetrahydro-2H-indeno[5,6-b]furan-8-yl)carbamoyl)-4-(2-hydroxypropan-2-yl)furan-2-sulfonamide | C19H21BrN2O6S | C 19 H 20 Br 1 N 2 O 6 S 1 | ESI− | 483.0231 | 483.0232 | ++++ | ND | ND |
| 4-(2-hydroxypropan-2-yl)-N-((3,5,6,7-tetrahydro-2H-indeno[5,6-b]furan-4-yl)carbamoyl)furan-2-sulfonamide | C19H22N2O6S | C 19 H 21 N 2 O 6 S 1 | ESI− | 405.1126 | 405.1116 | ++++ | ND | ND |

TABLE 2-continued

Compound HRMS characterisation data; Inhibition of IL-1β release IC50 in nM cell based assay using either HMDM or BMDM (<100 nM = '++++'/ <1 µM = '+++'/<10 µM = '++'/<50 µM = '+'); Inhibition of IL-18 release IC50 in nM cell based assay using HMDM (<100 nM = '++++'/<1 µM = '+++'/<10 µM = '++'/<50 µM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| 4-(2-hydroxypropan-2-yl)-N-((2,3,6,7-tetrahydrobenzo[1,2-b:4,5-b']difuran-4-yl)carbamoyl)furan-2-sulfonamide | C18H20N2O7S | C 18 H 19 N 2 O 7 S 1 | ESI− | 407.0918 | 407.0915 | +++ | ND | ND |
| N-(benzo[1,2-b:4,5-b']difuran-4-yl)carbamoyl)-4-(2-hydroxypropan-2-yl)furan-2-sulfonamide | C18H16N2O7S | C 18 H 15 N 2 O 7 S 1 | ESI− | 403.0605 | 403.0604 | ++++ | ND | ND |
| N-(anthracen-9-yl)carbamoyl)-4-(2-hydroxypropan-2-yl)furan-2-sulfonamide | C22H20N2O5S | C 22 H 19 N 2 O 5 S 1 | ESI− | 423.102 | 423.1038 | ++ | ND | ND |
| 4-(2-hydroxypropan-2-yl)-N-((quinolin-8-yl)carbamoyl)furan-2-sulfonamide | C17H17N3O5S | C 17 H 16 N 3 O 5 S 1 | ESI− | 374.0816 | 374.0805 | ND | ++ | ND |
| 4-(2-hydroxypropan-2-yl)-N-(((6-methoxyquinolin-8-yl)carbamoyl)furan-2-sulfonamide | C18H19N3O6S | C 18 H 18 N 3 O 6 S 1 | ESI− | 404.0922 | 404.0913 | ND | ++ | ND |
| N-((2,3-dihydrobenzo[b][1,4]dioxin-5-yl)carbamoyl)-4-(2-hydroxypropan-2-yl)furan-2-sulfonamide | C16H18N2O7S | C 16 H 17 N 2 O 7 S 1 | ESI− | 381.0762 | 381.078 | ++ | ND | ND |
| N-((2,3-dihydrobenzofuran-7-yl)carbamoyl)-4-(2-hydroxypropan-2-yl)furan-2-sulfonamide | C16H18N2O6S | C 16 H 17 N 2 O 6 S 1 | ESI− | 365.0813 | 365.0823 | + | ND | ND |
| N-((2,4-bis(trifluoromethyl)phenyl)carbamoyl)-4-(2-hydroxypropan-2-yl)furan-2-sulfonamide | C16H14F6N2O5S | C 16 H 13 F 6 N 2 O 5 S 1 | ESI− | 459.0455 | 459.0476 | +++ | ++ | ND |
| N-((2,5-bis(trifluoromethyl)phenyl)carbamoyl)-4-(2-hydroxypropan-2-yl)furan-2-sulfonamide | C16H14F6N2O5S | C 16 H 13 F 6 N 2 O 5 S 1 | ESI− | 459.0455 | 459.0453 | +++ | ++ | ND |

TABLE 2-continued

Compound HRMS characterisation data; Inhibition of IL-1β release IC50 in nM cell based assay using either HMDM or BMDM (<100 nM = '++++'/ <1 μM = '+++'/<10 μM = '++'/<50 μM = '+'); Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| 4-(2-hydroxypropan-2-yl)-N-((2-methoxyphenyl)carbamoyl)furan-2-sulfonamide | C15H18N2O6S | C 15 H 17 N 2 O 6 S 1 | ESI− | 353.0813 | 353.0828 | ++ | ND | ND |
| N-((2,5-dimethoxyphenyl)carbamoyl)-4-(2-hydroxypropan-2-yl)furan-2-sulfonamide | C16H20N2O7S | C 16 H 19 N 2 O 7 S 1 | ESI− | 383.0918 | 383.0935 | ++ | ND | ND |
| N-((1,2,3,5,6,7-hexahydro-s-indacen-4-yl)carbamoyl)-4-(2-hydroxypropan-2-yl)-5-methylfuran-2-sulfonamide | C21H26N2O5S | C 21 H 25 N 2 O 5 S 1 | ESI− | 417.149 | 417.1509 | ++++ | ND | ND |
| N-((2,6-diisopropylphenyl)carbamoyl)-4-(2-hydroxypropan-2-yl)-5-methylfuran-2-sulfonamide | C21H30N2O5S | C 21 H 29 N 2 O 5 S 1 | ESI− | 421.1803 | 421.18 | ND | ++++ | ND |
| N-((1,2,3,5,6,7-hexahydro-s-indacen-4-yl)carbamoyl)-4-(2-hydroxypropan-2-yl-1,1,1,3,3,3-d6)furan-2-sulfonamide | C20H18D6N2O5S | C 20 H 17 D 6 N 2 O 5 S 1 | ESI− | 409.171 | 409.1701 | ND | ++++ | ND |
| N-((1,2,3,5,6,7-hexahydro-s-indacen-4-yl)carbamoyl)-4-(2-hydroxypropan-2-yl-1,1,1,3,3,3-d6)-5-methylfuran-2-sulfonamide | C21H20D6N2O5S | C 21 H 19 D 6 N 2 O 5 S 1 | ESI− | 423.1866 | 423.1878 | ND | ++++ | ND |
| 4-(2-hydroxypropan-2-yl-1,1,1,3,3,3-d6)-5-methyl-N-(((3,5,6,7-tetrahydro-2H-indeno[5,6-b]furan-4-yl)carbamoyl)furan-2-sulfonamide | C20H18D6N2O6S | C 20 H 17 D 6 N 2 O 6 S 1 | ESI− | 425.1659 | 425.1665 | ND | ++++ | ND |
| N-((4-bromo-3,5,6,7-tetrahydro-2H-indeno[5,6-b]furan-8-yl)carbamoyl)-4-(2-hydroxypropan-2-yl-1,1,1,3,3,3-d6)-5-methylfuran-2-sulfonamide | C20H17D6BrN2O6S | C 20 H 16 Br 1 D 6 N 2 O 6 S 1 | ESI− | 503.0764 | 503.0748 | ND | ++++ | ND |
| N-((1,2,3,5,6,7-hexahydro-s-indacen-4-yl)carbamoyl)thiophene-2-sulfonamide | C17H18N2O3S2 | C17H19N2O3S2 | ESI+ | 363.0832 | 363.0819 | ND | ++++ | ++++ |

TABLE 2-continued

Compound HRMS characterisation data; Inhibition of IL-1β release IC50 in nM cell based assay using either HMDM or BMDM (<100 nM = '++++'/
<1 μM = '+++'/<10 μM = '++'/<50 μM = '+'); Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-((1,2,3,5,6,7-hexahydro-s-indacen-4-yl)carbamoyl)-5-methylthiophene-2-sulfonamide | C18H20N2O3S2 | C18H21N2O3S2 | ESI+ | 377.0988 | 377.0994 | ND | +++ | +++ |
| N-((1,2,3,5,6,7-hexahydro-s-indacen-4-yl)carbamoyl)thiazole-2-sulfonamide | C16H17N3O3S2 | | | | | | + | ND |
| 1-benzyl-N-((1,2,3,5,6,7-hexahydro-s-indacen-4-yl)carbamoyl)-1H-1,2,4-triazole-3-sulfonamide | C22H23N5O3S | C 22 H 22 N 5 O 3 S 1 | ESI− | 436.1449 | 436.1436 | ND | +++ | +++ |
| N-((1,2,3,5,6,7-hexahydro-s-indacen-4-yl)carbamoyl)-1-methyl-1H-pyrazole-5-sulfonamide | C17H20N4O3S | C 17 H 21 N 4 O 3 S 1 | ESI+ | 361.1329 | 361.1321 | ND | ++ | ND |
| N-((1,2,3,5,6,7-hexahydro-s-indacen-4-yl)carbamoyl)-1-methyl-1H-pyrazole-3-sulfonamide | C17H20N4O3S | C 17 H 19 N 4 O 3 S 1 | ESI− | 359.1183 | 359.1176 | ND | +++ | ND |
| N-((1,2,3,5,6,7-hexahydro-s-indacen-4-yl)carbamoyl)-1-(trifluoromethyl)-1H-pyrazole-3-sulfonamide | C17H17F3N4O3S | C 17 H 18 F 3 N 4 O 3 S 1 | ESI+ | 415.1046 | 415.1063 | ND | ++++ | ND |
| N-((1,2,3,5,6,7-hexahydro-s-indacen-4-yl)carbamoyl)-1-isopropyl-1H-pyrazole-3-sulfonamide | C19H24N4O3S | C 19 H 23 N 4 O 3 S 1 | ESI− | 387.1496 | 387.1514 | ND | ++++ | +++ |
| N-((1,2,3,5,6,7-hexahydro-s-indacen-4-yl)carbamoyl)-1-isopropyl-1H-pyrazole-4-sulfonamide | C19H24N4O3S | | | | | ND | ++++ | +++ |
| 1-cyclopropyl-N-(((1,2,3,5,6,7-hexahydro-s-indacen-4-yl)carbamoyl))-1H-pyrazole-3-sulfonamide | C19H22N4O3S | C 19 H 23 N 4 O 3 S 1 | ESI+ | 387.1485 | 387.1501 | ND | ++++ | ND |
| 1-(tert-butyl)-N-(((1,2,3,5,6,7-hexahydro-s-indacen-4-yl)carbamoyl))-1H-pyrazole-3-sulfonamide | C20H26N4O3S | C20H27N4O3S1 | ESI+ | 403.1798 | 403.1802 | ND | +++ | ++++ |
| 1-cyclohexyl-N-((1,2,3,5,6,7-hexahydro-s-indacen-4-yl)carbamoyl)-1H-pyrazole-3-sulfonamide | C22H28N4O3S | C 22 H 29 N 4 O 3 S 1 | ESI+ | 429.1955 | 429.1968 | ND | +++ | ND |

TABLE 2-continued

Compound HRMS characterisation data; Inhibition of IL-1β release IC50 in nM cell based assay using either HMDM or BMDM (<100 nM = '++++'/ <1 μM = '+++'/<10 μM = '++'/<50 μM = '+'); Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-((1,2,3,5,6,7-hexahydro-s-indacen-4-yl)carbamoyl)-1-phenyl-1H-pyrazole-3-sulfonamide | C22H22N4O3S | C 22 H 23 N 4 O 3 S 1 | ESI+ | 423.1485 | 423.1474 | ND | ++ | ND |
| 1-benzyl-N-((1,2,3,5,6,7-hexahydro-s-indacen-4-yl)carbamoyl)-1H-pyrazole-3-sulfonamide | C23H24N4O3S | C 23 H 25 N 4 O 3 S 1 | ESI+ | 437.1642 | 437.163 | ND | ++ | ND |
| N-((1,2,3,5,6,7-hexahydro-s-indacen-4-yl)carbamoyl)-1-(1-phenylethyl))-1H-pyrazole-3-sulfonamide | C24H26N4O3S | C 24 H 27 N 4 O 3 S 1 | ESI+ | 451.1798 | 451.1811 | ND | +++ | ND |
| N-((1,2,3,5,6,7-hexahydro-s-indacen-4-yl)carbamoyl)-1-(2-(piperidin-1-yl)ethyl)-1H-pyrazole-3-sulfonamide | C23H31N5O3S | C 23 H 30 N 5 O 3 S 1 | ESI− | 456.2075 | 456.2076 | ND | ++ | ND |
| N-((1,2,3,5,6,7-hexahydro-s-indacen-4-yl)carbamoyl)-1,5-dimethyl-1H-pyrazole-3-sulfonamide | C18H22N4O3S | C 18 H 21 N 4 O 3 S 1 | ESI− | 373.134 | 373.1334 | ND | +++ | ND |
| N-((1,2,3,5,6,7-hexahydro-s-indacen-4-yl)carbamoyl)-1-methyl-5-(trifluoromethyl)-1H-pyrazole-3-sulfonamide | C18H19F3N4O3S | C 18 H 18 F 3 N 4 O 3 S 1 | ESI− | 427.1057 | 427.1057 | ND | +++ | ND |
| N-(2,6-diisopropylphenyl)carbamoyl)-1-methyl-5-(trifluoromethyl)-1H-pyrazole-3-sulfonamide | C18H23F3N4O3S | C 18 H 22 F 3 N 4 O 3 S 1 | ESI− | 431.137 | 431.1388 | ND | ++ | ND |
| N-((1,2,3,5,6,7-hexahydro-s-indacen-4-yl)carbamoyl)-1-isopropyl-5-(trifluoromethyl)-1H-pyrazole-3-sulfonamide | C20H23F3N4O3S | C 20 H 24 F 3 N 4 O 3 S 1 | ESI+ | 457.1516 | 457.1528 | ND | +++ | ND |
| N-((1,2,3,5,6,7-hexahydro-s-indacen-4-yl)carbamoyl)-5-isopropyl-1-methyl-1H-pyrazole-3-sulfonamide | C20H26N4O3S | C 20 H 25 N 4 O 3 S 1 | ESI− | 401.1653 | 401.1637 | ND | +++ | ND |
| N-(2,6-diisopropylphenyl)carbamoyl)-5-(2-hydroxypropan-2-yl)-1-methyl-1H-pyrazole-3-sulfonamide | C20H30N4O4S | C 20 H 29 N 4 O 4 S 1 | ESI− | 421.1915 | 421.1904 | ND | ++++ | ++++ |

TABLE 2-continued

Compound HRMS characterisation data; Inhibition of IL-1β release IC50 in nM cell based assay using either HMDM or BMDM (<100 nM = '++++'/ <1 μM = '+++'/<10 μM = '++'/<50 μM = '+'); Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-((1,2,3,5,6,7-hexahydro-s-indacen-4-yl)carbamoyl)-5-(2-hydroxypropan-2-yl)-1-methyl-1H-pyrazole-3-sulfonamide | C20H26N4O4S | C 20 H 25 N 4 O 4 S 1 | ESI− | 417.1602 | 417.1603 | +++ | +++ | ++++ |
| N-((1,2,3,5,6,7-hexahydro-s-indacen-4-yl)carbamoyl)-5-(2-hydroxypropan-2-yl)-1-phenyl-1H-pyrazole-3-sulfonamide | C25H28N4O4S | C 25 H 27 N 4 O 4 S 1 | ESI− | 479.1758 | 479.1758 | ++++ | ++++ | ++++ |
| 1-benzyl-N-((1,2,3,5,6,7-hexahydro-s-indacen-4-yl)carbamoyl)-5-(2-hydroxypropan-2-yl)-1H-pyrazole-3-sulfonamide | C26H30N4O4S | C 26 H 29 N 4 O 4 S 1 | ESI− | 493.1915 | 493.1912 | ND | ++++ | ++++ |
| N-((1,2,3,5,6,7-hexahydro-s-indacen-4-yl)carbamoyl)benzenesulfonamide | C19H20N2O3S | C 19 H 19 N 2 O 3 S 1 | ESI− | 355.1122 | 355.1139 | ND | ++++ | ND |
| 5-(dimethylamino)-N-(((1,2,3,5,6,7-hexahydro-s-indacen-4-yl)carbamoyl)naphthalene-1-sulfonamide | C25H27N3O3S | C 25 H 28 N 3 O 3 S 1 | ESI+ | 450.1846 | 450.1859 | ND | +++ | ND |
| N-((1,2,3,5,6,7-hexahydro-s-indacen-4-yl)carbamoyl)-2,3-dihydrobenzo[b]thiophene-6-sulfonamide 1,1-dioxide | C21H22N2O5S2 | C 21 H 23 N 2 O 5 S 2 | ESI+ | 447.1043 | 447.1034 | ND | +++ | ND |
| N-((1,2,3,5,6,7-hexahydro-s-indacen-4-yl)carbamoyl)-2-methoxybenzenesulfonamide | C20H22N2O4S | C 20 H 23 N 2 O 4 S 1 | ESI− | 387.1373 | 387.1378 | ND | ++++ | ND |
| N-((1,2,3,5,6,7-hexahydro-s-indacen-4-yl)carbamoyl)-3-(trifluoromethyl)benzenesulfonamide | C20H19F3N2O3S | C 20 H 18 F 3 N 2 O 3 S 1 | ESI− | 423.0996 | 423.1009 | +++ | ++++ | ND |
| N-((1,2,3,5,6,7-hexahydro-s-indacen-4-yl)carbamoyl)-3-methoxybenzenesulfonamide | C20H22N2O4S | C 20 H 21 N 2 O 4 S 1 | ESI− | 385.1228 | 385.1211 | ++++ | ++++ | ND |
| N-((1,2,3,5,6,7-hexahydro-s-indacen-4-yl)carbamoyl)-3-(trifluoromethoxy)benzenesulfonamide | C20H19F3N2O4S | C 20 H 18 F 3 N 2 O 4 S 1 | ESI− | 439.0945 | 439.0955 | +++ | +++ | ND |
| 3-(difluoromethoxy)-N-(((1,2,3,5,6,7-hexahydro-s-indacen-4-yl)carbamoyl)benzenesulfonamide | C20H20F2N2O4S | C 20 H 19 F 2 N 2 O 4 S 1 | ESI− | 421.1039 | 421.1054 | ND | +++ | ND |

TABLE 2-continued

Compound HRMS characterisation data; Inhibition of IL-1β release IC50 in nM cell based assay using either HMDM or BMDM (<100 nM = '++++'/ <1 µM = '+++'/<10 µM = '++'/<50 µM = '+'); Inhibition of IL-18 release IC50 in nM cell based assay using HMDM (<100 nM = '++++'/<1 µM = '+++'/<10 µM = '++'/<50 µM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-((1,2,3,5,6,7-hexahydro-s-indacen-4-yl)carbamoyl)benzene-1,3-disulfonamide | C19H21N3O5S2 | C 19 H 20 N 3 O 5 S 2 | ESI− | 434.085 | 434.0862 | ++++ | ++++ | ND |
| N1-((1,2,3,5,6,7-hexahydro-s-indacen-4-yl)carbamoyl)-N3,N3-dimethylbenzene-1,3-disulfonamide | C21H25N3O5S2 | C 21 H 24 N 3 O 5 S 2 | ESI− | 462.1163 | 462.1149 | ND | ++++ | ND |
| 3-(N-((1,2,3,5,6,7-hexahydro-s-indacen-4-yl)carbamoyl)sulfamoyl)benzoic acid | C20H20N2O5S | C 20 H 19 N 2 O 5 S 1 | ESI− | 399.102 | 399.1034 | ND | ++++ | ND |
| 3-(N-((1,2,3,5,6,7-hexahydro-s-indacen-4-yl)sulfamoyl)benzamide | C20H21N3O4S | C 20 H 20 N 3 O 4 S 1 | ESI− | 398.118 | 398.1167 | ND | +++ | ND |
| N-((1,2,3,5,6,7-hexahydro-s-indacen-4-yl)carbamoyl)-3-(2-hydroxypropan-2-yl)benzenesulfonamide | C22H26N2O4S | C 22 H 25 N 2 O 4 S 1 | ESI+ | 413.1541 | 413.154 | ND | ++++ | ND |
| 3-azido-N-((1,2,3,5,6,7-hexahydro-s-indacen-4-yl)carbamoyl)benzenesulfonamide | C19H19N5O3S | C 19 H 20 N 5 O 3 S 1 | ESI+ | 398.1281 | 398.1272 | ND | ++ | ND |
| N-((1,2,3,5,6,7-hexahydro-s-indacen-4-yl)carbamoyl)-3-(4-phenyl-1H-1,2,3-triazol-1-yl)benzenesulfonamide | C27H25N5O3S | C 27 H 26 N 5 O 3 S 1 | ESI− | 500.1751 | 500.1735 | ND | ++++ | ND |
| N-(3-(N-((1,2,3,5,6,7-hexahydro-s-indacen-4-yl)carbamoyl)sulfamoyl)phenyl)pent-4-ynamide | C24H25N3O4S | C 24 H 26 N 3 O 4 S 1 | ESI+ | 452.1639 | 452.1658 | ND | +++ | ND |
| 3-(1-(3-aminopropyl)-1H-1,2,3-triazol-4-yl)-N-(3-(N-(((1,2,3,5,6,7-hexahydro-s-indacen-4-yl)carbamoyl)sulfamoyl)phenyl)propanamide | C27H33N7O4S | C 27 H 34 N 7 O 4 S 1 | ESI+ | 552.2387 | 552.2368 | ND | +++ | ND |
| N-(3-(N-((1,2,3,5,6,7-hexahydro-s-indacen-4-yl)carbamoyl)sulfamoyl)phenyl)-3-(1-(3-(7-nitrobenzo[c][1,2,5]oxadiazol-4-yl)amino)propyl)-1H-1,2,3-triazol-4-yl)propanamide | C33H34N10O7S | C33H33N10O7S1 | ESI− | 713.226 | 713.229 | ND | ++ | ND |

TABLE 2-continued

Compound HRMS characterisation data; Inhibition of IL-1β release IC50 in nM cell based assay using either HMDM or BMDM (<100 nM = '++++'/ <1 μM = '+++'/<10 μM = '++'/<50 μM = '+'); Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-(3-(4-(3-(N-((1,2,3,5,6,7-hexahydro-s-indacen-4-yl)carbamoyl)sulfamoyl)phenyl)amino)-3-oxopropyl)-1H-1,2,3-triazol-1-yl)propyl)-5-((3aS,4S,6aR)-2-oxohexahydro-1H-thieno[3,4-d]imidazol-4-yl)pentanamide | C37H47N9O6S2 | C37H48N9O6S2 | ESI+ | 778.3163 | 778.3145 | ++ | + | ND |
| N-((1-(3-(N-((1,2,3,5,6,7-hexahydro-s-indacen-4-yl)carbamoyl)sulfamoyl)phenyl)-1H-1,2,3-triazol-4-yl)methyl)-5-((3aS,4S,6aR)-2-oxohexahydro-1H-thieno[3,4-d]imidazol-4-yl)pentanamide | C32H38N8O5S2 | C32H39N8O5S2 | ESI+ | 679.2479 | 679.2456 | + | ++ | ND |
| N-(quinolin-6-ylcarbamoyl)-3-(3-(trifluoromethyl)-3H-diazirin-3-yl)benzenesulfonamide | C18H12F3N5O3S | C 18 H 11 F 3 N 5 O 3 S 1 | ESI− | 434.054 | 434.0558 | >50 uM | >50 uM | ND |
| N-(quinolin-5-ylcarbamoyl)-3-(3-(trifluoromethyl)-3H-diazirin-3-yl)benzenesulfonamide | C18H12F3N5O3S | C 18 H 11 F 3 N 5 O 3 S 1 | ESI− | 434.054 | 434.0547 | ND | + | ND |
| N-((6-methoxyquinolin-8-yl)carbamoyl)-3-(3-(trifluoromethyl)-3H-diazirin-3-yl)benzenesulfonamide | C19H14F3N5O4S | C 19 H 13 F 3 N 5 O 4 S 1 | ESI− | 464.0646 | 464.0664 | ND | + | ND |
| N-(quinolin-8-ylcarbamoyl)-3-(3-(trifluoromethyl)-3H-diazirin-3-yl)benzenesulfonamide | C18H12F3N5O3S | C 18 H 11 F 3 N 5 O 3 S 1 | ESI− | 434.054 | 434.0551 | ND | ++ | ND |
| N-((2,3,6,7-tetrahydrobenzo[1,2-b:4,5-b']difuran-4-yl)carbamoyl)-3-(3-(trifluoromethyl)-3H-diazirin-3-yl)benzenesulfonamide | C19H15F3N4O5S | C 19 H 14 F 3 N 5 O 4 S 1 | ESI− | 467.0642 | 467.0627 | ND | ++ | ND |
| 4-chloro-N-((1,2,3,5,6,7-hexahydro-s-indacen-4-yl)carbamoyl)benzenesulfonamide | C19H19ClN2O3S | C19H19ClN2O3S | ESI+ | 391.0878 | 391.0895 | ND | +++ | ND |

TABLE 2-continued

Compound HRMS characterisation data; Inhibition of IL-1β release IC50 in nM cell based assay using either HMDM or BMDM (<100 nM = '++++'/ <1 µM = '+++'/<10 µM = '++'/<50 µM = '+'); Inhibition of IL-18 release IC50 in nM cell based assay using HMDM (<100 nM = '++++'/<1 µM = '+++'/<10 µM = '++'/<50 µM = '+').

| Name | Chem Formula | HRMS formula | ESI+/- | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-((1,2,3,5,6,7-hexahydro-s-indacen-4-yl)carbamoyl)-4-methylbenzenesulfonamide | C20H22N2O3S | C 20 H 21 N 2 O 3 S 1 | ESI- | 369.1278 | 369.1296 | +++ | ++ | ND |
| 3-(4-(N-((1,2,3,5,6,7-hexahydro-s-indacen-4-yl)carbamoyl)sulfamoyl)phenyl)-N-(prop-2-yn-1-yl)propanamide | C25H27N3O4S | C 25 H 28 N 3 O 4 S 1 | ESI+ | 466.1795 | 466.1794 | ND | ++++ | ND |
| N-(4-(N-(1,2,3,5,6,7-Hexahydro-s-indacen-4-yl)carbamoyl)sulfamoyl)phenethyl)-2-(methyl(7-nitrobenzo[c][1,2,5]oxadiazol-4-yl)amino)acetamide | C30H34N7O7S | | | | | ND | ++ | ND |
| N-((1,2,3,5,6,7-hexahydro-s-indacen-4-yl)carbamoyl)-4-(2-(7-nitrobenzo[c][1,2,5]oxadiazol-4-yl)amino)ethyl)benzenesulfonamide | C27H26N6O6S | C 27 H 25 N 6 O 6 S 1 | ESI- | 561.1562 | 561.1579 | +++ | +++ | ND |
| 2-(7-(dimethylamino)-2-oxo-2H-chromen-4-yl)-N-(4-(N-(1,2,3,5,6,7-hexahydro-s-indacen-4-yl)carbamoyl)sulfamoyl)phenethyl)acetamide | C34H36N4O6S | | | | | ND | +++ | ND |
| N-((1,2,3,5,6,7-hexahydro-s-indacen-4-yl)carbamoyl)benzo[d][1,3]dioxole-5-sulfonamide | C20H20N2O5S | C 20 H 21 N 2 O 5 S 1 | ESI+ | 401.1166 | 401.1182 | ND | +++ | ND |
| N-((1,2,3,5,6,7-hexahydro-s-indacen-4-yl)carbamoyl)-4-(2-hydroxypropan-2-yl)pyridine-2-sulfonamide | C21H25N3O4S | C 21 H 24 N 3 O 4 S 1 | ESI- | 414.1493 | 414.1497 | ND | ++++ | ND |
| N-((1,2,3,5,6,7-hexahydro-s-indacen-4-yl)carbamoyl)-6,7-dihydro-5H-cyclopenta[b]pyridine-3-sulfonamide | C21H23N3O3S | C 21 H 24 N 3 O 3 S 1 | ESI+ | 398.1533 | 398.1538 | ND | ++++ | ND |
| N-((1,2,3,5,6,7-hexahydro-s-indacen-4-yl)carbamoyl)pyridine-2-sulfonamide | C18H19N3O3S | C 18 H 18 N 3 O 3 S 1 | ESI- | 356.1074 | 356.1079 | ND | ++++ | ND |

TABLE 2-continued

Compound HRMS characterisation data; Inhibition of IL-1β release IC50 in nM cell based assay using either HMDM or BMDM (<100 nM = '++++'/ <1 µM = '+++'/<10 µM = '++'/<50 µM = '+'); Inhibition of IL-18 release IC50 in nM cell based assay using HMDM (<100 nM = '++++'/<1 µM = '+++'/<10 µM = '++'/<50 µM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-((1,2,3,5,6,7-hexahydro-s-indacen-4-yl)carbamoyl)pyridine-3-sulfonamide | C18H19N3O3S | C 18 H 18 N 3 O 3 S 1 | ESI− | 356.1074 | 356.1087 | ND | ++ | ND |
| N-((1,2,3,5,6,7-hexahydro-s-indacen-4-yl)carbamoyl)-4-(trifluoromethyl)pyridine-2-sulfonamide | C19H18F3N3O3S | C 19 H 17 F 3 N 3 O 3 S 1 | ESI− | 424.0948 | 424.0955 | ND | ++++ | ND |
| N-((1,2,3,5,6,7-hexahydro-s-indacen-4-yl]carbamothioyl)-4-(2-hydroxypropan-2-yl)furan-2-sulfonamide | C20H24N2O4S2 | C 20 H 23 N 2 O 4 S 2 | ESI− | 419.1105 | 419.1123 | ND | +++ | ND |
| N-((4-chloro-2,6-dimethylphenyl)carbamoyl)-4-(2-hydroxypropan-2-yl)furan-2-sulfonamide | C16H19ClN2O5S | C 16 H 18 Cl 1 N 2 O 5 S 1 | ESI− | 385.0630 | 385.0621 | ++ | ND | ND |
| N-((4-chloro-2-methyl-6-(trifluoromethyl)phenyl)carbamoyl)-4-(2-hydroxypropan-2-yl)furan-2-sulfonamide | C16H16ClF3N2O5S | C 16 H 15 Cl 1 F 3 N 2 O 5 S 1 | ESI− | 439.0348 | 439.0339 | >10,000 | ND | ND |
| sodium ((4-chloro-2,6-diisopropylphenyl)carbamoyl)((4-(2-hydroxypropan-2-yl)furan-2-yl)sulfonyl)amide | C20H26ClN2NaO5S | C 20 H 26 Cl 1 N 2 O 5 S 1 | ESI− | 441.1256 | 441.1264 | ND | ++++ | ND |
| N-((4-chloro-2,6-dicyclopropylphenyl)carbamoyl)-4-(2-hydroxypropan-2-yl)furan-2-sulfonamide | C20H23ClN2O5S | C 20 H 22 Cl 1 N 2 O 5 S 1 | ESI− | 437.0943 | 437.0945 | ++++ | ND | ND |
| 4-(2-hydroxypropan-2-yl)-N-(((5-methoxy-2,3-dihydro-1H-inden-4-yl)carbamoyl)furan-2-sulfonamide | C18H22N2O6S | C 18 H 21 N 2 O 6 S 1 | ESI− | 393.1126 | 392.1113 | +++ | +++ | ND |
| N-((7-chloro-5-cyclopropyl-2,3-dihydro-1H-inden-4-yl)carbamoyl)-4-(2-hydroxypropan-2-yl)furan-2-sulfonamide | C20H23ClN2O5S | C 20 H 22 Cl 1 N 2 O 5 S 1 | ESI− | 437.0943 | 437.0927 | ++++ | ND | ND |
| N-((3-hydroxy-1,2,3,5,6,7-hexahydro-s-indacen-4-yl)carbamoyl)-4-(2-hydroxypropan-2-yl)furan-2-sulfonamide | C20H24N2O6S | C 20 H 23 N 2 O 6 S 1 | ESI− | 419.1282 | 419.1263 | ND | +++ | ND |

TABLE 2-continued

Compound HRMS characterisation data; Inhibition of IL-1β release IC50 in nM cell based assay using either HMDM or BMDM (<100 nM = '++++'/ <1 μM = '+++'/<10 μM = '++'/<50 μM = '+'); Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| hydroxypropan-2-yl)furan-2-sulfonamide | | | | | | | | |
| N-((1-hydroxy-1,2,3,5,6,7-hexahydro-s-indacen-4-yl)carbamoyl)-4-(2-hydroxypropan-2-yl)furan-2-sulfonamide | C20H24N2O6S | C 20 H 23 N 2 O 6 S 1 | ESI− | 419.1282 | 419.1265 | ND | ++ | ND |
| N-((4,6-dimethylpyrimidin-2-yl)carbamoyl)-4-(2-hydroxypropan-2-yl)furan-2-sulfonamide | C14H18N4O5S | C 14 H 17 N 4 O 5 S 1 | ESI− | 353.0925 | 353.0921 | >10,000 | >50000 | ND |
| N-((4,6-dimethylpyrimidin-2-yl)carbamoyl)-4-(2-hydroxypropan-2-yl)furan-2-sulfonamide | C14H18N4O5S | C 14 H 17 N 4 O 5 S 1 | ESI− | 353.0925 | 353.0923 | >10,000 | >50000 | ND |
| N-((4-cyclopropyl-6-methylpyrimidin-2-yl)carbamoyl)-4-(2-hydroxypropan-2-yl)furan-2-sulfonamide | C16H20N4O5S | C 16 H 19 N 4 O 5 S 1 | ESI− | 379.1082 | 379.1082 | ND | +++ | ND |
| N-((4,6-di-tert-butylpyrimidin-2-yl)carbamoyl)-4-(2-hydroxypropan-2-yl)furan-2-sulfonamide | C20H30N4O5S | C 20 H 29 N 4 O 5 S 1 | ESI− | 437.1864 | 437.1846 | ND | + | ND |
| N-((1,2,3,5,6,7-hexahydro-s-indacen-4-yl)carbamoyl)-2-methylthiazole-5-sulfonamide | C17H19N3O3S2 | C 17 H 18 N 3 O 3 S 2 | ESI− | 376.0795 | 376.0791 | ++++ | ND | ND |
| N-((1,2,3,5,6,7-hexahydro-s-indacen-4-yl)carbamoyl)-1H-1,2,4-triazole-3-sulfonamide | C15H17N5O3S | C 15 H 16 N 5 O 3 S 1 | ESI− | 346.0979 | 346.0983 | ++++ | ND | ND |
| N-((1,2,3,5,6,7-hexahydro-s-indacen-4-yl)carbamoyl)-1-isopropyl-1H-1,2,3-triazole-4-sulfonamide | C18H23N5O3S | C 18 H 22 N 5 O 3 S 1 | ESI− | 388.1449 | 388.1457 | +++ | ++++ | ND |
| sodium ((4-chloro-2,6-diisopropylphenyl)carbamoyl)((5-(2-hydroxypropan-2-yl)-1-methyl-1H-pyrazol-3-yl)sulfonyl)amide | C20H28ClN4NaO4S | C 20 H 28 Cl 1 N 4 O 4 S 1 | ESI− | 455.1525 | 455.1515 | ND | ++++ | ND |

TABLE 2-continued

Compound HRMS characterisation data; Inhibition of IL-1β release IC50 in nM cell based assay using either HMDM or BMDM (<100 nM = '++++'/ <1 μM = '+++'/<10 μM = '++'/<50 μM = '+'). Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| sodium ((4-chloro-2,6-diisopropylphenyl)carbamoyl)((5-(2-hydroxypropan-2-yl)-1-phenyl-1H-pyrazol-3-yl)sulfonyl)amide | C25H30ClN4NaO4S | C 25 H 30 Cl 1 N 4 O 4 S 1 | ESI− | 517.1682 | 517.1671 | ND | +++ | ND |
| N-((4-chloro-2,6-dimethylphenyl)carbamoyl)-1-isopropyl-1H-pyrazole-3-sulfonamide | C15H19ClN4O3S | C 15 H 18 Cl 1 N 4 O 3 S 1 | ESI− | 369.0794 | 369.0785 | >10,000 | ++ | ND |
| N-((4-chloro-2,6-dimethoxyphenyl)carbamoyl)-1-isopropyl-1H-pyrazole-3-sulfonamide | C15H19ClN4O5S | C 15 H 18 Cl 1 N 4 O 5 S 1 | ESI− | 401.0692 | 401.0684 | >10,000 | + | ND |
| N-((4-chloro-2-methyl-6-(trifluoromethyl)phenyl)carbamoyl)-1-isopropyl-1H-pyrazole-3-sulfonamide | C15H16ClF3N4O3S | C 15 H 15 Cl 1 F 3 N 4 O 3 S 1 | ESI− | 423.0511 | 423.0513 | >10,000 | ++ | ND |
| N-((4-chloro-2-methoxy-6-(trifluoromethyl)phenyl)carbamoyl)-1-isopropyl-1H-pyrazole-3-sulfonamide | C15H16ClF3N4O4S | C 15 H 15 Cl 1 F 3 N 4 O 4 S 1 | ESI− | 439.0460 | 439.0478 | ND | ND | ND |
| N-((4-chloro-2-methoxy-6-(trifluoromethyl)phenyl)carbamoyl)-1-isopropyl-1H-pyrazole-3-sulfonamide | C15H16ClF3N4O4S | C 15 H 15 Cl 1 F 3 N 4 O 4 S 1 | ESI− | 439.0460 | 439.0478 | >10,000 | ND | ND |
| N-((4-chloro-2,6-diethylphenyl)carbamoyl)-1-isopropyl-1H-pyrazole-3-sulfonamide | C17H23ClN4O3S | C 17 H 22 Cl 1 N 4 O 3 S 1 | ESI− | 397.1107 | 397.109 | ++ | ++ | ND |
| sodium ((4-chloro-2,6-diisopropylphenyl)carbamoyl)((1-isopropyl-1H-pyrazol-3-yl)sulfonyl)amide | C19H26ClN4NaO3S | C 19 H 26 Cl 1 N 4 O 3 S 1 | ESI− | 425.1420 | 425.1409 | ND | +++ | ND |
| N-((4-chloro-2,6-dicyclopropylphenyl)carbamoyl)-1-isopropyl-1H-pyrazole-3-sulfonamide | C19H23ClN4O3S | C 19 H 22 Cl 1 N 4 O 3 S 1 | ESI− | 421.1107 | 421.1107 | +++ | +++ | ND |
| N-((7-chloro-5-cyclopropyl-2,3-dihydro-1H-inden-4-yl)carbamoyl)-1-isopropyl-1H-pyrazole-3-sulfonamide | C19H23ClN4O3S | C 19 H 22 Cl 1 N 4 O 3 S 1 | ESI | 421.1107 | 421.111 | +++ | +++ | ND |

TABLE 2-continued

Compound HRMS characterisation data; Inhibition of IL-1β release IC50 in nM cell based assay using either HMDM or BMDM (<100 nM = '++++'/ <1 μM = '+++'/<10 μM = '++'/<50 μM = '+'); Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| 5-chloro-3-cyclopropyl-2-(3-(((1-isopropyl-1H-pyrazol-3-yl)sulfonyl)ureido)-N,N-dimethylbenzamide | C19H24ClN5O4S | C 19 H 23 Cl 1 N 5 O 4 S 1 | ESI− | 452.1165 | 452.118 | >10,000 | ND | ND |
| N-((4,6-dimethylpyrimidin-2-yl)carbamoyl)-1-isopropyl-1H-pyrazole-3-sulfonamide | C13H18N6O3S | C 13 H 17 N 6 O 3 S 1 | ESI− | 337.1088 | 337.1099 | >10,000 | ND | ND |
| N-((4,6-di-tert-butylpyrimidin-2-yl)carbamoyl)-1-isopropyl-1H-pyrazole-3-sulfonamide | C19H30N6O3S | C 19 H 29 N 6 O 3 S 1 | ESI− | 421.2027 | 421.2008 | >10,000 | ND | ND |
| N-((1,2,3,5,6,7-hexahydro-s-indacen-4-yl)carbamoyl)-6,7-dihydro-5H-pyrrolo[1,2-a]imidazole-2-sulfonamide | C19H22N4O3S | C 19 H 21 N 4 O 3 S 1 | ESI− | 385.1340 | 385.1331 | +++ | +++ | ND |
| 4-acetyl-N-((1,2,3,5,6,7-hexahydro-s-indacen-4-yl)carbamoyl)benzenesulfonamide | C21H22N2O4S | C 21 H 21 N 2 O 4 S 1 | ESI− | 397.1228 | 397.1225 | ++++ | +++ | ND |
| N-((1,2,3,5,6,7-hexahydro-s-indacen-4-yl)carbamoyl)-4-nitrobenzenesulfonamide | C19H19N3O5S | C 19 H 18 N 3 O 5 S 1 | ESI− | 400.0973 | 400.0979 | ++++ | ND | ND |
| 4-amino-N-((1,2,3,5,6,7-hexahydro-s-indacen-4-yl)carbamoyl)benzenesulfonamide | C19H21N3O3S | C 19 H 20 N 3 O 3 S 1 | ESI− | 370.1231 | 370.1225 | ++++ | +++ | ND |
| N-((1,2,3,5,6,7-hexahydro-s-indacen-4-yl)carbamoyl)-2,3-dihydro-1H-indene-5-sulfonamide | C22H24N2O3S | C 22 H 23 N 2 O 3 S 1 | ESI− | 395.1435 | 395.143 | ++++ | ++ | ND |
| N-((4-chlorophenyl)carbamoyl)-2,3-dihydro-1H-indene-5-sulfonamide | C16H15ClN2O3S | C 16 H 14 Cl 1 N 2 O 3 S 1 | ESI− | 349.0419 | 349.0418 | >10,000 | >100,000 | ND |
| N-((4-chloro-2,6-diisopropylphenyl)carbamoyl)quinoline-8-sulfonamide | C22H24ClN3O3S | C 22 H 25 Cl 1 N 3 O 3 S 1 | ESI+ | 446.1300 | 446.1314 | ND | ++ | ND |
| N-((4-chloro-2,6-diisopropylphenyl)carbamoyl)isoquinoline-5-sulfonamide | C22H24ClN3O3S | C 22 H 25 Cl 1 N 3 O 3 S 1 | ESI+ | 446.1300 | 446.1319 | ND | +++ | ND |
| N-((4-chloro-2,6-diisopropylphenyl)carbamoyl)quinoline-3-sulfonamide | C22H24ClN3O3S | C 22 H 25 Cl 1 N 3 O 3 S 1 | ESI+ | 446.1300 | 446.1315 | ND | ++++ | ND |

TABLE 2-continued

Compound HRMS characterisation data; Inhibition of IL-1β release IC50 in nM cell based assay using either HMDM or BMDM (<100 nM = '++++'/
<1 μM = '+++'/<10 μM = '++'/<50 μM = '+'); Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-((4-chloro-2,6-diisopropylphenyl)carbamoyl)quinoline-5-sulfonamide | C22H24ClN3O3S | C 22 H 25 Cl 1 N 3 O 3 S 1 | ESI+ | 446.1300 | 446.1317 | ND | ++ | ND |
| N-((1,2,3,5,6,7-hexahydro-s-indacen-4-yl)carbamoyl)quinoline-8-sulfonamide | C22H21N3O3S | C 22 H 22 N 3 O 3 S 1 | ESI+ | 408.1376 | 408.1371 | ND | +++ | ND |
| N-((4-chloro-2,6-diisopropylphenyl)carbamoyl)quinoxaline-5-sulfonamide | C21H23ClN4O3S | C 21 H 24 Cl 1 N 4 O 3 S 1 | ESI+ | 447.1252 | 447.1266 | ++++ | ND | ND |
| N-((4-chloro-2,6-diisopropylphenyl)carbamoyl)naphthalene-2-sulfonamide | C23H25ClN2O3S | C 23 H 26 Cl 1 N 2 O 3 S 1 | ESI+ | 445.1347 | 445.1349 | ND | ++ | ND |
| N-((4-chloro-2,6-diisopropylphenyl)carbamoyl)-6-methoxynaphthalene-2-sulfonamide | C24H27ClN2O4S | C 24 H 28 Cl 1 N 2 O 4 S 1 | ESI+ | 475.1453 | 475.1474 | ++++ | ND | ND |
| 6-chloro-N-((4-chloro-2,6-diisopropylphenyl)carbamoyl)naphthalene-2-sulfonamide | C23H24Cl2N2O3S | C 23 H 25 Cl 2 N 2 O 3 S 1 | ESI+ | 479.0957 | 479.0937 | ++++ | ND | ND |
| N-((4-chloro-2,6-diisopropylphenyl)carbamoyl)-5,6,7,8-tetrahydronaphthalene-2-sulfonamide | C23H29ClN2O3S | C 23 H 30 Cl 1 N 2 O 3 S 1 | ESI+ | 449.1660 | 449.1664 | ++ | ND | ND |
| N-((4-chloro-2,6-diisopropylphenyl)carbamoyl)-3-ethylisoxazolo[5,4-b]pyridine-5-sulfonamide | C21H25ClN4O4S | C 21 H 26 Cl 1 N 4 O 4 S 1 | ESI+ | 465.1358 | 465.1354 | +++ | ND | ND |
| N-((4-chloro-2,6-diisopropylphenyl)carbamoyl)thieno[3,2-b]pyridine-6-sulfonamide | C20H22ClN3O3S2 | C 20 H 23 Cl 1 N 3 O 3 S 2 | ESI+ | 452.0864 | 452.0884 | ++++ | +++ | ND |
| N-((1,2,3,5,6,7-hexahydro-s-indacen-4-yl)carbamoyl)benzofuran-2-sulfonamide | C21H20N2O4S | C 21 H 21 N 2 O 4 S 1 | ESI+ | 397.1217 | 397.1215 | ND | ND | ND |
| N-((4-chloro-2,6-diisopropylphenyl)carbamoyl)benzofuran-2-sulfonamide | C21H23ClN2O4S | C 21 H 24 Cl 1 N 2 O 4 S 1 | ESI+ | 435.1140 | 435.114 | ++++ | ++++ | ND |
| N-((4-chloro-2,6-diisopropylphenyl)carbamoyl)benzo[b]thiophene-2-sulfonamide | C21H23ClN2O3S2 | C 21 H 24 Cl 1 N 2 O 3 S 2 | ESI+ | 451.0911 | 451.09 | +++ | ++++ | ND |

TABLE 2-continued

Compound HRMS characterisation data; Inhibition of IL-1β release IC50 in nM cell based assay using either HMDM or BMDM (<100 nM = '++++'/ <1 μM = '+++'/<10 μM = '++'/<50 μM = '+'); Inhibition of IL-18 release IC50 in nM cell based assay using HMDM (<100 nM = '++++'/<1 μM = '+++'/<10 μM = '++'/<50 μM = '+').

| Name | Chem Formula | HRMS formula | ESI+/− | HRMS Calc | HRMS found | Avg. IL-1β IC50 Murine BMDM (nM) | Avg. IL-1β IC50 HMDM (nM) | Avg. IL-18 IC50 HMDM (nM) |
|---|---|---|---|---|---|---|---|---|
| N-((1,2,3,5,6,7-hexahydro-s-indacen-4-yl)carbamoyl)-4-(2-(7-methoxy-4,4-dimethyl-1,3-dioxo-3,4-dihydroisoquinolin-2(1H)-yl)ethyl)benzenesulfonamide | C33H35N3O6S | C 33 H 34 N 3 O 6 S 1 | ESI− | 600.2174 | 600.2183 | +++ | ++ | ND |
| N-(4-(N-((1,2,3,5,6,7-hexahydro-s-indacen-4-yl)carbamoyl)sulfamoyl)phenethyl)-5-methylisoxazole-3-carboxamide | C26H28N4O5S | C 26 H 27 N 4 O 5 S 1 | ESI− | 507.1708 | 507.1709 | +++ | +++ | ND |
| 3-ethyl-N-(4-(N-((1,2,3,5,6,7-hexahydro-s-indacen-4-yl)carbamoyl)sulfamoyl)phenethyl)-4-methyl-2-oxo-2,5-dihydro-1H-pyrrole-1-carboxamide | C29H34N4O5S | C 29 H 33 N 4 O 5 S 1 | ESI− | 549.2177 | 549.2169 | +++ | +++ | ND |
| 5-chloro-N-(4-(N-((1,2,3,5,6,7 hexahydro-s-indacen-4-yl)carbamoyl)sulfamoyl)phenethyl)-2-methoxybenzamide | C29H30ClN3O5S | C 29 H 29 Cl 1 N 3 O 5 S 1 | ESI− | 566.1522 | 566.1543 | +++ | +++ | ND |
| 4-(2-(7-methoxy-4,4-dimethyl-1,3-dioxo-3,4-dihydroisoquinolin-2(1H)-yl)ethyl)benzenesulfonamide | C20H22N2O5S | C 20 H 21 N 2 O 5 S 1 | ESI− | 401.1177 | 401.1174 | >10,000 | >200,000 | ND |
| 5-methyl-N-(4-sulfamoylphenethyl)isoxazole-3-carboxamide | C13H15N3O4S | C 13 H 14 N 3 O 4 S 1 | ESI− | 308.0711 | 308.0708 | >10,000 | ND | ND |
| N-(4-(N-((1,2,3,5,6,7-hexahydro-s-indacen-4-yl)carbamoyl)sulfamoyl)phenethyl)-5-methylpyrazine-2-carboxamide | C27H29N5O4S | C 27 H 28 N 5 O 4 S 1 | ESI− | 518.1867 | 518.1858 | ND | +++ | ND |

"ND" = not determined.

TABLE 3

Plasma levels of select test compounds at 2 hour timepoint after oral gavage at 20 mg/Kg

| | | | |
|---|---|---|---|
| Plasma Concentration (ng/mL) | 17490 | 28231 | 66260 |

TABLE 4

Properties of sulfonylureas, including increased BBB penetration, with and without hydroxylalkyl group on furan ring.

| | | |
|---|---|---|
| Brain Concentration (ng/g)* | 184 | 1339 |
| Plasma Concentration (ng/mL) | 17490 | 66260 |
| Brain/Plasma Ratio$^a$ | 0.0117 | 0.0203 |
| tPSA | 104.7 | 84.5 |

Plasma Concentration Post-Dosing

A single dose pharmacokinetic study of N-((1,2,3,5,6,7-hexahydro-s-indacen-4-yl)carbamoyl)-1-isopropyl-1H-pyrazole-3-sulfonamide (MCC7840 and being a compound of the first aspect) in comparison to N-((1,2,3,5,6,7-hexahydro-s-indacen-4-yl)carbamoyl)-4-(2-hydroxypropan-2-yl)furan-2-sulfonamide (MCC950) using an iv dose of 4 mg/Kg and po dose of 20 mg/Kg clearly indicated an extended half-life, increased maximum concentration ($C_{max}$) and area under the curve (AUC) for the pyrazole derivative in comparison to the furan. This is advantageous leading to comparatively lower doses or less frequent administration.

Figure 1B:
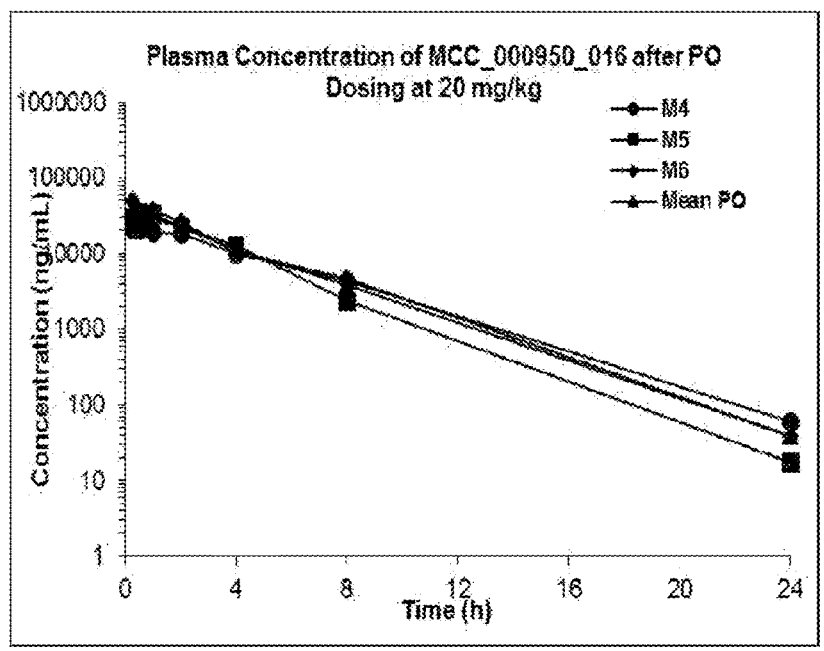
Figure 1C:
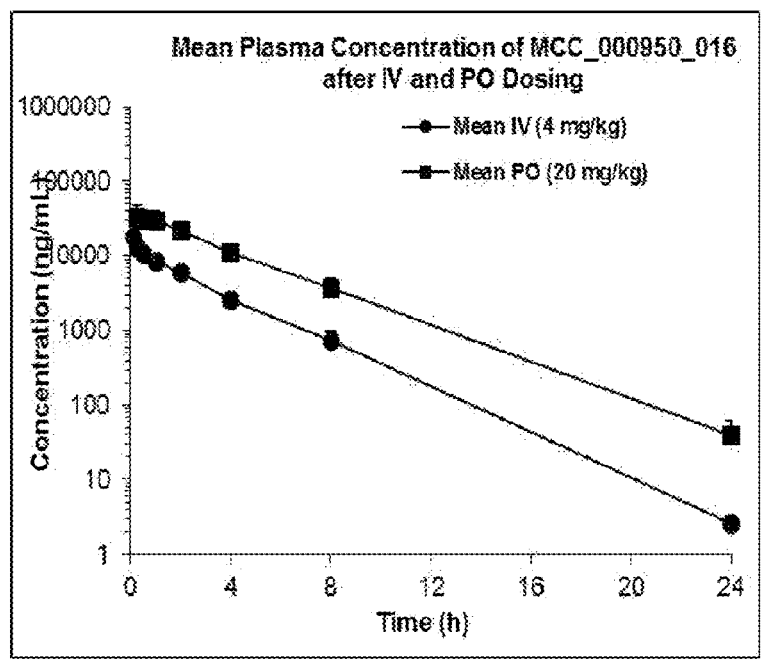
Figure 2A:
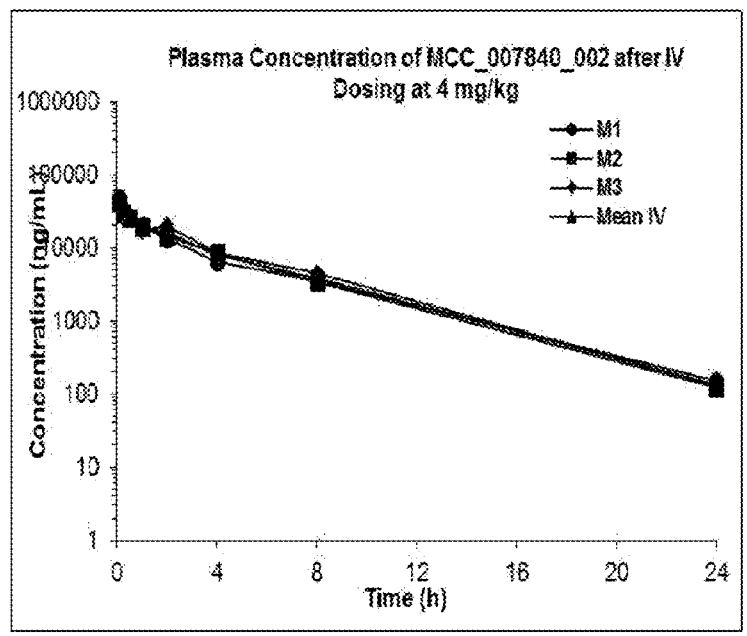
FIG. 2A to 2C is a series of graphical representations of the plasma concentrations of a sulfonylurea of the present invention (MCC7840) following different dosing levels in mice.
Figure 2B:
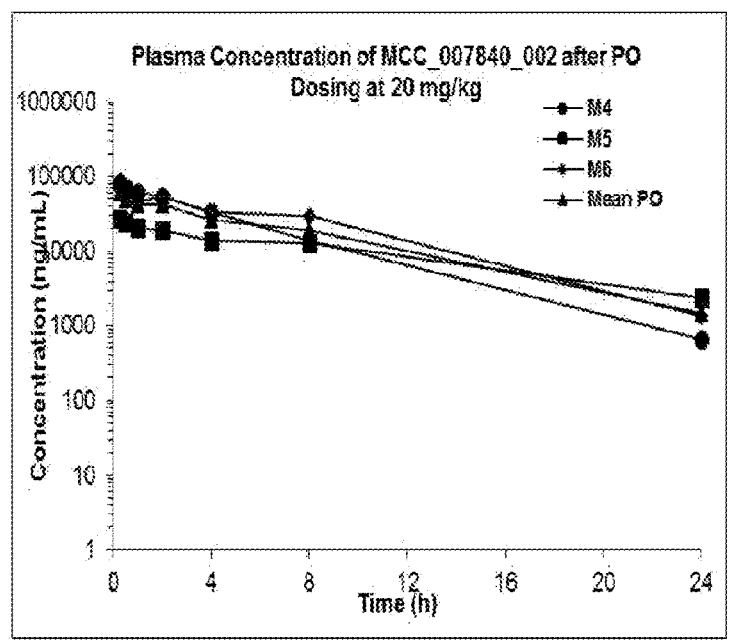
Figure 2C:
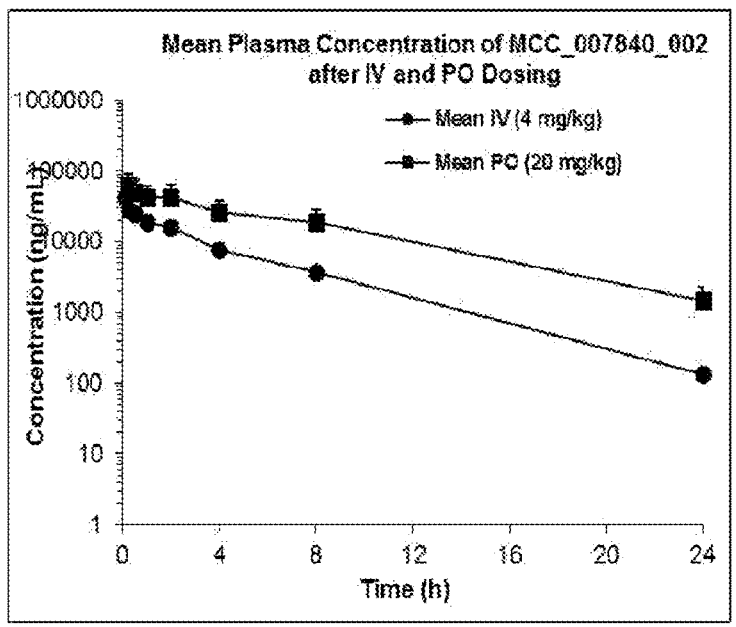

The procedure followed was: Male C57BL/6 mice were used at 7-9 weeks age with 3 animals per group. Mice were dosed with test compound using single intravenous bolus or oral gavage. Blood samples were taken via submandibular or saphenous vein for analysis of plasma concentrations of compound by LC-MS/MS at the following timepoints: IV (3 mice): 0.083, 0.25, 0.5, 1, 2, 4, 8 and 24 hours post dosing, PO (3 mice): 0.25, 0.5, 1, 2, 4, 8 and 24 hours post dosing. LC-MS/MS method for the quantitative determination of test compound in corresponding biological matrix was developed. PK parameters were calculated using Phoenix WinNonlin 6.3. The results are shown graphically in FIGS. 1A to 1C (MCC950) and FIGS. 2A to 2C (MCC7840).

The relevant compound structures are shown below and tables 5-8 contain the relevant data:

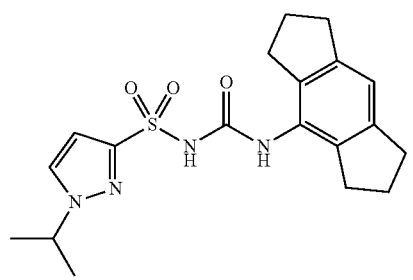

MCC7840

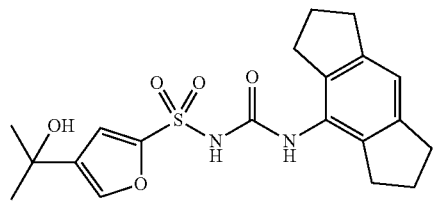

MCC950

Bioavailability of MCC_000950_016 in Mouse (ng/mL)
MCC_000950_016
IV

| | M1 | M2 | M3 | Mean IV | | SD | CV (%) |
|---|---|---|---|---|---|---|---|
| IV Time (h) | | | | | | | |
| 0.0833 | 20200 | 17200 | 17700 | 18367 | ± | 1607 | 8.75 |
| 0.250 | 16000 | 10200 | 12700 | 12967 | ± | 2909 | 22.4 |
| 0.500 | 11700 | 9420 | 10500 | 10540 | ± | 1141 | 10.8 |
| 1.00 | 9340 | 7730 | 8230 | 8433 | ± | 824 | 9.77 |
| 2.00 | 7410 | 6000 | 5010 | 6140 | ± | 1206 | 19.6 |
| 4.00 | 3280 | 2390 | 2130 | 2600 | ± | 603 | 23.2 |
| 8.00 | 905 | 843 | 480 | 743 | ± | 230 | 30.9 |
| 24.0 | 3.29 | 2.33 | 2.33 | 2.65 | ± | 0.554 | 20.9 |
| PK Parameters | | | | | | | |
| Rsq_adj | 1.000 | 0.998 | 0.999 | — | ± | — | — |
| No. points used for $T_{1/2}$ | 6.00 | 7.00 | 3.00 | ND | ± | — | — |
| $C_0$ (ng/mL) | 22695 | 22332 | 20894 | 21974 | ± | 953 | 4.34 |
| $T_{1/2}$ (h) | 2.00 | 1.97 | 2.05 | 2.00 | ± | 0.0394 | 1.97 |
| $Vd_{ss}$ (L/kg) | 0.265 | 0.339 | 0.313 | 0.306 | ± | 0.0376 | 12.3 |
| Cl (mL/min/kg) | 1.59 | 1.99 | 2.17 | 1.92 | ± | 0.295 | 15.4 |
| $T_{last}$ (h) | 24.0 | 24.0 | 24.0 | 24.0 | ± | — | — |
| $AUC_{0-last}$ (ng·h/mL) | 41880 | 33489 | 30751 | 35373 | ± | 5799 | 16.4 |
| $AUC_{0-inf}$ (ng·h/mL) | 41889 | 33496 | 30758 | 35381 | ± | 5800 | 16.4 |
| $MRT_{0-last}$ (h) | 2.77 | 2.83 | 2.40 | 2.67 | ± | 0.234 | 8.76 |
| $MRT_{0-inf}$ (h) | 2.78 | 2.84 | 2.41 | 2.67 | ± | 0.233 | 8.73 |
| $AUC_{Extra}$ (%) | 0.0226 | 0.0198 | 0.0224 | 0.0216 | ± | 0.00158 | 7.30 |
| $AUMC_{Extra}$ (%) | 0.219 | 0.187 | 0.251 | 0.219 | ± | 0.0318 | 14.6 |

Bioavailability of MCC_000950_016 in Mouse (ng/mL)
MCC_000950_016
PO

| | M4 | M5 | M6 | Mean PO | | SD | CV (%) |
|---|---|---|---|---|---|---|---|
| PO Time (h) | | | | | | | |
| 0.250 | 21900 | 29000 | 48900 | 33267 | ± | 13997 | 42.1 |
| 0.500 | 20400 | 34100 | 35800 | 30100 | ± | 8443 | 28.1 |
| 1.00 | 19300 | 33700 | 37000 | 30000 | ± | 9412 | 31.4 |
| 2.00 | 18500 | 22500 | 26200 | 22400 | ± | 3851 | 17.2 |
| 4.00 | 10200 | 13000 | 10500 | 11233 | ± | 1537 | 13.7 |
| 8.00 | 4330 | 2360 | 4670 | 3787 | ± | 1247 | 32.9 |
| 24.0 | 60.7 | 17.4 | 39.3 | 39.1 | ± | 21.7 | 55.3 |
| PK Parameters | | | | | | | |
| Rsq_adj | 0.999 | 0.996 | 0.996 | — | ± | — | — |
| No. points used for $T_{1/2}$ | 4.00 | 5.00 | 6.00 | ND | ± | — | — |
| $C_{max}$ (ng/mL) | 21900 | 34100 | 48900 | 34967 | ± | 13521 | 38.7 |
| $T_{max}$ (h) | 0.250 | 0.500 | 0.250 | 0.333 | ± | 0.144 | 43.3 |
| $T_{1/2}$ (h) | 2.67 | 2.11 | 2.37 | 2.39 | ± | 0.282 | 11.8 |
| $T_{last}$ (h) | 24.0 | 24.0 | 24.0 | 24.0 | ± | — | — |
| $AUC_{0-last}$ (ng·h/mL) | 108135 | 123399 | 144734 | 125422 | ± | 18383 | 14.7 |
| $AUC_{0-inf}$ (ng·h/mL) | 108369 | 123452 | 144868 | 125563 | ± | 18341 | 14.6 |
| $MRT_{0-last}$ (h) | 4.26 | 3.07 | 3.47 | 3.60 | ± | 0.603 | 16.8 |
| $MRT_{0-inf}$ (h) | 4.31 | 3.08 | 3.49 | 3.63 | ± | 0.624 | 17.2 |
| $AUC_{Extra}$ (%) | 0.216 | 0.0429 | 0.0929 | 0.117 | ± | 0.0892 | 76.0 |
| $AUMC_{Extra}$ (%) | 1.40 | 0.376 | 0.730 | 0.835 | ± | 0.519 | 62.1 |
| Bioavailability (%)[a] | — | — | — | 71.0 | ± | — | — |

Tables 5 and 6: PK and bioavailability data for N-((1,2,3,5,6,7-hexahydro-s-indacen-4-yl)carbamoyl)-4-(2-hydroxypropan-2-yl)furan-2-sulfonamide (MCC950)

| Bioavailability of MCC_007840_002 in Mouse (ng/mL) MCC_007840_002 IV | | | | | | | |
|---|---|---|---|---|---|---|---|
| | M1 | M2 | M3 | Mean IV | | SD | CV (%) |
| IV Time (h) | | | | | | | |
| 0.0833 | 47800 | 41900 | 38600 | 42767 | ± | 4661 | 10.9 |
| 0.250 | 28100 | 29300 | 29300 | 28900 | ± | 693 | 2.40 |
| 0.500 | 25200 | 25200 | 24500 | 24967 | ± | 404 | 1.62 |
| 1.00 | 19900 | 18900 | 17200 | 18667 | ± | 1365 | 7.31 |
| 2.00 | 13300 | 14700 | 19900 | 15967 | ± | 3478 | 21.8 |
| 4.00 | 6520 | 8550 | 8590 | 7887 | ± | 1184 | 15.0 |
| 8.00 | 3490 | 3360 | 4440 | 3763 | ± | 590 | 15.7 |
| 24.0 | 149 | 122 | 130 | 134 | ± | 13.9 | 10.4 |
| PK Parameters | | | | | | | |
| Rsq_adj | 0.998 | 0.999 | 0.996 | — | ± | — | — |
| No. points used for $T_{1/2}$ | 3.00 | 3.00 | 3.00 | 3.00 | ± | — | — |
| $C_0$ (ng/mL) | 62333 | 50100 | 44301 | 52245 | ± | 9205 | 17.6 |
| $T_{1/2}$ (h) | 3.62 | 3.29 | 3.26 | 3.39 | ± | 0.204 | 6.01 |
| $Vd_{ss}$ (L/kg) | 0.170 | 0.158 | 0.151 | 0.160 | ± | 0.00989 | 6.20 |
| Cl (mL/min/kg) | 0.659 | 0.633 | 0.571 | 0.621 | ± | 0.0455 | 7.33 |
| $T_{last}$ (h) | 24.0 | 24.0 | 24.0 | 24.0 | ± | — | — |
| $AUC_{0-last}$ (ng·h/mL) | 100364 | 104705 | 116222 | 107097 | ± | 8195 | 7.65 |
| $AUC_{0-inf}$ (ng·h/mL) | 101143 | 105283 | 116833 | 107753 | ± | 8132 | 7.55 |
| $MRT_{0-last}$ (h) | 4.11 | 4.01 | 4.28 | 4.13 | ± | 0.133 | 3.23 |
| $MRT_{0-inf}$ (h) | 4.30 | 4.15 | 4.40 | 4.29 | ± | 0.129 | 3.02 |
| $AUC_{Extra}$ (%) | 0.770 | 0.549 | 0.523 | 0.614 | ± | 0.136 | 22.1 |
| $AUMC_{Extra}$ (%) | 5.23 | 3.81 | 3.41 | 4.15 | ± | 0.957 | 23.1 |

| Bioavailability of MCC_007840_002 in Mouse (ng/mL) MCC_007840_002 PO | | | | | | | |
|---|---|---|---|---|---|---|---|
| | M4 | M5 | M6 | Mean PO | | SD | CV (%) |
| PO Time (h) | | | | | | | |
| 0.250 | 84300 | 27400 | 69700 | 60467 | ± | 29552 | 48.9 |
| 0.500 | 70300 | 24000 | 56600 | 50300 | ± | 23784 | 47.3 |
| 1.00 | 60400 | 20900 | 45700 | 42333 | ± | 19964 | 47.2 |
| 2.00 | 54900 | 19100 | 53600 | 42600 | ± | 20359 | 47.8 |
| 4.00 | 32900 | 14100 | 32800 | 26600 | ± | 10825 | 40.7 |
| 8.00 | 14100 | 12800 | 29900 | 18933 | ± | 9520 | 50.3 |
| 24.0 | 660 | 2370 | 1370 | 1467 | ± | 859 | 58.6 |
| PK Parameters | | | | | | | |
| Rsq_adj | 0.999 | 0.984 | 0.968 | — | ± | — | — |
| No. points used for $T_{1/2}$ | 3.00 | 6.00 | 4.00 | ND | ± | — | — |
| $C_{max}$ (ng/mL) | 84300 | 27400 | 69700 | 60467 | ± | 29552 | 48.9 |
| $T_{max}$ (h) | 0.250 | 0.250 | 0.250 | 0.250 | ± | 0.000 | 0.0 |
| $T_{1/2}$ (h) | 3.57 | 7.31 | 4.18 | 5.02 | ± | 2.01 | 40.1 |
| $T_{last}$ (h) | 24.0 | 24.0 | 24.0 | 24.0 | ± | — | — |
| $AUC_{0-last}$ (ng·h/mL) | 364947 | 226687 | 457808 | 349814 | ± | 116301 | 33.2 |
| $AUC_{0-inf}$ (ng·h/mL) | 368345 | 251697 | 466063 | 362035 | ± | 107323 | 29.6 |
| $MRT_{0-last}$ (h) | 4.80 | 8.07 | 6.41 | 6.43 | ± | 1.64 | 25.4 |
| $MRT_{0-inf}$ (h) | 5.03 | 10.7 | 6.83 | 7.52 | ± | 2.90 | 38.6 |
| $AUC_{Extra}$ (%) | 0.922 | 9.94 | 1.77 | 4.21 | ± | 4.98 | 118 |
| $AUMC_{Extra}$ (%) | 5.35 | 32.1 | 7.78 | 15.1 | ± | 14.8 | 98.1 |
| Bioavailability (%)[a] | — | — | — | 67.2 | ± | — | — |

Tables 7 and 8: PK and bioavailability data for N-((1,2,3,5,6,7-hexahydro-s-indacen-4-yl)carbamoyl)-1-isopropyl-1H-pyrazole-3-sulfonamide (MCC7840)

TABLE 9

Comparative IC$_{50}$ data for commercial compounds.

| Common names | Structure | HMDM IC50 vs NLRP3 | BMDM IC50 vs NLRP3 |
|---|---|---|---|
| Glibenclamide (Glyburide) | 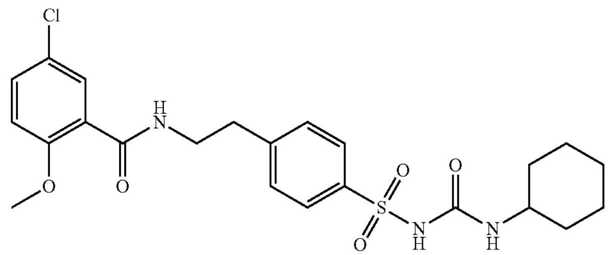 [SMILES: COc1ccc(Cl)cc1C(=O)NCCc1ccc(S(=O)(=O)NC(=O)NC2CCCCC2)cc1] | 6 μM | 22 μM |
| Glibenclamide precursor | 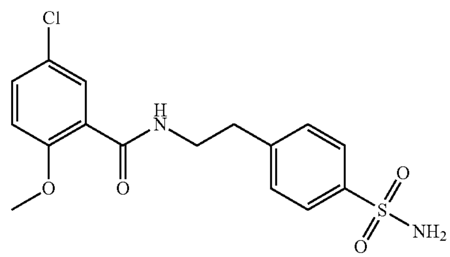 [SMILES: COc1ccc(Cl)cc1C(=O)NCCc1ccc(S(N)(=O)=O)cc1] | >200 μM | >200 μM |
| Glipizide | 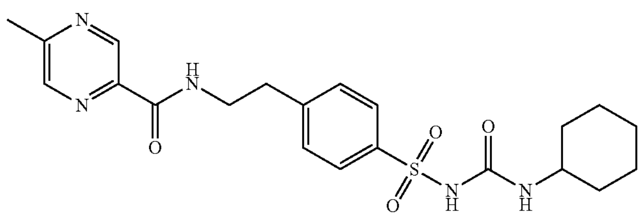 [SMILES: Cc1cnc(C(=O)NCCc2ccc(S(=O)(=O)NC(=O)NC3CCCCC3)cc2)cn1] | >200 μM | >200 μM |
| Glipizide precursor | 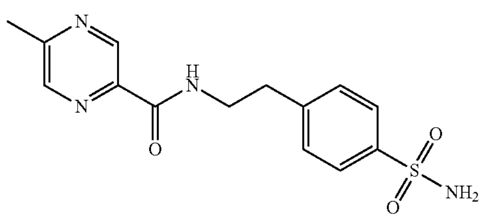 [SMILES: Cc1cnc(C(=O)NCCc2ccc(S(N)(=O)=O)cc2)cn1] | >50 μM | |
| Acetohexamide | 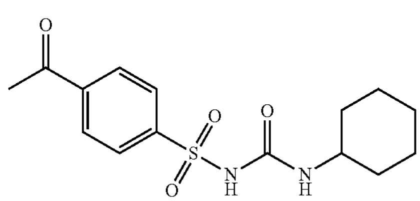 [SMILES: CC(=O)c1ccc(S(=O)(=O)NC(=O)NC2CCCCC2)cc1] | >200 μM | >200 μM |
| Tolazamide | 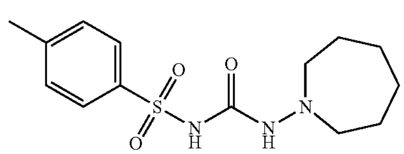 [SMILES: Cc1ccc(S(=O)(=O)NC(=O)NN2CCCCCC2)cc1] | >200 μM | |
| Gliclazide | 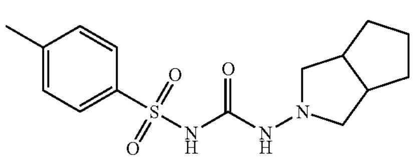 [SMILES: Cc1ccc(S(=O)(=O)NC(=O)NN2CC3CCCC3C2)cc1] | >200 μM | >200 μM |

TABLE 9-continued

Comparative IC$_{50}$ data for commercial compounds.

| Common names | Structure | HMDM IC50 vs NLRP3 | BMDM IC50 vs NLRP3 |
| --- | --- | --- | --- |
| Tolbutamide | 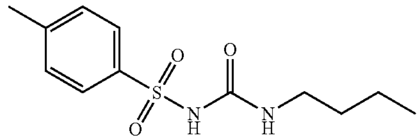 [SMILES: CCCCNC(=O)NS(=O)(=O)c1ccc(C)cc1] | >200 μM | >200 μM |
| Glimepiride | 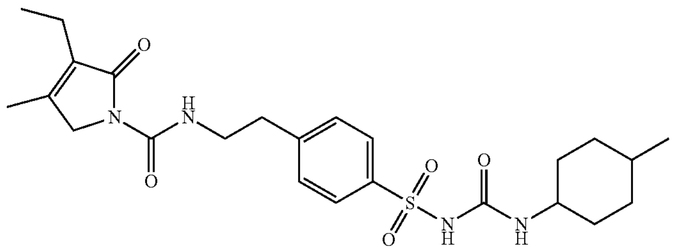 | | 92 μM |
| Glimespiride precursor | 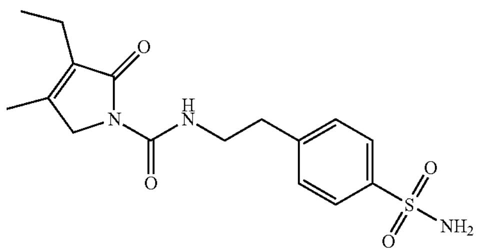 [SMILES: CCC1=C(C)CN(C(=O)NCCc2ccc(S(N)(=O)=O)cc2)C1=O] | >200 μM | |
| Gliquidone | 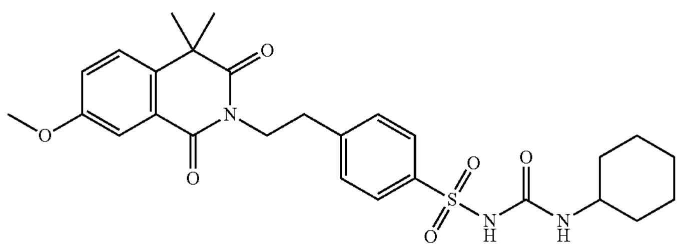 [SMILES: COc1ccc2c(c1)C(=O)N(CCc1ccc(S(=O)(=O)NC(=O)NC3CCCCC3)cc1)C(=O)C2(C)C] | | 32 μM |
| Gliquidone precursor | 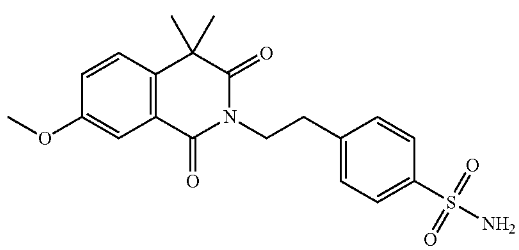 [SMILES: COc1ccc2c(c1)C(=O)N(CCc1ccc(S(N)(=O)=O)cc1)C(=O)C2(C)C] | >200 μM | >10 μM |
| Carbutamide | 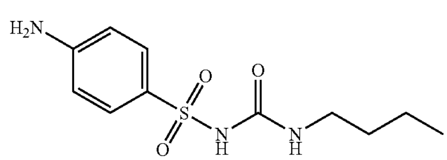 [SMILES: CCCCNC(=O)NS(=O)(=O)c1ccc(N)cc1] | >200 μM | |
| Chlorpropamide | 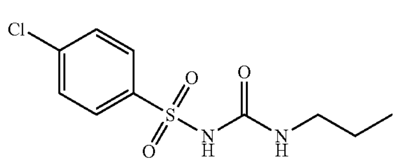 [SMILES: CCCNC(=O)NS(=O)(=O)c1ccc(Cl)cc1] | >200 μM | >200 μM |

TABLE 9-continued

Comparative IC$_{50}$ data for commercial compounds.

| Common names | Structure | HMDM IC50 vs NLRP3 | BMDM IC50 vs NLRP3 |
|---|---|---|---|
| Glisoxepide | 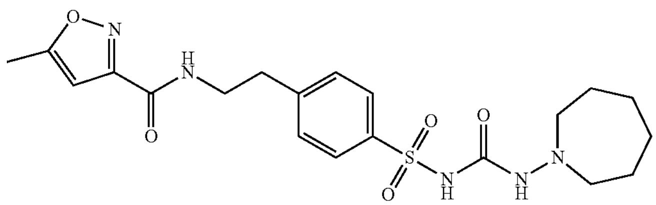 [SMILES: Cc1cc(C(=O)NCCc2ccc(S(=O)(=O)NC(=O)NN3CCCCCC3)cc2)no1] | | |
| Glisoxepide Precursor | 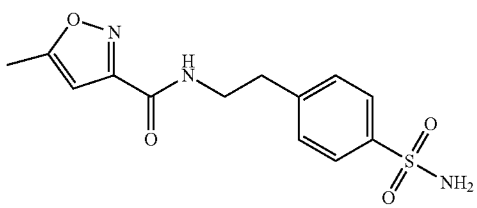 [SMILES: Cc1cc(C(=O)NCCc2ccc(S(N)(=O)=O)cc2)no1] | >10,000 μM | |
| Sulofenur | 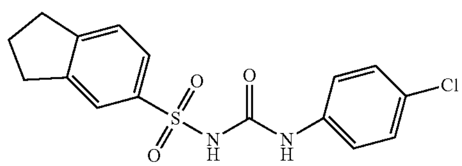 [SMILES: O=C(Nc1ccc(Cl)cc1)NS(=O)(=O)c1ccc2c(c1)CCC2] | >100 μM | >10 μM |

TABLE 10

Biological Activity data for select compounds of the first aspect (sorted by hybrid BMDM)

| Structure | HMDM IC50 vs NLRP3 | BMDM IC50 vs NLRP3 |
|---|---|---|
| 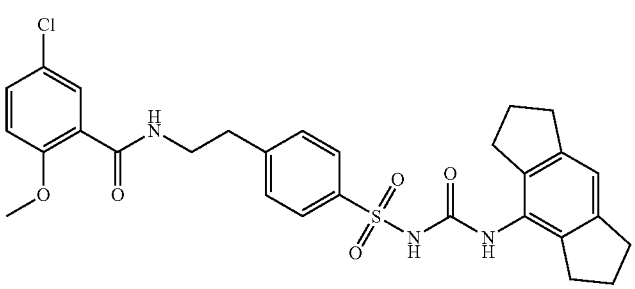 [SMILES: COc1ccc(Cl)cc1C(=O)NCCc1ccc(S(=O)(=O)NC(=O)Nc2c3c(cc4c2CCC4)CCC3)cc1] | 0.14 μM | 0.24 μM |
| | | 0.32 μM |

TABLE 10-continued

Biological Activity data for select compounds of the first aspect (sorted by hybrid BMDM)

| Structure | HMDM IC50 vs NLRP3 | BMDM IC50 vs NLRP3 |
|---|---|---|
| (structure) | 0.65 μM | 0.22 μM |
| (structure) | 2.3 μM | 0.26 μM |
| (structure) | 0.19 μM | 0.28 μM |
| (structure) | 0.31 μM | 0.036 μM |
| (structure) | 0.54 μM | 0.7 μM |
| (structure) | 0.31 μM | 0.014 μM |

TABLE 10-continued

Biological Activity data for select compounds of the first aspect (sorted by hybrid BMDM)

| Structure | HMDM IC50 vs NLRP3 | BMDM IC50 vs NLRP3 |
|---|---|---|
| 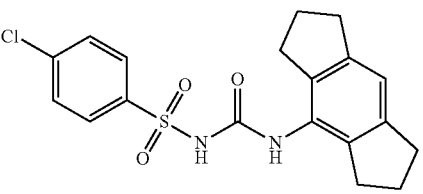 [SMILES: O=C(Nc1c2c(cc3c1CCC3)CCC2)NS(=O)(=O)c1ccc(Cl)cc1] | 0.3 µM | 0.03 µM |
| 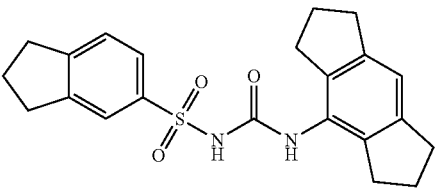 [SMILES: O=C(Nc1c2c(cc3c1CCC3)CCC2)NS(=O)(=O)c1ccc2c(c1)CCC2] | 1.46 µM | 0.05 µM |
| 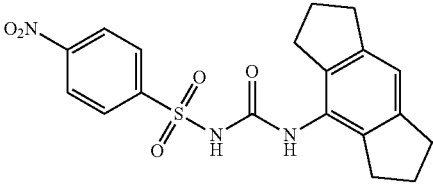 [SMILES: O=C(Nc1c2c(cc3c1CCC3)CCC2)NS(=O)(=O)c1ccc([N+](=O)[O-])cc1] | | 0.043 µM |

The invention claimed is:

1. A compound of formula (II), or a pharmaceutically acceptable salt, solvate or prodrug thereof:

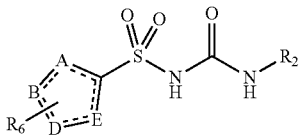

Formula (II)

wherein A, B, D and E are independently selected from C, N, O, S and Se, but at least one thereof is C and at least one thereof is N;
each dashed line may represent a bond;
each incidence of $R_6$ is independently selected from the group consisting of hydrogen, halide, cyano, $C_1$-$C_6$ alkyl, $C_1$-$C_6$ alkylamino, $C_1$-$C_6$ alkylhydroxy, $C_3$-$C_6$ cycloalkyl, alkylphenyl, phenyl, benzyl, $C_1$-$C_6$ ester, $C_2$-$C_6$ alkenyl, $C_1$-$C_6$ trifluoroalkyl and $C_1$-$C_6$ alkoxy, each of which may be optionally substituted, as appropriate, or $R_6$ is a fluorescent group; and
$R_2$ is selected from a 2,6-dialkylphenyl, a 2,6-dialkyl-4-halophenyl, a 2,6-dicycloalkylphenyl, a 2,6-dicycloalkyl-4-halophenyl, and:

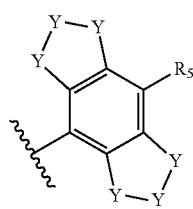

wherein each incidence of Y is independently selected from C, N, S and O, which may be optionally substituted as appropriate; and
$R_5$ is selected from the group consisting of hydrogen, halo, cyano, amide, sulphonamide, acyl, hydroxyl, $C_1$-$C_6$ alkyl, $C_1$-$C_6$ haloalkyl, $C_3$-$C_5$ cycloalkyl and $C_1$-$C_6$ alkoxy, all of which groups may be optionally substituted, as appropriate, with halo, cyano or $C_1$-$C_6$ alkoxy.

2. The compound of claim 1, wherein the compound of formula (II) is selected from the group consisting of:

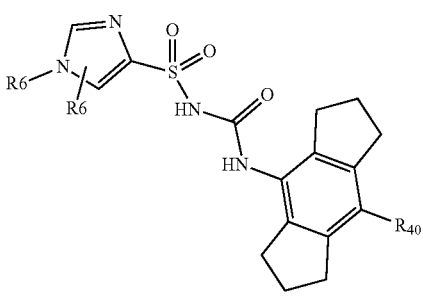

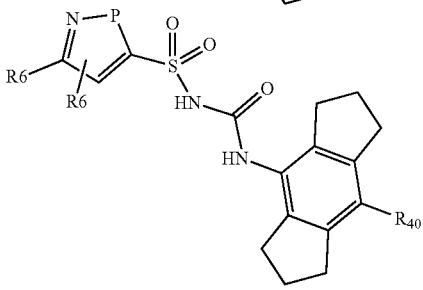

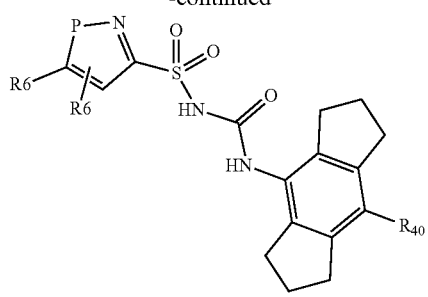
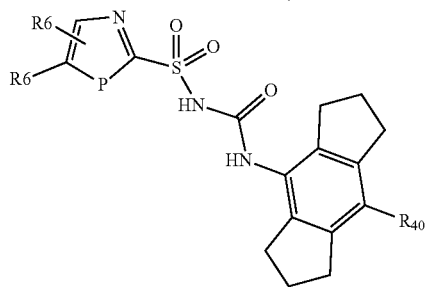
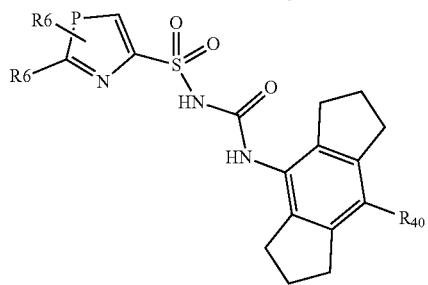
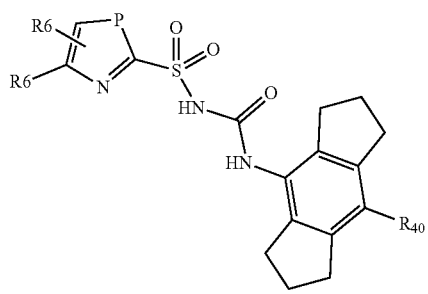
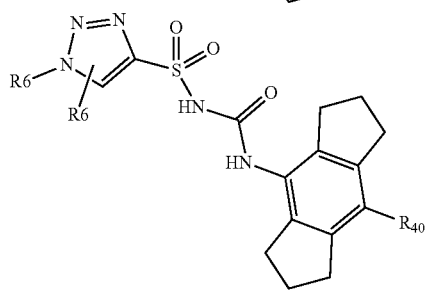
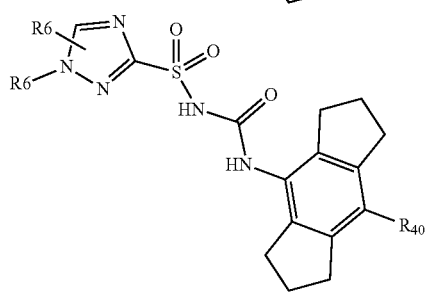
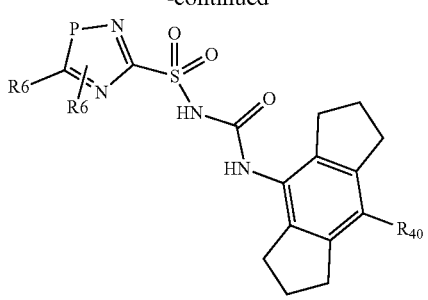
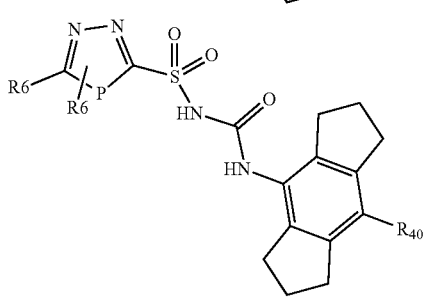
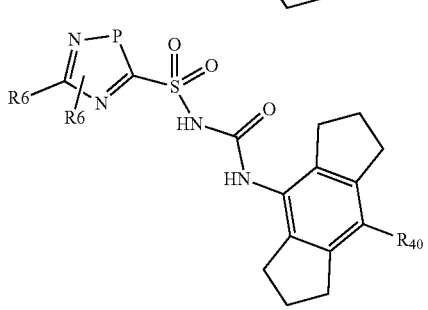
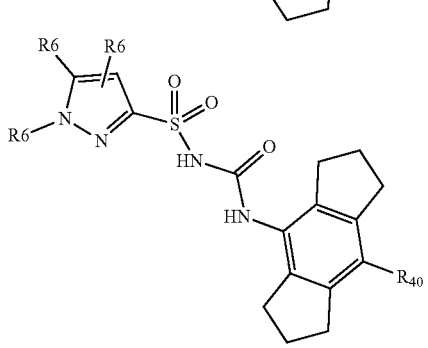
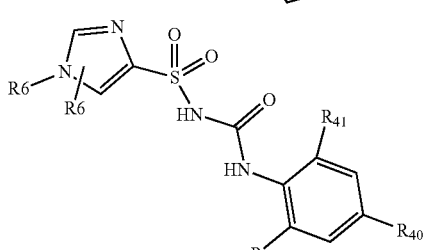
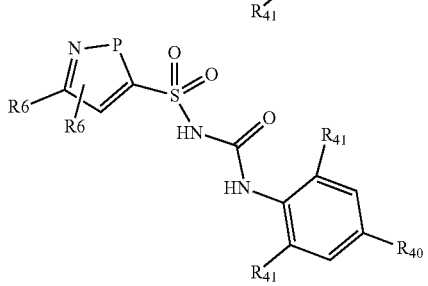

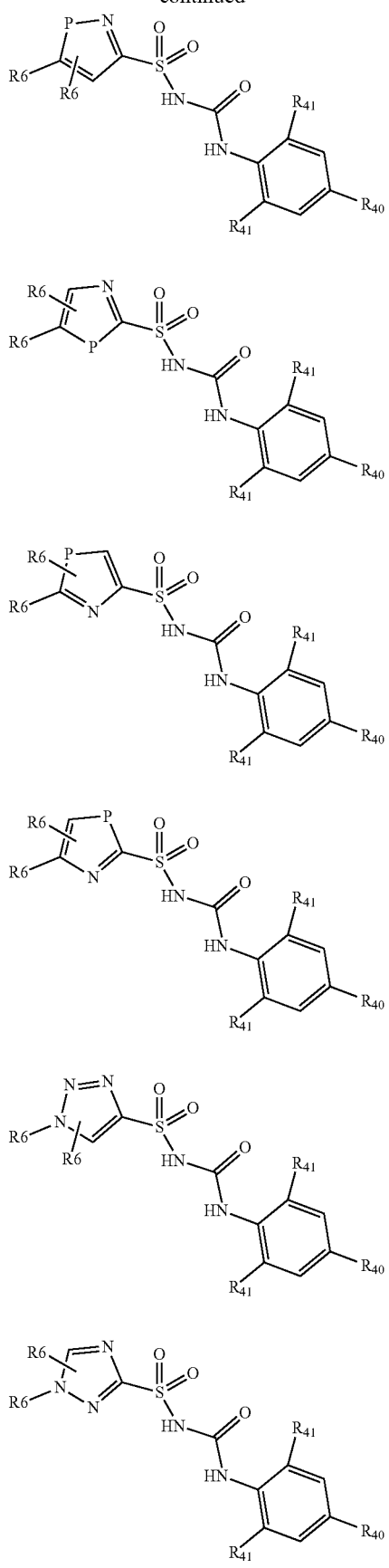

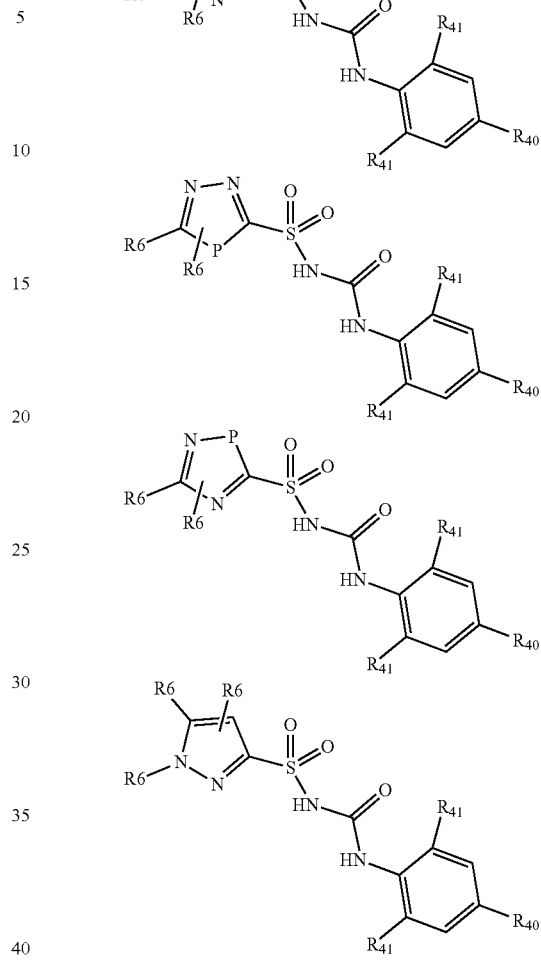

wherein $R_{40}$ is selected from H, $C_1$-$C_6$ alkyl and halo;
$R_{41}$ is selected from H, alkyl and cycloalkyl;
each incidence of P is independently selected from C, O and S; and
each incidence of $R_6$, when present, is independently selected from those groups defined in claim 1.

3. The compound of claim 1, wherein the compound is a compound of formula (IIb), or a pharmaceutically acceptable salt, solvate or prodrug thereof:

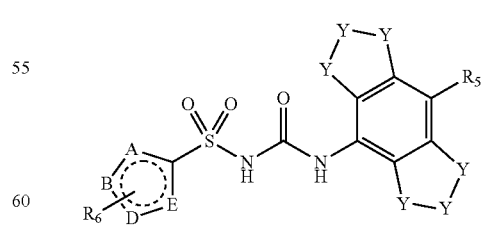

Formula (IIb)

wherein Y and $R_5$ are as defined in claim 1;
A, B, D and E are selected from N and C and at least two of A, B, D and E are N;
each incidence of $R_6$ is independently selected from the group consisting of hydrogen, halide, cyano, $C_1$-$C_6$ alkyl, $C_1$-$C_6$ alkylamino, $C_1$-$C_6$ alkylhydroxy, $C_3$-$C_6$ cycloalkyl, alkylphenyl, phenyl, benzyl, $C_1$-$C_6$ ester, $C_2$-$C_6$ alkenyl, $C_1$-$C_6$ trifluoroalkyl and $C_1$-$C_6$ alkoxy, each of which may be optionally substituted.

4. The compound of claim 1, wherein at least two of A, B, D and E are N.

5. The compound of claim 1, wherein A, B, D and E are selected from N and C.

6. The compound of claim 1, wherein A is C and at least two of B, D and E are N.

7. The compound of claim 1, wherein A, B, D and E form a ring selected from a pyrazole, an imidazole, a triazole, and a tetrazole.

8. The compound of claim 1, wherein A, B, D and E form a ring selected from a pyrazole and an imidazole ring.

9. The compound of claim 1, wherein A, B, D and E form a pyrazole ring.

10. The compound of claim 1, wherein the compound is a compound of formula (IIIa), (IIIb) or (IIIc), or a pharmaceutically acceptable salt, solvate or prodrug thereof:

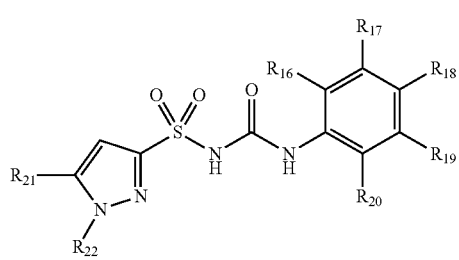

Formula (IIIa)

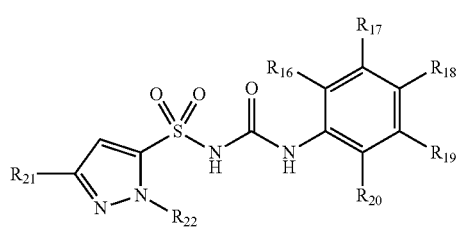

Formula (IIIb)

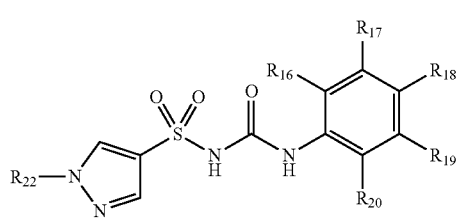

Formula (IIIc)

either wherein:
  $R_{21}$ is selected from H, alkyl, perhaloalkyl and hydroxylalkyl;
  $R_{22}$ is selected from H, alkyl, perhaloalkyl, $C_3$-$C_6$ cycloalkyl, phenyl and benzyl;
  $R_{16}$ and $R_{17}$, together with the atoms to which they are attached, form a cyclopentyl ring;
  $R_{19}$ and $R_{20}$, together with the atoms to which they are attached, form a cyclopentyl ring;
  $R_{18}$ is H or halogen; and
  provided that $R_{21}$ and $R_{22}$ are not both H;
or wherein:
  $R_{21}$ is selected from H, alkyl, perhaloalkyl and hydroxylalkyl;
  $R_{22}$ is selected from H, alkyl, perhaloalkyl, $C_3$-$C_6$ cycloalkyl, phenyl and benzyl;
  $R_{16}$ and $R_{20}$ are $C_{1-6}$ alkyl or $C_{3-5}$ cycloalkyl;
  $R_{17}$ and $R_{19}$ are H;
  $R_{18}$ is H or halogen; and
  provided that $R_{21}$ and $R_{22}$ are not both H.

11. The compound of claim 1, wherein the compound is a compound of formula (IVa), (IVb) or (IVc), or a pharmaceutically acceptable salt, solvate or prodrug thereof:

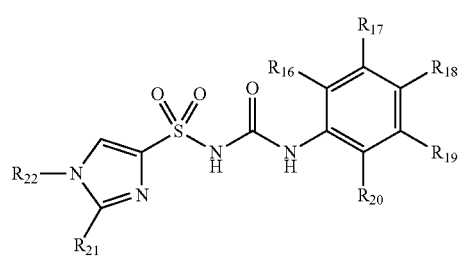

Formula (IVa)

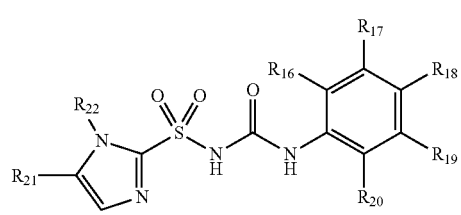

Formula (IVb)

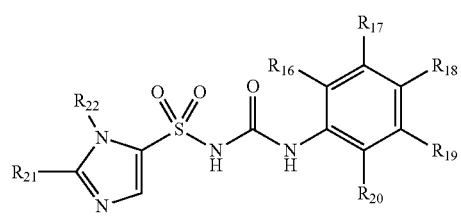

Formula (IVc)

either wherein:
  $R_{21}$ and $R_{22}$ are selected from H, alkyl, perhaloalkyl, hydroxylalkyl, $C_3$-$C_6$ cycloalkyl, phenyl and benzyl;
  $R_{16}$ and $R_{17}$, together with the atoms to which they are attached, form a cyclopentyl ring;
  $R_{19}$ and $R_{20}$, together with the atoms to which they are attached, form a cyclopentyl ring;
  $R_{18}$ is H or halogen; and
  provided that $R_{21}$ and $R_{22}$ are not both H;
or wherein:
  $R_{21}$ and $R_{22}$ are selected from H, alkyl, perhaloalkyl, hydroxylalkyl, $C_3$-$C_6$ cycloalkyl, phenyl and benzyl;
  $R_{16}$ and $R_{20}$ are $C_{1-6}$ alkyl or $C_{3-5}$ cycloalkyl;
  $R_{17}$ and $R_{19}$ are H;
  $R_{18}$ is H or halogen; and
  provided that $R_{21}$ and $R_{22}$ are not both H.

12. The compound of claim 1, wherein the compound is a compound of formula (Va), (Vb) or (Vc), or a pharmaceutically acceptable salt, solvate or prodrug thereof:

Formula (Va)

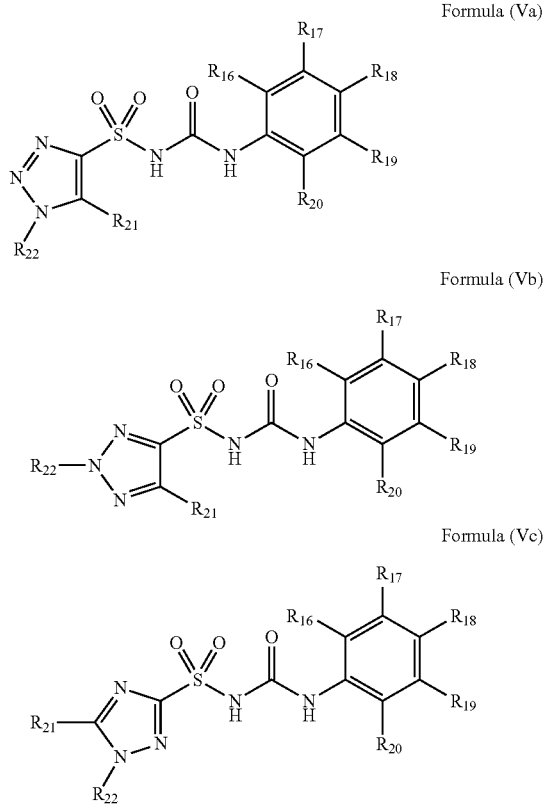

Formula (Vb)

Formula (Vc)

either wherein:
- R$_{21}$ and R$_{22}$ are selected from H, alkyl, perhaloalkyl, hydroxylalkyl, C$_3$-C$_6$ cycloalkyl, phenyl and benzyl;
- R$_{16}$ and R$_{17}$, together with the atoms to which they are attached, form a cyclopentyl ring;
- R$_{19}$ and R$_{20}$, together with the atoms to which they are attached, form a cyclopentyl ring;
- R$_{18}$ is H or halogen; and
- provided that R$_{21}$ and R$_{22}$ are not both H;

or wherein:
- R$_{21}$ and R$_{22}$ are selected from H, alkyl, perhaloalkyl, hydroxylalkyl, C$_3$-C$_6$ cycloalkyl, phenyl and benzyl;
- R$_{16}$ and R$_{20}$ are C$_{1-6}$alkyl or C$_{3-5}$cycloalkyl;
- R$_{17}$ and R$_{19}$ are H;
- R$_{18}$ is H or halogen; and
- provided that R$_{21}$ and R$_{22}$ are not both H.

13. The compound of claim 1, wherein the compound is a compound of formula (VIa) or (VIb), or a pharmaceutically acceptable salt, solvate or prodrug thereof:

Formula (VIa)

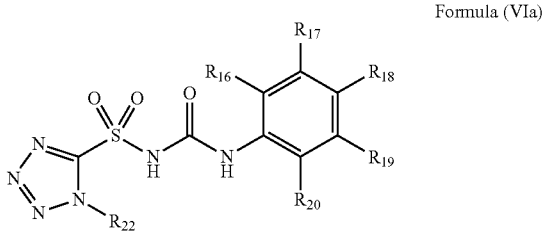

Formula (VIb)

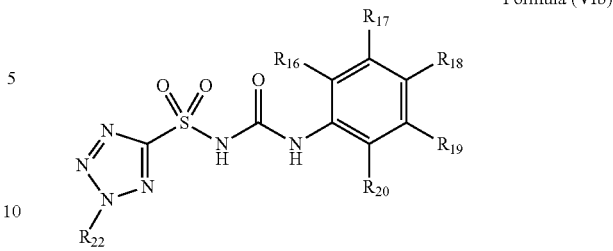

either wherein:
- R$_{22}$ is selected from alkyl, perhaloalkyl, hydroxylalkyl, C$_3$-C$_6$ cycloalkyl, phenyl and benzyl;
- R$_{16}$ and R$_{17}$, together with the atoms to which they are attached, form a cyclopentyl ring;
- R$_{19}$ and R$_{20}$, together with the atoms to which they are attached, form a cyclopentyl ring; and
- R$_{18}$ is H or halogen;

or wherein:
- R$_{22}$ is selected from alkyl, perhaloalkyl, hydroxylalkyl, C$_3$-C$_6$ cycloalkyl, phenyl and benzyl;
- R$_{16}$ and R$_{20}$ are C$_{1-6}$alkyl or C$_{3-5}$cycloalkyl;
- R$_{17}$ and R$_{19}$ are H; and
- R$_{18}$ is H or halogen.

14. The compound of claim 1, wherein

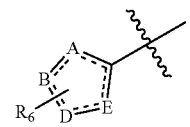

is selected from the group consisting of:

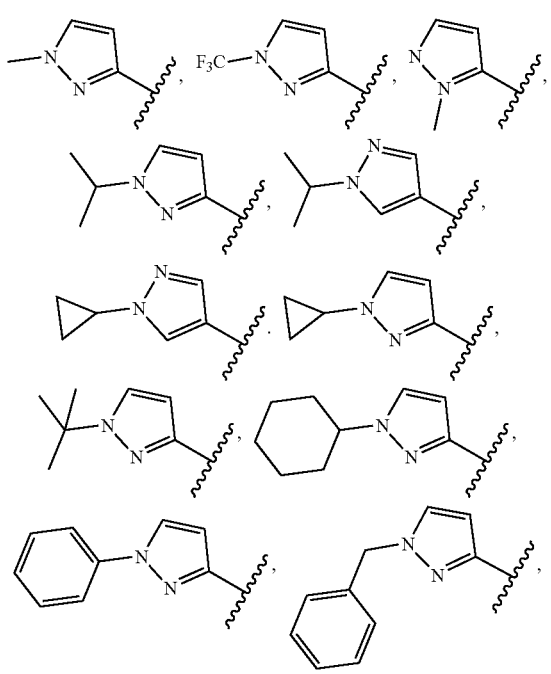

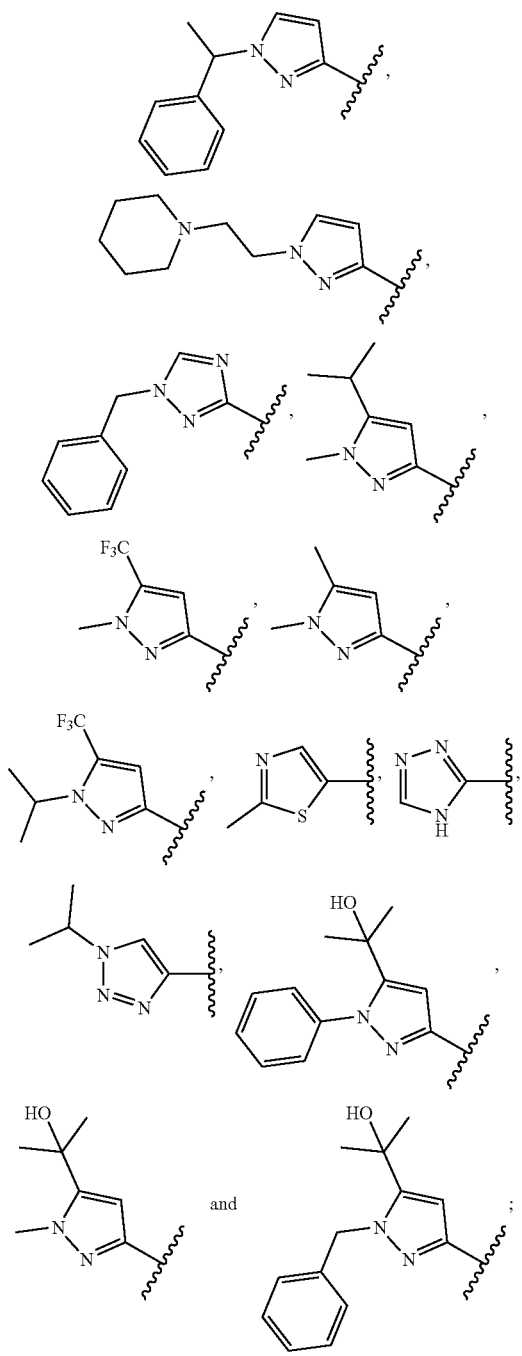

and in combination with each such group, $R_2$ is independently selected from the group consisting of:

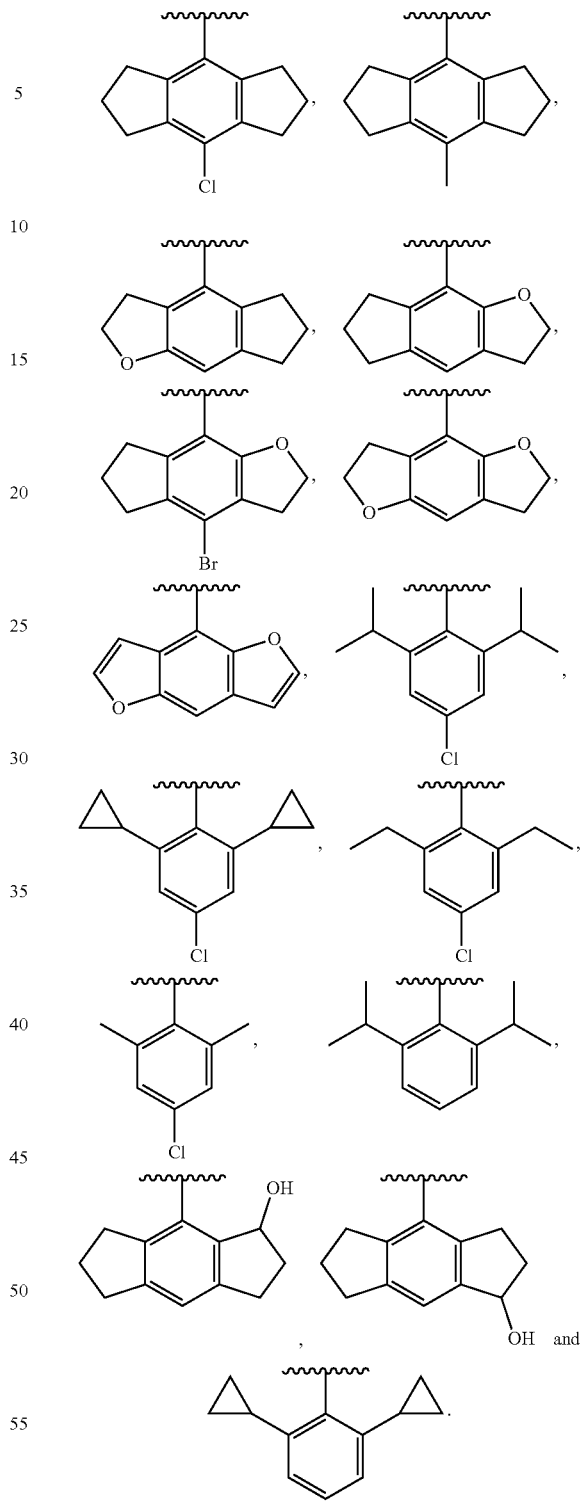

15. The compound of claim 1, wherein $R_2$ is selected from hexahydroindacene, 2,6-diisopropylphenyl, 2,6-diisopropyl-4-chlorophenyl, 2,6-dicyclopropylphenyl and 2,6-dicyclopropyl-4-chlorophenyl.

16. The compound of claim 1, wherein the compound is a compound of formula (Ia), (Ib) or (Ic), or a pharmaceutically acceptable salt, solvate or prodrug thereof:

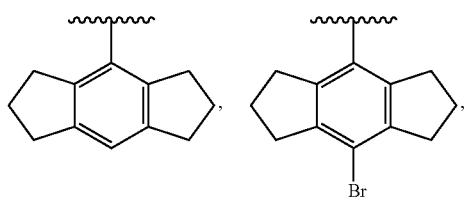

US 10,538,487 B2

301 formula (Ia)

formula (Ib)

formula (Ic)

wherein R₁ is and wherein A, B, D, E and R₆ are as defined in claim 1.

17. The compound of claim 16, wherein R₁ is selected from the group consisting of pyrazole, pyrrolidine, pyrrole, triazole, tetrazole and imidazole, all of which may be optionally substituted as appropriate.

18. The compound of claim 16, wherein R₁ is selected from the group consisting of:

302

-continued and

19. The compound of claim 1, wherein any optional substituent is independently selected from the group consisting of C1-10 alkyl; C3-6 cycloalkyl; hydroxyalkyl; C1-10 alkoxy; C2-10 alkenyl; C2-10 alkynyl; C6-C12 aryl; aryloxy; heteroaryl; heterocyclyl; halo; hydroxyl; halogenated alkyl; amino; alkylamino; arylamino; acyl; amido; CN; NO$_2$; N$_3$; CH$_2$OH; CONH$_2$; CONR$_{24}$R$_{25}$; CO$_2$R$_{24}$; CH$_2$OR$_{24}$; NHCOR$_{24}$; NHCO$_2$R$_{24}$; C1-3 alkylthio; sulfate; sulfonic acid; sulfonate esters; phosphonic acid; phosphate; phosphonate; mono-, di-, or triphosphate esters; trityl; monomethoxytrityl; R$_{24}$SO; R$_{24}$SO$_2$; CF$_3$S; CF$_3$SO$_2$; and trialkylsilyl; wherein R$_{24}$ and R$_{25}$ are each independently selected from H and C1-10 alkyl.

20. The compound of claim 1, wherein the compound is selected from the group consisting of:

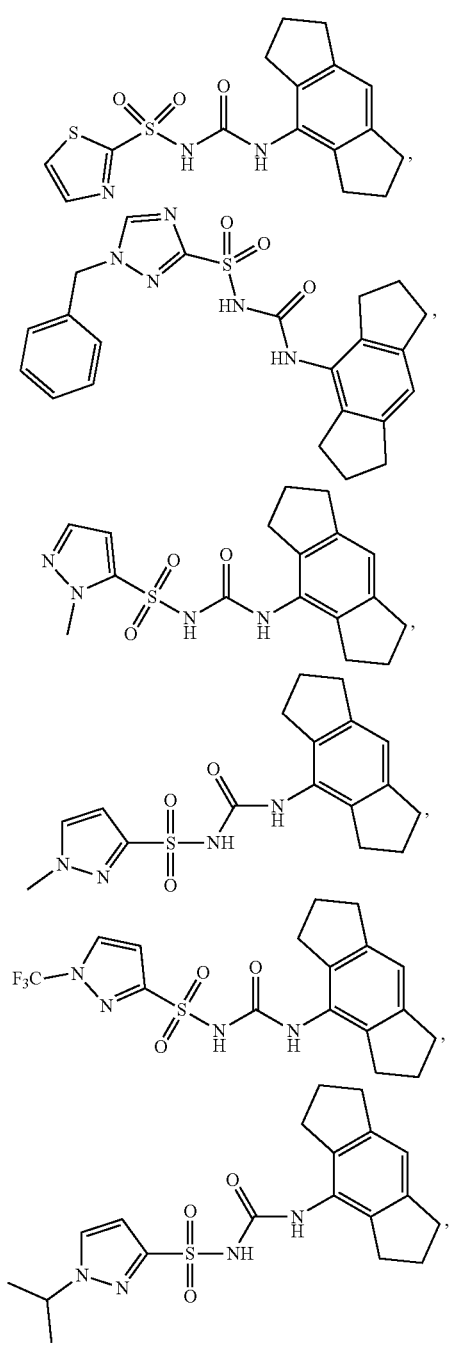

-continued

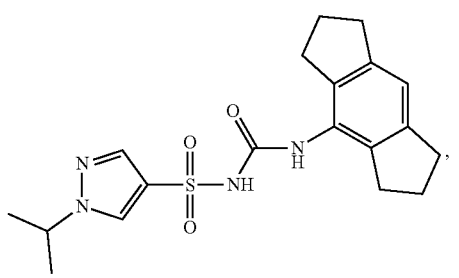

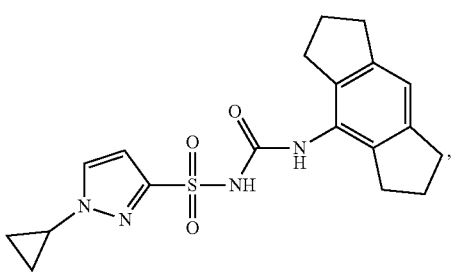

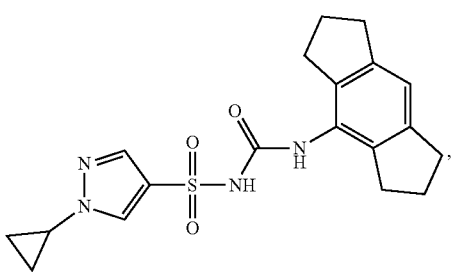

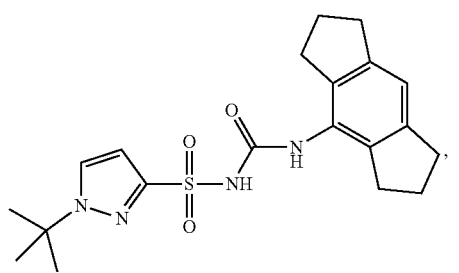

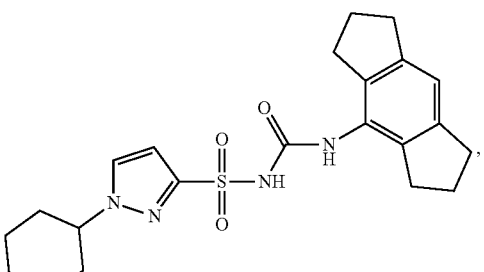

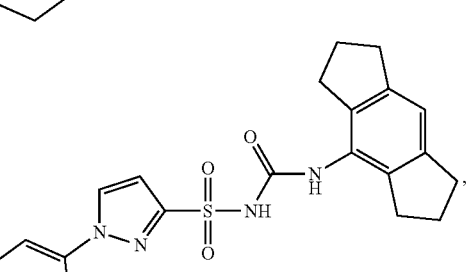

305
-continued
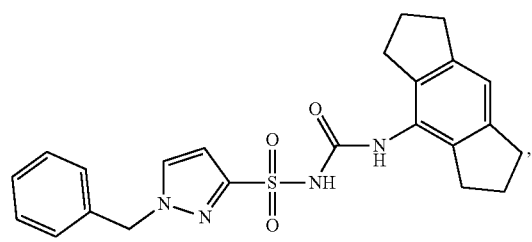
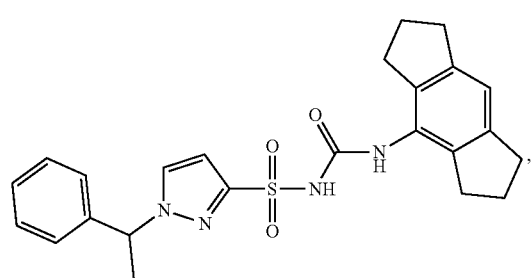
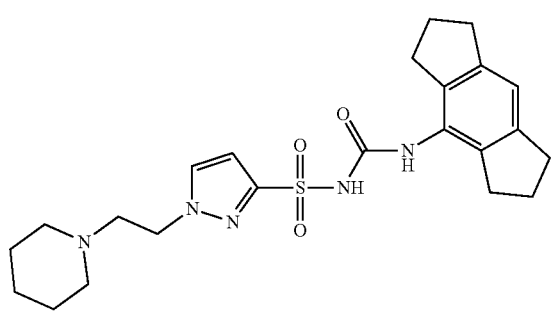
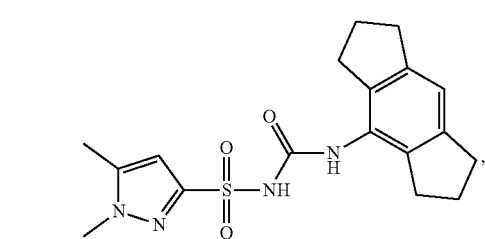
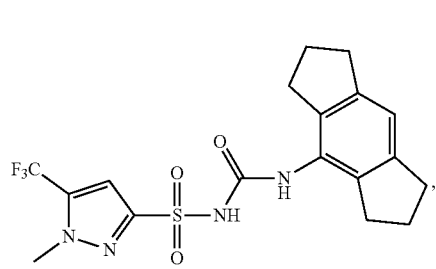
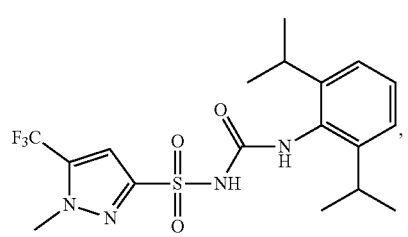
306
-continued
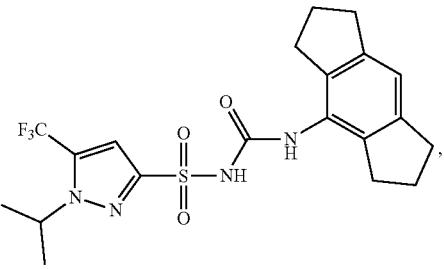
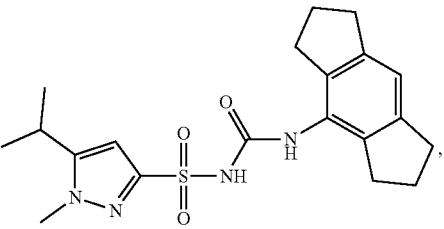
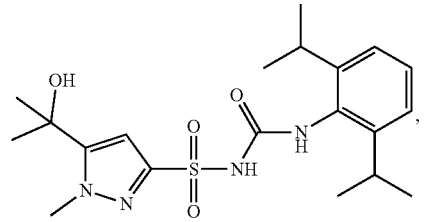
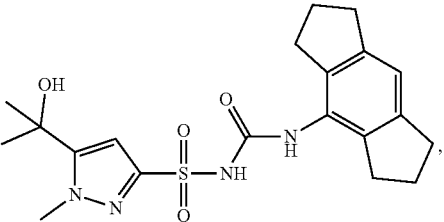
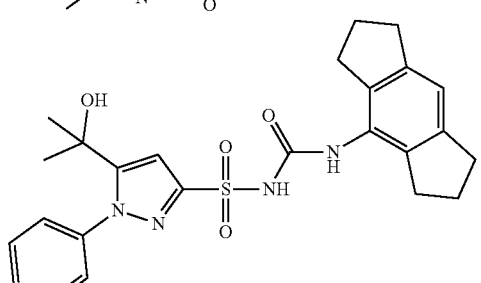
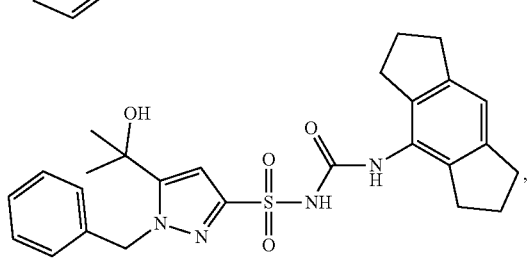
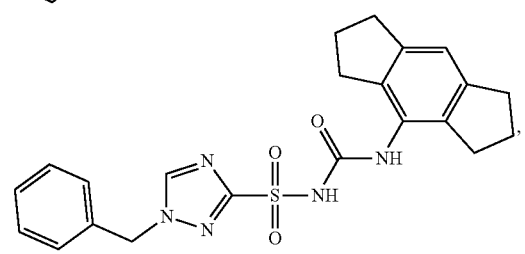

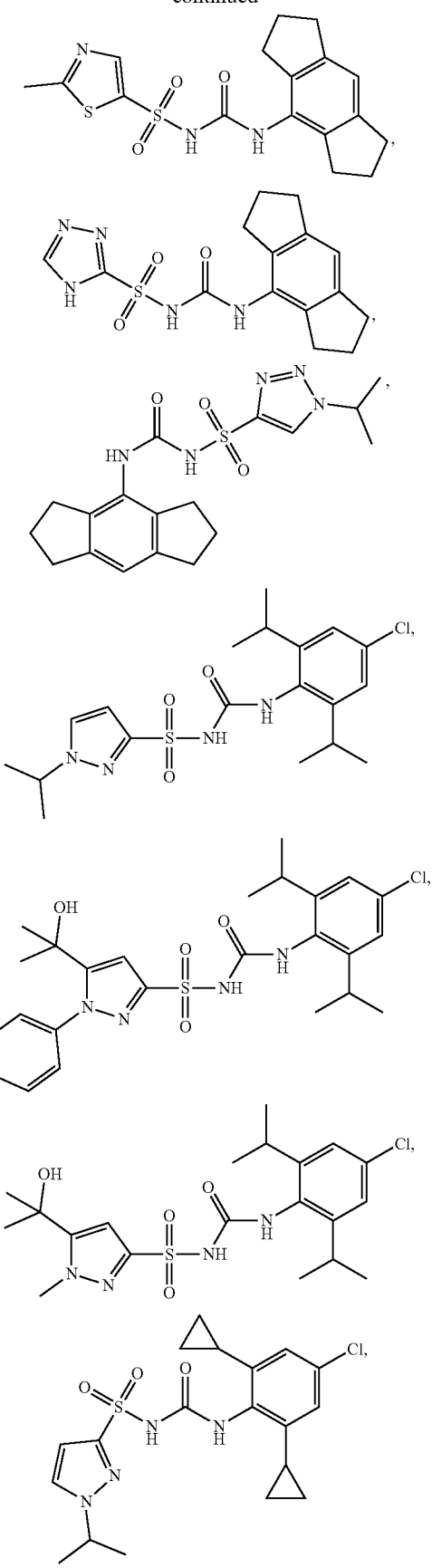

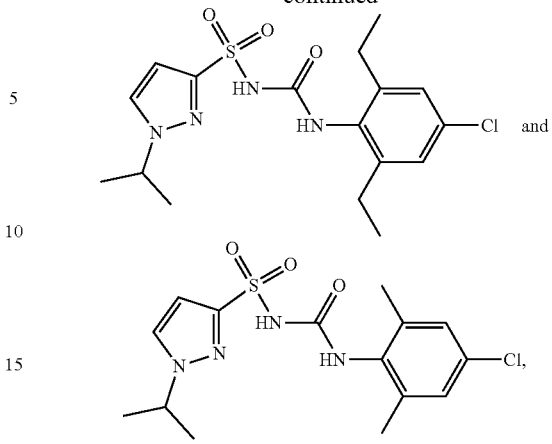

and pharmaceutically acceptable salts, solvates and prodrugs thereof.

21. The compound of claim 1, wherein the compound is

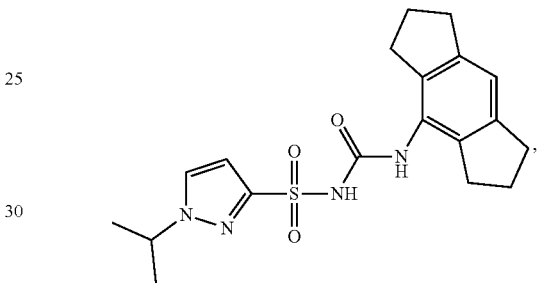

or a pharmaceutically acceptable salt, solvate or prodrug thereof.

22. The compound of claim 1, wherein the compound is

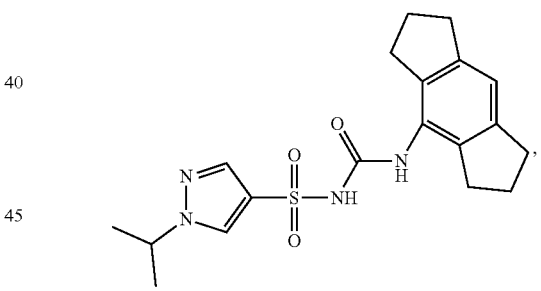

or a pharmaceutically acceptable salt, solvate or prodrug thereof.

23. The compound of claim 1, wherein the compound is

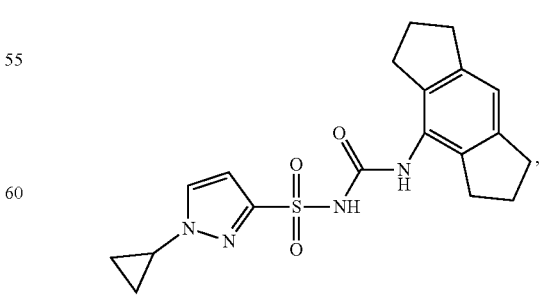

or a pharmaceutically acceptable salt, solvate or prodrug thereof.

24. The compound of claim 1, wherein the compound is

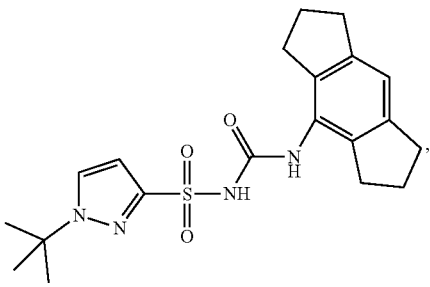 [SMILES: CC(C)(C)n1ccc(S(=O)(=O)NC(=O)Nc2c3c(cc4c2CCC4)CCC3)n1]

or a pharmaceutically acceptable salt, solvate or prodrug thereof.

25. The compound or the pharmaceutically acceptable salt, solvate or prodrug of claim 1, wherein the compound, or the pharmaceutically acceptable salt, solvate or prodrug thereof, is an inhibitor of the NLRP3 inflammasome.

26. A pharmaceutical composition comprising a compound of claim 1, or a pharmaceutically acceptable salt, solvate or prodrug thereof, and a pharmaceutically acceptable carrier, diluent and/or excipient.

27. A method of treatment of a disease, disorder or condition including the step of administering an effective amount of a compound of claim 1, or a pharmaceutically effective salt, solvate or prodrug thereof, to thereby treat the disease, disorder or condition, wherein the disease, disorder or condition is:
(a) one which is responsive to inhibition of activation of the NLRP3 inflammasome; and/or
(b) responsive to modulation of one or more of IL-1β, IL-17, IL-18, IL-1α, IL-37, IL-33 and Th17 cells.

28. The method of claim 27, wherein:
(a) the treatment of the disease, disorder or condition is performed on a mammal; and/or
(b) the treatment of the disease, disorder or condition is performed on a human subject.

29. A method of diagnosing a disease, disorder or condition in a mammal including the step of administering a labelled compound of claim 1, or a pharmaceutically effective salt, solvate or prodrug thereof, or metal ion chelate complex thereof, to the mammal or to a biological sample obtained from the mammal to facilitate diagnosis of the disease, disorder or condition in the mammal.

30. A method of modulating the activity of a biological target comprising the step of exposing the biological target to a compound of claim 1, or a pharmaceutically effective salt, solvate or prodrug thereof.

31. The method of claim 30, wherein the biological target is selected from the group consisting of the NLRP3 inflammasome, IL-1β, IL-17, IL-18, IL-1α, IL-37, IL-33 and Th17 cells.

32. The compound of claim 1, wherein A, B, D and E form a ring selected from a pyrazole, a pyrrolidine, a pyrrole, a triazole, a tetrazole and an imidazole.

33. The compound of claim 1, wherein $R_6$ is $C_1$-$C_6$ alkyl or $C_1$-$C_6$ alkylhydroxy.

34. The compound of claim 1, wherein $R_2$ is selected from hexahydroindacene, 2,6-diisopropylphenyl, 2,6-diisopropyl-4-chlorophenyl, 2,6-dicyclopropylphenyl, 2,6-dicyclopropyl-4-chlorophenyl, and

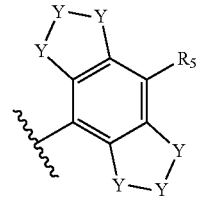

wherein each Y is CH and $R_5$ is H or halogen.

* * * * *

UNITED STATES PATENT AND TRADEMARK OFFICE
CERTIFICATE OF CORRECTION

PATENT NO. : 10,538,487 B2
APPLICATION NO. : 15/551264
DATED : January 21, 2020
INVENTOR(S) : Luke O'Neill et al.

Page 1 of 1

It is certified that error appears in the above-identified patent and that said Letters Patent is hereby corrected as shown below:

In the Claims

In Claim 11, at Column 296, Line 11:
Delete the text "prod rug" and replace it with the text --prodrug--.

In Claim 12, at Column 296, Line 67:
Delete the text "prod rug" and replace it with the text --prodrug--.

Signed and Sealed this
Fourteenth Day of April, 2020

Andrei Iancu
*Director of the United States Patent and Trademark Office*